US007060436B2

(12) United States Patent
Lyamichev et al.

(10) Patent No.: US 7,060,436 B2
(45) Date of Patent: Jun. 13, 2006

(54) NUCLEIC ACID ACCESSIBLE HYBRIDIZATION SITES

(75) Inventors: Victor Lyamichev, Madison, WI (US); Hatim Allawi, Madison, WI (US); Fang Dong, Broomfield, CO (US); Bruce P. Neri, Madison, WI (US); Tatiani I. Vener, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 402 days.

(21) Appl. No.: 09/882,945

(22) Filed: Jun. 15, 2001

(65) Prior Publication Data

US 2003/0143535 A1 Jul. 31, 2003

Related U.S. Application Data

(60) Provisional application No. 60/212,308, filed on Jun. 17, 2000.

(51) Int. Cl.

| | |
|---|---|
| *C12Q 1/68* | (2006.01) |
| *C12N 15/00* | (2006.01) |
| *C12N 15/63* | (2006.01) |
| *C12N 1/20* | (2006.01) |
| *C07H 21/04* | (2006.01) |

(52) U.S. Cl. .................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search .................... 435/6, 435/91.1, 91.2, 91.3; 536/24.3, 23.1, 24.33; 935/6; 436/518

See application file for complete search history.

(56) References Cited

U.S. PATENT DOCUMENTS

| | | | | | |
|---|---|---|---|---|---|
| 5,422,253 A | | 6/1995 | Dahlberg et al. | ........ | 435/91.53 |
| 5,427,930 A | | 6/1995 | Birkenmeyer et al. | ... | 435/91.52 |
| 5,429,807 A | | 7/1995 | Matson et al. | .............. | 422/131 |
| 5,436,327 A | | 7/1995 | Southern et al. | ......... | 536/25.34 |
| 5,494,810 A | | 2/1996 | Barany et al. | ........... | 435/91.52 |
| 5,599,695 A | | 2/1997 | Pease et al. | ............... | 435/91.1 |
| 5,770,373 A | * | 6/1998 | Britschgi et al. | .............. | 435/6 |
| 5,843,654 A | | 12/1998 | Heisler et al. | ................. | 435/6 |
| 5,846,717 A | | 12/1998 | Brow et al. | .................... | 435/6 |
| 5,846,723 A | * | 12/1998 | Kim et al. | ..................... | 435/6 |
| 5,985,557 A | | 11/1999 | Prudent et al. | ................ | 435/6 |
| 5,994,069 A | | 11/1999 | Hall et al. | ..................... | 435/6 |
| 6,001,567 A | | 12/1999 | Brow et al. | .................... | 435/6 |
| 6,060,310 A | | 5/2000 | Cho-Chung | ................. | 435/375 |
| 6,372,424 B1 | | 4/2002 | Brow et al. | .................... | 435/5 |

FOREIGN PATENT DOCUMENTS

| | | |
|---|---|---|
| WO | WO 97/27214 | 7/1972 |
| WO | WO 96/15267 | 6/1995 |
| WO | WO 98/23744 | 6/1998 |

OTHER PUBLICATIONS

Abrams et al., Genomics 7:463 [1990].
Allawi and SantaLucia, Biochemistry 36:10581 [1997].
Altamirano et al., J. Infect. Dis., 171:1034 [1995].
Bains and Smith, J. Theor. Biol., 135:303 [1988].
Banerjee et al., Science 263:227 [1994].
Barlow and Lehrach, Trends Genet., 3:167 [1987].
Bennett et al., J. Immunol., 152:3530 [1994]. This reference is not being supplied at this time but will be sent in a Supplement Information Disclosure Statement.
Bennett et al., J. Pharmacol. Exp. Ther., 280:988 [1997]. This reference is not being supplied at this time but will be sent in a Supplement Information Disclosure Statement.
Bidou et al., RNA 3:1153 [1997].
Borrensen et al., Proc. Natl. Acad. Sci. USA 88:8405 [1991].
Brow et al., J. Clin. Microbiol., 34:3129 [1996].
Bruice and Lima, Biochemistry 36:5004 [1997]. This reference is not being supplied at this time but will be sent in a Supplement Information Disclosure Statement.
Campbell and Cech, RNA 1:598 [1995]. This reference is not being supplied at this time but will be sent in a Supplement Information Disclosure Statement.
Chee et al., Science 274:610 [1996].
Chiang et al., J. Biol. Chem, 266:18162 [1991].
Cload and Shephartz, J. Am. Chem. Soc., 113:6324[1991].
Cockerill, III et al., J. Infect. Dis., 171:240 [1995].
Compton, *in PCR Protocols*, Innis et al. (Eds.), [1990], at p. 39.
Conner, Proc. Natl. Acad. Sci., 80:278 [1983].
Donnabella et al., Am. J. Respir. Dis., 11:639 [1994].
Doty et al., Proc. Natl. Acad. Sci. USA 46:461 [1960].
Drmanac et al., Genomics 4:114 [1989].
Duckett et al., Cell 55:79 [1988].
Eckstein and Lilley (eds.), *Nucleic Acids and Molecular Biology*, vol. 2, Springer–Verlag, Heidelberg [1988]. This reference is not being supplied at this time but will be sent in a Supplement Information Disclosure Statement.
Preier and Tinoco, Biochemistry 14:3310 [1975]. This reference is not being supplied at this time but will be sent in a Supplement Information Disclosure Statement.
Foder et al., Science 251:767 [1991].
Fodor et al., Nature 364:555 [1993].
Francois et al., Nucl. Acid. Res., 22: 3943 [1994].
Fried and Crothers, Nucleic Acids Res., 9:6505 [1981]. This reference is not being supplied at this time but will be sent in a Supplement Information Disclosure Statement.
Frieden et al., New Engl. J. Med., 328:521 [1993].
Gamper et al., J. Mol. Biol., 197:349 [1987].

(Continued)

*Primary Examiner*—Carla Myers
(74) *Attorney, Agent, or Firm*—Medlen & Carroll, LLP

(57) ABSTRACT

The present invention relates to methods and compositions for analyzing nucleic acids, and in particular, methods and compositions for detection and characterization of nucleic acid sequences and sequence changes. The present invention also provides methods and compositions for identifying oligonucleotides with desired hybridization properties to nucleic acid targets containing secondary structure.

40 Claims, 123 Drawing Sheets

OTHER PUBLICATIONS

Fedorova et al., FEBS Lett. 302:47 [1992].
Gaspin and Westhof, J. Mol. Biol. 254:163 [1995].
Girelli et al., Blood 90:2084 [1997].
Godard et al., Nucl. Acids Res., 22:4789 [1994].
Gogos et al., Nucl. Acids Res., 18:6807–6817 [1990].
Hanke et al., J. Mol. Biol., 246:63 [1995].
Harrington and Lieber, Genes and Develop., 3:1344 [1994].
Heym et al., Lancet 344:293 [1994].
Hiraro et al., Nucleic Acids Res. 22(4):576 [1994].
Ho et al., Nature Biotechnology 16:59 [1998].
Howe and Ares, Proc. Natl. Acad. Sci. USA 94:12467 [1997].
Hughes, Scrip Magazine May [1994].
Jacobs, Jr., Clin. Infect. Dis., 19:1 [1994].,
Jacobs, Jr. et al., Science 260:819 [1993].
Jaeger et al., Proc. Natl. Acad. Sci. USA, 86:7706 [1989].
Jaeger et al., Meth. Enzymol. 183:281[1990].
Kanai et al., Lancet 339:1543 [1992].
Kwok, et al., Nucl. Acids. Res. 18:999 [1990].
Lan et al., Science 280:1593 [1998]. This reference is not being supplied at this time but will be sent in a Supplement Information Disclosure Statement.
Lerman and Silverstein, Meth. Enzymol., 155:482 [1987].
Lima et al., Biochemistry 31:12055 1992.
Liu and Sommer, PCR Methods Applic, 4:97 [1994].
Lowman and Draper, J. Biol. Chem., 261:5396 [1986].
Lyarnichev et al., Nature Biotechnology 17:292 [1999].
Lyarnichev et al., Science 260: 778 [1993].
Mangada and Igarishi, Virus Genes 14:5 [1997].
Marmur and Lane, Proc. Natl. Acad. Sci. USA 46:453 [1960].
Maskos and Southern, Nucl. Acids Res., 20:1675 [1992].
Mateeva et al., Nucleic Acids Res., 25:5010 [1997].
Mateeva et al., Nature Biotechnology 16:1374 [1998]. This reference is not being supplied at this time but will be sent in a Supplement Information Disclosure Statement.
Mathews et al., RNA 5:1458 [1999]. This reference is not being supplied at this time but will be sent in a Supplement Information Disclosure Statement.
Mathews et al., J. Mol. Biol., 288:911 [1999].
Miller, et al. J Virol., 71:7648 [1997].
Milner et al., Nature Biotechnology 15:537 [1997].
Mir and Southern, Nature Biotechnology 17:788 [1999]. This reference is not being supplied at this time but will be sent in a Supplement Information Disclosure Statement.
Monia et al., Nature Med., 2:668 [1996]. This reference is not being supplied at this time but will be sent in a Supplement Information Disclosure Statement.
Morris et al., J. Infect. Dis., 171:954 [1995].
Murante et al., J. Biol. Chem., 269:1191 [1994].
Okamoto et al., J. Gen. Virol., 73:673 [1992].
OligoWalk (Mathews et al., RNA 5:1458 [1999].
Orita, et al., Genomics 5:874 [1999].
Parkhurst and Parkhurst, Biochem., 34:285 [1995].
Patel et al., Proc. Natl. Acad. Sci. USA 93:2969 [1996].
Patzel et al., Nucleic Acids Res., 27:4328 [1999].
Periman and Butow, Science 246:1106 [1989].
Peyman et al., Biol. Chem. Hoppe–Seyler 367:195 [1995]. This reference is not being supplied at this time but will be sent in a Supplement Information Disclosure Statement.
Proutski et al., J Gen Virol., 78( Pt 7):1543–1549 (1997).
Richardson et al., J. Am. Chem. Soc., 113:5109 [1991].
Sambrook et al. *Molecular Cloning: A Laboratory Manual*, 2nd ed. Cold Spring Harbor Laboratory Press, Cold Spring Harbor, NY [1989]. This reference is not being supplied at this time but will be sent in a Supplement Information Disclosure Statement.
Scholz et al., Hum. Mol. Genet., 2:2155 [1993].
Schwille et al., Biochem., 35:10182 [1996].
Sezakiel, Frontiers in Biosciences 5:194 [2000]. This reference is not being supplied at this time but will be sent in a Supplement Information Disclosure Statement.
Serano and Cohen, Develop., 121:3809–3818 [1995].
Sheffield et al., Proc. Natl. Acad. Sci., 86:232 [1989].
Shibata in *PCR: The Polymerase Chain Reaction*, Mullis et al., eds., Birkhauser, Boston [1994], pp. 47–54.
Shinnick and Jones in *Tuberculosis: Pathogenesis, Protection and Control*, Bloom, ed., American Society of Microbiology, Washington, D.C. [1994], pp. 517–530.
“Single–Strand Conformation Polymorphism” (SSCP) was developed by Hayashi, Sekya and colleagues (reviewed by Hayashi, PCR Meth. Appl., 1:34–38, [1991].
Smith et al., Genomics 3:217 [1988].
Sohail et al., RNA 5:646 [1999].
Southern et al., Genomics 13:1008 [1992].
Southern et al., Nucleic Acids Res., 22:1368 [1994]. This reference is not being supplied at this time but will be sent in a Supplement Information Disclosure Statement.
Sugimoto et al., Biochemistry 34:11211 [1995]. This reference is not being supplied at this time but will be sent in a Supplement Information Disclosure Statement.
Thompson et al., Oncogene 14:1715 [1997].
Uhlenbeck, J. Mol. Biol., 65:25 [1972]. This reference is not being supplied at this time but will be sent in a Supplement Information Disclosure Statement.
Veyrune et al,, Oncogene 11:2127 [1995].
Vickers et al., Nucleic Acids Res., 28:1340 [2000].
Wallace et al., Nucl. Acids Res., 6:3543 [1979].
Walton et al., Biotechnol. Bioeng., 65:1 [1999]. This reference is not being supplied at this time but will be sent in a Supplement Information Disclosure Statement.
Ward, et al., Virus Genes 10:91 [1995].
Wartell et al., Nucl. Acids Res., 18:2699–2701 [1990]. This reference is not being supplied at this time but will be sent in a Supplement Information Disclosure Statement.
Winter et al., Proc. Natl. Acad. Sci. USA 82:7575 [1985].
Woese and Pace (p. 91), Noller (p. 137), and Cech (p. 239) in Gesteland and Atkins (eds.), *The RNA World*, Cold Spring Harbor Laboratory Press, Cold Spring Harbor, NY [1993].
Woese, Microbiol. Rev., 51:221–271 [1987].
Yacyshyn et al., Gastroenterology 114:1133 [1998]. This reference is not being supplied at this time but will be sent in a Supplement Information Disclosure Statement.
Yang et al., Biochem., 35:7959 [1996].
Youil et al., Genomics 32:431 [1996].
Yoshioka et al., Hepatol., 16:293 [1992].
Yule, Bio/Technol., 12:1335 [1994].
Zarrinkar and Williamson, Science 265:928 [1994].
Zarrinkar and Williamson, Nat. Struct. Biol., 3:432 1996.
Zhong et al., Biochem., 32:6898 [1993].
Zuker, Science 244:48 [1989].
Zuker and Jacobson. Nucl. Acids Res. 23:2791 [1995].

* cited by examiner

FIGURE 6

```
Consensus:GATTCTGTCT TCACGCAGAA AGCGTCTAGC CATGGCGTTA GTATGAGTGT CGTGCAGCCT
 HCV 1a   ---------- ---------- ---------- ---------- ---------- ----------
 HCV 1b   ---------- ---------- ---------- ---------- ---------- ----------
 HCV 2c   ---------- ---------- ---------- ---------- ---------- ---A------
 HCV 3a   ---------- ---------- ----C----- ---------- ---C------ ----------

                              #249       #251
          CCAGGACCCC CCCTCCCGGG AGAGCCATAG TGGTCTGCGG AACCGGTGAG TACACCGGAA
          ---------- ---------- ---------- ---------- ---------- ----------
          -----T---- ---------- ---------- ---------- ---------- ----------
          -----C---- ---------- ---------- ---------- ---------- ----------
          ---------- ---------- ---A------ ---------- ---------- ----------

               #253                                          #257
          TTGCCAGGAC GACCGGGTCC TTTCTTGGAT CAACCCGCTC AATGCCTGGA GATTTGGGCG
          ---------- ---------- ---------- ---------- ---------- ----------
          ---------- ---------- ---------- ---------- ---------- ----------
          -----G---A ---T------ ---------- A-----A--- T-----C--C C---------
          -C--TG--GT ---------- ---------G ---------- ---A--CA-- A---------

              #40         #261        #263
          TGCCCCCGCA AGACTGCTAG CCGAGTAGTG TTGGGTCGCG AAAGGCCTTG TGGTACTGCC
          ---------- ---------- ---------- ---------- ---------- ----------
          ---------G ---------- ---------- ---------- ---------- ----------
          ---------- ---------- --------C- ------T--- ---------- ----------
          ---------G ---TCA---- ---------- ---------- ---------- ----------

          TGATAGGGTG CTTGCGAGTG CCCCGGGAGG TCTCGTAGAC CGTGCAATC
          ---------- ---------- ---------- ---------- ---------
          ---------- ---------- ---------- ---------- ------
          ---------- ---------A ---------- ---------- ---------
          ---------- ---------- ---------- ---------- ---------
```

FIGURE 8B
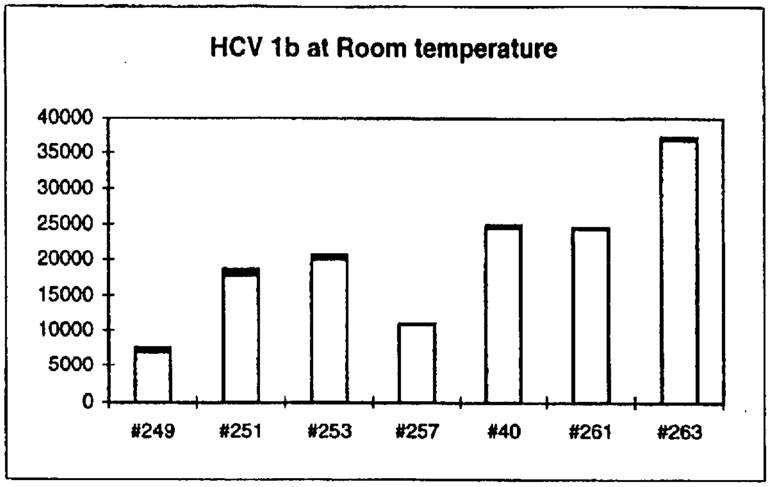
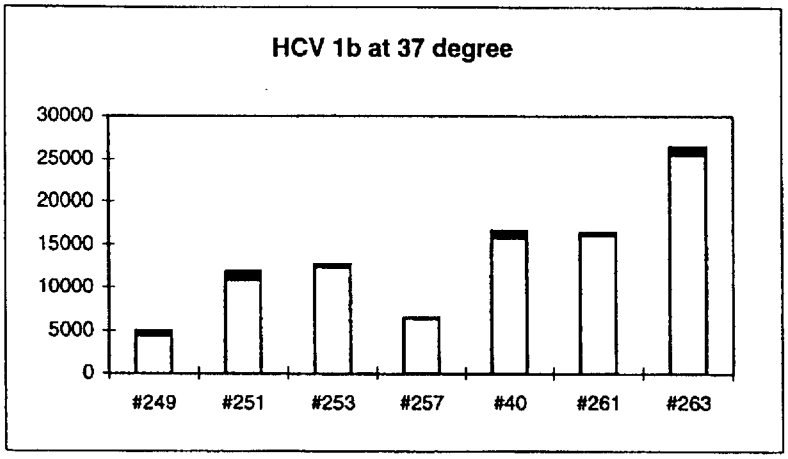
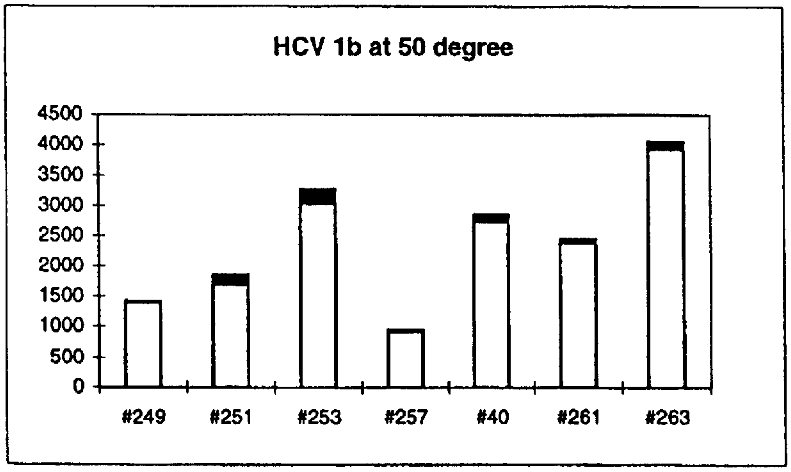

FIGURE 8C
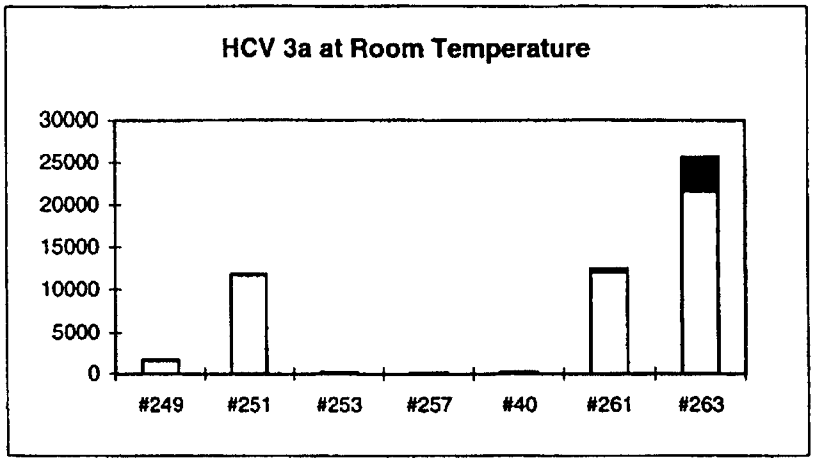
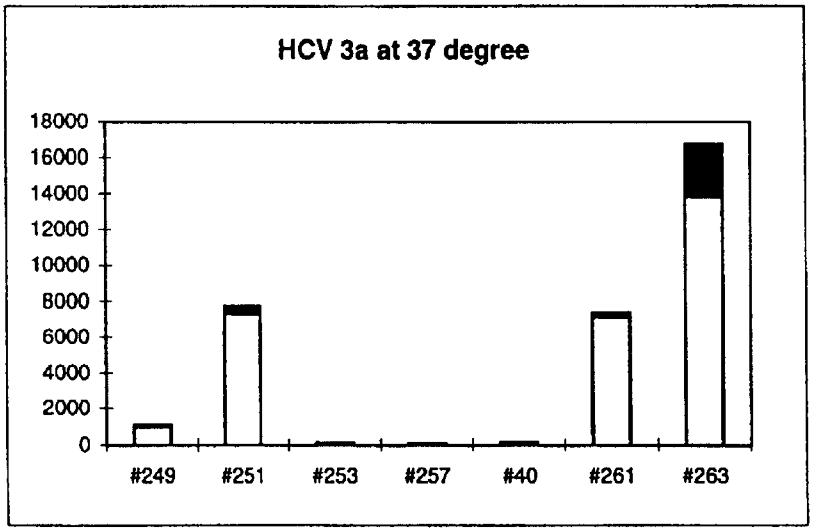
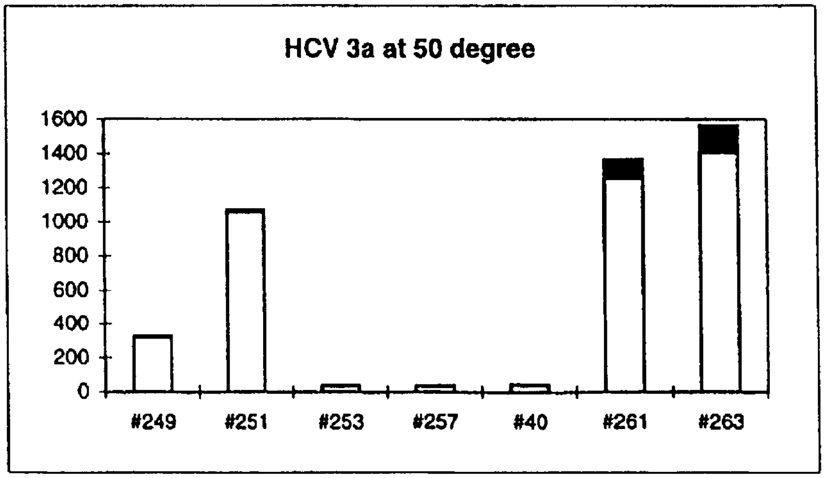

FIGURE 9D
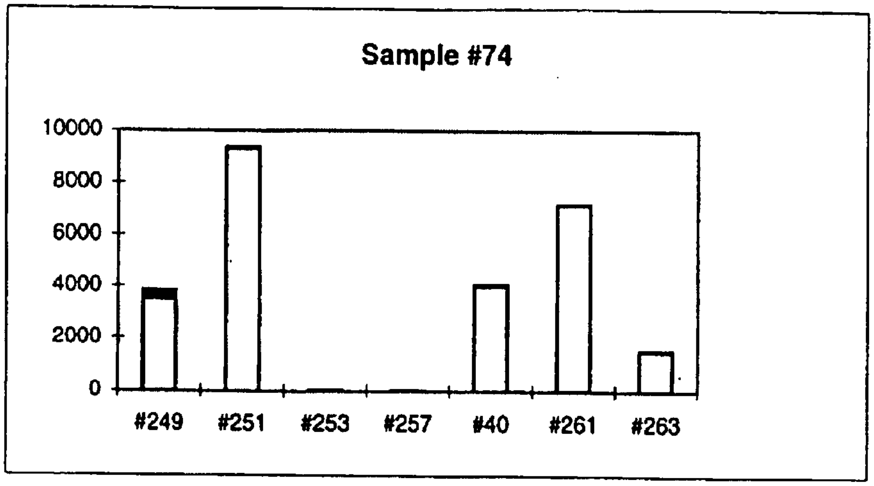
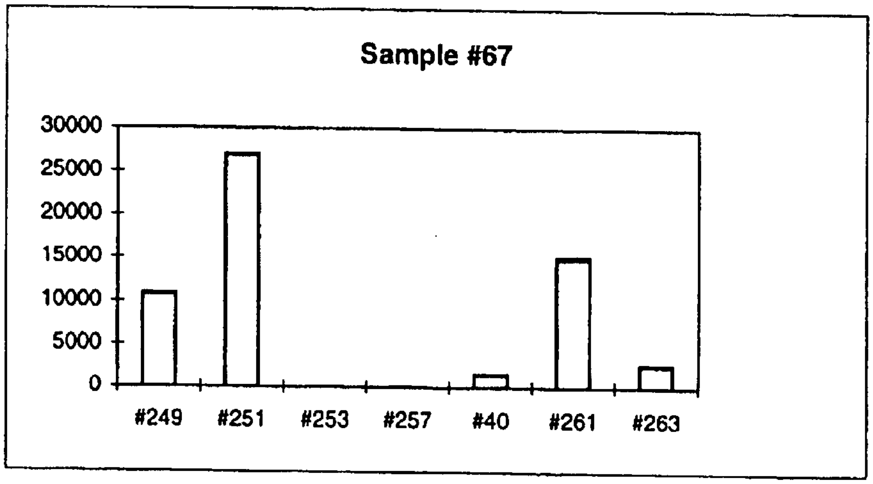

FIGURE 10
#80
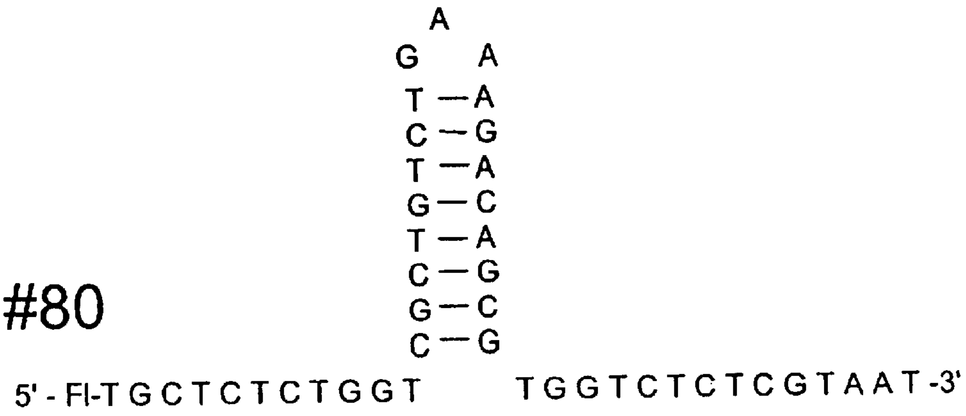
#81
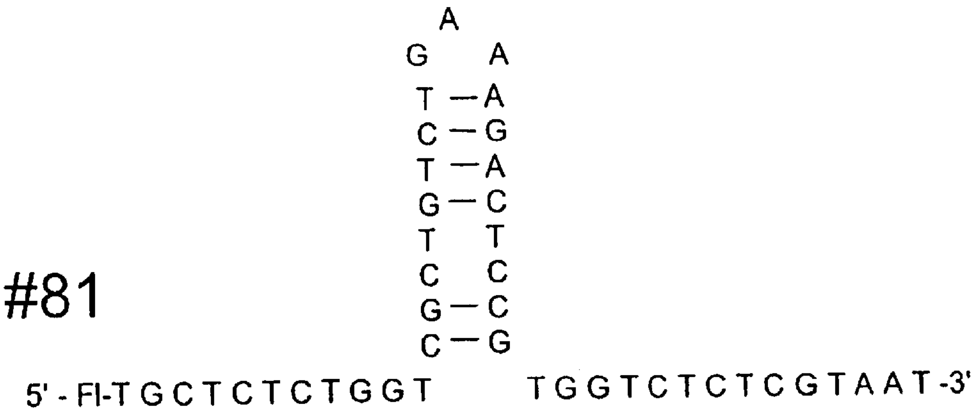
#82
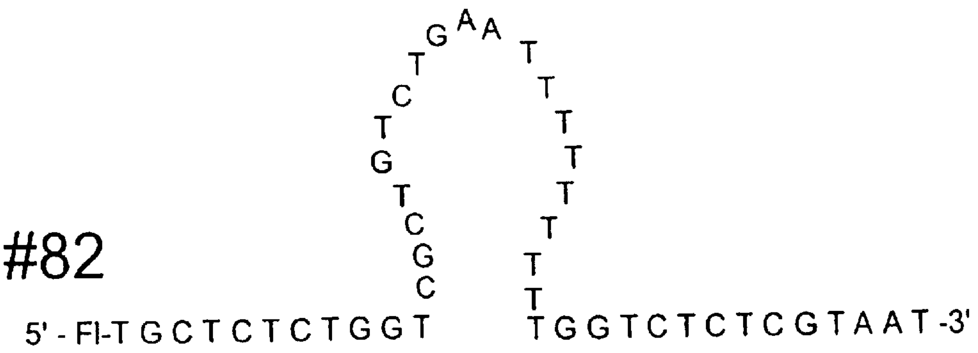
```
                A
            G       A
            T  — A
            C  — G
            T  — A
            G  — C
            T  — A
            C  — G
80         G  — C
            C  — G
  5'-FI-T G C T C T G G T      T G G T C T C T C G T A A T-3'
```
```
                A
            G       A
            T  — A
            C  — G
            T  — A
            G  — C
            T     T
81         C     C
            G  — C
            C  — G
  5'-FI-T G C T C T G G T      T G G T C T C T C G T A A T-3'
```
```
              G A A
           T        T
         C          T T
        T             T
        G              T
        T              T
        G              T
        C              T T
  5'-FI-T G C T C T G G T     T G G T C T C T C G T A A T-3'
```

```
              A
          G       A
          T — A
          C — G
          T — A
          G — C
          T — A
          C — G
          G — C
          C — G
80) 5'-FI-T G C T C T G G T      T G G T C T C T C G T A A T-3'
79) 3'-A G A G A C C A—T T—A C C A G A G A-Biotin 5'
```

```
              A
          G       A
          T — A
          C — G
          T — A
          G — C
          T — A
          C — G
          G — C
          C — G
80) 5'-FI-T G C T C T C T G G T      T G G T C T C T C G T A A T-3'
         3'-A G A G A C C A        A C C A G A G A-Biotin 5'
                        T          T
              #115      T          T      #114
                        A          A
                        C          C
              A ←→ C              C ←→ A
                        A          A
                        G          G
              C ←→ A              A ←→ C
                        G          G
                        A          A
                        /           \
                    Biotin 5'        3'
```

FIGURE 15

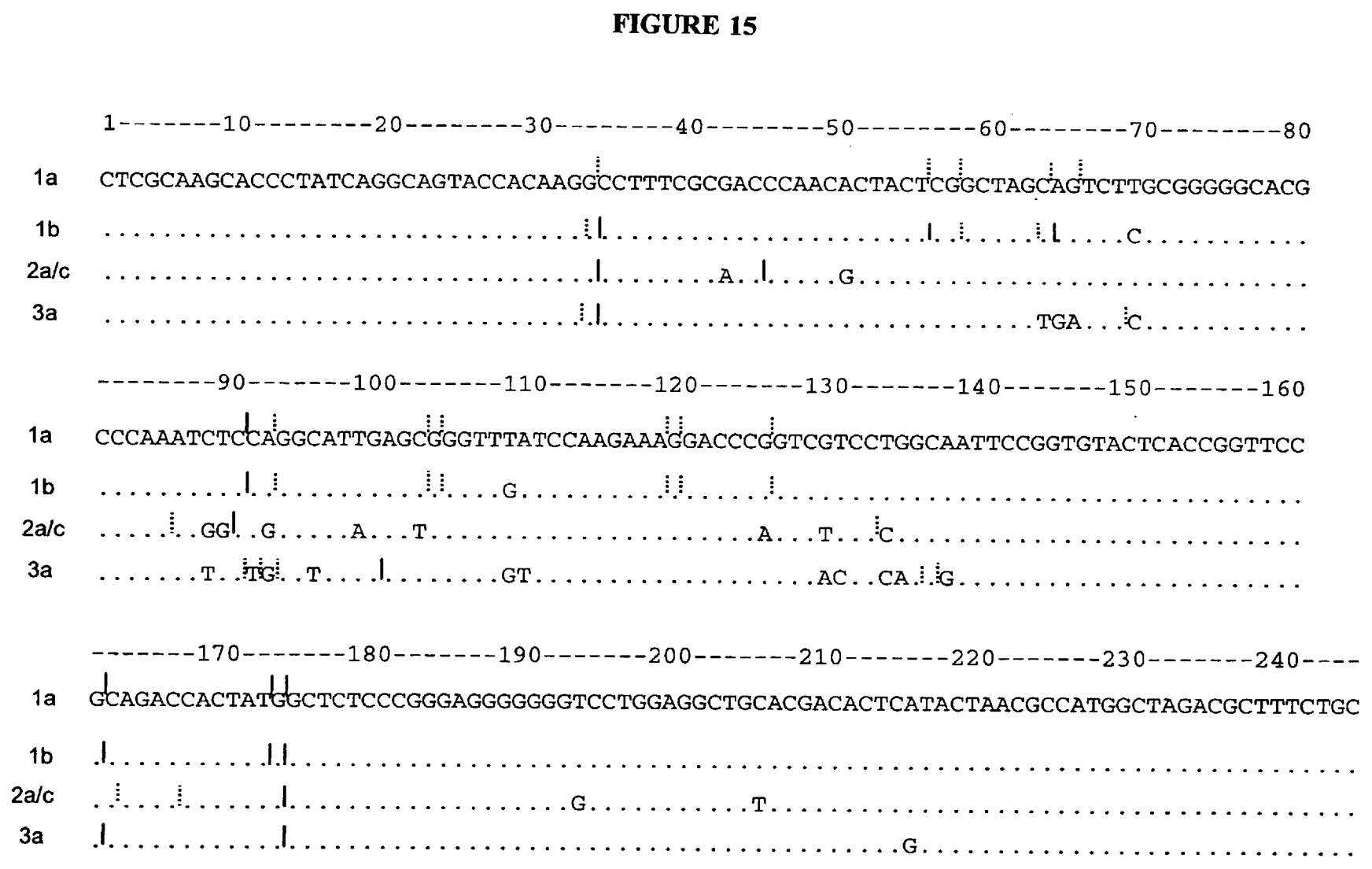

```
       1-------10--------20--------30--------40--------50--------60--------70--------80
1a     CTCGCAAGCACCCTATCAGGCAGTACCACAAGGCCTTTCGCGACCCAACACTACTCGGCTAGCAGTCTTGCGGGGGCACG
1b     ....................................................................C...........
2a/c   .........................................A.......G..............................
3a     ..............................................................TGA...C...........

--------90-------100-------110-------120-------130-------140-------150-------160
1a     CCCAAATCTCCAGGCATTGAGCGGGTTTATCCAAGAAAGGACCCGGTCGTCCTGGCAATTCCGGTGTACTCACCGGTTCC
1b     ...........................G....................................................
2a/c   .......GG..G.....A...T......................A...T...C...........................
3a     .......T..TG..T............GT...................AC..CA..G.......................

-------170-------180-------190-------200-------210-------220-------230-------240----
1a     GCAGACCACTATGGCTCTCCCGGGAGGGGGGTCCTGGAGGCTGCACGACACTCATACTAACGCCATGGCTAGACGCTTTCTGC
1b     ................................................................................
2a/c   ..............................G...........T.....................................
3a     ...................................................G............................
```

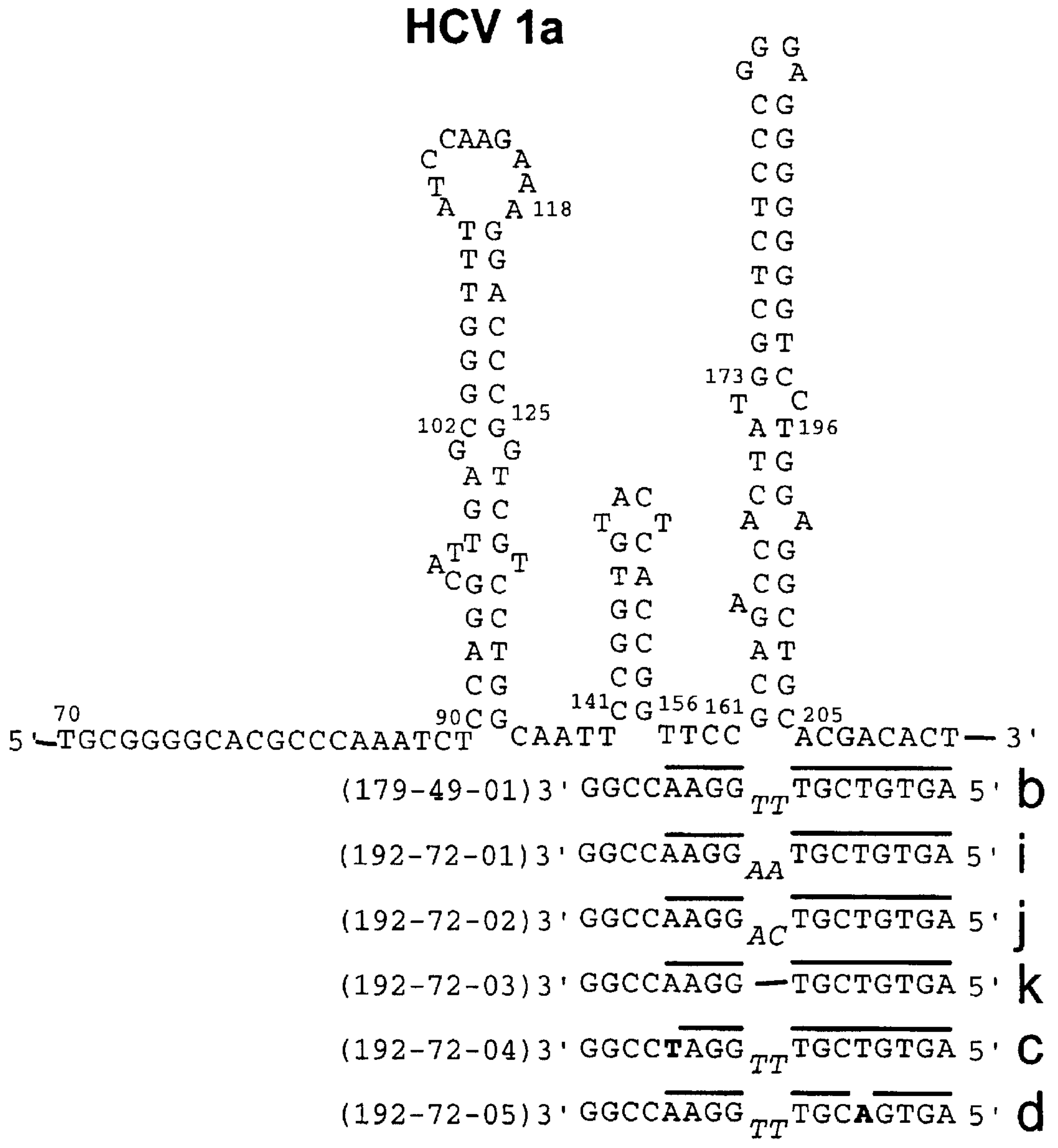

FIGURE 18A

HCV 1a

```
                                    G G
                                   G   A
                                   C G
        CAAG                       C G
       C    A                      C G
      T      A                     C G
     A        A 118                 T G
      T G                          C G
      T G                           T G
      T A                          C G
      G C                          C G
      G C                           G T
      G C                      173 G C
 102 C G 125                        T   C
      G  G                          A T 196
      A T                            T G
      G C        A C                C G
        T G   T     T                A  A
     A    T   G C                   C G
      C G C   T A                   C G
      G C     G C                A  C G
      A T     G C                 G C
      C G     C G                   A T
  70         C G        141        C G
          90 C G          C G 156 161 G C 205
5'-TGCGGGGCACGCCCAAATCT   CAATT    TTCC   ACGACACT—3'
   ─────────────────────  ─────    ────   ────────
(179-49-01) 3' GGCCAAGG    TGCTGTGA 5'   b
                        TT
(192-72-01) 3' GGCCAAGG    TGCTGTGA 5'   i
                        AA
(192-72-02) 3' GGCCAAGG    TGCTGTGA 5'   j
                        AC
(192-72-03) 3' GGCCAAGG  — TGCTGTGA 5'   k
(192-72-04) 3' GGCCTAGG    TGCTGTGA 5'   c
                        TT
(192-72-05) 3' GGCCAAGG    TGCAGTGA 5'   d
                        TT
```

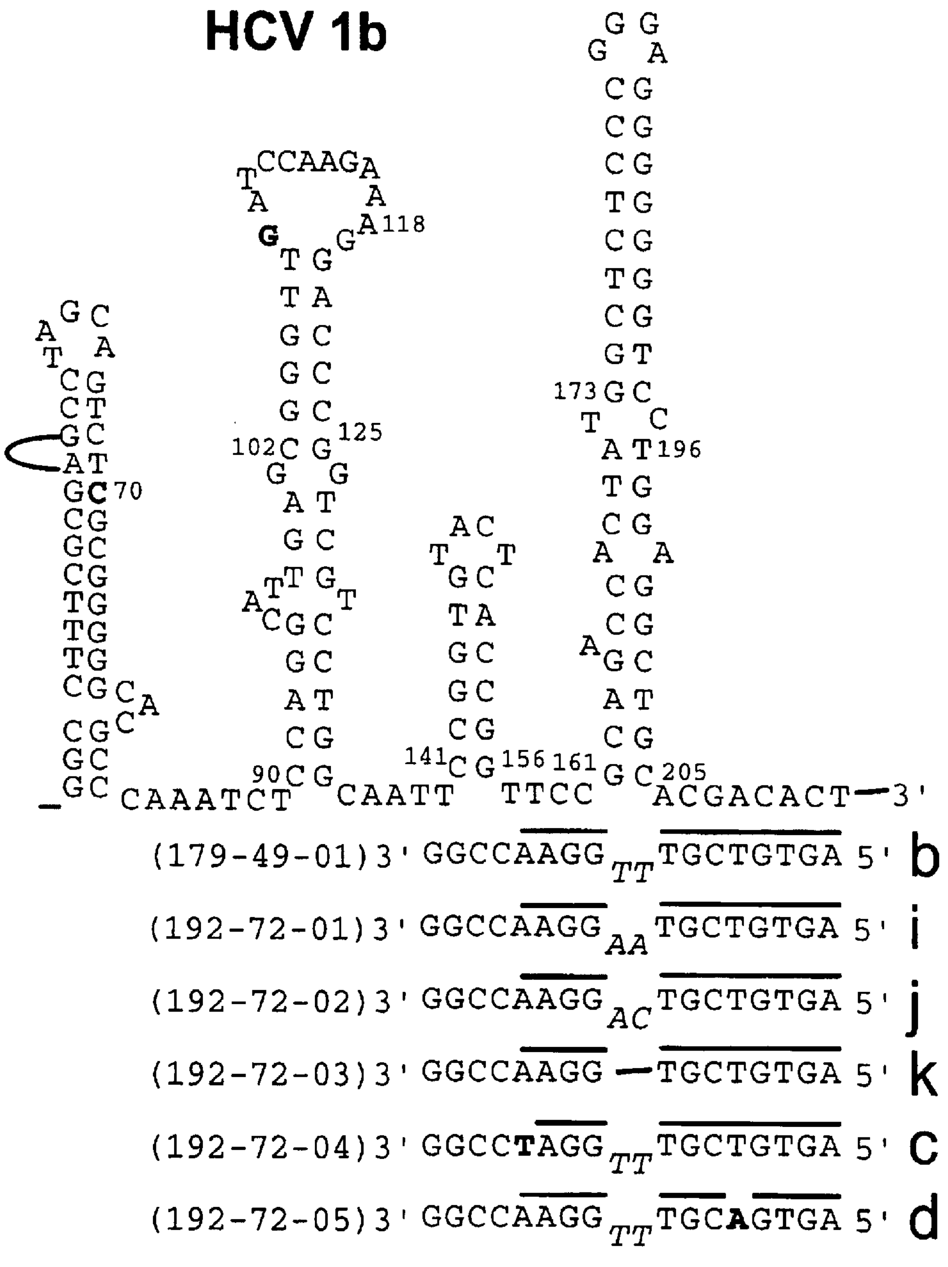

FIGURE 18B

HCV 1b

```
                                            G G
                                          G   G
                                        G     A
                                        C G
                                        C G
                                        C G
              CCAAGA                    C G
            T A     A                   T G
           T    A118A                   C G
           G  G G                       T G
           T G                          C G
           T A                          G T
           G C                       173G C
           G C                          T C
           G C                          A T196
      102C G  125                       T G
           G G                          C G
  A G C                              A C  A A
  T  A    A T                      T T    C G
  T C                              G C T  C G
  C G     G C                        T A  C G
  C T    T T G                       G C A G C
  G C A G C T                        G C  A T
  A T    C                            T   C G
  G C70  G C A                       A T  C G
  C G    C                           C G  C G
  G C    G C                         C G 205
  C G   90C G   141C G  156 161G C
  T G  CAAATCT  CAATT     TTCC  ACGACACT—3'
  T G
  T G
  C G C A
  C G C
  G C
 _G C
```

(179-49-01) 3' GGCCAAGG$_{TT}$TGCTGTGA 5'  b

(192-72-01) 3' GGCCAAGG$_{AA}$TGCTGTGA 5'  i

(192-72-02) 3' GGCCAAGG$_{AC}$TGCTGTGA 5'  j

(192-72-03) 3' GGCCAAGG —TGCTGTGA 5'  k

(192-72-04) 3' GGCCTAGG$_{TT}$TGCTGTGA 5'  c

(192-72-05) 3' GGCCAAGG$_{TT}$TGCAGTGA 5'  d

HCV 1a

```
         G G
        G   A
        C G
        C G
        C G
        T G
        C G
        T G
        C G
        G T
    173 G C
        T   C
        A T 196
        T G
        C G
        A   A
        C G
        C G
        A G C
        A T
        C G
        G C 205
5'—CAATTCCGGTGTACTCACCGGTTCC     ACGACACT—3'
```

3'-<u>GGCCAAGGCGTCTGGTGA</u>-F1 5' (205-13-02)    a

3'-<u>GGCCAAGG</u><sub>TT</sub><u>TGCTGTGA</u>-F1 5' (179-49-01)    b

3'-<u>GGCCAAGG</u>-F15' (205-27-01)    e

HCV 1a
5'-CAATTCCGGTGTACTCACCGGTTCC
ACGACACT-3'
173
196
205
f (192-96-01) 3'-TAAGGCCACATGAGT-5'
3'-GGCCAAGGCGTCTGGTGA-F1'5'(205-13-02) a
3'-GGCCAAGG TT TGCTGTGA-F1'5'(179-49-01) b
3'-GGCCTAGG TT TGCTGTGA-F1'5'(192-72-04) c
3'-GGCCAAGG TT TGCAGTGA-F1'5'(192-72-05) d
3'-GGCCAAGG-F15'(205-27-01) e

FIGURE 26

```
    5'-ATTCCGGTGTACTCACCGGTTCCAAACGACACT-3'(205-13-01)  S.T.
f (192-96-01)3'-TAAGGCCACATGAGT-5'
                3'-GGCCAAGGCGTCTGGTGA-F1'5'(205-13-02)   a
                3'-GGCCAAGG TT TGCTGTGA—F1'5'(179-49-01)  b
                3'-GGCCTAGG TT TGCTGTGA—F1'5'(192-72-04)  c
                3'-GGCCAAGG TT TGCAGTGA—F1'5'(192-72-05)  d
                3'-GGCCAAGG-F15'(205-27-01)               e
```

FIGURE 29B

```
S.T.  5'-ATTCCGGTGTACTCACCGGTTCCAAACGACACT-3'(205-13-01)
a     3'-GGCCAAGGCGTCTGGTGA-Fl'5'(205-13-02)
b     3'-GGCCAAGGTTTGCTGTGA—Fl'5'(179-49-01)
c     3'-GGCCTAGGTTTGCTGTGA—Fl'5'(192-72-04)
d     3'-GGCCAAGGTTTGCAGTGA—Fl'5'(192-72-05)
e     3'-GGCCAAGG-F15'(205-27-01)
g     3'-TAAGGCCACATGAGTGTTTT—Fl'5'(192-96-02)
```

FIGURE 37A
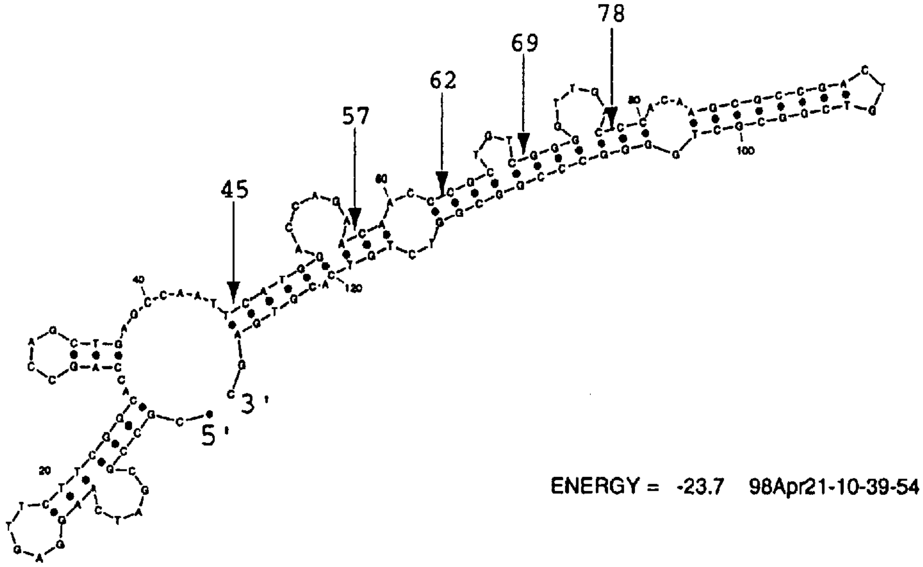
ENERGY = -23.7 98Apr21-10-39-54
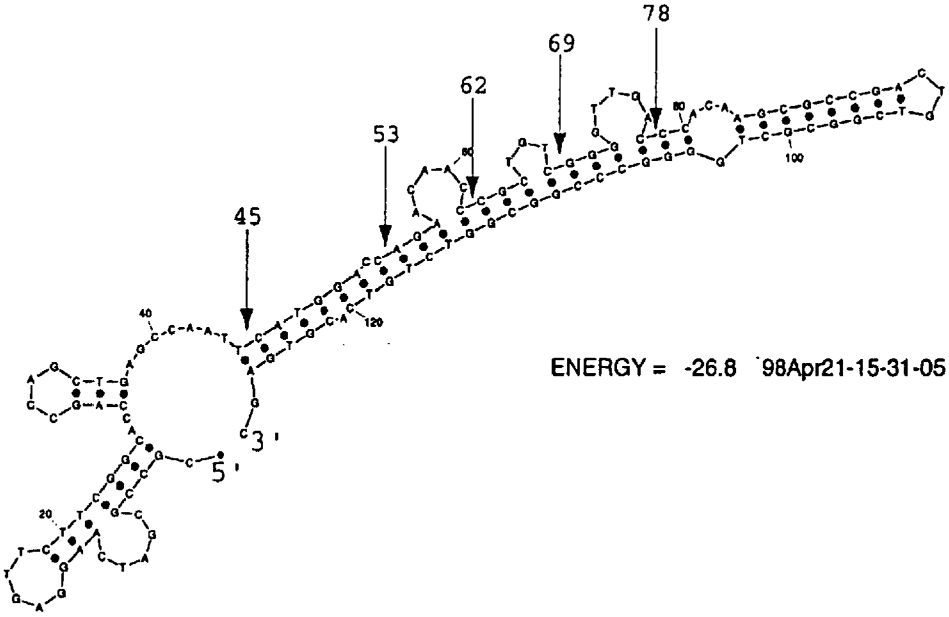
ENERGY = -26.8 98Apr21-15-31-05

FIGURE 37C
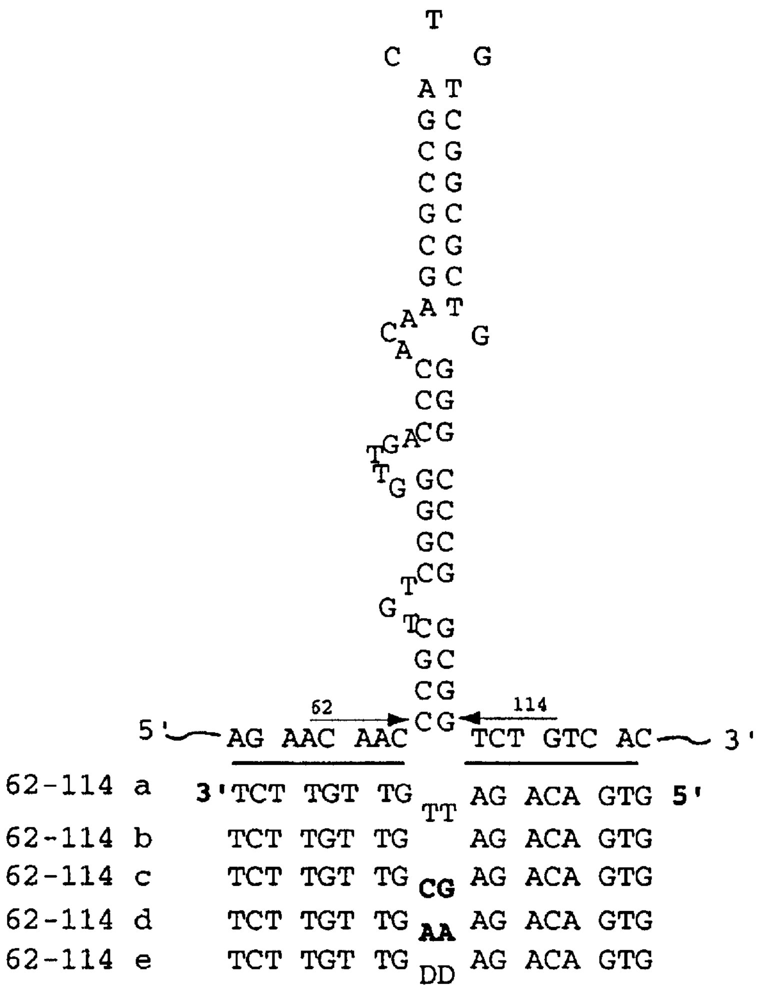
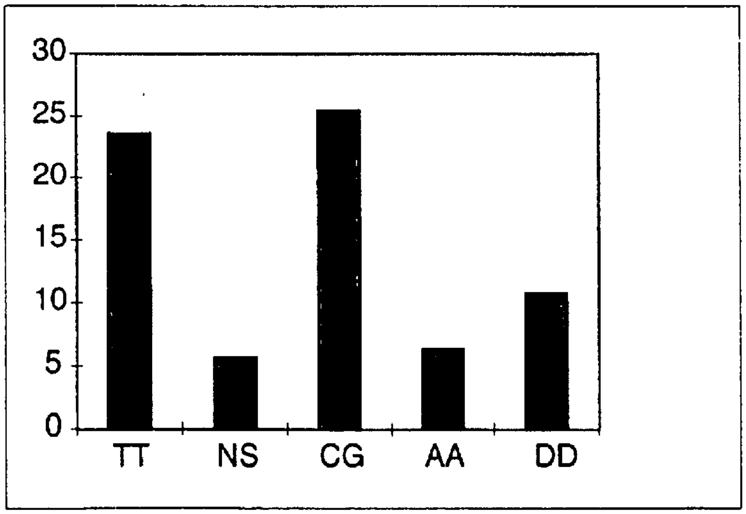

FIGURE 38A
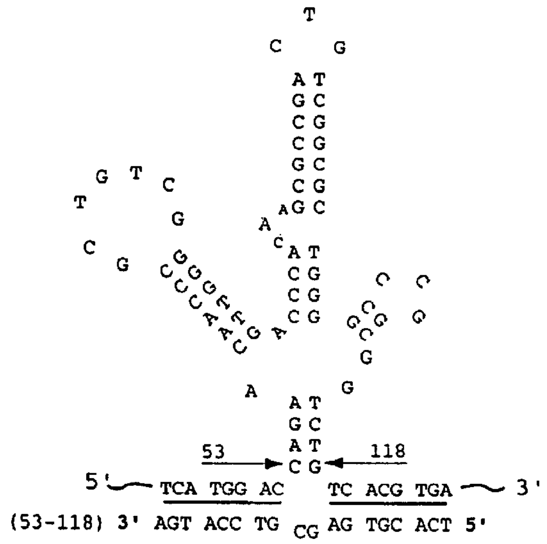
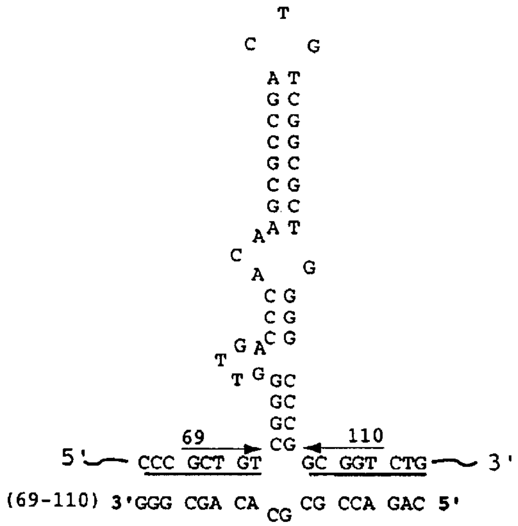
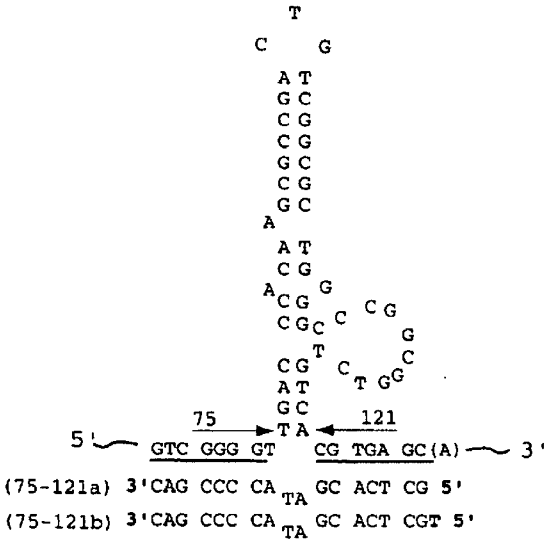
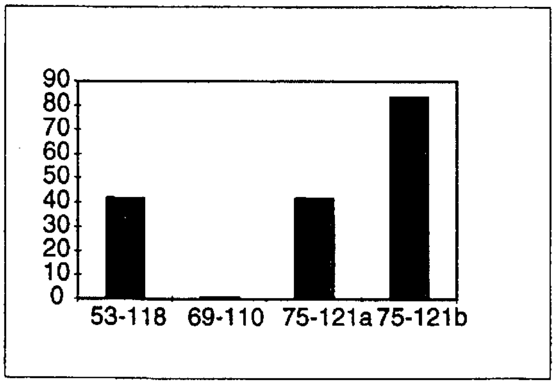

FIGURE 40
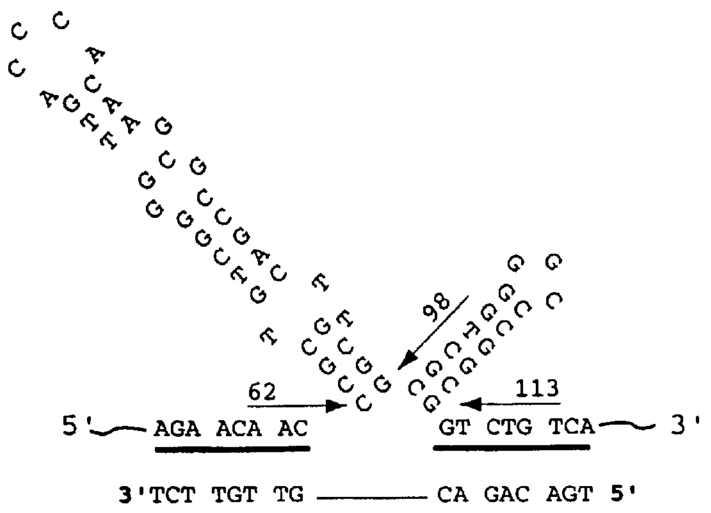
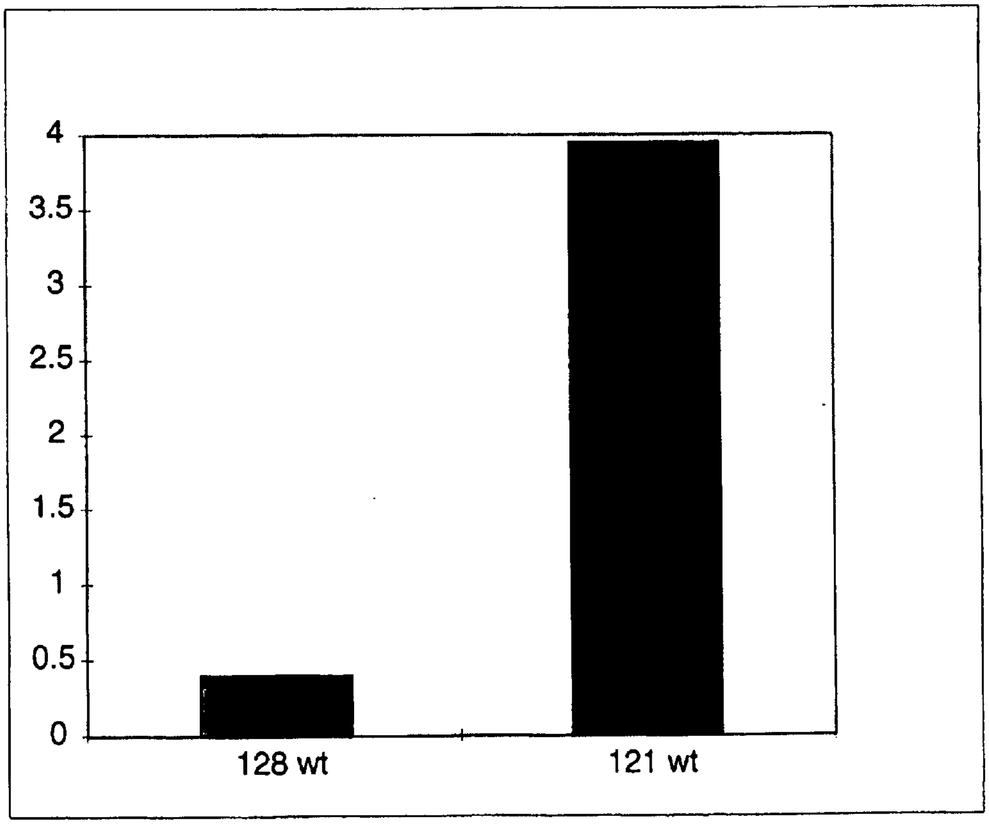

FIGURE 42
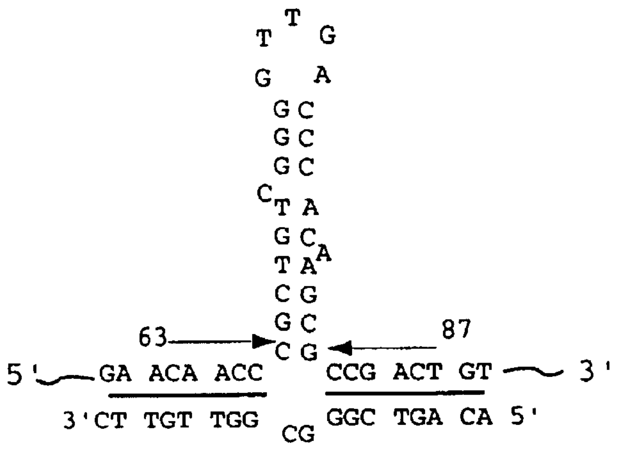
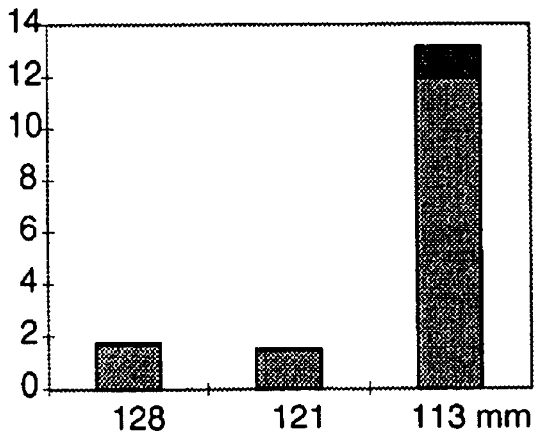

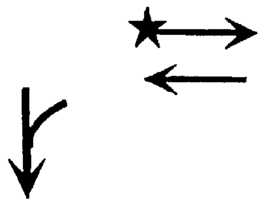
III) PCR
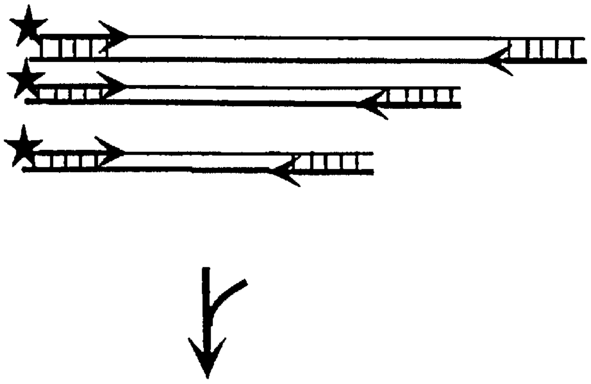
IV) PAGE with
Sequencing Ladder
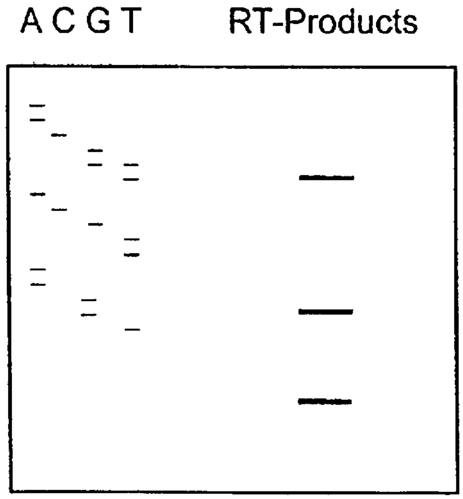
FIGURE 45B

SEQ ID 142

FIGURE 51

| | | | | | |
|---|---|---|---|---|---|
| | | | | 44-50 | |
| 1 | ACACUUGCUU | UUGACACAAC | UGUGUUUACU | UGCAAUCCCC | CAAAACAGAC |
| | 64-68 | | | 88-97 | |
| 51 | AGAAUGGUGC | AUCUGUCCAG | UGAGGAGAAG | UCUGCGGUCA | CUGCCCUGUG |
| 101 | GGGCAAGGUG | AAUGUGGAAG | AAGUUGGUGG | UGAGGCCCUG | GGCAGGCUGC |
| 151 | UGGUUGUCUA | CCCAUGGACC | CAGAGGUUCU | UCGAGUCCUU | UGGGGACCUG |

FIGURE 52A

```
                   ISIS 1571(-) ISIS 3067(+)
1     GCGCCCCAGT CGACGCTGAG CTCCTCTGCT ACTCAGAGTT

                 ISIS 1570(+)
41    GCAACCTCAG CCTCGCTATG GCTCCCAGCA GCCCCCGGCC

81    CGCGCTGCCC GCACTCCTGG TCCTGCTCGG GGCTCTGTTC

121   CCAGGACCTG GCAATGCCCA GACATCTGTG TCCCCCTCAA

161   AAGTCATCCT GCCCCGGGGA GGCTCCGTGC TGGTGACATG

201   CAGCACCTCC TGTGACCAGC CCAAGTTGTT GGGCATAGAG

241   ACCCCGTTGC CTAAAAAGGA GTTGCTCCTG CCTGGGAACA

281   ACCGGAAGGT GTATGAACTG AGCAATGTGC AAGAAGATAG

                                ISIS 1934(-)
321   CCAACCAATG TGCTATTCAA ACTGCCCTGA TGGGCAGTCA

361   ACAGCTAAAA CCTTCCTCAC CGTGTACTGG ACTCCAGAAC

401   GGGTGGAACT GGCACCCCTC CCCTCTTGGC AGCCAGTGGG

441   CAAGAACCTT ACCCTACGCT GCCAGGTGGA GGGTGGGGCA

481   CCCCGGGCCA ACCTCACCGT GGTGCTGCTC CGTGGGGAGA
```

FIGURE 52B

521 AGGAGCTGAA ACGGGAGCCA GCTGTGGGGG AGCCCGCTGA as 610

561 GGTCACGACC ACGGTGCTGG TGAGGAGAGA TCACCATGGA

601 GCCAATTTCT CGTGCCGCAC TGAACTGGAC CTGCGGCCCC

641 AAGGGCTGGA GCTGTTTGAG AACACCTCGG CCCCCTACCA

681 GCTCCAGACC TTTGTCCTGC CAGCGACTCC CCCACAACTT

721 GTCAGCCCCC GGGTCCTAGA GGTGGACACG CAGGGGACCG

761 TGGTCTGTTC CCTGGACGGG CTGTTCCCAG TCTCGGAGGC

801 CCAGGTCCAC CTGGCACTGG GGGACCAGAG GTTGAACCCC

841 ACAGTCACCT ATGGCAACGA CTCCTTCTCG GCCAAGGCCT

881 CAGTCAGTGT GACCGCAGAG GACGAGGGCA CCCAGCGGCT

921 GACGTGTGCA GTAATACTGG GGAACCAGAG CCAGGAGACA

961 CTGCAGACAG TGACCATCTA CAGCTTTCCG GCGCCCAACG

1001 TGATTCTGAC GAAGCCAGAG GTCTCAGAAG GGACCGAGGT

FIGURE 52C

1041 GACAGTGAAG TGTGAGGCCC ACCCTAGAGC CAAGGTGACG

1081 CTGAATGGGG TTCCAGCCCA GCCACTGGGC CCGAGGGCCC

1121 AGCTCCTGCT GAAGGCCACC CCAGAGGACA ACGGGCGCAG

1161 CTTCTCCTGC TCTGCAACCC TGGAGGTGGC CGGCCAGCTT as 1220 (+)

1201 ATACACAAGA ACCAGACCCG GGAGCTTCGT GTCCTGTATG

1241 GCCCCCGACT GGACGAGAGG GATTGTCCGG GAAACTGGAC

1281 GTGGCCAGAA AATTCCCAGC AGACTCCAAT GTGCCAGGCT

1321 TGGGGGAACC CATTGCCCGA GCTCAAGTGT CTAAAGGATG

ISIS 1547 (+)

1361 GCACTTTCCC ACTGCCCATC GGGGAATCAG TGACTGTCAC

1401 TCGAGATCTT GAGGGCACCT ACCTCTGTCG GGCCAGGAGC

1441 ACTCAAGGGG AGGTCACCCG CGAGGTGACC GTGAATGTGC

1481 TCTCCCCCCG GTATGAGATT GTCATCATCA CTGTGGTAGC

1521 AGCCGCAGTC ATAATGGGCA CTGCAGGCCT CAGCACGTAC

FIGURE 52D

1561 CTCTATAACC GCCAGCGGAA GATCAAGAAA TACAGACTAC as 1630 as 1630h(+++)

1601 AACAGGCCCA AAAAGGGACC CCCATGAAAC CGAACACACA

ISIS 1938 (+)

1641 AGCCACGCCT CCCTGAACCT ATCCCGGGAC AGGGCCTCTT

1681 CCTCGGCCTT CCCATATTGG TGGCAGTGGT GCCACACTGA

1721 ACAGAGTGGA AGACATATGC CATGCAGCTA CACCTACCGG

1761 CCCTGGGACG CCGGAGGACA GGGCATTGTC CTCAGTCAGA

1801 TACAACAGCA TTTGGGGCCA TGGTACCTGC ACACCTAAAA

1841 CACTAGGCCA CGCATCTGAT CTGTAGTCAC ATGACTAAGC

1881 CAAGAGGAAG GAGCAAGACT CAAGACATGA TTGATGGATG

ISIS 1939 (+)

1921 TTAAAGTCTA GCCTGATGAG AGGGGAAGTG GTGGGGGAGA

1961 CATAGCCCCA CCATGAGGAC ATACAACTGG GAAATACTGA

2001 AACTTGCTGC CTATTGGGTA TGCTGAGGCC CACAGACTTA

2041 CAGAAGAAGT GGCCCTCCAT AGACATGTGT AGCATCAAAA

FIGURE 52E

ISIS 2302 (+)

2081 CACAAAGGCC CACACTTCC<u>T GACGGATGCC AGCTTGGGC</u>A

2121 CTGCTGTCTA CTGACCCCAA CCCTTGATGA TATGTATTTA

ISIS 1572

2161 TTCATTTGTT ATTTT<u>ACCAG CTATTTATTG AGTGTC</u>TTTT

2201 ATGTAGGCTA AATGAACATA GGTCTCTGGC CTCACGGAGC

2241 TCCCAGTCCA TGTCACATTC AAGGTCACCA GGTACAGTTG

2281 TACAGGTTGT ACACTGCAGG AGAGTGCCTG GCAAAAAGAT

2321 CAAATGGGGC TGGGACTTCT CATTGGCCAA CCTGCCTTTC

2361 CCCAGAAGGA GTGATTTTTC TATCGGCACA AAAGCACTAT

2401 ATGGACTGGT AATGGTTCAC AGGTTCAGAG ATTACCCAGT

2441 GAGGCCTTAT TCCTCCCTTC CCCCCAAAAC TGACACCTTT

2481 GTTAGCCACC TCCCCACCCA CATACATTTC TGCCAGTGTT

2521 CACAATGACA CTCAGCGGTC ATGTCTGGAC ATGAGTGCCC

2561 AGGGAATATG CCCAAGCTAT GCCTTGTCCT CTTGTCCTGT

FIGURE 52F

2601 TTGCATTTCA CTGGGAGCTT GCACTATTGC AGCTCCAGTT

2641 TCCTGCAGTG ATCAGGGTCC TGCAAGCAGT GGGGAAGGGG

2681 GCCAAGGTAT TGGAGGACTC CCTCCCAGCT TTGGAAGGGT

2721 CATCCGCGTG TGTGTGTGTG TGTATGTGTA GACAAGCTCT

2761 CGCTCTGTCA CCCAGGCTGG AGTGCAGTGG TGCAATCATG

2801 GTTCACTGCA GTCTTGACCT TTTGGGCTCA AGTGATCCTC

2841 CCACCTCAGC CTCCTGAGTA GCTGGGACCA TAGGCTCACA

2881 ACACCACACC T

FIGURE 53A

```
1    CACAUUGUUC UGAUCAUCUG AAGAUCAGCU AUUAGAAGAG

                                            site 80
41   AAAGAUCAGU UAAGUCCUUU GGACCUGAUC AGCUUGAUAC

                                   site 120
81   AAGAACUACU GAUUUCAACU UCUUUGGCUU AAUUCUCUCG

121  GAAACGAUGA AAUAUACAAG UUAUAUCUUG GCUUUUCAGC

161  UCUGCAUCGU UUUGGGUUCU CUUGGCUGUU ACUGCCAGGA

                site 210
201  CCCAUAUGUA CAAGAAGCAG AAAACCUUAA GAAAUAUUUU

       site 240         site 260
241  AAUGCAGGUC AUUCAGAUGU AGCGGAUAAU GGAACUCUUU

281  UCUUAGGCAU UUUGAAGAAU UGGAAAGAGG AGAGUGACAG

               site 330
321  AAAAAUAAUG CAGAGCCAAA UUGUCUCCUU UUACUUCAAA

                               site 380    site 400
361  CUUUUUAAAA ACUUUAAAGA UGACCAGAGC AUCCAAAAGA

401  GUGUGGAGAC CAUCAAGGAA GACAUGAAUG UCAAGUUUUU

441  CAAUAGCAAC AAAAAGAAAC GAGAUGACUU CGAAAAGCUG
```

FIGURE 53B

```
481  ACUAAUUAUU CGGUAACUGA CUUGAAUGUC CAACGCAAAG

                                          site 560
521  CAAUACAUGA ACUCAUCCAA GUGAUGGCUG AACUGUCGCC

                     site 570
561  AGCAGCUAAA ACAGGGAAGC GAAAAAGGAG UCAGAUGCUG

601  UUUCGAGGUC GAAGAGCAUC CCAGUAAUGG UUGUCCUGCC

641  UACAAUAUUU GAAUUUUAAA UCUAAAUCUA UUUAUUAAUA

681  UUUAACAUUA UUUAUAUGGG GAAUAUAUUU UUAGACUCAU

721  CAAUCAAAUA AGUAUUUAUA AUAGCAACUU UUGUGUAAUG

761  AAAAUGAAUA UCUAUUAAUA UAUGUAUUAU UUAUAAUUCC

801  UAUAUCCUGU GACUGUCUCA CUUAAUCCUU UGUUUUCUGA

              site 850         site 860        site 880
841  CUAAUUAGGC AAGGCUAUGU GAUUACAAGG CUUUAUCUCA

                site 890            site 910
881  GGGGCCAACU AGGCAGCCAA CCUAAGCAAG AUCCCAUGGG

921  UUGUGUGUUU AUUUCACUUG AUGAUACAAU GAACACUUAU

961  AAGUGAAGUG AUACUAUCCA GUUACUA
```

FIGURE 55A

SEQ ID NO:158

```
     Primer 1
460  GGUCUCUCUG GUUAGACCAG AUCUGAGCCU GGGAGCUCUC UGGCUAACUA

510  GGGAACCCAC UGCUUAAGCC UCAAUAAAGC UUGCCUUGAG UGCUUCAAGU

560  AGUGUGUGCC CGUCUGUUGU GUGACUCUGG UAACUAGAGA UCCCUCAGAC

                                     Primer 2
610  CCUUUUAGUC AGUGUGGAAA AUCUCUAGCA GUGGCGCCCG AACAGGGACC

660  UGAAAGCGAA AGGGAAACCA GAGGAGCUCU CUCGACGCAG GACUCGGCUU

710  GCUGAAGCGC GCACGGCAAG AGGCGAGGGG CGGCGACUGG UGAGUACGCC

760  AAAAAUUUUG ACUAGCGGAG GCUAGAAGGA GAGAGAUGGG UGCGAGAGCG

                                     Primer 3
810  UCAGUAUUAA GCGGGGGAGA AUUAGAUCGA UGGGAAAAAA UUCGGUUAAG

860  GCCAGGGGGA AAGAAAAAAU AUAAAUUAAA ACAUAUAGUA UGGGCAAGCA

910  GGGAGCUAGA ACGAUUCGCA GUUAAUCCUG GCCUGUUAGA AACAUCAGAA

960  GGCUGUAGAC AAAUACUGGG ACAGCUACAA CCAUCCCUUC AGACAGGAUC

                                    Primer 4
1010 AGAAGAACUU AGAUCAUUAU AUAAUACAGU AGCAACCCUC UAUUGUGUGC

1060 AUCAAAGGAU AGAGAUAAAA GACACCAAGG AAGCUUUAGA CAAGAUAGAG
```

FIGURE 55B

1110 GAAGAGCAAA ACAAAAGUAA GAAAAAAGCA CAGCAAGCAG CAGCUGACAC

1160 AGGACACAGC AAUCAGGUCA GCCAAAAUUA CCCUAUAGUG CAGAACAUCC

Primer 5
1210 AGGGGCAAAU GGUACAUCAG GCCAUAUCAC CUAGAACUUU AAAUGCAUGG

1260 GUAAAAGUAG UAGAAGAGAA GGCUUUCAGC CCAGAAGUGA UACCCAUGUU

1310 UUCAGCAUUA UCAGAAGGAG CCACCCCACA AGAUUUAAAC ACCAUGCUAA

1360 ACACAGUGGG GGGACAUCAA GCAGCCAUGC AAAUGUUAAA AGAGACCAUC

Primer 6
1410 AAUGAGGAAG CUGCAGAAUG GGAUAGAGUG CAUCCAGUGC AUGCAGGGCC

1460 UAUUGCACCA GGCCAGAUGA GAGAACCAAG GGGAAGUGAC AUAGCAGGAA

1510 CUACUAGUAC CCUUCAGGAA CAAAUAGGAU GGAUGACAAA UAAUCCACCU

1560 AUCCCAGUAG GAGAAAUUUA UAAAAGAUGG AUAAUCCUGG GAUUAAAUAA

Primer 7
1610 AAUAGUAAGA AUGUAUAGCC CUACCAGCAU UCUGGACAUA AGACAAGGAC

1660 CAAAGGAACC CUUUAGAGAC UAUGUAGACC GGUUCUAUAA AACUCUAAGA

1710 GCCGAGCAAG CUUCACAGGA GGUAAAAAAU UGGAUGACAG AAACCUUGUU

FIGURE 55C

1760 GGUCCAAAAU GCGAACCCAG AUUGUAAGAC UAUUUUAAAA GCAUUGGGAC

Primer 8

1810 CAGCGGCUAC ACUAGAAGAA AUGAUGACAG CAUGUCAGGG AGUAGGAGGA

1860 CCCGGCCAUA AGGCAAGAGU UUUGGCUGAA GCAAUGAGCC AAGUAACAAA

1910 UUCAGCUACC AUAAUGAUGC AGAGAGGCAA UUUUAGGAAC CAAAGAAAGA

1960 UUGUUAAGUG UUUCAAUUGU GGCAAAGAAG GGCACACAGC CAGAAAUUGC

2010 AGGGCCCCUA GGAAAAAGGG CUGUUGGAAA UGUGGAAAGG AAGGACACCA

2060 AAUGAAAGAU UGUACUGAGA G

FIGURE 56
Tag A
neg 0 8 10 12
G A T C
Tag B
12 10 8 0 neg
Site 1850
Site 1840
Site 1850
Site 1840
Site 1800

FIGURE 57

```
(SEQ ID NO:188)              CGTATTCCGTTCTCAAAACCGACTTGCT-5'  13
(SEQ ID NO:187)             AGGTATTCCGTTCTCAAAACCGACT         12
(SEQ ID NO:186)            ACGGTATTCCGTTCTCAAAACCGAC          10=11
(SEQ ID NO:185)           CCCGGTATTCCGTTCTCAAAACCGA           9
(SEQ ID NO:184)          CGCCGGTATTCCGTTCTCAAAACCG            8
(SEQ ID NO:183)         CGGCCGGTATTCCGTTCTCAAAACC             7
(SEQ ID NO:182)        AGGGCCGGTATTCCGTTCTCAAAAC              6
(SEQ ID NO:181)       ATGGGCCGGTATTCCGTTCTCAAAA               5
(SEQ ID NO:180)      ACTGGGCCGGTATTCCGTTCTCAAA                4
(SEQ ID NO:179)     ACCTGGGCCGGTATTCCGTTCTCAA                 3
(SEQ ID NO:178)    ATCCTGGGCCGGTATTCCGTTCTCA                  2
(SEQ ID NO:177)   ACTCCTGGGCCGGTATTCCGTTCTC                   1
 5'-CAUGUCAGGGAGUAGGAGGACCCGGCCAUAAGGCAAGAGUUUUGGCUGAAGCAAUGAG-3'
                                                         (SEQ ID NO:158)
    1 CAGTCCCTCATC                  (SEQ ID NO:164)
    2  AGTCCCTCATCC                 (SEQ ID NO:165)
    3   GTCCCTCATCCT                (SEQ ID NO:166)
    4    TCCCTCATCCTC               (SEQ ID NO:167)
    5     CCCTCATCCTCC              (SEQ ID NO:168)
    6      CCTCATCCTCCT             (SEQ ID NO:169)
    7       CTCATCCTCCTG            (SEQ ID NO:170)
    8        TCATCCTCCTGG           (SEQ ID NO:171)
    9         CATCCTCCTGGG          (SEQ ID NO:172)
   10          ATCCTCCTGGGC         (SEQ ID NO:173)
   11           TCCTCCTGGGC         (SEQ ID NO:174)
   12            CCTCCTGGGCC        (SEQ ID NO:175)
   13             CTCCTGGGCCGAAAA-FL-5'  (SEQ ID NO:176)
```

FIGURE 61A

SEQ ID NO:159

```
        primer 1
3300  AGCUGGACUG UCAAUGACAU ACAGAAGUUA GUGGGGAAAU UGAAUUGGGC

3350  AAGUCAGAUU UACCCAGGGA UUAAAGUAAG GCAAUUAUGU AAACUCCUUA

3400  GAGGAACCAA AGCACUAACA GAAGUAAUAC CACUAACAGA AGAAGCAGAG

3450  CUAGAACUGG CAGAAAACAG AGAGAUUCUA AAAGAACCAG UACAUGGAGU

        primer 2
3500  GUAUUAUGAC CCAUCAAAAG ACUUAAUAGC AGAAAUACAG AAGCAGGGGC

3550  AAGGCCAAUG GACAUAUCAA AUUUAUCAAG AGCCAUUUAA AAAUCUGAAA

3600  ACAGGAAAAU AUGCAAGAAU GAGGGGUGCC CACACUAAUG AUGUAAAACA

3650  AUUAACAGAG GCAGUGCAAA AAAUAACCAC AGAAAGCAUA GUAAUAUGGG

        primer 3
3700  GAAAGACUCC UAAAUUUAAA CUGCCCAUAC AAAAGGAAAC AUGGGAAACA

3750  UGGUGGACAG AGUAUUGGCA AGCCACCUGG AUUCCUGAGU GGGAGUUUGU

3800  UAAUACCCCU CCCUUAGUGA AAUUAUGGUA CCAGUUAGAG AAAGAACCCA

3850  UAGUAGGAGC AGAAACCUUC UAUGUAGAUG GGGCAGCUAA CAGGGAGACU

        primer 4
3900  AAAUUAGGAA AAGCAGGAUA UGUUACUAAU AGAGGAAGAC AAAAAGUUGU
```

FIGURE 61B

3950 CACCCUAACU GACACAACAA AUCAGAAGAC UGAGUUACAA GCAAUUUAUC

4000 UAGCUUUGCA GGAUUCGGGA UUAGAAGUAA ACAUAGUAAC AGACUCACAA

4050 UAUGCAUUAG GAAUCAUUCA AGCACAACCA GAUCAAAGUG AAUCAGAGUU primer 5
4100 AGUCAAUCAA AUAAUAGAGC AGUUAAUAAA AAAGGAAAAG GUCUAUCUGG

4150 CAUGGGUACC AGCACACAAA GGAAUUGGAG GAAAUGAACA AGUAGAUAAA

4200 UUAGUCAGUG CUGGAAUCAG GAAAGUACUA UUUUUAGAUG GAAUAGAUAA

4250 GGCCCAAGAU GAACAUGAGA AAUAUCACAG UAAUUGGAGA GCAAUGGCUA primer 6
4300 GUGAUUUUAA CCUGCCACCU GUAGUAGCAA AAGAAAUAGU AGCCAGCUGU

4350 GAUAAAUGUC AGCUAAAAGG AGAAGCCAUG CAUGGACAAG UAGACUGUAG

4400 UCCAGGAAUA UGGCAACUAG AUUGUACACA UUUAGAAGGA AAAGUUAUCC

4450 UGGUAGCAGU UCAUGUAGCC AGUGGAUAUA UAGAAGCAGA AGUUAUUCCA primer 7
4500 GCAGAAACAG GGCAGGAAAC AGCAUAUUUU CUUUUAAAAU UAGCAGGAAG

4550 AUGGCCAGUA AAAACAAUAC AUACUGACAA UGGCAGCAAU UUCACCGGUG

4600 CUACGGUUAG GGCCGCCUGU UGGUGGGCGG GAAUCAAGCA GGAAUUUGGA

FIGURE 61C

4650 AUUCCCUACA AUCCCCAAAG UCAAGGAGUA GUAGAAUCUA UGAAUAAAGA primer 8

4700 AUUAAAGAAA AUUAUAGGAC AGGUAAGAGA UCAGGCUGAA CAUCUUAAGA

4750 CAGCAGUACA AAUGGCAGUA UUCAUCCACA AUUUUAAAAG AAAAGGGGGG

4800 AUUGGGGGGU ACAGUGCAGG GGAAAGAAUA GUAGACAUAA UAGCAACAGA

4850 CAUACAAACU AAAGAAUUAC AAAAACAAAU UACAAAAAUU CAAAAUUUUC primer 9

4900 GGGUUUAUUA CAGGGACAGC AGAAAUCCAC UUUGGAAAGG ACCAGCAAAG

4950 CUCCUCUGGA AAGGUGAAGG GGCAGUAGUA AUACAAGAUA AUAGUGACAU

5000 AAAAGUAGUG CCAAGAAGAA AAGCAAAGAU CAUUAGGGAU UAUGGAAAAC

5050 AGAUGGCAGG UGAUGAUUGU G

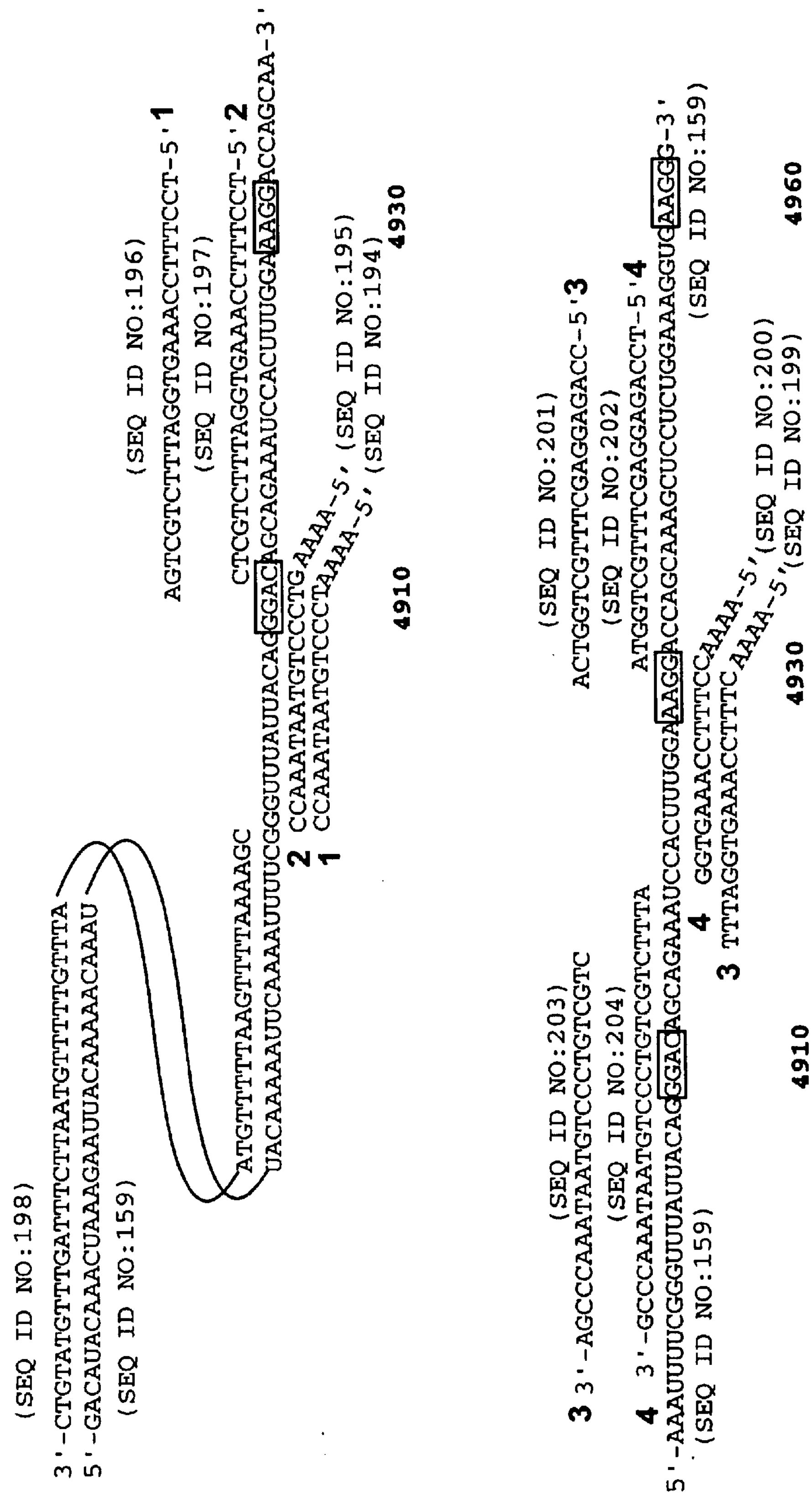

FIGURE 62

(SEQ ID NO:198)
3'-CTGTATGTTTGATTTCTTAATGTTTTGTTTA
5'-GACAUACAAACUAAAGAAUUACAAAAACAAAU
(SEQ ID NO:159)

```
                                                              (SEQ ID NO:196)
                                         AGTCGTCTTTAGGTGAAACCTTTCCT-5'  1
                                                              (SEQ ID NO:197)
                                        CTCGTCTTTAGGTGAAACCTTTCCT-5'  2
ATGTTTTTAAGTTTTAAAAGC                                                    AAGGACCAGCAA-3'
UACAAAAAUUCAAAAUUUCGGGUUUAUUACAGGAC AGAAAUCCACUUUGGA                         (SEQ ID NO:194)
                                   2 CCAAATAATGTCCCTG AAAA-5'  (SEQ ID NO:195)
                                 1 CCAAATAATGTCCCTAAAAA-5'
                                                       4910        4930
```

```
                                              (SEQ ID NO:201)
                                  ACTGGTCGTTTCGAGGAGACC-5' 3
                                              (SEQ ID NO:202)
                                  ATGGTCGTTTCGAGGAGACCT-5' 4
5'-AAAUUUCGGGUUUAUUACAGGACAGAAAUCCACUUUGGAACCAGCAAAGCUCCUCUGGAAAGGUCAAGG-3'
  (SEQ ID NO:159)                               4 GGTGAAACCTTTCCAAAA-5'(SEQ ID NO:200)
                                             3 TTTAGGTGAAACCTTTC AAAA-5'(SEQ ID NO:199)
                                                              4930        4960
```

(SEQ ID NO:203)
3'-AGCCCAAATAATGTCCCTGTCTTTA
(SEQ ID NO:204)
4 3'-GCCCAAATAATGTCCCTGTCTTTA

5'-AAAUUUCGGGUUUAUUACAGGACAGAAAUCCACUUUGGA
(SEQ ID NO:159)
                4910

FIGURE 63
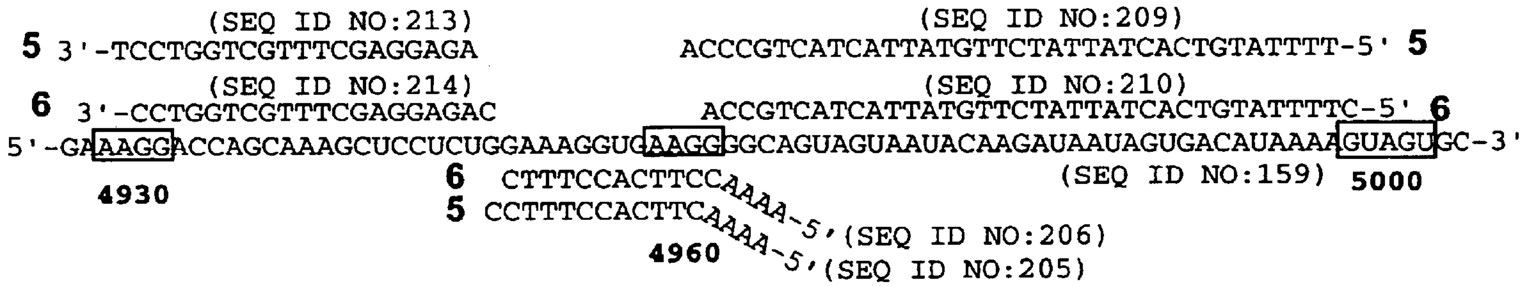
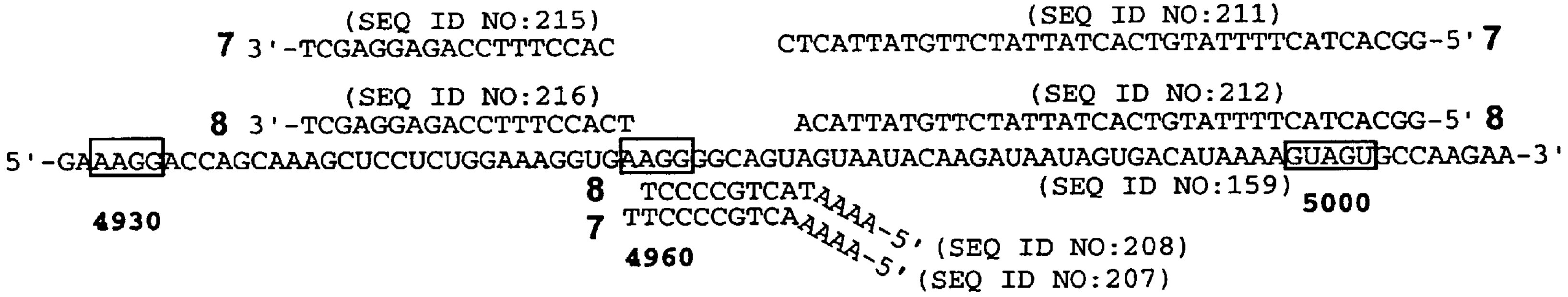

(SEQ ID NO:224)
3'-TCCCCCCTAACCCCCCATG ATTTCTTATCATCTGTATTATCGTTGTCTGTATGT-5' (SEQ ID NO:221)
5'-AAGAAAAGGGGGGAUUGGGGGGUACAGUGCAGGGGAAAGAAUAGUAGACAUAAUAGCAACAGACAUACAAACU-3' (SEQ ID NO:159)
TCACGTCCCCAAAA-5' (SEQ ID NO:217)

2, 4

4790 4810

(SEQ ID NO:225)
3'-CTGTCGTCATGTTTACCGTCATAAGTAGGT ACCCTAACCCCCCATGTCAC-5' (SEQ ID NO:222)
5'-AGACAGCAGUACAAAUGGCAGUAUUCAUCCACAAUUUUAAAAGAAAAGGGGGGAUUGGGGGGUACAGUGCAGGGGAAAG-3' (SEQ ID NO:159)
GTTAAAATTTTCTTTTCCCTATATA-5' (SEQ ID NO:220)
GTTAAAATTTTCTTTTCCCAAAA-5' (SEQ ID NO:218)

3

4790 4810

(SEQ ID NO:222)
ACCCTAACCCCCCATGTCAC-5' CATCATCTGTATTATCGTTGTCTGTATGTTTGATTTC (SEQ ID NO:223)
5'-AAAAGGGGGGAUUGGGGGGUACAGUGCAGGGGAAAGAAUAGUAGACAUAAUAGCAACAGACAUACAAACUAAAGAA-3 (SEQ ID NO:159)
GTCCCCTTTCTTAAAA-5' (SEQ ID NO:219)

```
                           4810
         4790
(SEQ ID NO:224)                    ATTTCTTATCATCTGTATTATCGTTGTCTGTATGT-5'
3'-TCCCCCCTAACCCCCATG              AAGAAUAGUAGACAACAGACAUACAAACUA-3'
5'-GAAAAGGGGGGAUUGGGGUACAGUGCAGGGGA                     (SEQ ID NO:159)
                    TCACGTCCCCCTCCCGCACTGCC-5'
                              ↑    (SEQ ID NO:221)
                     (SEQ ID NO:226)
```

```
                                    5'-AGTGCAGGGGGGCGCG-3'
                                        (SEQ ID NO:227)

(SEQ ID NO:193)
                                      Ⓠ  CAAC GCTTCCTCCG-3'
                                      ↑
                                      Ⓕ
5'-CCGTCACGCCTCC
3'-TGGCAGTGCGGGAGGTTGACGAAGAAGGC-5'
(SEQ ID NO:191)     (SEQ ID NO:192)
```

FIGURE 69

(SEQ ID NO:213) 4960 (SEQ ID NO:209)

3'-TCCTGGTCGTTTCGAGGAGA ACCCGTCATCATTATGTTCTATTATCACTGTATTTT-5'

5'-GAAAGGACCAGCAAAGCUCCUCUGGAAAGGUGAAGGGGCAGUAGUAAUACAAGAUAAUAGUGACAUAAAAGUAGUGC-3'

CCTTTCCACTTCCTCCGCACTGCC-5' (SEQ ID NO:159)

4930 (SEQ ID NO:228) 5000

5'-GGAAAGGTGAAGGAGGC-3'
(SEQ ID NO:229)

F Q (SEQ ID NO:193)

(SEQ ID NO:191) CAAC GCTTCCTCCG-3'

5'-CCGTCACGCCTCC

3'-TGGCAGTGCGGAGGTTGACGAAGAAGGC-5'

(SEQ ID NO:192)

FIGURE 71

Human PSP94

383-31-1 5'-TET-CCTGCTTATCACAATGAA-3' (SEQ ID NO:230)
383-31-3 5'-TET-ACATGCACTTGCTACGAAAC-3' (SEQ ID NO:231)

SEQ ID NO:232
CCUGCUUAUCACAAUGAAUGUUCUCCUGGGCAGCGUUGUGAUCUUUGCCACCUUCGUGA
CUUUAUGCAAUGCAUCAUGCUAUUUCAUACCUAAUGAGGGAGUUCCAGGAGAUUCAACCA
GGAAAUGCAUGGAUCUCAAAGGAAACAAACACCCAAUAAACUCGGAGUGGCAGACUGAC
AACUGUGAGACAUGCACUUGCUACGAAACAGAAAUUUCAUGUUGCACCCUUGUUUCUAC
ACCUGUGGGUUAUGACAAAGACAACUGCCAAAGAAUCUUCAAGAAGGAGGACUGCAAGU
AUAUCGUGGUGGAGAAGAAGGACCCAAAAAAGACCUGUUCUGUCAGUGAAUGGAUAAUC
UAAUGUGCUUCUAGUAGGCACAGGGCUCCCAGGCCAGGCCUCAUUCUCCUCUGGCCUCUA
AUAGUCAAUGAUUGUGUAGCCAUGCCUAUCAGUAAAAAGAUUUUUG

FIGURE 72

Human ubiquitin:

520-77-1 5'-TET-CCGCCACCAAAATGC-3' (SEQ ID NO:233)
520-59-2 5'-TET-GCTGGAAGATGGACG-3' (SEQ ID NO:234)

SEQ ID NO:235
CCGCCACCAAAAUGCAGAUUUUCGUGAAAACCCUUACGGGGAAGACCAUCACCCUCGAG
GUUGAACCCUCGGAUACGAUAGAAAAUGUAAAGGCCAAGAUCCAGGAUAAGGAAGGAAU
UCCUCCUGACAGCAGAGACUGAUCUUUGCUGGCAAGCAGCUGGAAGAUGGACGUACUUUG
UCUGACUACAAUAUUCAAAAGGAGUCUACUCUUCAUCUUGUGUUGAGACUUCGUGGUGG
UGCUAAGAAAAGGAAGAAGAAGUCUUACACCACUCCCAAGAAGAAUAAGCACAAGAGAAA
GAAGGUUAAGCUGGCUGUCCUGAAAUAUUAUAAGGUGGAUGAGAAUGGCAAAAUUAGUC
GCCUUCGUCGAGAGUGCCCUUCUGAUGAAUGUGGUGCUGGGGUGUUUAUGGCAAGUCACU
UUGACAGACAUUAUUGUGGCAAAUGUUGUCUGA

FIGURE 73

HCV-1a 5'-UTR:

898-28-01 5'-TET-GGGACACTCCACCATGAATCACTC-3' (SEQ ID NO:236)
898-35-01 5'-TET-CGGGAGAGCCATAGTGGTCTGCGG-3' (SEQ ID NO:237)
898-35-02 5'-TET-ATTTGGGCGTGCCCCCGC-3' (SEQ ID NO:238)
898-35-03 5'-TET-GACCGGGTCCTTTCTTGGA-3' (SEQ ID NO:239)

SEQ ID NO:240
GGGACACUCCACCAUGAAUCACUCCCCUGUGAGGAACUACUGUCUUCACGCAGAAAGCGU
CUAGCCAUGGCGUUAGUAUGAGUGUCGUGCAGCCUCCAGGACCCCCCCUCCCGGGAGAG
CCAUAGUGGUCUGCGGAACCGGUGAGUACACCGGAAUUGCCAGGACGACCGGGUCCUUUC
UUGGAUAAACCCGCUCAAUGCCUGGAGAUUUGGGCGUGCCCCCGCAAGACUGCUAGCCG
AGUAGUGUUGGGUCGCGAAAGGCCUUGUGGUACUGCCUGAUAGGGUGCUUGCGAGUGCC
CCGGGAGGUCUCGUAGACCGUGCACCAUGAG

FIGURE 74

HCV-1b 5'-UTR:

| | | |
|---|---|---|
| 898-28-02 | 5'-TET-GGGACACTCCACCATAGATCACTC-3' | (SEQ ID NO:241) |
| 898-35-01 | 5'-TET-CGGGAGAGCCATAGTGGTCTGCGG-3' | (SEQ ID NO:237) |
| 898-35-02 | 5'-TET-ATTTGGGCGTGCCCCCGC-3' | (SEQ ID NO:238) |
| 898-35-03 | 5'-TET-GACCGGGTCCTTTCTTGGA-3' | (SEQ ID NO:239) |

SEQ ID NO:242

GGGACACUCCACCAUAGAUCACUCCCCUGUGAGGAACUACUGUCUUCACGCAGAAAGCGU
CUAGCCAUGGCGUUAGUAUGAGUGUCGUGCAGCCUCCAGGACCCCCCCUCCCGGGAGAG
CCAUAGUGGUCUGCGGAACCGGUGAGUACACCGGAAUUGCCAGGACGACCGGGUCCUUUC
UUGGAUCAACCCGCUCAAUGCCUGGAGAUUUGGGCGUGCCCCCGCGAGACUGCUAGCCG
AGUAGUGUUGGGUCGCGAAAGGCCUUGUGGUACUGCCUGAUAGGGUGCUUGCGAGUGCC
CCGGGAGGUCUCGUAGACCGUGCACCAUGAG

FIGURE 75

HCV 2a/c 5'-UTR:

898-28-01 5'-TET-GGGACACTCCACCATGAATCACTC-3' (SEQ ID NO:236)
898-35-01 5'-TET-CGGGAGAGCCATAGTGGTCTGCGG-3' (SEQ ID NO:237)
898-35-02 5'-TET-ATTTGGGCGTGCCCCCGC-3' (SEQ ID NO:238)
898-35-03 5'-TET-GACCGGGTCCTTTCTTGGA-3' (SEQ ID NO:239)

SEQ ID NO:243
GGGACACUCCACCAUGAAUCACUCCCCUGUGAGGAACUACUGUCUUCACGCAGAAAGCGU
CUAGCCAUGGCGUUAGUAUGAGUGUCGUACAGCCUCCAGGCCCCCCCCUCCCGGGAGAG
CCAUAGUGGUCUGCGGAACCGGUGAGUACACCGGAAUUGCCGGGAAGACUGGGUCCUUUC
UUGGAUAAACCCACUCUAUGCCCGGCCAUUUGGGCGUGCCCCCGCAAGACUGCUAGCCGA
GUAGCGUUGGGUUGCGAAAGGCCUUGUGGUACUGCCUGAUAGGGUGCUUGCGAGUGCCCC
GGGAGGUCUCGUAGACCGUGCACCAUGAG

FIGURE 76

HCV 3a 5'-UTR:

898-28-03 5'-TET-GGGACACTCCACCATGGATCACTC-3' (SEQ ID NO:244)
898-35-01 5'-TET-CGGGAGAGCCATAGTGGTCTGCGG-3' (SEQ ID NO:237)
898-35-02 5'-TET-ATTTGGGCGTGCCCCCGC-3' (SEQ ID NO:238)
898-35-03 5'-TET-GACCGGGTCCTTTCTTGGA-3' (SEQ ID NO:239)

SEQ ID NO:245
GGGACACUCCACCAUGGAUCACUCCCCUGUGAGGAACUUCUGUCUUCACGCGGAAAGCGC
CUAGCCAUGGCGUUAGUACGAGUGUCGUGCAGCCUCCAGGCCCCCCCCUCCCGGGAGAG
CCAUAGUGGUCUGCGGAACCGGUGAGUACACCGGAAUCGCUGGGGUGACCGGGUCCUUUC
UUGGAACAACCCGCUCAAUACCCAGAAAUUUGGGCGUGCCCCCGCGAGAUCACUAGCCG
AGUAGUGUUGGGUCGCGAAAGGCCUUGUGGUACUGCCUGAUAGGGUGCUUGCGAGUGCC
CCGGGAGGUCUCGUAGACCGUGCACCAUGAG

FIGURE 77A

Human Antigen CD36 mRNA Oligonucleotides

| | | |
|---|---|---|
| 726-38-01 | 5'-ACAAGGGAAGAGAGATGAGGAACCAG-3' | (SEQ ID NO:246) |
| 666-33-01 | 5'-TTTGCCTTCTCATCACCAATGG-3' | (SEQ ID NO:247) |
| 937-03-01 | 5'-TET- aagggaagagagatgag-3' | (SEQ ID NO:248) |
| 937-03-02 | 5'-TET-aggagtttgcaagaaac-3' | (SEQ ID NO:249) |
| 937-03-03 | 5'-TET-ggtgctgtcctgg-3' | (SEQ ID NO:250) |
| 937-03-04 | 5'-TET-cagttttggatctttgatg-3' | (SEQ ID NO:251) |
| 937-03-05 | 5'-TET-aggacgctgagga-3' | (SEQ ID NO:252) |
| 937-03-06 | 5'-TET-aacaagtcaaaatcttctatg-3' | (SEQ ID NO:253) |
| 937-03-07 | 5'-TET-caatactgcagatggag-3' | (SEQ ID NO:254) |
| 937-03-08 | 5'-TET-aagccaggtattgca-3' | (SEQ ID NO:255) |
| 937-03-09 | 5'-TET-ctattgtttctgcacaga-3' | (SEQ ID NO:256) |
| 937-03-10 | 5'-TET-aaatgaagaagaacatagga-3' | (SEQ ID NO:257) |
| 937-03-11 | 5'-TET-ggtcaagccatcaga-3' | (SEQ ID NO:258) |

FIGURE 77B

Human Antigen CD36 mRNA (SEQ ID NO:259)

ACAAGGGAAGAGAGAUGAGGAACCAGAGCUUGUAGAAACCACUUUAAUCAUAUCCAGGA
GUUUGCAAGAAACAGGUGCUUAACACUAAUUCACCUCCUGAACAAGAAAAAUGGGCUGU
GACCGGAACUGUGGGCUCAUCGCUGGGGCUGUCAUUGGUGCUGUCCUGGCUGUGUUUGG
AGGUAUUCUAAUGCCAGUUGGAGACCUGCUUAUCCAGAAGACAAUUAAAAAGCAAGUUG
UCCUCGAAGAAGGUACAAUUGCUUUUAAAAAUUGGGUUAAAACAGGCACAGAAGUUUAC
AGACAGUUUUGGAUCUUUGAUGUGCAAAAUCCACAGGAAGUGAUGAUGAACAGCAGCAA
CAUUCAAGUUAAGCAAAGAGGUCCUUAUACGUACAGAGUUCGUUUUCUAGCCAAGGAAA
AUGUAACCCAGGACGCUGAGGACAACACAGUCUCUUUCCUGCAGCCCAAUGGUGCCAUC
UUCGAACCUUCACUAUCAGUUGGAACAGAGGCUGACAACUUCACAGUUCUCAAUCUGGC
UGUGGCAGCUGCAUCCCAUAUCUAUCAAAAUCAAUUUGUUCAAAUGAUCCUCAAUUCAC
UUAUUAACAAGUCAAAAUCUUCUAUGUUCCAAGUCAGAACUUUGAGAGAACUGUUAUGG
GGCUAUAGGGAUCCAUUUUUGAGUUUGGUUCCGUACCCUGUUACUACUACAGUUGGUCUG
UUUUAUCCUUACAACAAUACUGCAGAUGGAGUUUAUAAAGUUUUCAAUGGAAAAGAUAA
CAUAAGUAAAGUUGCCAUAAUCGACACAUAUAAAGGUAAAAGGAAUCUGUCCUAUUGGG
AAAGUCACUGCGACAUGAUUAAUGGUACAGAUGCAGCCUCAUUUCCACCUUUUGUUGAG
AAAAGCCAGGUAUUGCAGUUCUUUUCUUCUGAUAUUUGCAGGUCAAUCUAUGCUGUAUU
UGAAUCCGACGUUAAUCUGAAAGGAAUCCCUGUGUAUAGAUUCGUUCUUCCAUCCAAGG
CCUUUGCCUCUCCAGUUGAAAACCCAGACAACUAUUGUUUCUGCACAGAAAAAAUUAUC
UCAAAAAAUUGUACAUCAUAUGGUGUGCUAGACAUCAGCAAAUGCAAAGAAGGGAGACC
UGUGUACAUUUCACUUCCUCAUUUUCUGUAUGCAAGUCCUGAUGUUUCAGAACCUAUUGA
UGGAUUAAACCCAAAUGAAGAAGAACAUAGGACAUACUUGGAUAUUCAACCUAUAACUG
GAUUCACUUUACAAUUUGCAAAACGGCUGCAGGUCAACCUAUUGGUCAAGCCAUCAGAA
AAAAUUCAAGUAUUAAAGAAUCUGAAGAGGAACUAUAUUGUGCCUAUUCUUUGGCUUAA
UGAGACUGGGACCAUUGGUGAUGAGAAGGCAAA

FIGURE 78

Human Ribosomal Protein L5 mRNA

| | | |
|---|---|---|
| 761-47-01 | 5'-ATGGGGTTTGTTAAAGTTG-3' | (SEQ ID NO:260) |
| 761-47-02 | 5'-GCTGGGTTTAGCTCTCAGCAGCCCGC-3' | (SEQ ID NO:261) |
| 937-05-01 | 5'-TET- atggggtttgttaaagtt-3' | (SEQ ID NO:262) |
| 937-05-02 | 5'-TET- gaagacgacgagagg-3' | (SEQ ID NO:263) |
| 937-05-03 | 5'-TET- ggatgatagttcgtgtg-3' | (SEQ ID NO:264) |
| 937-05-04 | 5'-TET- gctgcagcatattgta-3' | (SEQ ID NO:265) |
| 937-05-05 | 5'-TET- ctgctatttggatgca-3' | (SEQ ID NO:266) |
| 937-05-06 | 5'-TET- gcagaagtacatcgga-3' | (SEQ ID NO:267) |
| 937-05-07 | 5'-TET- gacatgatggaggaga-3' | (SEQ ID NO:268) |
| 937-05-08 | 5'-TET- agaagaaggatcggg-3' | (SEQ ID NO:269) |

SEQ ID NO:270

AUGGGGUUUGUUAAAGUUGUUAAGAAUAAGGCCUACUUUAAGAGAUACCAAGUGAAAUU
UAGAAGACGACGAGAGGGUAAAACUGAUUAUUAUGCUCGGAAACGCUUGGUGAUACAAG
AUAAAAAUAAAUACAACACACCCAAAUACAGGAUGAUAGUUCGUGUGACAAACAGAGAU
AUCAUUUGUCAGAUUGCUUAUGCCCGUAUAGAGGGGGAUAUGAUAGUCUGCGCACGUUA
UGCACACGAACUGCCAAAAUAUGGUGUGAAGGUUGGCCUGACAAAUUAUGCUGCAGCAU
AUUGUACUGGCCUGCUGCUGGCCCGCAGGCUUCUCAAUAGGUUUGGCAUGGACAAGAUC
UAUGAAGGCCAAGUGGAGGUGACUGGUGAUGAAUACAAUGUGGAAAGCAUUGAUGGUCAG
CCAGGUGCCUUCACCUGCUAUUUGGAUGCAGGCCUUGCCAGAACUACCACUGGCAAUAA
AGUUUUUGGUGCCCUGAAGGGAGCUGUGGAUGGAGGCUUGUCUAUCCCUCACAGUACCA
AACGAUUCCCUGGUUAUGAUUCUGAAAGCAAGGAAUUUAAUGCAGAAGUACAUCGGAAG
CACAUCAUGGGCCAGAAUGUUGCAGAUUACAUGCGCUACUUAAUGGAAGAAGAUGAAGA
UGCUUACAAGAAACAGUUCUCUCAAUACAUAAAGAACAGCGUAACUCCAGACAUGAUGG
AGGAGAUGUAUAAGAAAGCUCAUGCUGCUAUACGAGAGAAUCCAGUCUAUGAAAAGAAG
CCCAAGAAAGAAGUUAAAAAGAAGAGGUGGAACCGUCCCAAAAUGUCCCUUGCUCAGAA
GAAGGAUCGGGUAGCUCAAAAGAAGGCAAGCUUCCUCAGAGCUCAGGAGCGGGCUGCUG
AGAGCUAAACCCAGC

FIGURE 79A

Mouse Scavenger Receptor Class B Type I mRNA

Oligonucleotides

| | | |
|---|---|---|
| 726-39-01 | 5'-GCTCAAGAATGTCCGCATAGACCCG-3' | (SEQ ID NO:271) |
| 666-34-01 | 5'-CTGGTCCCTGAGTTGTTTTTGC-3' | (SEQ ID NO:272) |
| 937-01-01 | 5'-TET- GCTCAAGAATGTCCG-3' | (SEQ ID NO:273) |
| 937-01-02 | 5'-TET- gggatgtggaaggag-3' | (SEQ ID NO:274) |
| 937-01-03 | 5'-TET- ggaccctatgtctacag-3' | (SEQ ID NO:275) |
| 937-01-04 | 5'-TET- acatcttggtcctgg-3' | (SEQ ID NO:276) |
| 937-01-05 | 5'-TET- tctcaacacgtacctc-3' | (SEQ ID NO:277) |
| 937-01-06 | 5'-TET- cggactcagcaaga-3' | (SEQ ID NO:278) |
| 937-01-07 | 5'-TET- caagggtgtttgaagg-3' | (SEQ ID NO:279) |
| 937-01-08 | 5'-TET- ctctgtttctctccca-3' | (SEQ ID NO:280) |
| 937-01-09 | 5'-TET- gtgaagatgcagctg-3' | (SEQ ID NO:281) |
| 937-01-10 | 5'-TET- agctggtgctgatg-3' | (SEQ ID NO:282) |
| 937-01-11 | 5'-TET- caggcctactctgag-3' | (SEQ ID NO:283) |
| 937-01-12 | 5'-TET- ggactctctcagcg-3' | (SEQ ID NO:284) |

FIGURE 79B

Mouse Scavenger Receptor Class B Type I mRNA (SEQ ID NO:285)

GCUCAAGAAUGUCCGCAUAGACCCGAGCAGCCUGUCCUUCGGGAUGUGGAAGGAGAUCC
CCGUCCCUUUCUACUUGUCUGUCUACUUCUUCGAAGUGGUCAACCCAAACGAGGUCCUC
AACGGCCAGAAGCCAGUAGUCCGGGAGCGUGGACCCUAUGUCUACAGGGAGUUCAGACA
AAAGGUCAACAUCACCUUCAAUGACAACGACACCGUGUCCUUCGUGGAGAACCGCAGCC
UCCAUUUCCAGCCUGACAAGUCGCAUGGCUCAGAGAGUGACUACAUUGUACUGCCUAACA
UCUUGGUCCUGGGGGGCUCGAUAUUGAUGGAGAGCAAGCCUGUGAGCCUGAAGCUGAUG
AUGACCUUGGCGCUGGUCACCAUGGGCCAGCGUGCUUUUAUGAACCGCACAGUUGGUGA
GAUCCUGUGGGGCUAUGACGAUCCCUUCGUGCAUUUUCUCAACACGUACCUCCCAGACAU
GCUUCCCAUAAAGGGCAAAUUUGGCCUGUUUGUUGGGAUGAACAACUCGAAUUCUGGGG
UCUUCACUGUCUUCACGGGCGUCCAGAAUUUCAGCAGGAUCCAUCUGGUGGACAAAUGG
AACGGACUCAGCAAGAUCGAUUAUUGGCAUUCAGAGCAGUGUAACAUGAUCAAUGGGAC
UUCCGGGCAGAUGUGGGCACCCUUCAUGACACCCGAAUCCUCGCUGGAAUUCUUCAGCC
CGGAGGCAUGCAGGUCCAUGAAGCUGACCUACAACGAAUCAAGGGUGUUUGAAGGCAUU
CCCACGUAUCGCUUCACGGCCCCCGAUACUCUGUUUGCCAACGGGUCCGUCUACCCACC
CAACGAAGGCUUCUGCCCAUGCCGAGAGUCUGGCAUUCAGAAUGUCAGCACCUGCAGGUU
UGGUGCGCCUCUGUUUCUCUCCCACCCCCACUUUUACAACGCCGACCCUGUGUUGUCAG
AAGCUGUUCUUGGUCUGAACCCUAACCCAAAGGAGCAUUCCUUGUUCCUAGACAUCCAU
CCGGUCACUGGGAUCCCCAUGAACUGUUCUGUGAAGAUGCAGCUGAGCCUCUACAUCAA
AUCUGUCAAGGGCAUCGGGCAAACAGGGAAGAUCGAGCCAGUAGUUCUGCCGUUGCUGUG
GUUCGAACAGAGCGGAGCAAUGGGUGGCAAGCCCCUGAGCACGUUCUACACGCAGCUGGU
GCUGAUGCCCCAGGUUCUUCACUACGCGCAGUAUGUGCUGCUGGGGCUUGGAGGCCUCCU
GUUGCUGGUGCCCAUCAUCUGCCAACUGCGCAGCCAGGAGAAAUGCUUUUUGUUUUGGA
GUGGUAGUAAAAAGGGCUCCCAGGAUAAGGAGGCCAUUCAGGCCUACUCUGAGUCCCUGA
UGUCACCAGCUGCCAAGGGCACGGUGCUGCAAGAAGCCAAGCUAUAGGGUCCUGAAGACA
CUAUAAGCCCCCCAAACCUGAUAGCUUGGUCAGACCAGCCACCCAGUCCCUACACCCCG
CUUCUUGAGGACUCUCUCAGCGGACAGCCCACCAGUGCCAUGGCCUGAGCCCCCAGAUGU
CACACCUGUCCGCACGCACGGCACAUGGAUGCCCACGCAUGUGCAAAAACAACUCAGGGA
CCAG

FIGURE 80A

Rat CX3CR1 Accession No. U04808 Oligonucleotides

| | | |
|---|---|---|
| 761-57-01 | 5'-taatacgactcactatagggacggaagtccaagagcatcactg-3' | (SEQ ID NO:286) |
| 761-57-03 | 5'-gcaggtacctggtccgta-3' | (SEQ ID NO:287) |
| 781-65-01 | 5'-TET-ggaagtccaagagca-3' | (SEQ ID NO:288) |
| 781-65-02 | 5'-TET-aatggcttctttggg-3' | (SEQ ID NO:289) |
| 781-65-03 | 5'-TET-ggcgtcgccc-3' | (SEQ ID NO:290) |
| 781-65-04 | 5'-TET-tacttccgcatcgtc-3' | (SEQ ID NO:291) |
| 781-65-05 | 5'-TET-cttcttccctagttgtg-3' | (SEQ ID NO:292) |
| 781-65-06 | 5'-TET-tgcctggccgt-3' | (SEQ ID NO:293) |
| 781-65-07 | 5'-TET-gactctactaagaaccca-3' | (SEQ ID NO:294) |
| 781-73-01 | 5'-TET-ccatcttagtggcgt-3' | (SEQ ID NO:295) |
| 781-73-02 | 5'-TET-caacaagtgcctgg-3' | (SEQ ID NO:296) |
| 781-85-01 | 5'-TET-aacacggcgtcac-3' | (SEQ ID NO:297) |
| 781-85-02 | 5'-TET-tgattaccccgagg-3' | (SEQ ID NO:298) |
| 781-85-03 | 5'-TET-acgctgttttcctg-3' | (SEQ ID NO:299) |
| 781-85-04 | 5'-TET-tgagacacctgtacaa-3' | (SEQ ID NO:300) |
| 781-85-05 | 5'-TET-gacggagacagtgg-3' | (SEQ ID NO:301) |
| 781-85-06 | 5'-TET-caagcgagggagag-3' | (SEQ ID NO:302) |

FIGURE 80B

Rat CX3CR1 Accession No. U04808 (SEQ ID NO:303)

GGAAGUCCAAGAGCAUCACUGACAUCUACCUCCUGAACCUGGCCUUGAGCGACCUGCUC
UUUGUGGCCACUUUGCCCUUCUGGACUCACUACCUCAUCAGCCAUGAGGGCCUCCACAA
CGCCAUGUGCAAGCUCACGACUGCUUUCUUCUUCAUUGGCUUCUUUGGGGGCAUAUUCU
UCAUCACCGUCAUCAGCAUCGACCGGUACCUCGCCAUCGUCCUGGCCGCCAACUCCAUG
AACAACCGGACAGUGCAACACGGCGUCACCAUCAGUCUGGGCGUCUGGGCGGCGGCCAU
CUUAGUGGCGUCGCCCCAGUUCAUGUUCACAAAGAGAAAGGACAACGAAUGUUUGGGUG
AUUACCCCGAGGUCCUGCAGGAAAUCUGGCCCGUGCUCCGCAACUCGGAGGUCAACAUC
CUGGGCUUCGUCCUGCCCUUGCUUAUCAUGAGCUUUUGCUACUUCCGCAUCGUCCGGAC
GCUGUUUUCCUGCAAGAACCGGAAGAAGGCCAGAGCCAUUAGGCUCAUCCUCUUGGUGGU
UGUUGUCUUCUUCCUCUUCUGGACGCCUUACAACAUCGUGAUUUUCCUGGAGACUCUCA
AAUUCUACAACUUCUUCCCUAGUUGUGGCAUGAAGAGGGACCUGAGGUGGGCCCUUAGU
GUGACGGAGACAGUGGCGUUUAGCCACUGCUGCCUCAACCCCUUUAUCUACGCUUUCGC
UGGGGAAAAGUUCAGAAGGUACCUGAGACACCUGUACAACAAGUGCCUGGCCGUCCUGU
GCGGUCGUCCUGUCCACGCCGGCUUCUCAACAGAGUCCCAGAGGAGCAGGCAGGACAGC
AUUCUGAGCAGCUUGACUCACUACACAAGCGAGGGAGAGGGAUCUCUCCUGCUCUGAAGG
GUCUCCCCGACCCCGACUCUACUAAGAACCCAGAGUUCCUGCAUCUGACUCUGUGUAAUG
AAAACAGAUUCACACACACACACACACACACACACACACACACACACACACACACACCCG
CUCCUCCUGCAUUUUAUGUGCAAGAAAUACGGACCAGGUACCUGC

FIGURE 81A

Human Interleukin-1 beta (IL-1ß) Oligonucleotides

720-82-01 5'-
gtaatttaatacgactcactatagggaaggtgcagttttgccaaggagtgctaaag-3'
(SEQ ID NO:304)

562-15-01 5'-ctgattgaaatttatctaataaaacatcat-3'
(SEQ ID NO:305)

| | | |
|---|---|---|
| 781-50-01 | 5'-TET-acttccaagctggc-3' | (SEQ ID NO:306) |
| 781-50-02 | 5'-TET-gagagtggaccacac-3' | (SEQ ID NO:307) |
| 781-50-03 | 5'-TET-gaatcagtgaagatgcc-3' | (SEQ ID NO:308) |
| 781-50-04 | 5'-TET-cattgtaccatgaaatatcc-3' | (SEQ ID NO:309) |
| 781-50-05 | 5'-TET-gaactttaatttcaggaattg-3' | (SEQ ID NO:310) |
| 781-50-06 | 5'-TET-ccctagtctgctagc-3' | (SEQ ID NO:311) |
| 781-50-07 | 5'-TET-ttcaagtgtaacttattaacc-3' | (SEQ ID NO:312) |
| 781-72-01 | 5'-TET-aagctggccgtg-3' | (SEQ ID NO:313) |
| 781-72-02 | 5'-TET-tgcagttttgccaag-3' | (SEQ ID NO:314) |

FIGURE 81B

Human Interleukin-1 beta (IL-1ß) (GenBank Accession # M15330) (SEQ ID NO:315)

GGCAGAAGUACCUGAGCUCGCCAGUGAAAUGAUGGCUUAUUACAGUGGCAAUGAGGAUG
ACUUGUUCUUUGAAGCUGAUGGCCCUAAACAGAUGAAGUGCUCCUUCCAGGACCUGGAC
CUCUGCCCUCUGGAUGGCGGCAUCCAGCUACGAAUCUCCGACCACCACUACAGCAAGGG
CUUCAGGCAGGCCGCGUCAGUUGUUGUGGCCAUGGACAAGCUGAGGAAGAUGCUGGUUC
CCUGCCCACAGACCUUCCAGGAGAAUGACCUGAGCACCUUCUUUCCCUUCAUCUUUGAA
GAAGAACCUAUCUUCUUCGACACAUGGGAUAACGAGGCUUAUGUGCACGAUGCACCUGU
ACGAUCACUGAACUGCACGCUCCGGGACUCACAGCAAAAAAGCUUGGUGAUGUCUGGUC
CAUAUGAACUGAAAGCUCUCCACCUCCAGGGACAGGAUAUGGAGCAACAAGUGGUGUUC
UCCAUGUCCUUUGUACAAGGAGAAGAAAGUAAUGACAAAAUACCUGUGGCCUUGGGCCUC
AAGGAAAAGAAUCUGUACCUGUCCUGCGUGUUGAAAGAUGAUAAGCCCACUCUACAGCU
GGAGAGUGUAGAUCCCAAAAAUUACCCAAAGAAGAAGAUGGAAAAGCGAUUUGUCUUCAA
CAAGAUAGAAAUCAAUAACAAGCUGGAAUUUGAGUCUGCCCAGUUCCCCAACUGGUACA
UCAGCACCUCUCAAGCAGAAAACAUGCCCGUCUUCCUGGGAGGGACCAAAGGCGGCCAG
GAUAUAACUGACUUCACCAUGCAAUUUGUGUCUUCCUAAAGAGAGCUGUACCCAGAGAG
UCCUGUGCUGAAUGUGGACUCAAUCCCUAGGGCUGGCAGAAAGGGAACAGAAAGGUUUU
UGAGUACGGCUAUAGCCUGGACUUUCCUGUUGUCUACACCAAUGCCCAACUGCCUGCCUU
AGGGUAGUGCUAAGAGGAUCUCCUGUCCAUCAGCCAGGACAGUCAGCUCUCUCCUUUCA
GGGCCAAUCCCCAGCCCUUUUGUUGAGCCAGGCCUCUCUCACCUCUCCUACUCACUUAA
AGCCCGCCUGACAGAAACCACGGCCACAUUUGGUUCUAAGAAACCCUCUGUCAUUCGCU
CCCACAUUCUGAUGAGCAACCGCUUCCCUAUUUAUUUAUUUAUUUGUUUGUUUGUUUUA
UUCAUUGGUCUAAUUUAUUCAAAGGGGGCAAGAAGUAGCAGUGUCUGUAAAAGAGCCUA
GUUUUUAAUAGCUAUGGAAUCAAUUCAAUUUGGACUGGUGUGCUCUCUUUAAAUCAAGU
CCUUUAAUUAAGACUGAAAAUAUAUAAGCUCAGAUUAUUUAAAUGGGAAUAUUUAUAAA
UGAGCAAAUAUCAUACUGUUCA

FIGURE 82A

Human Interferon gamma Oligonucleotides

| | | |
|---|---|---|
| 448-59-01 | 5'-TET-GCATCGTTTTGGGTTCTCTT | (SEQ ID NO:316) |
| 448-59-02 | 5'-TET-ACTTTAAAGATGACCAGAGC | (SEQ ID NO:317) |
| 448-79-01 | CACATTGTTCTGATCATCTG | (SEQ ID NO:318) |
| 448-79-02 | CGGTAACTGACTTGAATGTC | (SEQ ID NO:319) |
| 448-79-03 | TAGTAACTGGATAGTATCAC | (SEQ ID NO:320) |
| 448-79-04 | GACATTCAAGTCAGTTACCG | (SEQ ID NO:321) |
| 498-20-01 | AATTTAATACGACTCACTATACACATTGTTCTGATCATCTG | (SEQ ID NO:322) |
| 498-20-02 | AATTTAATACGACTCACTATACGGTAACTGACTTGAATGTC | (SEQ ID NO:323) |
| 498-20-03 | 5'-TET-CACATTGTTCTGATCATCTG | (SEQ ID NO:324) |
| 498-20-04 | 5'-TET-CGGTAACTGACTTGAATGTC | (SEQ ID NO:325) |
| 498-40-01 | 5'-AGTAATTTACGACTCACTATAGGGACACATTGTTCTGATCATCTGAAGA | (SEQ ID NO:326) |
| 498-40-02 | 5'-AGTAATTTACGACTCACTATAGGGACGGTAACTGACTTGAATGTCCAAC | (SEQ ID NO:327) |
| 498-84-01 | 5'-TET-CATTCAGATGTAGCG | (SEQ ID NO:328) |
| 498-84-02 | 5'-TET-GACTCATCAATCAAA | (SEQ ID NO:329) |
| 498-84-03 | 5'-TET-GATTACAAGGCTTTA | (SEQ ID NO:330) |

FIGURE 82B

Human Interferon gamma (SEQ ID NO:141)

CACAUUGUUCUGAUCAUCUGAAGAUCAGCUAUUAGAAGAGAAAGAUCAGUUAAGUCCUUU
GGACCUGAUCAGCUUGAUACAAGAACUACUGAUUUCAACUUCUUUGGCUUAAUUCUCUC
GGAAACGAUGAAAUAUACAAGUUAUAUCUUGGCUUUUCAGCUCUGCAUCGUUUUGGGUUC
UCUUGGCUGUUACUGCCAGGACCCAUAUGUACAAGAAGCAGAAAACCUUAAGAAAUAUU
UUAAUGCAGGUCAUUCAGAUGUAGCGGAUAAUGGAACUCUUUUCUUAGGCAUUUUGAAG
AAUUGGAAAGAGGAGAGUGACAGAAAAAUAAUGCAGAGCCAAAUUGUCUCCUUUUACUU
CAAACUUUUUAAAAACUUUAAAGAUGACCAGAGCAUCCAAAAGAGUGUGGAGACCAUCA
AGGAAGACAUGAAUGUCAAGUUUUUCAAUAGCAACAAAAAGAAACGAGAUGACUUCGAAA
AGCUGACUAAUUAUUCGGUAACUGACUUGAAUGUCCAACGCAAAGCAAUACAUGAACUCA
UCCAAGUGAUGGCUGAACUGUCGCCAGCAGCUAAAACAGGGAAGCGAAAAAGGAGUCAG
AUGCUGUUUCGAGGUCGAAGAGCAUCCCAGUAAUGGUUGUCCUGCCUACAAUAUUUGAAU
UUUAAAUCUAAAUCUAUUUAUUAAUAUAACAUUAUUUAUAUGGGGAAUAUAUUUUUAGAC
UCAUCAAUCAAAUAAGUAUUUAUAAUAGCAACUUUUGUGUAAUGAAAAUGAAUAUCUAUU
AAUAUAUGUAUUAUUUAUAAUUCCUAUAUCCUGUGACUGUCUCACUUAAUCCUUUGUUUU
CUGACUAAUUAGGCAAGGCUAUGUGAUUACAAGGCUUUAUCUCAGGGGCCAACUAGGCA
GCCAACCUAAGCAAGAUCCCAUGGGUUGUGUGUUUAUUUCACUUGAUGAUACAAUGAAC
ACUUAUAAGUGAAGUGAUACUAUCCAGUUACUA

FIGURE 83A

Pneumocystis carinii (NUCLEODTIDES 84-415 OF ACCESSION # AF236872) (SEQ ID NO:331)

GAGGGUCAUGAAAGCGGCGUGAAAACGUUAGCUAGUGAUCUGGAAUAAAUUCAGAUUGC
GACACUGUCAAAUUGCGGGGAAGCCCUAAAGAUUCAACUACUAAGCAGUUUGUGGAAAC
ACAGCUGUGGCCGAGUUAAUAGCCCUGGGUAUAGUAACAAUGUUGAAUAUGAAUCUUUU
GCGAGAUGAAAUGGGUGAUCCGCAGCCAAGUCCUAAGGGCAUUUUUGUCUAUGGAUGCAG
UUCAACGACUAGAUGGCAGUGGGUAUUGUAAGGAAUUGCAGUUUUCUUGCAGUGCUUAA
GGUAUAGUCUAUCCUCUUUCGAAAGAAAGAGUAUAU

Candida albicans (NUCLEOTIDES 72-418 OF ACCESSION # X74272)(SEQ ID NO:332)

GGGAGGCAAAAGUAGGGACGCCAUGGUUUCCAGAAAUGGGCCGCGGUGUUUUUGACCUGC
UAGUCGAUCUGGCCAGACGUAUCUGUGGGUGGCCAGCGGCGACAUAACCUGGUACGGGG
AAGGCCUCGAAGCAGUGUUCACCUUGGGAGUGCGCAAGCACAAAGAGGUGAGUGGUGUA
UGGGGUUAAUCCCGUGGCGAGCCGUCAGGGCGCGAGUUCUGGCAGUGGCCGUCGUAGAG
CACGGAAAGGUAUGGGCUGGCUCUCUGAGUCGGCUUAAGGUACGUGCCGUCCCACACGA
UGAAAAGUGUGCGGUGCAGAAUAGUUCCCACAGAACGAAGCUGCGCCGGAGAAAGCGAUU
UCUUGGAGCAAU

FIGURE 83B

Earwig R2 element (SEQ ID NO:333)

UAGGAUGAUAGCGCACCUGGUCAUCGUCUCUCUCAGCUGCUCACUUGCUGUUCUAAGUG
AUAAUACCGUUGUUUUUUUAGUGGGUAUUCUUUUACGCUUUCGUAGGAGCGAGUCCCAC
ACUCUUGGAGCAAUCCGGGGUAGUGCCUAAACGCAUUUCUUCAACGU

Bombyx mori R2 element (SEQ ID NO:334)

GCCUUGCACAGUAGUCCAGCGGUAAGGGUGUAGAUCAGGCCCGUCUGUUUCUCCCCCGGA
GCUCGCUCCCUUGGCUUCCCUUAUAUAUUUUAACAUCAGAAACAGACAUUAAACAUCUA
CUGAUCCAAUUUCGCCGGCGUACGGCCACGAUCGGGAGGGUGGGAAUCUCGGGGGUCUU
CCGAUCCUAAUCCAUGAUGAUUACGACCUGAGUCACUAAAGACGAUGGCAUGAUGAUCC
GGCGAUG

SEQUENCE LISTING

<160> NUMBER OF SEQ ID NOS: 334

<210> SEQ ID NO 1
<211> LENGTH: 391
<212> TYPE: DNA
<213> ORGANISM: Artificial Sequence
<220> FEATURE:
<223> OTHER INFORMATION: Synthetic

<400> SEQUENCE: 1
agctcgtatg gcaccggaac cggtaaggac gcgatcacca gcggcatcga ggtcgtatgg 60
acgaacaccc cgacgaaatg ggacaacagt ttcctcgaga tcctgtacgg ctacgagtgg 120
gagctgacga agagccctgc tggcgcttgg caatacaccg ccaaggacgg cgccggtgcc 180
ggcaccatcc cggacccgtt cggcgggcca gggcgctccc cgacgatgct ggccactgac 240
ctctcgctgc gggtggatcc gatctatgag cggatcacgc gtcgctggct ggaacacccc 300
gaggaattgg ccgacgagtt cgccaaggcc tggtacaagc tgatccaccg agacatgggt 360
cccgttgcga gataccttgg gccggtggtc c 391

<210> SEQ ID NO 2
<211> LENGTH: 391
<212> TYPE: DNA
<213> ORGANISM: Artificial Sequence -continued
<220> FEATURE:
<223> OTHER INFORMATION: Synthetic

<400> SEQUENCE: 2
agctcgtatg gcaccggaac cggtaaggac gcgatcacca ccggcatcga ggtcgtatgg 60
acgaacaccc cgacgaaatg ggacaacagt ttcctcgaga tcctgtacgg ctacgagtgg 120
gagctgacga agagccctgc tggcgcttgg caatacaccg ccaaggacgg cgccggtgcc 180
ggcaccatcc cggacccgtt cggcgggcca gggcgctccc cgacgatgct ggccactgac 240
ctctcgctgc gggtggatcc gatctatgag cggatcacgc gtcgctggct ggaacacccc 300
gaggaattgg ccgacgagtt cgccaaggcc tggtacaagc tgatccaccg agacatgggt 360
cccgttgcga gataccttgg gccgctggtc c 391

<210> SEQ ID NO 3
<211> LENGTH: 391
<212> TYPE: DNA
<213> ORGANISM: Artificial Sequence
<220> FEATURE:
<223> OTHER INFORMATION: Synthetic

<400> SEQUENCE: 3
agctcgtatg gcaccggaac cggtaaggac gcgatcacca gcggcatcga ggtcgtatgg 60
acgaacaccc cgacgaaatg ggacaacagt ttcctcgaga tcctgtacgg ctacgagtgg 120
gagctgacga agagccctgc tggcgcttgg caatacaccg ccaaggacgg cgccggtgcc 180
ggcaccatcc cggacccgtt cggcgggcca gggcgctccc cgacgatgct ggccactgac 240
ctctcgctgc gggtggatcc gatctatgag cggatcacgc gtcgctggct ggaacacccc 300
gaggaattgg ccgacgagtt cgccaaggcc tggtacaagc tgatccaccg agacatgggt 360
cccgttgcga gataccttgg gccgctggtc c 391

<210> SEQ ID NO 4
<211> LENGTH: 391
<212> TYPE: DNA
<213> ORGANISM: Artificial Sequence
<220> FEATURE:
<223> OTHER INFORMATION: Synthetic

<400> SEQUENCE: 4
agctcgtatg gcaccggaac cggtaaggac gcgatcacca ccggcatcga ggtcgtatgg 60
acgaacaccc cgacgaaatg ggacaacagt ttcctcgaga tcctgtacgg ctacgagtgg 120
gagctgacga agagccctgc tggcgcttgg caatacaccg ccaaggacgg cgccggtgcc 180
ggcaccatcc cggacccgtt cggcgggcca gggcgctccc cgacgatgct ggccactgac 240
ctctcgctgc gggtggatcc gatctatgag cggatcacgc gtcgctggct ggaacacccc 300
gaggaattgg ccgacgagtt cgccaaggcc tggtacaagc tgatccaccg agacatgggt 360
cccgttgcga gataccttgg gccggtggtc c 391

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agctcgtatg gcaccggaac 20

-continued

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ttgacctccc acccgacttg 20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
agctcgtatg gcaccggaac c 21

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ggaccagcgg cccaaggtat 20

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
ggaccaccgg cccaaggtat ct 22

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
tttttgccgc tggtgatcgc g 21

<210> SEQ ID NO 11
<211> LENGTH: 12
<212> TYPE: DNA
<213> ORGANISM: Artificial Sequence
<220> FEATURE:
<223> OTHER INFORMATION: Synthetic

<400> SEQUENCE: 11
ggagagccat ag 12

<210> SEQ ID NO 12
<211> LENGTH: 11
<212> TYPE: DNA
<213> ORGANISM: Artificial Sequence
<220> FEATURE:
<223> OTHER INFORMATION: Synthetic -continued

<400> SEQUENCE: 12
tggtctgcgg a 11

<210> SEQ ID NO 13
<211> LENGTH: 11
<212> TYPE: DNA
<213> ORGANISM: Artificial Sequence
<220> FEATURE:
<223> OTHER INFORMATION: Synthetic

<400> SEQUENCE: 13
ggacgaccgg g 11

<210> SEQ ID NO 14
<211> LENGTH: 11
<212> TYPE: DNA
<213> ORGANISM: Artificial Sequence
<220> FEATURE:
<223> OTHER INFORMATION: Synthetic

<400> SEQUENCE: 14
ggagatttgg g 11

<210> SEQ ID NO 15
<211> LENGTH: 11
<212> TYPE: DNA
<213> ORGANISM: Artificial Sequence
<220> FEATURE:
<223> OTHER INFORMATION: Synthetic

<400> SEQUENCE: 15
ccgcgagact g 11

<210> SEQ ID NO 16
<211> LENGTH: 12
<212> TYPE: DNA
<213> ORGANISM: Artificial Sequence
<220> FEATURE:
<223> OTHER INFORMATION: Synthetic

<400> SEQUENCE: 16
ctagccgagt ag 12

<210> SEQ ID NO 17
<211> LENGTH: 11
<212> TYPE: DNA
<213> ORGANISM: Artificial Sequence
<220> FEATURE:
<223> OTHER INFORMATION: Synthetic

<400> SEQUENCE: 17
tgttgggtcg c 11

<210> SEQ ID NO 18
<211> LENGTH: 11
<212> TYPE: DNA
<213> ORGANISM: Artificial Sequence
<220> FEATURE:
<223> OTHER INFORMATION: Synthetic

<400> SEQUENCE: 18
ccgcgagacc g 11

<210> SEQ ID NO 19

-continued

<211> LENGTH: 11
<212> TYPE: DNA
<213> ORGANISM: Artificial Sequence
<220> FEATURE:
<223> OTHER INFORMATION: Synthetic

<400> SEQUENCE: 19
ccgcaagacc g 11

<210> SEQ ID NO 20
<211> LENGTH: 289
<212> TYPE: DNA
<213> ORGANISM: Artificial Sequence
<220> FEATURE:
<223> OTHER INFORMATION: Synthetic

<400> SEQUENCE: 20
gattctgtct tcacgcagaa agcgtctagc catggcgtta gtatgagtgt cgtgcagcct 60
ccaggacccc ccctcccggg agagccatag tggtctgcgg aaccggtgag tacaccggaa 120
ttgccaggac gaccgggtcc tttcttggat caacccgctc aatgcctgga gatttgggcg 180
tgcccccgca agactgctag ccgagtagtg ttgggtcgcg aaaggccttg tggtactgcc 240
tgatagggtg cttgcgagtg ccccgggagg tctcgtagac cgtgcaatc 289

<210> SEQ ID NO 21
<211> LENGTH: 286
<212> TYPE: DNA
<213> ORGANISM: Artificial Sequence
<220> FEATURE:
<223> OTHER INFORMATION: Synthetic

<400> SEQUENCE: 21
gattctgtct tcacgcagaa agcgtctagc catggcgtta gtatgagtgt cgtgcagcct 60
ccaggtcccc ccctcccggg agagccatag tggtctgcgg aaccggtgag tacaccggaa 120
ttgccaggac gaccgggtcc tttcttggat caacccgctc aatgcctgga gatttgggcg 180
tgcccccgcg agactgctag ccgagtagtg ttgggtcgcg aaaggccttg tggtactgcc 240
tgatagggtg cttgcgagtg ccccgggagg tctcgtagac cgtgca 286

<210> SEQ ID NO 22
<211> LENGTH: 289
<212> TYPE: DNA
<213> ORGANISM: Artificial Sequence
<220> FEATURE:
<223> OTHER INFORMATION: Synthetic

<400> SEQUENCE: 22
gattctgtct tcacgcagaa agcgtctagc catggcgtta gtatgagtgt cgtacagcct 60
ccaggccccc ccctcccggg agagccatag tggtctgcgg aaccggtgag tacaccggaa 120
ttgccgggaa gactgggtcc tttcttggat aaacccactc tatgcccggc catttgggcg 180
tgcccccgca agactgctag ccgagtagcg ttgggttgcg aaaggccttg tggtactgcc 240
tgatagggtg cttgcgagta ccccgggagg tctcgtagac cgtgcaatc 289

<210> SEQ ID NO 23
<211> LENGTH: 289
<212> TYPE: DNA
<213> ORGANISM: Artificial Sequence
<220> FEATURE:
<223> OTHER INFORMATION: Synthetic

<400> SEQUENCE: 23

-continued

```
gattctgtct tcacgcagaa agcgcctagc catggcgtta gtacgagtgt cgtgcagcct     60

ccaggacccc ccctcccggg agaaccatag tggtctgcgg aaccggtgag tacaccggaa    120

tcgctggggt gaccgggtcc tttcttggag caacccgctc aatacccaga aatttgggcg    180

tgcccccgcg agatcactag ccgagtagtg ttgggtcgcg aaaggccttg tggtactgcc    240

tgatagggtg cttgcgagtg ccccgggagg tctcgtagac cgtgcaatc                289


<210> SEQ ID NO 24
<211> LENGTH: 18
<212> TYPE: DNA
<213> ORGANISM: Artificial Sequence
<220> FEATURE:
<223> OTHER INFORMATION: Synthetic

<400> SEQUENCE: 24

ctcgcaagca ccctatca                                                   18


<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25

gcagaaagcg tctagccatg g                                               21


<210> SEQ ID NO 26
<211> LENGTH: 244
<212> TYPE: DNA
<213> ORGANISM: Artificial Sequence
<220> FEATURE:
<223> OTHER INFORMATION: Synthetic

<400> SEQUENCE: 26

gcagaaagcg tctagccatg gcgttagtat gagtgtcgtg cagcctccag gacccccccct     60

cccgggagag ccatagtggt ctgcggaacc ggtgagtaca ccggaattgc caggacgacc    120

gggtcctttc ttggatcaac ccgctcaatg cctggagatt tgggcgtgcc cccgcaagac    180

tgctagccga gtagtgttgg gtcgcgaaag gccttgtggt actgcctgat agggtgcttg    240

cgag                                                                 244


<210> SEQ ID NO 27
<211> LENGTH: 244
<212> TYPE: DNA
<213> ORGANISM: Artificial Sequence
<220> FEATURE:
<223> OTHER INFORMATION: Synthetic

<400> SEQUENCE: 27

gcagaaagcg tctagccatg gcgttagtat gagtgtcgtg cagcctccag gtccccccct     60

cccgggagag ccatagtggt ctgcggaacc ggtgagtaca ccggaattgc caggacgacc    120

gggtcctttc ttggatcaac ccgctcaatg cctggagatt tgggcgtgcc cccgcgagac    180

tgctagccga gtagtgttgg gtcgcgaaag gccttgtggt actgcctgat agggtgcttg    240

cgag                                                                 244


<210> SEQ ID NO 28
<211> LENGTH: 244
<212> TYPE: DNA
```

-continued

<213> ORGANISM: Artificial Sequence
<220> FEATURE:
<223> OTHER INFORMATION: Synthetic

<400> SEQUENCE: 28
gcagaaagcg tctagccatg gcgttagtat gagtgtcgta cagcctccag gccccccct 60 cccgggagag ccatagtggt ctgcggaacc ggtgagtaca ccggaattgc cgggaagact 120
gggtcctttc ttggataaac ccactctatg cccggccatt tgggcgtgcc cccgcaagac 180
tgctagccga gtagcgttgg gttgcgaaag gccttgtggt actgcctgat agggtgcttg 240
cgag 244

<210> SEQ ID NO 29
<211> LENGTH: 244
<212> TYPE: DNA
<213> ORGANISM: Artificial Sequence
<220> FEATURE:
<223> OTHER INFORMATION: Synthetic

<400> SEQUENCE: 29
gcagaaagcg cctagccatg gcgttagtac gagtgtcgtg cagcctccag gacccccct 60 cccgggagaa ccatagtggt ctgcggaacc ggtgagtaca ccggaatcgc tggggtgacc 120
gggtcctttc ttggagcaac ccgctcaata cccagaaatt tgggcgtgcc cccgcgagat 180
cactagccga gtagtgttgg gtcgcgaaag gccttgtggt actgcctgat agggtgcttg 240
cgag 244

<210> SEQ ID NO 30
<211> LENGTH: 216
<212> TYPE: DNA
<213> ORGANISM: Artificial Sequence
<220> FEATURE:
<223> OTHER INFORMATION: Synthetic

<400> SEQUENCE: 30
cagaaagggt ttagccatgg ggttagtatg agtgtcgtac agcctccagg cccccccctc 60
ccgggagagc catagtggtc tgcggaaccg gtgagtacac cggaattgcc gggaagactg 120
ggtcctttct tggataaacc cactctatgc ccggccattt gggcgtgccc ccgcaagact 180
gctagccgag tagcgttggg ttgcgaaagg ccttgt 216

<210> SEQ ID NO 31
<211> LENGTH: 244
<212> TYPE: DNA
<213> ORGANISM: Artificial Sequence
<220> FEATURE:
<223> OTHER INFORMATION: Synthetic

<400> SEQUENCE: 31
cagaaagggt ttagccatgg cgttagtatg agtgtcgtgc agcctccagg acccccctc 60 ccgggagagc catagtggtc tgcggaaccg gtgagtacac cggaattgcc aggacgaccg 120
ggtcctttct tggataaaac ccgctcaatg cctggagatt tgggcgtgcc cccgcaagac 180
tgctagccga gtagtgttgg gtcgcgaaag gccttgtggt actgcctgat agggtgcttg 240
caag 244

<210> SEQ ID NO 32
<211> LENGTH: 239
<212> TYPE: DNA
<213> ORGANISM: Artificial Sequence -continued
<220> FEATURE:
<223> OTHER INFORMATION: Synthetic

<400> SEQUENCE: 32
gcagaaaggt ttagccatgg gttagtatga gtgtcgtgca gcctccagga cccccctcc 60 cgggagagcc atagtggtct gcggaaccgg tgagtacacc ggaattgcca ggacgaccgg 120
gtcctttctt ggattaaccc gctcaatgcc tggagatttg ggcgtgcccc cgcaagactg 180
ctagccgagt agtgttgggt cgcgaaaggc cttgtggtac tgcctgatag ggtgcttgc 239

<210> SEQ ID NO 33
<211> LENGTH: 240
<212> TYPE: DNA
<213> ORGANISM: Artificial Sequence
<220> FEATURE:
<223> OTHER INFORMATION: Synthetic

<400> SEQUENCE: 33
gcagaaaggt ttagccatgg ggttagtatg agtgtcgtac agcctccagg acccccctc 60 ccgggagagc catagtggtc tgcggaaccg gtgagtacac cggaattgcc aggacgaccg 120
ggtcctttct tggataaacc cgctcaatgc ctggagattt gggcgtgccc ccgcaagact 180
gctagccgag tagtgttggg tcgcgaaagg ccttgtggta ctgcctgata gggtgcttgc 240

<210> SEQ ID NO 34
<211> LENGTH: 240
<212> TYPE: DNA
<213> ORGANISM: Artificial Sequence
<220> FEATURE:
<223> OTHER INFORMATION: Synthetic

<400> SEQUENCE: 34
gcagaaaggg tttagccatg gcgttagtat gagtgtcgta cagcctccag gcccccccct 60
cccgggagag ccatagtggt ctgcggaacc ggtgagtaca ccggaattac cggaaagact 120
gggtcctttc ttggataaac ccactctatg tccggtcatt tgggcgtgcc cccgcaagac 180
tgctagccga gtagcgttgg gttgcaaagg ccttgtggta ctgcctgata gggtgcttgc 240

<210> SEQ ID NO 35
<211> LENGTH: 240
<212> TYPE: DNA
<213> ORGANISM: Artificial Sequence
<220> FEATURE:
<223> OTHER INFORMATION: Synthetic

<400> SEQUENCE: 35
cagaaagggt ttagccatgg ggttagtacg agtgtcgtgc agcctccagg cccccccctc 60
ccgggagagc catagtggtc tgcggaaccg gtgagtacac cggaatcgct ggggtgaccg 120
ggtcctttct tggagcaacc cgctcaatac ccagaaattt gggcgtgccc ccgcgagatc 180
actagccgag tagtgttggg tcgcgaaagg ccttgtggta ctgcctgata gggtgcttgc 240

<210> SEQ ID NO 36
<211> LENGTH: 239
<212> TYPE: DNA
<213> ORGANISM: Artificial Sequence
<220> FEATURE:
<223> OTHER INFORMATION: Synthetic

<400> SEQUENCE: 36
agaaagcgtt tagccatggc gttagtatga gtgttgtgca gcctccagga cccccctcc 60

-continued

```
cgggagagcc atagtggtct gcggaaccgg tgagtacacc ggaattgcca ggacgaccgg    120

gtcctttctt ggatcaaccc gctcaatgcc tggagatttg ggcgtgcccc cgcaagactg    180

ctagccgagt agtgttgggt cgcgaaaggc cttgtggtac tgcctgatag ggtgcttgc     239
```

<210> SEQ ID NO 37
<211> LENGTH: 232
<212> TYPE: DNA
<213> ORGANISM: Artificial Sequence
<220> FEATURE:
<223> OTHER INFORMATION: Synthetic

<400> SEQUENCE: 37

```
gtttagccat ggcgttagta tgagtgtcgt gcagcctcca ggaccccccc tcccgggaga     60

gccatagtgg tctgcggaac cggtgagtac accggaattg ccaggacgac cgggtccttt    120

cttggatcaa cccgctcaat gcctggagat ttgggcgtgc ccccgcgaga ccgctagccg    180

agtagtgttg ggtcgcgaaa ggccttgtgg tactgcctga tagggtgctt gc            232
```

<210> SEQ ID NO 38
<211> LENGTH: 240
<212> TYPE: DNA
<213> ORGANISM: Artificial Sequence
<220> FEATURE:
<223> OTHER INFORMATION: Synthetic

<400> SEQUENCE: 38

```
gcagaaagcg tttagccatg gcgttagtac gagtgtcgtg cagcctccag gacccccccct    60

cccgggagag ccatagtggt ctgcggaacc ggtgagtaca ccggaatcgc tggggtgacc    120

gggtcctttc ttggaacaac ccgctcaata cccagaaatt tgggcgtgcc cccgcgagat    180

cactagccga gtagtgttgg gtcgcgaaag gccttgtggt actgcctgat agggtgcttg    240
```

<210> SEQ ID NO 39
<211> LENGTH: 44
<212> TYPE: DNA
<213> ORGANISM: Artificial Sequence
<220> FEATURE:
<223> OTHER INFORMATION: Synthetic

<400> SEQUENCE: 39

```
tgctctctgg tcgctgtctg aaagacagcg tggtctctcg taat                      44
```

<210> SEQ ID NO 40
<211> LENGTH: 44
<212> TYPE: DNA
<213> ORGANISM: Artificial Sequence
<220> FEATURE:
<223> OTHER INFORMATION: Synthetic

<400> SEQUENCE: 40

```
tgctctctgg tcgctgtctg aaagactccg tggtctctcg taat                      44
```

<210> SEQ ID NO 41
<211> LENGTH: 44
<212> TYPE: DNA
<213> ORGANISM: Artificial Sequence
<220> FEATURE:
<223> OTHER INFORMATION: Synthetic

<400> SEQUENCE: 41

```
tgctctctgg tcgctgtctg aattttttttt tggtctctcg taat                     44
```

-continued

<210> SEQ ID NO 42
<211> LENGTH: 14
<212> TYPE: DNA
<213> ORGANISM: Artificial Sequence
<220> FEATURE:
<223> OTHER INFORMATION: Synthetic

<400> SEQUENCE: 42
agaccattac caga 14

<210> SEQ ID NO 43
<211> LENGTH: 16
<212> TYPE: DNA
<213> ORGANISM: Artificial Sequence
<220> FEATURE:
<223> OTHER INFORMATION: Synthetic

<400> SEQUENCE: 43
gagaccatta ccagag 16

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
agagaccatt accagaga 18

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
agagaccatt acaagcga 18

<210> SEQ ID NO 46
<211> LENGTH: 18
<212> TYPE: DNA
<213> ORGANISM: Artificial Sequence
<220> FEATURE:
<223> OTHER INFORMATION: Synthetic

<400> SEQUENCE: 46
agcgaacatt accagaga 18

<210> SEQ ID NO 47
<211> LENGTH: 16
<212> TYPE: DNA
<213> ORGANISM: Artificial Sequence
<220> FEATURE:
<223> OTHER INFORMATION: Synthetic

<400> SEQUENCE: 47
agagaccaac cagaga 16

<210> SEQ ID NO 48
<211> LENGTH: 9
<212> TYPE: DNA
<213> ORGANISM: Artificial Sequence
<220> FEATURE:
<223> OTHER INFORMATION: Synthetic -continued

<400> SEQUENCE: 48 agagaccat 9

<210> SEQ ID NO 49
<211> LENGTH: 9
<212> TYPE: DNA
<213> ORGANISM: Artificial Sequence
<220> FEATURE:
<223> OTHER INFORMATION: Synthetic

<400> SEQUENCE: 49 taccagaga 9

<210> SEQ ID NO 50
<211> LENGTH: 10
<212> TYPE: DNA
<213> ORGANISM: Artificial Sequence
<220> FEATURE:
<223> OTHER INFORMATION: Synthetic

<400> SEQUENCE: 50
accagagagc 10

<210> SEQ ID NO 51
<211> LENGTH: 10
<212> TYPE: DNA
<213> ORGANISM: Artificial Sequence
<220> FEATURE:
<223> OTHER INFORMATION: Synthetic

<400> SEQUENCE: 51
tcagacagcg 10

<210> SEQ ID NO 52
<211> LENGTH: 18
<212> TYPE: DNA
<213> ORGANISM: Artificial Sequence
<220> FEATURE:
<223> OTHER INFORMATION: Synthetic

<400> SEQUENCE: 52
agtggtctgc ggaaccgg 18

<210> SEQ ID NO 53
<211> LENGTH: 18
<212> TYPE: DNA
<213> ORGANISM: Artificial Sequence
<220> FEATURE:
<223> OTHER INFORMATION: Synthetic

<400> SEQUENCE: 53
agtgtcgttt ggaaccgg 18

<210> SEQ ID NO 54
<211> LENGTH: 18
<212> TYPE: DNA
<213> ORGANISM: Artificial Sequence
<220> FEATURE:
<223> OTHER INFORMATION: Synthetic

<400> SEQUENCE: 54
agtgtcgtaa ggaaccgg 18

<210> SEQ ID NO 55
<211> LENGTH: 18

-continued

<212> TYPE: DNA
<213> ORGANISM: Artificial Sequence
<220> FEATURE:
<223> OTHER INFORMATION: Synthetic

<400> SEQUENCE: 55
agtgtcgtca ggaaccgg 18

<210> SEQ ID NO 56
<211> LENGTH: 16
<212> TYPE: DNA
<213> ORGANISM: Artificial Sequence
<220> FEATURE:
<223> OTHER INFORMATION: Synthetic

<400> SEQUENCE: 56
agtgtcgtgg aaccgg 16

<210> SEQ ID NO 57
<211> LENGTH: 18
<212> TYPE: DNA
<213> ORGANISM: Artificial Sequence
<220> FEATURE:
<223> OTHER INFORMATION: Synthetic

<400> SEQUENCE: 57
agtgtcgttt ggatccgg 18

<210> SEQ ID NO 58
<211> LENGTH: 18
<212> TYPE: DNA
<213> ORGANISM: Artificial Sequence
<220> FEATURE:
<223> OTHER INFORMATION: Synthetic

<400> SEQUENCE: 58
agtgacgttt ggaaccgg 18

<210> SEQ ID NO 59
<211> LENGTH: 8
<212> TYPE: DNA
<213> ORGANISM: Artificial Sequence
<220> FEATURE:
<223> OTHER INFORMATION: Synthetic

<400> SEQUENCE: 59 ggaaccgg 8

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
ttttgtgagt acaccggaat 20

<210> SEQ ID NO 61
<211> LENGTH: 14
<212> TYPE: DNA
<213> ORGANISM: Artificial Sequence
<220> FEATURE:
<223> OTHER INFORMATION: Synthetic

<400> SEQUENCE: 61

-continued ttttgtgagt acac 14

<210> SEQ ID NO 62
<211> LENGTH: 15
<212> TYPE: DNA
<213> ORGANISM: Artificial Sequence
<220> FEATURE:
<223> OTHER INFORMATION: Synthetic

<400> SEQUENCE: 62
tgagtacacc ggaat 15

<210> SEQ ID NO 63
<211> LENGTH: 33
<212> TYPE: DNA
<213> ORGANISM: Artificial Sequence
<220> FEATURE:
<223> OTHER INFORMATION: Synthetic

<400> SEQUENCE: 63
attccggtgt actcaccggt tccaaacgac act 33

<210> SEQ ID NO 64
<211> LENGTH: 18
<212> TYPE: DNA
<213> ORGANISM: Artificial Sequence
<220> FEATURE:
<223> OTHER INFORMATION: Synthetic

<400> SEQUENCE: 64
cagcctcccc ttcttgga 18

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
agtgtcgttt ggaattaatt 20

<210> SEQ ID NO 66
<211> LENGTH: 16
<212> TYPE: DNA
<213> ORGANISM: Artificial Sequence
<220> FEATURE:
<223> OTHER INFORMATION: Synthetic

<400> SEQUENCE: 66
gcgaaaggcc ttgtgg 16

<210> SEQ ID NO 67
<211> LENGTH: 16
<212> TYPE: DNA
<213> ORGANISM: Artificial Sequence
<220> FEATURE:
<223> OTHER INFORMATION: Synthetic

<400> SEQUENCE: 67
acagcctcca ggaccc 16

<210> SEQ ID NO 68
<211> LENGTH: 16
<212> TYPE: DNA
<213> ORGANISM: Artificial Sequence -continued
<220> FEATURE:
<223> OTHER INFORMATION: Synthetic

<400> SEQUENCE: 68
gcagcctcca ggaccc 16

<210> SEQ ID NO 69
<211> LENGTH: 193
<212> TYPE: DNA
<213> ORGANISM: Artificial Sequence
<220> FEATURE:
<223> OTHER INFORMATION: Synthetic

<400> SEQUENCE: 69
cgtggaggcg atcacaccgc agacgttgat caacatccgg ccggtggtcg ccgcgatcaa 60
ggagttcttc ggcaccagcc agctgagcca attcatggac cagaacaacc cgctgtcggg 120
gttgacccac aagcgccgac tgtcggcgct ggggcccggc ggtctgtcac gtgagcgtgc 180
cgggctggag gtc 193

<210> SEQ ID NO 70
<211> LENGTH: 26
<212> TYPE: DNA
<213> ORGANISM: Artificial Sequence
<220> FEATURE:
<223> OTHER INFORMATION: Synthetic

<400> SEQUENCE: 70
cgtggaggcg atcacaccgc agacgt 26

<210> SEQ ID NO 71
<211> LENGTH: 25
<212> TYPE: DNA
<213> ORGANISM: Artificial Sequence
<220> FEATURE:
<223> OTHER INFORMATION: Synthetic

<400> SEQUENCE: 71
gacctccagc ccggcacgct cacgt 25

<210> SEQ ID NO 72
<211> LENGTH: 128
<212> TYPE: DNA
<213> ORGANISM: Artificial Sequence
<220> FEATURE:
<223> OTHER INFORMATION: Synthetic

<400> SEQUENCE: 72
cgccgcgatc aaggagttct tcggcaccag ccagctgagc caattcatgg accagaacaa 60
cccgctgtcg gggttgaccc acaagcgccg actgtcggcg ctggggcccg gcggtctgtc 120
acgtgagc 128

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
cgccgcgatc aaggagttct 20

<210> SEQ ID NO 74

```
<211> LENGTH: 20
<212> TYPE: DNA
<213> ORGANISM: Artificial Sequence
<220> FEATURE:
<223> OTHER INFORMATION: Synthetic

<400> SEQUENCE: 74

gctcacgtga cagaccgccg                                                   20

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

tgacagaccg ccgggccc                                                     18

<210> SEQ ID NO 76
<211> LENGTH: 121
<212> TYPE: DNA
<213> ORGANISM: Artificial Sequence
<220> FEATURE:
<223> OTHER INFORMATION: Synthetic

<400> SEQUENCE: 76

cgccgcgatc aaggagttct tcggcaccag ccagctgagc caattcatgg accagaacaa       60

cccgctgtcg gggttgaccc acaagcgccg actgtcggcg ctggggcccg gcggtctgtc      120

a                                                                      121

<210> SEQ ID NO 77
<211> LENGTH: 18
<212> TYPE: DNA
<213> ORGANISM: Artificial Sequence
<220> FEATURE:
<223> OTHER INFORMATION: Synthetic

<400> SEQUENCE: 77

agacagaccg ccgggccc                                                     18

<210> SEQ ID NO 78
<211> LENGTH: 121
<212> TYPE: DNA
<213> ORGANISM: Artificial Sequence
<220> FEATURE:
<223> OTHER INFORMATION: Synthetic

<400> SEQUENCE: 78

cgccgcgatc aaggagttct tcggcaccag ccagctgagc caattcatgg accagaacaa       60

cccgctgtcg gggttgaccc acaagcgccg actgtcggcg ctggggcccg gcggtctgtc      120

t                                                                      121

<210> SEQ ID NO 79
<211> LENGTH: 18
<212> TYPE: DNA
<213> ORGANISM: Artificial Sequence
<220> FEATURE:
<223> OTHER INFORMATION: Synthetic

<400> SEQUENCE: 79

acagaccgcc gggcccca                                                     18
```

<210> SEQ ID NO 80
<211> LENGTH: 119
<212> TYPE: DNA
<213> ORGANISM: Artificial Sequence
<220> FEATURE:
<223> OTHER INFORMATION: Synthetic

<400> SEQUENCE: 80
cgccgcgatc aaggagttct tcggcaccag ccagctgagc caattcatgg accagaacaa    60
cccgctgtcg gggttgaccc acaagcgccg actgtcggcg ctggggcccg gcggtctgt   119

<210> SEQ ID NO 81
<211> LENGTH: 18
<212> TYPE: DNA
<213> ORGANISM: Artificial Sequence
<220> FEATURE:
<223> OTHER INFORMATION: Synthetic

<400> SEQUENCE: 81
ccagaccgcc gggcccca                                                  18

<210> SEQ ID NO 82
<211> LENGTH: 119
<212> TYPE: DNA
<213> ORGANISM: Artificial Sequence
<220> FEATURE:
<223> OTHER INFORMATION: Synthetic

<400> SEQUENCE: 82
cgccgcgatc aaggagttct tcggcaccag ccagctgagc caattcatgg accagaacaa    60
cccgctgtcg gggttgaccc acaagcgccg actgtcggcg ctggggcccg gcggtctgg   119

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83
cagaccgccg ggccccag                                                  18

<210> SEQ ID NO 84
<211> LENGTH: 118
<212> TYPE: DNA
<213> ORGANISM: Artificial Sequence
<220> FEATURE:
<223> OTHER INFORMATION: Synthetic

<400> SEQUENCE: 84
cgccgcgatc aaggagttct tcggcaccag ccagctgagc caattcatgg accagaacaa    60
cccgctgtcg gggttgaccc acaagcgccg actgtcggcg ctggggcccg gcggtctg    118

<210> SEQ ID NO 85
<211> LENGTH: 18
<212> TYPE: DNA
<213> ORGANISM: Artificial Sequence
<220> FEATURE:
<223> OTHER INFORMATION: Synthetic

<400> SEQUENCE: 85
gagaccgccg ggccccag                                                  18

<210> SEQ ID NO 86

-continued

<211> LENGTH: 118
<212> TYPE: DNA
<213> ORGANISM: Artificial Sequence
<220> FEATURE:
<223> OTHER INFORMATION: Synthetic

<400> SEQUENCE: 86
cgccgcgatc aaggagttct tcggcaccag ccagctgagc caattcatgg accagaacaa 60
cccgctgtcg gggttgaccc acaagcgccg actgtcggcg ctggggcccg gcggtctc 118

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
ccgccgggcc ccagcgccga 20

<210> SEQ ID NO 88
<211> LENGTH: 114
<212> TYPE: DNA
<213> ORGANISM: Artificial Sequence
<220> FEATURE:
<223> OTHER INFORMATION: Synthetic

<400> SEQUENCE: 88
cgccgcgatc aaggagttct tcggcaccag ccagctgagc caattcatgg accagaacaa 60
cccgctgtcg gggttgaccc acaagcgccg actgtcggcg ctggggcccg gcgg 114

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
gcgccgggcc ccagcgccga 20

<210> SEQ ID NO 90
<211> LENGTH: 114
<212> TYPE: DNA
<213> ORGANISM: Artificial Sequence
<220> FEATURE:
<223> OTHER INFORMATION: Synthetic

<400> SEQUENCE: 90
cgccgcgatc aaggagttct tcggcaccag ccagctgagc caattcatgg accagaacaa 60
cccgctgtcg gggttgaccc acaagcgccg actgtcggcg ctggggcccg gcgc 114

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
cggccgggcc ccagcgccga 20

<210> SEQ ID NO 92
<211> LENGTH: 114

```
<212> TYPE: DNA
<213> ORGANISM: Artificial Sequence
<220> FEATURE:
<223> OTHER INFORMATION: Synthetic

<400> SEQUENCE: 92

cgccgcgatc aaggagttct tcggcaccag ccagctgagc caattcatgg accagaacaa    60

cccgctgtcg gggttgaccc acaagcgccg actgtcggcg ctggggcccg gccg          114

<210> SEQ ID NO 93
<211> LENGTH: 18
<212> TYPE: DNA
<213> ORGANISM: Artificial Sequence
<220> FEATURE:
<223> OTHER INFORMATION: Synthetic

<400> SEQUENCE: 93

cgggccccag cgccgaca                                                   18

<210> SEQ ID NO 94
<211> LENGTH: 110
<212> TYPE: DNA
<213> ORGANISM: Artificial Sequence
<220> FEATURE:
<223> OTHER INFORMATION: Synthetic

<400> SEQUENCE: 94

cgccgcgatc aaggagttct tcggcaccag ccagctgagc caattcatgg accagaacaa    60

cccgctgtcg gggttgaccc acaagcgccg actgtcggcg ctggggcccg                110

<210> SEQ ID NO 95
<211> LENGTH: 18
<212> TYPE: DNA
<213> ORGANISM: Artificial Sequence
<220> FEATURE:
<223> OTHER INFORMATION: Synthetic

<400> SEQUENCE: 95

agggccccag cgccgaca                                                   18

<210> SEQ ID NO 96
<211> LENGTH: 110
<212> TYPE: DNA
<213> ORGANISM: Artificial Sequence
<220> FEATURE:
<223> OTHER INFORMATION: Synthetic

<400> SEQUENCE: 96

cgccgcgatc aaggagttct tcggcaccag ccagctgagc caattcatgg accagaacaa    60

cccgctgtcg gggttgaccc acaagcgccg actgtcggcg ctggggccct                110

<210> SEQ ID NO 97
<211> LENGTH: 18
<212> TYPE: DNA
<213> ORGANISM: Artificial Sequence
<220> FEATURE:
<223> OTHER INFORMATION: Synthetic

<400> SEQUENCE: 97

ccccagcgcc gacagtcg                                                   18

<210> SEQ ID NO 98
<211> LENGTH: 106
<212> TYPE: DNA
```

<213> ORGANISM: Artificial Sequence
<220> FEATURE:
<223> OTHER INFORMATION: Synthetic

<400> SEQUENCE: 98
cgccgcgatc aaggagttct tcggcaccag ccagctgagc caattcatgg accagaacaa    60
cccgctgtcg gggttgaccc acaagcgccg actgtcggcg ctgggg                  106

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99
tcccagcgcc gacagtcg                                                  18

<210> SEQ ID NO 100
<211> LENGTH: 106
<212> TYPE: DNA
<213> ORGANISM: Artificial Sequence
<220> FEATURE:
<223> OTHER INFORMATION: Synthetic

<400> SEQUENCE: 100
cgccgcgatc aaggagttct tcggcaccag ccagctgagc caattcatgg accagaacaa    60
cccgctgtcg gggttgaccc acaagcgccg actgtcggcg ctggga                  106

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
cgcttgtggg tcaaccccga                                                20

<210> SEQ ID NO 102
<211> LENGTH: 87
<212> TYPE: DNA
<213> ORGANISM: Artificial Sequence
<220> FEATURE:
<223> OTHER INFORMATION: Synthetic

<400> SEQUENCE: 102
cgccgcgatc aaggagttct tcggcaccag ccagctgagc caattcatgg accagaacaa    60
cccgctgtcg gggttgaccc acaagcg                                        87

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
agcttgtggg tcaaccccga                                                20

<210> SEQ ID NO 104
<211> LENGTH: 87
<212> TYPE: DNA
<213> ORGANISM: Artificial Sequence -continued

```
<220> FEATURE:
<223> OTHER INFORMATION: Synthetic

<400> SEQUENCE: 104

cgccgcgatc aaggagttct tcggcaccag ccagctgagc caattcatgg accagaacaa      60

cccgctgtcg gggttgaccc acaagct                                         87

<210> SEQ ID NO 105
<211> LENGTH: 16
<212> TYPE: DNA
<213> ORGANISM: Artificial Sequence
<220> FEATURE:
<223> OTHER INFORMATION: Synthetic

<400> SEQUENCE: 105

gtgacagagt tgttct                                                     16

<210> SEQ ID NO 106
<211> LENGTH: 18
<212> TYPE: DNA
<213> ORGANISM: Artificial Sequence
<220> FEATURE:
<223> OTHER INFORMATION: Synthetic

<400> SEQUENCE: 106

gtgacagatt gttgttct                                                   18

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107

gtgacagagc gttgttct                                                   18

<210> SEQ ID NO 108
<211> LENGTH: 18
<212> TYPE: DNA
<213> ORGANISM: Artificial Sequence
<220> FEATURE:
<223> OTHER INFORMATION: Synthetic

<400> SEQUENCE: 108

gtgacagaaa gttgttct                                                   18

<210> SEQ ID NO 109
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: The residues at these positions are spacers
      with abasic sugar labels.

<400> SEQUENCE: 109

gtgacagann gttgttct                                                   18

<210> SEQ ID NO 110
<211> LENGTH: 18
<212> TYPE: DNA
<213> ORGANISM: Artificial Sequence
```

-continued

<220> FEATURE:
<223> OTHER INFORMATION: Synthetic

<400> SEQUENCE: 110
tcacgtgagc gtccatga 18

<210> SEQ ID NO 111
<211> LENGTH: 18
<212> TYPE: DNA
<213> ORGANISM: Artificial Sequence
<220> FEATURE:
<223> OTHER INFORMATION: Synthetic

<400> SEQUENCE: 111
cagaccgcgc acagcggg 18

<210> SEQ ID NO 112
<211> LENGTH: 17
<212> TYPE: DNA
<213> ORGANISM: Artificial Sequence
<220> FEATURE:
<223> OTHER INFORMATION: Synthetic

<400> SEQUENCE: 112
gctcacgata ccccgac 17

<210> SEQ ID NO 113
<211> LENGTH: 18
<212> TYPE: DNA
<213> ORGANISM: Artificial Sequence
<220> FEATURE:
<223> OTHER INFORMATION: Synthetic

<400> SEQUENCE: 113
tgctcacgat accccgac 18

<210> SEQ ID NO 114
<211> LENGTH: 18
<212> TYPE: DNA
<213> ORGANISM: Artificial Sequence
<220> FEATURE:
<223> OTHER INFORMATION: Synthetic

<400> SEQUENCE: 114
cgccgggcgc tcaacccc 18

<210> SEQ ID NO 115
<211> LENGTH: 18
<212> TYPE: DNA
<213> ORGANISM: Artificial Sequence
<220> FEATURE:
<223> OTHER INFORMATION: Synthetic

<400> SEQUENCE: 115
acagtcgggc ggttgttc 18

<210> SEQ ID NO 116
<211> LENGTH: 18
<212> TYPE: DNA
<213> ORGANISM: Artificial Sequence
<220> FEATURE:
<223> OTHER INFORMATION: Synthetic

<400> SEQUENCE: 116
cgggccccta tgtgggtc 18

-continued

<210> SEQ ID NO 117
<211> LENGTH: 18
<212> TYPE: DNA
<213> ORGANISM: Artificial Sequence
<220> FEATURE:
<223> OTHER INFORMATION: Synthetic

<400> SEQUENCE: 117
ctcacgtgta tctggtcc 18

<210> SEQ ID NO 118
<211> LENGTH: 16
<212> TYPE: DNA
<213> ORGANISM: Artificial Sequence
<220> FEATURE:
<223> OTHER INFORMATION: Synthetic

<400> SEQUENCE: 118
tgacagacgt tgttct 16

<210> SEQ ID NO 119
<211> LENGTH: 18
<212> TYPE: DNA
<213> ORGANISM: Artificial Sequence
<220> FEATURE:
<223> OTHER INFORMATION: Synthetic

<400> SEQUENCE: 119
ccccagcggc gttgttct 18

<210> SEQ ID NO 120
<211> LENGTH: 16
<212> TYPE: DNA
<213> ORGANISM: Artificial Sequence
<220> FEATURE:
<223> OTHER INFORMATION: Synthetic

<400> SEQUENCE: 120
gtgtcgtttg gaaccg 16

<210> SEQ ID NO 121
<211> LENGTH: 16
<212> TYPE: DNA
<213> ORGANISM: Artificial Sequence
<220> FEATURE:
<223> OTHER INFORMATION: Synthetic

<400> SEQUENCE: 121
tgggcgttgc ttgtgg 16

<210> SEQ ID NO 122
<211> LENGTH: 18
<212> TYPE: DNA
<213> ORGANISM: Artificial Sequence
<220> FEATURE:
<223> OTHER INFORMATION: Synthetic

<400> SEQUENCE: 122
ttgggcgttg cttgtggt 18

<210> SEQ ID NO 123
<211> LENGTH: 13
<212> TYPE: DNA
<213> ORGANISM: Artificial Sequence
<220> FEATURE:
<223> OTHER INFORMATION: Synthetic -continued

<400> SEQUENCE: 123
tccttgatcg cgg 13

<210> SEQ ID NO 124
<211> LENGTH: 16
<212> TYPE: DNA
<213> ORGANISM: Artificial Sequence
<220> FEATURE:
<223> OTHER INFORMATION: Synthetic

<400> SEQUENCE: 124
cttaaggtag gactac 16

<210> SEQ ID NO 125
<211> LENGTH: 16
<212> TYPE: DNA
<213> ORGANISM: Artificial Sequence
<220> FEATURE:
<223> OTHER INFORMATION: Synthetic

<400> SEQUENCE: 125
cattttccaa ccttaa 16

<210> SEQ ID NO 126
<211> LENGTH: 14
<212> TYPE: DNA
<213> ORGANISM: Artificial Sequence
<220> FEATURE:
<223> OTHER INFORMATION: Synthetic

<400> SEQUENCE: 126
taaggtagga ctac 14

<210> SEQ ID NO 127
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(16)
<223> OTHER INFORMATION: The residue at this position can be any nucleotide.

<400> SEQUENCE: 127
taaggtagga ctacnn 16

<210> SEQ ID NO 128
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(18)
<223> OTHER INFORMATION: The residue at this position can be any nucleotide.

<400> SEQUENCE: 128
taaggtagga ctacnnnn 18

<210> SEQ ID NO 129
<211> LENGTH: 20
<212> TYPE: DNA

-continued

<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(20)
<223> OTHER INFORMATION: The residue at this position can be any nucleotide.

<400> SEQUENCE: 129
taaggtagga ctacnnnnnn 20

<210> SEQ ID NO 130
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(22)
<223> OTHER INFORMATION: The residue at this position can be any nucleotide.

<400> SEQUENCE: 130
taaggtagga ctacnnnnnn nn 22

<210> SEQ ID NO 131
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(24)
<223> OTHER INFORMATION: The residue at this position can be any nucleotide.

<400> SEQUENCE: 131
taaggtagga ctacnnnnnn nnnn 24

<210> SEQ ID NO 132
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(26)
<223> OTHER INFORMATION: The residue at this position can be any nucleotide.

<400> SEQUENCE: 132
taaggtagga ctacnnnnnn nnnnnn 26

<210> SEQ ID NO 133
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(30)
<223> OTHER INFORMATION: The residue at this position can be any nucleotide.

<400> SEQUENCE: 133

-continued

```
taaggtagga ctacnnnnnn nnnnnnnnnn                                        30


<210> SEQ ID NO 134
<211> LENGTH: 14
<212> TYPE: DNA
<213> ORGANISM: Artificial Sequence
<220> FEATURE:
<223> OTHER INFORMATION: Synthetic

<400> SEQUENCE: 134

ttttccaacc ttaa                                                         14


<210> SEQ ID NO 135
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(22)
<223> OTHER INFORMATION: The residue at this position can be any
      nucleotide.

<400> SEQUENCE: 135

ttttccaacc ttaannnnnn nn                                                22


<210> SEQ ID NO 136
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(26)
<223> OTHER INFORMATION: The residue at this position can be any
      nucleotide.

<400> SEQUENCE: 136

ttttccaacc ttaannnnnn nnnnnn                                            26


<210> SEQ ID NO 137
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(14)
<223> OTHER INFORMATION: The residues in these positions are 2'-O-
      methylnucleotides.

<400> SEQUENCE: 137

gtagtcctac ctta                                                         14


<210> SEQ ID NO 138
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(14)
<223> OTHER INFORMATION: The residues in these positions are 2'-O-
      methyl nucleotides.

<400> SEQUENCE: 138
```

-continued ttaaggttgg aaaa 14

<210> SEQ ID NO 139
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(24)
<223> OTHER INFORMATION: The residue at this position can be any nucleotide.

<400> SEQUENCE: 139
ttttccaacc ttaannnnnn nnnn 24

<210> SEQ ID NO 140
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this 5' end has a tetrachlorofluorescein label.

<400> SEQUENCE: 140
ngcatcgttt tgggttctct t 21

<210> SEQ ID NO 141
<211> LENGTH: 987
<212> TYPE: RNA
<213> ORGANISM: Artificial Sequence
<220> FEATURE:
<223> OTHER INFORMATION: Synthetic

<400> SEQUENCE: 141
cacauuguuc ugaucaucug aagaucagcu auuagaagag aaagaucagu uaaguccuuu 60
ggaccugauc agcuugauac aagaacuacu gauuucaacu ucuuuggcuu aauucucucg 120
gaaacgauga aauauacaag uuauaucuug gcuuuucagc ucugcaucgu uuuggguucu 180
cuuggcuguu acugccagga cccauaugua caagaagcag aaaaccuuaa gaaauauuuu 240
aaugcagguc auucagaugu agcggauaau ggaacucuuu ucuuaggcau uuugaagaau 300
uggaaagagg agagugacag aaaaauaaug cagagccaaa uugucuccuu uuacuucaaa 360
cuuuuuaaaa acuuuaaaga ugaccagagc auccaaaaga guguggagac caucaaggaa 420
gacaugaaug ucaaguuuuu caauagcaac aaaaagaaac gagaugacuu cgaaaagcug 480
acuaauuauu cgguaacuga cuugaauguc caacgcaaag caauacauga acucauccaa 540
gugauggcug aacugucgcc agcagcuaaa acagggaagc gaaaaaggag ucagaugcug 600
uuucgagguc gaagagcauc ccaguaaugg uuguccugcc uacaauauuu gaauuuuaaa 660
ucuaaaucua uuuauuaaua uuuaacauua uuuauauggg gaauauauuu uuagacucau 720
caaucaaaua aguauuuaua auagcaacuu uuguguaaug aaaaugaaua ucuauuaaua 780
uauguauuau uuauaauucc uauauccugu gacugucuca cuuaauccuu uguuuucuga 840
cuaauuaggc aaggcuaugu gauuacaagg cuuuaucuca ggggccaacu aggcagccaa 900
ccuaagcaag aucccauggg uuguguguuu auuucacuug augauacaau gaacacuuau 960

-continued aagugaagug auacuaucca guuacua 987

<210> SEQ ID NO 142
<211> LENGTH: 47
<212> TYPE: RNA
<213> ORGANISM: Artificial Sequence
<220> FEATURE:
<223> OTHER INFORMATION: Synthetic

<400> SEQUENCE: 142
ggugguggug ggcgccgucg gugugggcaa gagugcgcug accaucc 47

<210> SEQ ID NO 143
<211> LENGTH: 589
<212> TYPE: RNA
<213> ORGANISM: Oryctolagus cuniculus

<400> SEQUENCE: 143
acacuugcuu uugacacaac uguguuuacu ugcaaucccc caaaacagac agaauggugc 60
aucuguccag ugaggagaag ucugcgguca cugcccugug gggcaaggug aauguggaag 120
aaguuggugg ugaggcccug ggcaggcugc ugguugucua cccauggacc cagagguucu 180
ucgaguccuu uggggaccug uccucugcaa augcuguuau gaacaauccu aaggugaagg 240
cucauggcaa gaaggugcug gcugccuuca gugagggucu gagucaccug gacaaccuca 300
aaggcaccuu ugcuaagcug agugaacugc acugugacaa gcugcacgug gauccugaga 360
acuucaggcu ccugggcaac gugcugguua uugugcuguc ucaucauuuu ggcaaagaau 420
ucacuccuca ggugcaggcu gccuaucaga agguggugge ugguguggcc aaugcccugg 480
cucacaaaua ccacugagau cuuuuucccu cugccaaaaa uuauggggac aucaugaagc 540
cccuugagca ucugacuucu ggcuaauaaa ggaaauuuau uuucauugc 589

<210> SEQ ID NO 144
<211> LENGTH: 2891
<212> TYPE: DNA
<213> ORGANISM: Homo sapiens

<400> SEQUENCE: 144
gcgccccagt cgacgctgag ctcctctgct actcagagtt gcaacctcag cctcgctatg 60
gctcccagca gcccccggcc cgcgctgccc gcactcctgg tcctgctcgg ggctctgttc 120
ccaggacctg gcaatgccca gacatctgtg tccccctcaa aagtcatcct gccccgggga 180
ggctccgtgc tggtgacatg cagcacctcc tgtgaccagc ccaagttgtt gggcatagag 240
accccgttgc ctaaaaagga gttgctcctg cctgggaaca accggaaggt gtatgaactg 300
agcaatgtgc aagaagatag ccaaccaatg tgctattcaa actgccctga tgggcagtca 360
acagctaaaa ccttcctcac cgtgtactgg actccagaac gggtggaact ggcacccctc 420
ccctcttggc agccagtggg caagaacctt accctacgct gccaggtgga gggtggggca 480
ccccgggcca acctcaccgt ggtgctgctc cgtggggaga aggagctgaa acgggagcca 540
gctgtggggg agcccgctga ggtcacgacc acggtgctgg tgaggagaga tcaccatgga 600
gccaatttct cgtgccgcac tgaactggac ctgcggcccc aagggctgga gctgtttgag 660
aacacctcgg ccccctacca gctccagacc tttgtcctgc cagcgactcc cccacaactt 720
gtcagccccc gggtcctaga ggtggacacg caggggaccg tggtctgttc cctggacggg 780
ctgttcccag tctcggaggc ccaggtccac ctggcactgg gggaccagag gttgaacccc 840
acagtcacct atggcaacga ctccttctcg gccaaggcct cagtcagtgt gaccgcagag 900

-continued

```
gacgagggca cccagcggct gacgtgtgca gtaatactgg ggaaccagag ccaggagaca    960
ctgcagacag tgaccatcta cagctttccg gcgcccaacg tgattctgac gaagccagag   1020
gtctcagaag ggaccgaggt gacagtgaag tgtgaggccc accctagagc caaggtgacg   1080
ctgaatgggg ttccagccca gccactgggc ccgagggccc agctcctgct gaaggccacc   1140
ccagaggaca acgggcgcag cttctcctgc tctgcaaccc tggaggtggc cggccagctt   1200
atacacaaga accagacccg ggagcttcgt gtcctgtatg gcccccgact ggacgagagg   1260
gattgtccgg gaaactggac gtggccagaa aattcccagc agactccaat gtgccaggct   1320
tgggggaacc cattgcccga gctcaagtgt ctaaaggatg gcactttccc actgcccatc   1380
ggggaatcag tgactgtcac tcgagatctt gagggcacct acctctgtcg ggccaggagc   1440
actcaagggg aggtcacccg cgaggtgacc gtgaatgtgc tctccccccg gtatgagatt   1500
gtcatcatca ctgtggtagc agccgcagtc ataatgggca ctgcaggcct cagcacgtac   1560
ctctataacc gccagcggaa gatcaagaaa tacagactac aacaggccca aaaagggacc   1620
cccatgaaac cgaacacaca agccacgcct ccctgaacct atcccgggac agggcctctt   1680
cctcggcctt cccatattgg tggcagtggt gccacactga acagagtgga agacatatgc   1740
catgcagcta cacctaccgg ccctgggacg ccggaggaca gggcattgtc ctcagtcaga   1800
tacaacagca tttggggcca tggtacctgc acacctaaaa cactaggcca cgcatctgat   1860
ctgtagtcac atgactaagc caagaggaag gagcaagact caagacatga ttgatggatg   1920
ttaaagtcta gcctgatgag aggggaagtg gtgggggaga catagcccca ccatgaggac   1980
atacaactgg gaaatactga aacttgctgc ctattgggta tgctgaggcc cacagactta   2040
cagaagaagt ggccctccat agacatgtgt agcatcaaaa cacaaaggcc cacacttcct   2100
gacggatgcc agcttgggca ctgctgtcta ctgaccccaa cccttgatga tatgtattta   2160
ttcatttgtt attttaccag ctatttattg agtgtctttt atgtaggcta aatgaacata   2220
ggtctctggc ctcacggagc tcccagtcca tgtcacattc aaggtcacca ggtacagttg   2280
tacaggttgt acactgcagg agagtgcctg gcaaaaagat caaatggggc tgggacttct   2340
cattggccaa cctgcctttc cccagaagga gtgatttttc tatcggcaca aaagcactat   2400
atggactggt aatggttcac aggttcagag attacccagt gaggccttat tcctcccttc   2460
cccccaaaac tgacaccttt gttagccacc tccccaccca catacatttc tgccagtgtt   2520
cacaatgaca ctcagcggtc atgtctggac atgagtgccc agggaatatg cccaagctat   2580
gccttgtcct cttgtcctgt ttgcatttca ctgggagctt gcactattgc agctccagtt   2640
tcctgcagtg atcagggtcc tgcaagcagt ggggaagggg gccaaggtat tggaggactc   2700
cctcccagct ttggaagggt catccgcgtg tgtgtgtgtg tgtatgtgta gacaagctct   2760
cgctctgtca cccaggctgg agtgcagtgg tgcaatcatg gttcactgca gtcttgacct   2820
tttgggctca agtgatcctc ccacctcagc ctcctgagta gctgggacca taggctcaca   2880
acaccacacc t                                                        2891
```

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145

-continued cccccaccac ttcccctctc 20

<210> SEQ ID NO 146
<211> LENGTH: 18
<212> TYPE: DNA
<213> ORGANISM: Artificial Sequence
<220> FEATURE:
<223> OTHER INFORMATION: Synthetic

<400> SEQUENCE: 146
tgggagccat agcgaggc 18

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
gaggagctca gcgtcgactg 20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
tgcccatcag ggcagtttga 20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
gcccaagctg gcatccgtca 20

<210> SEQ ID NO 150
<211> LENGTH: 18
<212> TYPE: DNA
<213> ORGANISM: Artificial Sequence
<220> FEATURE:
<223> OTHER INFORMATION: Synthetic

<400> SEQUENCE: 150
ctctctcaat ttggctct 18

<210> SEQ ID NO 151
<211> LENGTH: 33
<212> TYPE: DNA
<213> ORGANISM: Artificial Sequence
<220> FEATURE:
<223> OTHER INFORMATION: Synthetic

<400> SEQUENCE: 151
aaagttttta aaaagtttga agtaaaagga gaa 33

<210> SEQ ID NO 152
<211> LENGTH: 14
<212> TYPE: DNA
<213> ORGANISM: Artificial Sequence
<220> FEATURE:
<223> OTHER INFORMATION: Synthetic

<400> SEQUENCE: 152 ccccctttttg gggg 14

<210> SEQ ID NO 153
<211> LENGTH: 30
<212> TYPE: DNA
<213> ORGANISM: Artificial Sequence
<220> FEATURE:
<223> OTHER INFORMATION: Synthetic

<400> SEQUENCE: 153
ccctatcttt aaagttttta aaaagtttga 30

<210> SEQ ID NO 154
<211> LENGTH: 74
<212> TYPE: DNA
<213> ORGANISM: Artificial Sequence
<220> FEATURE:
<223> OTHER INFORMATION: Synthetic

<400> SEQUENCE: 154
ccctatcttt aaagttttta aaaagtttga cccccttttg ggggccctat ctttaaagtt 60
tttaaaaagt ttga 74

<210> SEQ ID NO 155
<211> LENGTH: 15
<212> TYPE: DNA
<213> ORGANISM: Artificial Sequence
<220> FEATURE:
<223> OTHER INFORMATION: Synthetic

<400> SEQUENCE: 155
cgcgcggaac gcgcg 15

<210> SEQ ID NO 156
<211> LENGTH: 16
<212> TYPE: DNA
<213> ORGANISM: Artificial Sequence
<220> FEATURE:
<223> OTHER INFORMATION: Synthetic

<400> SEQUENCE: 156
cccgggtttt cccggg 16

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
aggcgcacca atttggtgtt 20

<210> SEQ ID NO 158
<211> LENGTH: 1621
<212> TYPE: RNA
<213> ORGANISM: Human immunodeficiency virus

<400> SEQUENCE: 158
ggucucucug guuagaccag aucugagccu gggagcucuc uggcuaacua gggaacccac 60

-continued ugcuuaagcc ucaauaaagc uugccuugag ugcuucaagu agugugugcc cgucuguugu 120
gugacucugg uaacuagaga ucccucagac ccuuuuaguc aguguggaaa aucucuagca 180
guggcgcccg aacagggacc ugaaagcgaa agggaaacca gaggagcucu cucgacgcag 240
gacucggcuu gcugaagcgc gcacggcaag aggcgagggg cggcgacugg ugaguacgcc 300
aaaaauuuug acuagcggag gcuagaagga gagagauggg ugcgagagcg ucaguauuaa 360
gcgggggaga auuagaucga ugggaaaaaa uucgguuaag gccaggggga aagaaaaaau 420
auaaauuaaa acauauagua ugggcaagca gggagcuaga acgauucgca guuaauccug 480
gccuguuaga aacaucagaa ggcuguagac aaauacuggg acagcuacaa ccaucccuuc 540
agacaggauc agaagaacuu agaucauuau auaauacagu agcaacccuc uauugugugc 600
aucaaaggau agagauaaaa gacaccaagg aagcuuuaga caagauagag gaagagcaaa 660
acaaaaguaa gaaaaaagca cagcaagcag cagcugacac aggacacagc aaucagguca 720
gccaaaauua cccuauagug cagaacaucc aggggcaaau gguacaucag gccauaucac 780
cuagaacuuu aaaugcaugg guaaaaguag uagaagagaa ggcuuucagc ccagaaguga 840
uacccauguu uucagcauua ucagaaggag ccaccccaca agauuuaaac accaugcuaa 900
acacaguggg gggacaucaa gcagccaugc aaauguuaaa agagaccauc aaugaggaag 960
cugcagaaug ggauagagug cauccagugc augcagggcc uauugcacca ggccagauga 1020
gagaaccaag gggaagugac auagcaggaa cuacuaguac ccuucaggaa caaauaggau 1080
ggaugacaaa uaauccaccu aucccaguag gagaaauuua uaaaagaugg auaauccugg 1140
gauuaaauaa aauaguaaga auguauagcc cuaccagcau ucuggacaua agacaaggac 1200
caaaggaacc cuuuagagac uauguagacc gguucuauaa aacucuaaga gccgagcaag 1260
cuucacagga gguaaaaaau uggaugacag aaaccuuguu gguccaaaau gcgaacccag 1320
auuguaagac uauuuuaaaa gcauugggac cagcggcuac acuagaagaa augaugacag 1380
caugucaggg aguaggagga cccggccaua aggcaagagu uuuggcugaa gcaaugagcc 1440
aaguaacaaa uucagcuacc auaaugaugc agagaggcaa uuuuaggaac caaagaaaga 1500
uuguuaagug uuucaauugu ggcaaagaag ggcacacagc cagaaauugc agggccccua 1560
ggaaaaaggg cuguuggaaa uguggaaagg aaggacacca aaugaaagau uguacugaga 1620
g 1621

<210> SEQ ID NO 159
<211> LENGTH: 1771
<212> TYPE: RNA
<213> ORGANISM: Human immunodeficiency virus

<400> SEQUENCE: 159
agcuggacug ucaaugacau acagaaguua guggggaaau ugaauugggc aagucagauu 60
uacccaggga uuaaaguaag gcaauuaugu aaacuccuua gaggaaccaa agcacuaaca 120
gaaguaauac cacuaacaga agaagcagag cuagaacugg cagaaaacag agagauucua 180
aaagaaccag uacauggagu guauuaugac ccaucaaaag acuuaauagc agaaauacag 240
aagcaggggc aaggccaaug gacauaucaa auuuaucaag agccauuuaa aaaucugaaa 300
acaggaaaau augcaagaau gaggggugcc cacacuaaug auguaaaaca auuaacagag 360
gcagugcaaa aaauaaccac agaaagcaua guaauauggg gaaagacucc uaaauuuaaa 420
cugcccauac aaaaggaaac augggaaaca ugguggacag aguauuggca agccaccugg 480
auuccugagu gggaguuugu uaauaccccu cccuuaguga aauuauggua ccaguuagag 540

-continued

```
aaagaaccca uaguaggagc agaaaccuuc uauguagaug gggcagcuaa cagggagacu    600
aaauuaggaa aagcaggaua uguuacuaau agaggaagac aaaaaguugu cacccuaacu    660
gacacaacaa aucagaagac ugaguuacaa gcaauuuauc uagcuuugca ggauucggga    720
uuagaaguaa acauaguaac agacucacaa uaugcauuag gaaucauuca agcacaacca    780
gaucaaagug aaucagaguu agucaaucaa auaauagagc aguuaauaaa aaaggaaaag    840
gucuaucugg cauggguacc agcacacaaa ggaauuggag gaaaugaaca aguagauaaa    900
uuagucagug cuggaaucag gaaaguacua uuuuuagaug gaauagauaa ggcccaagau    960
gaacaugaga aauaucacag uaauuggaga gcaauggcua gugauuuuaa ccugccaccu   1020
guaguagcaa aagaaauagu agccagcugu gauaaauguc agcuaaaagg agaagccaug   1080
cauggacaag uagacuguag uccaggaaua uggcaacuag auuguacaca uuuagaagga   1140
aaaguuaucc ugguagcagu ucauguagcc aguggauaua uagaagcaga aguuauucca   1200
gcagaaacag ggcaggaaac agcauauuuu cuuuuaaaau uagcaggaag auggccagua   1260
aaaacaauac auacugacaa uggcagcaau uucaccggug cuacgguuag ggccgccugu   1320
ugguggggcgg gaaucaagca ggaauuugga auucccuaca auccccaaag ucaaggagua   1380
guagaaucua ugaauaaaga auuaaagaaa auuauaggac agguaagaga ucaggcugaa   1440
caucuuaaga cagcaguaca aauggcagua uucauccaca auuuuaaaag aaaagggggg   1500
auuggggggu acagugcagg ggaaagaaua guagacauaa uagcaacaga cauacaaacu   1560
aaagaauuac aaaaacaaau uacaaaaauu caaaauuuuc ggguuuauua cagggacagc   1620
agaaauccac uuuggaaagg accagcaaag cuccucugga aaggugaagg ggcaguagua   1680
auacaagaua auagugacau aaaaguagug ccaagaagaa aagcaaagau cauuagggau   1740
uauggaaaac agauggcagg ugaugauugu g                                   1771
```

```
<210> SEQ ID NO 160
<211> LENGTH: 54
<212> TYPE: DNA
<213> ORGANISM: Artificial Sequence
<220> FEATURE:
<223> OTHER INFORMATION: Synthetic

<400> SEQUENCE: 160

ggtaatacga ctcactatag gctggactgt caatgacata cagaagttag tggg           54


<210> SEQ ID NO 161
<211> LENGTH: 34
<212> TYPE: DNA
<213> ORGANISM: Artificial Sequence
<220> FEATURE:
<223> OTHER INFORMATION: Synthetic

<400> SEQUENCE: 161

cacaatcatc acctgccatc tgttttccat aatc                                 34


<210> SEQ ID NO 162
<211> LENGTH: 37
<212> TYPE: DNA
<213> ORGANISM: Artificial Sequence
<220> FEATURE:
<223> OTHER INFORMATION: Synthetic

<400> SEQUENCE: 162

ggtaatacga ctcactatag gtctctctgg ttagacc                              37
```

-continued

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
ctctcagtac aatctttcat 20

<210> SEQ ID NO 164
<211> LENGTH: 16
<212> TYPE: DNA
<213> ORGANISM: Artificial Sequence
<220> FEATURE:
<223> OTHER INFORMATION: Synthetic

<400> SEQUENCE: 164
aaaactactc cctgac 16

<210> SEQ ID NO 165
<211> LENGTH: 16
<212> TYPE: DNA
<213> ORGANISM: Artificial Sequence
<220> FEATURE:
<223> OTHER INFORMATION: Synthetic

<400> SEQUENCE: 165
aaaacctact ccctga 16

<210> SEQ ID NO 166
<211> LENGTH: 16
<212> TYPE: DNA
<213> ORGANISM: Artificial Sequence
<220> FEATURE:
<223> OTHER INFORMATION: Synthetic

<400> SEQUENCE: 166
aaaatcctac tccctg 16

<210> SEQ ID NO 167
<211> LENGTH: 16
<212> TYPE: DNA
<213> ORGANISM: Artificial Sequence
<220> FEATURE:
<223> OTHER INFORMATION: Synthetic

<400> SEQUENCE: 167
aaaactccta ctccct 16

<210> SEQ ID NO 168
<211> LENGTH: 16
<212> TYPE: DNA
<213> ORGANISM: Artificial Sequence
<220> FEATURE:
<223> OTHER INFORMATION: Synthetic

<400> SEQUENCE: 168
aaaacctcct actccc 16

<210> SEQ ID NO 169
<211> LENGTH: 16
<212> TYPE: DNA
<213> ORGANISM: Artificial Sequence
<220> FEATURE:
<223> OTHER INFORMATION: Synthetic -continued

<400> SEQUENCE: 169
aaaatcctcc tactcc 16

<210> SEQ ID NO 170
<211> LENGTH: 16
<212> TYPE: DNA
<213> ORGANISM: Artificial Sequence
<220> FEATURE:
<223> OTHER INFORMATION: Synthetic

<400> SEQUENCE: 170
aaaagtcctc ctactc 16

<210> SEQ ID NO 171
<211> LENGTH: 16
<212> TYPE: DNA
<213> ORGANISM: Artificial Sequence
<220> FEATURE:
<223> OTHER INFORMATION: Synthetic

<400> SEQUENCE: 171
aaaaggtcct cctact 16

<210> SEQ ID NO 172
<211> LENGTH: 16
<212> TYPE: DNA
<213> ORGANISM: Artificial Sequence
<220> FEATURE:
<223> OTHER INFORMATION: Synthetic

<400> SEQUENCE: 172
aaaagggtcc tcctac 16

<210> SEQ ID NO 173
<211> LENGTH: 16
<212> TYPE: DNA
<213> ORGANISM: Artificial Sequence
<220> FEATURE:
<223> OTHER INFORMATION: Synthetic

<400> SEQUENCE: 173
aaaacgggtc ctccta 16

<210> SEQ ID NO 174
<211> LENGTH: 15
<212> TYPE: DNA
<213> ORGANISM: Artificial Sequence
<220> FEATURE:
<223> OTHER INFORMATION: Synthetic

<400> SEQUENCE: 174
aaaacgggtc ctcct 15

<210> SEQ ID NO 175
<211> LENGTH: 15
<212> TYPE: DNA
<213> ORGANISM: Artificial Sequence
<220> FEATURE:
<223> OTHER INFORMATION: Synthetic

<400> SEQUENCE: 175
aaaaccgggt cctcc 15

<210> SEQ ID NO 176

-continued

<211> LENGTH: 15
<212> TYPE: DNA
<213> ORGANISM: Artificial Sequence
<220> FEATURE:
<223> OTHER INFORMATION: Synthetic

<400> SEQUENCE: 176
aaaagccggg tcctc 15

<210> SEQ ID NO 177
<211> LENGTH: 25
<212> TYPE: DNA
<213> ORGANISM: Artificial Sequence
<220> FEATURE:
<223> OTHER INFORMATION: Synthetic

<400> SEQUENCE: 177
ctcttgcctt atggccgggt cctca 25

<210> SEQ ID NO 178
<211> LENGTH: 25
<212> TYPE: DNA
<213> ORGANISM: Artificial Sequence
<220> FEATURE:
<223> OTHER INFORMATION: Synthetic

<400> SEQUENCE: 178
actcttgcct tatggccggg tccta 25

<210> SEQ ID NO 179
<211> LENGTH: 25
<212> TYPE: DNA
<213> ORGANISM: Artificial Sequence
<220> FEATURE:
<223> OTHER INFORMATION: Synthetic

<400> SEQUENCE: 179
aactcttgcc ttatggccgg gtcca 25

<210> SEQ ID NO 180
<211> LENGTH: 25
<212> TYPE: DNA
<213> ORGANISM: Artificial Sequence
<220> FEATURE:
<223> OTHER INFORMATION: Synthetic

<400> SEQUENCE: 180
aaactcttgc cttatggccg ggtca 25

<210> SEQ ID NO 181
<211> LENGTH: 25
<212> TYPE: DNA
<213> ORGANISM: Artificial Sequence
<220> FEATURE:
<223> OTHER INFORMATION: Synthetic

<400> SEQUENCE: 181
aaaactcttg ccttatggcc gggta 25

<210> SEQ ID NO 182
<211> LENGTH: 25
<212> TYPE: DNA
<213> ORGANISM: Artificial Sequence
<220> FEATURE:
<223> OTHER INFORMATION: Synthetic

<400> SEQUENCE: 182

-continued caaaactctt gccttatggc cggga 25

<210> SEQ ID NO 183
<211> LENGTH: 25
<212> TYPE: DNA
<213> ORGANISM: Artificial Sequence
<220> FEATURE:
<223> OTHER INFORMATION: Synthetic

<400> SEQUENCE: 183
ccaaaactct tgccttatgg ccggc 25

<210> SEQ ID NO 184
<211> LENGTH: 25
<212> TYPE: DNA
<213> ORGANISM: Artificial Sequence
<220> FEATURE:
<223> OTHER INFORMATION: Synthetic

<400> SEQUENCE: 184
gccaaaactc ttgccttatg gccgc 25

<210> SEQ ID NO 185
<211> LENGTH: 25
<212> TYPE: DNA
<213> ORGANISM: Artificial Sequence
<220> FEATURE:
<223> OTHER INFORMATION: Synthetic

<400> SEQUENCE: 185
agccaaaact cttgccttat ggccc 25

<210> SEQ ID NO 186
<211> LENGTH: 25
<212> TYPE: DNA
<213> ORGANISM: Artificial Sequence
<220> FEATURE:
<223> OTHER INFORMATION: Synthetic

<400> SEQUENCE: 186
cagccaaaac tcttgcctta tggca 25

<210> SEQ ID NO 187
<211> LENGTH: 25
<212> TYPE: DNA
<213> ORGANISM: Artificial Sequence
<220> FEATURE:
<223> OTHER INFORMATION: Synthetic

<400> SEQUENCE: 187
tcagccaaaa ctcttgcctt atgga 25

<210> SEQ ID NO 188
<211> LENGTH: 28
<212> TYPE: DNA
<213> ORGANISM: Artificial Sequence
<220> FEATURE:
<223> OTHER INFORMATION: Synthetic

<400> SEQUENCE: 188
tcgttcagcc aaaactcttg ccttatgc 28

<210> SEQ ID NO 189
<211> LENGTH: 24
<212> TYPE: DNA

-continued

<213> ORGANISM: Artificial Sequence
<220> FEATURE:
<223> OTHER INFORMATION: Synthetic

<400> SEQUENCE: 189
ccgtcacgcc tcctcctact ccct 24

<210> SEQ ID NO 190
<211> LENGTH: 16
<212> TYPE: DNA
<213> ORGANISM: Artificial Sequence
<220> FEATURE:
<223> OTHER INFORMATION: Synthetic

<400> SEQUENCE: 190
agggagtagg aggagg 16

<210> SEQ ID NO 191
<211> LENGTH: 13
<212> TYPE: DNA
<213> ORGANISM: Artificial Sequence
<220> FEATURE:
<223> OTHER INFORMATION: Synthetic

<400> SEQUENCE: 191
ccgtcacgcc tcc 13

<210> SEQ ID NO 192
<211> LENGTH: 28
<212> TYPE: DNA
<213> ORGANISM: Artificial Sequence
<220> FEATURE:
<223> OTHER INFORMATION: Synthetic

<400> SEQUENCE: 192
cggaagaagc agttggaggc gtgacggt 28

<210> SEQ ID NO 193
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: The residue at this position is a cy3
linker group.

<400> SEQUENCE: 193
caacngcttc ctccg 15

<210> SEQ ID NO 194
<211> LENGTH: 19
<212> TYPE: DNA
<213> ORGANISM: Artificial Sequence
<220> FEATURE:
<223> OTHER INFORMATION: Synthetic

<400> SEQUENCE: 194
aaaatccctg taataaacc 19

<210> SEQ ID NO 195
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 195
aaaagtccct gtaataaacc 20

<210> SEQ ID NO 196
<211> LENGTH: 26
<212> TYPE: DNA
<213> ORGANISM: Artificial Sequence
<220> FEATURE:
<223> OTHER INFORMATION: Synthetic

<400> SEQUENCE: 196
tcctttccaa agtggatttc tgctga 26

<210> SEQ ID NO 197
<211> LENGTH: 25
<212> TYPE: DNA
<213> ORGANISM: Artificial Sequence
<220> FEATURE:
<223> OTHER INFORMATION: Synthetic

<400> SEQUENCE: 197
tcctttccaa agtggatttc tgctc 25

<210> SEQ ID NO 198
<211> LENGTH: 53
<212> TYPE: DNA
<213> ORGANISM: Artificial Sequence
<220> FEATURE:
<223> OTHER INFORMATION: Synthetic

<400> SEQUENCE: 198
cgaaaatttt gaatttttgt aatttgtttt tgtaattctt tagtttgtat gtc 53

<210> SEQ ID NO 199
<211> LENGTH: 21
<212> TYPE: DNA
<213> ORGANISM: Artificial Sequence
<220> FEATURE:
<223> OTHER INFORMATION: Synthetic

<400> SEQUENCE: 199
aaaactttcc aaagtggatt t 21

<210> SEQ ID NO 200
<211> LENGTH: 18
<212> TYPE: DNA
<213> ORGANISM: Artificial Sequence
<220> FEATURE:
<223> OTHER INFORMATION: Synthetic

<400> SEQUENCE: 200
aaaacctttc caaagtgg 18

<210> SEQ ID NO 201
<211> LENGTH: 21
<212> TYPE: DNA
<213> ORGANISM: Artificial Sequence
<220> FEATURE:
<223> OTHER INFORMATION: Synthetic

<400> SEQUENCE: 201
ccagaggagc tttgctggtc a 21

-continued

<210> SEQ ID NO 202
<211> LENGTH: 21
<212> TYPE: DNA
<213> ORGANISM: Artificial Sequence
<220> FEATURE:
<223> OTHER INFORMATION: Synthetic

<400> SEQUENCE: 202
tccagaggag ctttgctggt a 21

<210> SEQ ID NO 203
<211> LENGTH: 24
<212> TYPE: DNA
<213> ORGANISM: Artificial Sequence
<220> FEATURE:
<223> OTHER INFORMATION: Synthetic

<400> SEQUENCE: 203
ctgctgtccc tgtaataaac ccga 24

<210> SEQ ID NO 204
<211> LENGTH: 27
<212> TYPE: DNA
<213> ORGANISM: Artificial Sequence
<220> FEATURE:
<223> OTHER INFORMATION: Synthetic

<400> SEQUENCE: 204
atttctgctg tccctgtaat aaacccg 27

<210> SEQ ID NO 205
<211> LENGTH: 16
<212> TYPE: DNA
<213> ORGANISM: Artificial Sequence
<220> FEATURE:
<223> OTHER INFORMATION: Synthetic

<400> SEQUENCE: 205
aaaacttcac ctttcc 16

<210> SEQ ID NO 206
<211> LENGTH: 16
<212> TYPE: DNA
<213> ORGANISM: Artificial Sequence
<220> FEATURE:
<223> OTHER INFORMATION: Synthetic

<400> SEQUENCE: 206
aaaaccttca cctttc 16

<210> SEQ ID NO 207
<211> LENGTH: 14
<212> TYPE: DNA
<213> ORGANISM: Artificial Sequence
<220> FEATURE:
<223> OTHER INFORMATION: Synthetic

<400> SEQUENCE: 207
aaaaactgcc cctt 14

<210> SEQ ID NO 208
<211> LENGTH: 14
<212> TYPE: DNA
<213> ORGANISM: Artificial Sequence
<220> FEATURE:
<223> OTHER INFORMATION: Synthetic -continued

<400> SEQUENCE: 208
aaaatactgc ccct 14

<210> SEQ ID NO 209
<211> LENGTH: 36
<212> TYPE: DNA
<213> ORGANISM: Artificial Sequence
<220> FEATURE:
<223> OTHER INFORMATION: Synthetic

<400> SEQUENCE: 209
ttttatgtca ctattatctt gtattactac tgccca 36

<210> SEQ ID NO 210
<211> LENGTH: 36
<212> TYPE: DNA
<213> ORGANISM: Artificial Sequence
<220> FEATURE:
<223> OTHER INFORMATION: Synthetic

<400> SEQUENCE: 210
cttttatgtc actattatct tgtattacta ctgcca 36

<210> SEQ ID NO 211
<211> LENGTH: 37
<212> TYPE: DNA
<213> ORGANISM: Artificial Sequence
<220> FEATURE:
<223> OTHER INFORMATION: Synthetic

<400> SEQUENCE: 211
ggcactactt ttatgtcact attatcttgt attactc 37

<210> SEQ ID NO 212
<211> LENGTH: 36
<212> TYPE: DNA
<213> ORGANISM: Artificial Sequence
<220> FEATURE:
<223> OTHER INFORMATION: Synthetic

<400> SEQUENCE: 212
ggcactactt ttatgtcact attatcttgt attaca 36

<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
agaggagctt tgctggtcct 20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
cagaggagct ttgctggtcc 20

<210> SEQ ID NO 215
<211> LENGTH: 18

-continued

<212> TYPE: DNA
<213> ORGANISM: Artificial Sequence
<220> FEATURE:
<223> OTHER INFORMATION: Synthetic

<400> SEQUENCE: 215
cacctttcca gaggagct 18

<210> SEQ ID NO 216
<211> LENGTH: 19
<212> TYPE: DNA
<213> ORGANISM: Artificial Sequence
<220> FEATURE:
<223> OTHER INFORMATION: Synthetic

<400> SEQUENCE: 216
tcacctttcc agaggagct 19

<210> SEQ ID NO 217
<211> LENGTH: 14
<212> TYPE: DNA
<213> ORGANISM: Artificial Sequence
<220> FEATURE:
<223> OTHER INFORMATION: Synthetic

<400> SEQUENCE: 217 aaaaccccctg cact 14

<210> SEQ ID NO 218
<211> LENGTH: 23
<212> TYPE: DNA
<213> ORGANISM: Artificial Sequence
<220> FEATURE:
<223> OTHER INFORMATION: Synthetic

<400> SEQUENCE: 218
aaaacccttt tcttttaaaa ttg 23

<210> SEQ ID NO 219
<211> LENGTH: 16
<212> TYPE: DNA
<213> ORGANISM: Artificial Sequence
<220> FEATURE:
<223> OTHER INFORMATION: Synthetic

<400> SEQUENCE: 219
aaaattcttt cccctg 16

<210> SEQ ID NO 220
<211> LENGTH: 25
<212> TYPE: DNA
<213> ORGANISM: Artificial Sequence
<220> FEATURE:
<223> OTHER INFORMATION: Synthetic

<400> SEQUENCE: 220
atatatccct tttcttttaa aattg 25

<210> SEQ ID NO 221
<211> LENGTH: 35
<212> TYPE: DNA
<213> ORGANISM: Artificial Sequence
<220> FEATURE:
<223> OTHER INFORMATION: Synthetic

<400> SEQUENCE: 221

-continued tgtatgtctg ttgctattat gtctactatt cttta 35

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
cactgtaccc cccaatccca 20

<210> SEQ ID NO 223
<211> LENGTH: 37
<212> TYPE: DNA
<213> ORGANISM: Artificial Sequence
<220> FEATURE:
<223> OTHER INFORMATION: Synthetic

<400> SEQUENCE: 223
ctttagtttg tatgtctgtt gctattatgt ctactac 37

<210> SEQ ID NO 224
<211> LENGTH: 19
<212> TYPE: DNA
<213> ORGANISM: Artificial Sequence
<220> FEATURE:
<223> OTHER INFORMATION: Synthetic

<400> SEQUENCE: 224 gtaccccca atcccccct 19

<210> SEQ ID NO 225
<211> LENGTH: 30
<212> TYPE: DNA
<213> ORGANISM: Artificial Sequence
<220> FEATURE:
<223> OTHER INFORMATION: Synthetic

<400> SEQUENCE: 225
tggatgaata ctgccatttg tactgctgtc 30

<210> SEQ ID NO 226
<211> LENGTH: 22
<212> TYPE: DNA
<213> ORGANISM: Artificial Sequence
<220> FEATURE:
<223> OTHER INFORMATION: Synthetic

<400> SEQUENCE: 226
ccgtcacgcc tccccctgca ct 22

<210> SEQ ID NO 227
<211> LENGTH: 16
<212> TYPE: DNA
<213> ORGANISM: Artificial Sequence
<220> FEATURE:
<223> OTHER INFORMATION: Synthetic

<400> SEQUENCE: 227
agtgcagggg gcggcg 16

<210> SEQ ID NO 228
<211> LENGTH: 24
<212> TYPE: DNA
<213> ORGANISM: Artificial Sequence -continued

```
<220> FEATURE:
<223> OTHER INFORMATION: Synthetic

<400> SEQUENCE: 228

ccgtcacgcc tccttcacct ttcc                                            24

<210> SEQ ID NO 229
<211> LENGTH: 17
<212> TYPE: DNA
<213> ORGANISM: Artificial Sequence
<220> FEATURE:
<223> OTHER INFORMATION: Synthetic

<400> SEQUENCE: 229

ggaaaggtga aggaggc                                                    17

<210> SEQ ID NO 230
<211> LENGTH: 18
<212> TYPE: DNA
<213> ORGANISM: Artificial Sequence
<220> FEATURE:
<223> OTHER INFORMATION: Synthetic

<400> SEQUENCE: 230

cctgcttatc acaatgaa                                                   18

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231

acatgcactt gctacgaaac                                                 20

<210> SEQ ID NO 232
<211> LENGTH: 461
<212> TYPE: RNA
<213> ORGANISM: Artificial Sequence
<220> FEATURE:
<223> OTHER INFORMATION: Synthetic

<400> SEQUENCE: 232

ccugcuuauc acaaugaaug uucuccuggg cagcguugug aucuuugcca ccuucgugac      60

uuuaugcaau gcaucaugcu auuucauacc uaaugaggga guuccaggag auucaaccag     120

gaaaugcaug gaucucaaag gaaacaaaca cccaauaaac ucggaguggc agacugacaa     180

cugugagaca ugcacuugcu acgaaacaga aauuucaugu ugcacccuug uuucuacacc     240

uguggguuau gacaaagaca acugccaaag aaucuucaag aaggaggacu gcaaguauau     300

cgugguggag aagaaggacc caaaaaagac cuguucuguc agugaaugga uaaucuaaug     360

ugcuucuagu aggcacaggg cucccaggcc aggccucauu cuccucuggc cucuaauagu     420

caaugauugu guagccaugc cuaucaguaa aaagauuuuu g                        461

<210> SEQ ID NO 233
<211> LENGTH: 15
<212> TYPE: DNA
<213> ORGANISM: Artificial Sequence
<220> FEATURE:
<223> OTHER INFORMATION: Synthetic

<400> SEQUENCE: 233
```

-continued

```
ccgccaccaa aatgc                                                  15


<210> SEQ ID NO 234
<211> LENGTH: 15
<212> TYPE: DNA
<213> ORGANISM: Artificial Sequence
<220> FEATURE:
<223> OTHER INFORMATION: Synthetic

<400> SEQUENCE: 234

gctggaagat ggacg                                                  15


<210> SEQ ID NO 235
<211> LENGTH: 449
<212> TYPE: RNA
<213> ORGANISM: Artificial Sequence
<220> FEATURE:
<223> OTHER INFORMATION: Synthetic

<400> SEQUENCE: 235

ccgccaccaa aaugcagauu uucgugaaaa cccuuacggg gaagaccauc acccucgagg     60

uugaacccuc ggauacgaua gaaaauguaa aggccaagau ccaggauaag gaaggaauuc    120

cuccugacag cagagacuga ucuuugcugg caagcagcug gaagauggac guacuuuguc    180

ugacuacaau auucaaaagg agucuacucu ucaucuugug uugagacuuc gugguggugc    240

uaagaaaagg aagaagaagu cuuacaccac ucccaagaag aauaagcaca agagaaagaa    300

gguuaagcug gcuguccuga aauauuauaa gguggaugag aauggcaaaa uuagucgccu    360

ucgucgagag ugcccuucug augaaugugg ugcuggggug uuuauggcaa gucacuuuga    420

cagacauuau uguggcaaau guugucuga                                     449


<210> SEQ ID NO 236
<211> LENGTH: 24
<212> TYPE: DNA
<213> ORGANISM: Artificial Sequence
<220> FEATURE:
<223> OTHER INFORMATION: Synthetic

<400> SEQUENCE: 236

gggacactcc accatgaatc actc                                          24


<210> SEQ ID NO 237
<211> LENGTH: 24
<212> TYPE: DNA
<213> ORGANISM: Artificial Sequence
<220> FEATURE:
<223> OTHER INFORMATION: Synthetic

<400> SEQUENCE: 237

cgggagagcc atagtggtct gcgg                                          24


<210> SEQ ID NO 238
<211> LENGTH: 18
<212> TYPE: DNA
<213> ORGANISM: Artificial Sequence
<220> FEATURE:
<223> OTHER INFORMATION: Synthetic

<400> SEQUENCE: 238

atttgggcgt gccccgc                                                  18


<210> SEQ ID NO 239
<211> LENGTH: 19
```

-continued

<212> TYPE: DNA
<213> ORGANISM: Artificial Sequence
<220> FEATURE:
<223> OTHER INFORMATION: Synthetic

<400> SEQUENCE: 239
gaccgggtcc tttcttgga 19

<210> SEQ ID NO 240
<211> LENGTH: 328
<212> TYPE: RNA
<213> ORGANISM: Hepatitis C virus

<400> SEQUENCE: 240
gggacacucc accaugaauc acuccccugu gaggaacuac ugucuucacg cagaaagcgu 60
cuagccaugg cguuaguaug agugucgugc agccuccagg accccccuc ccgggagagc 120 cauaguggúc ugcggaaccg gugaguacac cggaauugcc aggacgaccg gguccuuucu 180
uggauaaacc cgcucaaugc cuggagauuu gggcgugccc ccgcaagacu gcuagccgag 240
uaguguuggg ucgcgaaagg ccuuguggua cugccugaua gggugcuugc gagugccccg 300
ggaggucucg uagaccgugc accaugag 328

<210> SEQ ID NO 241
<211> LENGTH: 24
<212> TYPE: DNA
<213> ORGANISM: Artificial Sequence
<220> FEATURE:
<223> OTHER INFORMATION: Synthetic

<400> SEQUENCE: 241
gggacactcc accatagatc actc 24

<210> SEQ ID NO 242
<211> LENGTH: 328
<212> TYPE: RNA
<213> ORGANISM: Hepatitis C virus

<400> SEQUENCE: 242
gggacacucc accauagauc acuccccugu gaggaacuac ugucuucacg cagaaagcgu 60
cuagccaugg cguuaguaug agugucgugc agccuccagg accccccuc ccgggagagc 120 cauagugguc ugcggaaccg gugaguacac cggaauugcc aggacgaccg gguccuuucu 180
uggaucaacc cgcucaaugc cuggagauuu gggcgugccc ccgcgagacu gcuagccgag 240
uaguguuggg ucgcgaaagg ccuuguggua cugccugaua gggugcuugc gagugccccg 300
ggaggucucg uagaccgugc accaugag 328

<210> SEQ ID NO 243
<211> LENGTH: 328
<212> TYPE: RNA
<213> ORGANISM: Hepatitis C virus

<400> SEQUENCE: 243
gggacacucc accaugaauc acuccccugu gaggaacuac ugucuucacg cagaaagcgu 60
cuagccaugg cguuaguaug agugucguac agccuccagg cccccccuc ccgggagagc 120 cauagugguc ugcggaaccg gugaguacac cggaauugcc gggaagacug gguccuuucu 180
uggauaaacc cacucuaugc ccggccauuu gggcgugccc ccgcaagacu gcuagccgag 240
uagcguuggg uugcgaaagg ccuuguggua cugccugaua gggugcuugc gagugccccg 300

```
ggaggucucg uagaccgugc accaugag                                      328
```

<210> SEQ ID NO 244
<211> LENGTH: 24
<212> TYPE: DNA
<213> ORGANISM: Artificial Sequence
<220> FEATURE:
<223> OTHER INFORMATION: Synthetic

<400> SEQUENCE: 244

```
gggacactcc accatggatc actc                                           24
```

<210> SEQ ID NO 245
<211> LENGTH: 328
<212> TYPE: RNA
<213> ORGANISM: Hepatitis C virus

<400> SEQUENCE: 245

```
gggacacucc accauggauc acuccccugu gaggaacuuc ugucuucacg cggaaagcgc    60
cuagccaugg cguuaguacg agugucgugc agccuccagg ccccccccuc ccgggagagc   120
cauagugguc ugcggaaccg gugaguacac cggaaucgcu ggggugaccg gguccuuucu   180
uggaacaacc cgcucaauac ccagaaauuu gggcgugccc ccgcgagauc acuagccgag   240
uaguguuggg ucgcgaaagg ccuugugguu cugccugaua gggugcuugc gagugccccg   300
ggaggucucg uagaccgugc accaugag                                     328
```

<210> SEQ ID NO 246
<211> LENGTH: 26
<212> TYPE: DNA
<213> ORGANISM: Artificial Sequence
<220> FEATURE:
<223> OTHER INFORMATION: Synthetic

<400> SEQUENCE: 246

```
acaagggaag agagatgagg aaccag                                         26
```

<210> SEQ ID NO 247
<211> LENGTH: 22
<212> TYPE: DNA
<213> ORGANISM: Artificial Sequence
<220> FEATURE:
<223> OTHER INFORMATION: Synthetic

<400> SEQUENCE: 247

```
tttgccttct catcaccaat gg                                             22
```

<210> SEQ ID NO 248
<211> LENGTH: 17
<212> TYPE: DNA
<213> ORGANISM: Artificial Sequence
<220> FEATURE:
<223> OTHER INFORMATION: Synthetic

<400> SEQUENCE: 248

```
aagggaagag agatgag                                                   17
```

<210> SEQ ID NO 249
<211> LENGTH: 17
<212> TYPE: DNA
<213> ORGANISM: Artificial Sequence
<220> FEATURE:
<223> OTHER INFORMATION: Synthetic

<400> SEQUENCE: 249

-continued aggagtttgc aagaaac 17

<210> SEQ ID NO 250
<211> LENGTH: 13
<212> TYPE: DNA
<213> ORGANISM: Artificial Sequence
<220> FEATURE:
<223> OTHER INFORMATION: Synthetic

<400> SEQUENCE: 250
ggtgctgtcc tgg 13

<210> SEQ ID NO 251
<211> LENGTH: 19
<212> TYPE: DNA
<213> ORGANISM: Artificial Sequence
<220> FEATURE:
<223> OTHER INFORMATION: Synthetic

<400> SEQUENCE: 251
cagttttgga tctttgatg 19

<210> SEQ ID NO 252
<211> LENGTH: 13
<212> TYPE: DNA
<213> ORGANISM: Artificial Sequence
<220> FEATURE:
<223> OTHER INFORMATION: Synthetic

<400> SEQUENCE: 252
aggacgctga gga 13

<210> SEQ ID NO 253
<211> LENGTH: 21
<212> TYPE: DNA
<213> ORGANISM: Artificial Sequence
<220> FEATURE:
<223> OTHER INFORMATION: Synthetic

<400> SEQUENCE: 253
aacaagtcaa aatcttctat g 21

<210> SEQ ID NO 254
<211> LENGTH: 17
<212> TYPE: DNA
<213> ORGANISM: Artificial Sequence
<220> FEATURE:
<223> OTHER INFORMATION: Synthetic

<400> SEQUENCE: 254
caatactgca gatggag 17

<210> SEQ ID NO 255
<211> LENGTH: 15
<212> TYPE: DNA
<213> ORGANISM: Artificial Sequence
<220> FEATURE:
<223> OTHER INFORMATION: Synthetic

<400> SEQUENCE: 255
aagccaggta ttgca 15

<210> SEQ ID NO 256
<211> LENGTH: 18
<212> TYPE: DNA

-continued

<213> ORGANISM: Artificial Sequence
<220> FEATURE:
<223> OTHER INFORMATION: Synthetic

<400> SEQUENCE: 256
ctattgtttc tgcacaga 18

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
aaatgaagaa gaacatagga 20

<210> SEQ ID NO 258
<211> LENGTH: 15
<212> TYPE: DNA
<213> ORGANISM: Artificial Sequence
<220> FEATURE:
<223> OTHER INFORMATION: Synthetic

<400> SEQUENCE: 258
ggtcaagcca tcaga 15

<210> SEQ ID NO 259
<211> LENGTH: 1024
<212> TYPE: RNA
<213> ORGANISM: Homo sapiens

<400> SEQUENCE: 259
acaagggaag agagaugagg aaccagagcu uguagaaacc acuuuaauca uauccaggag 60
uuugcaagaa acaggugcuu aacacuaauu caccuccuga acaagaaaaa ugggcuguga 120
ccggaacugu gggcucaucg cuggggcugu cauuggugcu guccuggcug uguuuggagg 180
uauucuaaug ccaguuggag accugcuuau ccagaagaca auuaaaaagc aaguuguccu 240
cgaagaaggu acaauugcuu uuaaaaauug gguuaaaaca ggcacagaag uuuacagaca 300
guuuuggauc uuugaugugc aaaauccaca ggaagugaug augaacagca gcaacauuca 360
aguuaagcaa agagguccuu auacguacag aguucguuuu cuagccaagg aaaauguaac 420
ccaggacgcu gaggacaaca cagucucuuu ccugcagccc aauggugcca ucuucgaacc 480
uucacuauca guuggaacag aggcugacaa cuucacaguu cucaaucugg cuguggcagc 540
ugcaucccau aucuaucaaa aucaauuugu ucaaaugauc cucaauucac uuauuaacaa 600
gucaaaaucu ucuauguucc aagucagaac uuugagagaa cuguuauggg gcuauaggga 660
uccauuuuug aguuugguuc cguacccugu uacuacuaca guuggucugu uuuauccuua 720
caacaauacu gcagauggag uuuauaaagu uuucaaugga aaagauaaca uaaguaaagu 780
ugccauaauc gacacauaua aagguaaaag gaaucugucc uauugggaaa gucacugcga 840
caugauuaau gguacagaug cagccucauu uccaccuuuu guugagaaaa gccagguauu 900
gcaguucuuu ucuucugaua uuugcagguc aaucuaugcu guauuugaau ccgacguuaa 960
ucugaaagga aucccugugu auagauucgu ucuuccaucc aaggccuuug ccucuccagu 1020
ugaa 1024

<210> SEQ ID NO 260
<211> LENGTH: 19

-continued

<212> TYPE: DNA
<213> ORGANISM: Artificial Sequence
<220> FEATURE:
<223> OTHER INFORMATION: Synthetic

<400> SEQUENCE: 260
atggggtttg ttaaagttg 19

<210> SEQ ID NO 261
<211> LENGTH: 26
<212> TYPE: DNA
<213> ORGANISM: Artificial Sequence
<220> FEATURE:
<223> OTHER INFORMATION: Synthetic

<400> SEQUENCE: 261
gctgggttta gctctcagca gcccgc 26

<210> SEQ ID NO 262
<211> LENGTH: 18
<212> TYPE: DNA
<213> ORGANISM: Artificial Sequence
<220> FEATURE:
<223> OTHER INFORMATION: Synthetic

<400> SEQUENCE: 262
atggggtttg ttaaagtt 18

<210> SEQ ID NO 263
<211> LENGTH: 15
<212> TYPE: DNA
<213> ORGANISM: Artificial Sequence
<220> FEATURE:
<223> OTHER INFORMATION: Synthetic

<400> SEQUENCE: 263
gaagacgacg agagg 15

<210> SEQ ID NO 264
<211> LENGTH: 17
<212> TYPE: DNA
<213> ORGANISM: Artificial Sequence
<220> FEATURE:
<223> OTHER INFORMATION: Synthetic

<400> SEQUENCE: 264
ggatgatagt tcgtgtg 17

<210> SEQ ID NO 265
<211> LENGTH: 16
<212> TYPE: DNA
<213> ORGANISM: Artificial Sequence
<220> FEATURE:
<223> OTHER INFORMATION: Synthetic

<400> SEQUENCE: 265
gctgcagcat attgta 16

<210> SEQ ID NO 266
<211> LENGTH: 16
<212> TYPE: DNA
<213> ORGANISM: Artificial Sequence
<220> FEATURE:
<223> OTHER INFORMATION: Synthetic

<400> SEQUENCE: 266

-continued

```
ctgctatttg gatgca                                                    16


<210> SEQ ID NO 267
<211> LENGTH: 16
<212> TYPE: DNA
<213> ORGANISM: Artificial Sequence
<220> FEATURE:
<223> OTHER INFORMATION: Synthetic

<400> SEQUENCE: 267

gcagaagtac atcgga                                                    16


<210> SEQ ID NO 268
<211> LENGTH: 16
<212> TYPE: DNA
<213> ORGANISM: Artificial Sequence
<220> FEATURE:
<223> OTHER INFORMATION: Synthetic

<400> SEQUENCE: 268

gacatgatgg aggaga                                                    16


<210> SEQ ID NO 269
<211> LENGTH: 15
<212> TYPE: DNA
<213> ORGANISM: Artificial Sequence
<220> FEATURE:
<223> OTHER INFORMATION: Synthetic

<400> SEQUENCE: 269

agaagaagga tcggg                                                     15


<210> SEQ ID NO 270
<211> LENGTH: 901
<212> TYPE: RNA
<213> ORGANISM: Homo sapiens

<400> SEQUENCE: 270

auggggguuug uuaaaguugu uaagaauaag gccuacuuua agagauacca agugaaauuu     60

agaagacgac gagaggguaa aacugauuau uaugcucgga aacgcuuggu gauacaagau    120

aaaaauaaau acaacacacc caaauacagg augauaguuc gugugacaaa cagagauauc    180

auuugucaga uugcuuaugc ccguauagag ggggauauga uagucugcgc acguuaugca    240

cacgaacugc caaaauaugg ugugaagguu ggccugacaa auuaugcugc agcauauugu    300

acuggccugc ugcuggcccg caggcuucuc aauagguuug gcauggacaa gaucuaugaa    360

ggccaagugg aggugacugg ugaugaauac aauguggaaa gcauugaugg ucagccaggu    420

gccuucaccu gcuauuugga ugcaggccuu gccagaacua ccacuggcaa uaaaguuuuu    480

ggugcccuga agggagcugu ggauggaggc uugucuaucc cucacaguac caaacgauuc    540

ccugguuaug auucugaaag caaggaauuu aaugcagaag uacaucggaa gcacaucaug    600

ggccagaaug uugcagauua caugcgcuac uuaauggaag aagaugaaga ugcuuacaag    660

aaacaguucu cucaauacau aaagaacagc guaacuccag acaugaugga ggagauguau    720

aagaaagcuc augcugcuau acgagagaau ccagucuaug aaaagaagcc caagaaagaa    780

guuaaaaaga agagguggaa ccgucccaaa augucccuug cucagaagaa ggaucgggua    840

gcucaaaaga aggcaagcuu ccucagagcu caggagcggg cugcugagag cuaaacccag    900

c                                                                    901
```

-continued

<210> SEQ ID NO 271
<211> LENGTH: 25
<212> TYPE: DNA
<213> ORGANISM: Artificial Sequence
<220> FEATURE:
<223> OTHER INFORMATION: Synthetic

<400> SEQUENCE: 271
gctcaagaat gtccgcatag acccg 25

<210> SEQ ID NO 272
<211> LENGTH: 22
<212> TYPE: DNA
<213> ORGANISM: Artificial Sequence
<220> FEATURE:
<223> OTHER INFORMATION: Synthetic

<400> SEQUENCE: 272
ctggtccctg agttgttttt gc 22

<210> SEQ ID NO 273
<211> LENGTH: 15
<212> TYPE: DNA
<213> ORGANISM: Artificial Sequence
<220> FEATURE:
<223> OTHER INFORMATION: Synthetic

<400> SEQUENCE: 273
gctcaagaat gtccg 15

<210> SEQ ID NO 274
<211> LENGTH: 15
<212> TYPE: DNA
<213> ORGANISM: Artificial Sequence
<220> FEATURE:
<223> OTHER INFORMATION: Synthetic

<400> SEQUENCE: 274
gggatgtgga aggag 15

<210> SEQ ID NO 275
<211> LENGTH: 17
<212> TYPE: DNA
<213> ORGANISM: Artificial Sequence
<220> FEATURE:
<223> OTHER INFORMATION: Synthetic

<400> SEQUENCE: 275
ggaccctatg tctacag 17

<210> SEQ ID NO 276
<211> LENGTH: 15
<212> TYPE: DNA
<213> ORGANISM: Artificial Sequence
<220> FEATURE:
<223> OTHER INFORMATION: Synthetic

<400> SEQUENCE: 276
acatcttggt cctgg 15

<210> SEQ ID NO 277
<211> LENGTH: 16
<212> TYPE: DNA
<213> ORGANISM: Artificial Sequence
<220> FEATURE:
<223> OTHER INFORMATION: Synthetic -continued

<400> SEQUENCE: 277
tctcaacacg tacctc 16

<210> SEQ ID NO 278
<211> LENGTH: 14
<212> TYPE: DNA
<213> ORGANISM: Artificial Sequence
<220> FEATURE:
<223> OTHER INFORMATION: Synthetic

<400> SEQUENCE: 278
cggactcagc aaga 14

<210> SEQ ID NO 279
<211> LENGTH: 16
<212> TYPE: DNA
<213> ORGANISM: Artificial Sequence
<220> FEATURE:
<223> OTHER INFORMATION: Synthetic

<400> SEQUENCE: 279
caagggtgtt tgaagg 16

<210> SEQ ID NO 280
<211> LENGTH: 16
<212> TYPE: DNA
<213> ORGANISM: Artificial Sequence
<220> FEATURE:
<223> OTHER INFORMATION: Synthetic

<400> SEQUENCE: 280
ctctgtttct ctccca 16

<210> SEQ ID NO 281
<211> LENGTH: 15
<212> TYPE: DNA
<213> ORGANISM: Artificial Sequence
<220> FEATURE:
<223> OTHER INFORMATION: Synthetic

<400> SEQUENCE: 281
gtgaagatgc agctg 15

<210> SEQ ID NO 282
<211> LENGTH: 14
<212> TYPE: DNA
<213> ORGANISM: Artificial Sequence
<220> FEATURE:
<223> OTHER INFORMATION: Synthetic

<400> SEQUENCE: 282
agctggtgct gatg 14

<210> SEQ ID NO 283
<211> LENGTH: 15
<212> TYPE: DNA
<213> ORGANISM: Artificial Sequence
<220> FEATURE:
<223> OTHER INFORMATION: Synthetic

<400> SEQUENCE: 283
caggcctact ctgag 15

<210> SEQ ID NO 284
<211> LENGTH: 14

-continued

<212> TYPE: DNA
<213> ORGANISM: Artificial Sequence
<220> FEATURE:
<223> OTHER INFORMATION: Synthetic

<400> SEQUENCE: 284
ggactctctc agcg 14

<210> SEQ ID NO 285
<211> LENGTH: 1607
<212> TYPE: RNA
<213> ORGANISM: Mus musculus

<400> SEQUENCE: 285
gcucaagaau guccgcauag acccgagcag ccuguccuuc gggaugugga aggagauccc 60
cgucccuuuc uacuugucug ucuacuucuu cgaagugguc aacccaaacg agguccucaa 120
cggccagaag ccaguagucc gggagcgugg acccuauguc uacagggagu ucagacaaaa 180
ggucaacauc accuucaaug acaacgacac cguguccuuc guggagaacc gcagccucca 240
uuuccagccu gacaagucgc auggcucaga gagugacuac auuguacugc cuaacaucuu 300
gguccugggg ggcucgauau ugauggagag caagccugug agccugaagc ugaugaugac 360
cuuggcgcug gucaccaugg gccagcgugc uuuuaugaac cgcacaguug gugagauccu 420 gugggggcuau gacgaucccu ucgugcauuu ucucaacacg uaccucccag acaugcuucc 480
cauaaagggc aaauuuggcc uguuuguugg gaugaacaac ucgaauucug ggucuucac 540 ugucuucacg ggcguccaga auuucagcag gauccaucug guggacaaau ggaacggacu 600
cagcaagauc gauuauuggc auucagagca guguaacaug aucaauggga cuuccgggca 660
gaugugggca cccuucauga cacccgaauc cucgcuggaa uucuucagcc cggaggcaug 720
cagguccaug aagcugaccu acaacgaauc aagggguguu gaaggcauuc ccacguaucg 780
cuucacggcc cccgauacuc uguuugccaa cggguccguc uacccaccca acgaaggcuu 840
cugcccaugc cgagagucug gcauucagaa ugucagcacc ugcagguuug gugcgccucu 900
guuucucucc cacccccacu uuuacaacgc cgacccugug uugucagaag cuguucuugg 960
ucugaacccu aacccaaagg agcauuccuu guuccuagac auccauccgg ucacugggau 1020
ccccaugaac uguucuguga agaugcagcu gagccucuac aucaaaucug ucaagggcau 1080
cgggcaaaca gggaagaucg agccaguagu ucugccguug cugugguucg aacagagcgg 1140
agcaaugggu ggcaagcccc ugagcacguu cuacacgcag cuggugcuga ugccccaggu 1200
ucuucacuac gcgcaguaug ugcugcuggg gcuuggaggc cuccuguugc uggugcccau 1260
caucugccaa cugcgcagcc aggagaaaug cuuuuuguuu uggaguggua guaaaaaggg 1320
cucccaggau aaggaggcca uucaggccua cucugagucc cugaugucac cagcugccaa 1380
gggcacggug cugcaagaag ccaagcuaua ggguccugaa gacacuauaa gccccccaaa 1440
ccugauagcu uggucagacc agccacccag ucccuacacc ccgcuucuug aggacucucu 1500
cagcggacag cccaccagug ccauggccug agcccccaga ugucacaccu guccgcacgc 1560
acggcacaug gaugcccacg caugugcaaa aacaacucag ggaccag 1607

<210> SEQ ID NO 286
<211> LENGTH: 43
<212> TYPE: DNA
<213> ORGANISM: Artificial Sequence
<220> FEATURE:
<223> OTHER INFORMATION: Synthetic -continued

<400> SEQUENCE: 286
taatacgact cactataggg acggaagtcc aagagcatca ctg 43

<210> SEQ ID NO 287
<211> LENGTH: 18
<212> TYPE: DNA
<213> ORGANISM: Artificial Sequence
<220> FEATURE:
<223> OTHER INFORMATION: Synthetic

<400> SEQUENCE: 287
gcaggtacct ggtccgta 18

<210> SEQ ID NO 288
<211> LENGTH: 15
<212> TYPE: DNA
<213> ORGANISM: Artificial Sequence
<220> FEATURE:
<223> OTHER INFORMATION: Synthetic

<400> SEQUENCE: 288
ggaagtccaa gagca 15

<210> SEQ ID NO 289
<211> LENGTH: 15
<212> TYPE: DNA
<213> ORGANISM: Artificial Sequence
<220> FEATURE:
<223> OTHER INFORMATION: Synthetic

<400> SEQUENCE: 289
aatggcttct ttggg 15

<210> SEQ ID NO 290
<211> LENGTH: 10
<212> TYPE: DNA
<213> ORGANISM: Artificial Sequence
<220> FEATURE:
<223> OTHER INFORMATION: Synthetic

<400> SEQUENCE: 290
ggcgtcgccc 10

<210> SEQ ID NO 291
<211> LENGTH: 15
<212> TYPE: DNA
<213> ORGANISM: Artificial Sequence
<220> FEATURE:
<223> OTHER INFORMATION: Synthetic

<400> SEQUENCE: 291
tacttccgca tcgtc 15

<210> SEQ ID NO 292
<211> LENGTH: 17
<212> TYPE: DNA
<213> ORGANISM: Artificial Sequence
<220> FEATURE:
<223> OTHER INFORMATION: Synthetic

<400> SEQUENCE: 292
cttcttccct agttgtg 17

<210> SEQ ID NO 293
<211> LENGTH: 11

-continued

<212> TYPE: DNA
<213> ORGANISM: Artificial Sequence
<220> FEATURE:
<223> OTHER INFORMATION: Synthetic

<400> SEQUENCE: 293
tgcctggccg t 11

<210> SEQ ID NO 294
<211> LENGTH: 18
<212> TYPE: DNA
<213> ORGANISM: Artificial Sequence
<220> FEATURE:
<223> OTHER INFORMATION: Synthetic

<400> SEQUENCE: 294
gactctacta agaaccca 18

<210> SEQ ID NO 295
<211> LENGTH: 15
<212> TYPE: DNA
<213> ORGANISM: Artificial Sequence
<220> FEATURE:
<223> OTHER INFORMATION: Synthetic

<400> SEQUENCE: 295
ccatcttagt ggcgt 15

<210> SEQ ID NO 296
<211> LENGTH: 14
<212> TYPE: DNA
<213> ORGANISM: Artificial Sequence
<220> FEATURE:
<223> OTHER INFORMATION: Synthetic

<400> SEQUENCE: 296
caacaagtgc ctgg 14

<210> SEQ ID NO 297
<211> LENGTH: 13
<212> TYPE: DNA
<213> ORGANISM: Artificial Sequence
<220> FEATURE:
<223> OTHER INFORMATION: Synthetic

<400> SEQUENCE: 297
aacacggcgt cac 13

<210> SEQ ID NO 298
<211> LENGTH: 14
<212> TYPE: DNA
<213> ORGANISM: Artificial Sequence
<220> FEATURE:
<223> OTHER INFORMATION: Synthetic

<400> SEQUENCE: 298
tgattacccc gagg 14

<210> SEQ ID NO 299
<211> LENGTH: 14
<212> TYPE: DNA
<213> ORGANISM: Artificial Sequence
<220> FEATURE:
<223> OTHER INFORMATION: Synthetic

<400> SEQUENCE: 299

-continued acgctgtttt cctg 14

<210> SEQ ID NO 300
<211> LENGTH: 16
<212> TYPE: DNA
<213> ORGANISM: Artificial Sequence
<220> FEATURE:
<223> OTHER INFORMATION: Synthetic

<400> SEQUENCE: 300
tgagacacct gtacaa 16

<210> SEQ ID NO 301
<211> LENGTH: 14
<212> TYPE: DNA
<213> ORGANISM: Artificial Sequence
<220> FEATURE:
<223> OTHER INFORMATION: Synthetic

<400> SEQUENCE: 301
gacggagaca gtgg 14

<210> SEQ ID NO 302
<211> LENGTH: 14
<212> TYPE: DNA
<213> ORGANISM: Artificial Sequence
<220> FEATURE:
<223> OTHER INFORMATION: Synthetic

<400> SEQUENCE: 302
caagcgaggg agag 14

<210> SEQ ID NO 303
<211> LENGTH: 1051
<212> TYPE: RNA
<213> ORGANISM: Rattus rattus

<400> SEQUENCE: 303
ggaaguccaa gagcaucacu gacaucuacc uccugaaccu ggccuugagc gaccugcucu 60
uuguggccac uuugcccuuc uggacucacu accucaucag ccaugagggc cuccacaacg 120
ccaugugcaa gcucacgacu gcuuucuucu ucauuggcuu cuuugggggc auauucuuca 180
ucaccgucau cagcaucgac cgguaccucg ccaucguccu ggccgccaac uccaugaaca 240
accggacagu gcaacacggc gucaccauca gucugggcgu cugggcggcg gccaucuuag 300
uggcgucgcc ccaguucaug uucacaaaga gaaaggacaa cgaauguuug ggugauuacc 360
ccgagguccu gcaggaaauc uggcccgugc uccgcaacuc ggaggucaac auccugggcu 420
ucguccugcc cuugcuuauc augagcuuuu gcuacuuccg caucguccgg acgcuguuuu 480
ccugcaagaa ccggaagaag gccagagcca uuaggcucau ccucuuggug guuguugucu 540
ucuuccucuu cuggacgccu uacaacaucg ugauuuuccu ggagacucuc aaauucuaca 600
acuucuuccc uaguuguggc augaagaggg accugaggug ggcccuuagu gugacggaga 660
caguggcguu uagccacugc ugccucaacc ccuuuaucua cgcuuucgcu ggggaaaagu 720
ucagaaggua ccugagacac cuguacaaca agugccuggc cguccugugc ggucguccug 780
uccacgccgg cuucucaaca gagucccaga ggagcaggca ggacagcauu cugagcagcu 840
ugacucacua cacaagcgag ggagagggau cucuccugcu cugaaggguc uccccgaccc 900
cgacucuacu aagaacccag aguuccugca ucugacucug uguaaugaaa acagauucac 960
acacacacac acacacacac acacacacac acacacacac accccgcucc uccugcauuu 1020
uaugugcaag aaauacggac cagguaccug c 1051

<210> SEQ ID NO 304
<211> LENGTH: 56
<212> TYPE: DNA
<213> ORGANISM: Artificial Sequence
<220> FEATURE:
<223> OTHER INFORMATION: Synthetic

<400> SEQUENCE: 304
gtaatttaat acgactcact atagggaagg tgcagttttg ccaaggagtg ctaaag 56

<210> SEQ ID NO 305
<211> LENGTH: 30
<212> TYPE: DNA
<213> ORGANISM: Artificial Sequence
<220> FEATURE:
<223> OTHER INFORMATION: Synthetic

<400> SEQUENCE: 305
ctgattgaaa tttatctaat aaaacatcat 30

<210> SEQ ID NO 306
<211> LENGTH: 14
<212> TYPE: DNA
<213> ORGANISM: Artificial Sequence
<220> FEATURE:
<223> OTHER INFORMATION: Synthetic

<400> SEQUENCE: 306
acttccaagc tggc 14

<210> SEQ ID NO 307
<211> LENGTH: 15
<212> TYPE: DNA
<213> ORGANISM: Artificial Sequence
<220> FEATURE:
<223> OTHER INFORMATION: Synthetic

<400> SEQUENCE: 307
gagagtggac cacac 15

<210> SEQ ID NO 308
<211> LENGTH: 17
<212> TYPE: DNA
<213> ORGANISM: Artificial Sequence
<220> FEATURE:
<223> OTHER INFORMATION: Synthetic

<400> SEQUENCE: 308
gaatcagtga agatgcc 17

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
cattgtacca tgaaatatcc 20

<210> SEQ ID NO 310
<211> LENGTH: 21
<212> TYPE: DNA

-continued

<213> ORGANISM: Artificial Sequence
<220> FEATURE:
<223> OTHER INFORMATION: Synthetic

<400> SEQUENCE: 310
gaactttaat ttcaggaatt g 21

<210> SEQ ID NO 311
<211> LENGTH: 15
<212> TYPE: DNA
<213> ORGANISM: Artificial Sequence
<220> FEATURE:
<223> OTHER INFORMATION: Synthetic

<400> SEQUENCE: 311
ccctagtctg ctagc 15

<210> SEQ ID NO 312
<211> LENGTH: 21
<212> TYPE: DNA
<213> ORGANISM: Artificial Sequence
<220> FEATURE:
<223> OTHER INFORMATION: Synthetic

<400> SEQUENCE: 312
ttcaagtgta acttattaac c 21

<210> SEQ ID NO 313
<211> LENGTH: 12
<212> TYPE: DNA
<213> ORGANISM: Artificial Sequence
<220> FEATURE:
<223> OTHER INFORMATION: Synthetic

<400> SEQUENCE: 313
aagctggccg tg 12

<210> SEQ ID NO 314
<211> LENGTH: 15
<212> TYPE: DNA
<213> ORGANISM: Artificial Sequence
<220> FEATURE:
<223> OTHER INFORMATION: Synthetic

<400> SEQUENCE: 314
tgcagttttg ccaag 15

<210> SEQ ID NO 315
<211> LENGTH: 1382
<212> TYPE: RNA
<213> ORGANISM: Homo sapiens

<400> SEQUENCE: 315
ggcagaagua ccugagcucg ccagugaaau gauggcuuau uacaguggca augaggauga 60
cuuguucuuu gaagcugaug gcccuaaaca gaugaagugc uccuuccagg accuggaccu 120
cugcccucug gauggcggca uccagcuacg aaucuccgac caccacuaca gcaagggcuu 180
caggcaggcc gcgucaguug uuguggccau ggacaagcug aggaagaugc ugguucccug 240
cccacagacc uuccaggaga augaccugag caccuucuuu cccuucaucu uugaagaaga 300
accuaucuuc uucgacacau gggauaacga ggcuuaugug cacgaugcac cuguacgauc 360
acugaacugc acgcuccggg acucacagca aaaaagcuug gugaugucug guccauauga 420
acugaaagcu cuccaccucc agggacagga uauggagcaa caaguggugu ucuccauguc 480

-continued

```
cuuuguacaa ggagaagaaa guaaugacaa aauaccugug gccuugggcc ucaaggaaaa    540

gaaucuguac cuguccugcg uguugaaaga ugauaagccc acucuacagc uggagagugu    600

agaucccaaa aauuacccaa agaagaagau ggaaaagcga uuugucuuca acaagauaga    660

aaucaauaac aagcuggaau uugagucugc ccaguucccc aacugguaca ucagcaccuc    720

ucaagcagaa aacaugcccg ucuuccuggg agggaccaaa ggcggccagg auauaacuga    780

cuucaccaug caauuugugu cuuccuaaag agagcuguac ccagagaguc cugugcugaa    840

uguggacuca aucccuaggg cuggcagaaa gggaacagaa agguuuuuga guacggcuau    900

agccuggacu uuccuguugu cuacaccaau gcccaacugc cugccuuagg guagugcuaa    960

gaggaucucc uguccaucag ccaggacagu cagcucucuc cuuucagggc caaucccag    1020

cccuuuuguu gagccaggcc ucucucaccu cuccuacuca cuuaaagccc gccugacaga   1080

aaccacggcc acauuugguu cuaagaaacc cucugucauu cgcucccaca uucugaugag   1140

caaccgcuuc ccuauuuauu uauuuauuug uuuguuuguu uuauucauug gucuaauuua   1200

uucaaagggg gcaagaagua gcagugucug uaaaagagcc uaguuuuuaa uagcuaugga   1260

aucaauucaa uuuggacugg ugugcucucu uuaaaucaag ucccuuuaauu aagacugaaa  1320

auauauaagc ucagauuauu uaaaugggaa uauuuauaaa ugagcaaaua ucauacuguu   1380

ca                                                                  1382
```

<210> SEQ ID NO 316
<211> LENGTH: 20
<212> TYPE: DNA
<213> ORGANISM: Artificial Sequence
<220> FEATURE:
<223> OTHER INFORMATION: Synthetic

<400> SEQUENCE: 316
gcatcgtttt gggttctctt 20

<210> SEQ ID NO 317
<211> LENGTH: 20
<212> TYPE: DNA
<213> ORGANISM: Artificial Sequence
<220> FEATURE:
<223> OTHER INFORMATION: Synthetic

<400> SEQUENCE: 317
actttaaaga tgaccagagc 20

<210> SEQ ID NO 318
<211> LENGTH: 20
<212> TYPE: DNA
<213> ORGANISM: Artificial Sequence
<220> FEATURE:
<223> OTHER INFORMATION: Synthetic

<400> SEQUENCE: 318
cacattgttc tgatcatctg 20

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319

-continued cggtaactga cttgaatgtc 20

<210> SEQ ID NO 320
<211> LENGTH: 20
<212> TYPE: DNA
<213> ORGANISM: Artificial Sequence
<220> FEATURE:
<223> OTHER INFORMATION: Synthetic

<400> SEQUENCE: 320
tagtaactgg atagtatcac 20

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
gacattcaag tcagttaccg 20

<210> SEQ ID NO 322
<211> LENGTH: 41
<212> TYPE: DNA
<213> ORGANISM: Artificial Sequence
<220> FEATURE:
<223> OTHER INFORMATION: Synthetic

<400> SEQUENCE: 322
aatttaatac gactcactat acacattgtt ctgatcatct g 41

<210> SEQ ID NO 323
<211> LENGTH: 41
<212> TYPE: DNA
<213> ORGANISM: Artificial Sequence
<220> FEATURE:
<223> OTHER INFORMATION: Synthetic

<400> SEQUENCE: 323
aatttaatac gactcactat acggtaactg acttgaatgt c 41

<210> SEQ ID NO 324
<211> LENGTH: 20
<212> TYPE: DNA
<213> ORGANISM: Artificial Sequence
<220> FEATURE:
<223> OTHER INFORMATION: Synthetic

<400> SEQUENCE: 324
cacattgttc tgatcatctg 20

<210> SEQ ID NO 325
<211> LENGTH: 20
<212> TYPE: DNA
<213> ORGANISM: Artificial Sequence
<220> FEATURE:
<223> OTHER INFORMATION: Synthetic

<400> SEQUENCE: 325
cggtaactga cttgaatgtc 20

<210> SEQ ID NO 326
<211> LENGTH: 49
<212> TYPE: DNA
<213> ORGANISM: Artificial Sequence -continued
<220> FEATURE:
<223> OTHER INFORMATION: Synthetic

<400> SEQUENCE: 326
agtaatttac gactcactat agggacacat tgttctgatc atctgaaga 49

<210> SEQ ID NO 327
<211> LENGTH: 49
<212> TYPE: DNA
<213> ORGANISM: Artificial Sequence
<220> FEATURE:
<223> OTHER INFORMATION: Synthetic

<400> SEQUENCE: 327
agtaatttac gactcactat agggacggta actgacttga atgtccaac 49

<210> SEQ ID NO 328
<211> LENGTH: 15
<212> TYPE: DNA
<213> ORGANISM: Artificial Sequence
<220> FEATURE:
<223> OTHER INFORMATION: Synthetic

<400> SEQUENCE: 328
cattcagatg tagcg 15

<210> SEQ ID NO 329
<211> LENGTH: 15
<212> TYPE: DNA
<213> ORGANISM: Artificial Sequence
<220> FEATURE:
<223> OTHER INFORMATION: Synthetic

<400> SEQUENCE: 329
gactcatcaa tcaaa 15

<210> SEQ ID NO 330
<211> LENGTH: 15
<212> TYPE: DNA
<213> ORGANISM: Artificial Sequence
<220> FEATURE:
<223> OTHER INFORMATION: Synthetic

<400> SEQUENCE: 330
gattacaagg cttta 15

<210> SEQ ID NO 331
<211> LENGTH: 332
<212> TYPE: RNA
<213> ORGANISM: Pneumocystis carinii

<400> SEQUENCE: 331
gagggucaug aaagcggcgu gaaaacguua gcuagugauc uggaauaaau ucagauugcg 60
acacugucaa auugcgggga agcccuaaag auucaacuac uaagcaguuu guggaaacac 120
agcuguggcc gaguuaauag cccuggguau aguaacaaug uugaauauga aucuuuugcg 180
agaugaaaug ggugauccgc agccaagucc uaagggcauu uuugucuaug gaugcaguuc 240
aacgacuaga uggcaguggg uauuguaagg aauugcaguu uucuugcagu gcuuaaggua 300
uagucuaucc ucuuucgaaa gaaagaguau au 332

<210> SEQ ID NO 332
<211> LENGTH: 368
<212> TYPE: RNA

-continued

```
<213> ORGANISM: Candida albicans

<400> SEQUENCE: 332

gggaggcaaa aguagggacg ccaugguuuc cagaaauggg ccgcggugwu uuugaccugc     60

uagucgaucu ggccagacgu aucugugggu ggccagcggc gacauaaccu gguacgggga    120

aggccucgaa gcaguguuca ccuugggagu gcgcaagcac aaagagguga gugguguaug    180

ggguuaaucc cguggcgagc cgucagggcg cgaguucugg caguggccgu cguagagcac    240

ggaaagguau gggcuggcuc ucugagucgg cuuaagguac gugccguccc acacgaugaa    300

aagugugcgg ugcagaauag uucccacaga acgaagcugc gccggagaaa gcgauuucuu    360

ggagcaau                                                             368

<210> SEQ ID NO 333
<211> LENGTH: 165
<212> TYPE: RNA
<213> ORGANISM: Earwig R2 element

<400> SEQUENCE: 333

uaggaugaua gcgcaccugg ucaucgucuc ucucagcugc ucacuugcug uucuaaguga     60

uaauaccguu guuuuuuuag uggguauucu uuuacgcuuu cguaggagcg agucccacac    120

ucuuggagca auccggggua gugccuaaac gcauuucuuc aacgu                    165

<210> SEQ ID NO 334
<211> LENGTH: 244
<212> TYPE: RNA
<213> ORGANISM: Bombyx mori

<400> SEQUENCE: 334

gccuugcaca guaguccagc gguaagggug uagaucaggc ccgucuguuu cucccccgga     60

gcucgcuccc uuggcuuccc uuauauauuu uaacaucaga aacagacauu aaacaucuac    120

ugauccaauu ucgccggcgu acggccacga ucgggagggu gggaaucucg ggggucuucc    180

gauccuaauc caugaugauu acgaccugag ucacuaaaga cgauggcaug augauccggc    240

gaug                                                                 244
```

NUCLEIC ACID ACCESSIBLE HYBRIDIZATION SITES

The present invention claims priority to U.S. provisional application No. 60/212,308, filed Jun. 17, 2000.

FIELD OF THE INVENTION

The present invention relates to methods and compositions for analyzing nucleic acids, and in particular, methods and compositions for detection and characterization of nucleic acid sequences and sequence changes. The present invention also provides methods and compositions for identifying oligonucleotides with desired hybridization properties to nucleic acid targets containing secondary structure.

BACKGROUND OF THE INVENTION

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations. As nucleic acid sequence data for genes from humans and pathogenic organisms accumulates, the demand for fast, cost-effective, and easy-to-use tests for as yet unknown, as well as known, mutations within specific sequences is rapidly increasing.

A handful of methods have been devised to scan nucleic acid segments for mutations. One option is to determine the entire gene sequence of each test sample (e.g., a clinical sample suspected of containing bacterial strain). For sequences under approximately 600 nucleotides, this may be accomplished using amplified material (e.g., PCR reaction products). This avoids the time and expense associated with cloning the segment of interest. However, specialized equipment and highly trained personnel are required for DNA sequencing, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or, as noted above, the precise nucleotide sequence can be determined by partial chemical degradation or by primer extension in the presence of chain-terminating nucleotide analogs.

For detection of single-base differences between like sequences (e.g., the wild type and a mutant form of a gene), the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis). In this way, single point mutations can be detected by the creation or destruction of RFLPs.

Single-base mutations have also been identified by cleavage of RNA—RNA or RNA-DNA heteroduplexes using RNaseA (Myers et al., Science 230:1242 [1985] and Winter et al., Proc. Natl. Acad. Sci. USA 82:7575 [1985]). Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817 [1990]). However, this method requires the use of osmium tetroxide and piperidine, two highly noxious chemicals that are not suited for use in a clinical laboratory. Enzymes such as the bacteriophage T4 endonuclease VII have been used in Enzymatic Mismatch Cleavage (EMC) (Youil et al, Genomics 32:431 [1996]). However, all of the mismatch cleavage methods lack sensitivity to some mismatch pairs, and all are prone to background cleavage at sites removed from the mismatch. Furthermore, the generation of purified fragments to be used in heteroduplex formation is both labor intensive and time consuming.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), *Nucleic Acids and Molecular Biology*, vol. 2, Springer-Verlag, Heidelberg [1988]). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167 [1987]). Recently, endonucleases encoded by group I introns have been discovered that might have greater than 12 base-pair specificity (Perlman and Butow, Science 246:1106 [1989]), but again, these are few in number.

If the change is not in a restriction enzyme recognition sequence, then allele-specific oligonucleotides (ASOs) can be designed to hybridize in proximity to the unknown nucleotide, such that a primer extension or ligation event can be used as the indicator of a match or a mismatch. Hybridization with radioactively labeled ASOs also has been applied to the detection of specific point mutations (Conner, Proc. Natl. Acad. Sci., 80:278 [1983]). The method is based on the differences in the melting temperature of short DNA fragments differing by a single nucleotide (Wallace et al., Nucl. Acids Res., 6:3543 [1979]). Similarly, hybridization with large arrays of short oligonucleotides is now used as a method for DNA sequencing (Bains and Smith, J. Theor. Biol., 135:303 [1988]; Drmanac et al., Genomics 4:114 [1989]). To perform either method it is necessary to work under conditions in which the formation of mismatched duplexes is eliminated or reduced while perfect duplexes still remain stable. Such conditions are termed "high stringency" conditions. The stringency of hybridization conditions can be altered in a number of ways known in the art. In general, changes in conditions that enhance the formation of nucleic acid duplexes, such as increases in the concentration of salt, or reduction in the temperature of the solution, are considered to reduce the stringency of the hybridization conditions. Conversely, reduction of salt and elevation of temperature are considered to increase the stringency of the conditions. Because it is easy to change and control, variation of the temperature is commonly used to control the stringency of nucleic acid hybridization reactions.

Discrimination of hybridization based solely on the presence of a mismatch imposes a limit on probe length because effect of a single mismatch on the stability of a duplex is smaller for longer duplexes. For oligonucleotides designed to detect mutations in genomes of high complexity, such as human DNA, it has been shown that the optimal length for hybridization is between 16 and 22 nucleotides, and the temperature window within which the hybridization stringency will allow single base discrimination can be as large as 10° C. (Wallace [1979], supra). Usually, however, it is much narrower, and for some mismatches, such as G-T, it may be as small as 1 to 2° C. These windows may be even smaller if any other reaction conditions, such as temperature, pH, concentration of salt and the presence of destabilizing agents (e.g., urea, formamide, dimethylsulfoxide) alter the stringency. Thus, for successful detection of mutations using such high stringency hybridization methods, a tight control of all parameters affecting duplex stability is critical.

In addition to the degree of homology between the oligonucleotide probe and the target nucleic acid, efficiency of hybridization also depends on the secondary structure of the target molecule. Indeed, if the region of the target molecule that is complementary to the probe is involved in the formation of intramolecular structures with other regions of the target, this will reduce the binding efficiency of the probe. Interference with hybridization by such secondary structure is another reason why high stringency conditions are so important for sequence analysis by hybridization. High stringency conditions reduce the probability of secondary structure formation (Gamper et al., J. Mol. Biol., 197:349 [1987]). Another way to of reducing the probability of secondary structure formation is to decrease the length of target molecules, so that fewer intrastrand interactions can occur. This can be done by a number of methods, including enzymatic, chemical or thermal cleavage or degradation. Currently, it is standard practice to perform such a step in commonly used methods of sequence analysis by hybridization to fragment the target nucleic acid into short oligonucleotides (Fodor et al., Nature 364:555 [1993]).

ASOs have also been adapted to the PCR method. In this, or in any primer extension-based assay, the nucleotide to be investigated is positioned opposite the 3' end of a primer oligonucleotide. If the bases are complementary, then a DNA polymerase can extend the primer with ease; if the bases are mismatched, the extension may be blocked. Blocking of PCR by this method has had some degree of success, but not all mismatches are able to block extension. In fact, a "T" residue on the 3' end of a primer can be extended with reasonable efficiency when mis-paired with any of the non-complementary nucleotide when Taq DNA polymerase, a common PCR enzyme, is used (Kwok, et al, Nucl. Acids. Res. 18:999 [1990]). Further, if any of the enzymes having 3'–5' exonuclease "proofreading" activity (e.g., Vent DNA polymerase, New England Biolabs, Beverly Mass.) are used, the mismatch is first removed, then filled in with a matched nucleotide before further extension. This dramatically limits the scope of application of PCR in this type of direct mutation identification.

Two other methods of mutation detection rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in the melting properties of homoduplexes versus heteroduplexes differing in a single nucleotide can be used to detect the presence of mutations in the target sequences because of the corresponding changes in the electrophoretic mobilities of the hetero- and homoduplexes. The fragments to be analyzed, usually PCR products, are "clamped" at one end by a long stretch of G-C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463 [1990]). Attaching a GC clamp to one primer is critical to ensure that the amplified sequence has a low dissociation temperature (Sheffield et al., Proc. Natl. Acad. Sci., 86:232 [1989]; and Lerman and Silverstein, Meth. Enzymol., 155:482 [1987]). Modifications of the technique have been developed, using temperature gradient gels (Wartell et al., Nucl. Acids Res., 18:2699–2701 [1990]), and the method can be also applied to RNA:RNA duplexes (Smith et al., Genomics 3:217 [1988]).

Limitations on the utility of DGGE include the requirement that the denaturing conditions must be optimized for each specific nucleic acid sequence to be tested. Furthermore, the method requires specialized equipment to prepare the gels and maintain the high temperatures required during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405 [1991]). CDGE requires that gels be performed under different denaturant conditions in order to reach high efficiency for the detection of unknown mutations. Both DGGE and CDGE are unsuitable for use in clinical laboratories.

A technique analogous to DGGE, termed temperature gradient gel electrophoresis (TGGE), uses a thermal gradient rather than a chemical denaturant gradient (Scholz et al., Hum. Mol. Genet., 2:2155 [1993]). TGGE requires the use of specialized equipment that can generate a temperature gradient perpendicularly oriented relative to the electrical field. TGGE can detect mutations in relatively small fragments of DNA therefore scanning of large gene segments requires the use of multiple PCR products prior to running the gel.

Another common method, called "Single-Strand Conformation Polymorphism" (SSCP) was developed by Hayashi, Sekya and colleagues (reviewed by Hayashi, PCR Meth. Appl., 1:34–38, [1991]) and is based on the observation that single strands of nucleic acid can take on characteristic conformations under non-denaturing conditions, and these conformations influence electrophoretic mobility. The complementary strands assume sufficiently different structures that the two strands may be resolved from one another. Changes in the sequence of a given fragment will also change the conformation, consequently altering the mobility and allowing this to be used as an assay for sequence variations (Orita, et al., Genomics 5:874 [1989]).

The SSCP process involves denaturing a DNA segment (e.g., a PCR product) that is usually labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

The dideoxy fingerprinting (ddF) technique is another technique developed to scan genes for the presence of unknown mutations (Liu and Sommer, PCR Methods Applic, 4:97 [1994]). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200–300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion subcloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Another method of detecting sequence polymorphisms based on the conformation assumed by strands of nucleic acid is the CLEAVASE Fragment Length Polymorphism (CFLP) method (Brow et al., J. Clin. Microbiol., 34:3129 [1996]; PCT Publication WO 96/15267; U.S. Pat. Nos. 5,843,654; and co-pending application Ser. No. 08/520,946, herein incorporated by reference in their entireties). This method uses the actions of a structure specific nuclease to cleave the folded structures, thus creating a set of product fragments that can by resolved by size (e.g., by electrophoresis). This method is much less sensitive to size so that entire genes, rather than gene fragments, may be analyzed.

In many situations (e.g., in many clinical laboratories), electrophoretic separation and analysis may not be technically feasible, or may not be able to accommodate the processing of a large number of samples in a cost-effective manner. There is a clear need for a method of analyzing the characteristic conformations of nucleic acids without the need for either electrophoretic separation of conformations or fragments or for elaborate and expensive methods of visualizing gels (e.g., darkroom supplies, blotting equipment or fluorescence imagers).

In addition to the apparently fortuitous folded conformations that may be assumed by any nucleic acid segment, as noted above, the folded structures assumed by some nucleic acids are linked in a variety of ways to the function of that nucleic acid. For example, tRNA structure is critical to its proper function in protein assembly, ribosomal RNA (rRNA) structures are essential to the correct function of the ribosome, and correct folding is essential to the catalytic function of Group I self-splicing introns (See e.g., the chapters by Woese and Pace (p. 91), Noller (p. 137), and Cech (p. 239) in Gesteland and Atkins (eds.), *The RNA World*, Cold Spring Harbor Laboratory Press, Cold Spring Harbor, N.Y. [1993]). Folded structures in viral RNAs have been linked to infectivity (Proutski et al., J Gen Virol., 78(Pt 7):1543–1549 [1997], altered splicing (Ward, et al., Virus Genes 10:91 [1995]), translational frameshifting (Bidou et al., RNA 3:1153 [1997]), packaging (Miller, et al. J. Virol., 71:7648 [1997]), and other functions. In both prokaryotes and eukaryotes, RNA structures are linked to post-transcriptional control of gene expression through mechanisms including attenuation of translation (Girelli et al., Blood 90:2084 [1997], alternative splicing (Howe and Ares, Proc. Natl. Acad. Sci. USA 94:12467 [1997]) and signaling for RNA degradation (Veyrune et al, Oncogene 11:2127 [1995]). Messenger RNA secondary structure has also been associated with localization of that RNA within cells (Serano and Cohen, Develop., 121:3809–3818 [1995]). In DNA, it has been shown that cruciform structures have also been tied to control of gene expression (Hanke et al., J. Mol. Biol., 246:63 [1995]). It can be seen from these few examples that the use of folded structures as signals within organisms is not uncommon, nor is it limited to non-protein-encoding RNAs, such as rRNAs, or to non-protein-encoding regions of genomes or messenger RNAs.

Some mutations and polymorphisms associated with altered phenotype act by altering structures assumed by nucleic acids. Any of the functions and pathways cited above may be altered, e.g., decreased or increased in efficacy, by such a structural alteration. Such alterations in function may be associated with medically relevant effects, including but not limited to tumor growth or morphology (Thompson et al., Oncogene 14:1715 [1997]), drug resistance, or virulence (Mangada and Igarishi, Virus Genes 14:5 [1997], Ward et al., supra) in pathogens. For example, the iron availability in blood in controlled by the protein ferritin, an iron storage protein. Ferritin levels are controlled post-transcriptionally by binding of iron-regulatory proteins to a structure (an iron-responsive element, or IRE) on 5' untranslated region of the ferritin mRNA, thereby blocking translation when iron levels are low. Hereditary hyperferritinemia, an iron storage disorder linked to cataract formation, had been found in some cases to be caused by mutations in the IRE that alter or delete the structure, preventing translational regulation.

It can easily be appreciated from these few examples that ability to rapidly analyze nucleic acid structure would be a useful tool for both basic and clinical research and for diagnostics. Further, accurate identification of nucleic acid structures would facilitate the design and application of therapeutic agents targeted directly at nucleic acids, such as antisense oligonucleotides, aptamers and peptide nucleic acid agents.

Targeting mRNA with sequence-specific deoxyoligonucleotides has recently gained attention for purposes of antisense research, oligomer hybridization for various gene expression assays such as the INVADER assay (Lyamichev et al., Nature Biotechnology 17:292 [1999]), and primer selection for reverse transcription and extension experiments. One of the major problems associated with such experiments is the ability to define regions of the RNA that can be efficiently targeted for oligonucleotide hybridization. To simply use randomly selected complementary oligonucleotides for a given RNA target without prior knowledge of regions of the RNA that allow efficient hybridization has been proven to be an ineffective approach. It is estimated that targeting RNA with antisense oligonucleotides based on random design results in one out of 18–20 tested oligonucleotides showing significant inhibition of gene expression (Sczakiel, Fronteirs in Biosciences 5:194 [2000]; Patzel et al., Nucleic Acids Res., 27:4328 [1999]; Peyman et al., Biol. Chem. Hoppe-Seyler 367:195 [1995]; Monia et al, Nature Med., 2:668 [1996]). Secondary and tertiary structures of RNA are thought of to be the major reasons that influence the ability of an oligonucleotide to bind targeted regions of the RNA (Vickers et al., Nucleic Acids Res., 28:1340 [2000]; Lima et al., Biochemistry 31:12055 [1992]; Uhlenbeck, J. Mol. Biol., 65:25 [1972]; Freier and Tinoco, Biochemistry 14:3310 [1975]). This is due to the hybridization kinetics and thermodynamics of destroying any structural motifs of the RNA and, in return, hybridizing the complementary DNA oligonucleotide (Patzel et al., Nucleic Acids Res., 27:4328 [1999]; Mathews et al., RNA 5:1458 [1999]). Thus, the ability to identify regions of RNA that are “accessible” for hybridization is of crucial importance for design and selection of effective oligonucleotides.

To date, there are few experimental and theoretical methods available for identifying accessible regions in RNA. These include the use of RNase-H footprinting (Ho et al., Nature Biotechnology 16:59 [1998]; Mateeva et al., Nucleic Acids Res., 25:5010 [1997]; Mateeva et al., Nature Biotechnology 16:1374 [1998]), complementary arrays of oligonucleotide libraries (Southern et al., Nucleic Acids Res., 22:1368 [1994]; Mir and Southern, Nature Biotechnology 17:788 [1999]), ribozyme libraries with random hexamer internal guide sequences (Campbell and Cech, RNA 1:598 [1995]; Lan et al., Science 280:1593 [1998]), and RNA and DNA structure prediction computer programs (Sczakiel, Frontiers in Biosciences 5:194 [2000]; Patzel et al., Nucleic Acids Res., 27:4328 [1999]; Zuker, Science 244:48 [1989]; Walton et al., Biotechnol. Bioeng., 65:1 [1999]). Thus, the art is in need of realiable and efficient methods for identifying and characterizing accessible regions of RNA.

SUMMARY OF THE INVENTION

The present invention relates to methods and compositions for treating nucleic acid, and in particular, methods and compositions for detection and characterization of nucleic acid sequences and sequence changes. The present invention provides methods for examining the conformations assumed by single strands of nucleic acid, forming the basis of novel methods of detection of specific nucleic acid sequences. The present invention contemplates use of novel detection methods for, among other uses, clinical diagnostic purposes, including but not limited to the detection and identification of pathogenic organisms. The present invention also provides methods for identifying oligonucleotides with desired hybridization properties to nucleic acid targets containing secondary structure.

For example, the present invention provides methods for designing oligonucleotides that interact with folded nucleic acids. It is contemplated that such oligonucleotides may be used for either diagnostic (e.g., detection or analysis of structure) or therapeutic (e.g., alteration of structure function) purposes. When used to detect nucleic acid structure, it is contemplated that the resulting oligonucleotide/folded nucleic acid target complexes may be detected directly (e.g., by capture), or may be detected as the result of a further catalyzed reaction that is enabled by the complex formation, including but not limited to a ligation, a primer extension, or a nuclease cleavage reaction. It will easily be appreciated by those skilled in the art that performance of bridging oligonucleotides in these basic enzymatic reactions is indicative of their utility in assays that are based on reiterative performance of these basic reactions, including but not limited to cycle sequencing, polymerase chain reaction, ligase chain reaction, cycling probe reaction and the INVADER invasive cleavage reaction. The present invention provides methods of using the bridging oligonucleotides in each of the basic enzymatic reaction systems, and in the INVADER invasive cleavage system.

The present invention further provides an alternative experimental method, based on reverse transcription and polymerase chain reaction (RT-PCR) for determining regions of RNA targets that are readily available for participation in oligonucleotide hybridization. Such available regions are termed “accessible sites.” Determination of accessible sites finds use, for example, in identifying and designing antisense oligonucleotide that efficiently hybridize to target structures and in identifying and designing oligonucleotides for use in the structure-probing methods disclosed herein.

The present invention contemplates using the interactions between probe oligonucleotides and folded nucleic acid strands in methods for detection and characterization of nucleic acid sequences and sequence changes. In another embodiment, the present invention contemplates the use of structure based nucleic acid interactions in the analysis of particular structured regions of nucleic acids, as a determination of function or alteration of function. A complex formed by the specific interaction (i.e., reproducible and predictable under a given set of reaction conditions) of a probe with a target nucleic acid sequence is referred to herein as a “probe/folded target nucleic acid complex.” The interactions contemplated may be a combination of standard hybridization of oligonucleotides to contiguous, co-linear complementary bases, or may include standard base-pairing to non-contiguous regions of complementarity on a strand of nucleic acid to be analyzed. In this context, the term “standard base pairing” refers to hydrogen bonding that occurs between complementary bases, adenosine to thymidine or uracil and guanine to cytosine to form double helical structures of the A or B form. Such standard base pairing may also be referred to as Watson-Crick base pairing. It is contemplated that the interactions between the oligonucleotides of the present invention (i.e., the probes and the targets) may include non-standard nucleic acid interactions known in the art, such as triplex structures, quadraplex aggregates, and the multibase hydrogen bonding such as is observed within nucleic acid tertiary structures, such as those found in tRNAs. It is contemplated that in one embodiment, the interactions between the oligonucleotides of the present invention may consist primarily of non-standard nucleic acid interactions. In one embodiment, the specific probe/folded target nucleic acid complex uses oligonucleotides that lack unique complementarity to each other (e.g., the shorter nucleic acid probe lacks segments that are long enough to be complementary to only a single site within the longer nucleic acid or its complement).

The present invention contemplates the use of probes that are designed to interact with non-contiguous regions of complementarity. In one embodiment, such probes are constructed by incorporating within a single oligonucleotide segments that are complementary to two or more non-contiguous regions in the target nucleic acid of interest.

In another embodiment, this mixture is present in an aqueous solution. The invention is not limited by the nature of the aqueous solution employed. The aqueous solution may contain mono- and divalent ions, non-ionic detergents, buffers, stabilizers, etc.

The present invention provides a method, comprising: a) providing: i) a folded target having a nucleic acid (e.g., deoxyribonucleic acid [DNA] sequence) comprising one or more double stranded regions and one or more single stranded regions; and ii) one or more oligonucleotide probes complementary to at least a portion of said folded target; and b) mixing said folded target and said one or more probes under conditions such that said probe hybridizes to said folded target to form a probe/folded target complex. The degree of complementarity between the probes and the target nucleic acids may be complete or partial (e.g., contain at least one mismatched base pair). The method is not limited by the nature of the target DNA employed to provide the folded target DNA. In one embodiment, the target DNA comprises single-stranded DNA. In another embodiment, the target DNA comprises double-stranded DNA. Folded target DNAs may be produced from either single-stranded or double-stranded target DNAs by denaturing (e.g., heating) the DNA and then permitting the DNA to form intra-strand secondary structures. The method is not limited by the manner in which the folded target DNA is generated. The target DNA may be denatured by a variety of methods known to the art including heating, exposure to alkali, etc. and then permitted to renature under conditions that favor the formation of intra-strand duplexes (e.g., cooling, diluting the DNA solution, neutralizing the pH, etc.).

The method is also not limited by the nature of the oligonucleotide probes; these probes may comprise DNA, RNA, PNA and combinations thereof as well as comprise modified nucleotides, universal bases, adducts, etc.

In a preferred embodiment, the method further comprises detecting the presence of said probe/folded target complex. When a detection step is employed either the probe or the target DNA (or both) may comprise a label (i.e., a detectable moiety); the invention is not limited by the nature of the label employed or the location of the label (i.e., 5' end, 3' end, internal to the DNA sequence). A wide variety of suitable labels are known to the art and include fluorescein, tetrachlorofluorescein, hexachlorofluorescein, Cy3, Cy5, digoxigenin, and radioisotopes (e.g., $^{32}P$, $^{35}S$). In another preferred embodiment, the method further comprises quantitating the amount of probe/folded target complex formed. The method is not limited by the means used for quantitification; when a labeled folded target DNA is employed (e.g., fluorescein or $^{32}P$), the art knows means for quantification (e.g., determination of the amount of fluorescence or radioactivity present in the probe/folded target complex).

In a preferred embodiment, the probe in the probe/folded target complex is hybridized to a single stranded region of said folded target. In another preferred embodiment, the probe comprises an oligonucleotide having a moiety that permits its capture by a solid support. The invention is not limited by the nature of the moiety employed to permit capture. Numerous suitable moieties are known to the art, including but not limited to, biotin, avidin and streptavidin. Further, it is known in the art that many small compounds, such as fluorescein and digoxigenin may serve as haptens for specific capture by appropriate antibodies. Protein conjugates may also be used to allow specific capture by antibodies.

In a preferred embodiment the detection of the presence of said probe/folded target complex comprises exposing said probe/folded target complex to a solid support under conditions such that said probe is captured by said solid support. As discussed in further detail below, numerous suitable solid supports are known to the art (e.g., beads, particles, dipsticks, wafers, chips, membranes or flat surfaces composed of agarose, nylon, plastics such as polystyrenes, glass or silicon) and may be employed in the present methods.

In a particularly preferred embodiment, the moiety comprises a biotin moiety and said solid support comprises a surface having a compound capable of binding to said biotin moiety, said compound selected from the group consisting of avidin and streptavidin.

In another embodiment, the folded target comprises a deoxyribonucleic acid sequence having a moiety that permits its capture by a solid support; as discussed above a number of suitable moieties are known and may be employed in the present method. In yet another embodiment, the detection of the presence of said probe/folded target complex comprises exposing said probe/folded target complex to a solid support under conditions such that said folded target is captured by said solid support. In a preferred embodiment, the moiety comprises a biotin moiety and said solid support comprises a surface having a compound capable of binding to said biotin moiety, said compound selected from the group consisting of avidin and streptavidin.

In a preferred embodiment, the probe is attached to a solid support; the probe is attached to the solid support in such a manner that the probe is available for hybridization with the folded target nucleic acid. The invention is not limited by the means employed to attach the probe to the solid support. The probe may be synthesized in situ on the solid support or the probe may be attached (post-synthesis) to the solid support via a moiety present on the probe (e.g., using a biotinylated probe and solid support comprising avidin or streptavidin). In another preferred embodiment, the folded target nucleic acid is attached to a solid support; this may be accomplished for example using a moiety present on the folded target (e.g., using a biotinylated target nucleic acid and solid support comprising avidin or streptavidin).

The present invention also provides a method, comprising: a) providing: i) a first folded target having a nucleic acid sequence comprising first and second portions, said first and second portions each comprising one or more double stranded regions and one or more single stranded regions; ii) a second folded target having a nucleic acid sequence comprising a first portion that is identical to said first portion of said first folded target and a second portion that differs from said second portion of said first folded target because of a variation in nucleic acid sequence relative to said first folded target, said first and second portions each comprising one or more double stranded regions and one or more single stranded regions; iii) first and second oligonucleotide probes, said first oligonucleotide probe complementary to said first portion of said first and second folded targets and said second oligonucleotide probe complementary to said second portion of said first and second folded targets; and iv) a solid support comprising first, second, third and fourth testing zones, each zone capable of capturing and immobilizing said first and second oligonucleotide probes; b) contacting said first folded target with said first oligonucleotide probe under conditions such that said first probe binds to said first folded target to form a probe/folded target complex in a first mixture; c) contacting said first folded target with said second oligonucleotide probes under conditions such that said second probe binds to said first folded target to form a probe/folded target complex in a second mixture; d) contacting said second folded target with said first oligonucleotide probe to form a third mixture; e) contacting said second folded target with said second oligonucleotide probe to form fourth mixture; and f) adding said first, second, third and fourth mixtures to said first, second, third and fourth testing zones of said solid support, respectively, under conditions such that said probes are captured and immobilized. The degree of complementarity between the probes and the target nucleic acids may be complete or partial (e.g., contain at least one mismatched base pair).

In a preferred embodiment, the first probe in step d) does not substantially hybridize to said second folded target; that is while it is not required that absolutely no formation of a first probe/second folded target complex occurs, very little of this complex is formed. In another preferred embodiment, the hybridization of said first probe in step d) to said second folded target is reduced relative to the hybridization of said first probe in step c) to said first folded target.

The method is not limited by the nature of the first and second targets. The first and second targets may comprise double- or single-stranded DNA or RNA. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA. The present invention further provides a method, comprising: a) providing: i) a first folded target having a nucleic acid sequence comprising first and second portions, said first and second portions each comprising one or more double stranded regions and one or more single stranded regions; ii) a second folded target having a nucleic acid sequence comprising a first portion that is identical to said first portion of said first folded target and a second portion that differs from said second portion of said first folded target because of a variation in nucleic acid sequence relative to said first folded target, said first and second portions each comprising one or more double stranded regions and one or more single stranded regions; iii) a solid support comprising first and second testing zones, each of said zones comprising immobilized first and second oligonucleotide probes, said first oligonucleotide probe complementary to said first portion of said first and second folded targets and second oligonucleotide probe complementary to said second portion of said first and second folded targets; and b) contacting said first and second folded targets with said solid support under conditions such that said first and second probes hybridize to said first folded target to form a probe/folded target complex. The invention is not limited by the nature of the first and second folded targets. The first and second targets may be derived from double- or single-stranded DNA or RNA. The probes may be completely or partially complementary to the target nucleic acids. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA. The invention is not limited by the nature of the solid support employed as discussed above.

In a preferred embodiment, the contacting of step b) comprises adding said first folded target to said first testing zone and adding said second folded target to said second testing zone. In another preferred embodiment, the first and second probes are immobilized in separate portions of said testing zones.

In a preferred embodiment, the first probe in said second testing zone does not substantially hybridize to said second folded target; that is while it is not required that absolutely no formation of a first probe/second folded target complex occurs, very little of this complex is formed. In another preferred embodiment, the first probe in said second testing zone hybridizes to said second folded target with a reduced efficiency compared to the hybridization of said first probe in first testing zone to said first folded target.

In one embodiment, the first and second folded targets comprise DNA. In another embodiment, the first and second folded targets comprise RNA.

The present invention also provides a method for treating nucleic acid, comprising: a) providing: i) a nucleic acid target and ii) one or more oligonucleotide probes; b) treating the nucleic acid target and the probes under conditions such that the target forms one or more folded structures and interacts with one or more probes; and c) analyzing the complexes formed between the probes and the target. In a preferred embodiment, the method further comprises providing a solid support for the capture of the target/probe complexes. Such capture may occur after the formation of the structures, or either the probe or the target may be bound to the support before complex formation.

The method is not limited by the nature of the nucleic acid target employed. In one embodiment, the nucleic acid of step (a) is substantially single-stranded. In another embodiment, the nucleic acid is RNA or DNA. It is contemplated that the nucleic acid target comprise a nucleotide analog, including but not limited to the group comprising 7-deaza-dATP, 7-deaza-dGTP and dUTP. The nucleic acid target may be double stranded. When double-stranded nucleic acid targets are employed, the treating of step (b) comprises: i) rendering the double-stranded nucleic acid substantially single-stranded; and ii) exposing the single-stranded nucleic acid to conditions such that the single-stranded nucleic acid has secondary structure. The invention is not limited by the method employed to render the double-stranded nucleic acid substantially single-stranded; a variety of means known to the art may be employed. A preferred means for rendering double stranded nucleic acid substantially single-stranded is by the use of increased temperature.

In a preferred embodiment, the method further comprises the step of detecting said one or more target/probe complexes. The invention is not limited by the methods used for the detection of the complex(es).

In some embodiments of the present invention, the methods of the present invention are used for the detection and identification of microorganisms. It is contemplated that the microorganism(s) of the present invention be selected from a variety of microorganisms; it is not intended that the present invention be limited to any particular type of microorganism. Rather, it is intended that the present invention is used with organisms including, but not limited to, bacteria, fungi, protozoa, ciliates, and viruses. It is not intended that the microorganisms be limited to a particular genus, species, strain, or serotype. Indeed, it is contemplated that the bacteria be selected from the group comprising, but not limited to members of the genera Campylobacter, Escherichia, Mycobacterium, Salmonella, Shigella, and Staphylococcus. In one preferred embodiment, the microorganism(s) comprise strains of multi-drug resistant *Mycobacterium tuberculosis*. It is also contemplated that the present invention be used with viruses, including but not limited to hepatitis C virus, human immunodeficiency virus and simian immunodeficiency virus.

Another embodiment of the present invention contemplates a method for detecting and identifying strains of microorganisms, comprising the steps of extracting nucleic acid from a sample suspected of containing one or more microorganisms; and contacting the extracted nucleic acid with one or more oligonucleotide probes under conditions such that the extracted nucleic acid forms one or more secondary structures and interacts with one or more probes. In one embodiment, the method further comprises the step of capturing the complexes to a solid support. In yet another embodiment, the method further comprises the step of detecting the captured complexes. In one preferred embodiment, the present invention further comprises comparing the detected from the extracted nucleic acid isolated from the sample with separated complexes derived from one or more reference microorganisms. In such a case the sequence of the nucleic acids from one or more reference microorganisms may be related but different (e.g., a wild type control for a mutant sequence or a known or previously characterized mutant sequence).

In an alternative preferred embodiment, the present invention further comprises the step of isolating a polymorphic locus from the extracted nucleic acid after the extraction step, so as to generate a nucleic acid target, wherein the target is contacted with one or more probe oligonucleotides. In one embodiment, the isolation of a polymorphic locus is accomplished by polymerase chain reaction amplification. In an alternate embodiment, the polymerase chain reaction is conducted in the presence of a nucleotide analog, including but not limited to the group comprising 7-deaza-dATP, 7-deaza-dGTP and dUTP. It is contemplated that the polymerase chain reaction amplification will employ oligonucleotide primers matching or complementary to consensus gene sequences derived from the polymorphic locus. In one embodiment, the polymorphic locus comprises a ribosomal RNA gene. In a particularly preferred embodiment, the ribosomal RNA gene is a 16S ribosomal RNA gene.

The present invention also contemplates a process for creating a record reference library of genetic fingerprints characteristic (i.e., diagnostic) of one or more alleles of the various microorganisms, comprising the steps of providing a nucleic acid target derived from microbial gene sequences; comprising the steps of extracting nucleic acid from a sample suspected of containing one or more microorganisms; and contacting the extracted nucleic acid with one or more oligonucleotide probes under conditions such that the extracted nucleic acid forms one or more secondary structures and interacts with one or more probes; detecting the captured complexes; and maintaining a testable record reference of the captured complexes.

By the term “genetic fingerprint” it is meant that changes in the sequence of the nucleic acid (e.g., a deletion, insertion or a single point substitution) alter both the sequences detectable by standard base pairing, and alter the structures formed, thus changing the profile of interactions between the target and the probe oligonucleotides (e.g., altering the identity of the probes with which interaction occurs and/or altering the site/s or strength of the interaction). The measure of the identity of the probes bound and the strength of the interactions constitutes an informative profile that can serve as a “fingerprint” of the nucleic acid, reflecting the sequence and allowing rapid detection and identification of variants.

The methods of the present invention allow for simultaneous analysis of both strands (e.g., the sense and antisense strands) and are ideal for high-level multiplexing. The products produced are amenable to qualitative, quantitative and positional analysis. The present methods may be automated and may be practiced in solution or in the solid phase (e.g., on a solid support). The present methods are powerful in that they allow for analysis of longer fragments of nucleic acid than currently available methodologies.

The present invention also provides a method, comprising: a) providing: i) a folded target having a deoxyribonucleic acid (DNA) sequence comprising one or more double stranded regions and one or more single stranded regions; and ii) one or more oligonucleotide probes complementary to at least a portion of the folded target; and b) mixing the folded target and the one or more probes under conditions such that the probe hybridizes to the folded target to form a probe/folded target complex. The degree of complementarity between the probes and the target nucleic acids may be complete or partial (e.g., contain at least one mismatched base pair). The method is not limited by the nature of the target DNA employed to provide the folded target DNA. In one embodiment, the target DNA comprises single-stranded DNA. In another embodiment, the target DNA comprises double-stranded DNA. Folded target DNAs may be produced from either single-stranded or double-stranded target DNAs by denaturing (e.g., heating) the DNA and then permitting the DNA to form intra-strand secondary structures. The method is not limited by the manner in which the folded target DNA is generated. The target DNA may be denatured by a variety of methods known to the art including heating, exposure to alkali, etc. and then permitted to renature under conditions that favor the formation of intra-strand duplexes (e.g., cooling, diluting the DNA solution, neutralizing the pH, etc.).

The present invention also provides a method, comprising: a) providing: i) a first folded target having a nucleic acid sequence comprising first and second portions, said first and second portions each comprising one or more double stranded regions, and one or more single stranded regions, and further comprising two or more non-contiguous portions, and one or more intervening regions; ii) a second folded target having a nucleic acid sequence comprising a first portion that is identical to said first portion of said first folded target and a second portion that differs from said second portion of said first folded target because of a variation in nucleic acid sequence relative to said first folded target, said first and second portions each comprising one or more double stranded regions, and one or more single stranded regions, and further comprising two or more non-contiguous portions, and one or more intervening regions; iii) first and second bridging oligonucleotides, said first bridging oligonucleotide complementary to said two or more non-contiguous portions of said first portion of said first and second folded targets and said second bridging oligonucleotide complementary to said two or more non-contiguous portions of said second portion of said first and second folded targets; and iv) a solid support comprising first, second, third and fourth testing zones, each zone capable of capturing and immobilizing said first and second bridging oligonucleotides; b) contacting the first folded target with the first oligonucleotide probe under conditions such that the first probe binds to the first folded target to form a probe/folded target complex in a first mixture; c) contacting the first folded target with the second oligonucleotide probes under conditions such that the second probe binds to the first folded target to form a probe/folded target complex in a second mixture; d) contacting the second folded target with the first oligonucleotide probe to form a third mixture; e) contacting the second folded target with the second oligonucleotide probe to form a fourth mixture; and f) adding the first, second, third and fourth mixtures to the first, second, third and fourth testing zones of the solid support, respectively, under conditions such that the probes are captured and immobilized. The degree of complementarity between the probes and the target nucleic acids may be complete or partial (e.g., contain at least one mismatched base pair).

In a preferred embodiment, the first probe in step d) does not substantially hybridize to the second folded target; that is while it is not required that absolutely no formation of a first probe/second folded target complex occurs, very little of this complex is formed. In another preferred embodiment, the hybridization of the first probe in step d) to the second folded target is reduced relative to the hybridization of the first probe in step c) to the first folded target.

The method is not limited by the nature of the first and second targets. The first and second targets may comprise double- or single-stranded DNA or RNA. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA.

The present invention further provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second oligonucleotide probes, the first oligonucleotide probe complementary to the first portion of the first and second folded targets and second oligonucleotide probe complementary to the second portion of the first and second folded targets; and b) contacting the first and second folded targets with the solid support under conditions such that the first and second probes hybridize to the first folded target to form a probe/folded target complex. The invention is not limited by the nature of the first and second folded targets. The first and second targets may be derived from double- or single-stranded DNA or RNA. The probes may be completely or partially complementary to the target nucleic acids. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA. The invention is not limited by the nature of the solid support employed as discussed above.

In a preferred embodiment, the contacting of step b) comprises adding the first folded target to the first testing zone and adding the second folded target to the second testing zone. In another preferred embodiment, the first and second probes are immobilized in separate portions of the testing zones.

In a preferred embodiment, the first probe in the second testing zone does not substantially hybridize to the second folded target; that is while it is not required that absolutely no formation of a first probe/second folded target complex occurs, very little of this complex is formed. In another preferred embodiment, the first probe in the second testing zone hybridizes to the second folded target with a reduced efficiency compared to the hybridization of the first probe in first testing zone to the first folded target.

In one embodiment, the first and second folded targets comprise DNA. In another embodiment, the first and second folded targets comprise RNA.

The present invention also provides a method for treating nucleic acid, comprising: a) providing: i) a nucleic acid target and ii) one or more oligonucleotide probes; b) treating the nucleic acid target and the probes under conditions such that the target forms one or more folded structures and interacts with one or more probes; and c) analyzing the complexes formed between the probes and the target. In a preferred embodiment, the method further comprises providing a solid support for the capture of the target/probe complexes. Such capture may occur after the formation of the structures, or either the probe or the target may be bound to the support before complex formation.

The present invention further provides methods for determination of structure formation in nucleic acid targets, comprising the steps of: a) providing: i) a folded target having a deoxyribonucleic acid sequence comprising one or more double stranded regions, and one or more single stranded regions, and further comprising two or more non-contiguous portions, and one or more intervening regions; and ii) one or more bridging oligonucleotide probes complementary to two or more non-contiguous portions of the folded target; and b) mixing the folded target and one or more bridging oligonucleotide probes under conditions such that the bridging oligonucleotide probes hybridize to the folded target to form a probe/folded target complex.

In preferred embodiments, the one or more intervening regions of the folded targets comprise at least five nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In alternative embodiments, the method further comprises detecting the presence of the probe/folded target complex. In yet other embodiments, the method further comprises quantitating the amount of probe/folded target complex formed. In yet other embodiments of the method, the bridging oligonucleotide probe in the probe/folded target complex is hybridized to at least one single stranded region of the folded target.

The method is not limited by the nature of the target DNA employed to provide the folded target DNA, nor is the method limited by the manner in which the folded target DNA is generated. The method is also not limited by the nature of the bridging oligonucleotide probes; these probes may comprise DNA, RNA, PNA and combinations thereof as well as comprise modified nucleotides, universal bases, adducts, etc.

In a preferred embodiment, the method further comprises detecting the presence of the probe/folded target complex. When a detection step is employed either the bridging oligonucleotide probe or the target DNA (or both) may comprise a label (i.e., a detectable moiety); the invention is not limited by the nature of the label employed or the location of the label (i.e., 5' end, 3' end, internal to the DNA sequence). In another preferred embodiment, the bridging oligonucleotide probe comprises a bridging oligonucleotide having a moiety that permits its capture by a solid support. In a preferred embodiment the detection of the presence of the probe/folded target complex comprises exposing the probe/folded target complex to a solid support under conditions such that the bridging oligonucleotide probe is captured by the solid support.

The present invention also provides methods for analyzing the structure of nucleic acid targets, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second bridging oligonucleotides, wherein the first bridging oligonucleotide is complementary to the first portion of the first and second folded targets and the second bridging oligonucleotide is complementary to the second portion of the first and second folded targets; and iv) a solid support comprising first, second, third and fourth testing zones, each zone capable of capturing and immobilizing the first and second bridging oligonucleotides; b) contacting the first folded target with the first bridging oligonucleotide under conditions such that the first bridging oligonucleotide binds to the first folded target to form a probe/folded target complex in a first mixture; c) contacting the first folded target with the second bridging oligonucleotide under conditions such that the second bridging oligonucleotide binds to the first folded target to form a probe/folded target complex in a second mixture; d) contacting the second folded target with the first bridging oligonucleotide to form a third mixture; e) contacting the second folded target with the second bridging oligonucleotide to form fourth mixture; and f) adding the first, second, third and fourth mixtures to the first, second, third and fourth testing zones of the solid support, respectively, under conditions such that the first and second bridging oligonucleotides are captured and immobilized.

The method is not limited by the nature of the first and second targets. The first and/or second target may comprise one or more non-contiguous regions, as well as one or more intervening regions. In preferred embodiments, the intervening regions comprise at least five nucleotides. The method is also not limited by the nature of the bridging oligonucleotide probes; these bridging oligonucleotide probes may comprise DNA, RNA, PNA and combinations thereof as well as comprise modified nucleotides, universal bases, adducts, etc. In some embodiments, the first and/or second bridging oligonucleotide probes comprise one or more intervening regions. In alternative embodiments, the intervening region of the bridging oligonucleotide probes comprises at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In a preferred embodiment, the first and second bridging oligonucleotide probes comprise DNA.

In alternative embodiments, the first bridging oligonucleotide in step d) does not substantially hybridize to the second folded target. In yet another embodiment, the hybridization of the first bridging oligonucleotide in step d) to the second folded target is reduced relative to the hybridization of the first bridging oligonucleotide in step c) to the first folded target. In further embodiments, the first and second targets comprise DNA, and/or the first and second bridging oligonucleotides comprise DNA.

The present invention also provides methods for analyzing folded nucleic acid targets, comprising: a) providing: i) a first folded target having a nucleic acid sequence comprising first and second portions, wherein the first and second portions each comprise one or more double stranded regions and one or more single stranded regions; ii) a second folded target having a nucleic acid sequence comprising a first portion that is identical to the first portion of the first folded target, and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second bridging oligonucleotides, the first bridging oligonucleotide being complementary to the first portion of the first and second folded targets and second bridging oligonucleotide being complementary to the second portion of the first and second folded targets; and b) contacting the first and second folded targets with the solid support under conditions such that the first and second bridging oligonucleotides hybridize to the first folded target to form a probe/folded target complex.

In some embodiments, the contacting of step b) comprises adding the first folded target to the first testing zone and adding the second folded target to the second testing zone. In alternative embodiments, the first and second bridging oligonucleotides are immobilized in separate portions of the testing zones. In yet other embodiments, the first bridging oligonucleotide in the second testing zone does not substantially hybridize to the second folded target. In further embodiments, the first bridging oligonucleotide in the second testing zone hybridizes to the second folded target with a reduced efficiency compared to the hybridization of the first bridging oligonucleotide in first testing zone to the first folded target.

The method is not limited by the nature of, nor the method of generating the first and second folded targets. The method is also not limited by the nature of, or the method of generating the oligonucleotide probes; these probes may comprise DNA, RNA, PNA and combinations thereof as well as comprise modified nucleotides, universal bases, adducts, etc. In some embodiments, the first and/or second folded target comprises one or more intervening region comprised of at least five nucleotides. In yet other embodiments, the first and/or second bridging oligonucleotide probe comprises one or more intervening regions comprised of at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. The invention is not limited by the nature of the solid support employed as discussed above. In some preferred embodiments of the method, the first and second folded targets comprise DNA. In alternative embodiments, the first and second folded targets comprise RNA. In yet other embodiments, the first and second bridging oligonucleotides comprise DNA.

In one embodiment, the present invention provides a method, comprising: a) providing: i) a folded target having a deoxyribonucleic acid (DNA) sequence comprising one or more double stranded regions and one or more single stranded regions; and ii) one or more oligonucleotide probes complementary to at least a portion of the folded target; and b) mixing the folded target and the one or more probes under conditions such that the probe hybridizes to the folded target to form a probe/folded target complex. The degree of complementarity between the probes and the target nucleic acids may be complete or partial (e.g., contain at least one mismatched base pair). The method is not limited by the nature of the target DNA employed to provide the folded target DNA. In one embodiment, the target DNA comprises single-stranded DNA. In another embodiment, the target DNA comprises double-stranded DNA. Folded target DNAs may be produced from either single-stranded or double-stranded target DNAs by denaturing (e.g., heating) the DNA and then permitting the DNA to form intra-strand secondary structures. The method is not limited by the manner in which the folded target DNA is generated. The target DNA may be denatured by a variety of methods known to the art including heating, exposure to alkali, etc. and then permitted to renature under conditions that favor the formation of intra-strand duplexes (e.g., cooling, diluting the DNA solution, neutralizing the pH, etc.).

The present invention also provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second oligonucleotide probes, the first oligonucleotide probe complementary to the first portion of the first and second folded targets and the second oligonucleotide probe complementary to the second portion of the first and second folded targets; and iv) a solid support comprising first, second, third and fourth testing zones, each zone capable of capturing and immobilizing the first and second oligonucleotide probes; b) contacting the first folded target with the first oligonucleotide probe under conditions such that the first probe binds to the first folded target to form a probe/folded target complex in a first mixture; c) contacting the first folded target with the second oligonucleotide probes under conditions such that the second probe binds to the first folded target to form a probe/folded target complex in a second mixture; d) contacting the second folded target with the first oligonucleotide probe to form a third mixture; e) contacting the second folded target with the second oligonucleotide probe to form fourth mixture; and f) adding the first, second, third and fourth mixtures to the first, second, third and fourth testing zones of the solid support, respectively, under conditions such that the probes are captured and immobilized. The degree of complementarity between the probes and the target nucleic acids may be complete or partial (e.g., contain at least one mismatched base pair).

In a preferred embodiment, the first probe in step d) does not substantially hybridize to the second folded target; that is while it is not required that absolutely no formation of a first probe/second folded target complex occurs, very little of this complex is formed. In another preferred embodiment, the hybridization of the first probe in step d) to the second folded target is reduced relative to the hybridization of the first probe in step c) to the first folded target.

The present invention further provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second oligonucleotide probes, the first oligonucleotide probe complementary to the first portion of the first and second folded targets and second oligonucleotide probe complementary to the second portion of the first and second folded targets; and b) contacting the first and second folded targets with the solid support under conditions such that the first and second probes hybridize to the first folded target to form a probe/folded target complex. The invention is not limited by the nature of the first and second folded targets. The first and second targets may be derived from double- or single-stranded DNA or RNA. The probes may be completely or partially complementary to the target nucleic acids. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA. The invention is not limited by the nature of the solid support employed as discussed above.

In a preferred embodiment, the contacting of step b) comprises adding the first folded target to the first testing zone and adding the second folded target to the second testing zone. In another preferred embodiment, the first and second probes are immobilized in separate portions of the testing zones.

In a preferred embodiment, the first probe in the second testing zone does not substantially hybridize to the second folded target; that is while it is not required that absolutely no formation of a first probe/second folded target complex occurs, very little of this complex is formed. In another preferred embodiment, the first probe in the second testing zone hybridizes to the second folded target with a reduced efficiency compared to the hybridization of the first probe in first testing zone to the first folded target.

In one embodiment, the first and second folded targets comprise DNA. In another embodiment, the first and second folded targets comprise RNA.

The present invention also provides a method for treating nucleic acid, comprising: a) providing: i) a nucleic acid target and ii) one or more oligonucleotide probes; b) treating the nucleic acid target and the probes under conditions such that the target forms one or more folded structures and interacts with one or more probes; and c) analyzing the complexes formed between the probes and the target. In a preferred embodiment, the method further comprises providing a solid support for the capture of the target/probe complexes. Such capture may occur after the formation of the structures, or either the probe or the target may be bound to the support before complex formation.

The method is not limited by the nature of the nucleic acid target employed. In one embodiment, the nucleic acid of step (a) is substantially single-stranded. In another embodiment, the nucleic acid is RNA or DNA. It is contemplated that the nucleic acid target comprise a nucleotide analog, including but not limited to the group comprising 7-deaza-dATP, 7-deaza-dGTP and dUTP. The nucleic acid target may be double stranded. When double-stranded nucleic acid targets are employed, the treating of step (b) comprises: i) rendering the double-stranded nucleic acid substantially single-stranded; and ii) exposing the single-stranded nucleic acid to conditions such that the single-stranded nucleic acid has secondary structure. The invention is not limited by the method employed to render the double-stranded nucleic acid substantially single-stranded; a variety of means known to the art may be employed. A preferred means for rendering double stranded nucleic acid substantially single-stranded is by the use of increased temperature.

In a preferred embodiment, the method further comprises the step of detecting the one or more target/probe complexes. The invention is not limited by the methods used for the detection of the complex(es).

The present invention further provides methods for determination of structure formation in nucleic acid targets, comprising the steps of: a) providing: i) a folded target having a deoxyribonucleic acid sequence comprising one or more double stranded regions, and one or more single stranded regions, and further comprising two or more non-contiguous portions, and one or more intervening regions; and ii) one or more bridging oligonucleotide probes complementary to two or more non-contiguous portions of the folded target; and b) mixing the folded target and one or more bridging oligonucleotide probes under conditions such that the bridging oligonucleotide probes hybridize to the folded target to form a probe/folded target complex.

In preferred embodiments, the one or more intervening regions of the folded targets comprise at least five nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In alternative embodiments, the method further comprises detecting the presence of the probe/folded target complex. In yet other embodiments, the method further comprises quantitating the amount of probe/folded target complex formed. In yet other embodiments of the method, the bridging oligonucleotide probe in the probe/folded target complex is hybridized to at least one single stranded region of the folded target. In a preferred embodiment, the method further comprises detecting the presence of the probe/folded target complex.

Detection of the probe/folded target complex may also involve a catalyzed reaction on the probe that can only occur upon binding. It is contemplated that such catalyzed reaction may be mediated by an enzyme. By way of example, but not by way of limitation, the bound bridging oligonucleotide probe may be extended by a DNA polymerase, joined to another nucleic acid by the action of a ligase, or cleaved by a structure-specific nuclease. It is further contemplated that the catalytic action may be chemical, rather then enzymatic. For example, the cleavage of nucleic acid by compounds such as phenanthroline-Cu is specific for duplexed structures. It is contemplated that any chemical that can act upon nucleic acid in a manner that is responsive to the strandedness or other structural feature of the complex of the target may be used in the detection of the probe/folded target complex.

It is contemplated that any catalyzed reaction that is specifically operative on a duplex formed between a target nucleic acid and a substantially complementary probe may be configured to perform on the bridging probe/folded target complex.

In another embodiment the bound probe may participate in a reaction requiring a one or more additional nucleic acids, such as ligation reaction a polymerase chain reaction, a 5' nuclease reaction, (Lyamichev et al., Science 260: 778 [1993]; U.S. Pat. No. 5,422,253, herein incorporated by reference), or an INVADER invasive cleavage reaction (PCT Publications WO 97/27214 and 98/42873; and U.S. Pat. Nos. 5,846,717, 6,001,567, 5,985,557, 6,090,543, and 5,994,069, all of which are herein incorporated by reference in their entireties). In one embodiment, the additional nucleic acid includes another hybridized probe. In another embodiment, the additional nucleic acid includes the target. In a preferred embodiment, the additional nucleic acid includes a bridging oligonucleotide probe complementary to two or more non-contiguous portions of the folded target.

It is contemplated that a nucleic acid on which the catalyzed reaction acts may be labeled. Thus detection of the complex on which the catalyzed reaction has acted may comprise detection of a labeled product or products of that reaction. The invention is not limited by the nature of the label used, including, but not limited to, labels that comprise a dye or a radionuclide (e.g., $^{32}P$), fluorescein moiety, a biotin moiety, luminogenic, fluorogenic, phosphorescent, or fluorophores in combination with moieties that can suppress emission by fluorescence resonance energy transfer (FRET). Numerous methods are available for the detection of nucleic acids containing any of the above-listed labels. For example, biotin-labeled oligonucleotide(s) may be detected using non-isotopic detection methods that employ streptavidin-alkaline phosphatase conjugates. Fluorescein-labeled oligonucleotide(s) may be detected using a fluorescein-imager. The oligonucleotides may be labeled with different labels. The different labels may be present on the probe before the catalytic reaction. In this embodiment the release of the labels from attachment to the same complex (e.g., by FRET analysis), may be used to detect formation of the probe/folded target complex. Alternatively, one or more of the labels may be added to the complex as a result of the catalytic reaction (e.g., by ligation to a labeled nucleic acid or by polymerization using labeled nucleoside triphosphates).

It is also contemplated that labeled oligonucleotides (reacted or unreacted) may be separated by means other than electrophoresis. For example, biotin-labeled oligonucleotides may be separated from nucleic acid present in the reaction mixture using para-magnetic or magnetic beads, or particles that are coated with avidin (or streptavidin). In this manner, the biotinylated oligonucleotide/avidin-magnetic bead complex can be physically separated from the other components in the mixture by exposing the complexes to a magnetic field. Additionally, the signal from the reacted oligonucleotides may be resolved from that of the unreacted oligonucleotides without physical separation. For example, a change in size as may be caused by binding to another oligonucleotide, or by cleavage, ligation or polymerase extension of at least one nucleic acid in the complex, will change the rate of rotation in solution, allowing of fluorescently labeled complexes or product molecules to be detected by fluorescence polarization analysis. However, it is not intended that the means of analysis be limited to those methods of cited above. Those skilled in the art of nucleic acid analysis will appreciate that there are numerous additional methods for the analysis of both of labeled and unlabeled nucleic acids that are readily adaptable for the detection of the probe/folded target complexes of the present invention. In another preferred embodiment, the bridging oligonucleotide probe comprises a bridging oligonucleotide having a moiety that permits its capture by a solid support.

The present invention also provides methods for analyzing the structure of nucleic acid targets, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second bridging oligonucleotides, wherein the first bridging oligonucleotide is complementary to the first portion of the first and second folded targets and the second bridging oligonucleotide is complementary to the second portion of the first and second folded targets; and iv) a solid support comprising first, second, third and fourth testing zones, each zone capable of capturing and immobilizing the first and second bridging oligonucleotides; b) contacting the first folded target with the first bridging oligonucleotide under conditions such that the first bridging oligonucleotide binds to the first folded target to form a probe/folded target complex in a first mixture; c) contacting the first folded target with the second bridging oligonucleotide under conditions such that the second bridging oligonucleotide binds to the first folded target to form a probe/folded target complex in a second mixture; d) contacting the second folded target with the first bridging oligonucleotide to form a third mixture; e) contacting the second folded target with the second bridging oligonucleotide to form fourth mixture; and f) adding the first, second, third and fourth mixtures to the first, second, third and fourth testing zones of the solid support, respectively, under conditions such that the first and second bridging oligonucleotides are captured and immobilized.

The method is not limited by the nature of the first and second targets. The first and/or second target may comprise one or more non-contiguous regions, as well as one or more intervening regions. In preferred embodiments, the intervening regions comprise at least five nucleotides. The method is also not limited by the nature of the bridging oligonucleotide probes; these bridging oligonucleotide probes may comprise DNA, RNA, PNA and combinations thereof as well as comprise modified nucleotides, universal bases, adducts, etc. In some embodiments, the first and/or second bridging oligonucleotide probes comprise one or more intervening regions. In alternative embodiments, the intervening region of the bridging oligonucleotide probes comprises at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In a preferred embodiment, the first and second bridging oligonucleotide probes comprise DNA.

In alternative embodiments, the first bridging oligonucleotide in step d) does not substantially hybridize to the second folded target. In yet another embodiment, the hybridization of the first bridging oligonucleotide in step d) to the second folded target is reduced relative to the hybridization of the first bridging oligonucleotide in step c) to the first folded target. In further embodiments, the first and second targets comprise DNA, and/or the first and second bridging oligonucleotides comprise DNA.

The present invention also provides methods for analyzing folded nucleic acid targets, comprising: a) providing: i) a first folded target having a nucleic acid sequence comprising first and second portions, wherein the first and second portions each comprise one or more double stranded regions and one or more single stranded regions; ii) a second folded target having a nucleic acid sequence comprising a first portion that is identical to the first portion of the first folded target, and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second bridging oligonucleotides, the first bridging oligonucleotide being complementary to the first portion of the first and second folded targets and second bridging oligonucleotide being complementary to the second portion of the first and second folded targets; and b) contacting the first and second folded targets with the solid support under conditions such that the first and second bridging oligonucleotides hybridize to the first folded target to form a probe/folded target complex.

In some embodiments, the contacting of step b) comprises adding the first folded target to the first testing zone and adding the second folded target to the second testing zone. In alternative embodiments, the first and second bridging oligonucleotides are immobilized in separate portions of the testing zones. In yet other embodiments, the first bridging oligonucleotide in the second testing zone does not substantially hybridize to the second folded target. In further embodiments, the first bridging oligonucleotide in the second testing zone hybridizes to the second folded target with a reduced efficiency compared to the hybridization of the first bridging oligonucleotide in first testing zone to the first folded target. The method is not limited by the nature of, nor the method of generating the first and second folded targets. The method is also not limited by the nature of, or the method of generating the oligonucleotide probes; these probes may comprise DNA, RNA, PNA and combinations thereof as well as comprise modified nucleotides, universal bases, adducts, etc. In some embodiments, the first and/or second folded target comprises one or more intervening region comprised of at least five nucleotides. In yet other embodiments, the first and/or second bridging oligonucleotide probe comprises one or more intervening regions comprised of at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. The invention is not limited by the nature of the solid support employed as discussed above. In some preferred embodiments of the method, the first and second folded targets comprise DNA. In alternative embodiments, the first and second folded targets comprise RNA. In yet other embodiments, the first and second bridging oligonucleotides comprise DNA.

The present invention provides methods for detection of structured nucleic acid targets, comprising the steps of: a) providing: i) a folded target having a nucleic acid sequence comprising one or more double stranded regions, and one or more single stranded regions, and further comprising two or more non-contiguous portions, and one or more intervening regions; ii) at least one bridging oligonucleotide probe capable of binding to two or more non-contiguous portions of said folded target; and iii) a reactant; b) mixing said folded target and said probe under conditions such that said probe hybridizes to said folded target to form a probe/folded target complex; and c) treating said probe/folded target complex with said reactant to produce at least one modified probe. In one embodiment the method further provides for the detection of said modified probe.

The present invention further provides a method, comprising: a) providing target nucleic acid comprising first and second non-contiguous single-stranded regions separated by an intervening region comprising a double-stranded portion; a bridging oligonucleotide capable of binding to said first and second non-contiguous single-stranded regions; and a reactant selected from the group consisting of polymerases and ligases; and mixing said target nucleic acid, said bridging oligonucleotide and said reactant under conditions such that said bridging oligonucleotide is modified to produce a modified oligonucleotide.

In some embodiments of the methods, the reactant is a polymerase, while in yet other embodiments, the modified oligonucleotide comprises an extended oligonucleotide. In still other embodiments, the reactant is a polymerase and the modified oligonucleotide comprises extended oligonucleotide. In yet other embodiments, the reactant is a ligase, while in yet other embodiments, the modified oligonucleotide comprises a ligated oligonucleotide. In still other embodiments, the reactant is a ligase and the modified oligonucleotide comprises a ligated oligonucleotide.

In yet other embodiments of the method, the bridging oligonucleotide is capable of binding to fewer than ten nucleotides of each of said first and second non-contiguous single-stranded regions. In still other embodiments, the bridging oligonucleotide is capable of binding to eight or fewer nucleotides of each of said first and second non-contiguous single-stranded regions.

In further embodiments of the method the target nucleic acid is DNA, while in some preferred embodiments, the DNA is viral DNA. In yet other preferred embodiments, the virus is selected from the group consisting of Parvoviridae, Papovaviridae, Adenoviridae, Hepadnaviridae, Herpesviridae, Iridoviridae, and Poxviridae. For example, it is intended that the present invention encompass methods for the detection of any DNA-containing virus, including, but not limited to parvoviruses, dependoviruses, papillomaviruses, polyomaviruses, mastadenoviruses, aviadenoviruses, hepadnaviruses, simplexviruses [such as herpes simplex virus 1 and 2], varicelloviruses, cytomegaloviruses, muromegaloviruses, lymphocryptoviruses, thetalymphocryptoviruses, rhadinoviruses, iridoviruses, ranaviruses, pisciniviruses, orthopoxviruses, parapoxviruses, avipoxviruses, capripoxviruses, leporipoxviruses, suipoxviruses, yatapoxviruses, and mulluscipoxvirus). Thus, it is not intended that the present invention be limited to any DNA virus family.

In further embodiments of the method the target nucleic acid is RNA, while in some preferred embodiments, the RNA is viral RNA. In yet other preferred embodiments, the virus is selected from the group consisting of Picornaviridae, Caliciviridae, Reoviridae, Togaviridae, Flaviviridae, Orthomyxoviridae, Paramyxoviridae, Arenaviridae, Rhabdoviridae, Coronaviridae, Bunyaviridae, and Retroviridae. For example, it is intended that the present invention encompass methods for the detection of RNA-containing virus, including, but not limited to enteroviruses (e.g., polioviruses, Coxsackieviruses, echoviruses, enteroviruses, hepatitis A virus, encephalomyocarditis virus, mengovirus, rhinoviruses, and aphthoviruses), caliciviruses, reoviruses, orbiviruses, rotaviruses, birnaviruses, alphaviruses, rubiviruses, pestiviruses, flaviviruses (e.g., hepatitis C virus, yellow fever viruses, dengue, Japanese, Murray Valley, and St. Louis encephalitis viruses, West Nile fever virus, Kyanasur Forest disease virus, Omsk hemorrhagic fever virus, European and Far Eastern tick-borne encephalitis viruses, and louping ill virus), influenzaviruses (e.g, types A, B, and C), paramyxoviruses, morbilliviruses, pneumoviruses, veisculoviruses, lyssaviruses, filoviruses, coronaviruses, bunyaviruses, phleboviruses, nairoviruses, uukuviruses, hantaviruses, sarcoma and leukemia viruses, oncoviruses, HTLV, spumaviruses, lentiviruses, and arenaviruses).

The present invention also provides a method, comprising: a) providing target nucleic acid comprising first and second non-contiguous single-stranded regions separated by an intervening region comprising a double-stranded region; a bridging oligonucleotide capable of binding to said first and second non-contiguous single-stranded regions; a second oligonucleotide capable of binding to a portion of said first non-contiguous single-stranded region; and a cleavage means; b) mixing said target nucleic acid, said bridging oligonucleotide, said second oligonucleotide, and said cleavage means under conditions such that either said second oligonucleotide or said bridging oligonucleotide is cleaved.

In some preferred embodiments, the cleavage means comprises a nuclease. In other preferred embodiments, the cleavage means comprises a thermostable 5' nuclease. In still other preferred embodiments, the thermostable 5' nuclease comprises an altered polymerase derived from a native polymerases of Thermus species.

In other embodiments of the method, the conditions of mixing allow for hybridization of said bridging oligonucleotide and said second oligonucleotide to said target nucleic acid so as to define a region of overlap of said oligonucleotides. In some embodiments, the region of overlap comprises one base, while in other embodiments, the region of overlap comprises more than one base.

The present invention also provides a method, comprising: a) providing target nucleic acid comprising first and second non-contiguous single-stranded regions separated by an intervening region, said intervening region comprising a first double-stranded portion and a second double-stranded portion separated by a connecting single-stranded portion; and a bridging oligonucleotide capable of binding to said first and second non-contiguous single-stranded regions; and b) mixing said target nucleic acid and said bridging oligonucleotide under conditions such that said bridging oligonucleotide hybridizes to said target to form an oligonucleotide/target complex.

The present invention further provides a method for the analysis of nucleic acid structures comprising; providing a sequence data input means (defined as any means [e.g., a computer input device and software for receiving and storing the sequence information] for entering nucleic acid sequence information into a device capable of storing and/or processing the data), a cleavage data input means (defined as any means [e.g., a computer input device and software for receiving and storing the sequence information] for entering information regarding the location of a cleavage site in a nucleic acid into a device capable of storing and/or processing the data), and a nucleic acid structure prediction means (defined as any means [e.g., software designed to predict the structure of nucleic acids or proteins based on sequence data and other data inputs] capable of predicting nucleic acid sequence based on input data); providing nucleic acid sequence data (defined as any data relating to the sequence of one or more nucleic acid compositions) to said sequence data input means to produce sequence data results; providing structure-specific cleavage data (defined as any data relating to the cleavage status of one or more nucleic acid compositions) to said cleavage data input means to produce cleavage data results; and providing said sequence data results and said cleavage data results to said nucleic acid structure prediction means to produce a predicted nucleic acid structure (defined as any structure capable of interpretation by users [e.g., a pictographic display] or by a device capable of relaying the structural information to a user in any interpretable form).

In some embodiments, the present invention further provides methods for the analysis of nucleic acid structures comprising the steps of e) providing a basepair data input means and a second nucleic acid structure prediction means; f) providing basepair data to said basepair data input means to produce basepair data results; and g) providing said sequence data results, said cleavage data results, and said basepair data results to said second nucleic acid structure prediction means to produce a second predicted nucleic acid structure.

The present invention also provides novel methods for the determination of regions of a nucleic acid of interest that are sequestered (i.e., unavailable for hybridization to other nucleic acid molecules [e.g., oligonucleotide probes and antisense oligonucleotides]) by folding and which are not. This can be referred to as the identification and mapping of accessible sites of folded nucleic acid targets. In the methods of the present invention, accessible sites are quickly mapped (e.g., in a few hours or less) resulting in an accurate map of the accessible sites of the folded target (e.g., a one to two nucleotide precision map). In some embodiments of the present invention, the information derived from such methods is used to select and design antisense oligonucleotides and oligonucleotide probes for any number of uses (e.g., for use in the structure probing methods described above).

In some embodiments, the present invention provides a method for selecting a primer (e.g., a primer capable of binding to an accessible region of a nucleic acid and being extended), comprising providing: 1) a target nucleic acid having at least one accessible site and at least one inaccessible site; a plurality of extension primers (e.g., degenerate primers), each of said primers comprising a first region, wherein the first regions of the plurality of primers differ in sequence from each other, and wherein the plurality of primers comprise first regions that are complementary to different portions of the target nucleic acid; and 3) an extension agent (e.g., a template-dependent nucleic acid extension agent); exposing the plurality of extension primers and the extension agent to the target nucleic acid under conditions wherein primers comprising first regions that are complementary only to an inaccessible site in the target nucleic acid are not extended by said extension agent (e.g., are not detectably extended), and wherein primers comprising first regions that are complementary to at least one accessible site of the target nucleic acid form an extension product; and selecting a primer complementary to at least one accessible site by identifying a member of the plurality of primers that forms an extension product.

The present invention is not limited by the nature of the target nucleic acid. For example, the target nucleic acid may comprise DNA (e.g., folded DNA) or RNA. The target nucleic acid may be from a natural source or may be synthetic. In some embodiments, a DNA may be converted to RNA and the RNA processed in the above steps. In some embodiments of the present invention, the sequence of the target nucleic acid or a portion of the sequence of the target nucleic acid is unknown.

In some preferred embodiments of the present invention, the plurality of primers further comprise a second region located 5' of the first region. In particularly preferred embodiments, the second regions of the plurality of primers are identical in sequence to one another. Such primers find use in methods where the extension products are amplified prior to selection of primers. For example, in some embodiments, the method further comprises providing: 1) first and second amplification primers, said first amplification primer complementary to at least a portion of the second regions of the plurality of extension primers and said second amplification primer capable of hybridizing to a sequence complementary to a first domain of the target nucleic acid, and 2) an amplification agent; and further comprising the step of treating the extension products with the first and second amplification primers and the amplification agents to produce amplification products prior to the selecting step.

Although the present invention is not limited by the number of different primers in the plurality of primers, in certain embodiments of the present invention the plurality of primers comprises at least 10 different primers, at least 100 different primers, at least 1000 different primers, or a sufficient number of primers to encompass every sequence variation within the first region. Although the present invention is not limited by the size of the first region of the extension primers, in preferred embodiments, the first region is six or more nucleotides in length.

The present invention is not limited by the nature of the extension agent. "Extension agents" include any agent capable of adding nucleotides to an oligonucleotide primer. In preferred embodiments, the extension agent is a template-dependent nucleic acid extension agent. In particularly preferred embodiments, the extension agent comprises a polymerase or a reverse transcriptase. The present invention is also not limited by the nature of the amplification agent. In preferred embodiments, the amplification agent is a polymerase (e.g., a thermostable polymerase) and amplification is conducted using the polymerase chain reaction.

The present invention also provides a method for identifying accessible sites on a target nucleic acid comprising providing: 1) a target nucleic acid having at least one accessible site and at least one inaccessible site; 2) a plurality of extension primers, each of the primers comprising a first region, wherein the first regions of the plurality of primers differ in sequence from each other, and wherein the plurality of primers comprise first regions that are complementary to different portions of the target nucleic acid; and 3) a template-dependent nucleic acid extension agent; exposing the plurality of extension primers and the extension agent to the target nucleic acid under conditions wherein primers comprising first regions that are complementary only to an inaccessible site in said target nucleic acid are not extended by the extension agent, and wherein primers comprising first regions that are complementary to at least one accessible site of the target nucleic acid form an extension product that is complementary to the target nucleic acid adjacent to the accessible site; determining at least a portion of the sequence of an extension product; and identifying the accessible site by locating a region of the target nucleic acid adjacent to sequence that is complementary to the extension product.

The present invention further provides a method of locating accessible sites on a target nucleic acid comprising providing: 1) a target nucleic acid having at least one accessible site and at least one inaccessible site, 2) a plurality of extension primers, each of said primers comprising first region and second regions, wherein the first regions of the plurality of primers differ in sequence from each other, wherein the plurality of primers comprise first regions that are complementary to different portions of the target nucleic acid, and wherein the second region is located 5' of the first region; 3) an extension agent; 4) an amplification agent; and 5) first and second amplification primers, said first amplification primer complementary to at least a portion of the second regions of the plurality of extension primers and said second amplification primer capable of hybridizing to a sequence complementary to a first domain of the target nucleic acid; exposing the plurality of extension primers and the extension agent to the target nucleic acid under conditions wherein primers comprising first regions that are complementary only to an inaccessible site in the target nucleic acid are not extended by said extension agent, and wherein primers comprising first regions that are complementary to at least one accessible site of the target nucleic acid form an extension product; treating the extension products with the amplification agent and the first and second amplification primers to generate one or more amplification products, the amplification products having a length, wherein the length of the amplification products provides a distance of an accessible site on the target nucleic acid from the first domain of the target nucleic acid; and determining a location of one or more accessible sites on the target nucleic acid using the distance (e.g., determining the size of one or more of said amplification products).

The above methods may also be used to identify inaccessible regions of the target nucleic acids. For example, extension product may be displayed on an agarose gel. Regions of the gel having no extension products (e.g., regions devoid of extension products comprising a particular length) may be used to determine the location of the inaccessible sites. Any suitable method may also be used to identify these sites.

The present invention also provides oligonucleotides capable of binding to accessible sites of the target nucleic acids using (e.g., determined by) any of the above methods. For example, oligonucleotides are provided that contain a sequence comprising a sequence of a first region of a primer selected by the above methods. The present invention also provides a variety of methods for using oligonucleotides capable of binding to accessible sites as described in detail below. For example, the present invention provides a method comprising, providing any of the oligonucleotides identified by the above methods and a target nucleic acid and exposing the target nucleic acid to the oligonucleotide (e.g., wherein the oligonucleotide is used as a probe or an therapeutic antisense oligonucleotide). In some embodiments, the target nucleic acid is present in a cell (in vitro or in vivo), including plant and animal (e.g., human) cells.

The present invention also provides systems, compositions, and kits containing one or more oligonucleotide selected from SEQ ID NOs:164–231, 236–239, 241, 242, 244, 246–258, 260–269, 271–284, 286–302, 304–314, and 316–330. Such oligonucleotide find use in detection methods for detecting the presence of a target nucleic acid (e.g., an HIV target nucleic acid) in a sample, wherein the oligonucleotide, alone or combined with other detection assay components (e.g., invasive cleavage assay components) are exposed to the sample and the presence or absence of the target nucleic acid is detected.

DESCRIPTION OF THE DRAWINGS

FIGS. 2A–2D show portions of SEQ ID NOS:1–4 (structures 2A–2D, respectively).

FIG. 6 provides an alignment of sequences that have been determined for the HCV genotypes examined in Example 3. The sites within the HCV targets that the probes have been designed to complement are underlined and shown in bold. The numbers of the probes are indicated above each site. SEQ ID NOS:20–23 are shown in FIG. 6.

FIGS. 9A–9D show graphs depicting the fluorescence signal measured after the solid support capture of different HCV types from clinical samples, by the indicated probes.

FIG. 10 shows schematic representations of the folded structures that would be assumed by each of the three test molecules, #80 (SEQ ID NO:39), #81 (SEQ ID NO:40) and #82 (SEQ ID NO:41).

FIG. 15 shows an alignment of four 244 nt segments of HCV, representing types 1a, 1b, 2a/c and 3a. Type 1a is shown in its entirety, while only the differences are indicated for the other types. Cleavage sites generated by CFLP cleavage are indicated by vertical lines along the sequence, with the weakest cleavage sites shown as broken lines.

FIGS. 18A–D show schematic diagrams of the predicted structures for a region of the 244 nt amplicon derived from HCV types 1a, 1b, 2a/c and 3a, respectively. In 18 B–D the bases that differ from the type 1a sequence are shown in bold. Each is aligned with bridging oligonucleotides of six different designs (SED ID NOS:53, 54, 55, 56, 57, and 58). The regions that are complementary as aligned to the target are indicated by a black line between the strands. The 3' terminal contact sequence of each probe (excepting “c”) is complementary to eight contiguous target bases upstream of the right most stem, but representation of the small central stem prevents showing this alignment.

FIG. 26 shows a schematic diagram of an unstructured synthetic target (SEQ ID NO:63) aligned with non-bridging probes “a” and “e” and bridging probes “b”–“d” and ligation oligonucleotide “f” (SEQ ID NOS:52, 59, 53, 57, and 58, respectively). The regions that are complementary as aligned to the target are indicated by a black line between the strands.

FIGS. 29A and 29B show a schematic diagram of either a structure in the amplicon derived from HCV type 1a, or an unstructured synthetic target (SEQ ID NO:63) respectively, aligned with non-bridging probes “a” and “e”, bridging probes “b”–“d” and invasive cleavage probe “g” (SEQ ID NOS:52, 53, 57, 59, and 58, respectively). The regions that are complementary as aligned to the targets are indicated by a black line between the strands.

FIG. 37A shows two schematic diagrams of two possible secondary structures for a 128 nucleotide fragment derived from the rpoB gene of *M tuberculosis*.

FIG. 37C shows a schematic diagram of a structured site in the amplicon derived from the rpoB gene of *M. tuberculosis* having a basepair between nucleotides 62 and 114, aligned with bridging probes having different spacer regions (SEQ ID NOS: 106, 107, 108, and 109). The regions of the target that are complementary to the probes are indicated by a black line below the target structure. A graph depicts the fluorescence signal measured after the solid support capture of this amplicon by the indicated probes. The numbers identifying the probes used in each capture test are indicated above each bar and the spacer in each probe is indicated below each bar. The fluorescence signal is shown on the left of the panel as a percentage of the signal measured in experiments using a linear (non-bridging) control probe for capture of this target.

FIG. 38A shows schematic diagrams of a three structured sites in the amplicon derived from the rpoB gene of *M. tuberculosis* aligned with bridging probes 17–20 (SEQ ID NOS:110, 111, 112, and 113). The regions that are complementary as aligned to the target are indicated by a black line between the strands. A graph depicts the fluorescence signal measured after the solid support capture of these amplicons by the indicated probes. The numbers identifying the probes used in each capture test are indicated below each bar, and the fluorescence signal is shown on the left of the panel as a percentage of the signal measured in experiments using a linear (non-bridging) control probe for capture of these targets.

FIG. 40 shows a schematic diagram of structure "b" from FIG. 39 aligned with a bridging probe (SEQ ID NO:118) that could create a four-way junction. A graph depicts the fluorescence signal measured after the solid support capture of two different sized amplicons by this probe. The fluorescence signal is shown on the left of the panel as a percentage of the signal measured in experiments using a linear (non-bridging) control probe for capture of these targets.

FIG. 42 shows a schematic diagram of structure "c" from FIG. 39 aligned with bridging probe 63–87 (SEQ ID NO:115), and a graph depicting the fluorescence signal measured after the solid support capture of three different sizes of amplicon by the indicated probe. The fluorescence signal is shown on the left of the panel as a percentage of the signal measured in experiments using a linear (non-bridging) control probe for capture of these targets.

FIGS. 45A and 45B show schematic representations of the steps of one embodiment of the accessible site determination method of the present invention.

FIG. 51 shows sites within the first 200 nucleotides of the rabbit β-globin mRNA, indicated in bolt type, that were found to be accessible using the degenerate primer RT-PCR method of the present invention.

FIG. 52 shows sites within the human I-CAM-1 mRNA that were found to be accessible using the degenerate primer RT-PCR method of the present invention, indicated in bold type. Underlined and boxed nucleotides indicate regions where antisense oligonucleotide inhibition studies were performed by others (Patzel et al., supra; Chiang et al., J. Biol. Chem., 266:181 [1991]; Bennett et al., J. Immunol., 152:3530 [1994]).

FIG. 53 shows sequence of the hIFN-γ mRNA. Bold type nucleotides are regions that were determined as accessible using degenerate-primer RT-PCR. Underlined nucleotides are regions that are predicted to be accessible by the computer program OligoWalk (Mathews et al., RNA 5:1458 [1999]).

FIGS. 55A–C shows the sequence of Transcript 1 derived from the HIV gag gene (SEQ ID NO:158). Locations of primers used for mapping are indicated by underlining; sites found to be accessible using the degenerate primer RT-PCR method of the present invention are shown in bold.

FIG. 57 shows an example of INVADER assay design for site 1840–1850 of HIV-1 with the probe sets walking across an accessible site in one-nucleotide steps. Each signal probe included the 'AAAA' 5' arm and a 5' fluorescein, as indicated on Signal Probe 13, and each was used with the INVADER oligonucleotide having the same number (i.e., Signal Probe 12 was used with INVADER oligonucleotide 12).

FIGS. 61A–C shows the sequence of Transcript 3 derived from the HIV pol gene, (SEQ ID NO:159). Locations of primers used for mapping are indicated by underlining; sites found to be accessible using the degenerate primer RT-PCR method of the present invention are shown in bold.

FIG. 62 shows a schematic diagram of four sets of INVADER assay oligonucleotides aligned on a portion of HIV transcript 3 (SEQ ID NO: 159). Each set comprises a probe, a stacker and an INVADER oligonucleotide. Set 1 comprises probe 1 (SEQ ID NO:194) and INVADER oligonucleotide 1 (SEQ ID NO:196); set 2 comprises probe 2 (SEQ ID NO:195) and INVADER oligonucleotide 2 (SEQ ID NO:197). Sets 1 and 2 use the same stacker oligonucleotide (SEQ ID NO: 198). Set 3 comprises probe 3 (SEQ ID NO:199), INVADER oligonucleotide 3 (SEQ ID NO:201) and stacker oligonucleotide 3 (SEQ ID NO:203); Set 4 comprises probe 4 (SEQ ID NO:200), INVADER oligonucleotide 4 (SEQ ID NO:202) and stacker oligonucleotide 4 (SEQ ID NO:204).

Figure 1:
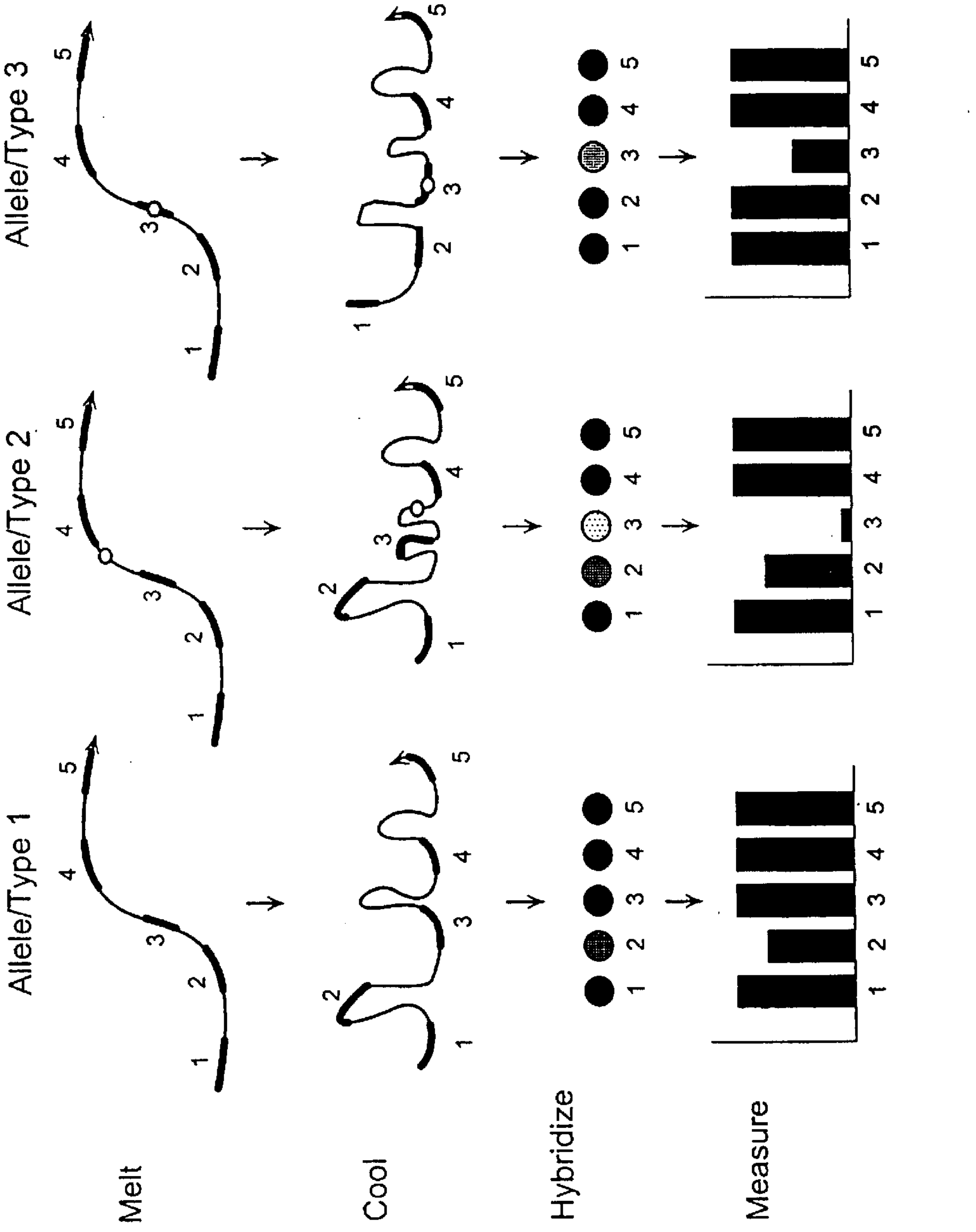
FIG. 1 provides a schematic of one embodiment of the detection methods of the present invention.

FIG. 63 shows a schematic diagram of four sets of INVADER assay oligonucleotides aligned on a portion of HIV transcript 3 (SEQ ID NO:159). Each set comprises a probe, a stacker and an INVADER oligonucleotide. Set 5 comprises probe 5 (SEQ ID NO:205), INVADER oligonucleotide 5 (SEQ ID NO:209) and stacker oligonucleotide 5 (SEQ ID NO:213); Set 6 comprises probe 6 (SEQ ID NO:206), INVADER oligonucleotide 6 (SEQ ID NO:210) and stacker oligonucleotide 6 (SEQ ID NO:214); Set 7 comprises probe 7 (SEQ ID NO:207), INVADER oligonucleotide 7 (SEQ ID NO:211) and stacker oligonucleotide 7 (SEQ ID NO:215); Set 8 comprises probe 8 (SEQ ID NO:208), INVADER oligonucleotide 8 (SEQ ID NO:212) and stacker oligonucleotide 8 (SEQ ID NO:216).

FIG. 64 shows a schematic diagram of four sets of INVADER assay oligonucleotides aligned on a portion of HIV transcript 3 (SEQ ID NO:159). Each set comprises a probe, a stacker and an INVADER oligonucleotide. The probe, stacker and INVADER oligonucleotides of Set 1 are SEQ ID NOS:217, 224 and 221, respectively; for Sets 2 and 4, the stacker and INVADER oligonucleotides are SEQ ID NOS: 225 and 222, respectively, with Set 2 using probe oligonucleotide SEQ ID NO:218 and set 4 using probe oligonucleotide SEQ ID NO:220; The probe, stacker and INVADER oligonucleotides of Set 3 are SEQ ID NOS:219, 222 and 223, respectively.

Figure 65:
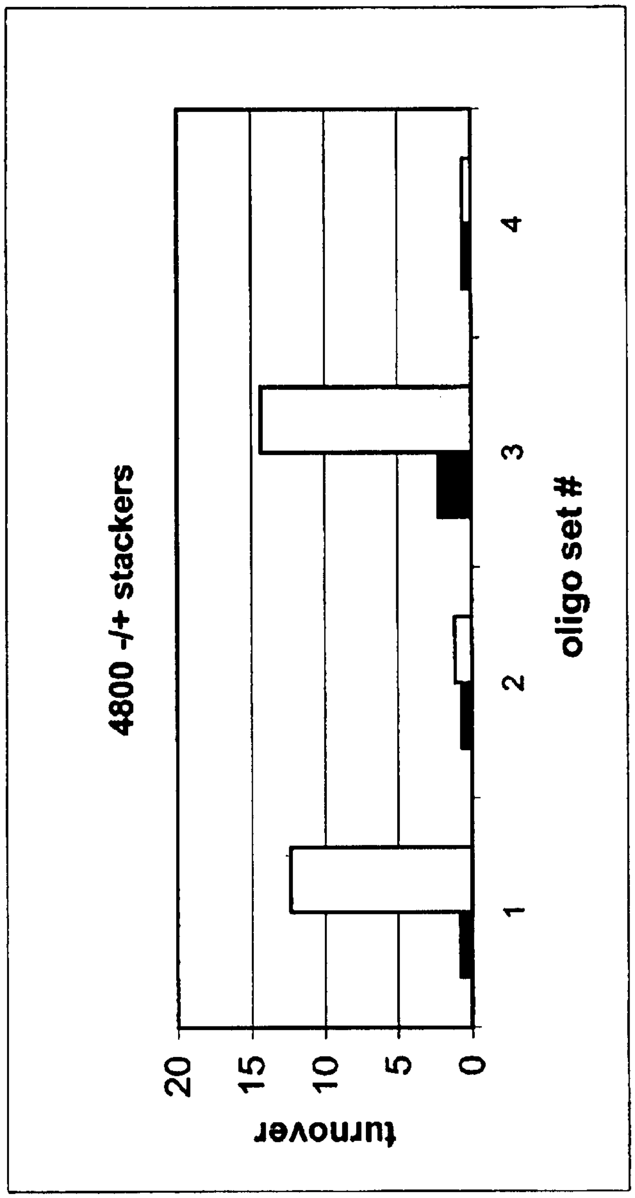

FIG. 65 shows probe turnover rates ($min^{-1}$) as determined in the INVADER assay for each of the probe sets shown in FIG. 64, and the effects of using the sets without or with the corresponding stacker oligonucleotide.

Figure 66:
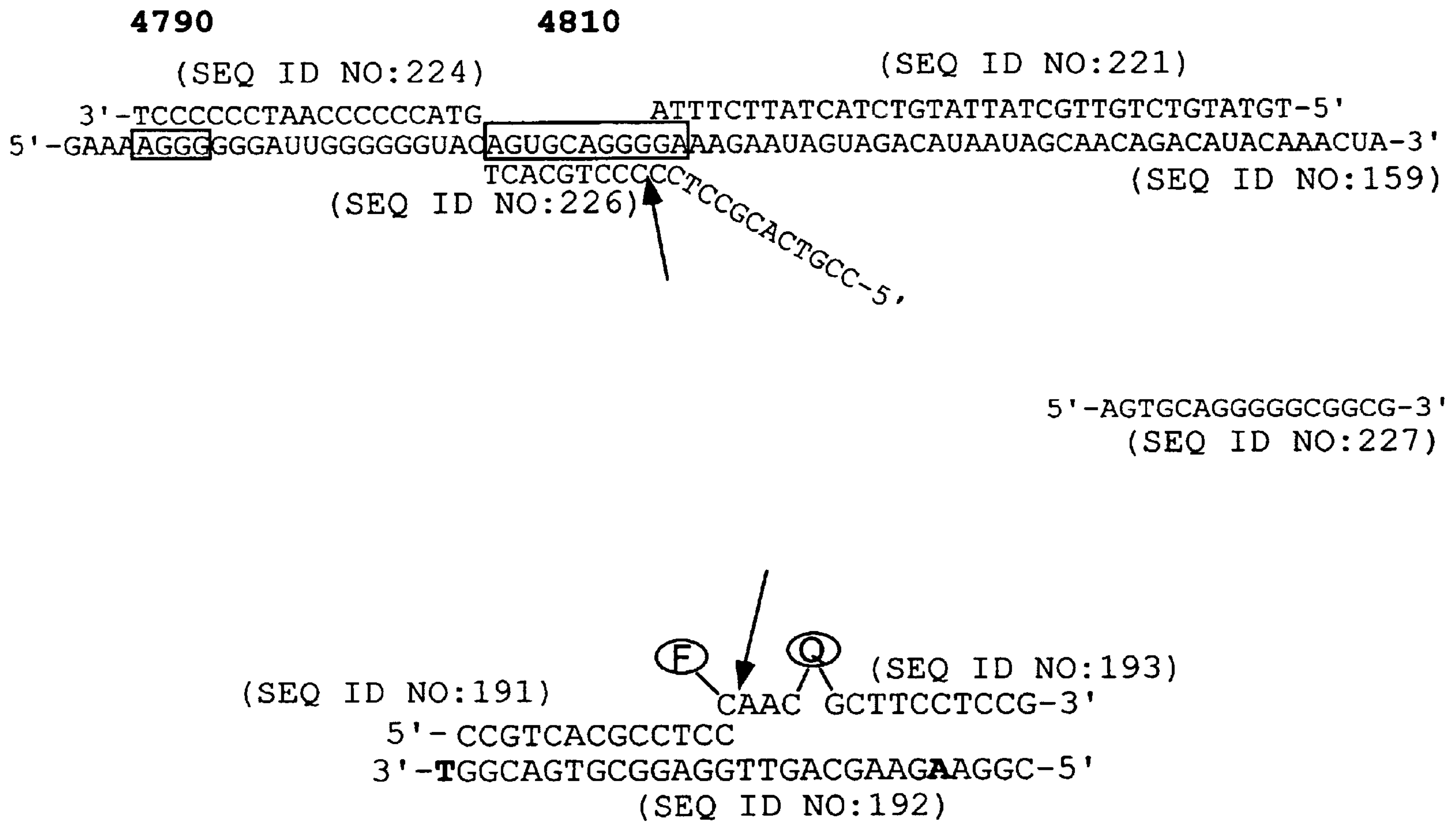

FIG. 66 shows a schematic diagram of an INVADER oligonucleotide (SEQ ID NO:221), primary probe oligonucleotide (SEQ ID NO:226), a stacker oligonucleotide (SEQ ID NO:224), an ARRESTOR oligonucleotide (SEQ ID NO:227), a secondary target oligonucleotide (SEQ ID NO:192) and FRET probe (SEQ ID NO:193) for the detection of HIV RNA. The primary probe and INVADER oligonucleotides are shown aligned with a portion of HIV transcript 3 (SEQ ID NO:159). Cleavage of the primary probe oligonucleotide produces the arm oligonucleotide having SEQ ID NO:191.

Figure 67:
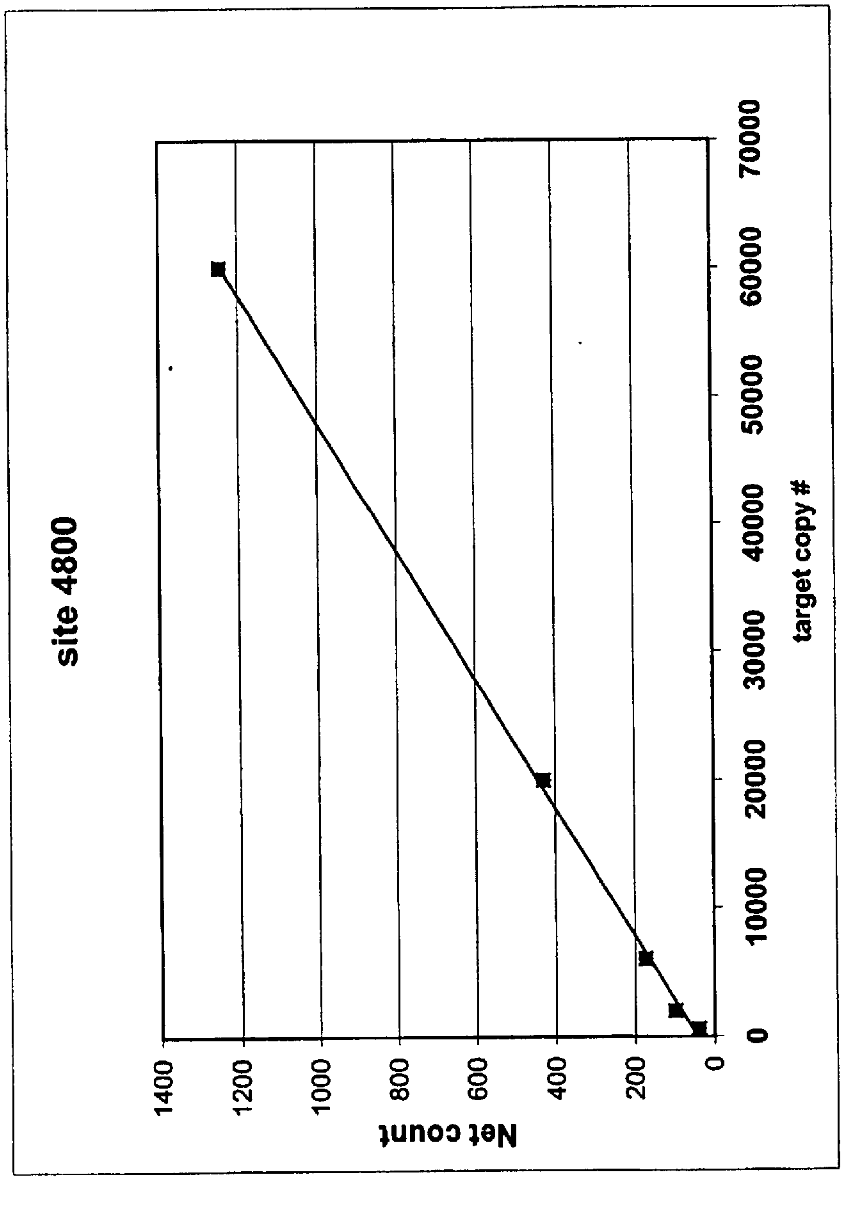

FIG. 67 shows the accumulated fluorescence signal from INVADER assay reactions using the oligonucleotides diagrammed in FIG. 66, over a range of concentrations of HIV viral RNA. Target copy number is indicated in copies per reaction.

Figure 68:
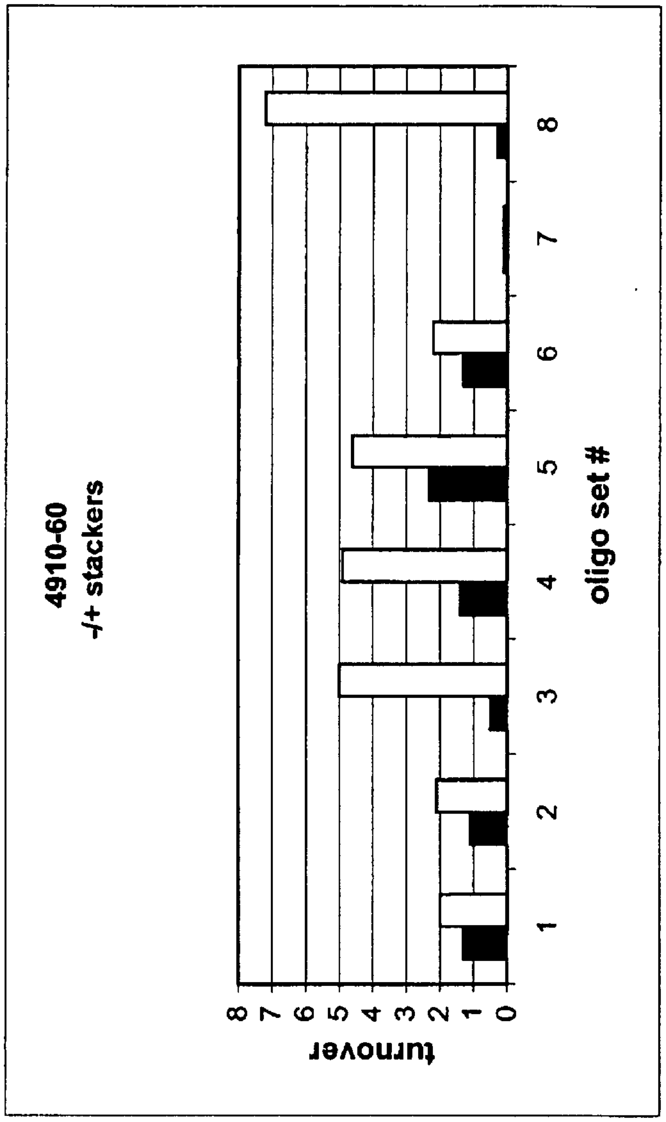

FIG. 68 shows probe turnover rates ($min^{-1}$) as determined in the INVADER assay for each of the probe sets shown in FIGS. 62 and 63, and the effects of using the sets without or with the corresponding stacker oligonucleotide.

FIG. 69 shows a schematic diagram of an INVADER oligonucleotide (SEQ ID NO:209), primary probe oligonucleotide (SEQ ID NO:228), a stacker oligonucleotide (SEQ ID NO:213), an ARRESTOR oligonucleotide (SEQ ID NO:229), a secondary target oligonucleotide (SEQ ID NO:192) and FRET probe (SEQ ID NO:193) for the detection of HIV RNA. The primary probe and INVADER oligonucleotides are shown aligned with a portion of HIV transcript 3 (SEQ ID NO:159). Cleavage of the primary probe oligonucleotide produces the arm oligonucleotide having SEQ ID NO:191.

Figure 70:
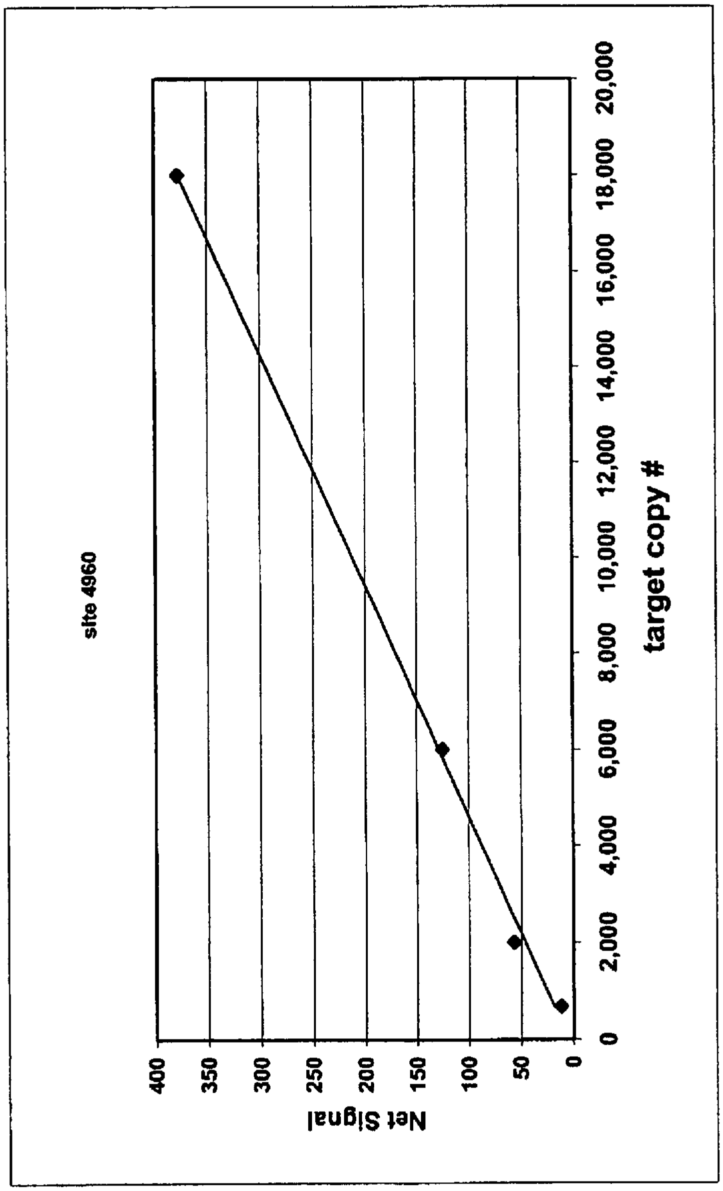

FIG. 70 shows the accumulated fluorescence signal from INVADER assay reactions using the oligonucleotides diagrammed in FIG. 69, over a range of concentrations of HIV viral RNA. Target copy number is indicated in copies per reaction.

FIG. 71 shows sites within the human PSP94 mRNA (SEQ ID NO:232), indicated by boxes, that were found to be accessible using the degenerate primer RT-PCR method of the present invention. Oligonucleotides used to generate cDNA and mRNA transcripts and for accessible sites mapping are shown (SEQ ID NOS:230–231). Only the RNA transcript region that was studied for accessibility is shown.

FIG. 72 shows sites within the human ubiquitin mRNA (SEQ ID NO:235), indicated by boxes, that were found to be accessible using the degenerate primer RT-PCR method of the present invention. Oligonucleotides used to generate cDNA and mRNA transcripts and for accessible sites mapping are shown (SEQ ID NOS:233–234). Only the RNA transcript region that was studied for accessibility is shown. Underlined regions in the RNA correspond to regions where accessible sites were studied but not mapped.

FIG. 73 shows sites within the HCV-1a 5'-UTR (SEQ ID NO:240), indicated by boxes, that were found to be accessible using the degenerate primer RT-PCR method of the present invention. Oligonucleotides used to generate cDNA and mRNA transcripts and for accessible sites mapping are shown (SEQ ID NOS:236–239). Only the RNA transcript region that was studied for accessibility is shown.

FIG. 74 shows sites within the HCV-1b 5'-UTR (SEQ ID NO:242), indicated by boxes, that were found to be accessible using the degenerate primer RT-PCR method of the present invention. Oligonucleotides used to generate cDNA and mRNA transcripts and for accessible sites mapping are shown (SEQ ID NOS:237–239, 241). Only the RNA transcript region that was studied for accessibility is shown.

FIG. 75 shows sites within the HCV-2 a/c 5'-UTR (SEQ ID NO:243), indicated by boxes, that were found to be accessible using the degenerate primer RT-PCR method of the present invention. Oligonucleotides used to generate cDNA and mRNA transcripts and for accessible sites mapping are shown (SEQ ID NOS:236–239). Only the RNA transcript region that was studied for accessibility is shown.

FIG. 76 shows sites within the HCV-3a 5'-UTR (SEQ ID NO:245), indicated by boxes, that were found to be accessible using the degenerate primer RT-PCR method of the present invention. Oligonucleotides used to generate cDNA and mRNA transcripts and for accessible sites mapping are shown (SEQ ID NOS:237–239, 244). Only the RNA transcript region that was studied for accessibility is shown.

FIG. 77A shows oligonucleotides used to generate cDNA and mRNA transcripts and for accessible sites mapping within Human Antigen CD36 mRNA (SEQ ID NOS:246–258).

FIG. 77B shows sites within the Human Antigen CD36 mRNA (SEQ ID NO:259), indicated by boxes, that were found to be accessible using the degenerate primer RT-PCR method of the present invention. Only the RNA transcript region that was studied for accessibility is shown.

FIG. 78 shows sites within the Human Ribosomal Protein L5 mRNA (SEQ ID NO:270), indicated by boxes, that were found to be accessible using the degenerate primer RT-PCR method of the present invention. Oligonucleotides used to generate cDNA and mRNA transcripts and for accessible sites mapping are shown (SEQ ID NOS:260–269). Only the RNA transcript region that was studied for accessibility is shown.

FIG. 79A shows oligonucleotides used to generate cDNA and mRNA transcripts and for accessible sites mapping within Mouse Scavenger Receptor Class B Type I mRNA (SEQ ID NOS:271–284).

FIG. 79B shows sites within the Mouse Scavenger Receptor Class B Type I mRNA (SEQ ID NO:285), indicated by boxes, that were found to be accessible using the degenerate primer RT-PCR method of the present invention. Only the RNA transcript region that was studied for accessibility is shown.

FIG. 80A shows oligonucleotides used to generate cDNA and mRNA transcripts and for accessible sites mapping within Rat CX3CR1 Accession No. U04808 mRNA (SEQ ID NOS:286–302).

FIG. 80B shows sites within the Rat CX3CR1 Accession No. U04808 mRNA (SEQ ID NO:303), indicated by boxes, that were found to be accessible using the degenerate primer RT-PCR method of the present invention. Only the RNA transcript region that was studied for accessibility is shown.

FIG. 81A shows oligonucleotides used to generate cDNA and mRNA transcripts and for accessible sites mapping within Human Interleukin-1 beta (IL-1β) mRNA (SEQ ID NOS:304–314).

FIG. 81B shows sites within the Human Interleukin-1 beta (IL-1β) mRNA (SEQ ID NO:315), indicated by boxes, that were found to be accessible using the degenerate primer RT-PCR method of the present invention. Only the RNA transcript region that was studied for accessibility is shown.

FIG. 82A shows oligonucleotides used to generate cDNA and mRNA transcripts and for accessible sites mapping within Human Interferon gamma mRNA (SEQ ID NOS:316–330).

FIG. 82B shows sites within the Human Interferon gamma mRNA (SEQ ID NO:141), indicated by boxes, that were found to be accessible using the degenerate primer RT-PCR method of the present invention. Only the RNA transcript region that was studied for accessibility is shown.

FIG. 83A shows sites within the *Pneumocystis carinii* RNA (nucleotides 84–415 of Accession # AF236872, SEQ ID NO:331) and *Candida albicans* RNA (nucleotides 72–418° F. Accession # X74272, SEQ ID NO:332), indicated by boxes, that were found to be accessible using the degenerate primer RT-PCR method of the present invention.

FIG. 83B shows sites within Earwig R2 element RNA (SEQ ID NO:333) and *Bombyx mori* R2 element RNA (SEQ ID NO:334), indicated by boxes, that were found to be accessible using the degenerate primer RT-PCR method of the present invention.

DEFINITIONS

To facilitate understanding of the invention, a number of terms are defined below.

The term "gene" refers to a DNA sequence that comprises control and coding sequences necessary for the production of a polypeptide or precursor. The polypeptide can be encoded by a full-length coding sequence or by any portion of the coding sequence so long as the desired enzymatic activity is retained.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "LTR" as used herein refers to the long terminal repeat found at each end of a provirus (i.e., the integrated form of a retrovirus). The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be the to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refer to the annealing of a complementary sequence to the target nucleic acid (the sequence to be detected) through base pairing interaction (Marmur and Lane, Proc. Natl. Acad. Sci. USA 46:453 [1960] and Doty et al., Proc. Natl. Acad. Sci. USA 46:461 [1960]). The terms "annealed" and "hybridized" are used interchangeably throughout, and are intended to encompass any specific and reproducible interaction between an oligonucleotide and a target nucleic acid, including binding of regions having only partial complementarity and binding interactions that make use of non-canonical interactions for stability and/or specificity.

The complement of a nucleic acid sequence as used herein refers to an oligonucleotide that, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "non-canonical" as used in reference to nucleic acids indicates interactions other than standard, or "Watson-Crick" base pairing, including but not limited to G-T and G-U base pairs, Hoogstein interactions, triplex structures, quadraplex aggregates, and multibase hydrogen bonding such as is observed within nucleic acid tertiary structures, such as those found in tRNAs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide that forms a duplex structure or other complex with a sequence in another nucleic acid, due to complementarity or other means of reproducible attractive interaction, of at least one sequence in the probe with a sequence in the other nucleic acid.

The terms "signal probe" and "signal oligonucleotide," as used herein, are used interchangeably in reference to any oligonucleotide that is provided to permit detection of the progress or products of a reaction or interaction. A signal probe may be labeled or unlabeled, and may be modified or left unmodified by the mechanism of the reaction.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

As used herein, the term "folded target" refers to a nucleic acid strand that contains at least one region of secondary structure (i.e., at least one double stranded region and at least one single-stranded region within a single strand of the nucleic acid). A folded target may comprise regions of tertiary structure in addition to regions of secondary structure.

The term "substantially single-stranded" when used in reference to a nucleic acid target means that the target molecule exists primarily as a single strand of nucleic acid in contrast to a double-stranded target that exists as two strands of nucleic acid that are held together by inter-strand base pairing interactions.

Nucleic acids form secondary structures that depend on base-pairing for stability. When single strands of nucleic acids (single-stranded DNA, denatured double-stranded DNA or RNA) with different sequences, even closely related ones, are allowed to fold on themselves, they assume characteristic secondary structures. An alteration in the sequence of the target may cause the destruction of a duplex region(s), or an increase in stability of a thereby altering the accessibility of some regions to hybridization of the probes oligonucleotides. While not being limited to any particular theory, it is thought that individual molecules in the target population may each assume only one or a few of the structures (i.e., duplexed regions), but when the sample is analyzed as a whole, a composite pattern from the hybridization of the probes can be created. Many of the structures that can alter the binding of the probes are likely to be only a few base-pairs long and would appear to be unstable. Some of these structures may be displaced by the hybridization of a probe in that region; others may by stabilized by the hybridization of a probe nearby, such that the probe/substrate duplex can stack coaxially with the target intrastrand duplex, thereby increasing the stability of both. The formation or disruption of these structures in response to small sequence changes results in changes in the patterns of probe/target complex formation. Temperatures in the range of 20 to 55° C., with the range of 20 to 40° C. being particularly preferred, are suitable temperatures for the practice of the method of the invention.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene vary in sequence from one another. A second mutant form of the structural gene may exist. This second mutant form varies in sequence from both the wild-type gene and the first mutant form of the gene. It is noted, however, that the invention does not require that a comparison be made between one or more forms of a gene to detect sequence variations. Because the method of the invention generates a characteristic and reproducible pattern of complex formation for a given nucleic acid target, a characteristic "fingerprint" may be obtained from any nucleic target without reference to a wild-type or other control. The invention contemplates the use of the method for both "fingerprinting" nucleic acids without reference to a control and identification of mutant forms of a target nucleic acid by comparison of the mutant form of the target with a wild-type or known mutant control.

The terms "structure probing signature," "hybridization signature" and "hybridization profile" are used interchangeably herein to indicate the measured level of complex formation between a folded target nucleic acid and a probe or set of probes, such measured levels being characteristic of the folded target nucleic acid when compared to levels of complex formation involving reference targets or probes.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is the to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

The term "cleavage structure" as used herein, refers to a structure that is formed by the interaction of at least one probe oligonucleotide and a target nucleic acid to form at least one region of duplex, the resulting structure being cleavable by a cleavage means, including but not limited to an enzyme. The cleavage structure is a substrate for specific cleavage by the cleavage means, in contrast to a nucleic acid molecule that is a substrate for non-specific cleavage by agents such as phosphodiesterases, which cleave nucleic acid molecules without regard to secondary structure (i.e., no formation of a duplexed structure is required).

The term "cleavage means" and "cleavage agent" are used interchangeably herein to refer to any means that is capable of cleaving nucleic acid (e.g., nucleic acid comprising a cleavage structure), including but not limited to enzymes. In some embodiments, the cleavage means may include native DNAPs having 5' nuclease activity (e.g., Taq DNA polymerase, *E. coli* DNA polymerase I) and, more specifically, modified DNAPs having 5' nuclease but lacking synthetic activity. The ability of 5' nucleases to cleave naturally occurring structures in nucleic acid templates (structure-specific cleavage) is useful to detect internal sequence differences in nucleic acids without prior knowledge of the specific sequence of the nucleic acid. In this manner, they are structure-specific enzymes. The cleavage means is not restricted to enzymes having solely 5' nuclease activity. The cleavage means may include nuclease activity provided from a variety of sources including the CLEAVASE enzymes, the FEN-1 endonucleases (including RAD2 and XPG proteins), Taq DNA polymerase and *E. coli* DNA polymerase I. In some embodiments, the cleavage means of the present invention cleave a nucleic acid molecule in response to the formation of cleavage structures; it is not necessary that the cleavage means cleave the cleavage structure at any particular location within the cleavage structure.

The term "structure-specific nucleases" or "structure-specific enzymes" refers to enzymes that recognize specific secondary structures in a nucleic molecule and cleave these structures without the regard to the specific sequences making up the structure.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule that contains a sequence that has at least partial complementarity with at least one probe oligonucleotide as well as nucleic acid molecules that comprise a folded target. The target nucleic acid may comprise single- or double-stranded DNA or RNA.

The term "probe oligonucleotide" refers to an oligonucleotide that interacts with a target nucleic acid to form a complex. The complex may also comprise a cleavage structure.

The term "non-target cleavage product" refers to a product of a cleavage reaction that is not derived from the target nucleic acid. In the methods of the present invention, cleavage of the cleavage structure may occur within the probe oligonucleotide. The fragments of the probe oligonucleotide generated by this target nucleic acid-dependent cleavage are "non-target cleavage products."

The term "INVADER oligonucleotide" refers to an oligonucleotide that hybridizes to a target nucleic acid upstream of a probe oligonucleotide, wherein the 3' end of the INVADER oligonucleotide contains a portion that overlaps (e.g., physically and/or by sequence) with a region of the target nucleic acid that is complementary to a probe oligonucleotide. In some embodiments, the 3' end of the INVADER oligonucleotide positions the site of structure-specific nuclease cleavage within an adjacently hybridized oligonucleotide probe. In one embodiment its 3' end has at least one nucleotide of sequence that is identical the first target-complementary nucleotide of the adjacent probe; these nucleotides will compete for hybridization to the same nucleotide in a complementary target nucleic acid. In another embodiment, the INVADER oligonucleotide has a single 3' mismatched nucleotide, and hybridizes to an adjacent, but not overlapping, site on the target nucleic acid.

The term "substantially single-stranded" when used in reference to a nucleic acid substrate means that the substrate molecule exists primarily as a single strand of nucleic acid in contrast to a double-stranded substrate that exists as two strands of nucleic acid that are held together by inter-strand base pairing interactions.

A "consensus gene sequence" refers to a gene sequence that is derived by comparison of two or more gene sequences and that describes the nucleotides most often present in a given segment of the genes; the consensus sequence is the canonical sequence.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "multi-drug resistant" or "multiple-drug resistant" refers to a microorganism that is resistant to more than one of the antibiotics or antimicrobial agents used in the treatment of the microorganism.

The term "non-contiguous," when used to describe regions within a target nucleic acid to be analyzed, is intended to mean that the regions are separated by intervening nucleic acid (or non-nucleic acid spacers). It is not intended that the present invention be limited by the size of the intervening nucleic acid (or the size of non-nucleic acid spacers). However, in preferred embodiments, the intervening sequence is at least five nucleotides in length.

The term "non-contiguous," when used to describe regions within a nucleic acid probe, means sequences capable of hybridizing to the non-contiguous regions of target nucleic acid. It is not intended that the present invention be limited to probes having intervening nucleic acid; that is to say, the non-contiguous regions of a probe are defined functionally, with reference to their binding to non-contiguous regions in a target, the target having intervening nucleic acid separating the non-contiguous regions. Nonetheless, the probes of the present invention may have (but need not have) intervening nucleic acid (or a non-nucleic acid spacer).

The terms "intervening nucleic acid," "intervening portion," "intervening region," "intervening nucleic acid sequence," and "intervening sequence," refer to nucleic acid (single-stranded or double-stranded), that separates two or more regions (e.g., non-contiguous regions) within a nucleic acid sequence. Where the present invention employs a probe having one or more intervening sequences, such intervening sequences are to be distinguished from mere single base mismatched nucleic acid, such that intervening sequences on the probe are at least two nucleic acids in length.

The term "bridging" when used in conjunction with a type of nucleic acid (e.g., oligonucleotide, probe, primer, etc.), refers to a nucleic acid that is made to contact non-contiguous sites on a folded target nucleic acid. For example, a bridging probe and a bridging primer may refer to oligonucleotides that hybridize across a structure for detection, or for subsequent primer extension, respectively, although "primer" and "probe" may also be used to indicate other types of interactions or reactions.

The term "non-bridging" when used in conjunction with a type of nucleic acid (e.g., oligonucleotide, probe, primer, etc.), refers to an nucleic acid that is not intended to hybridize across, a structure (i.e., it contains a region substantially complementary to its hybridization partner nucleic acid).

The term "reactant" refers to any agent that can act upon either the target or non-target nucleic acids to create a detectable alteration from the original nucleic acid chemical or nucleotide composition.

The terms "catalyzed reaction" or "catalytic reaction" refers to any action on a nucleic acid that is catalyzed or enacted by a reactant other than the nucleic acid.

The terms "modified probe" and "modified oligonucleotide" refer to probes that have been altered from their original composition by the action of a reactant. Such alterations include but are not limited to cleavage as by a nuclease, elongation as by a polymerase, or joining to another entity, either through a covalent interaction, such as by ligation to another nucleic acid, or by chemical cross-linking to an entity such as a protein, a nucleic acid, a detectable moiety, or a solid support.

The terms "inaccessible" and "inaccessible site," when used in reference to a nucleic acid, are used to indicate nucleic acids or portions of nucleic acids that exhibit reduced or minimal hybridization to a complementary oligonucleotide, as compared to the hybridization of the oligonucleotide to the nucleic acid under conditions where the nucleic acid is substantially single stranded and free of other molecules. Inaccessible sites may be determined functionally, for example, by exposing a nucleic acid (e.g., a folded nucleic acid) to an oligonucleotide complementary to the site in question and detecting the presence of a binding complex between the oligonucleotide and the nucleic acid. The absence of a binding complex under experimental conditions characterizes the site as an inaccessible site. Likewise, a detectable reduction in the amount of binding complex as compared to a control binding experiment conducted under conditions where the nucleic acid is substantially single stranded and free of other molecules characterizes the site as an inaccessible site. Conditions generally required for hybridization of nucleic acids, including, but not limited to, temperature ranges, salt and divalent ion concentrations, and size and concentration of complementary nucleic acids are well known in the art. It is contemplated that sites on a nucleic acid may be inaccessible for a variety of reason, including, but not limited to, being completely or partially double-stranded, or being bound by a binding agent such as an oligonucleotide, a protein, or reagent having an affinity for nucleic acid.

The term "accessible" and "accessible site" when used in reference to a nucleic acid, are used to indicate nucleic acids or portions of nucleic acids that exhibit hybridization to a complementary oligonucleotide. Accessible sites exhibit similar levels of hybridization to oligonucleotides under experimental conditions (e.g., environmental conditions) as compared to conditions where the nucleic is rendered substantially single stranded and free of other molecules.

The term "extendible site" refers to a site on a nucleic acid that has been determined to be accessible by hybridization and extension of a primer in the presence of a template-dependent nucleic acid extension agent.

The terms "degenerate primer" and "degenerate oligonucleotide" refer to primers and oligonucleotides comprising at least a region where, within a plurality of molecules, the individual members differ in sequence from one another within the region. In some embodiments, the region of degeneracy may comprise the entire primer or oligonucleotide. In other embodiments, the nucleic acids may be otherwise identical (i.e., identical, but for the region of variance). For example, a plurality of 12-mer oligonucleotides may comprise a region of degeneracy consisting of 6 consecutive nucleotides in the center of the 12-mer (e.g., TCANNNNNNGTC). In this example, the members of the plurality of degenerate oligonucleotides differ in sequence from each other within the positions identified as "N."

The term "tag" or "tag sequence" refers to a sequence provided on the 5' end of an extension primer that is not related to the nucleic acid sequence to be copied in a primer extension reaction (i.e., is not designed to be complementary to the target nucleic acid). A tag sequence may serve to provide a non-target sequence for primer binding during further amplification of the extended product (e.g., by PCR).

As used herein, the term "antisense" is used in reference to DNA or RNA sequences that are complementary to a specific DNA or RNA sequence (e.g., mRNA). Antisense RNA may be produced by any method, including synthesis by splicing the gene(s) or sequences of interest in a reverse orientation to a promoter that permits the synthesis of a coding strand. The specific hybridization of an oligomeric compound with its target nucleic acid may interfere with the normal function of the nucleic acid. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. Antisense molecules are sufficiently complementary to the target (i.e., hybridize sufficiently well and with sufficient specificity) to give the desired effect. In the context of the present invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (e.g., under physiological conditions in the case of in vivo assays or therapeutic treatment, and in the case of in vitro assays, under conditions in which the assays are performed). Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway. The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. While antisense oligonucleotides are a preferred form of antisense compound, the present invention contemplates other oligomeric antisense compounds, including but not limited to oligonucleotide mimetics. Specific examples of preferred antisense compounds useful with the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In other preferred antisense oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

As used herein, the term "reverse transcriptase" refers to an enzyme capable of producing DNA from an RNA template. A variety of DNA polymerases having the ability to use RNA as a template strand to generate DNA extension products are known. "Reverse transcription" refers to the process of producing a DNA copy of an RNA template.

As used herein, the term "template-dependent extension agent" refers to an extension agent that performs a nucleic acid extension reaction that creates extension product strands through the copying of a template strand and which does not synthesize nucleic in the absence of a template. This is in contrast to the activity of the template-independent nucleic acid agents that synthesize or extend nucleic acids without reference to a template, such as terminal deoxynucleotidyl transferase, or Poly A polymerase.

As used herein, the term "amplification agent" refers to any agent (e.g., enzyme) capable of increasing the population of a specific nucleic acid sequence in a sample. Amplification agents include, but are not limited to, nucleic acid polymerases (e.g., thermostable polymerases that find use in the polymerase chain reaction). The art is well aware of a variety of agents and conditions for amplifying specific nucleic acid sequences within a sample.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as nucleic acid molecules and proteins attached to solid supports. A biological material is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linker group." Such spacer molecules are molecules that have a first portion that attaches to the biological material and a second portion that attaches to the solid support. Thus, when attached to the solid support, the spacer molecule separates the solid support and the biological materials, but is attached to both.

DESCRIPTION OF THE INVENTION

The present invention provides methods for identifying oligonucleotides with desired hybridization properties to nucleic acid targets containing secondary structure. Some methods of the present invention also use the combined effects of mismatch and folded structure on hybridization to provide a tool for the detection of mutations and other polymorphisms in nucleic acids (e.g., DNA and RNA). The simultaneous probing of the primary (sequence), secondary (simple folded) and tertiary (interactions between secondary folds) structures of substrate molecules is referred herein simply as "structure probing." Rather than destroying secondary structures by high stringency conditions and target fragmentation, the methods of the present invention uses conditions in which the formation of intramolecular structures is favored, i.e., unfragmented target strands in conditions of low stringency. Thus, the present method of probing is designed to detect variations between nucleic acids at any of these levels in a single assay.

At temperatures below the melting range of duplexed nucleic acid (i.e., below the melting temperature of long [i.e., >100 bp] nucleic acids; this is generally taken to be temperatures below about 85° C. for a nucleic acid of average G-C content), single-stranded nucleic acids undergo a complex process of intramolecular folding. The first rapid step of this process involves formation of short-range, or local stem-loops structures. Later in the folding process, formation of tertiary or global structure occurs as a result of interactions between different local domains (Zarrinkar and Williamson, Science 265:928 [1994] and Zarrinkar and Williamson, Nat. Struct. Biol., 3:432 [1996]). The effects of secondary structure of the target on probe binding is well documented for DNA and RNA molecules (Gamper et al., supra; Fedorova et al., FEBS Lett. 302:47 [1992]; Lima et al., Biochem., 31:12055 [1992]; Godard et al., Nucl. Acids Res., 22:4789 [1994]; Zarrinkar and Williamson, [1994], supra; Parkhurst and Parkhurst, Biochem., 34:285 [1995]; and Schwille et al., Biochem., 35:10182 [1996]). Target sequences that form stable duplexes within intramolecular secondary structures can have probe binding constants $10^5$–$10^6$ times lower than sequences that exists as a single strands (Lima et al., supra). The reduction of the hybridization constant for structured regions is primarily due to a lower association rate constant rather than a higher dissociation rate constant (Lima et al., supra; Gamper et al., supra and Parkhurst and Parkhurst, supra), supporting the model that the structures in the target are blocking access of the probe to the complementary region within the target molecule.

Mutations in the target sequence change both local and global conformations of the molecule. It has been shown that the conformations assumed by single strands of nucleic acids can be probed using a structure-specific nuclease that cleaves in response to the structures that are formed in a number of test reaction conditions. (Brow et al., supra). Such cleavage creates a collection of product fragments that reflect those structures and which are characteristic of the particular strands. The structures that give rise to cleavage patterns are very sensitive to the precise nucleotide sequence of the strand, such that even single base differences in nucleic acids that are several hundred nucleotides long create sufficient changes in the folded conformations to be detectable in the resulting cleavage pattern (Brow et al., supra), and the changes in electrophoretic mobility in SSCP. As a result of these changes, some regions that were previously base paired may become unpaired and vice versa. By measuring probe hybridization rates it is possible to determine whether or not any region of a target molecule forms intramolecular structure. The examples below describe the use of multiple oligonucleotides to characterize DNA fragments (i.e., for structure probing). This approach is diagrammed schematically in FIG. 1.

In FIG. 1, three different, but related, target nucleic acids are analyzed using the structure probing assay of the present invention. Allele/Type 1 represents the prototypical target sequence (e.g., a wild type allele of gene X); Allele/Types 2 and 3 represent different alleles of the same target sequence (e.g., two different allelic variants of gene X). The thick regions labeled 1–5 along the three target nucleic acids represent the regions along the target that are complementary to probes 1–5. Allele/Type 2 contains a single-base variant (e.g., a point mutation) relative to Allele/Type 1 (represented by the small open circle between regions 3 and 4 of Allele/Type 2). This variant does not appear in a region where a probe binds to the Type 2 target; however, this variant alters the secondary structure of the Type 2 molecule relative to that of the Type 1 molecule such that region 3 of the Type 2 molecule is essentially unavailable for hybridization with probe 3. Allele/Type 3 also contains a single-base variant (e.g., a point mutation) relative to Allele/Type 1 (represented by the small open circle within region 3 of Allele/Type 3). The variant in this molecule is located within a probe binding region and reduces the efficiency with which probe 3 binds to the Type 3 molecule. The target nucleic acids are rendered substantially single-stranded (i.e., they are denatured, e.g., by heating) and then permitted to form secondary structures (e.g., by cooling) and then hybridized with probes 1–5. The probe/target complexes are captured onto a solid support and the amount of target that binds to each of probes 1–5 is determined for each target to generate a probe structure signature (also referred to as a hybridization signature or profile). The schematic shown in FIG. 1 is intended to illustrate that the signal variation may come from probe/target mismatch, or from the formation of local structures that block probe binding sites (i.e., regions on the target which are at least partially complementary to the probe). Tertiary structure, involving interactions between sequences at some distance (even several hundred nucleotides) may also block binding, i.e., mutations at one site may influence probe binding hundreds of nucleotides away, as is seen with the katG targets employed in Example 1.

In the Examples below, the oligonucleotide probes include a biotin moiety so that the labeled target DNAs that have formed a hybridization complex with the probes can be captured by exposure to a solid support coated with streptavidin. When used for immobilization in this way, the probes are referred to herein as "capture probes." The labels on the DNA can then be detected, with the amount of captured DNA reflecting the efficiency of the probe/target hybridization, and thus the strength of a particular binding interaction.

In the Examples below, the solid support employed is a well of a 96-well microtiter plate. This format was chosen for convenience; the methods of the present invention are not limited to the use of microtiter plates or any particular support. The present invention contemplates the use of many types of solid supports, including but not limited to beads, particles, dipsticks, membranes and silicon or glass flat surfaces. It is also contemplated that the binding of the probe/target complexes to surfaces may be through interactions with the target nucleic acid (e.g., the use of biotinylated target nucleic acids), while a detectable label may be included on the probes.

In the embodiments presented herein, the affinity of the target nucleic acid (e.g., a DNA fragment of interest) for different probes is assessed by performing separate hybridization and solid support capture determinations for each probe sequence. It is envisioned that differently labeled probes, e.g., with different fluorescent dyes or other detectable moieties, may be used together in a single complex formation reaction. Use of an instrument that can detect several types of signal, such as a fluorimeter with the capacity to excite and detect at a variety of wavelengths, allows the signal contribution from each of the bound probes to be assessed.

In some typing applications, variants may have any one of several sequences (and therefore structures) and still be classed as the same type (e.g., in HCV, there are numerous sequence variants that are classed as type 1b). If it is not necessary to separately identify the subtypes within a type, a mixture of probes may be provided such that at least one type of probe interacts with each of the different known variants. If the target interacts appropriately (i.e., with the expected affinity) with any probe in the mixture it can be deduced to be of a broad type without concern about the identity of the particular subtype variant. In this way, genetic materials known to vary in sequence without affecting function or type (as do many rapidly changing pathogens) may be analyzed in a single assay without the need for a complex matrix of probes or for sequence determination.

In the following discussion, the oligonucleotide probes are discussed as capture probes. The use of this term is for convenience only, to avoid repetition of the enumeration of the possible configurations for this method, and it is intended that each of the embodiments described below may be used in combination with any of the probe/target configurations (e.g., labeled probes and captured target DNA and vice versa) described above.

The probes used in the methods of the present invention may be used without any prior analysis of the structure assumed by a target nucleic acid. In designing such an assay, one designs probes that would span the entire length of the target sequence, (i.e., they would be complementary to regions of the target that are substantially evenly spaced across the entire length of the target). Probes designed in this way may be phased to a variety of densities. For example, the probes may each shift in hybridization site by one or a few nucleotides, to give a very high resolution fingerprint of the target, or they may be designed to hybridize to adjacent but not overlapping regions, to give thorough coverage at a slightly lower resolution. Alternatively, they may be spaced at much larger intervals for a lower resolution screen. The choice of spacing will be dependent on the needs of the assay. A higher density fingerprint will have a greater likelihood of identifying any possible polymorphism, and may be more suitable for situations where certainty in identification of single base changes is required (e.g., identification of mutations associated with cancers and other diseases). When genotyping is to be performed on targets in which more variation is expected (e.g., rapidly changing viruses), a lower density array may be sufficient for accurate identification. The examples below provide such an analysis for the identification of Hepatitis C viral types. For any given case, it can be determined empirically using appropriately selected reference target molecule whether a chosen probe or array of probes can distinguish between genetic variants sufficiently for the needs of a particular assay. Once a probe or array of probes is selected, the analysis of which probes bind to a target, and how efficiently these probes bind (i.e., how much of probe/target complex can be detected) allows a hybridization signature of the conformation of the target to be created. One possible format for such a signature is as a graph of the measured amounts of a complex formed between the target and each probe, as shown in FIGS. 4, 7, 8, and 9. It is not intended that the structure probing or hybridization signature be limited to the use of the column graphs shown in these figures. It is contemplated that the signature may be stored, represented or analyzed by any of the methods commonly used for the presentation of mathematical and physical information, including but not limited to line, pie, or area graphs or 3-dimensional topographic representations. The data may also be used as a numerical matrix, or any other format that may be analyzed either visually, mathematically or by computer-assisted algorithms.

The resulting signatures of the nucleic acid structures serve as sequence-specific identifiers of the particular molecule, without requiring the determination of the actual nucleotide sequence. While specific sequences may be identified by comparison of their signature to a reference signature, the use of algorithms to deduce the actual sequence of a molecule by sequence-specific hybridization (i.e., at high stringency to eliminate the influence of secondary and tertiary structures) to a complete matrix (i.e., probes that shift by a single nucleotide position at each location of an array), is not a feature or requirement, or within the bounds of the methods of the present invention.

It is contemplated that information on the structures assumed by a target nucleic acid may be used in the design of the probes, such that regions that are known or suspected to be involved in folding may be chosen as hybridization sites. Such an approach reduces the number of probes that are likely to be needed to distinguish between targets of interest.

There are many methods used to obtain structural information involving nucleic acids, including the use of chemicals that are sensitive to the nucleic acid structure, such as phenanthroline/copper, EDTA-$Fe^{2+}$, cisplatin, ethylnitrosourea, dimethyl pyrocarbonate, hydrazine, dimethyl sulfate, and bisulfite. Such chemical reagents may cause cleavage based on structure, or they may cause nucleotide modification that can subsequently be detected, such as by pausing or blocking of reverse transcriptase or other DNA polymerase copying, or by fingerprinting or other chromatography methods. Those skilled in the art are familiar with numerous additional methods for the detection of nucleotide modifications within a nucleic acid strand.

Enzymatic probing can be done using structure-specific nucleases from a variety of sources. Duplex-specific nucleases such as cobra venom $V_1$ nuclease have been widely used in the analysis of RNA structures (See e.g., Lowman and Draper, J. Biol. Chem., 261:5396 [1986]). In addition, suitable 5' nucleases include the CLEAVASE enzymes (Third Wave Technologies, Inc., Madison, Wis.), Taq DNA polymerase, *E. coli* DNA polymerase I, and eukaryotic structure-specific endonucleases (e.g., human, murine and Xenopus XPG enzymes, yeast RAD2 enzymes), murine FEN-1 endonucleases (Harrington and Lieber, Genes and Develop., 3:1344 [1994]) and calf thymus 5' to 3' exonuclease (Murante et al., J. Biol. Chem., 269:1191 [1994]). In addition, enzymes having 3' nuclease activity such as members of the family of DNA repair endonucleases (e.g., the RrpI enzyme from *Drosophila melanogaster*, the yeast RAD1/RAD10 complex and *E. coli* Exo III), are also suitable for examining the structures of nucleic acids. In Example 3, the use of the CFLP method for identifying regions of folding in PCR amplified segments of the HCV genome is described.

If analysis of structure as a step in probe selection is to be used for a segment of nucleic acid for which no information is available concerning regions likely to form secondary structures, the sites of structure-induced modification or cleavage must be identified. It is most convenient if the modification or cleavage can be done under partially reactive conditions (i.e., such that in the population of molecules in a test sample, each individual receives only one or a few cuts or modifications). When the sample is analyzed as a whole, each reactive site should be represented, and all the sites may be thus identified. Using a CFLP cleavage reaction as an example, when the partial cleavage products of an end labeled nucleic acid fragment are resolved by size (e.g., by electrophoresis), the result is a ladder of bands indicating the site of each cleavage, measured from the labeled end. Similar analysis can be done for chemical modifications that block DNA synthesis; extension of a primer on molecules that have been partially modified will yield a nested set of termination products. Determining the sites of cleavage/modification may be done with some degree of accuracy by comparing the products to size markers (e.g., commercially available fragments of DNA for size comparison) but a more accurate measure is to create a DNA sequencing ladder for the same segment of nucleic acid to resolve alongside the test sample. This allows rapid identification of the precise site of cleavage or modification.

Two approaches have commonly been applied to elucidate nucleic acid secondary structures: physical approaches, such as analysis of crystal structure or NMR, and analytical approaches, such as comparative or phylogenetic analysis. Physical analysis remains the only way to get a complete determination of a folded structure for any given nucleic acid. However, that level of analysis is impractical if the goal is to analyze a large number of molecules. By far, the most often used method of analyzing biological nucleic acids is a phylogenetic, or comparative approach. This method of analysis is based on the biological paradigm that functionally homologous sequences will adopt similar structures. Sequences are screened for sequence conservation, stem-loop conservation, and for compensatory sequence changes that preserve predicted structures. Unfortunately, such analysis can only be applied when the number of related sequences is large enough for statistical analysis.

The efficient analysis of single nucleic acids requires the use of multiple tools. Many of the available tools can give partial information on the possible structures assumed by a given molecule. As stated above, these methods include enzymatic analysis, chemical structure probing, and computer based analysis of regions of base pairing. In addition, deletion studies, in which portions of a linear molecule are deleted and the effects on the folding are analyzed by the above-cited methods, can help identify with more certainty those regions of a nucleic acid that interact with each other. None of these methods in isolation can provide sufficient physical information to identify with certainty any non-contiguous regions that will be in close enough proximity to be simultaneously contacted by a bridging oligonucleotide. For example, one of the most commonly used nucleic acid folding programs, "mfold" (Zuker, Science 244:48 [1989]; Jaeger et al., Proc. Natl. Acad. Sci. USA, 86:7706 [1989]; Jaeger et al., Meth. Enzymol. 183:281 [1990]) uses previously determined physical measurements for the effects of various secondary structure features, such as basepair combinations, loops, bulges, etc., on the stability of folded structures to predict structures that have the lowest possible free energy. This approach is referred to as an energy minimization approach (See, Gaspin and Westhof, J. Mol. Biol. 254:163 [1995] for review). While mfold and other computer-based folding algorithms can be made to present only those structures that are most likely to form (e.g., that are thermodynamically favored), when the software is permitted to show structures that are even slightly less energetically favorable, there are usually dozens of such structures predicted for any given nucleic acid strand. Even though these structures may be very stable, and may in fact be proven to exist in nature, they are referred to as "suboptimal" structures, because they are calculated to have a less favorable free energy based on the software parameters. Using information derived from the other methods (e.g., analyzing folded structures or by physical methods), allows the number of structures to be pared down dramatically, from many, many possible structures, to a few probable ones.

One additional software-based approach involves tallying the number of pairing partners available for each base within a collection of suboptimal structures predicted for a given nucleic acid strand (Zuker and Jacobson. Nucl. Acids Res. 23:2791 [1995]). The pairing number, or "p-num" for each base gives a quantitative measure of the fidelity of pairing, i.e., the number of possible pairing partners, of each base position. It has been observed that predicted structures containing bases with p-nums that are lower than those of surrounding regions have a stronger correlation with structures that have been verified by physical or phylogenetic conservation data. Therefore using mfold and p-num together can help simplify the task of identifying structures that may be assumed by a nucleic acid strand. Both p-num and mfold are available commercially (Genetics Computer Group, Madison, Wis.).

A significant limitation of the energy minimization programs for nucleic acids folding is that all of them, including mfold, use greatly simplified thermodynamic models that include energy parameters that are not well defined. The result is that the predicted optimal structures may not correspond to the actual conformation of the nucleic acid in solution. A partial solution to this is to extend the number of computed structures to include those that have suboptimal energies, thereby increasing the chances that one of them has better correlation with a real one. This step may produce a large number of possible structures, and identification of actual structures may be difficult without other analytical tools. For example, the mfold predictions done for the HCV type 1 a amplicon, as described in Example 8, resulted in 32 predicted structures.

Efficient screening of the suboptimal structures can be accomplished by incorporating constraints derived from experimental data or phylogenetic analysis into the computer algorithm. The use of structure specific nucleases having well characterized specificity have an advantage that the site of cleavage can convey additional information based on the structural requirements for cleavage. This is illustrated here by discussion of information potentially gained by cleavage with a 5' nuclease, CLEAVASE I nuclease, but the same deductive approach is equally applicable and useful for other structure-specific cleavage agents for which a substrate structure is well defined (i.e., it is known where in the structure the cleavage can occur). The specificity of CLEAVASE enzymes is such that cleavage occurs at the 5' ends of hairpin duplexes, after the first base pair (Lyamichev et al, supra). This means that any cleavage site identifies both a base that must be paired in the structure, and that the base to which it pairs must be downstream in the strand. This can expressed as follows: if there is a cleavage site at position i, then nucleotide i is base paired with nucleotide j where j>i. Entering into mfold the parameters ‘f i 0 2’ and ‘p i−i+1 1−i−1’ specifies that nucleotides i and i+1 should be basepaired to something (not to each other) and that i and i+1 can not be basepaired with nucleotides from 1 to i−1, respectively. This type of parameter can be considered a “soft” parameter because, while base pairing is required, the specific pairing partners of i and i+1 are left undefined, thereby allowing the suboptimal foldings generated using these parameters to predict multiple base-pairing partners of these nucleotides. This allows the use of existing constraint parameters without modification of the folding algorithm to predict only those structures that correlate with the cleavage data. If cleavage occurs at position i, then a series of structures can be calculated to explain it using the following constraints, ‘f i 0 1’ (nucleotide i is forced to be base paired) and ‘p 1 0 i−1’ (prohibiting nucleotides from 1 to i−1 to be base paired). For example, to generate structures that could be responsible for a major cleavage site at position 90 of HCV1a DNA, folding of 244 nt DNA fragment of HCV1a (FIG. 15) was done using mfold version 2.3 with constraints ‘f 90 0 1’ and ‘p 1 0 89’ predicting structure shown in FIG. 16A. It is important that this structure not only predicts a cleavage site at position 90, but also explains cleavages at positions 102–103, 161 and 173, making it a good candidate to represent actual base pairing in the DNA molecule. The structure shown in FIG. 16A does not explain cleavage sites at positions 118–119 and 173. To reveal corresponding structures, the folding was done using constraints ‘f 118 0 1’ and ‘p 1 0 117’ (nucleotides 1–117 are not base paired and nucleotide 118 is base paired) with one of resulting structures shown in FIG. 16B. Again this structure not only reasonably predicts cleavage site at position 117–118 but also shows how cleavage at position 123 may happen. The same two structures were identified in the development of the experiments described in Example 8, using manual comparison of the cleavage sites and the 32 suboptimal folds. By either method, the knowledge of the structure specificity of the 5' nuclease made it possible to eliminate from consideration, all predicted structures that would require the cleavage sites to vary from the known substrate structure. This reduced the field of possible structures from 32 to 2. Use of additional enzymes, such as 3' nucleases, or duplex specific chemical agents, that can identify other positions that must be base-paired within a structure can further narrow the field.

Among different baseparing partners predicted for nucleotide i, the one that is responsible for the CLEAVASE enzyme site at position i can be determined experimentally by using a combined deletion/mutation technique referred to as “PCR walking.” The PCR walking technique is based on CFLP analysis of PCR subfragments that are shorter variants of the analyzed sequence, variants that include only nucleotides from 1 to the selected partner of nucleotide i. For example, if the soft constraints cause mfold to predict that nucleotide 25 is paired with nucleotide 67, the PCR walk subfragments would include nucleotides 1–67. For each tested basepair, two subfragment variants are generated; one having a wild type sequence and another having the putative basepairing partner for nucleotide i (i.e., the 3' terminal nucleotide) substituted with a base that is not complementary to i. In the example above, the base to be substituted would be at position 67.

CFLP cleavage analysis is then performed on both of these subfragments. If the putative pairing partner does in fact basepair to i, then the wild type PCR subfragment would show cleavage immediately after i, but the substituted variant would show either a loss of cleavage, or a shifting of the cleavage site. If cleavage is the same in both subfragments, then i is pairing elsewhere; if cleavage at the original site is absent in both fragments, then the original pairing partner was likely to have been in the region deleted to make the subfragments. Once basepairing partner j of nucleotide i is determined, this information can be used as a “hard” constraint in the mfold program, forcing nucleotides i and i+1 be basepaired with nucleotides j and j−1.

Similar procedure can be repeated for each cleavage site, thereby generating a set of CFLP-defined constraints. Compatible constraints can be combined into groups so that each group would define an alternative structure of the molecule.

This procedure was used to find alternative secondary structures of 244 nucleotide RT-PCR fragment of HCV 1b 5'UTR region. Energy minimization folding of HCV1b fragment using the mfold program without constraints generated 29 structures, with difference in free energy between the two most stable structures of only 1.3%. Folding with soft constraints ‘f90 0 2’ and ‘p 90–91 1–89’, dictated by the major cleavage site at position 90, produced 28 structures (the difference between two most stable structures being 1.4%), 17 of which predicted baseparing between nucleotides 90 and 135, 4 of which predicted basepairing between nucleotides 90 and 105, another 4 predicted a 90–184 basepair, 2 predicted a 90-229 basepair, and 1 predicted a 90-198 basepair. PCR walking analysis showed that cleavage at position 90 can be explained by basepairing between nucleotides 90 and 135. Using this information as a “hard”

constraint ‘f90 135 2’ forces basepairing between nucleotides 90–91 and 134–135. Folding with this constraint resulted in 18 structures with difference in AG between optimal and suboptimal structures still only 1.4%.

A similar study for a cleavage site at position 161 showed it to pair with nucleotide 205. The constraints for cleavage sites 90 and 161 are compatible, meaning that they do not result in mutually exclusive structures, and can be combined together. Running the folding program with both constraints generated 13 structures and increased the discrimination between the two most stable structures to 3.4%. This process was continued by adding two new constraints for cleavage sites at positions 33 and 173, decreasing the number of predicted structures to 10, and increasing the difference in free energy between the optimal and first suboptimal structures to 7.2%, increasing the certainly that the optimal structure is likely to be form by the molecule.

In summary, the present invention provide a stepwise process for the analysis of nucleic acid structure without the use of the expensive and time consuming traditional techniques such as crystallography and nuclear magnetic resonance. In preferred embodiments, this process comprises the steps of: a) performing CFLP analysis to identify nucleotides that are basepaired on the 5' sides of stems; b) using this partial basepair information as a “soft constraint” in a fold-prediction program such as mfold to produce schematic diagrams (or other suitable output) of possible folded conformations that are consistent with the CFLP data; c) using PCR deletion and directed mutagenesis to confirm the identities of the nucleotides on the 3' sides of stems, to which the 5' side nucleotides are hydrogen bonded; and d) using this full basepair information as a “hard constraint” in the fold-prediction program to produce a highly refined set of predicted structures. Depending on the complexity of the data generated at each step, one or more of steps (a) through (d) may be omitted in any particular application. As noted above, a number of physical analytical methods may be combined with a number of secondary structure prediction algorithms to perform this type of analysis; the use of CFLP cleavage method in conjunction with the mfold software is discussed here as a convenient example and is not presented as a limitation on the scope of the present invention. The structure information gained in this process may be used not only is design of the structure probes of the present invention, but also in the improvement of CFLP, SSCP, and like mutation detection methods, and in the improvement of many hybridization-based methods that suffer as a consequence of target strand-structure interference, including but not limited to the polymerase chain reaction, dideoxynucleotide-chain termination sequencing, sequencing by hybridization, and other chip hybridization methods, ribozyme nucleic acid cleavage, and antisense manipulation of gene expression in vivo.

In addition to the structural mapping methods described above, there are several methods based on the actions of polymerizing enzymes that may be used to gain structural information. It has long been observed that reverse transcriptases can have difficulty polymerizing through RNA secondary structures. For this reason, reverse transcriptases that can be used at high temperatures have been sought (Myers et al., Biochem., 30:7661 [1991]), in order to facilitate full-length reverse transcription before cloning or PCR amplification. By intentionally using polymerases that produce such pausing effects, structures formed in a template strand may be mapped by the location of the pause sites (e.g., by extension of a labeled primer).

Another approach based on the use of DNA polymerases takes advantage of the observation that some DNA polymerases, upon encountering a fold in the template strand, will apparently polymerize across a structure by a mechanism that has been termed “strand switching,” thereby deleting the complement of the structured intermediate sequence. Though an understanding of the mechanism of strand switching is not necessary in order to practice the present invention, it is believed that strand switching involves some degree of displacement synthesis, such that a small portion of a sequence (even to the level of one base), is duplicated, followed by a branch migration that pairs the 3' end of the elongated strand with sequences on the far side of the template structure (Patel et al., Proc. Natl. Acad. Sci. USA 93:2969 [1996]). This mechanism can be used for structure mapping in at least two ways. For example, if the 3' side of a structure has been mapped using a 3' nuclease in a CFLP reaction, as discussed above, a primer may be designed such that the 3' end of the primer is poised to polymerize either along or across the structure-forming region. In addition to its template complementary sequence, the primer may be supplied with one or a few degenerate nucleotides (e.g., two or more nucleotides at the same position on different copies of the primer) on the 3' end, to provide opportunity for strand switching, regardless of the downstream sequence. The primer may then be extended under conditions favoring strand switching (Patel et al., supra). The isolation (e.g., by cloning and sequencing) of such sites should identify the sequences that are coming together to form the folded structures, thus facilitating bridge oligonucleotide design. A second approach is similar, but without the use of primers adjacent to any particular putative structure. In this embodiment, a strand to be analyzed is primed using a normal primer, and synthesis is carried out in the same or similar strand switch favoring conditions. The use of conditions that favor base misincorporation (e.g., by the use of manganese in the synthesis reactions), and therefore promote pausing of the polymerase, would provide additional opportunity for branch migration and strand switching. The analysis of the junction sites would then follow as with the first approach. By these methods, both sides of a cleavage structure could be identified. It is also expected that alternative pairing partners for various sequences would be represented in the collection of molecules created.

To distinguish between related nucleic acids, the regions that show different sites of cleavage or modification have the highest probability of having secondary structures that will respond differently to probes in the methods of the present invention. This is for two reasons. First, the cleavage or modification is physical evidence that a structure may form at a given site under the conditions of the cleavage or modification assay. Second, the structures that are detected by the CFLP method have been found to be predominantly local (i.e., formed from sequences that are close to each other along the nucleic acid strand, Brow et al., supra), so that changes observed are likely to be caused by base changes near the altered cleavage site. By designing oligonucleotide probes to hybridize or complex with the regions showing different sites of cleavage or modification there is a higher probability of finding either a base change (primary structure variation) or a folding change (secondary structure variation) that will affect the complexing of the probe to that site, thus facilitating the distinction between the comparison targets. Because of the complex nature of the folded structure formation as described above and because any given probe may interact with the target in a number of ways, choosing a probe in this way is not a guarantee that any particular probe will provide a diagnostic distinction. This is offered as a guide to increase the probability that it will. When working with an uncharacterized target or set of targets, the use of a multiplicity of such probes will give the most distinctive signature of probe/target complex formation.

In one embodiment, it is preferred that the probes used in the methods of the present invention be short enough to provide distinctive hybridization signatures for variants of a target. Probes longer than about 20 nt (e.g., 20 to 40 nt) can interact with target nucleic acids in a specific manner at elevated temperatures (e.g., higher than about 40° C.) and thus are suitable for use in the present methods. However, probes in this size range may interact with multiple sites on the target if the reaction is performed below about 40° C., reducing the distinction between variants. If this is the case, higher reaction temperatures or more stringent solution conditions (e.g., lower salt, the inclusion of helix-destabilizing agents such as dimethyl sulfoxide or formamide) may prove useful in enhancing the distinction between targets. In a particularly preferred embodiment, the method of the present invention is performed at ambient temperatures (e.g., 20 to 25° C.). When the assay is performed at room temperature, small probes with $T_m$s of 40° C. or less (e.g., 10 to 20 nt) can provide the discrimination necessary, as shown in the examples below. Probes in this size range are also less likely to fold on themselves under the reaction conditions, an effect that would reduce the binding efficacy of a probe without regard to the structure of the target.

As stated above, the capture probe may interact with the target in any number of ways. For example, in another embodiment, the capture probes may contact more than one region of the target nucleic acid. When the target nucleic acid is folded as described, two or more of the regions that remain single stranded may be sufficiently proximal to allow contact with a single capture probe. The capture oligonucleotide in such a configuration is referred to herein as a "bridge" or "bridging" oligonucleotide, to reflect the fact that it may interact with distal regions within the target nucleic acid. The use of the terms "bridge" and "bridging" is not intended to limit these distal interactions to any particular type of interaction. It is contemplated that these interactions may include non-canonical nucleic acid interactions known in the art, such as G-T base pairs, Hoogstein interactions, triplex structures, quadraplex aggregates, and the multibase hydrogen bonding such as is observed within nucleic acid tertiary structures, such as those found in tRNAs. The terms are also not intended to indicate any particular spatial orientation of the regions of interaction on the target strand, i.e., it is not intended that the order of the contact regions in a bridge oligonucleotide be required to be in the same sequential order as the corresponding contact regions in the target strand. The order may be inverted or otherwise shuffled.

It is known that synthetic oligonucleotides can be hybridized to non-contiguous sequences in both RNA and DNA strands, in a manner that either causes the intervening sequence to loop out, or that bridges the base of an internal folded structure (Richardson et al., J. Am. Chem. Soc., 113:5109 [1991]; Francois et al., Nucl. Acid. Res., 22: 3943 [1994]). However, these references do not suggest the design or use of bridging oligonucleotides that can distinguish between the different folded structures, or that bind with significantly reduced efficiency when the intervening sequence is unstructured. The present invention provides methods for the use and design of bridge capture probes with minimally stable regions of complementarity to make these bridge probes sensitive to changes in the target strand structure. Minimal stability (i.e., with a very low melting temperature), may be created in a number of ways, including by the use of short lengths of complementarity, low G-C basepair content, and/or the use of base analogs or mismatches to reduce the melting temperature. To test the effects of variations in the target structure on the efficiency of capture with different lengths of bridge probes, three test molecules were created; these are shown in schematic representation in FIG. 10. Test molecule #80 (SEQ ID NO:39) has a long segment of self complementarity and when folded as shown, the 8 basepair hairpin formed by this oligonucleotide is further stabilized by a "tri-loop" sequence in the loop end (i.e., three nucleotides form the loop portion of the hairpin) (Hiraro et al., Nucleic Acids Res. 22(4):576 [1994]). In test molecule #81 (SEQ ID NO:40), the stem is interrupted by 2 mismatches to form a less stable structure, and the region of self-complementarity is entirely removed in test molecule #82 (SEQ ID NO:41). All three of these molecules have identical target regions for the binding of the capture oligonucleotides, and an examination of their use is described in Example 6.

When a bridging oligonucleotide contacts sequences on either side of a basepaired stem, the structure formed is termed a three-way or three-arm junction. Such junctions have been studied extensively to determine their physical structure and to assess the differences that occur in the physical structure when additional nucleotides are included in these structures. When extra nucleotides are included at the junction site, where the three strands come together (i.e., when a 'bulged' structure is formed), it has been shown that the structure is more flexible and that some degree of coaxial stacking between the arms stabilized the structure compared to the unbulged structure (See e.g., Zhong et al., Biochem., 32:6898 [1993]; and Yang et al., Biochem., 35:7959 [1996]). The inclusion of two thymidine nucleotides in the portion of the probe that forms the junction is particularly preferred.

There are a number of approaches that may be used in the design or selection of bridging capture probes. As noted above, the term "capture probes" is not intended to limit the application of the bridging probes of the present invention to the capture of a target strand onto a solid support. Additional applications of the bridging probes are described in the Experimental Examples, below. Furthermore, for simplicity of discussion and to avoid repetition, this section describes one embodiment of the present invention, namely a process for creating bridge oligonucleotides that interact with only two regions of a target nucleic acid. It is not intended, however, that the invention be limited to the use of oligonucleotides that have only two sites of interaction. It is contemplated that bridge oligonucleotides may be created that can interact with many sites on a folded target molecule.

Bridge oligonucleotides may be created by the joining two or more short oligonucleotide sequences. The creation of bridge oligonucleotides may be based upon observations that these sequences have been determined to interact with a given folded target when used in isolation, without limitation to any particular nature of interaction, or they may be deduced to be capable of such interaction by virtue of sequence composition, complementarity, or like analysis. For convenience, such sequences are termed herein "contact sequences," to reflect the putative ability of such a sequence to contact the target molecule. The designation of a particular sequence as a contact sequence is not intended to imply that the sequence is in contact, or is required to contact a target in any particular embodiment.

In alternative embodiments, contact sequences may be joined by synthesizing or otherwise creating a new oligonucleotide that incorporates both sequences into a single molecule. In one embodiment, the sequences are joined contiguously within the bridge oligonucleotide (i.e., without any intervening nucleotides or other space-filling material). In another embodiment, the contact sequences are non-contiguous, with the spacing provided by additional nucleotides. In a preferred embodiment, the contact sequences are bridged by two thymidine nucleotides, as depicted in several of the bridging probes in FIG. 11A. In another preferred embodiment, the contact sequences in the bridging oligonucleotide are connected by a segment of nucleic acid containing a region of self-complementarity, such that the bridging oligonucleotide itself contains a folded structure. A stem-loop folded structure within the bridge oligonucleotide, if situated opposite a stem in the target nucleic acid, would permit the formation of a four-way Holliday structure, which is stabilized by coaxial stacking of the arms (Duckett et al., Cell 55:79 [1988]).

Alternatively, the bridge oligonucleotide may be created by linking the individual sequences with non-nucleotide spacers such as those commonly known in the art, such as d-spacers (Glen Research Corp. (Sterling, Va.), or other chemical chains, such as polyethers (Cload and Shephartz, J. Am. Chem. Soc., 113:6324[1991]).

Contact sequences may also be linked to form the bridge probes post synthetically, by enzymatic (e.g., ligation) or by chemical interaction to produce either covalent (e.g., cross-linked) or non-covalent bonds (e.g., affinity bonds such as formed in an antigen-antibody interaction).

The formation of the complexes between the probes and the targets may be performed using a wide variety of solution conditions. Conditions considered to be "low stringency" have been well defined in the areas of hybridization to filters and membranes (Sambrook et al, *Molecular Cloning: A Laboratory Manual,* 2nd ed. Cold Spring Harbor Laboratory Press, Cold Spring Harbor, N.Y. [1989]) and to other solid supports, such as silicon or glass wafers, chips or slides (Maskos and Southern, Nucl. Acids Res., 20:1675 [1992]). It is contemplated that the formation of the complexes may be done in solution, before the binding of either the target or the probe to a solid support, or it may be done after one of the molecules has been bound to the support. It is recognized, and considered to be within the scope of the invention, that the kinetics and mechanics of complex formation may differ depending on whether complex formation is performed in solution or on a solid support. However, as long as complexes can be made to form at detectable levels, a set of conditions is considered appropriate for use in the present methods.

It is further contemplated that the complexes may be formed on nucleic acids that have not been isolated from a sample source, such as in live cells (in vivo) or in tissue samples (in situ). It is also contemplated that a nucleic acid found within a cell may be native to that cell, or may be transferred into the cell (e.g., by viral infection, by laboratory-induced transfection, or by in vivo transcription from an introduced nucleic acid). The methods of the present invention as applied to nucleic acids within cells are not limited to nucleic acids of any particular origin or cell type.

A number of solid supports known in the art are contemplated for use with the methods of the present invention. In the examples below, a 96-well microtiter plate is used as a support medium. The method may also be applied to other supports nucleic acid commonly used for nucleic acid analyses, including but not limited to beads, particles, membranes, filters, dipsticks, slides, plates and microchips. Such supports may be composed of a number of materials known to be compatible with nucleic acids analyses, including but not limited to agarose, styrene, nylon, glass and silicon.

Individual complex formation (i.e., assessing a single target with a single probe) may be sufficiently informative for some applications. In other applications, it may be desirable to use a number of probes against a single target. For a large number of probes, it may be useful to use an array format, in which a large number of probes are bound to a surface in an ordered pattern. Means for creating such arrays on surfaces such as glass slides and microchips are known in the art (Southern et al., Genomics 13:1008 [1992]; Chee et al., Science 274:610 [1996]; and Foder et al., Science 251:767 [1991]; and U.S. Pat. No. 5,436,327 to Southern et al., U.S. Pat. No. 5,429,807 to Matson et al. and U.S. Pat. No. 5,599,695 to Pease et al., all of which are herein incorporated by reference).

A. Use of Bridging Oligonucleotides in Catalyzed Reactions

As discussed above, it is contemplated that any catalyzed reaction that is specifically operative on a duplex formed between a target nucleic acid and a substantially complementary probe may be configured to perform on the bridging probe/folded target complex. Examples demonstrating the use of bridging probes in primer extension, ligation and structure-specific nuclease cleavage are provided below. Primer extension reactions and ligation reactions are well known in the art and the basic method for performing these reactions are published (See e.g., Sambrook et al., supra), as well as often being provided by the manufactures of the enzymes. The INVADER invasive cleavage reaction is based on the use of a structure-specific nuclease that is used to cleave oligonucleotide probes once they hybridize to a target nucleic acid. The nature of the reaction allows the cleavage of many copies of the probe oligonucleotide for each copy of the target nucleic acid. Complete descriptions of the technology and its variables are included in PCT Publications WO 97/27214 and WO 98/05809 and U.S. Pat. Nos. 5,846,717, 6,001,567, 5,985,557, 6,090,543 and 5,994,069, all of which are herein incorporated by reference. Briefly, The INVADER assay is a method for detecting a specific target sequence within a nucleic acid mixture. The assay depends on the coordinate actions of at least two synthetic oligonucleotides, together constituting a probe system, and a structure-specific nuclease. The oligonucleotides of the probe system may be referred to as the signal oligonucleotide and the INVADER oligonucleotide. By the extent of their substantial complementarity to the target strand, each of these oligonucleotides defines a specific region of the target strand. These regions should be oriented such that when the probe system is hybridized to the target strand, the INVADER oligonucleotide is upstream of the signal oligonucleotide and such that the INVADER oligonucleotide sequence either overlaps with the probe oligonucleotide sequence by at least one nucleotide (i.e., the two regions of the target nucleic acid defined by the oligonucleotides of the probe system share at least one nucleotide), or, when there is no overlap, the two target regions defined by the oligonucleotides must abut, and the 3' terminus of the INVADER oligonucleotide preferably has a single additional nucleotide that is not complementary to the target strand at that site.

The nuclease recognizes the structure formed by hybridization of the probe system to the specific target nucleic acid and cleaves the signal oligonucleotide, the precise site of cleavage being dependent on the amount of its overlap with the INVADER oligonucleotide. If the reaction is run such that the structure can partially disassemble to allow cleaved signal oligonucleotide to be replaced by intact signal oligonucleotide (e.g., performed at an elevated temperature to promote rapid dissociation and association of signal probes), then multiple probes may be cleaved for each copy of the target nucleic acid, the amount of target present then being calculable from the rate of product accumulation and the time of incubation.

The nucleases of the INVADER assay include any nuclease capable of specifically recognizing the structure defined above, and cleaving within the signal oligonucleotide, thereby creating cleavage products. Such nucleases include, but are not limited to the 5' nucleases associated with eubacterial DNA polymerases, and the DNA repair-associated nucleases of the FEN1, RAD2 and XPG classes.

The oligonucleotides of the INVADER probe system may comprise DNA, RNA, PNA and combinations thereof, as well as modified nucleotides, universal bases, adducts, etc. They may be either fully or partially complementary to their cognate target sequences. In addition, they may be labeled or unlabeled.

Detection may be by analysis of cleavage products or by analysis of remaining uncleaved signal probe. Detection of the cleavage products may be through release of a label. Such labels comprise: dyes; radiolabels such as $^{32}P$; binding moieties such as biotin; haptens such as digoxgenin; luminogenic, phosphorescent or fluorogenic moieties; fluorescent dyes alone or in combination with moieties that can suppress or shift emission spectra by fluorescence resonance energy transfer (FRET).

Cleavage products may be analyzed by physical separation (e.g., by electrophoresis, hybridization or by selective binding to a support) or without physical separation (e.g., by changes in fluorescence in FRET-based analysis, or by change in rotation rate in solution in fluorescence polarization analysis).

Cleavage products can be used subsequently in any reaction or read-out method that can make use of oligonucleotides. Such reactions include enzyme dependent modification reaction, such as ligation, tailing with a template-independent nucleic acid polymerase and primer extension with a template-dependent nucleic acid polymerase. The modification of the products may serve to add one or more labels or binding moieties, to alter mass, to add specific sequences, or to otherwise facilitate specific analysis of the cleavage products.

Cleavage product may be used to complete a functional structure, such as a competent promoter for in vitro transcription or other protein binding site. The oligonucleotide product may also be used to complete a cleavage structure to enable a subsequent invasive cleavage reaction, the product of which may be detected or used by any of the methods described above, including the participation in further invasive cleavage reactions.

It is envisioned that any or all of the oligonucleotide probes used in the INVADER assay may be made to contact non-contiguous sequences in the target strand. In the Examples below, the upstream INVADER oligonucleotide is made to bridge a structure, thus directing the cleavage of a non-bridging probe.

Specific applications of the structure probing methods of the present invention are described below.

B. Detection and Identification of Pathogens Using the Structure Probing Method

1. Detection and Identification of Multi-Drug Resistant *M. tuberculosis*

In the past decade there has been a tremendous resurgence in the incidence of tuberculosis in this country and throughout the world. In the United States, the incidence of tuberculosis has risen steadily during past decade, accounting for 2000 deaths annually, with as many as 10 million Americans infected with the disease. The situation is critical in New York City, where the incidence has more than doubled in the past decade, accounting for 14% of all new cases in the United States in 1990 (Frieden et al., New Engl. J. Med., 328:521 [1993]).

The crisis in New York City is particularly dire because a significant proportion (as many as one-third) of the recent cases are resistant to one or more anti-tuberculosis drugs (Frieden et al, supra and Hughes, Scrip Magazine May [1994]). Multi-drug resistant tuberculosis (MDR-TB) is an iatrogenic disease that arises from incomplete treatment of a primary infection (Jacobs, Jr., Clin. Infect. Dis., 19:1 [1994]). MDR-TB appears to pose an especially serious risk to the immunocompromised, who are more likely to be infected with MDR-TB strains than are otherwise healthy individuals [Jacobs, Jr., supra]. The mortality rate of MDR-TB in immunocompromised individuals is alarmingly high, often exceeding 90%, compared to a mortality rate of <50% in otherwise uncompromised individuals (Donnabella et al., Am. J. Respir. Dis., 11:639 [1994]).

From a clinical standpoint, tuberculosis has always been difficult to diagnose because of the extremely long generation time of *Mycobacterium tuberculosis* as well as the environmental prevalence of other, faster growing mycobacterial species. The doubling time of *M. tuberculosis* is 20–24 hours, and growth by conventional methods typically requires 4 to 6 weeks to positively identify *M. tuberculosis* (Jacobs, Jr. et al., Science 260:819 [1993] and Shinnick and Jones in *Tuberculosis: Pathogenesis, Protection and Control*, Bloom, ed., American Society of Microbiology, Washington, D.C. [1994], pp. 517–530). It can take an additional 3 to 6 weeks to diagnose the drug susceptibility of a given strain (Shinnick and Jones, supra). Needless to say, the health risks to the infected individual, as well as to the public, during a protracted period in which the patient may or may not be symptomatic, but is almost certainly contagious, are considerable. Once a drug resistance profile has been elucidated and a diagnosis made, treatment of a single patient can cost up to $250,000 and require 24 months.

The recent explosion in the incidence of the disease, together with the dire risks posed by MDR strains, have combined to spur a burst of research activity and commercial development of procedures and products aimed at accelerating the detection of *M. tuberculosis* as well the elucidation of drug resistance profiles of *M. tuberculosis* clinical isolates. A number of these methods are devoted primarily to the task of determining whether a given strain is *M. tuberculosis* or a mycobacterial species other than tuberculosis. Both culture based methods and nucleic-acid based methods have been developed that allow *M. tuberculosis* to be positively identified more rapidly than by classical methods: detection times have been reduced from greater than 6 weeks to as little as two weeks (culture-based methods) or two days (nucleic acid-based methods). While culture-based methods are currently in wide-spread use in clinical laboratories, a number of rapid nucleic acid-based methods that can be applied directly to clinical samples are under development. For all of the techniques described below, it is necessary to first "decontaminate" the clinical samples, such as sputum (usually done by pretreatment with N-acetyl L-cysteine and NaOH) to reduce contamination by non-mycobacterial species (Shinnick and Jones, supra).

The polymerase chain reaction (PCR) has been applied to the detection of *M. tuberculosis* and can be used to detect its presence directly from clinical specimens within one to two days. The more sensitive techniques rely on a two-step procedure: the first step is the PCR amplification itself, the second is an analytical step such as hybridization of the amplicon to a *M. tuberculosis*-specific oligonucleotide probe, or analysis by RFLP or DNA sequencing (Shinnick and Jones, supra).

The Amplified *M. tuberculosis* Direct Test (AMTDT; Gen-Probe) relies on Transcription Mediated Amplification (TMA; essentially a self-sustained sequence reaction [3SR] amplification) to amplify target rRNA sequences directly from clinical specimens. Once the rRNA has been amplified, it is then detected by a dye-labeled assay such as the PACE2. This assay is highly subject to inhibition by substances present in clinical samples.

The Cycling Probe Reaction (CPR; ID Biomedical). This technique, which is under development as a diagnostic tool for detecting the presence of *M. tuberculosis*, measures the accumulation of signal probe molecules. The signal amplification is accomplished by hybridizing tripartite DNA-RNA-DNA probes to target nucleic acids, such as *M. tuberculosis*-specific sequences. Upon the addition of RNAse H, the RNA portion of the chimerical probe is degraded, releasing the DNA portions, which accumulate linearly over time to indicate that the target sequence is present (Yule, Bio/Technol., 12:1335 [1994]). The need to use RNA probes is a drawback, particularly for use in crude clinical samples, where RNase contamination is often rampant.

The above nucleic acid-based detection and differentiation methods offer a clear time savings over the more traditional, culture-based methods. While they are beginning to enter the clinical setting, their usefulness in the routine diagnosis of M tuberculosis is still in question, in large part because of problems with associated with cross-contamination and low-sensitivity relative to culture-based methods. In addition, many of these procedures are limited to analysis of respiratory specimens (Yule, supra).

i) Determination of the Antibiotic Resistance Profile of *M. tuberculosis* a) Culture-based methods: Once a positive identification of M tuberculosis has been made, it is necessary to characterize the extent and nature of the strain's resistance to antibiotics. The traditional method used to determine antibiotic resistance is the direct proportion agar dilution method, in which dilutions of culture are plated on media containing antibiotics and on control media without antibiotics. This method typically adds an additional 2–6 weeks to the time required for diagnosis and characterization of an unknown clinical sample (Jacobs, Jr., supra).

The Luciferase Reporter Mycobacteriophage (LRM) assay was first described in 1993 (Jacobs, Jr. et al. [1993], supra). In this assay, a mycobacteriophage containing a cloned copy of the luciferase gene is used to infect mycobacterial cultures. In the presence of luciferin and ATP, the expressed luciferase produces photons, easily distinguishable by eye or by a luminometer, allowing a precise determination of the extent of mycobacterial growth in the presence of antibiotics. Once sufficient culture has been obtained (usually 10–14 days post-inoculation), the assay can be completed in 2 days. This method suffers from the fact that the LRM are not specific for *M. tuberculosis*: they also infect *M. smegmatis* and *M. bovis* (e.g., BCG), thereby complicating the interpretation of positive results. Discrimination between the two species must be accomplished by growth on specialized media that does not support the growth of *M. tuberculosis* (e.g., NAP media). This confirmation requires another 2 to 4 days.

The above culture-based methods for determining antibiotic resistance will continue to play a role in assessing the effectiveness of putative new anti-mycobacterial agents and those drugs for which a genetic target has not yet been identified. However, recent success in elucidating the molecular basis for resistance to a number of anti-mycobacterial agents, including many of the front-line drugs, has made possible the use of much faster, more accurate and more informative DNA polymorphism-based assays.

b) DNA-based methods: Genetic loci involved in resistance to isoniazid, rifampin, streptomycin, fluoroquinolones, and ethionamide have been identified (Jacobs, Jr., supra; Heym et al., Lancet 344:293 [1994]; and Morris et al., J. Infect. Dis., 171:954 [1995]. A combination of isoniazid (inh) and rifampin (rif) along with pyrazinamide and ethambutol or streptomycin, is routinely used as the first line of attack against confirmed cases of *M. tuberculosis* (Banerjee et al., Science 263:227 [1994]). Consequently, resistance to one or more of these drugs can have disastrous implications for short course chemotherapy treatment. The increasing incidence of such resistant strains necessitates the development of rapid assays to detect them and thereby reduce the expense and community health hazards of pursuing ineffective, and possibly detrimental, treatments. The identification of some of the genetic loci involved in drug resistance has facilitated the adoption of mutation detection technologies for rapid screening of nucleotide changes that result in drug resistance. The availability of amplification procedures such as PCR and SDA, which have been successful in replicating large amounts of target DNA directly from clinical specimens, makes DNA-based approaches to antibiotic profiling far more rapid than conventional, culture-based methods.

The most widely employed techniques in the genetic identification of mutations leading to drug resistance are DNA sequencing, Restriction Fragment Length Polymorphism (RFLP), PCR-Single Stranded Conformational Polymorphism (PCR-SSCP), and PCR-dideoxyfingerprinting (PCR-ddF). All of these techniques have drawbacks as discussed above. None of them offers a rapid, reproducible means of precisely and uniquely identifying individual alleles.

In contrast, the structure probing methods of the present invention provide an approach that relies on interactions of oligonucleotide probes with the target nucleic acid on the primary, secondary and tertiary structure level. This method requires a fraction of the time, skill and expense of the techniques described above, and can be performed using instrumentation commonly found in the clinical lab (e.g., a microtiter plate reader).

The application of this method to the detection of MDR-TB is illustrated herein using segments of DNA amplified from katG gene. Other genes associated with MDR-TB, including but not limited to those involved in conferring resistance to isoniazid (inhA), streptomycin (rpsL and rrs), and fluoroquinoline (gyrA), are equally well suited to the structure probing assay of the present invention.

2. Detection and Identification of Hepatitis C Virus

Hepatitis C virus (HCV) infection is the predominant cause of post-transfusion non-A, non-B (NANB) hepatitis around the world. In addition, HCV is the major etiologic agent of hepatocellular carcinoma (HCC) and chronic liver disease world wide. HCV infection is transmitted primarily to blood transfusion recipients and intravenous drug users although maternal transmission to offspring and transmission to recipients of organ transplants have been reported.

The genome of the positive-stranded RNA hepatitis C virus comprises several regions including 5' and 3' noncoding regions (i.e., 5' and 3' untranslated regions) and a polyprotein coding region that encodes the core protein (C), two envelope glycoproteins (E1 and E2/NS1) and six non-structural glycoproteins (NS2–NS5b). Molecular biological analysis of the small (9.4 kb) RNA genome has showed that some regions of the genome are very highly conserved between isolates, while other regions are fairly rapidly changeable. The 5' noncoding region (NCR) is the most highly conserved region in the HCV. These analyses have allowed these viruses to be divided into six basic genotype groups, and then further classified into over a dozen subtypes (the nomenclature and division of HCV genotypes is evolving; See Altamirano et al., J. Infect. Dis., 171:1034 [1995] for a recent classification scheme). These viral groups are associated with different geographical areas, and accurate identification of the agent in outbreaks is important in monitoring the disease. While only Group 1 HCV has been observed in the United States, multiple HCV genotypes have been observed in both Europe and Japan.

The ability to determine the genotype of viral isolates also allows comparisons of the clinical outcomes from infection by the different types of HCV, and from infection by multiple types in a single individual. HCV type has also been associated with differential efficacy of treatment with interferon, with Group 1 infected individuals showing little response (Kanai et al., Lancet 339:1543 [1992] and Yoshioka et al, Hepatol., 16:293 [1992]). Pre-screening of infected individuals for the viral type will allow the clinician to make a more accurate diagnosis, and to avoid costly but fruitless drug treatment.

Existing methods for determining the genotype of HCV isolates include traditional serotyping, PCR amplification of segments of the HCV genome coupled with either DNA sequencing or hybridization to HCV-specific probes and RFLP analysis of PCR amplified HCV DNA. All of these methods suffer from the limitations discussed above (i.e., DNA sequencing is too labor-intensive and expensive to be practical in clinical laboratory settings; RFLP analysis suffers from low sensitivity).

Universal and genotype specific primers have been designed for the amplification of HCV sequences from RNA extracted from plasma or serum (Okamoto et al., J. Gen. Virol., 73:673 [1992]; Yoshioka et al., Hepatol., 16:293 [1992] and Altamirano et al., supra). These primers can be used to generate PCR products that serve as substrates in the structure probing assay of the present invention. As shown herein, the structure probing assay provides a rapid and accurate method of typing HCV isolates. The structure probing analysis of HCV substrates allows a distinction to be made between the major genotypes and subtypes of HCV thus providing improved methods for the genotyping of HCV isolates.

3. Detection and Identification of Bacterial Pathogens

Identification and typing of bacterial pathogens is critical in the clinical management of infectious diseases. Precise identity of a microbe is used not only to differentiate a disease state from a healthy state, but is also fundamental to determining whether and which antibiotics or other antimicrobial therapies are most suitable for treatment. Traditional methods of pathogen typing have used a variety of phenotypic features, including growth characteristics, color, cell or colony morphology, antibiotic susceptibility, staining, smell and reactivity with specific antibodies to identify bacteria. All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained. In many cases the pathogens are very similar to the organisms that make up the normal flora, and may be indistinguishable from the innocuous strains by the methods cited above. In these cases, determination of the presence of the pathogenic strain may require the higher resolution afforded by more recently developed molecular typing methods.

A number of methods of examining the genetic material from organisms of interest have been developed. One way of performing this type of analysis is by hybridization of species-specific nucleic acid probes to the DNA or RNA from the organism to be tested. This is done by immobilizing the denatured nucleic acid to be tested on a membrane support, and probing with labeled nucleic acids that will bind only in the presence of the DNA or RNA from the pathogen. In this way, pathogens can be identified. Organisms can be further differentiated by using the RFLP method described above, in which the genomic DNA is digested with one or more restriction enzymes before electrophoretic separation and transfer to a nitrocellulose or nylon membrane support. Probing with the species-specific nucleic acid probes will reveal a banding pattern that, if it shows variation between isolates, can be used as a reproducible way of discriminating between strains. However, these methods are susceptible to the drawbacks outlined above: assays based on sequence-specific hybridization to complex (i.e., whole genome) targets are time-consuming and may give false or misleading results if the stringency of the hybridization is not well controlled, and RFLP identification is dependent on the presence of suitable restriction sites in the DNA to be analyzed.

To address these concerns about hybridization and RFLP as diagnostic tools, several methods of molecular analysis based on polymerase chain reaction (PCR) amplification have gained popularity. In one well-accepted method, called PCR fingerprinting, the size of a fragment generated by PCR is used as an identifier. In this type of assay, the primers are targeted to regions containing variable numbers of tandem repeated sequences (referred to as VNTRs an eukaryotes). The number of repeats, and thus the length of the PCR amplicon, can be characteristic of a given pathogen, and co-amplification of several of these loci in a single reaction can create specific and reproducible fingerprints, allowing discrimination between closely related species.

In some cases where organisms are very closely related, however, the target of the amplification does not display a size difference, and the amplified segment must be further probed to achieve more precise identification. This may be done on a solid support, in a fashion analogous to the whole-genome hybridization described above, but this has the same problem with variable stringency as that assay.

Alternatively, the interior of the PCR fragment may be used as a template for a sequence-specific ligation event. As outlined above for the LCR, in this method, single stranded probes to be ligated are positioned along the sequence of interest on either side of an identifying polymorphism, so that the success or failure of the ligation will indicate the presence or absence of a specific nucleotide sequence at that site. With either hybridization or ligation methods of PCR product analysis, knowledge of the precise sequence in the area of probe binding must be obtained in advance, and differences outside the probe binding area are not detected. These methods are poorly suited to the examination and typing of new isolates that have not been fully characterized.

In the methods of the present invention, primers that recognize conserved regions of bacterial ribosomal RNA genes allow amplification of segments of these genes that include sites of variation. The variations in ribosomal gene sequences have become an accepted method not only of differentiating between similar organisms on a DNA sequence level, but their consistent rate of change allows these sequences to be used to evaluate the evolutionary relatedness of organisms. That is to say, the more similar the nucleic acid is at the sequence level, the more closely related the organisms in discussion are considered to be (Woese, Microbiol. Rev., 51:221–271 [1987]). The present invention allows the amplification products derived from these sequences to be used to create highly individual structural fingerprints (e.g., profiles of the complex formation with an array of probes), allowing the detection of sequence polymorphisms without prior knowledge of the site, character or even the presence of the polymorphisms. With appropriate selection of primers, the PCR amplification can be made to be either all-inclusive (e.g., using the most highly conserved ribosomal sequences) to generate PCR products that, when analyzed using the methods of the present invention, allow comparison of distantly related organisms, or the primers can be chosen to be very specific for a given genus, to allow examination at the species and subspecies level. While the examination of ribosomal genes is extremely useful in these characterizations, the use of the structure probing method in bacterial typing is not limited to these genes. Other genes, including but not limited to those associated with specific growth characteristics, (e.g., carbon source preference, antibiotic resistance, resistance to methicillin or antigen production), or with particular cell morphologies (such as pilus formation) are equally well suited to the structure probing of the present invention.

C. Identification of Sites Accessible for Hybridization by Degenerate-Primer Reverse Transcription (DP-RT)

The present invention further provides methods for determining and characterizing the accessibility of regions contained in nucleic acids to hybridization by oligonucleotides or other desired binding partners. Such methods find use, for example, in the identification, characterization, and design of antisense oligonucleotides that optimally bind to folded RNA targets. These methods also find use in the identification, characterization, and design of oligonucleotides in the structure probing assays described above. For example, the methods allow for the selection of oligonucleotides that bind at or near folded structures, such that they are particularly sensitive to differences in sequence (e.g., local or distal) between two or more target nucleic acids that are compared.

Figure 45A:
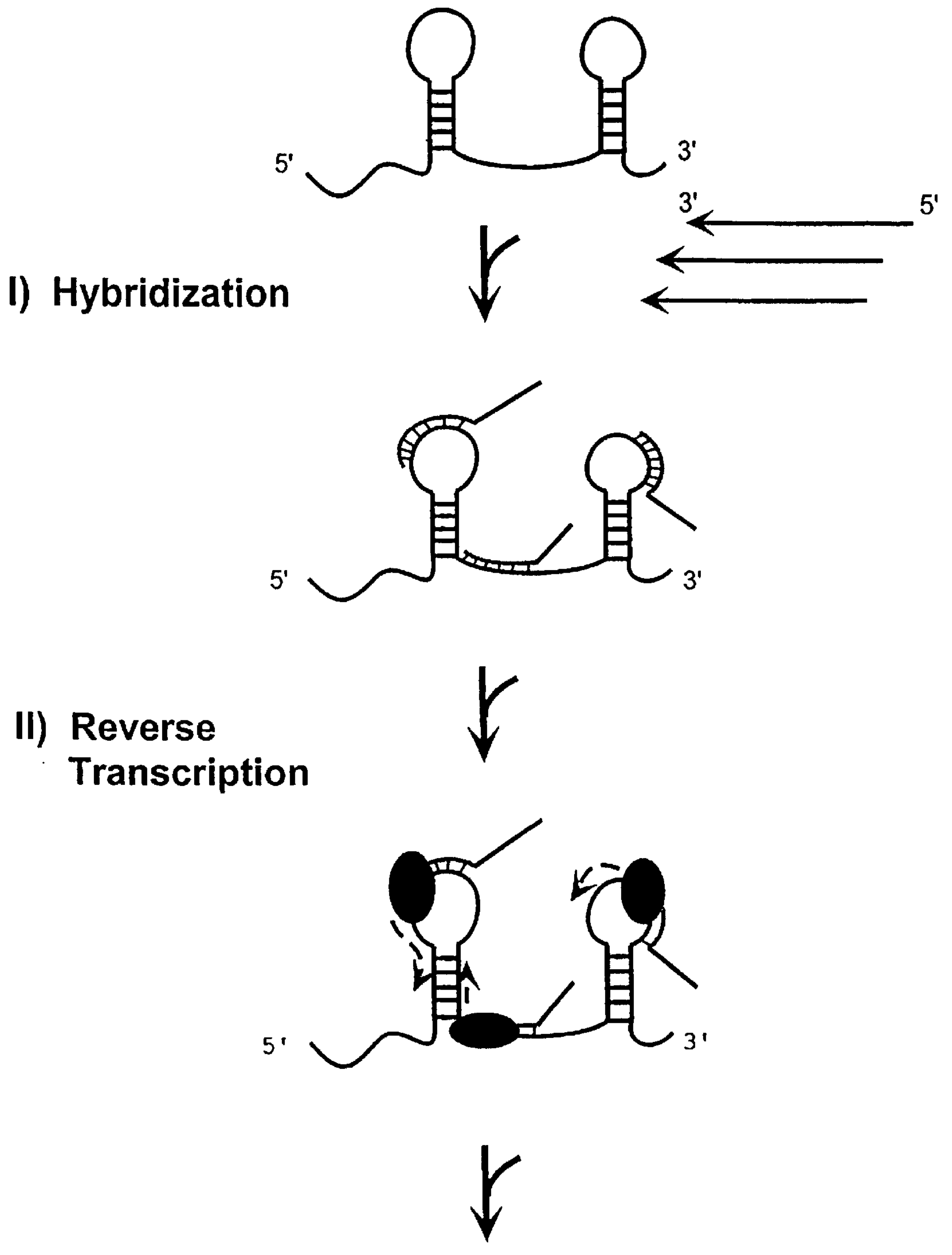

In preferred embodiments of the present invention, target nucleic acids (e.g., mRNA target nucleic acids) are contacted with a plurality of primers containing a region of degenerate sequence and primer extension reactions are conducted (See e.g., FIGS. 45A and 45B). Where the target nucleic acid is an RNA molecule, preferred enzymes for use in the extension reactions are reverse transcriptases, which produce a DNA copy of the RNA template. Folded structures present in the target nucleic acid affect the initiation and/or efficiency of the extension reaction. For example, certain extension products are not generated where the primer is complementary to a sequence that is present in a folded structure. As described in detail below, the extension products of the primers are analyzed to provide a map of the accessible sites. For example, the presence of an extension product indicates that the corresponding primer used to generate the extension product was able to bind to an accessible region of the target nucleic acid. Regions of the target nucleic acid that do not allow hybridization of the primer and do not result in the production of an extension product are considered inaccessible sites. Such methods are referred to herein as "degenerate primer reverse transcription" or "DP-RT."

In preferred embodiments of the present invention, the primers used to generate extension products contain a region of degeneracy. In such embodiments, a plurality of primers are used so that multiple regions of the target are primed. In particularly preferred embodiments, a sufficient number of different primers are used such that every combination of nucleotides in the region of degeneracy is represented within the mixture of oligonucleotides. For example, where the primers have a region of degeneracy that is six nucleotides in length, a sufficient number of primers is used such that an A, T, C, or G is located in each of the six positions, in every combination possible. For a region of degeneracy that is two nucleotides in length, this would mean the following sequences are present in different, individual members of the oligonucleotide mixture: AA, AT, AG, AC, TT, TA, TG, TC, GG, GA, GT, GC, CC, CA, CG, and CT. Having such a collection of primers with a region of degeneracy maximizes the number of regions of the target that are potentially bound by the primers. In preferred embodiments, the mixture of primers is capable of binding to every region of the target, in single-base staggered increments, assuming the target lacks folded structure (e.g., for a target nucleic acid having the sequence 5'-ATGGCGT-3', the corresponding degenerate regions of the primers would include the sequences [5'-3'] AC, CG, GC, CC, CA, and AT).

The extension products generated from the plurality of extension primers may be analyzed in any suitable manner. In preferred embodiments of the present invention, the extension products are amplified prior to further analysis. Any amplification method may be utilized. In some embodiments, the nucleic acid amplification is conducted (e.g., using the polymerase chain reaction). In yet other embodiments, a portion of the extension product is used to generate an amplifiable signal. For example, each extension primer, in addition to having the region of degeneracy, may further comprise a second region comprising an INVADER oligonucleotide. Following the generation of the extension products, the extension products or fragments thereof (e.g., fragments generated by cleavage of the extension product to release the INVADER oligonucleotide portion) are used as an INVADER oligonucleotide in an INVADER assay to detect the presence of extension product (e.g., with a predetermined INVADER target sequences based on the known sequence of the INVADER oligonucleotide). One skilled in the art will appreciate a wide array of amplification methods that find use in the detection of the extension products of the present invention.

The presence or absence of an extension product (or an amplification product or signal corresponding to an extension product) provides information about the folded structure of the target nucleic acid and about the accessibility of the target nucleic acid to hybridization by oligonucleotide probes. For example, as discussed in detail below, an amplification product can be correlated to the exact sequence of the target nucleic acid that hybridized to an extension primer used to generate the amplification product. This identified region of the folded target is accessible to oligonucleotide binding. The sub-set of extension primers that do not produce extension products can be correlated to regions of the target that are not accessible to oligonucleotide binding (e.g., regions of secondary or higher order structures).

While any folded nucleic acid may be used with the present invention, in preferred embodiments, the folded nucleic acid comprises RNA. In certain preferred methods of the present invention, oligonucleotides with a minimum of six degenerate bases at their 3'-end and a known 5'-end sequence (as described in detail below), herein referred to as 5'-tag, are allowed to hybridize with the target RNA. Libraries containing each of the possible sequences in the degenerate portion are obtained or generated. Since all possible sequences complementary to accessible regions of the RNA are present in the degenerate oligonucleotide library, oligonucleotides complementary to accessible regions of the target RNA will hybridize. By taking advantage of reverse transcriptase recognition and extension of these randomly hybridized oligonucleotides, a reverse transcription (RT) reaction is then initiated by adding reverse transcriptase and its appropriate reagents. Afterward, a standard polymerase chain reaction (PCR) is performed on the RT products using primers that are specific for the target RNA (e.g., 5'-end of the cDNA) and the known 5'-tag sequence of the degenerate oligonucleotides. Using the target cDNA and the same sense-strand primer used for the PCR reaction, sequencing reactions are then performed and their products are loaded side by side with the RT-PCR products on PAGE. The 3'-end of the sequences of the extended products that correspond to regions where the degenerate oligonucleotides bound the RNA, are then mapped. This gives an accessible sites map of the target RNA where the degenerate primer bound and extended. FIGS. 45A and 45B present an outline of the principles of this method.

Thus, the present invention provides methods based on a the degenerate-primer RT (DP-RT) approach for determining extendible/accessible regions of RNA targets. Experiments conducted during the development of the present invention have shown that the method gives extendible sites that correlate well with previously determined accessible regions for both human ha-ras and rabbit β-globin mRNA obtained using RNase H footprinting and libraries of complementary oligonucleotide arrays, respectively. Compared with these other experimental methods for determining accessible sites, the accessible sites determination of the present invention relies on a very simple, well established, and straight forward technique (i.e., RT-PCR) and provides accurate results in few hours with little cost and labor efforts.

Comparison with antisense inhibition data published on hICAM-1 also indicate that sites obtained using DP-RT can readily and successfully be used for antisense oligonucleotide design. This is of great importance to the antisense technology since one of the major hurdles that antisense researchers face is determining accessible regions of their targeted mRNA.

Additionally, experiments conducted during the development of the present invention show that results obtained using DP-RT can be directly used in RNA INVADER assays. This allows for a more efficient probe and INVADER oligonucleotide designs to regions of RNA that allow proficient probe cycling. The ability to do so is important for gene expression assays that require lower levels of detection of total mRNA. Additionally, these probe/INVADER oligonucleotide design principles can applied for INVADER assays designed to detect viral loads allowing lower detection limits of RNA targets in a time and cost efficient manner.

Recently, several computer assisted predictions of accessible RNA regions have been developed such as mfold (Zucker, Science 244:48 [1989]), OligoWalk (Mathews et al., RNA 5:1458 [1999]), and variations of both (Sczakiel, Frontiers in Biosciences 5:194 [2000]; Patzel et al., Nucleic Acids Res., 27:4328 [1999]; Walton et al., Biotechnol. Bioeng., 65:1 [1999]). The quality of the computer-assisted prediction of accessible regions in RNA was tested versus results obtained with the DP-RT method described herein. The program OligoWalk—a module of the software RNAstructure of the Turner laboratory (Mathews et al., RNA 5:1458 [1999]) was used since it uses the latest set of thermodynamic parameters for both RNA, DNA, and their hybrids (Allawi and SantaLucia, Biochemistry 36:10581 [1997]; Mathews et al., J. Mol. Biol., 288:911 [1999]; Sugimoto et al., Biochemistry 34:11211 [1995]) in an algorithm that relies on mfold for RNA secondary structure prediction (Zucker, Science 244:48 [1989]). hIFN-γ was used as a model for OligoWalk predictions. A set secondary structures of the hIFN-γ were predicted using RNAstructure (Zucker, Science 244:48 [1989]; Mathews et al., J. Mol. Biol., 288:911 [1999]) and were used to perform OligoWalk. OligoWalk is designed to predict the most favorable regions of an RNA target for designing antisense oligonucleotides by estimating the overall thermodynamics of hybridizing an antisense oligomer to the RNA by taking into account the thermodynamics of destroying any structural motifs in the RNA target or the antisense oligonucleotide. OligoWalk was performed using 12mer oligonucleotides with oligomer concentration of 0.5 μM and considering local target structure only and the set of suboptimal target structures predicted with a 25% maximum energy difference. Results are shown on FIG. 53. No obvious correlation can be concluded when comparing OligoWalk results with the DP-RT results obtained. This suggests that, while theoretical prediction of accessible sites in RNA is a good initial step towards narrowing the possibilities of effective antisense oligonucleotide designs, it is not guaranteed that all sites predicted using such approach will work. As can be seen in the case of hIFN-γ, OligoWalk over-predicts the number of accessible regions in the RNA. Also, whenever OligoWalk is correct about the location of an accessible site, it is almost always the case that it is predicted to be wider (i.e., longer stretch of nucleotides) than it actually is. This is not surprising since theoretical models and algorithms of accessible sites predictions are dependent on the degree of accuracy of RNA secondary structure prediction and, among others, ignore the effects of tertiary interactions. Thus more accurate experimental methods such as DP-RT are superior to computer modeling in terms of guaranteeing that all accessible sites determined are truly accessible.

While the above discussion focuses on RNA, the DP-RT method may also be used on DNA. Folded DNA may be used as a target directly. However, in some embodiments of the present invention, the DNA is converted to RNA and DP-RT is performed on the RNA target. It is contemplated that accessibility information obtained from an RNA copy of a DNA provides useful information regarding the accessible sites on the DNA itself. Even without a 100% correlation, the technique finds use in reducing the number of candidate oligonucleotides that need to be tested to confirm accessibility to the DNA. This technique finds particular use in regions of DNA that have significant amounts of folded structure, such as promoter and upstream 5' regulatory regions of genes. In such embodiments, the region of the DNA to be tested is placed in an expression system and exposed to RNA polymerase to generate an RNA copy of the DNA. DP-RT is then performed on the RNA copy. Accessible sites determined by this method can be confirmed by testing whether an oligonucleotide complementary to the corresponding site on the DNA will bind to the DNA. Sites that are determined to be inaccessible, particularly in 5' upstream regulatory regions of genes, provide regions that may be involved in regulation of gene expression, since many such folded structures provide recognition sites for transcription factors. Thus, in some embodiments of the present invention, sequences representing inaccessible regions find use in characterizing transcription factor binding or in generating oligonucleotide decoys that inhibit the binding of regulatory factors to native DNA (See e.g., U.S. Pat. No. 6,060,310, herein incorporated by reference in its entirety).

D. Extraction of Nucleic Acids from Clinical Samples

To provide nucleic acid substrates for use in the detection and identification of microorganisms in clinical samples using the methods of the present invention, nucleic acid is extracted from the sample. The nucleic acid may be extracted from a variety of clinical samples (fresh or frozen tissue, suspensions of cells [e.g., blood], cerebral spinal fluid, sputum, urine, etc.) using a variety of standard techniques or commercially available kits. For example, kits that allow the isolation of RNA or DNA from tissue samples are available from Qiagen, Inc. (Chatsworth, Calif.) and Stratagene (La Jolla, Calif.). For example, the QIAamp Blood kits permit the isolation of DNA from blood (fresh, frozen or dried) as well as bone marrow, body fluids or cell suspensions. QIAamp tissue kits permit the isolation of DNA from tissues such as muscles, organs and tumors.

It has been found that crude extracts from relatively homogenous specimens (such as blood, bacterial colonies, viral plaques, or cerebral spinal fluid) are better suited to severing as templates for the amplification of unique PCR products than are more composite specimens (such as urine, sputum or feces) (Shibata in *PCR: The Polymerase Chain Reaction*, Mullis et al., eds., Birkhauser, Boston [1994], pp. 47–54). Samples that contain relatively few copies of the material to be amplified (i.e., the target nucleic acid), such as cerebral spinal fluid, can be added directly to a PCR. Blood samples have posed a special problem in PCRs due to the inhibitory properties of red blood cells. The red blood cells must be removed prior to the use of blood in a PCR; there are both classical and commercially available methods for this purpose (e.g., QIAamp Blood kits, passage through a Chelex 100 column [BioRad], etc.). Extraction of nucleic acid from sputum, the specimen of choice for the direct detection of *M. tuberculosis*, requires prior decontamination to kill or inhibit the growth of other bacterial species. This decontamination is typically accomplished by treatment of the sample with N-acetyl L-cysteine and NaOH (Shinnick and Jones, supra). This decontamination process is necessary only when the sputum specimen is to be cultured prior to analysis.

E. Design of INVADER Assay Directed to Accessible Sites. Oligonucleotide Design a. Target-Specific Regions: Length and Melting Temperature In some embodiments, the length of the analyte-specific regions (ASRs) are defined by the temperature selected for running the reaction. Starting from the desired position (e.g., a variant position or splice junction in a target RNA, or a site corresponding to a low free energy value in an OligoWalk analysis) an iterative procedure is used by which the length of the ASR is increased by one base pair until a calculated optimal reaction temperature ($T_m$ plus salt correction to compensate for enzyme and any other reaction conditions effects, as shown below) matching the desired reaction temperature is reached.

The melting temperature ($T_m$) of an oligonucleotide is calculated using the nearest-neighbor model and published parameters for either DNA/DNA (Allawi and SantaLucia, Biochemistry, 36:10581 [1997]) or DNA/RNA [Sugimoto, et al., Biochemistry 34:11211 (1995)] duplex formation. Because the assay's salt concentrations are often different than the solution conditions in which the nearest-neighbor parameters were obtained (1M NaCl and no divalent metals), and because the presence and concentration of the enzyme influence optimal reaction temperature, an adjustment should be made to the calculated $T_m$ to determine the optimal temperature at which to perform a reaction. One way of compensating for these factors is to vary the value provided for the salt concentration within the melting temperature calculations. This adjustment is termed a 'salt correction'. As used herein, the term "salt correction" refers to a variation made in the value provided for a salt concentration for the purpose of reflecting the effect on a $T_m$ calculation for a nucleic acid duplex of a non-salt parameter or condition affecting said duplex. Variation of the values provided for the strand concentrations will also affect the outcome of these calculations. By using a value of 0.5 M NaCl (SantaLucia, Proc Natl Acad Sci USA, 95:1460 [1998]) and strand concentrations of about 1 mM of the probe and 1 fM target, the algorithm used for calculating probe-DNA target melting temperature has been adapted for use in predicting optimal INVADER assay reaction temperature.

In general probes are selected to have an ASR with a calculated $T_m$ of about 60° C. if a stacking oligonucleotide is not used, and a $T_m$ of about 50 to 55° C. if a stacking oligonucleotide is used (a stacking oligonucleotide typically raises the $T_m$ of a flanking probe oligonucleotide by about 5 to 15° C.). If the position of variation or a splice junction is a starting position, then the additions are made to the 3' end of the probe. Alternatively, if the 3' end of the probe is to be positioned at the most accessible site, the additions are in the 5' direction. In some embodiments, wherein a stacker oligonucleotide is to be used, it is preferred that the probe be designed to have a 3' base that has stable stacking interaction interface with the 5' base of the stacker oligonucleotide. The stability of coaxial stacking is highly dependent on the identity of the stacking bases. Overall, the stability trend of coaxial stacking in decreasing order is purine:purine>purine:pyrimidine≈pyrimidne:purine> pyrimidine:pyrimidine. In other embodiments employing a stacker, a less stable stacking interaction is preferred; in such cases the probe 3' base and/or the stacker 5' base are selected to provide a less stable stacking interaction. In some embodiments, the probe 3' base and/or the stacker 5' base are selected to have a mismatch with respect to the target strand, to reduce the strength of the stacking interaction.

The same principles are also followed for INVADER oligonucleotide design. Briefly, starting from the position N, additional residues complementary to the target RNA starting from residue N−1 are then added in the upstream direction until the stability of the INVADER-target hybrid exceeds that of the probe (and therefore the planned assay reaction temperature). In preferred embodiments, the stability of the INVADER-target hybrid exceeds that of the probe by 12–15° C. In general, INVADER oligonucleotides are selected to have a $T_m$ near 75° C. Software applications, such as INVADERCREATOR (Third Wave Technologies, Madison, Wis.) or Oligonucleotide 5.0 may be used to assist in such calculations.

If a stacking oligonucleotide is to be used, similar design principles are applied. The stacking oligonucleotide is generally designed to hybridize at the site adjacent to the 3' end of the probe oligonucleotide, such that the stacker/target helix formed can coaxially stack with the probe/target helix (U.S. Pat. No. 5,985,557, incorporated herein by reference). The sequence is selected to have a calculated $T_m$ of about 60 to 65° C., with the calculation based on the use of natural bases. However, stacking oligonucleotides are generally synthesized using only 2'-O-methyl nucleotides, and consequently, have actual $T_m$s that are higher than calculated by about 0.8° C. per base, for actual $T_m$s close to 75° C.

In some embodiments, ARRESTOR oligonucleotides are included in a secondary reaction. ARRESTOR oligonucleotides are provided in a secondary reaction to sequester any remaining uncleaved probe from the primary reaction, to preclude interactions between the primary probe and the secondary target strand. ARRESTOR oligonucleotides are generally 2'-O-methylated, and comprise a portion that is complementary to essentially all of their respective probe's target-specific region, and a portion that is complementary to at least a portion of the probe's flap regions (e.g., six nucleotides, counted from the +1 base towards the 5' end of the arm).

b. Non-Complementary Regions

Probe 5' Arm Selection

The non-complementary arm of the probe, if present, is preferably selected (e.g., by an iterative process as described above) to allow the secondary reaction to be performed at a particular reaction temperature. In the secondary reaction, the secondary probe is generally cycling, and the cleaved 5' arm (serving as an INVADER oligonucleotide) should stably bind to the secondary target strand.

INVADER Oligonucleotide 3' Terminal Mismatch Selection

In preferred embodiments, the 3' base of the INVADER oligonucleotide is not complementary to the target strand, and is selected in the following order of preference (listed as INVADER oligonucleotide 3' base/target base):

| | |
|---|---|
| C in target: | C C > A C > T C > G C |
| A in target: | A A > C A > G A > T A |
| G in target: | A G > G G > T G > C G |
| U in target: | C U > A U > T U > G U |

C. Folding and Dimer Analysis

In some embodiments, the oligonucleotides proposed for use in the INVADER assay are examined for possible inter- and intra-molecular structure formation in the absence of the target RNA. In general, it is desirable for assay probes to have fewer predicted inter- or intra molecular interactions. In some embodiments, the program OLIGO (e.g., OLIGO 5.0, Molecular Biology Insights, Inc., Cascade, Colo.) is used for such analysis. In other embodiments, the program mfold is used for the analysis. In yet other embodiments, the RNAStructure program can be used for dimer analysis. The following sections provide stepwise instructions for the use of these programs for analysis of INVADER assay oligonucleotides.

OLIGO 5.0 Analysis for Probe Structure and Interaction Prediction.

Analysis of INVADER oligonucleotides using OLIGO 5.0 comprises the following steps. All menu choices are shown in UPPER CASE type.

1. Launch OLIGO 5.0 and open a sequence file for each mRNA to be analyzed. This is done by using a menu to select the following Choose FILE->NEW Paste in longest available sequence Choose ACCEPT & QUIT (F6)

2. Set Program settings to default

Choose FILE->RESET->ORIGINAL DEFAULTS

3. Identify Probe Oligonucleotide

Select OLIGO LENGTH to be around 16 nucleotides (open the menu for this option by using ctrl-L keystrokes).

Move the cursor indicating the 5' end of the Current Oligo until the 3' end is located at the candidate cleavage site residue.

Choose ANALYSE->DUPLEX FORMATION->CURRENT OLIGO (ctrl-D) for a rough determination of the extent of dimer and hairpin formation.

Confirm length of analyte region corresponds with desired reaction temperature [e.g., through the use of $T_m$ calculation as described in the Optimization of Reaction Conditions, I (c) of the Detailed Description of the Invention]

Select the "LOWER" button in OLIGO 5.0 to copy the anti-sense sequence (this will be the analyte-specific region of the actual probe oligonucleotide and is anti-sense to the RNA strand.)

Import into a database file.

Save to computer memory.

4. Identify INVADER Oligonucleotide

Choose sequence adjacent to the probe oligonucleotide identified from step 3.

Select OLIGO LENGTH to ~24 nucleotides

Confirm length of analyte region corresponds with desired reaction temperature [e.g., through the use of $T_m$ calculation as described in the Optimization of Reaction Conditions, I (c) of the Detailed Description of the Invention, about 75° C. for INVADER oligonucleotides). Select the "LOWER" button in OLIGO 5.0 to copy the corresponding anti-sense sequence (this will be the analyte-specific region of the actual INVADER oligonucleotide.)

Import into a database file.

Save to computer memory.

5. Addition of Cleaved Arm Sequence and INVADER Oligonucleotide Mismatch Sequence.

Export the Probe oligonucleotide as Upper Primer.

Export the INVADER oligonucleotide as Lower Primer.

EDIT UPPER PRIMER to add in a candidate arm sequence (selected, for example, as described above).

Check that the arm sequence does not create new secondary structures (analysis performed as described above).

EDIT LOWER PRIMER to add in the 3' mismatched nucleotide that will overlap into the cleavage site (selected according to the guidelines for this mismatched bases, provided above).

Select all Upper and Lower Primer boxes in the "Print/Save Options"

PRINT ANALYSIS of Upper (Probe) and Lower (INVADER) oligonucleotides and check for lack of stable secondary structures.

Save both mRNA sequence and oligonucleotide sequence database files before quitting the program.

Generally, oligonucleotides having detected intramolecular formations with stabilities of less than −6 ΔG are preferred. Less stable structures represent poor substrates for CLEAVASE enzymes, and thus cleavage of such structures is less likely to contribute to background signal. Probe and INVADER oligonucleotides having less affinity for each other are more available to bind to the target, ensuring the best cycling rates.

The $T_m$ of dimerized probes (i.e., probes wherein one probe molecule is hybridized to another probe molecule) should ideally be lower than the $T_m$ for the probe hybridized to the target, to ensure that the probes preferentially hybridize to the target sequence at the elevated temperatures at which INVADER assay reactions are generally conducted. Similarly, the $T_m$ for the INVADER oligonucleotide hybridized either to itself or to a probe molecule should be lower than the INVADER oligonucleotide/target $T_m$. It is preferred that dimer $T_m$s (i.e., Probe/Probe and Probe/INVADER oligonucleotide) be 25° C. or less to ensure that they will be unlikely to form at the planned reaction temperature.

The melting temperatures for each of these complexes can be determined as described above in Optimization of Reaction Conditions, I (c) of the Detailed Description of the Invention, or by using the OLIGO software. Once RNAs sites and several candidate INVADER assay oligonucleotide sets are selected according to the process outlined above, the candidate oligonucleotide sets can be ranked according to the degree to which they comply with preferred selection rules, e.g., their location on the SS-Count average plot (peak, valley, neither), and the energetic predictions of probe and INVADER oligonucleotide interactions. In some embodiments, the ranked probe sets are tested in order of rank to identify one or more sets having suitable performance in an RNA INVADER assay. In other embodiments, several of the top ranked sets (e.g., two, three or more) are selected for testing, to rapidly identify one or more sets having suitable or desireable performance.

Mfold Analysis for Probe Structure and Interaction Prediction

Analysis of probe and INVADER oligonucleotide interactions may be performed using mfold for DNA provided by Michael Zuker, available through Rensselaer Polytechnic Institute at bioinfo.math.rpi.edu/~mfold/dna/form1.cgi. The analysis is performed without changing the default ionic conditions, and with a selected temperature of 37° C. and with % suboptimality set to 75. Each sequence (e.g., probe, INVADER oligonucleotide, stacker, etc.) is folded using the program to check for any unimolecular structure formation (e.g., hairpins). The energies provided by mfold gives for unimolecular structures can be used as provided, without further calculations.

Bimolecular structure formation for a given oligonucleotide is assessed by typing in the oligonucleotide sequence (5' to 3') followed by the sequence of a small, stable hairpin forming sequence (e.g., CCCCCTTTTGGGGG [SEQ ID NO:]), followed by the same oligonucleotide sequence, again listed 5' to 3. Constraints are entered to require that these Ts remain single-stranded and the strings of Cs and Gs in this spacer are basepaired. The command "F" is used to force basepairing, while the command "P" is used to prohibit basepairing, and the positions of the forced or prohibited basepairs are counted from the 5' end. For example, if the sequence of interest is a 20-mer, then the following is entered:

F 21 0 5 [this forces the C's, C21 to C25, to base pair]

P 26 0 4 [this forces the T's, T26 to T29, to be single stranded]

F 30 0 5 [this forces the G's, G30 to G34, to base pair]

On examination of the resulting structures, the stability of each can be estimated by subtracting the stability (i.e., the thermodynamic measures) of the central spacer hairpin from the total result (i.e., Thermodynamics of possible structure= mfold structure thermodynamics−core hairpin thermodynamics). For convenience, in some embodiments, any nearest neighbor interactions between the central hairpin and dimers formed by the test sequence are ignored for this calculation; a more accurate analysis would require consideration of this interaction. The core hairpin formed by CCCCCTTTTGGGGG (SEQ ID NO:152) has the following thermodynamics: ΔG=−5.3; ΔH=−37.8; ΔS=−104.8.

The process can be demonstrated using the following probe sequence: 5'-CCCTATCTTTAAAGTTTTTAAAAAGTTTGA-3' (SEQ ID NO:153). The oligonucleotide sequence is examined by mfold analysis for bimolecular structures using the following steps.

1—In mfold sequence box type:

```
                                          (SEQ ID NO:154)
CCCTATCTTTAAAGTTTTTAAAAAGTTTGACCCCCTTTTGGGGGCCC
TATCTTTAAAGTTTTTAAAAAGTTTGA
```

2—In the constraint box type:

P 36 0 4

F 31 0 5

F 40 0 5

Results (showing one):

```
Structure 1
dG = -14.2 dH = -150.5 dS = -439.5 Tm = 69.3

CCCTATCTTT    |G                  G      ------
     T

           AAA TTTTTAAAAA TTTGA          CCCCC T

           TTT AAAAATTTTT AAATT          GGGGG T

---------AG  G           G      TCTATCCC       T

To evaluate the stability of the duplex:
      CCCTATCTTT    |G      G

           AAA TTTTTAAAAA TTTGA

           TTT AAAAATTTTT AAATT

---------AG G           G     TCTATCCC
```

the thermodyanamic values for the hairpin alone are subtracted from the values for the complete structure:

ΔG=−14.2−(−5.3)=−8.9,

ΔH=−150.5−(−37.8)=−112.7,

ΔS=−439.5−(−104.8)=−334.7,

Using a calculation wherein $T_m$(° C.)={ΔH/[ΔS+R ln (CT/4)]}−273.15, wherein R is the gas constant 1.987 (cal/

K.mol), ln is the natural log, and CT is the total single strand concentration in Molar, this results in a calculated $T_m$ of 46.1° C. for the non-hairpin portion of the structure.

The above method is not limited to the use of the core hairpin sequence CCCCCTTTTGGGGG but rather any stable hairpin sequences can be used. For example, CGCGCGGAACGCGCG (SEQ ID NO:155) or CCCGGGTTTTCCCGGG (SEQ ID NO:156). However, if a different hairpin sequence is used, one needs to calculate its stability using mfold and use its thermodynamics in the subsequent calculations.

RNAStructure for Oligonucleotide Interaction Prediction

Dimer formation can also be evaluated using the RNAStructure program. Unlike mfold, RNAStructure allows the calculation of all possible oligonucleotide—oligonucleotide interactions and provides an output .ct file. One can then view the structures using any .ct viewing program such as RNAStructure or RNAvis (1997, P. Rijk, University of Antwerp (UIA), available on the Internet at rma.uia.ac.be/rnavis) and evaluate the stability of any dimer formation using the nearest-neighbor model (Borer et al., 1974) and DNA nearest-neighbor parameters (Allawi & SantaLucia, 1997).

For example, to evaluate the propensity of the sequence 5' AGGCGCACCAATTTGGTGTT 3' (SEQ ID NO:157) for dimer formation using the DNA Fold Intermolecular module of RNAStructure, the sequence is saved into a file (e.g., probe.seq) and the following parameters are set:

Sequence file 1: probe.seq
Sequence file 2: probe.seq
CT file: dimer.ct
Max % Energy difference: 50
Max number of structures: 20
Window size: do not change After the calculation is done, one can view the resulting .ct file using the "view" module of RNAStructure. Generally, there will be several structures within the ct file. The view module is used to view them individually. One of the dimers that the test sequece, above, can form according to RNAStructure is:

```
AGGCG           TT
     CACCAATTTGGTG
     GTGGTTTAACCAC
  TT            GCGGA
```

According to the nearest-neighbor model (i.e., using DNA nearest-neighbor and mismatch parameters [Allawi & SantaLucia, 1997]), the stability of this duplex in 1M NaCl and at a probe concentration of 100 μM is:

$\Delta G°_{37}=-10.07$
$\Delta H=-87.6$
$\Delta S=-250.1$
$T_m=50.1°$ C.

By changing the identities of Sequence Files 1 & 2, RNAStructure can be used to evaluate the possibility of any dimer formation between pairs of all of the DNA oligonucleotides present in an INVADER assay reaction.

iv. Assay Performance Evaluation

Probe sets selected according to the guidelines provided above can be tested in the INVADER assay to evaluate performance. While the oligonucleotides are designed to perform at or near a particular desired reaction temperature, the best performance for a given design may not be precisely at the intended temperature. Thus, in evaluating any new INVADER assay probe set, it can be helpful to examine the performance in the INVADER assay conducted at several different reaction temperatures, over a range of about 10 to 15° C., centered around the designed temperature. For convenience, temperature optimization can be performed on a temperature gradient thermocycler with a fixed amount of RNA (e.g., 2.5 amoles of an in vitro transcript per reaction), and for a fixed amount of time (e.g., 1 hour each for Primary and Secondary reactions). The temperature gradient test will reveal the temperature at which the designed probe set produces the best performance (e.g., the highest level of target-specific signal compared to background signal, generally expressed as a multiple of the zero-target background signal, or "fold over zero").

The results can be examined to see how close the measured temperature optimum is to the intended temperature of operation. In some embodiments, it is desirable to have probe sets that operate at or near a pre-selected temperature. If the measured temperature optimum is higher than the desired reaction temperature, a probe design can be altered in ways that tend to reduce the probe/target $T_m$ (e.g., shortened by one or more bases, or altered to contain one or more mismatched bases). In some embodiments, wherein a stacker oligonucleotide is not used, wherein the reaction temperature is more than 7° C. above the desired reaction temperature, and wherein the performance (e.g., the fold over zero) is acceptable, use of a 3' mismatch on the probe oligonucleotide is likely to lower the reaction temperature without otherwise altering the assay performance.

An LOD determination can be made by performing reactions on varying amounts of target RNA (e.g., an in vitro transcript control RNA of known concentration). In preferred embodiments, a designed assay has an LOD of less than 0.05 attomole. In particularly preferred embodiments, a designed assay has an LOD of less than 0.01 attomole. It is contemplated that the same guideline provided above for reducing the LOD of a designed assay may be used for the purpose of raising the LOD of a designed assay, i.e., to make it LESS sensitive to the presence of a target RNA. For example, it may be desirable to detect an abundant RNA and a rare RNA in the same reaction. In such a reaction, it may be desirable to attenuate the signal generated for the abundant RNA so that it does not overwhelm the signal from the rarer species. In some embodiments this may be done by designing probe sets for reduced signal generation, e.g., an LOD of at least (not less than) 0.5 attomoles. In some embodiments, a single step INVADER assay may be used for detection of abundant targets in a sample, while sequential INVADER reactions to amplify signal, as described, may be used for less abundant analytes in the same sample. In preferred embodiments, the single step and the sequential INVADER assay reactions for the different analytes are performed in a single reaction.

In some embodiments, time course reactions are run, wherein the accumulation of signal for a known amount of target is measured for reactions run for different lengths of time. This measurement will establish the linear ranges, i.e., the ranges in which accurate quantitative measurements can be made using a given assay design, with respect to time and starting target RNA level.

v. Design and Assay Optimization

Some designed assays may not meet the preferred performance criteria described above. A number of variations on the performance of INVADER assay reactions have been described herein. In optimizing performance of the INVADER assay for the detection of RNA targets, these variations may be used alone or in combination. For example, in some embodiments, a stacker oligonucleotide is employed. While not limiting the present invention to any particular mechanism of action, in some embodiments, a stacker oligonucleotide may enhance performance of an assay by altering the hybridization characteristics (e.g., $T_m$) of a probe or an INVADER oligonucleotide. In some embodiments, a stacker oligonucleotide may increase performance by enabling the use of a shorter probe. In other embodiments, a stacker oligonucleotide may enhance performance by altering the folded structure of the target nucleic acid. In yet other embodiments, the enhancing activity of the stacker oligonucleotide may involve these and other mechanisms in combination.

In other embodiments, the target site may be shifted. In some embodiments, reactions are optimized by testing multiple probe sets that shift along a suspected accessible site. In preferred embodiments, such probe sets shift along the accessible site in one to two base increments. In embodiments wherein accessible sites have previously been predicted only by computer analysis, physical detection of the accessible sites may be employed to optimize a probe set design. In preferred embodiments, the ACCESSIBLE SITES method of detecting accessible sites is employed. In some embodiments, optimization of a probe set design may require shifting of the target site to a newly identified accessible site.

In some embodiments, e.g., wherein an accessible site has been identified yet probe set performance is low, a change in the design of a probe 5' arm may improve assay performance without altering the site targeted. In other embodiments, altering the length of an ARRESTOR oligonucleotide (e.g., increasing the length of the portion that is complementary to the 5' arm region of the probe) may reduce background signal, thus increasing the probe stet performance.

Other variations on oligonucleotide design may be employed to alter performance in an assay. Some modifications may be employed to shift the ideal operating temperature of a probe set design into a preferred temperature range. For example, the use of shorter oligonucleotides and the incorporation of mismatches generally act to reduce the $T_m$s, and thus reduce the ideal operating temperatures, of designed oligonucleotides. Conversely, the use of longer oligonucleotides and the employment of stacking oligonucleotides generally act to increase the $T_m$s, and thus increase the ideal operating temperatures of the designed oligonucleotides.

Other modifications may be employed to alter other aspects of oligonucleotide performance in an assay. For example, the use of base analogs or modified bases can alter enzyme recognition of the oligonucleotide. In some embodiments, such modified bases are used to protect a region of an oligonucleotide from nuclease cleavage. In other embodiments, modified bases are used to affect the ability of an oligonucleotide to participate as a member of a cleavage structure that is not in a position to be cleaved (e.g., to serve as an INVADER oligonucleotide to enable cleavage of a probe). These modified bases may be referred to as "blocker" or "blocking" modifications. In some embodiments, assay oligonucleotides incorporate 2'-O-methyl modifications. In other embodiments, assay oligonucleotides incorporate 3' terminal modifications (e.g., $NH_2$, 3' hexanol, 3' phosphate, 3' biotin).

In yet other embodiments, the components of the reaction may be altered to affect assay performance. For example, oligonucleotide concentrations may be varied. Oligonucleotide concentrations can affect multiple aspects of the reaction. Since melting temperatures of complexes are partly a function of the concentrations of the components of the complex, variation of the concentrations of the oligonucleotide components can be used as one facet of reaction optimization. In the methods of the present invention, ARRESTOR oligonucleotides may be used to modulate the availability of the primary probe oligonucleotides in an INVADER assay reaction. In some embodiments, an ARRESTOR oligonucleotide may be excluded. Other reaction components may also be varied, including enzyme concentration, salt and divalent ion concentration and identity.

Experimental

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); IVS (intervening sequence); p (plasmid); ml (microliters); ml (milliliters); mg (micrograms); pmoles (picomoles); mg (milligrams); MOPS (3-[N-Morpholino]propanesulfonic acid); M (molar); mM (milliMolar); mM (microMolar); nm (nanometers); nt (nucleotide); bp (base pair); kb (kilobase pair); kdal (kilodaltons); OD (optical density); EDTA (ethylene diamine tetra-acetic acid); FITC (fluorescein isothiocyanate); IPTG (isopropylthiogalactoside); X-Gal (5-bromo-4-chloro-3-indolyl-b-D-galactosidase); SDS (sodium dodecyl sulfate); $NaPO_4$ (sodium phosphate); Tris (tris(hydroxymethyl)aminomethane); PMSF (phenylmethyl-sulfonylfluoride); TBE (Tris-Borate-EDTA, i.e., Tris buffer titrated with boric acid rather than HCl and containing EDTA); PBS (phosphate buffered saline); Ab Peptides (Ab Peptides, St. Louis, Mo.); PPBS (phosphate buffered saline containing 1 mM PMSF); PAGE (polyacrylamide gel electrophoresis); TWEEN (polyoxyethylene-sorbitan); hICAM-1 (human intercellular adhesion molecule 1); hIFN-γ (human interferon-γ); PCR (polymerase chain reaction); RT (reverse transcription); DP-RT (degenerate primer reverse transcription); TET (tetrachlorofluorecsein); TMA-Cl (tetramethylammonium chloride); JBL (JBL, San Louis Obispo, Calif.); Boehringer Mannheim (Boehringer Mannheim, Indianapolis, Ind.); Dynal (Dynal A. S., Oslo, Norway); Epicentre (Epicentre Technologies, Madison, Wis.); MJ Research (MJ Research, Inc., Watertown, Mass.); National Biosciences (National Biosciences, Plymouth, Minn.); New England Biolabs (New England Biolabs, Beverly, Mass.); Novagen (Novagen, Inc., Madison, Wis.); Perkin Elmer (Perkin Elmer, Norwalk, Conn.); Promega Corp. (Promega Corp., Madison, Wis.); Stratagene (Stratagene Cloning Systems, La Jolla, Calif.); Third Wave (Third Wave Technologies, Inc., Madison, Wis.); and USB (U.S. Biochemical, Cleveland, Ohio).

20×SSPE (sodium chloride, sodium phosphate, EDTA) contains per liter: 174 grams NaCl, 27.6 grams $NaH_2PO_4.H_2O$ and 7.4 grams EDTA; the pH is adjusted to 7.4 with NaOH. PBS (phosphate-buffered saline) contains per liter: 8 grams NaCl, 0.2 grams KCl, 1.44 grams $Na_2PO_4$ and 0.24 grams $KH_2PO_4$; the pH is adjusted to 7.4 with HCl.

EXAMPLE 1

Figure 2:
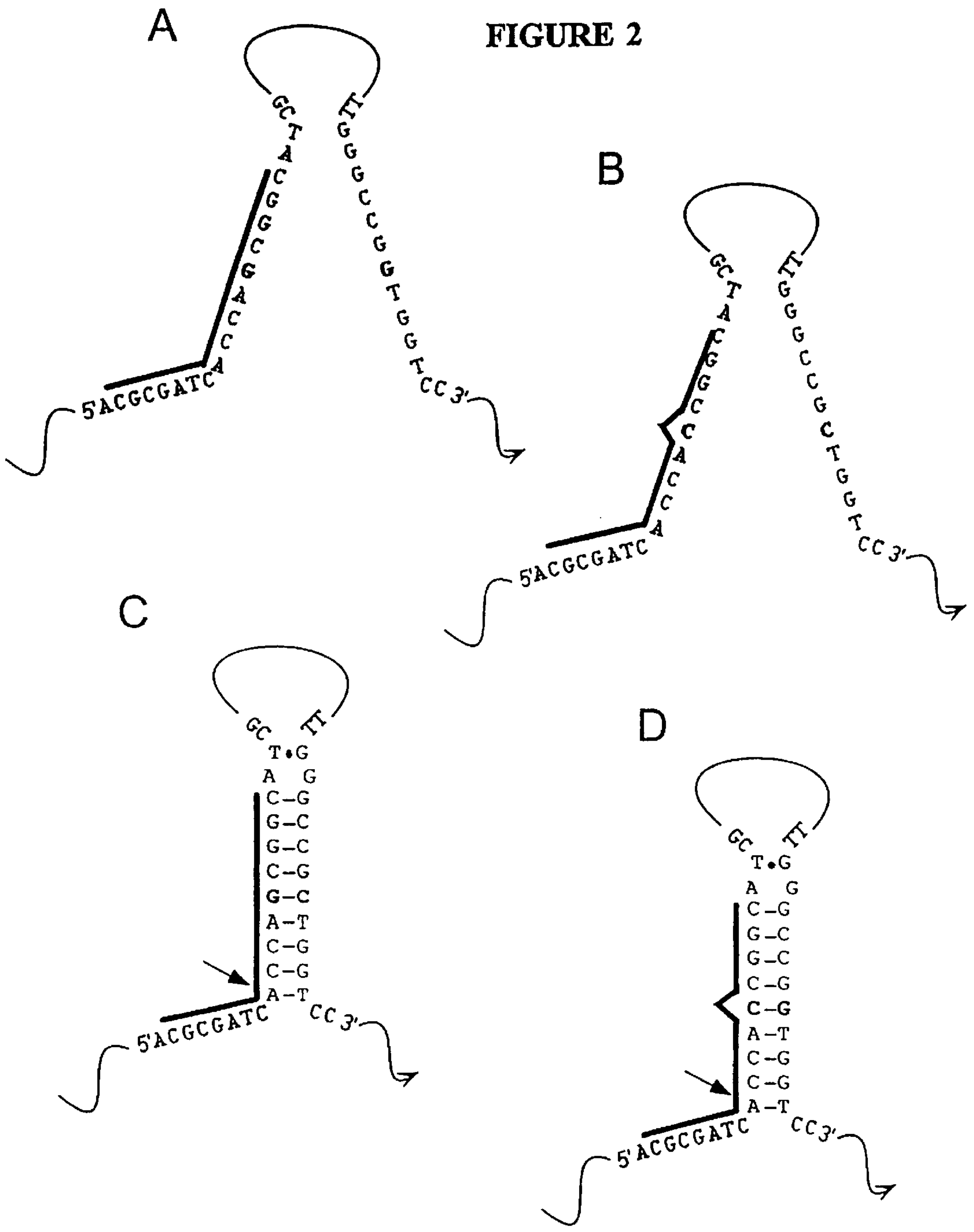
FIGS. 2A–2D provide a schematic of representation of a segment of the katG gene from *M. tuberculosis*. Depending on the sequence, the segment of the DNA can form the stem-loop structures depicted in 2C and 2D. The arrows in 2C and 2D show the sites that are cleaved when these structures are treated by the structure specific CLEAVASE I nuclease. The black bar to the left of each structure indicates the region to which the katG probe would bind, with the pointed kink in the bar indicating a site of mismatch between the probe and the katG target.

The Presence of a Structure and a Probe Mismatch in Combination Provide More Sensitive Discrimination than Does Either Effect Alone In this Example, the effects on oligonucleotide binding of either the formation of an occlusive structure, the presence of a single-base mismatch, or the presence of both at once were examined. To separate the effects on the efficiency of binding of structure from the effects of mismatches, four katG DNA target variants were chosen (SEQ ID NOS:1, 2, 3 and 4). The structures of these four targets in the region of the probe hybridization sites are shown in FIG. 2 and the existence of the large stem-loop in structures 2C and 2D (SEQ ID NOS:3 and 4, respectively) was confirmed by digestion with the structure-specific CLEAVASEI nuclease (Third Wave) and the cleavage sites are indicated by the arrows on structures 2C and 2D. The dark bar on the left of each structure in FIG. 2 indicates the region to which the capture probe is expected to bind. The pointed kink in the black bar in structures 2B and 2D indicates a site of mismatch between the capture probe and the katG target.

a) CFLP Analysis of Mutations in the katG Gene of *M. tuberculosis* i) Generation of Plasmids Containing katG Gene Sequences

Genomic DNA isolated from wild-type *M. tuberculosis* or *M. tuberculosis* strains containing mutations in the katG gene associated with isoniazid resistance were obtained from Dr. J. Uhl (Mayo Clinic, Rochester, Minn.). These strains are termed wild-type and S315T (Cockerill, III et al., J. Infect. Dis., 171:240 [1995]). Strain S315T contains a G to C mutation in codon 315 of the wild-type katG gene.

A 620 bp region of the *M. tuberculosis* katG gene was amplified using the PCR from DNA derived from the above strains. The primers used to amplify the katG gene sequences were KatG904 (5'-AGCTCGTATGGCACCGGAAC-3')(SEQ ID NO:5) and KatG1523 (5'-TTGACCTCCCACCCGACTTG-3') (SEQ ID NO:6); these primers amplify a 620 bp region of katG gene. The PCRs were conducted in a final reaction volume of 100 μl and contained the KatG904 and KatG1523 primers at 0.5 mM, 1.5 mM $MgCl_2$, 20 mM Tris-HCl, pH 8.3,50 mM KCl, 0.05% each TWEEN-20 and NONIDET P-40 non-ionic detergents, 60 mM of all 4 dNTPs. The reaction mixtures were heated at 95° C. for 3 min, then amplification was started with addition of 5 units of Taq DNA polymerase and continued for 35 cycles at 95° C. for 1 min, 60° C. for 1 min and 72° C. for 2 min.

To clone the PCR-amplified katG fragments, 1 μl of each PCR product was used for ligation into the linear pT7Blue T-vector (Novagen, Madison, Wis.). The ligation products were used to transform competent JM109 cells and clones containing pT7Blue T-vector with an insert were selected by white color on LB plates containing 40 mg/ml X-Gal, 40 mg/ml IPTG and 50 mg/ml ampicillin. For each of the PCR samples, four colonies were picked and grown overnight in 2 ml LB media containing 50 mg/ml carbenicillin. Plasmid DNA was isolated using an alkaline miniprep protocol (Sambrook et al., supra).

To analyze the cloned katG fragments, 1 μl of plasmid DNA from each clone was amplified by PCR using 100 μl reactions containing the KatG904 and KatG1523 primers at 0.5 mM, 1.5 mM $MgCl_2$, 20 mM Tris-HCl, pH 8.3, 50 mM KCl, 0.05% each TWEEN-20 and NONIDET P-40 non-ionic detergents, 60 mM of all 4 dNTPs and 5 units of Taq DNA polymerase. The PCRs were cycled 35 times at 95° C. for 1 min, 60° C. for 1 min and 72° C. for 2 min. PCR products were separated by electrophoresis on a 6% native polyacrylamide gel in 0.5×TBE buffer and clones that gave rise to a 620 bp fragment were selected for further analysis.

Fragments of DNA (391 bp), labeled on the 5' end of the sense strand with tetrachlorofluorescein (TET), were created from the cloned katG genes using primers 5'-TET-AGCTCGTATGGCACCGGAACC-3' (SEQ ID NO:7) and 5'-GGACCAGC GGCCCAAGGTAT-3' (SEQ ID NO:8). When the wild type katG DNA fragment of this size is denatured by heating and allowed to fold, nucleotides A37–C45 base pair with nucleotides G381–T389 (measured from the 5' end of the sense strand). The wild type sequence has a G at bp 41 (G41) which is complimentary to the C at bp 385 (C385) as shown in FIG. 2C; the S315T mutant sequence contains a C at bp 41 (C41) which is non-complimentary to C385 and disrupts the formation of the hairpin, as shown in FIG. 2B. Two additional non-wild type sequences were created by using an alternative primer at the 3' end (5'-GGACCACCGGCCCAAGGTATCT-3'; SEQ ID NO:9) which changed C385 to G385. This allowed creation of fragments with a G41 to G385 mismatch (FIG. 2A) and a C41 to G385 base pair (FIG. 2D).

The PCR reactions were performed as follows: PCR mixtures contained 5 ng of plasmid DNA template, 1×PCR buffer, 200 mM of each dNTP, 0.5 mM of each primer, 5 units of Taq Polymerase and water to final volume of 100 ml. The PCR cycling conditions were: 95° C. for 45", 65° C. for 1'30" and 72° C. for 2' for a total of 30 cycles, followed by a 4° C. soak. The 391 bp PCR products were purified using "High Pure PCR Product Purification Kit" (Boehringer Mannheim). This set of fragments (SEQ ID NOS:1–4) allowed a single probe to be used to assess the effects of mismatch, secondary structure or a combination of both on the formation of the complex between the probe and target.

ii) CFLP Reactions

CFLP reactions were performed on each 5'-TET labeled amplification product from the four KatG variants (2A–2D). Each CFLP reaction contained approximately 20 fmole of the amplified product, 50 units of CLEAVASE I nuclease in 10 μl of IX CFLP buffer (10 mM MOPS pH 7.5, 0.05% TWEEN 20 and 0.05% NONIDET P40 non-ionic detergents) with 0.2 mM $MnCl_2$. Reactions were assembled with all components except the enzyme and the $MnCl_2$, heated to 95° C. for 15 seconds, then cooled to the reaction temperature of 50° C. The cleavage reactions were started with the addition of the enzyme and the $MnCl_2$, and incubated for 5 minutes. The reactions were terminated by the addition of 4 ml of 95% formamide with 10 mM EDTA and 0.02% Methyl Violet. The products were heated at 95° C. for 30 sec, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the left panel of FIG. 3. Lanes A–D contain CFLP reaction products from reactions containing structures 2A–2D, respectively. Lanes C and D contain a product (37 nt; indicated by the arrowhead) not present in lanes A and B which indicates the presence of the large stem-loop in structures 2C and 2D shown in FIG. 2.

b) Structure Probing Analysis of *M. tuberculosis* katG Gene Targets

In these experiments, the capture probes are bound to the target DNAs in solution and then immobilized on a solid support. The 391 bp fragment of katG described above was created by PCR using a 5'-fluorescein labelled primer (SEQ ID NO:7). A hybridization mixture was assembled, containing 40 fmoles of heat-denatured, 391 bp katG PCR product having one of the four sequences depicted in FIG. 2 (SEQ ID NOS: 1–4), labelled on the 5' end of the sense strand, 1.5 pmole of the biotinylated capture probe (SEQ ID NO:10), 0.01 mg/ml tRNA, 0.2% acetylated BSA, 4.5×SSPE and $H_2O$ to 150 μl.

Figure 3:
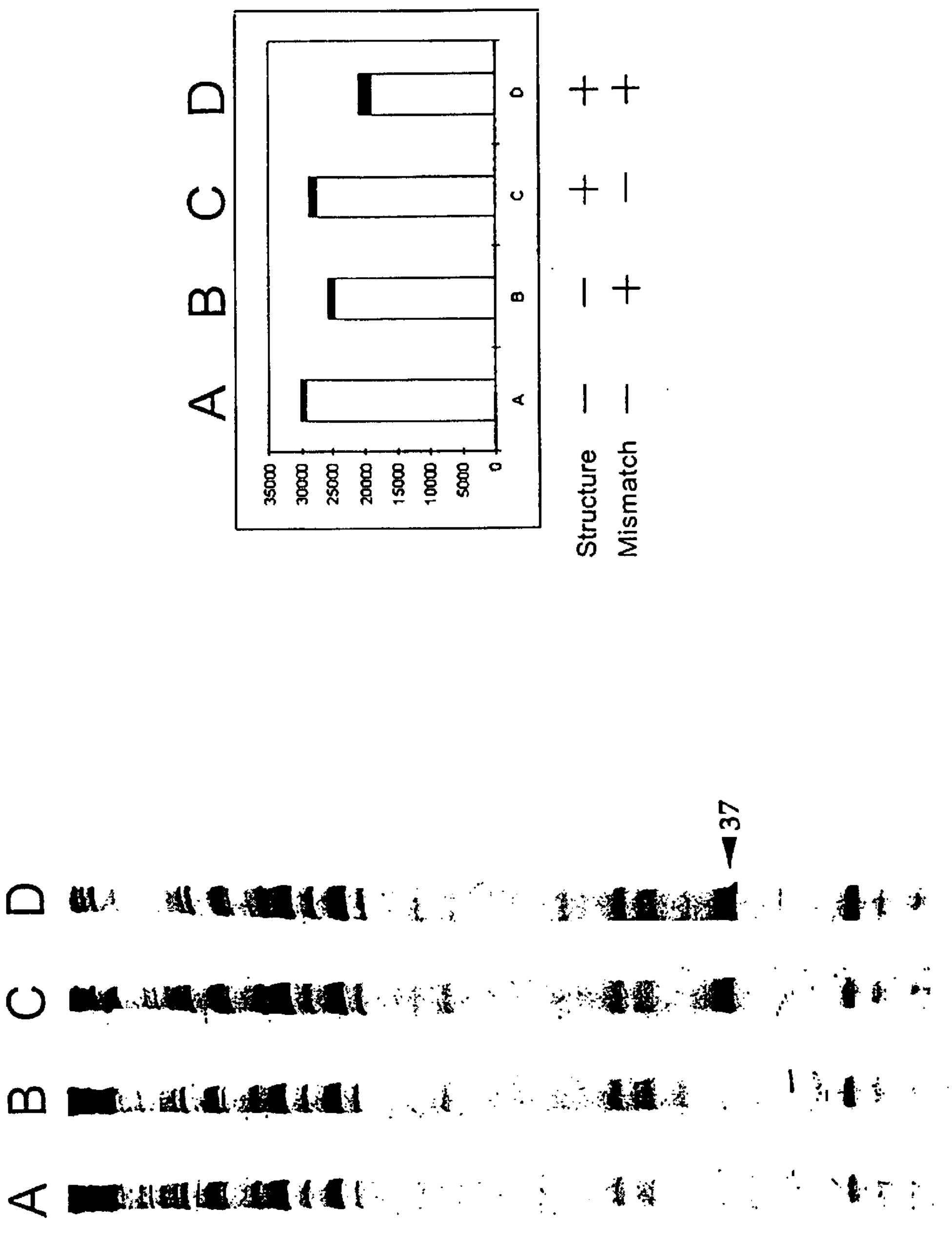
FIG. 3 shows at left a fluorescence imager scan of the cleavage patterns generated using the CFLP® method on the katG substrates. The letters above the lanes indicate that these DNA fragments corresponding to structures diagrammed in FIG. 2. An arrow indicates the 37 nucleotide (nt) product of cleavage at the site indicated by the arrows in FIG. 2. The graph at the right depicts the fluorescence intensity measured when each of the molecules depicted in FIG. 2 was complexed to the katG capture probe and bound to a solid support in a structure probing assay.

Aliquots (100 μl) of the mixture were then transferred to wells in a streptavidin-coated 96-well plate (Boehringer Mannheim) and incubated at room temperature for 30 min. The plate was then washed three times with 1×PBS, with 0.01% TWEEN-20 non-ionic detergent, then treated with a solution containing 0.2% I-Block (Tropix, Bedford, Mass.) and 0.05% TWEEN-20 non-ionic detergent in PBS for 30 minutes to block. After blocking, the plate was washed three times with PBS with 0.1% TWEEN-20 non-ionic detergent. A 1:5000 dilution of 0.75 u/ml anti-fluorescein antibody conjugated with alkaline-phosphatase in 0.2% I-block buffer was added to the plate in 100 μl/well volumes. After ½ hour, the plate was washed three times with TBS (25 mM Tris-Cl, 0.15 M NaCl, pH 7.2). One hundred microliters of ATTOPHOS fluorescent substrate (JBL) was added to each well and the plate was incubated at room temperature for 1 hour before fluorescence readings were taken using a Perkin-Elmer Cytofluor-4000 set to excite at 450/50 nm and to and detect emission at 580/50 nm. Each assay was performed in triplicate and the standard deviation is represented by the black bar at the top of each column in the right panel of FIG. 3. The fluorescence intensity is indicated in arbitrary fluorescence units. In FIG. 3, "A–D" indicates the use of structures 2A–2D, respectively in the structure probing assay.

The results, shown in FIG. 3, indicate that not only the mismatch between target DNA and probe, but also differences in secondary structure, leads to a better discrimination between wild type and mutant DNA.

EXAMPLE 2

Figure 4:
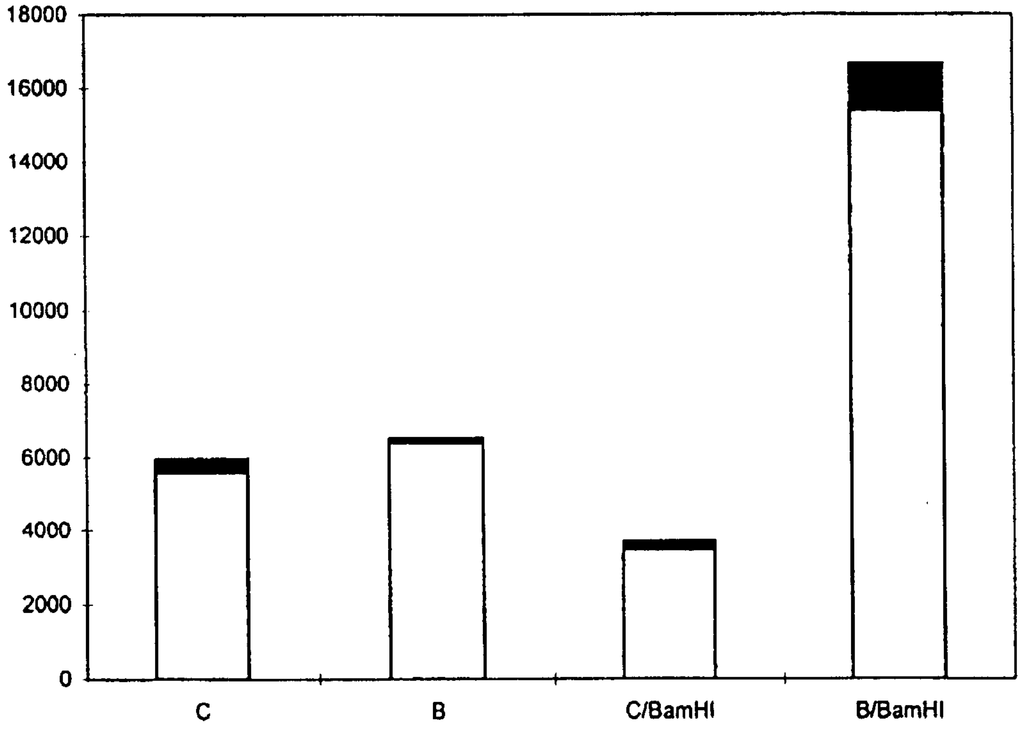
FIG. 4 show a graph that depicts the fluorescence intensity measured when two variants of the katG target DNA with different amounts of flanking sequence were bound to a microtiter plate using a single capture probe.

Changes in DNA Secondary Structure Leads to Different Binding Abilities Between the Target DNA and the Capture Probe The context of a target sequence (i.e., the length and identity of the flanking nucleic acid), can influence the secondary structure, and therefore the hybridization accessibility of the target segment. To illustrate this effect, a target segment of DNA was exposed, either with or without pretreatment with a restriction enzyme, to a capture probe that is complementary to a site that is unaffected by the restriction cleavage. The restriction enzyme BamHI was used to digest the 391 bp 5'-fluorescein labeled fragments of katG DNA, either wild-type (FIG. 2C) or the S315T mutant (FIG. 2B), prepared as described in Example 1. The restriction enzyme shortens the 5' labelled fragment from 391 nt to 256 nt. The capture probe is complementary to sequence located within the first 50 nt of these katG DNA targets. Equal amounts of the DNA targets were used in all the reactions. The restriction digests included 2 pmoles of 5'-Fluorescein labeled DNA, 10 μl of 10×BamHI buffer, 160 units of BamHI enzyme and $H_2O$ to a final volume of 100 μl. The reactions were incubated at 37° C. for 2 hours. After digestion, the hybridization assay was performed as described above, using the capture probe (SEQ ID NO:10). The results are shown in FIG. 4. In FIG. 4, the amount of labeled target captured (as a target/probe complex) is shown for each target/probe complex examined (shown using arbitrary fluorescence units). In FIG. 4, the following abbreviations are used: C (structure 2C); B (structure 2B); C/BamHI (BamHI-digested structure 2C); B/BamHI (BamHI-digested structure 2B).

The 2C DNA target (SEQ ID NO:3) has a site perfectly complementary to the capture probe, while the 2B DNA target (SEQ ID NO:2) has a single base mismatch near the middle of the region of complementarity with the capture probe. Despite this mismatch, discrimination between these two 391 nt DNAs (i.e., not digested with BamHI) by hybridization to this probe is very weak. As shown in FIG. 4, the difference in the binding efficiency between wild type and mutant DNA after enzyme digestion is increased. Because the segment of the katG DNA to which the probe hybridizes is not cleaved by the enzyme, it can be concluded that it is the change in the folded structure of the target DNA that accounts for the change in the hybridization pattern. This shows that, while mismatches may enhance discrimination between nucleic acid variants, they are not necessary for discrimination between DNAs by hybridization. These results also demonstrate that variables other than the degree of complementarity (e.g., complete or partial) between the probe and target (e.g., the secondary and tertiary structure of the target) may provide a better means of discriminating between related sequences.

EXAMPLE 3

Hybridization Analysis Using Multiple Capture Probes for HCV Genotyping

Figure 5:
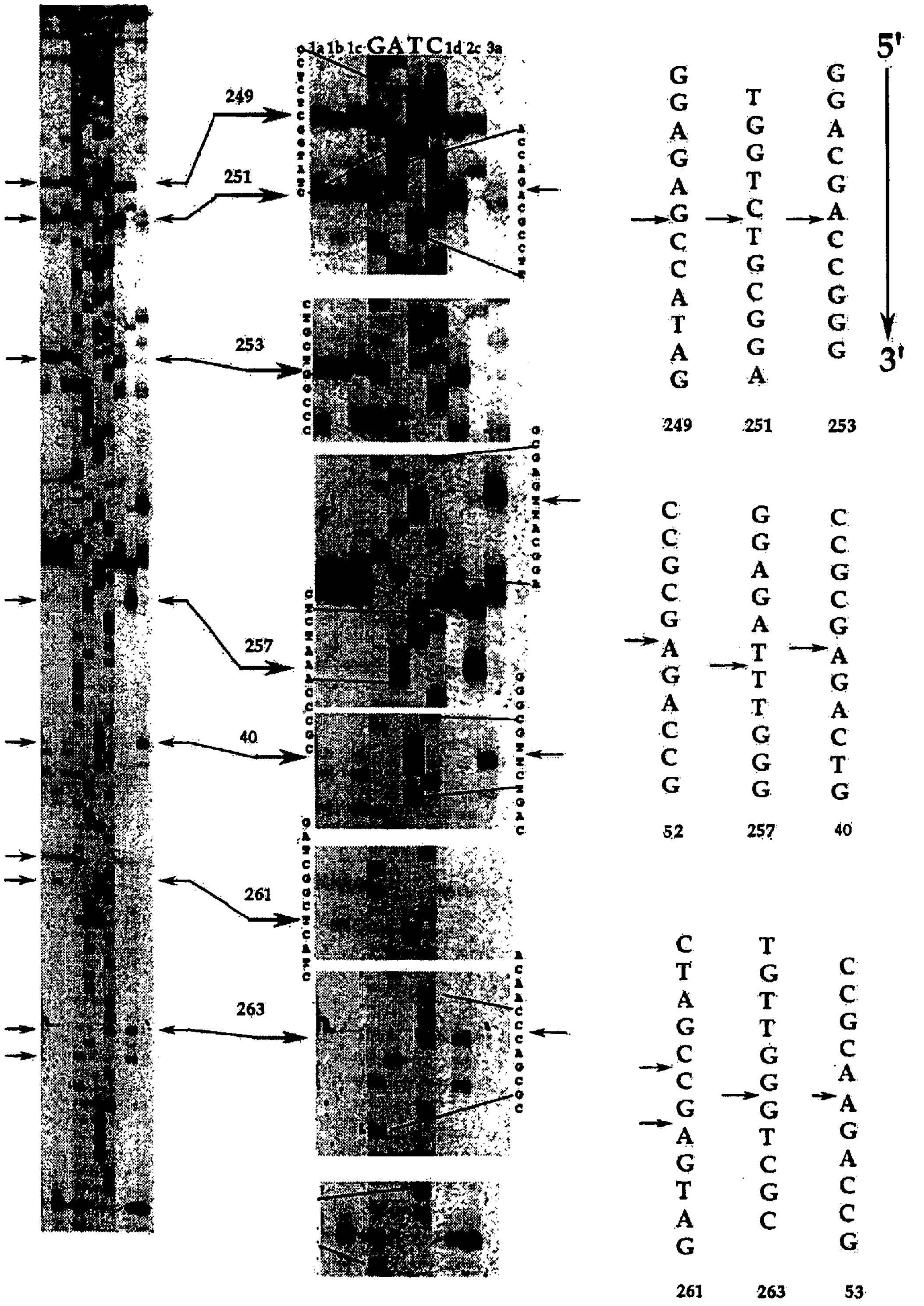
FIG. 5 shows an analysis of several types of HCV by both the CFLP method and by DNA sequencing. The sequence lanes were resolved beside the lanes showing the products of CFLP cleavage. This allowed precise identification of the sites cleaved, and therefore the regions of structure, in the analysis of each of the HCV genotypes. The probes selected to interact in these regions are indicated to the right (SEQ ID NOS:11–119).

Because both mismatches and structures are used in the method of the present invention for discrimination between similar nucleic acids by hybridization, the patterns created by the use of a structure specific nuclease, e.g., CLEAVASE I nuclease can be used as a way of selecting regions likely to demonstrate different binding behaviors with different variants. Because the CFLP method indicates the presence of structure in a DNA fragment of interest, and because the variations in the structures tend to be proximal to the actual sequence changes, choosing capture probes at or near the CFLP cleavage sites increases the probability of choosing a sequence that changes in accessibility in the different variants. FIG. 5 shows a diagram depicting this means of probe selection as applied to the comparison of fragments from the Hepatitis C virus. In FIG. 5, the left panel shows an fluoroimager scan of sequencing gel in which products of CFLP cleavage reactions are resolved next to a sequencing ladder generated using the same target DNA employed in the CFLP cleavage reactions. The middle panel provides an enlargement of sections of the gel shown in the left panel. The right panel provides the sequence of nine HCV probes (SEQ ID NOS:11–19); these probe were synthesized such that they contained a 5'-biotin moiety.

Five subtypes of HCV; 1a, 1b, 2b, 2c, and 3a were analyzed using both the CFLP cleavage method, and cycle sequencing. The CFLP reactions were performed on each 5'-fluorescein labeled amplification product from each HCV isolate as follows. Each CFLP reaction contained approximately 20 fmole of the amplified product, 25 units of CLEAVASE I nuclease in 10 μl of 1×CFLP buffer (10 mM MOPS pH 7.5, 0.05% TWEEN 20 and 0.05% NONIDET P40 non-ionic detergents) with 0.2 mM $MnCl_2$. Reactions were assembled with all components except the enzyme and the $MnCl_2$, heated to 95° C. for 15 seconds, then cooled to the reaction temperature of 55° C. The cleavage reactions were started with the addition of the enzyme and the $MnCl_2$, and incubated for 2 minutes. The reactions were terminated by the addition of 4 μl of 95% formamide with 10 mM EDTA and 0.02% Methyl Violet. The products were heated at 85° C. for 2 min, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi).

The CFLP patterns for these HCV subtypes are shown in FIG. 5. Different subtypes of HCV give different CFLP patterns, which means that they also have different internal secondary structure. Probes were designed to detect structure differences between the 1a, 1b, 2c and 3a HCV subtypes. The capture probes are shown in the right panel of FIG. 5. The region to which each of these HCV capture probes can bind along the sequence of the HCV targets is shown in FIG. 6. In FIG. 6, the location of the probe binding regions are indicated using bold type, underlining and by placing the probe designation above the sequence. The consensus HCV sequence (SEQ ID NO:20), and the sequence of HCV subtypes 1a, 1b, 2c and 3a (SEQ ID NOS:20–23, respectively) are provided.

Figure 7:
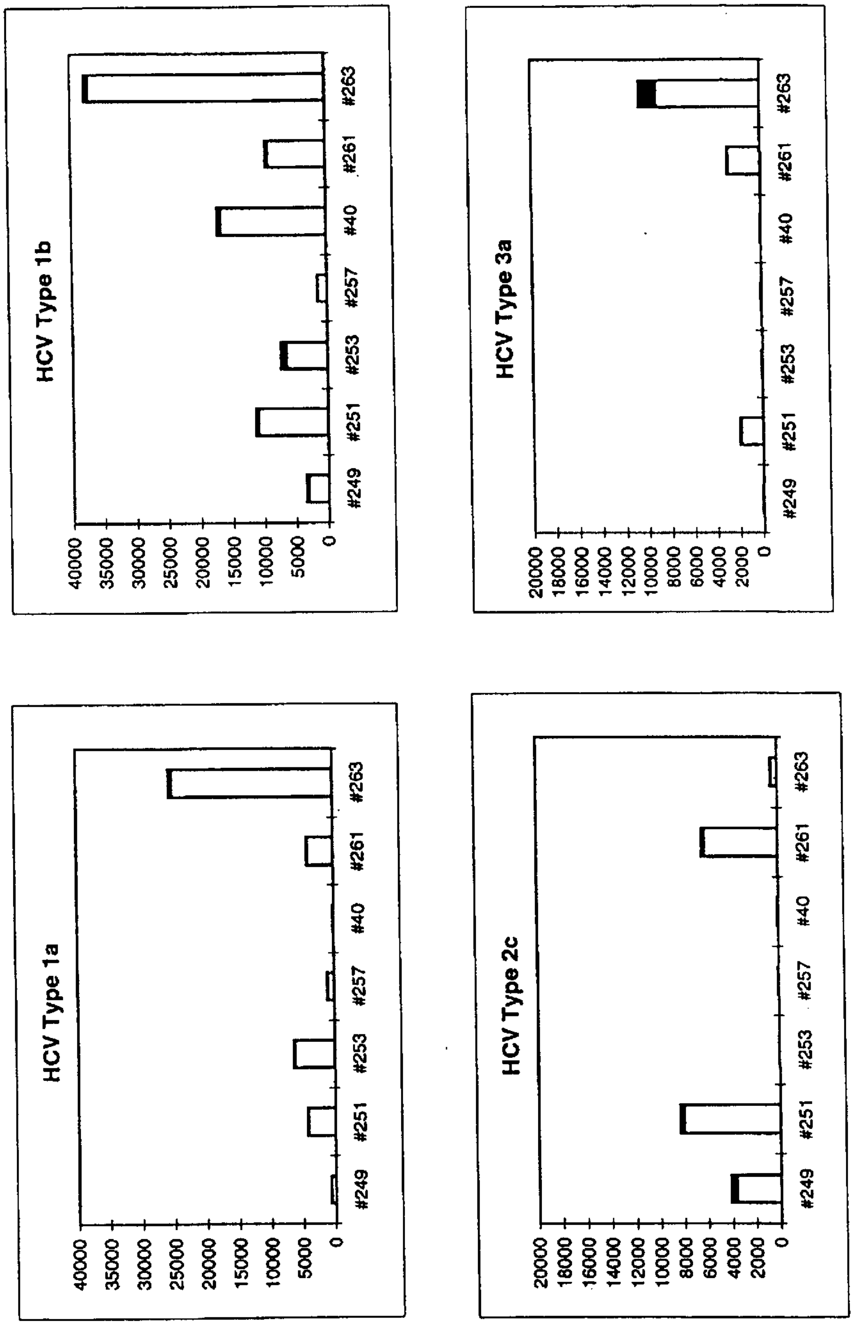
FIG. 7 shows four graphs depicting the fluorescence signal measured after the solid support capture of the indicated HCV types by the indicated probes.

The capture probes (SEQ ID NOS:11–19) were synthetically labeled with biotin at their 5' end and purified by gel-electrophoresis. The HCV target DNA was labeled with fluorescein at the 5' end of the antisense strand by PCR using a 5'-fluorescein labeled primer. The primers employed for the amplification of HCV target DNAs were: 5' primer: 5'-FI-CTCGCAAGCACCCTATCA (SEQ ID NO:24) and 3' primer: 5'-GCAGAAAGCGTCTAGCCATGG (SEQ ID NO:25). The PCR reactions included 5 ng of plasmid DNA template, 1×PCR buffer (Boehringer Mannheim), 200 mM of each dNTP, 0.5 mM of each primer (SEQ ID NOS:24 and 25), 5 units Taq DNA polymerase (Boehringer Mannheim) and water to a final volume of 100 μl. The PCR cycling conditions were: 95° C. for 45", 55° C. for 45", and 72° C. for 1', for 30 cycles followed by a 72° C. for 5' extension and a 4° C. soak. The resulting 244 bp PCR products (SEQ ID NOS:26–29 for types 1a, 1b, 2c and 3a, respectively) were purified using "High Pure PCR Product Purification Kit" (Boehringer Mannheim) and eluted in $dH_2O$ according to the manufacturer's instructions. The same amount of DNA, based on optical absorbance, was used for each sample in the capture assay. Structure probing analysis on streptavidin-coated 96-well micro-titer plates was performed as described above. Each assay was performed in triplicate and the standard deviation is shown as a black bar at the top of each column in FIG. 7. The results are shown in FIG. 7.

The column graphs of the measured fluorescence intensity for the complexes between each probe and a given target constitute a characteristic "signature" that is distinctive for each HCV subtype. The effects of structure can be illustrated by examining the signal strengths from targets binding to probe #40 (SEQ ID NO:16). While both the 1b and 3a targets are completely complementary to probe #40, the 3a target shows nearly undetectable signal, while the type 1b target signal is very strong. The binding of probe #251 (SEQ ID NO:12) to the HCV targets shows similar signal variation even though this probe is completely complementary to all four of the HCV subtype targets.

EXAMPLE 4

Effect of Temperature on Structure Probing with Oligonucleotides

Most traditional hybridization methods have a small window of temperature (i.e., about less than 10° C.) in which to produce the expected discrimination between targets. The structure probing analysis of the four HCV subtypes (describe above) under different hybridization temperatures was performed to examine the effect of temperature on both the secondary structure of DNA and the stability of the probe/target complex. Three different temperatures were used; room temperature (approx. 20 to 25° C.), 37° C. and 50° C.

Figure 8A:
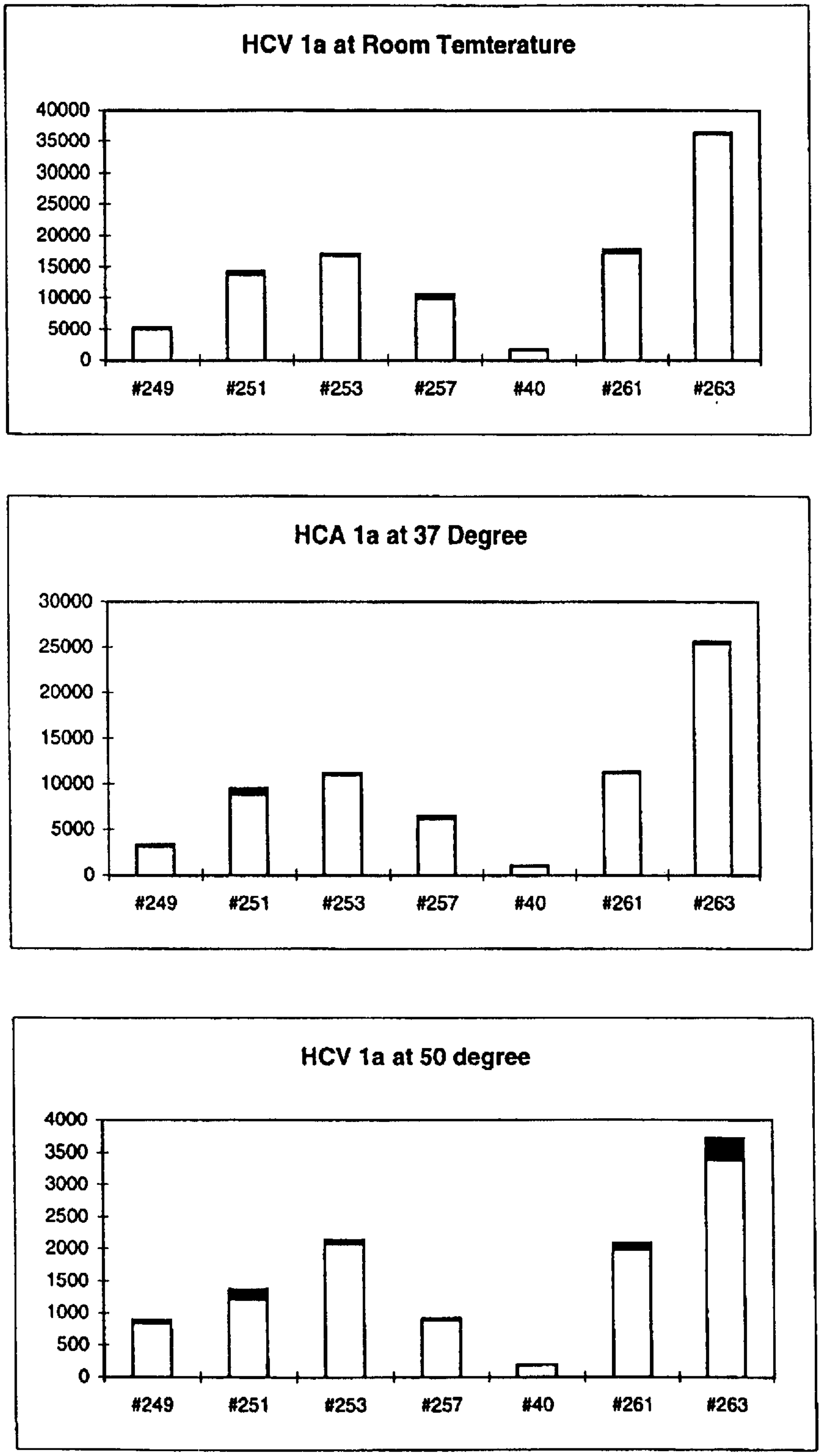
FIGS. 8A, B and C show graphs depicting the fluorescence signal measured after the solid support capture of the indicated HCV types by the indicated probes, at temperatures ranging from room temperature (approximately 22° C.) to 50° C.

The profile of the HCV subtypes 1a, 1b and 3a are shown in FIG. 7. The profiles of the HCV subtype 1b are shown in FIG. 8B. The profiles of the HCV subtype 3a are shown in FIG. 8C. The hybridization profiles of these three HCV subtypes over a 25° C. range of temperature (~25–50° C.) are shown in FIGS. 8A–8C (the numbers below each column indicates the capture probe employed; note the change in scale for each temperature tested). The profiles for these three HCV subtypes are essentially the same over the 25° C. range of temperature tested. However, the higher the temperature employed, the less stable the probe-DNA target binding becomes, so the overall fluorescence intensity was reduced. These results show that the discrimination capability of the structure probing method is very robust, maintaining consistency over a broad range of temperature.

EXAMPLE 5

Structure Probing Analysis of HCV Clinical Isolates

Structure probing analysis of HCV clinical isolates at a room temperature hybridization temperature was performed to examine the feasibility of developing a diagnostic test for HCV genotyping. Twelve HCV amplification products generated from clinical samples were obtained (Molecular Pathology Dept, Univ. of Wisconsin Clinics, Madison, Wis.) and employed in the structure probe assay. These targets were RT-PCR products of viral RNA from different patient samples amplified using the Amplicor HCV detection kit (Roche Molecular Systems, Alameda, Calif.). Further PCR reactions were performed on these clinical amplification products using the primer pair described in Example 4 (SEQ ID NOS:24 and 25) to create ds PCR products comprising 5' fluorescein labels on the anti-sense strands. The PCR conditions were as described in Example 4. The resulting HCV targets were employed in the structure probing assay which was carried out as described in Example 1.

The resulting profiles were sorted by type (based on the profiles determined for the HCV subtypes as described in Examples 3 and 4 and FIG. 7) and are shown in FIGS. 9A–9D (the types were independently determined by single pass DNA sequencing. The resulting partial sequences, sufficient to identify types are as follows: #67 (SEQ ID NO:30), #69 (SEQ ID NO:31), #72 (SEQ ID NO:32), #73 (SEQ ID NO:33), #74 (SEQ ID NO:34), #81 (SEQ ID NO:35), #85 (SEQ ID NO:36), #86 (SEQ ID NO:37) and #91 (SEQ ID NO:38).

Figure 9A:
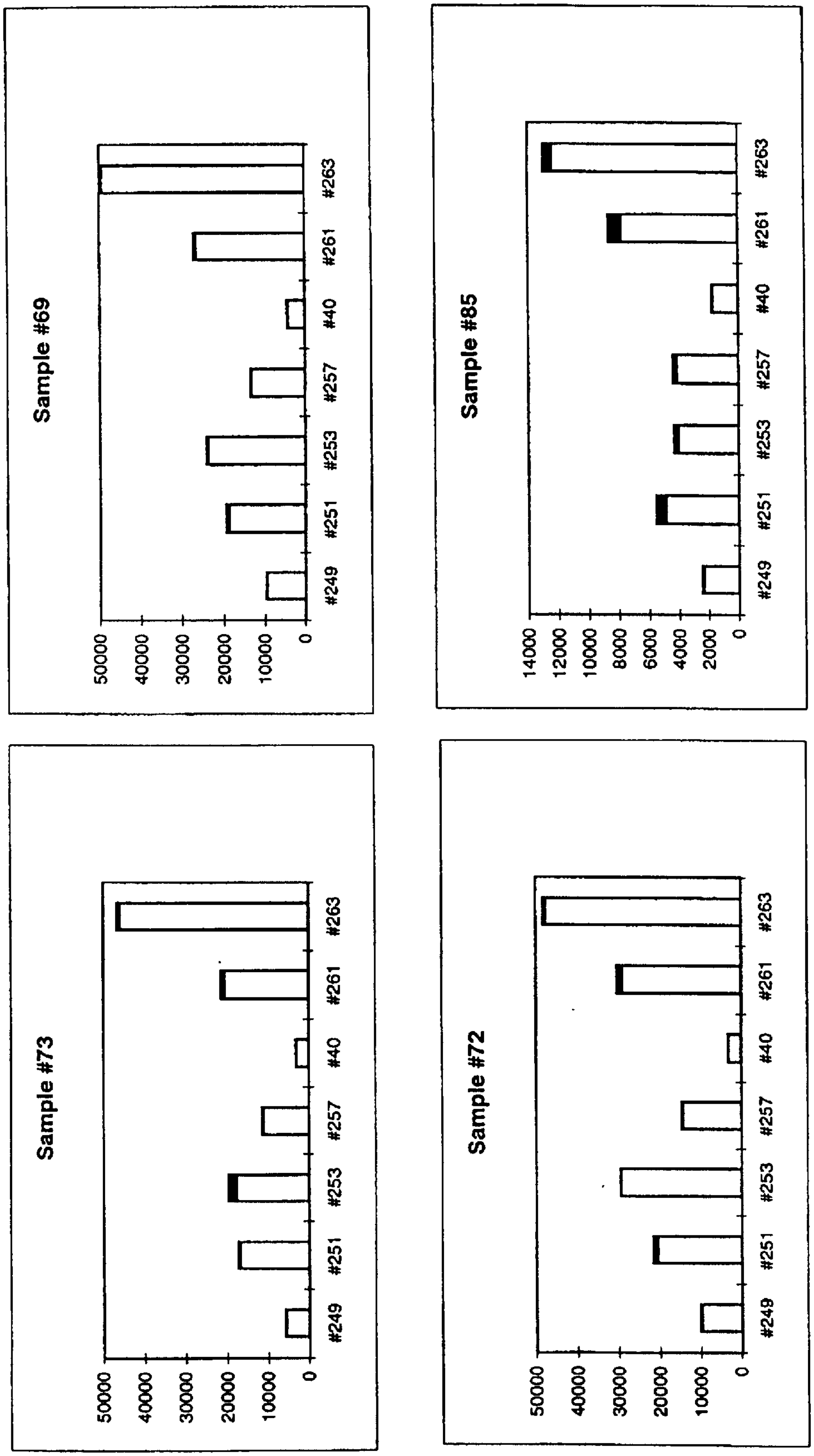
Figure 9B:
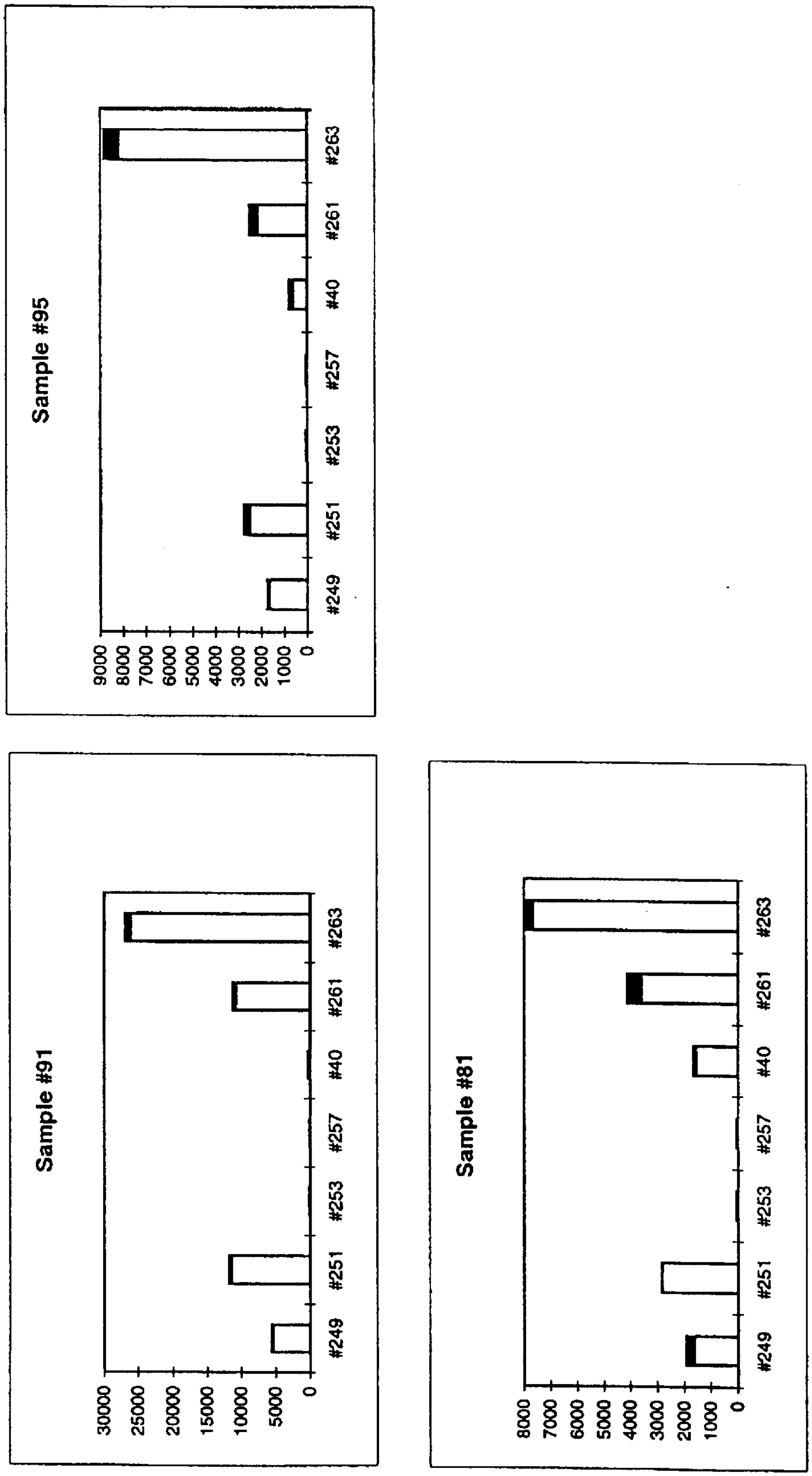
Figure 9C:
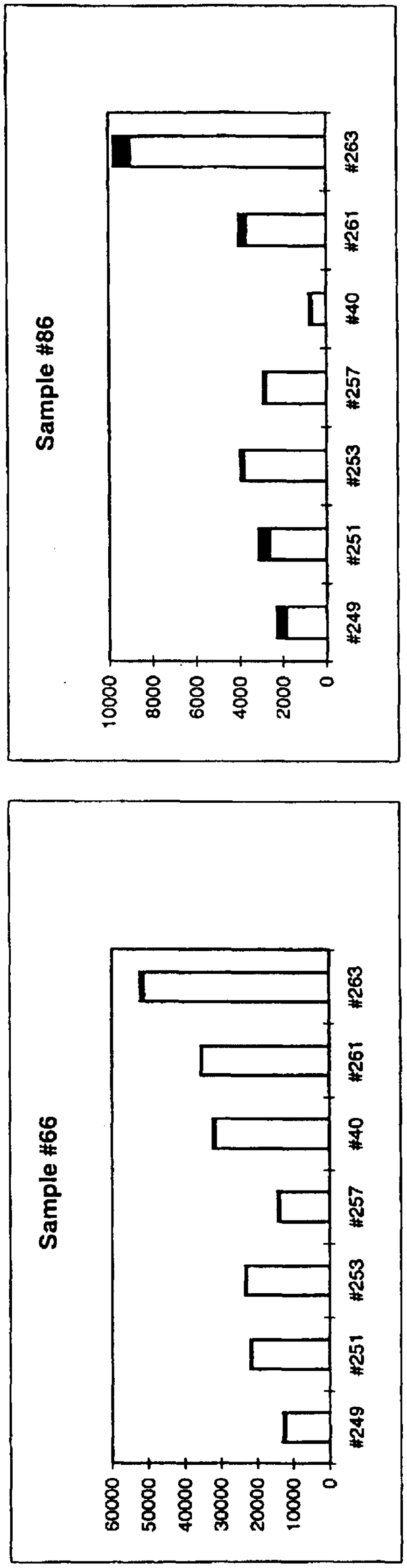

The profiles for four different amplicons of HCV type 1a are shown in FIG. 9A (#69, #72, #73 and #85) and all have a profile similar to the type la profile shown in FIG. 7. The profiles of three different amplicons of HCV type 3a are shown in FIG. 9B (#81, #91 and #95) and their profiles are all similar to each other and to the type 3a profile shown in FIG. 7. The profile of an amplicon of HCV type 2c (#67) and an amplicon of HCV type 2b (#74) are shown in FIG. 9D. The profiles for two amplicons of HCV 1b are shown in FIG. 9C (#66 and #86).

The profile for amplicon #86 was more similar to that of type 1a rather than type 1b. Based on CFLP analysis, amplicon #86 was classified as type 1b. However, using the probe set shown in FIG. 9C, the hybridization profile obtained in the structure probing assay appeared more similar to that of type 1a. Sequence analysis showed that there is an extra mutation in this sample, which changed its hybridization response to probe #40, creating a profile more like that of type 1a. Based on this T to C mutation in amplicon #86, an additional capture probe having a sequence completely complimentary to amplicon #86 was tested (probe #53; SEQ ID NO:19). A structure probing assay using the amplicon #86 target and capture probe #53 generated a profile similar to a more typical type 1b profile. These results demonstrate that additional information concerning the structure of the amplicon #86 target was obtained using the structure probing assay.

These data demonstrate that an unknown (i.e., uncharacterized) set of HCV isolates can be identified by HCV type through the use of the structure probing assay, with comparison of the resulting profiles to those of previously characterized isolates (i.e., reference profiles).

It is clear from the above that the present invention provides methods for the analysis of the characteristic conformations of nucleic acids without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within human genes as well as the detection and identification of pathogens in clinical samples.

Thus, the previous Examples that oligonucleotide binding is affected by the formation of an occlusive structure in the target DNA. In each of these cases, the oligonucleotides used to bind and capture the target nucleic acid were designed to be substantially complementary to a single region of the target. The following two Examples demonstrate the use of oligonucleotides that are designed to interact with multiple, non-contiguous regions of the target DNA. In some embodiments of the methods of the present invention, the oligonucleotides (i.e., bridging oligonucleotides) are designed to interact with regions that are brought into close proximity by the formation of folded structure in the target strand. By using short sections of complementarity on either side of the connecting segment, it is intended that the bridge oligonucleotides be dependent on the binding of both of the sections of complementarity, and that changes in, or the absence of, the intervening folded structure cause a significant change in the affinity between the bridge oligonucleotide and the target DNA.

EXAMPLE 6

Size of Complementary Regions Affects the Ability of Bridging Oligonucleotides to Discriminate Between Targets that Contain Identical Regions of Complementarity, but Different Folded Structures In this Example, the effect of length of complementarity on each side of the bridge oligonucleotides on the ability of the bridge oligonucleotide to distinguish between test molecule #80, 81 and 82 (SEQ ID NOS:39–41) was examined. As noted above, these oligonucleotides have identical regions of complementarity to which the bridge oligonucleotides of this Example may hybridize. The bridge oligonucleotides used in this test are shown in the lower half of FIG. 11A, arranged in the orientation in which they would hybridize to test molecule #80 (SEQ ID NO:39). Three bridging oligonucleotides, shown as #78, #4 and #79 (SEQ ID NOS:42, 43, 44), were used, and these had 6, 7 or 8 nucleotides of complementarity, respectively, to each side of the hairpin formed in target #80 (SEQ ID NO:39). The two regions of target complementarity were separated by a pair of thymidine nucleotides in each oligonucleotides to provide additional flexibility to the three-leg junction (Zhong et al., Biochem., 32:6898 [1993]; and Yang et al., Biochem., 35:7959 [1996]). All the biotinylated oligonucleotides were gel-purified after synthesis using the standard oligonucleotide purification methods.

In these hybridization analyses, the capture probes were bound to the target DNAs in solution and then immobilized on a solid support, as described in the previous Examples. For each of these tests (each of the three bridge oligonucleotides listed above was tested on each of the three test molecules), a 150 µl hybridization mixture was assembled containing 20 fmols of a fluorescein-labeled test molecule as depicted in FIG. 10 (SEQ ID NOS:39–41), 1.5 pmole of one of the biotinylated capture probe 78, 4 or 79 (SEQ ID NOS:42–44), 10 mg/ml tRNA and 0.2% acetylated BSA, in 150 ml of 4.5×SSPE. The mixture was incubated at room temperature for 30 min.

Aliquots (100 ul) of the mixtures were then transferred to wells in a streptavidin-coated 96-well plate (Boehringer Mannheim) and incubated at room temperature for 20 min. The plate was then washed three times with TBS (25 mM Tris-Cl, 0.15 M NaCl, pH 7.2) with 0.01% TWEEN-20 non-ionic detergent. Then, 100 µl of a 1:5000 dilution of 0.75 u/ml anti-fluorescein antibody conjugated with alkaline-phosphatase in 0.2% I-block buffer (Tropix, Bedford, Mass.) was added to each well. After 20 min at room temperature, the plate was washed three times with TBS with 0.01% TWEEN-20. Then, 100 µl of Attophos fluorescent substrate (JBL, San Louis Obisbo, Calif.) were added to each well and the plate was incubated at 370C for 1 hour, before fluorescence readings were taken using a Perkin-Elmer Cytofluor-4000 set to excite at 450/50 nm and to and detect emission at 580/50 nm. Each assay was performed in duplicate and the standard deviation is represented by the black bar at the top of each column in the right panel of FIG. 12. In this Figure, the fluorescence intensity is indicated in arbitrary fluorescence units.

Figure 12:
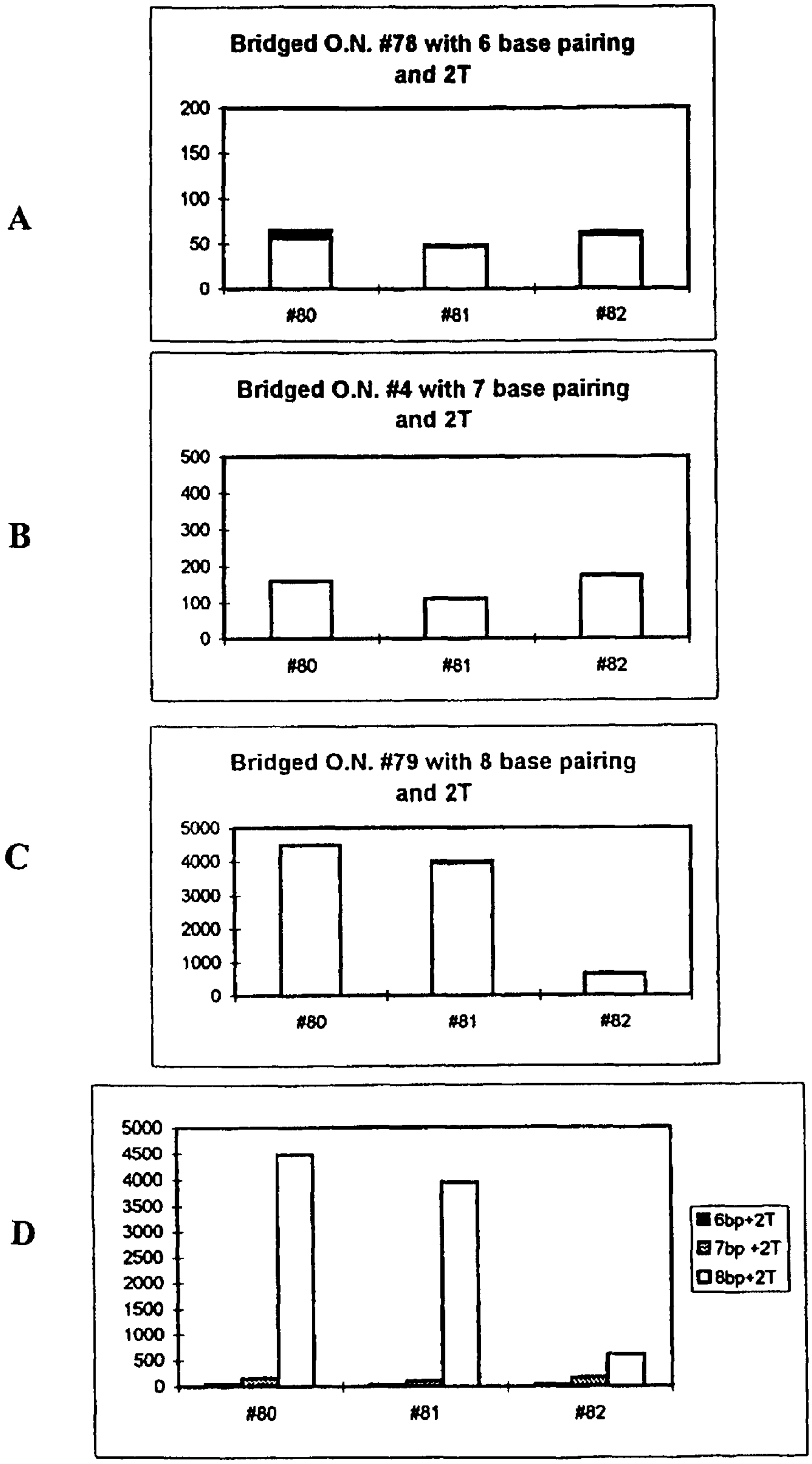
FIGS. 12A–12D show graphs depicting the fluorescence signal measured after the solid support capture of the three test molecules, #80 (SEQ ID NO:39), #81 (SEQ ID NO:40), and #82 (SEQ ID NO:41) by the indicated probes. The wider fourth panel (FIG. 12D), shows the fluorescence signal from each of the first three panels re-drawn together on a single scale of fluorescence intensity, for ease of comparison.

The results, shown in FIG. 12, indicate that the bridging oligonucleotide #79 (SEQ ID NO:44), having 8 bases pairing to each side of the hairpin in the DNA target, gives better binding activity to the target DNA than oligonucleotides that have 7 bases pairing (#4; SEQ ID NO:43), which is better than oligonucleotides that have only 6 bases pairing (#78; SEQ ID NO:42). Furthermore, the oligonucleotides with the shorter flanking sequences did not show any significant difference in binding to the different test molecules, indicating that the presence or absence of structure was immaterial to their binding under these test conditions. In contrast, the oligonucleotide with the 8 bp flanks had a 6 to 7-fold higher affinity for the folded molecules #80 (SEQ ID NO:39) and #81 (SEQ ID NO:40), when compared to the unstructured #82 (SEQ ID NO:41) molecule. This demonstrated that bridge oligonucleotides are suitable for the assessment of differences in folded structure of a target molecule, in contrast to previous reports (Francois et al., Nucl. Acid. Res. 22: 3943 [1994]).

While the 8-bp flanks are clearly the preferred size in this experimental system, the absolute number of basepairs required for any particular bridge oligonucleotide system may vary other factors affecting the stability of the interaction, as discussed above, such as with the G-C content of the hybridization site, the temperature and solution conditions under which the reaction is performed, and the nature of the structure to be bridged. Thus, it is contemplated that in some systems, bridge oligonucleotides comprise any appropriate length suitable for the assay system.

EXAMPLE 7

Bridging Oligonucleotides

Figure 11A:
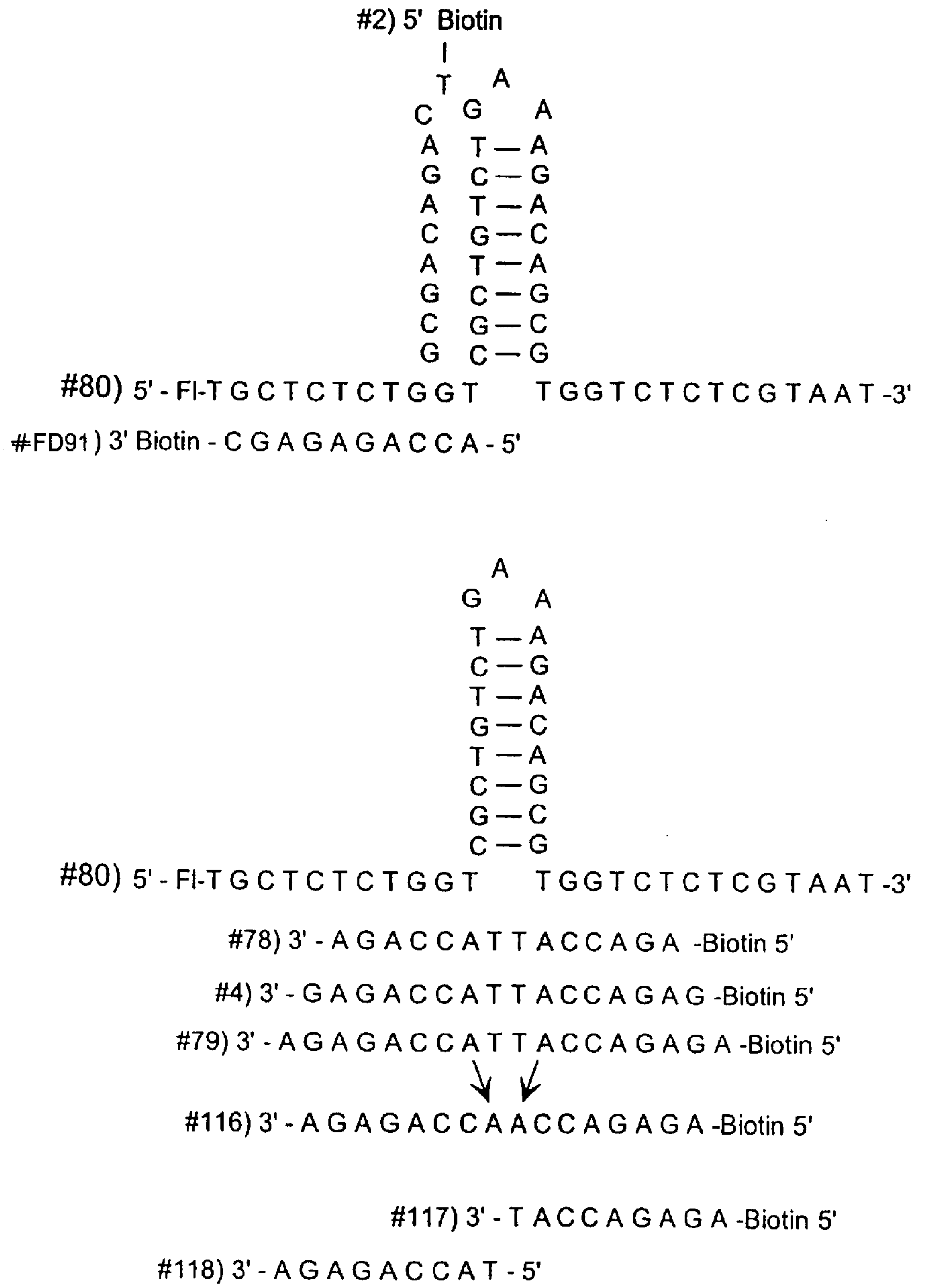
FIGS. 11A and 11B show schematic representations of the capture oligonucleotides used in these studies. While they were tested with all three of the test molecules depicted in FIG. 10, for convenience they are shown aligned with their complementary regions in test molecule #80 (SEQ ID NO:39).
Figure 11B:
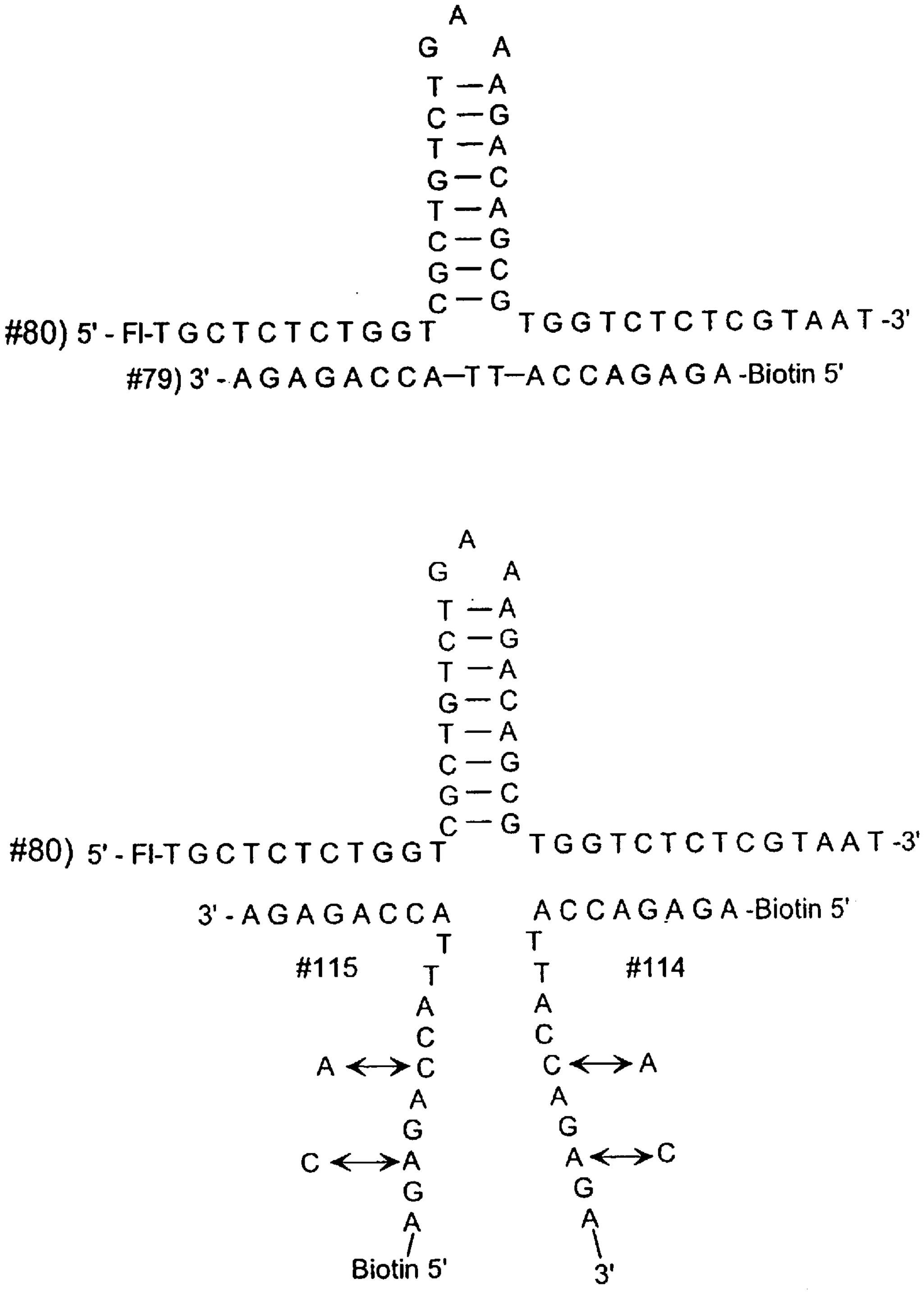

In this Example, two schemes were investigated in order to determine how the bridging oligonucleotide might bind to the targeted hairpin structure, as illustrated in FIG. 11B. Although an understanding of the mechanism is not necessary in order to make and use the present invention, nor is it intended that the present invention be limited to any particular mechanism, one possibility is that one bridging oligonucleotide molecule binds to one DNA target molecule, as diagrammed in the top half of the Figure. A second possibility is that two or more of the bridging oligonucleotide molecules bind to one DNA target molecule, with the apparent increase in signal resulting from the presence of two biotin moieties on the complex facilitating binding or detection, rather than successfully spanning of a structure by a single bridge oligonucleotide.

To differentiate these two possibilities, two additional oligonucleotides were synthesized (oligonucleotide #114 and #115 [SEQ ID NOS:45 and 46, respectively]), as shown in FIG. 11B. Oligonucleotide #114 (SEQ ID NO:45) is almost identical to #79 (SEQ ID NO:44), except that two mutations have been introduced in such way that it cannot hybridize to the right side of the hairpin on the target DNA. Similarly, oligonucleotide #115 (SEQ ID NO:46) is a version of #79 (SEQ ID NO:44) having two base mutations so that it can't hybridize to the left side if the hairpin on the target DNA. If the ability of oligonucleotide #79 (SEQ ID NO:44) to bind to the folded molecules is truly dependent on a single oligonucleotide bridging the structure then neither of the 'pseudo' bridge oligonucleotides, #114 or #115 (SEQ ID NOS:45 and 46, respectively), should be able to perform in this way. However, if the increased binding is in fact due to the presence of two copies of # 79 (SEQ ID NO:44), which would be arranged as depicted for #114 and #115 (SEQ ID NOS:45 and 46, respectively) in the bottom half of FIG. 11B, then #114 and #115 (SEQ ID NOS:45 and 46, respectively) used together should give the same result.

In addition to the test of the bridging function, the necessity of the spacing thymidines in the center of each bridge oligonucleotide was assessed. An oligonucleotide having the same complementary flanking sequences as oligonucleotide #79, but lacking the two T's in the middle, was created. This oligonucleotide (#116 [SEQ ID NO:47]), is depicted in the bottom half of FIG. 11A. In addition, to test the necessity of having a physical linkage between the binding halves of #79 (SEQ ID NO:44), to half molecules were created, each having complementarity to one of side of the test molecules, #117 (SEQ ID NO:48) to the right side and #118 (SEQ ID NO:49) to left side, as depicted in FIG. 11A, and each having one of the two spacer T residues. Finally, two 10-mer oligonucleotides were created, each with sufficient contiguous complementarity to bind without any bridging activity. One of these was complementary to the left flank (#FD91; SEQ ID NO:50), which is unstructured in all cases, while the other was complementary to the sequence involved in the structures of the folded test molecules (#2; SEQ ID NO:51). These are depicted in the top half of FIG. 11A.

The hybridization analyses were performed as described in Example 6, except that 15 fmoles of the fluorescein labeled test molecules were used, and the amount of bridge oligonucleotide was held to a total of 1.5 pmole when #114 and #115 (SEQ ID NOS:45 and 46, respectively) were used in combination. The results are shown in FIGS. 13A and 13B.

Taking the results in reverse order: the 10-mer control oligonucleotides showed the expected profiles in binding i.e., the oligonucleotide complementary to the unstructured region, #FD91 (SEQ ID NO:50), bound with nearly equal affinity to each of the test molecules, while the oligonucleotide complementary to the portion that forms structure in molecules #80 and #81 (SEQ ID NOS:39 and 40, respectively) bound well only to unstructured test molecule #82 (SEQ ID NO:41). This further illustrates that structure alone is an important determinant in the binding of the capture probes in embodiments of the methods of the present invention.

Figure 13A:
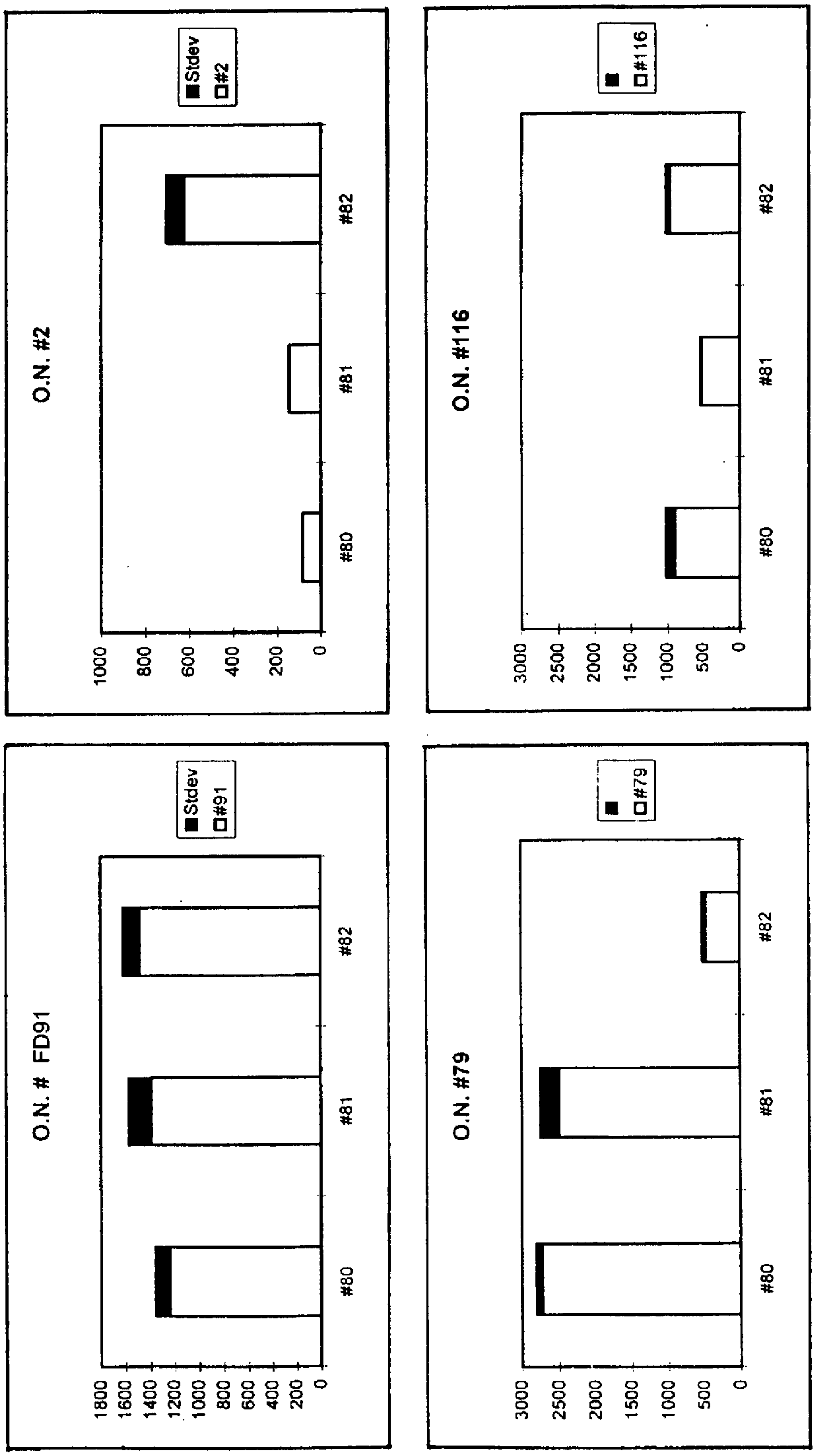
FIGS. 13A and 13B show graphs depicting the fluorescence signal measured after the solid support capture of the three test molecules, #80 (SEQ ID NO:39), #81 (SEQ ID NO:40), and #82 (SEQ ID NO:41) by the indicated probes. The names of the probes used in each capture test are indicated above each individual panel in these Figure panels.

When the oligonucleotide without any spacer residues, #116 (SEQ ID NO:47), was tested for its ability to bind the test molecules, it was found that this oligonucleotide could not distinguish between the folded and unfolded molecules (See, FIG. 13A). This demonstrated that hybridization across structures is greatly enhanced by the presence of some spacing material between the segments of complementarity.

Figure 13B:
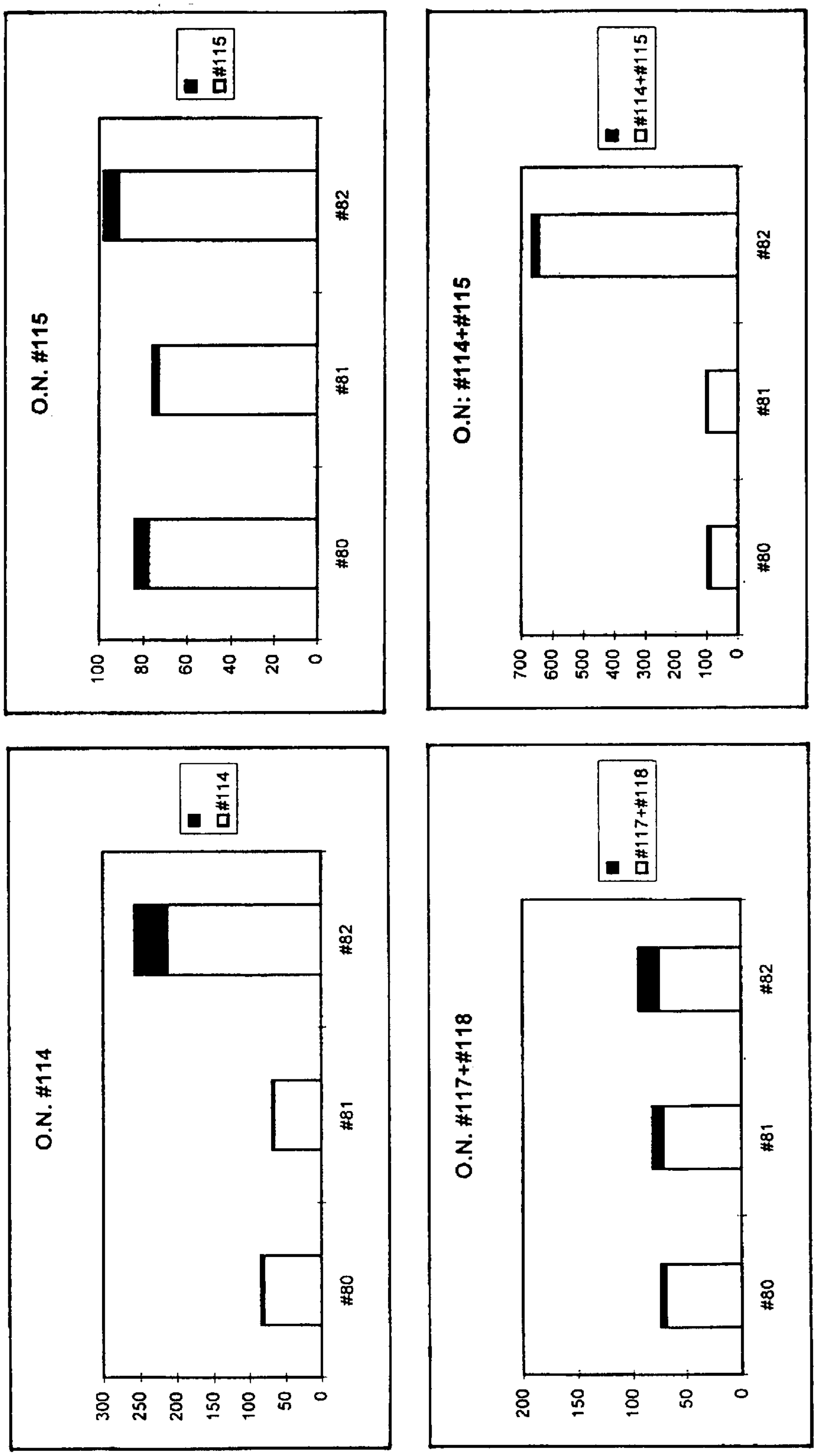
Figure 14:
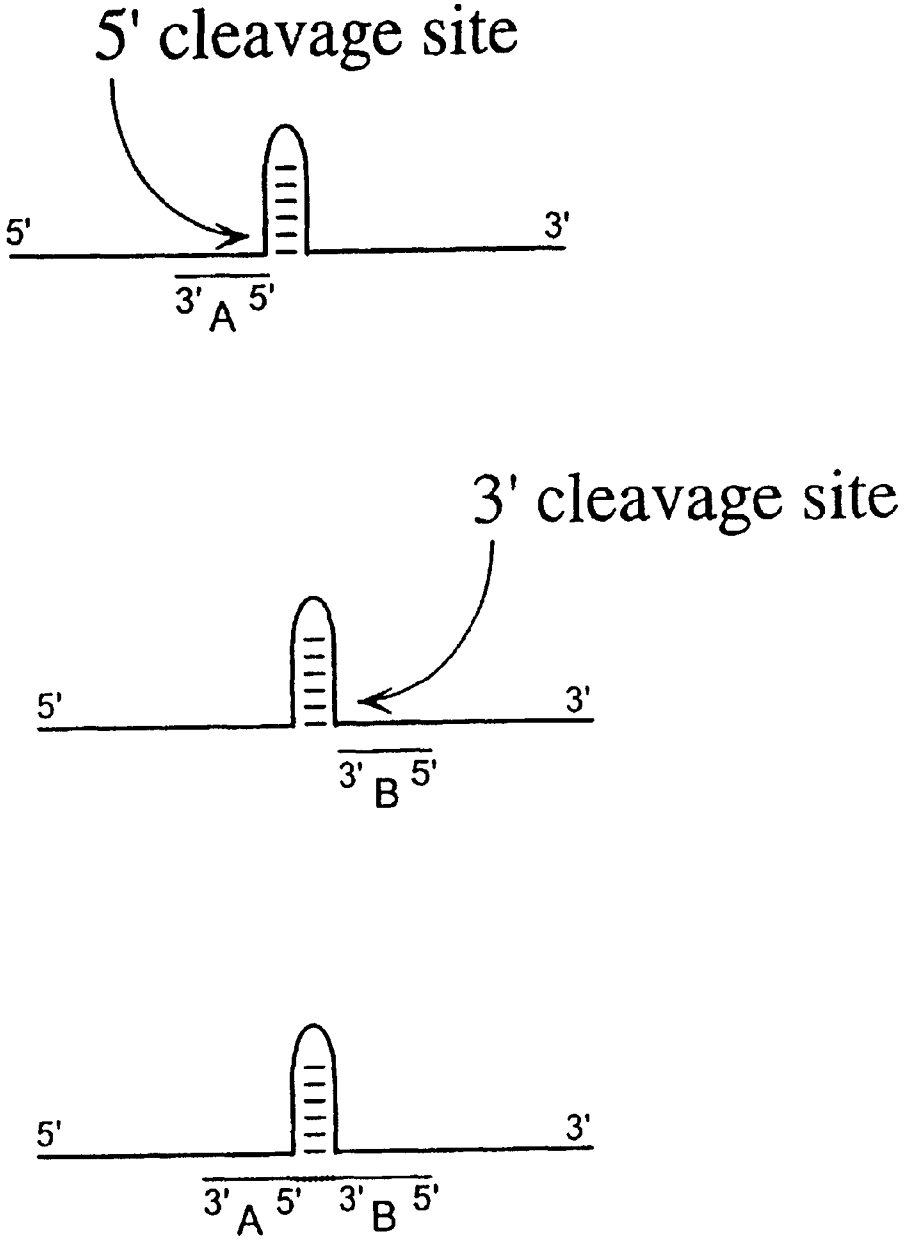
FIG. 14 shows a schematic diagram of the process for selecting two segments of bridging oligonucleotide based on the data from the use of 5' and 3' nucleases to cleave a folded structure. Such cleavage reactions can be used to locate regions that are either upstream or downstream of folded structures, facilitating selection of complementary sequences to compose bridging oligonucleotides.

Finally, the results of testing the pseudo bridge oligonucleotides, separately and in combination, are shown in FIG. 13B. It can be seen by these data, that oligonucleotides #114 and #115 (SEQ ID NOS:45 and 46, respectively) are not capable, either alone or in combination, to duplicate the binding profile of the true bridge, #79 (SEQ ID NO:44). The enhanced binding to the unstructured test molecule #82 (SEQ ID NO:41) is possibly attributable to the accessibility of this molecule for binding both oligonucleotides. Note that the fluorescence signal seen with the combination of #s 114, 115 and molecule #82 (SEQ ID NOS: 45, 46, and 41, respectively), about 650 fluorescence units, is nearly identical to the signal seen when #79 (SEQ ID NO:44) is combined with #82 (SEQ ID NO:41). This supports the idea that two copies of #79 (SEQ ID NO:44) may be involved in creating the signal with # 82 (SEQ ID NO:41).

It is clear from the above that the present invention provides methods for the analysis of the characteristic conformations of nucleic acids without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within human genes as well as the detection and identification of pathogens in clinical samples.

The previous examples demonstrated the use of bridging oligonucleotides to capture specific target molecules through hybridization to non-contiguous complementary sequences. However, the use of bridging oligonucleotides is not limited to hybrid capture. Bridging oligonucleotides hybridizing to folded target molecules can be used in place of standard oligonucleotides in almost any application, including applications in which enzymes modify probes that have found their target complement. Such enzymatic modifications include, but are not limited to primer extension, ligation and structure-specific nuclease cleavage. It will easily be appreciated by those skilled in the art that performance of bridging oligonucleotides in these basic enzymatic reactions is indicative of their utility in assays that are based on reiterative performance of these reactions, including but not limited to cycle sequencing, polymerase chain reaction, ligase chain reaction, cycling probe reaction and the INVADER invasive cleavage reaction. The examples below demonstrate the use of bridging oligonucleotides in each of the basic enzymatic reaction systems.

EXAMPLE 8

Analysis of Folded Structures of a Hepatitis C Virus-Derived Amplicon and Design of Bridging Oligonucleotides The process of identifying candidate structures for bridging with probes involves i) pinpointing all modification or cleavage sites; ii) predicting a set of most probable structures, and selecting those that fit with the specificity of the modification means; and iii) designing and testing probes to span the most probably structures. If desired, the information deduced at step ii) can be confirmed by deletion analysis such as PCR walking, or any equivalent method that allows the selective repression or removal of one half of a suspected basepair from interaction.

This stepwise approach is illustrated here for a 244 nt amplicon derived from HCV type 1a. The identification of the cleavage sites in all four types of HCV amplicon is described in Example 3. FIG. 15 shows sequence of 5' UTR region of HCV genotypes 1a, 1b, 2a/c and 3a with marked cleavage sites. Note that the designations 2a and 2a/c are used interchangeably throughout, and refer to the same HCV viral type, the amplicon of which is SEQ ID NO:22.

Figure 16A:
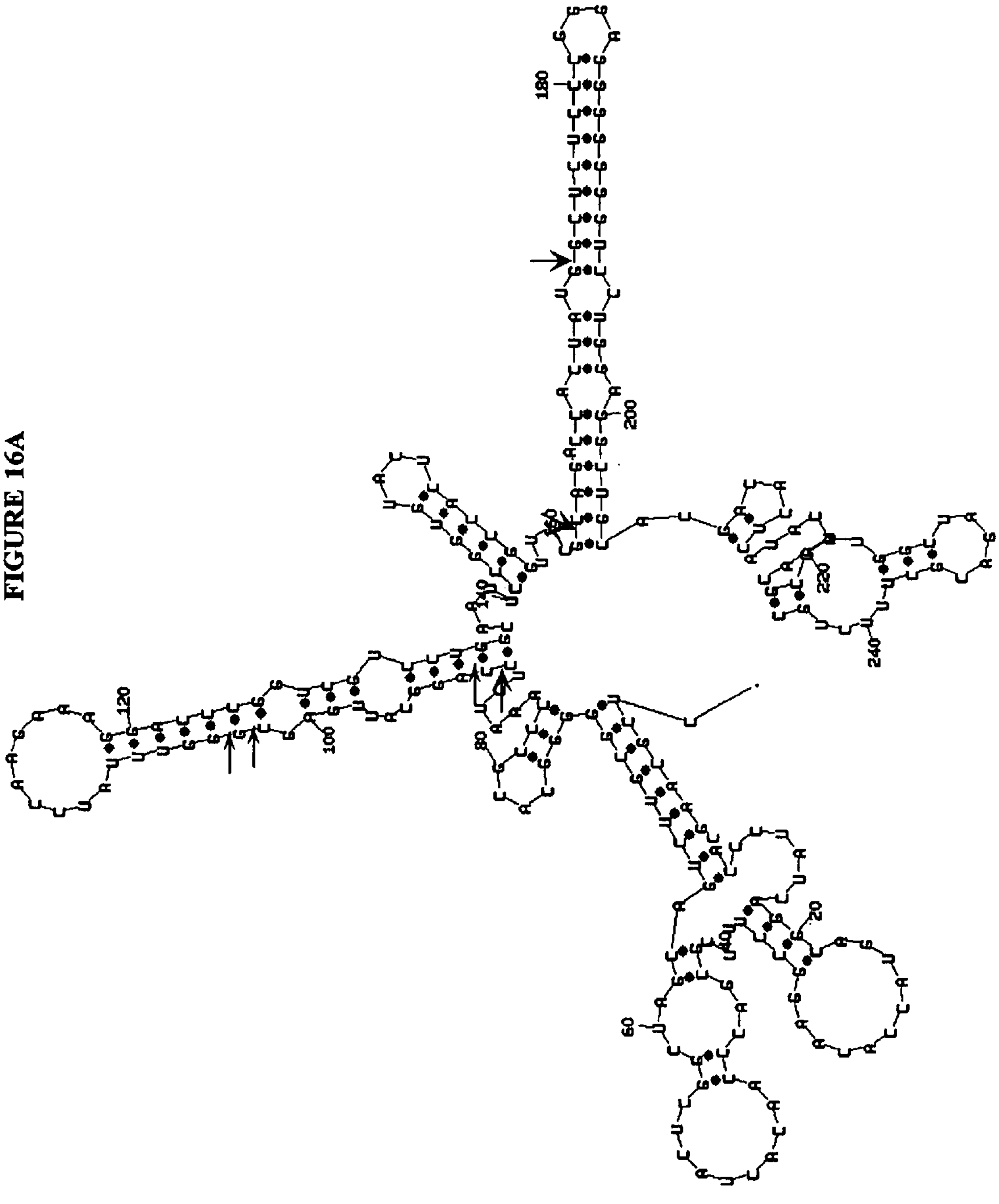
FIGS. 16A and 16B show schematic diagrams of two possible secondary structures for a 244 nt fragment derived from HCV type 1a FIG. 17A shows an analysis by the CFLP method of a 244 nt fragment derived from HCV type 1a and two 205 nt truncated fragments. The sizes of the significant cleavage bands are indicated to the right of the panel.
Figure 16B:
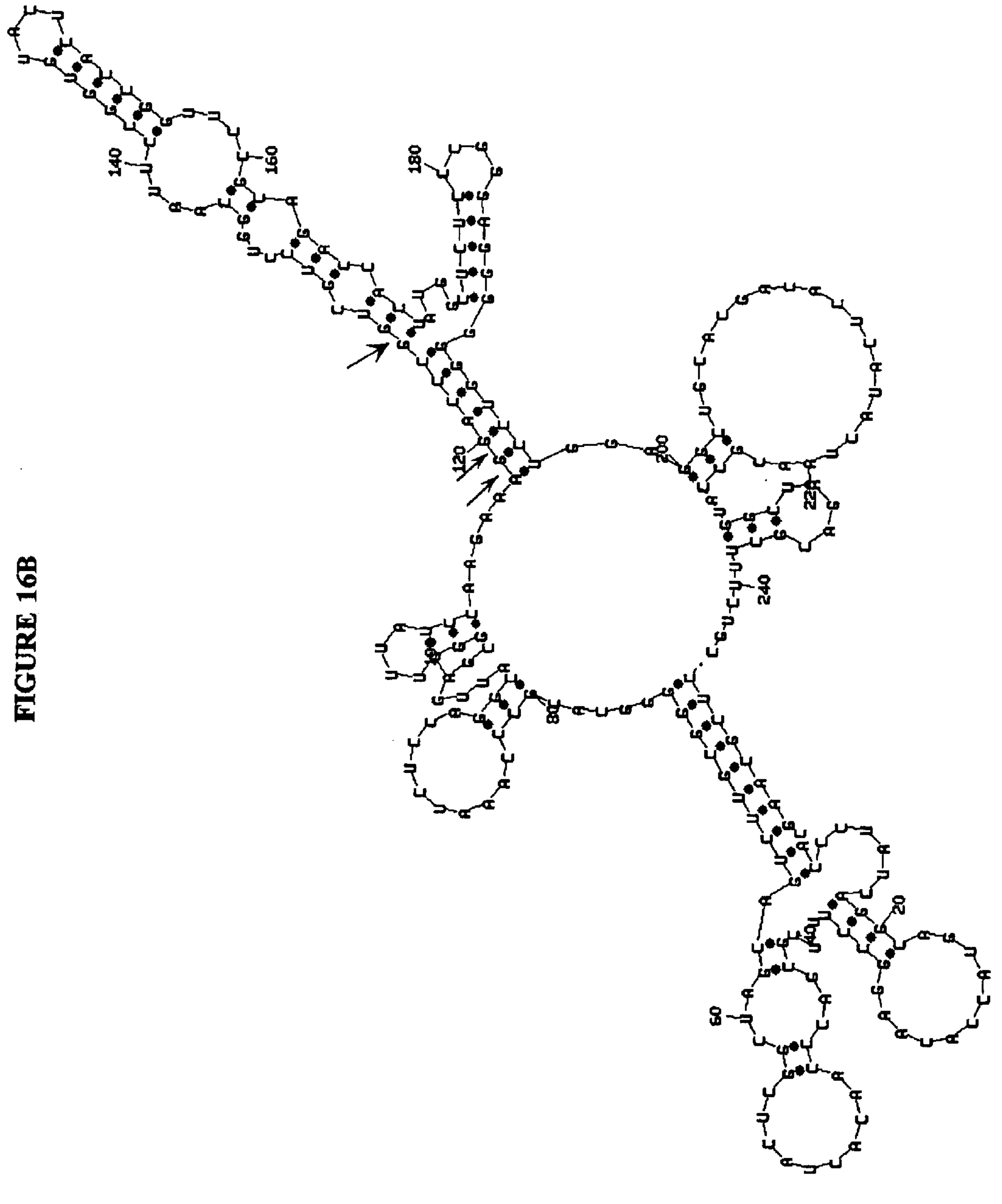

The type 1a sequence as then subjected to folding predictions using the mfold version 2.3 program, which is available either through Genetics Computer Group (Madison, Wis.) or through public access to the authors' web site (the wustl.edu web site, zuker page). Folding was done with using either DNA or RNA parameters with a selected folding temperature of 37° C. The output was set to include the optimal structure (lowest free energy) and any structure with a 20 percent or lower increase in calculated free energy (termed a "suboptimality of 20%"). All other program parameters used the default values. Folding with the RNA parameters generated 32 possible structures, while the DNA parameters gave 18 structures. Two of the structures predicted with the RNA parameters showed the best agreement with the cleavage data from the CFLP analysis. These structures, the first and the thirtieth out of 32, are depicted in FIGS. 16A and 16B.

Figure 17A:
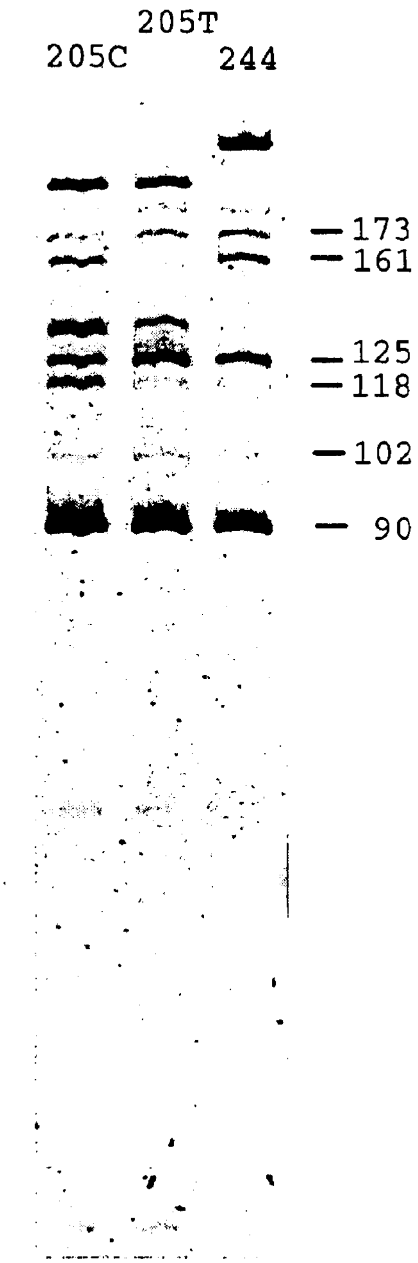
FIG. 17B shows schematic diagrams of two of the predicted structures for a region of the 244 nt amplicon derived from HCV type 1a. The CFLP data indicates that the target DNA assumes multiple conformations in solution, each contributing to the cleavage pattern (Brow et al., supra)
FIG. 17C shows schematic diagram of three bridging oligonucleotides designed two interact with the predicted structures for this region (SEQ ID NOS:53, 64, and 65). The regions that are complementary as aligned to the target are indicated by a black line between the strands.
Figure 17B:
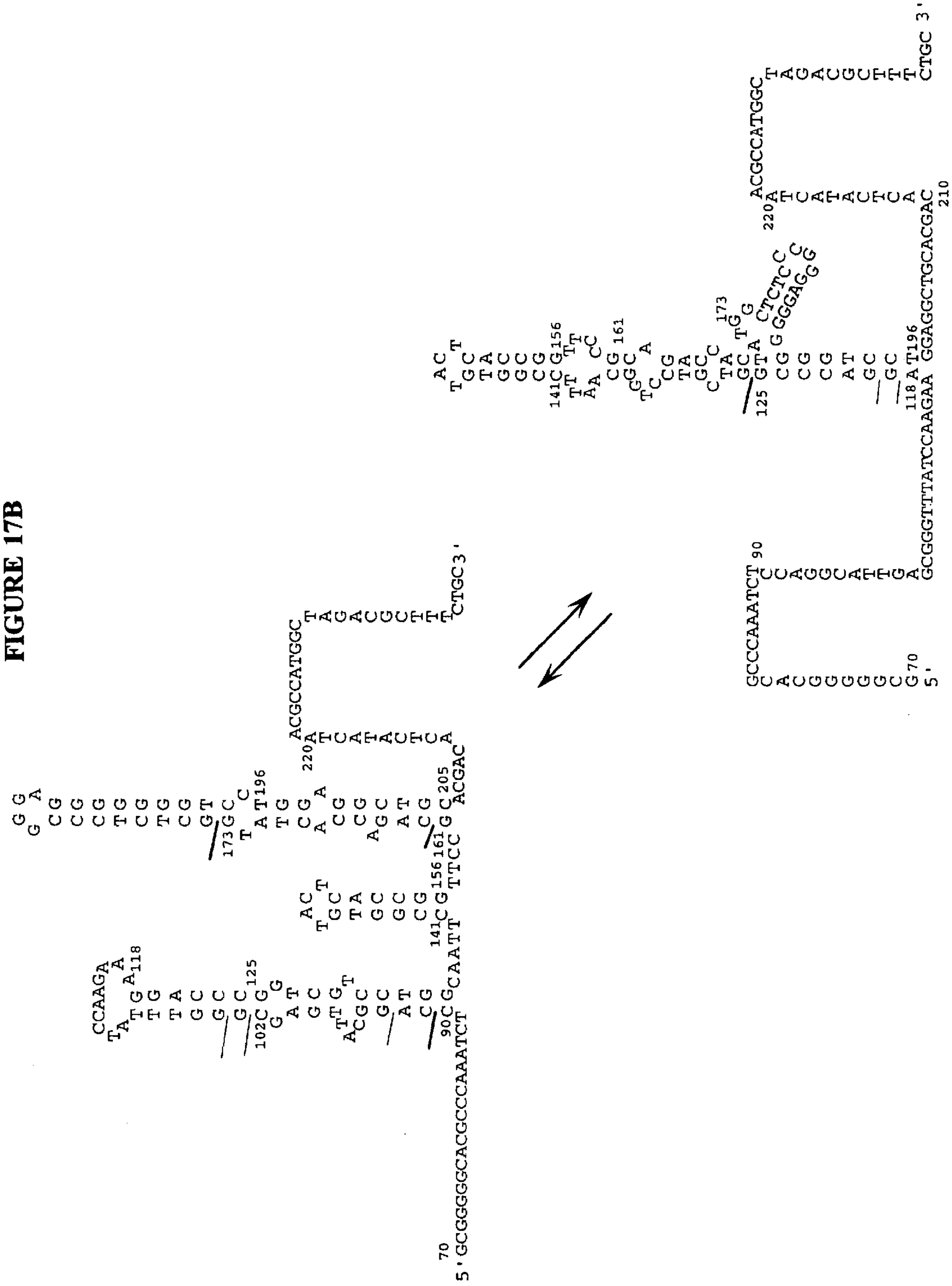

Structures predicted by the above analysis can be confirmed through the use of CFLP analysis on fragments that delete the putative downstream pairing partner (Brow et al., supra). This approach, termed PCR walking, is illustrated here by the confirmation of the pairing partner responsible for the CFLP cleavage at position 161 in the HCV type 1a 244 nt amplicon. The mfold program predicted a structure that paired a G at 161 with a C at position 205 (FIG. 17A, left conformer). To confirm this two deletion amplicons were made. Each amplicon was 205 nt long. One included the C205 at the 3' end, while the other substituted a T at 205 to disrupt the basepair. PCR was conducted as described in Example 3, except the downstream primers 67 (SEQ ID NO:67) and 68 (SEQ ID NO:68) were substituted for (SEQ ID NO:25) used to amplify the full length amplicons. The resulting DNAs were purified and subjected to CFLP analysis, resolved and visualized as described in Example 3. The resulting image is shown in FIG. 17B. The identity of residue 205 in the deletion fragments is indicated above each lane, and the sizes of selected cleavage bands, as determined by comparison to a sequencing ladder in Example 3, are indicated on the right.

Focusing on the band that was the subject of this analysis, at 161 nt, it can be seen that the amplicon having the natural 205C maintained the 161 cleavage, while disruption of this base pair in the 205T fragment caused a loss of that band, thus supporting the existence of the 161/205 interaction. It should be noted that it is possible that the 205 nt base does not interact directly with the 161G, and that the C to T change caused a conformational change elsewhere, which altered the 161-containing structure as a secondary effect. While this is less likely, the possibility should always be kept in mind when analyzing the data, especially if unexpected results arise. Not surprisingly, the deletions and mutations also give rise to pattern changes elsewhere in the pattern, indicating how little change is required to be detectable by CFLP.

Figure 17C:
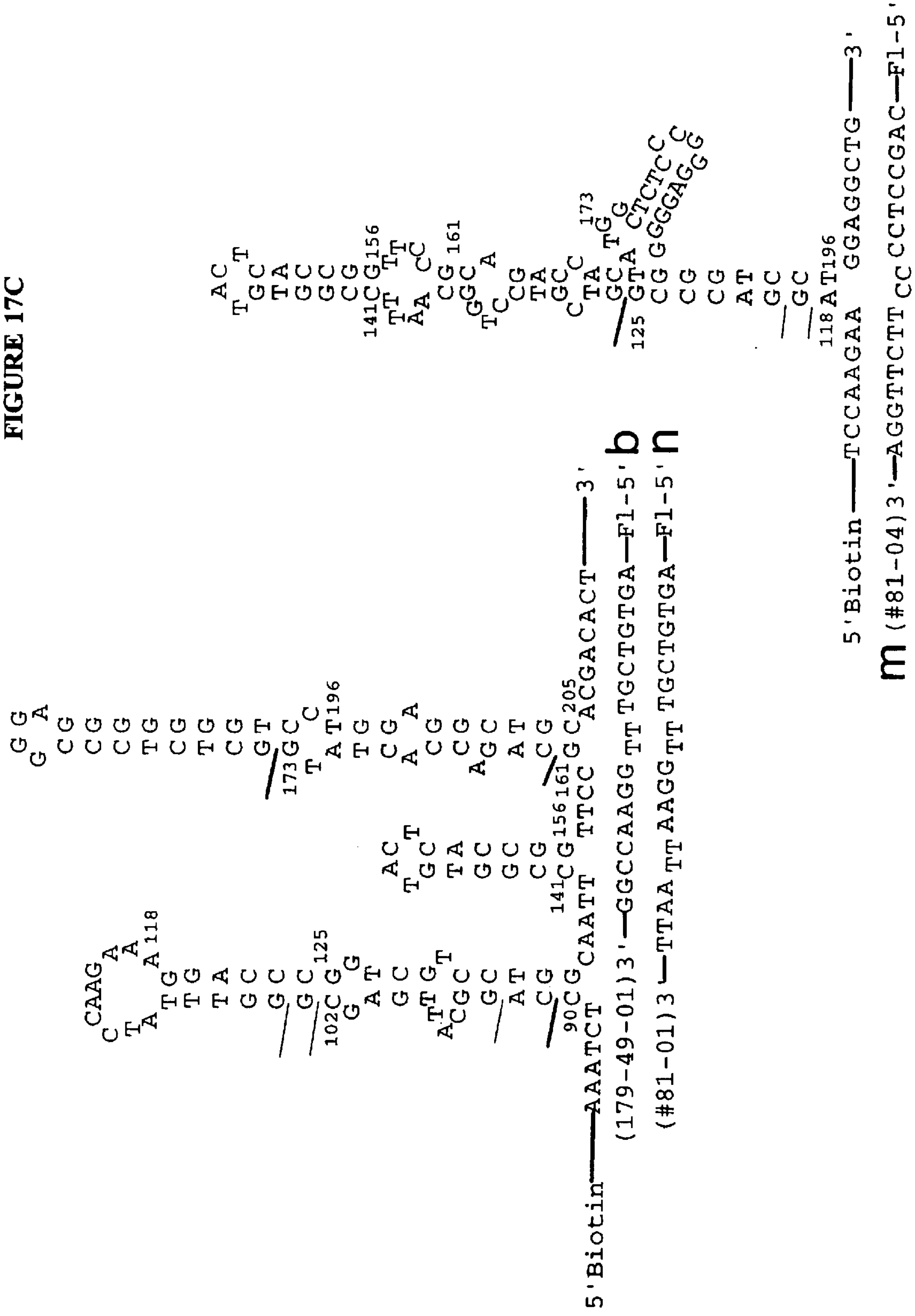

Based on the combined CFLP, mfold, and PCR walking data, three of the most likely conformations for this region were chosen and three bridge oligonucleotides were designed to span the structures. These are shown schematically in FIG. 17C. The "b" (SEQ ID NO:53) and "n" (SEQ ID NO:65) variants address essentially the same conformation with a difference related to the small central stem. Though predicted by mfold, the presence of this structure is not predicted by the CFLP pattern for the 244-mer (FIG. 17A, right lane). Consequently, bridge probes were designed that either spanned that structure ("n"; SEQ ID NO:65) or that complemented the 8 contiguous bases upstream of the larger stem ("b"; SEQ ID NO:53). The "m" (SEQ ID NO:64) bridge probe was designed to cross the base of the single stem of the other conformer. Each of the these probes was tested for binding to the HCV 1a amplicon as described in Example 6. While the "m" (SEQ ID NO:64) and "n" (SEQ ID NO:65) probes failed to capture significant amounts of target, the "b" (SEQ ID NO:53) probe was found to be effective, as will be illustrated in the following examples.

Using the "b" oligonucleotide (SEQ ID NO:53) as a model, a number of variant bridges were designed to compare the effects of different intervening sequences in the probes and on the inclusion of mismatches in either contact sequence. These bridge probes are diagrammed schematically as they would align with the HCV 1a predicted structure are shown in FIG. 18A. The connecting line in the center of the "k" probe (SEQ ID NO:56) indicates that the two portions are linked directly together without any intervening sequence. Modifications to the intervening region included the use of alternative nucleotides in to link the contact sequences and the omission of additional intervening nucleotides. A mismatch was included in the middle of either of the two contact sequences to assess whether the binding of both is necessary for capture.

The 244 bp target DNAs were created by PCR and isolated as described in Example 3 (SEQ ID NOS:26–29 for types 1a, 1b, 2c and 3a, respectively). The capture probes were synthetically labeled with fluorescein at their 5' end and purified by gel-electrophoresis. The target DNA was labeled with biotin at the 5' end of the antisense strand. Each of the these probes was tested for binding to the of the HCV amplicons (as shown schematically in FIGS. 18A–18D), as described in Example 6. Each assay was performed in duplicate and the standard deviation is represented by the black bar at the top of each column in FIG. 19. The fluorescence intensity is indicated in arbitrary fluorescence units, shown on the left side of each chart panel. The probe included in each capture reaction are indicated below each graph column. A control probe not shown in the schematic diagram (49-3; 5'Fl-GCGAAAGGCCTTGTGG; SEQ ID NO:66) that hybridizes to all HCV variants was used with each target to verify the presence and amount of DNA in each reaction. The rightmost column in each panel shows the signal from the control reaction.

These data show that functional bridge oligonucleotides may be designed with different intervening sequences, or without any intervening sequence at all ("k"; SEQ ID NO:56), although those having extra nucleotides showed greater signal in most tests. The low signal seen when a mismatch is included on either side verifies that both contact sequences participate in the binding. It is interesting to note that the signal from oligonucleotide "i" (SEQ ID NO:54) is greater than "b" (SEQ ID NO:53) in the type 2a/c test.

Figure 18C:
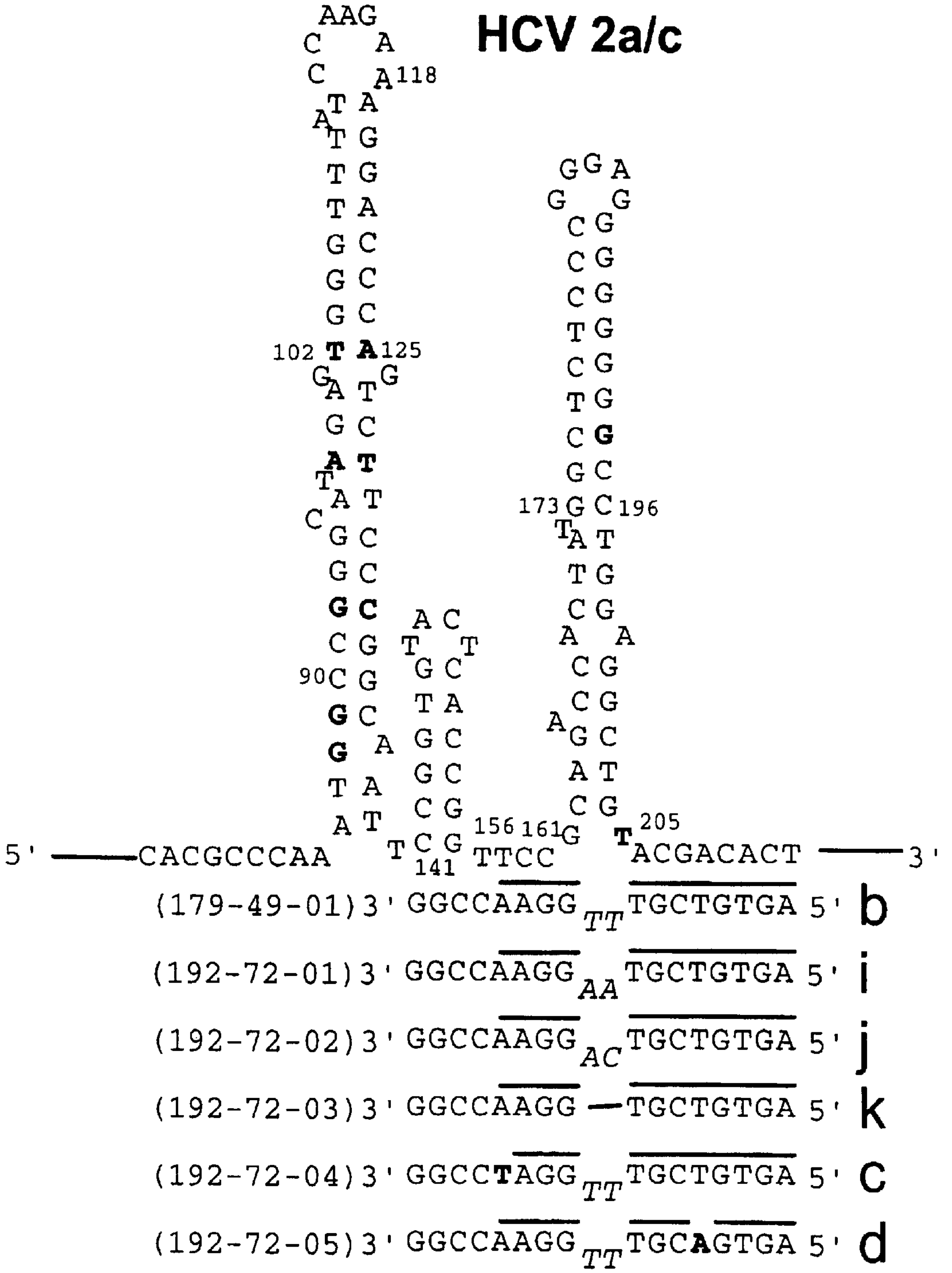
Figure 18D:
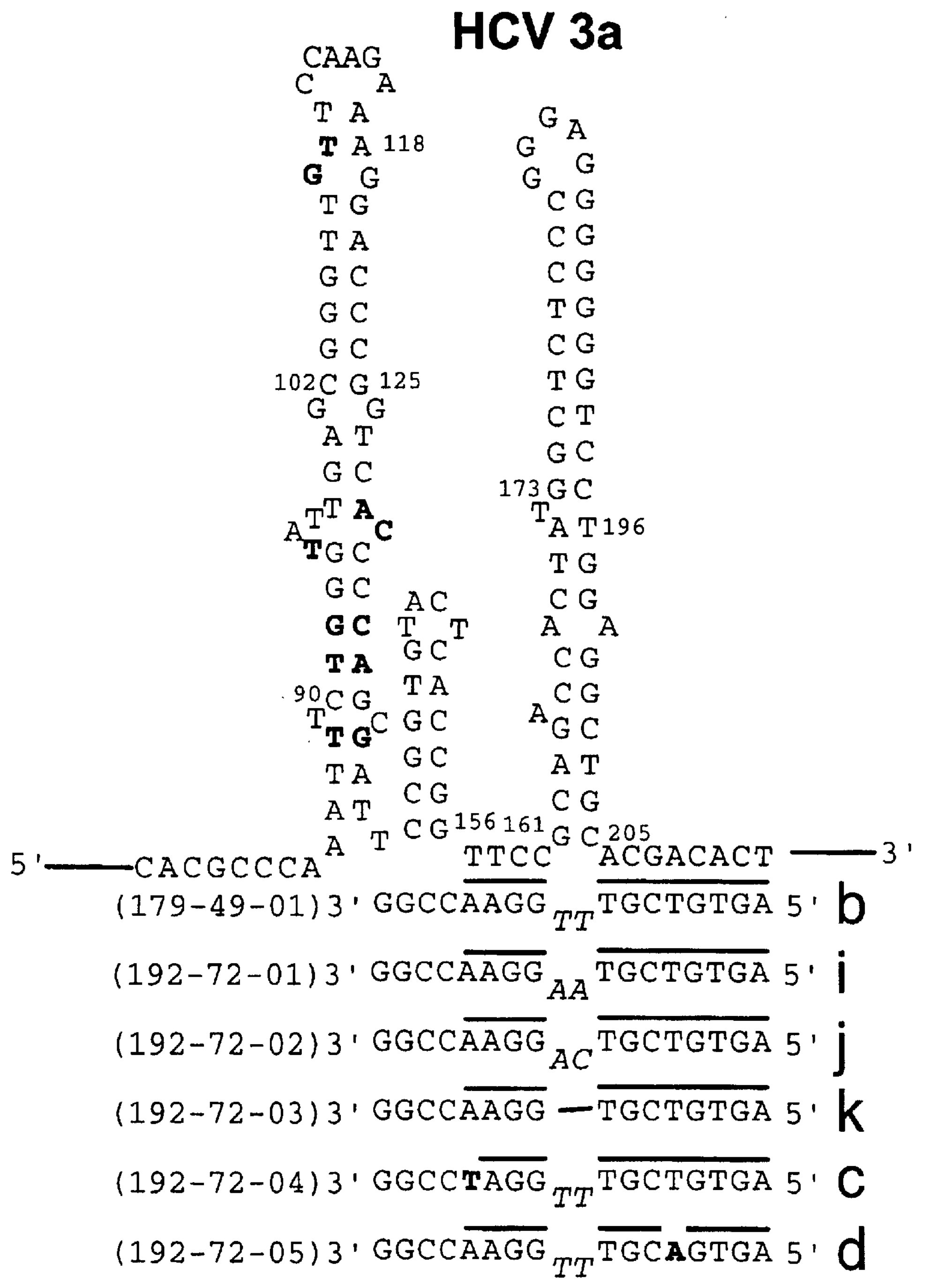
Figure 19:
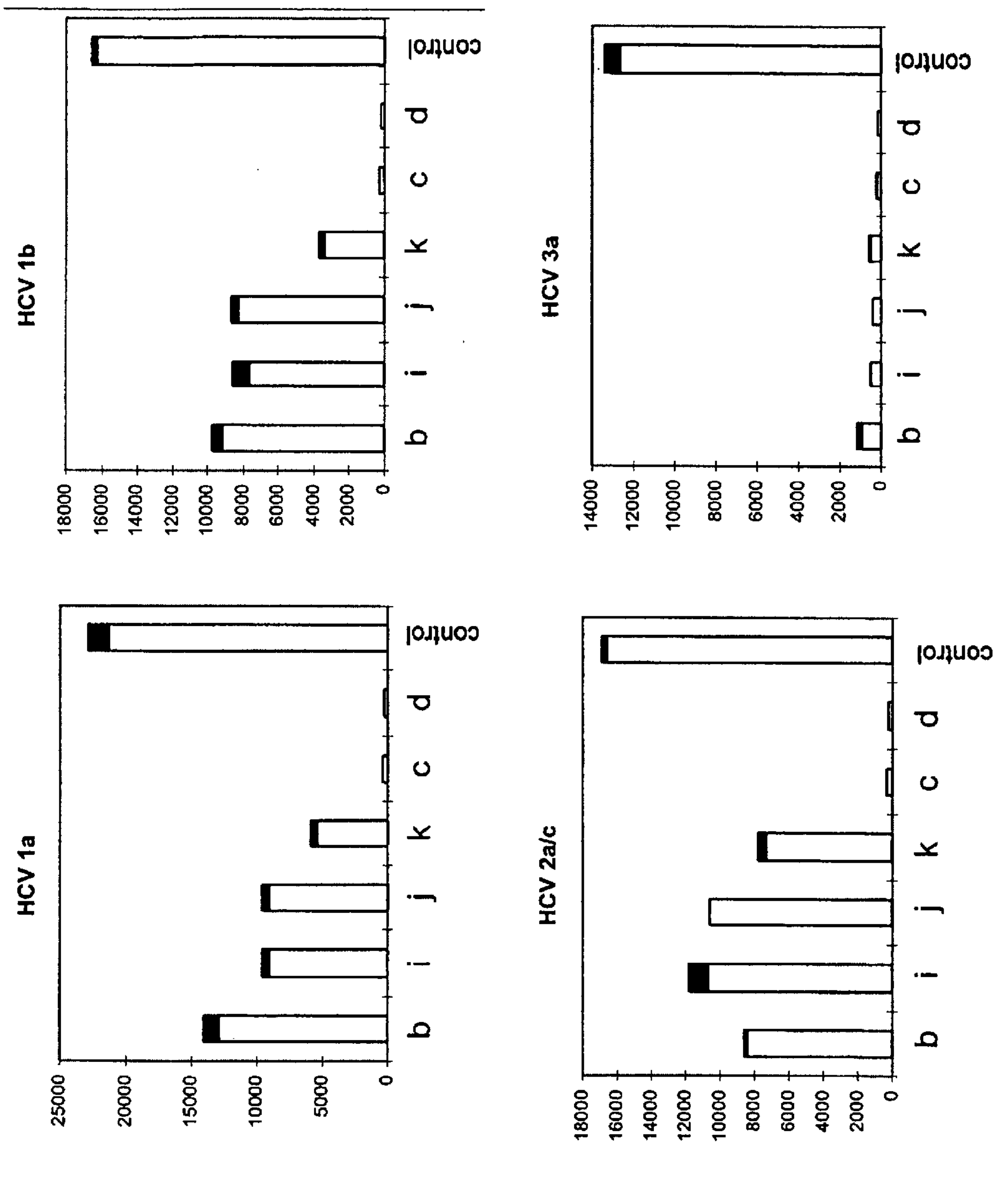
FIG. 19 shows graphs depicting the fluorescence signal measured after the solid support capture of the amplicons derived from HCV types 1a, 1b, 2a/c and 3a by the indicated probes. The letters identifying the probes used in each capture test are indicated below each bar, and the signal in arbitrary fluorescence units is shown on the left of each panel.

Examination of this junction in FIG. 18C shows that this type has a C to T change relative to the type 1a, a T that may interact with one of the A residues in the intervening sequence of the "i" probe (SEQ ID NO:54), thereby strengthening the interaction. It can be seen here and in later Examples, that this bridging design does not interact well with the type 3a amplicon, suggesting that this may not be a favored conformation for this particular variant. Nonetheless, these data demonstrate the flexibility available to the user in designing suitable bridging probes.

EXAMPLE 9

Primer Extension of Bridging Oligonucleotides

Figure 20A:
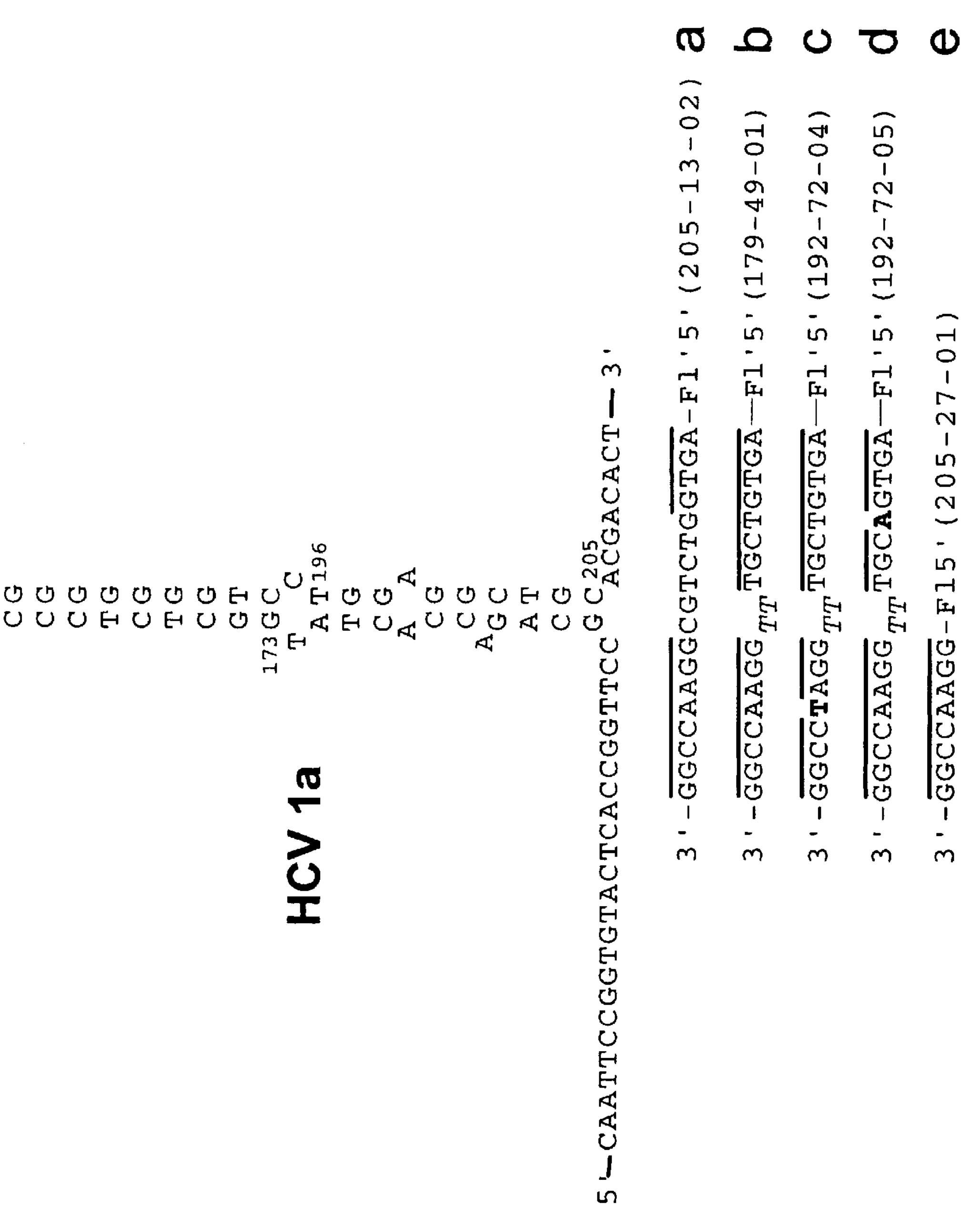
FIG. 20A shows a schematic diagram of a structure in the amplicon derived from HCV type 1a aligned with non-bridging probes “a” and “e” and bridging probes “b”“d”. The regions that are complementary as aligned to the target are indicated by a black line between the strands.
Figure 20B:
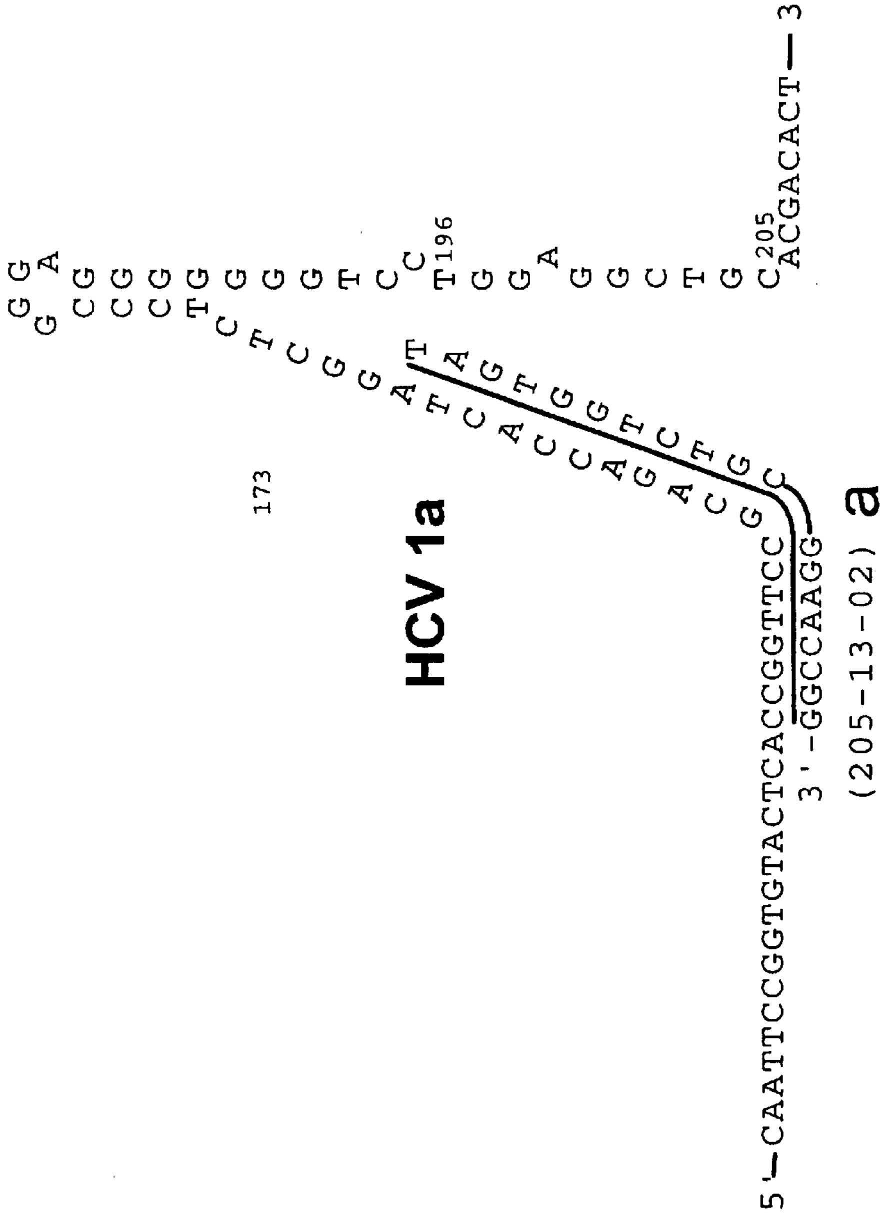
FIG. 20B shows a schematic diagram of a structure in the amplicon derived from HCV type la as it might be expected to pair with the fully complementary non-bridging oligonucleotide “a” (SEQ ID NO:52). The regions that are complementary as aligned to the target are indicated by a black line between the strands.

The folding of the 244 bp DNA copy of a segment of the hepatitis C viral genome is described above. The bridging oligonucleotides designed to hybridize across the deduced structures were used in a primer extension reaction to show that the presence of folded structures within the target would not prevent extension of the probe by a template-dependent DNA polymerase. The 244 bp target DNAs were created by PCR and isolated as described in Example 8. The bridging primers (a, b, c, d, and e, SEQ ID NOS:52, 53, 57, 58, and 59, respectively) are shown in FIG. 20A as they would be expected to hybridize to a folded structure of the HCV type 1a amplicon. The oligonucleotide indicated as "a" (SEQ ID NO:52), while it may have some complementarity that suggest it may serve as a bridge in some conditions, was designed as a non-bridging primer, intended to fully-hybridize to a non-folded target. This is shown schematically in FIG. 20B.

Figure 21:
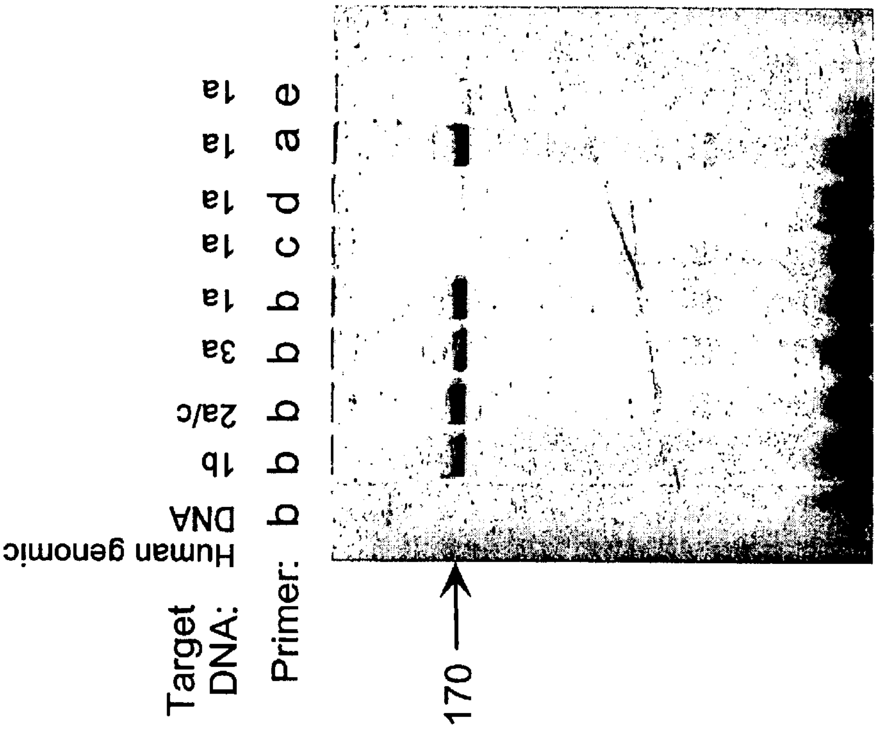
FIG. 21 shows a fluorescence imager scan of the products of primer extension reactions using the probes depicted in FIG. 20A and the folded target strands derived from HCV types 1 a, 1b, 2a/c and 3a, or using human genomic DNA as a control, as indicated above each lane. An arrow indicates the 170 nucleotide (nt) product of extension.

Each primer extension reaction contained either 50 fmole of the 244 bp target DNA or 10 ng of human genomic DNA (Novagen #69237-1, Madison, Wis.), 1 pmole of the fluorescein-labeled bridge oligonucleotide, 5 units of KlenTaq polymerase (Ab Peptides), and 0.1 mM of each dNTP in 10 μl of 1×PCR Buffer containing $Mg^{++}$ (Boehringer Mannheim). The assembled reaction mixtures with all the components were heated to 95° C. for 2 minutes, then cooled to the 40° C. for 1 hour. The reactions were terminated by the addition of 5 μl of 95% formamide with 10 mM EDTA and 0.02% Methyl Violet. The samples were then heated at 90° C. for 1 minute, and aliquots were resolved by electrophoresis through 10% denaturing polyacrylamide (19:1 cross link) with 7 M urea in a buffer of 45 mM Tris-Borate, pH 8.3, 1.4 mM EDTA. The gel was visualized using an M.D. Scanner (Molecular Dynamics, Sunnyvale, Calif.). The resulting image is shown in the panel of FIG. 21.

The target DNAs and the bridging primer/probe used in each reaction are indicated. The product of primer extension is indicated by an arrow on the left of the panel as a 170 bp band. It can be seen from these data that the "b" bridging oligonucleotide (SEQ ID NO:53) is able to prime synthesis on the folded HCV target of from all viral types, generating essentially the same level of signal as the non-bridging "a" primer (SEQ ID NO:52). Examination of the first (left most) lane, in which human genomic DNA was used in place of the HCV target shows little or no non specific priming, demonstrating the specificity of the primers for the HCV folded sequence. When single base mismatches are introduced on either side of the bridge (as in "c" and "d" primers; SEQ ID NOS:57 and 58, respectively) the signal is dramatically reduced. When only the 3' portion of the bridging primer is provided ("e"; SEQ ID NO:59) the extension is also nearly non-existent. These data demonstrate: a) that both complementary portions of these bridging oligonucleotides are required for the primers extension, demonstrating that the oligonucleotide is truly bridging; and b) that bridging oligonucleotides with no more than eight contiguous nucleotides of complementarity in single region can be used to specifically recognize an HCV viral sequence by use of its folded structure.

Figure 22:
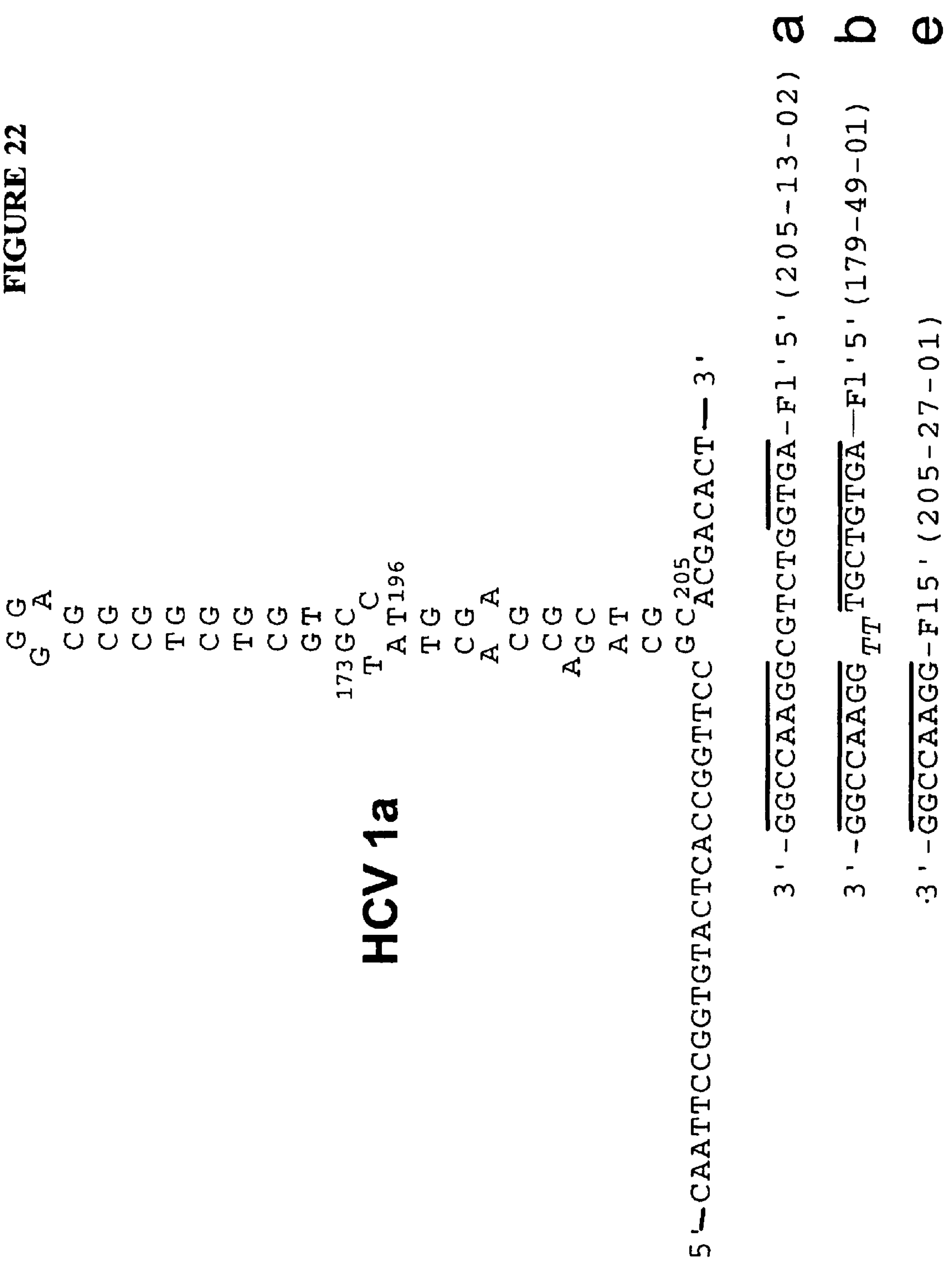
FIG. 22 shows a schematic diagram of a structure in the amplicon derived from HCV type la aligned with non-bridging probes “a” and “e” and bridging probe “b” (SEQ ID NOS:52, 53, and 59, respectively). The regions that are complementary as aligned to the target are indicated by a black line between the strands.

Above, the performance of a non-bridging oligonucleotide (i.e., an oligonucleotide that hybridizes to a region of contiguous, complementary bases in the target strand), was compared to the performance of the bridging oligonucleotides to assess the effect of the folded target structure on the enzyme activity. However, at elevated temperatures the folded structures may denature, reducing the binding efficiency of the bridging oligonucleotide relative to the non-bridging oligonucleotide. To demonstrate this effect, primer extension experiments were performed at a range of temperatures selected to decrease the presence of such structures as diagrammed in FIG. 22.

Figure 23:
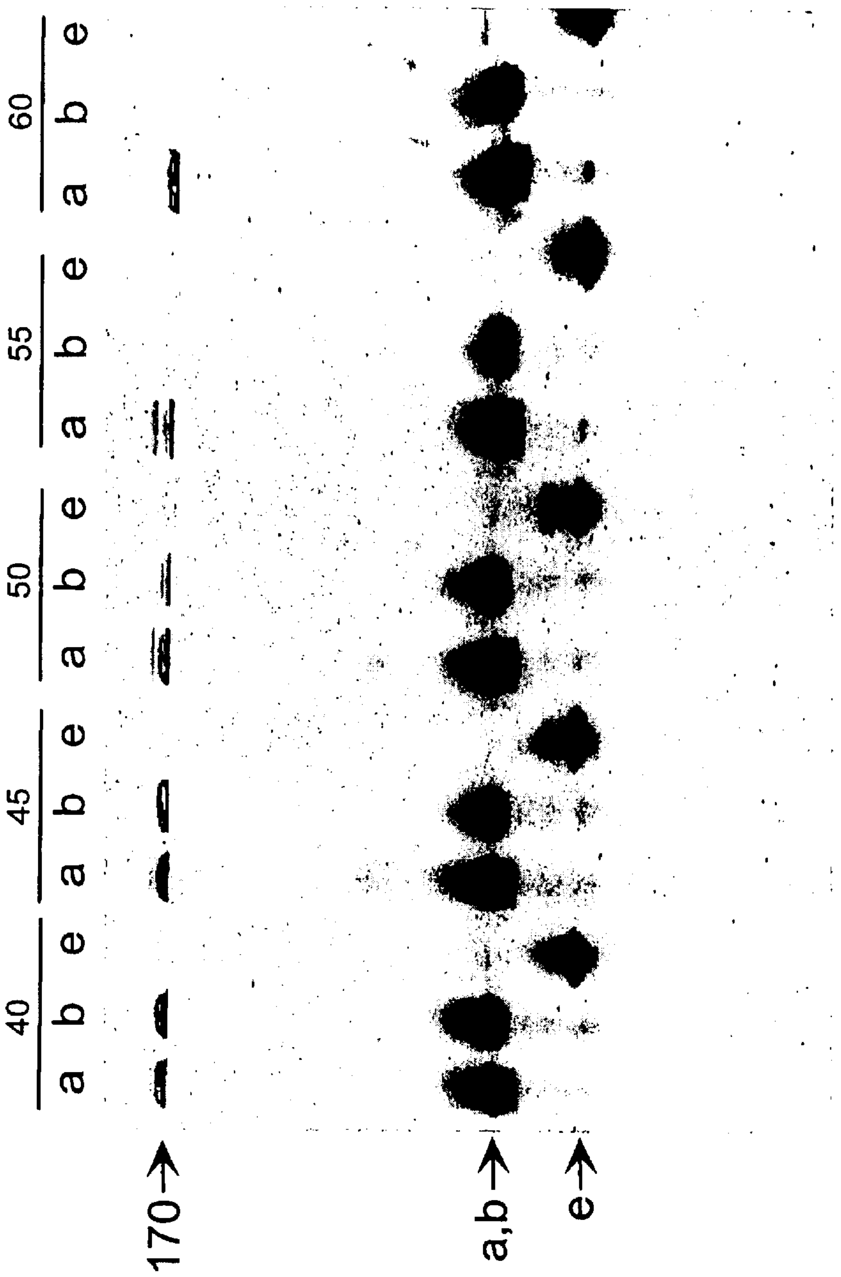
FIG. 23 shows a fluorescence imager scan of the products of primer extension reactions using the probes and target depicted in FIG. 22 in reactions performed over a range of temperatures. The temperatures of each reaction are indicated at the top of the panel, and the unreacted probes are indicated by arrows and their letters on the left. An arrow indicates the 170 nucleotide (nt) product of extension.

For this test, only the bridging, the non bridging and the half primer ("a", "b" and "e"; SEQ ID NOS:52, 53, and 59) were tested. Each primer extension reaction contained 50 fmole of the 244 bp target DNA, 1 pmole of the fluorescein-labeled bridge oligonucleotide, 5 units of KlenTaq polymerase (Ab Peptides) and 0.1 mM of each dNTP in 10 ml of 1×PCR Buffer containing Mg++ (Boehringer Mannheim). Reaction mixtures with all the components were heated to 95° C. for 2 minutes, then cooled to the various extension temperatures for 1 hour. Reactions were performed at 40° C., 45° C., 50° C., 55° C. and 60° C. The reactions were terminated by the addition of 5 ml of 95% formamide with 10 mM EDTA and 0.02% Methyl Violet. The products were heated at 90° C. for 1 minute, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the M.D. Scanner (Molecular Dynamics, Sunnyvale, Calif.). The resulting image is shown in the panel of FIG. 23. The temperatures (° C.) and the primers used for each reaction are indicated above each lane.

The extended products are indicated by an arrow on the left side of the panel as a 170 bp band. It can be seen from these data that the non-bridging oligonucleotide ("a"; SEQ ID NO:52) can prime synthesis at each of the test temperatures. The bridging oligonucleotide ("b"; SEQ ID NO:53), however, loses its ability to prime synthesis as the temperature of the reaction rises. This further demonstrates that the bridging oligonucleotides require the presence of the fold within the target strand. This also shows that the use of target folded structure to either support bridging oligonucleotide binding, or to allow structure-based discrimination of sequences as described in previous examples, is preferably done at lower temperature that those used for non-bridging applications. The precise temperature required to maintain a given structure will vary widely depending on the size and stability of a given structure, but a simple temperature titration such as is shown here will serve to identify optimal reaction conditions.

Figure 34:
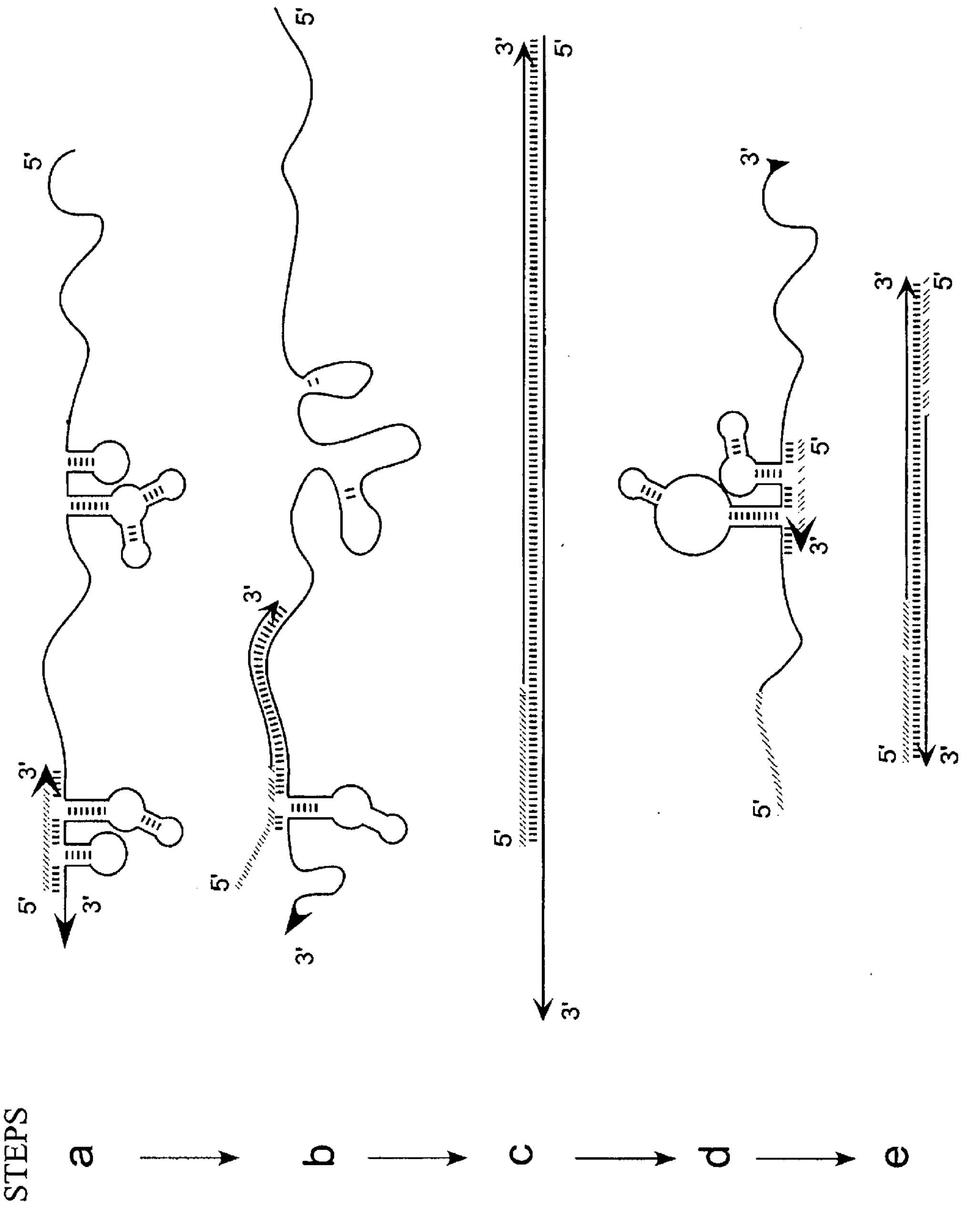
FIG. 34 is a schematic diagram showing one example of the use of bridging oligonucleotides as primers in a polymerase chain reaction. The "a–e" designations in this Figure are used to indicate the general steps in the reaction.

It will be appreciated by those skilled in the art that the target dependent extension of a bridging oligonucleotide can be adapted to the polymerase chain reaction method of target sequence amplification, using standard methods with minimal adaptation. In a PCR, either or both of the primers may be selected to perform the initial target recognition through the specific recognition of non-contiguous sequences. A schematic representation of a reaction in which both primers are thus configured in shown in FIG. 34. This is a simplified version of a PCR diagram that does not show all products at each step; the products shown are selected to demonstrate the manner in which a pair of bridging oligonucleotides may be designed. This example as described is intended as an illustrative example and not as a limitation on the mechanisms of application of the present invention. As shown in 34*a*, the first strand would be copied from a folded target strand as described above. The bridging oligonucleotide would anneal to the target at low temperature (relative to the temperature at which strand extension takes place). As the temperature of the reaction increases toward a chosen extension temperature (FIG. 34*b*), the folded structures would be disrupted, but the now partially extended primer would not disassociate due to its increased length. This would allow the polymerase to fully extend the primer, creating a double strand (FIG. 34*c*). In the next PCR cycle, after the strands have been denatured by heating, and the reaction has again cooled to an appropriate annealing temperature, the newly synthesized strand would likewise assume distinct folded structures, which can serve as binding sites for a second bridging primer (FIG. 34*d*). When the second primer is fully extended it would fill in the original bridging oligonucleotide with perfectly complementary sequence. In subsequent cycles of the PCR, the former bridge oligonucleotides would now operate as standard, fully complementary oligonucleotides, amplifying the target region between the 3' ends of the original binding sites. The resulting flanking sequences added by the bridge oligonucleotides would be unique to the bridge sequences.

The selection of conditions for using bridging primers in PCR is not dissimilar in reactions designed to use mismatched or degenerate oligonucleotides (Compton, in *PCR Protocols*, Innis et al. (Eds.), [1990], at p. 39). In the first few cycles of PCR it would be desirable to use an annealing temperature that would be permissive of the bridge contact formation. This reaction temperature could be determined empirically for any bridge oligonucleotide by a number of methods known in the art, including direct measurement (e.g., in a temperature controlled spectrophotometer), or by the use of the methods presented here, such as by plate capture, described in numerous examples above, or by temperature titration, as described in this Example. The principles of oligonucleotide design for maximum specificity are also similar to standard practices known in the art. For example, for maximum specificity of PCR oligonucleotides, it is a common practice to skew the stability such that the 5' end of the oligonucleotides has a higher local stability and the 3' end has a lower local stability. Conditions (e.g., sufficiently high annealing temperature), are then selected so that the 3' terminal sequence is unlikely to successfully bind unless the 5' end also binds. This prevents mis-priming caused by unintended hybridization of the 3' terminal residues at non-target sites.

The bridge oligonucleotides can be designed with a similar skew. In addition, it is contemplated that the bridge oligonucleotides be selected such that the 3' end is less stable (e.g., through the use of A/T base pairs or a short contact sequence) so that it is unlikely to find its target site without the successful binding of the other contact sequences, thereby increasing the discriminating power of the bride oligonucleotides in a PCR assay.

EXAMPLE 10

Hybridization Analysis of the Bridge Oligonucleotide in Combination with a Flanking Oligonucleotide Several reactions using involving standard probes require hybridization of two or more oligonucleotides in close proximity. For example, a ligation reactions to join oligonucleotide probes requires that at least two probes hybridize adjacently (i.e., without a gap), on a target or template strand. The INVADER reaction requires oligonucleotides to hybridize either adjacently, or with one or more nucleotides of overlap. In both of these scenarios, the binding of adjacent sites on a complementary strand means that resulting individual duplex regions are cooperatively stabilized by the coaxial stacking of the helices. In other words, each duplex will be more stable, i.e., will have a higher apparent melting temperature, in the presence of the other than it would in isolation. In the hybridization-based discrimination of genotypes based on the stability of folded target structure, the increased stability of binding of the bridge probe may reduce the ability to discriminate, absent compensating changes in the design of the probe.

Figure 24:
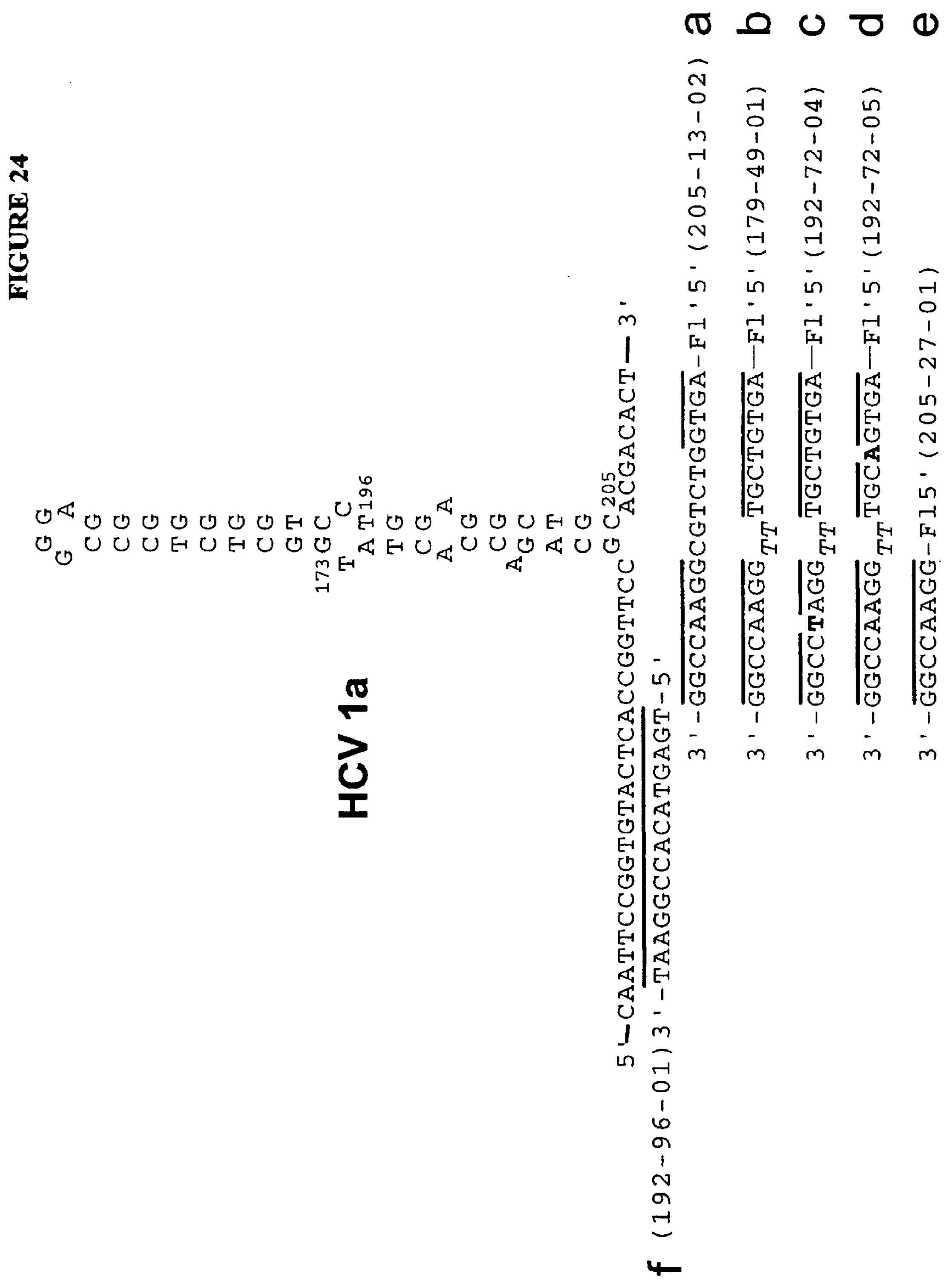
FIG. 24 shows a schematic diagram of a structure in the amplicon derived from HCV type la aligned with non-bridging probes “a” and “e” and bridging probes “b”–“d” and ligation oligonucleotide “f” (SEQ ID NOS:52, 59, 53, 57, 58, and 62, respectively). The regions that are complementary as aligned to the target are indicated by a black line between the strands.

To examine the effect of a neighboring oligonucleotide, hybridization capture tests were used on the bridging oligonucleotides and neighbor oligonucleotides designed for the ligation assay. The oligonucleotides were tested either alone, or in the pairs as they would be used in the enzymatic assays. For these tests the capture probes (SEQ ID NOS:52, 53, 60, and 66) were synthetically labeled with fluorescein at their 5' end and purified by gel electrophoresis. These probes are among those shown schematically in FIG. 24, identified by lower case letter. The HCV target DNA was amplified by PCR as described in Example 3, but the 5' end of the antisense strand was labeled with biotin, instead of fluorescein. The primers employed for the amplification of HCV target DNAs were: 5' primer: 5'-B-CTCGCAAGCACCCTATCA (SEQ ID NO:24)-and 3' primer: 5'-GCAGAAAGCGTCTAGCCATGG (SEQ ID NO:25). The PCR reactions were performed as described in Example 3, and the resulting 244 bp PCR products (SEQ ID NOS:20–23) for types 1a, 1b, 2c and 3a, respectively) were purified using "High Pure PCR Product Purification Kit" (Boehringer Mannheim) and eluted in $dH_2O$ according to the manufacturer's instructions. The same amount of DNA was used for each sample in the capture assay.

Figure 25:
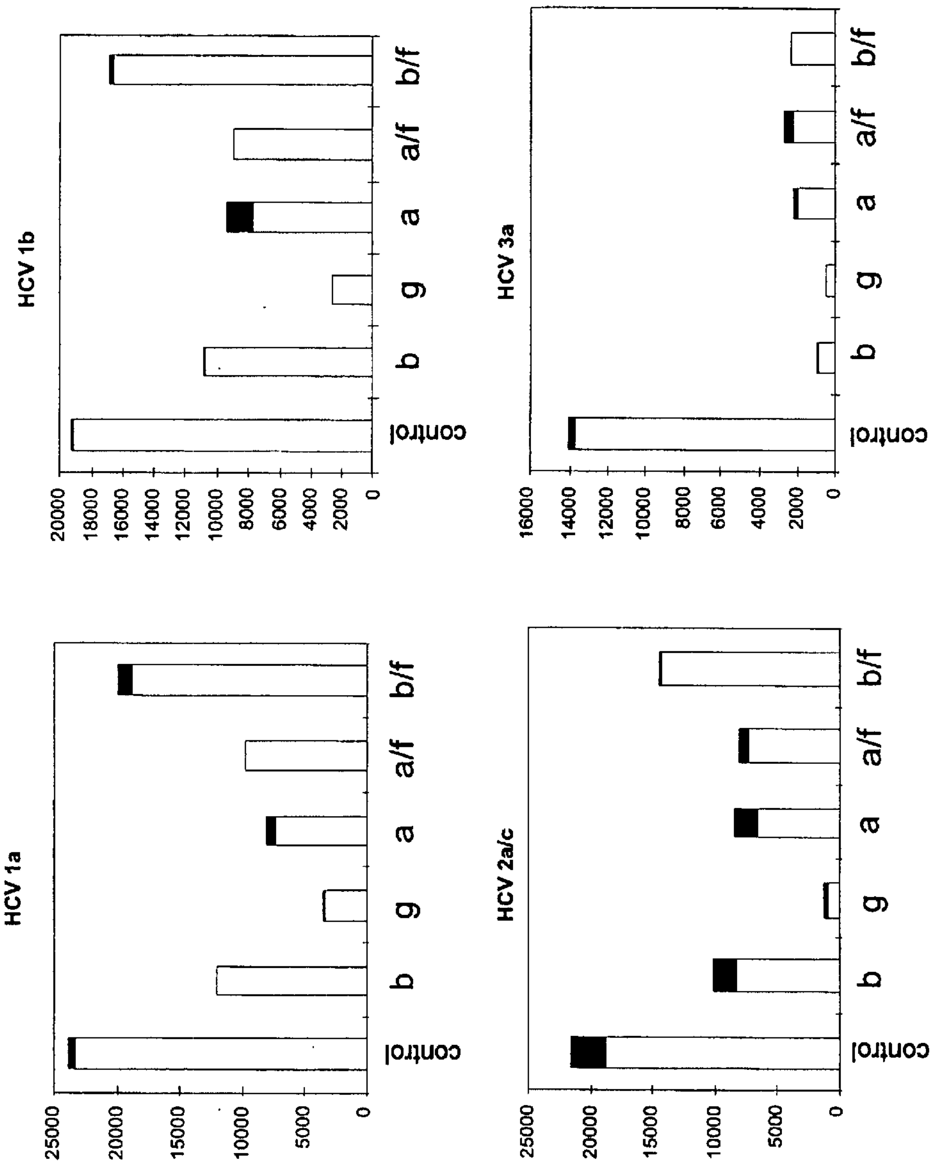
FIG. 25 shows graphs depicting the fluorescence signal measured after the solid support capture of the amplicons derived from HCV types 1a, 1b, 2a/c and 3a by the indicated probes and combinations of probes. The letters identifying the probes used in each capture test are indicated below each bar, and the signal in arbitrary fluorescence units is shown on the left of each panel.

The hybridization analyses were similar to these described in previous examples. For each test, a hybridization mixture was assembled containing 20 fmoles of heat-denatured, 244 bp HCV PCR product, 1 pmole each of the fluorescein-labeled bridge oligonucleotides and the ligation oligonucleotide probe depicted in FIG. 24 ("b," "a," and "f", SEQ ID NO:53, 52, and 62, respectively), and 0.01 mg/ml tRNA, in 100 μl of a solution of 0.2% acetylated BSA, 4.5×SSPE. After incubating the mixture at room temperature for 30 min., the mixtures were transferred into wells of a streptavidin-coated 96-well plate (Boehringer Mannheim) and incubated at room temperature for 30 min. The plate was then washed three times with 1×PBS, with 0.01% TWEEN-20 non-ionic detergent, containing 0.2% I-Block (Tropix, Bedford, Mass.). A 1:5000 dilution of 0.75 u/ml anti-fluorescein antibody conjugated with alkaline-phosphatase in 0.2% I-block buffer was added to each well. After 20 min at room temperature, the plate was washed three times with TBS (25 mM Tris-Cl, 0.15 M NaCl, pH 7.2). One hundred microliters of ATTOPHOS fluorescent substrate (JBL) was added to each well and the plate was incubated at room temperature for 1 hour before fluorescence readings were taken using a Perkin-Elmer Cytofluor-4000 set to excite at 450/50 nm and to and detect emission at 580/50 nm. Each assay was performed in duplicate, and the standard deviation is represented by the black bar at the top of each column in FIG. 25. In this Figure, the fluorescence intensity is indicated in arbitrary fluorescence units, shown on the left side of each chart panel. The probes included in each capture reaction are indicated below each graph column. A control probe not shown in the schematic diagram ("49-3"; 5'Fl-GCGAAAGGCCTTGTGG; SEQ ID NO:66) that hybridizes to all HCV variants was used with each target to verify the presence and amount of DNA in each reaction. The leftmost column in each panel shows the signal from the control reaction.

In addition, a comparison of bridging and non-bridging oligonucleotides for HCV capture was conducted. It can be seen by comparing the signals from the "a" (non-bridging) and "b" probes (SEQ ID NO:52 and 53, respectively), that the bridge oligonucleotide, having only 8 nts of uninterrupted complementarity to the target, binds to the targets with nearly the same affinity as the 18 nt, fully complementary oligonucleotide, demonstrating the efficacy of the bridge design. Each of the oligonucleotides binds most strongly to HCV type 1a, slightly less efficiently to types 1b and 2a/c, and not very strongly to type 3a. The degree to which this differential binding is out of proportion to variations seen with the control oligonucleotide, particularly evident with type 3a, further illustrated the ability of these probes to differentiate types based on folding of the target nucleic acid.

Figure 29A:
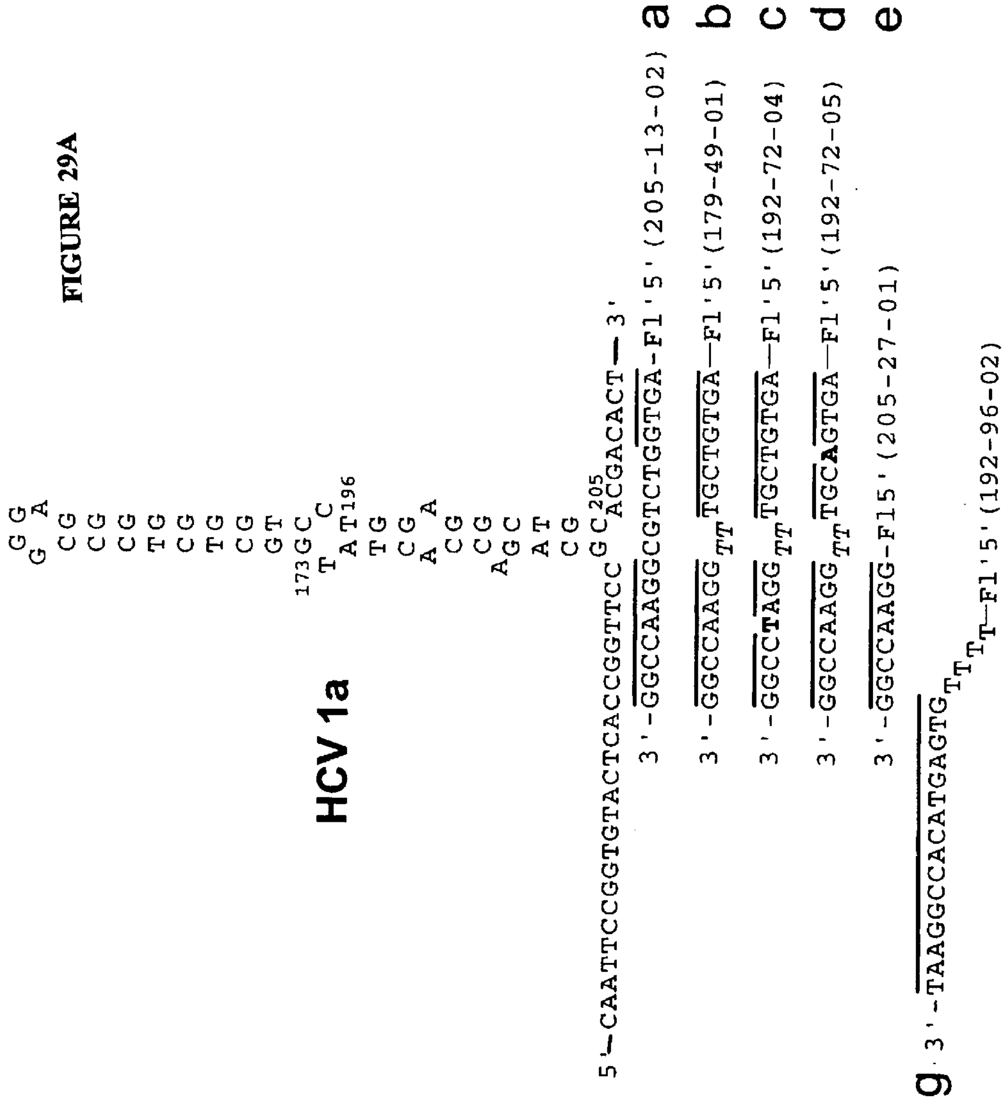

Effect of a neighboring oligonucleotide on the bridge binding signal. The Probe "g" (SEQ ID NO:60), a probe used in an INVADER cleavage assay and diagrammed in FIG. 29, was included because it has the same target-complementary sequence as the "f" probe (SEQ ID NO:62), but it also has a 5' fluorescein label to allow it to serve as a capture probe, whereas "f" does not, because it is intended for ligation. The "g" probe (SEQ ID NO:60) also comprises a short 5' tail of 4 T residues that are not included in "f" (SEQ ID NO:62). While not identical in composition, the capture signal from "g" (SEQ ID NO:60) should be a good indicator of the strength of the interaction between the HCV targets and the "f" (SEQ ID NO:62) oligonucleotide. The base signal from each of the capture oligonucleotides (columns marked underneath as "b" and "a"), and the effect of the addition of a neighboring oligonucleotide can be seen by examining the signal in reactions that included the ligation probe "f" (SEQ ID NO:62). It can be seen by comparing "a" to "a/f" that the presence of the second oligonucleotide has little or no effect on the capture of these HCV targets with the non-bridging "a" probe (SEQ ID NO:52). In contrast, in all cases the addition of the "f" oligonucleotide (SEQ ID NO:62) substantially increases the binding by the bridging "b" (SEQ ID NO:53) oligonucleotide. Because "f" (SEQ ID NO:62) is unlabeled and does not contribute to either the plate binding or the signal generation, the additional signal seen in these columns must come from increased binding of "b" (SEQ ID NO:53). This increased stability of binding using a flanking oligonucleotide may be used to enhance the performance of the bridge oligonucleotides in capturing all types of a target. Conversely, the increased stability must be considered in the design of the bridge oligonucleotides only if the goal is to create a system that is maximally sensitive to subtle structural changes, as described in Example 7. When maximum discrimination is desired in an assay that requires the binding of an adjacent oligonucleotide, it may be desirable to shorten or otherwise reduce the stability of the contact segment of the bridge that is nearest to the neighboring oligonucleotide. Common methods of reducing oligonucleotide binding affinity, such as through the use of base analogs or mismatches are well known in the art.

EXAMPLE 11

Target Dependent Ligation of a Bridging Oligonucleotide to an Adjacent Oligonucleotide.

To examine the mismatch effect on the ligation between a bridging oligonucleotide and the ligation oligonucleotides, a linear (i.e., non-folded) oligonucleotide target having appropriately oriented regions of complementarity was synthesized for use as a control target (SEQ ID NO:63)(i.e., to examine the effect of ligation in the presence of a stem). This control target aligned with the ligation and bridging oligonucleotides is depicted in FIG. 26. The PCR conditions to prepare 244 bp ds HCV target DNA were the same as described above.

Figure 27:
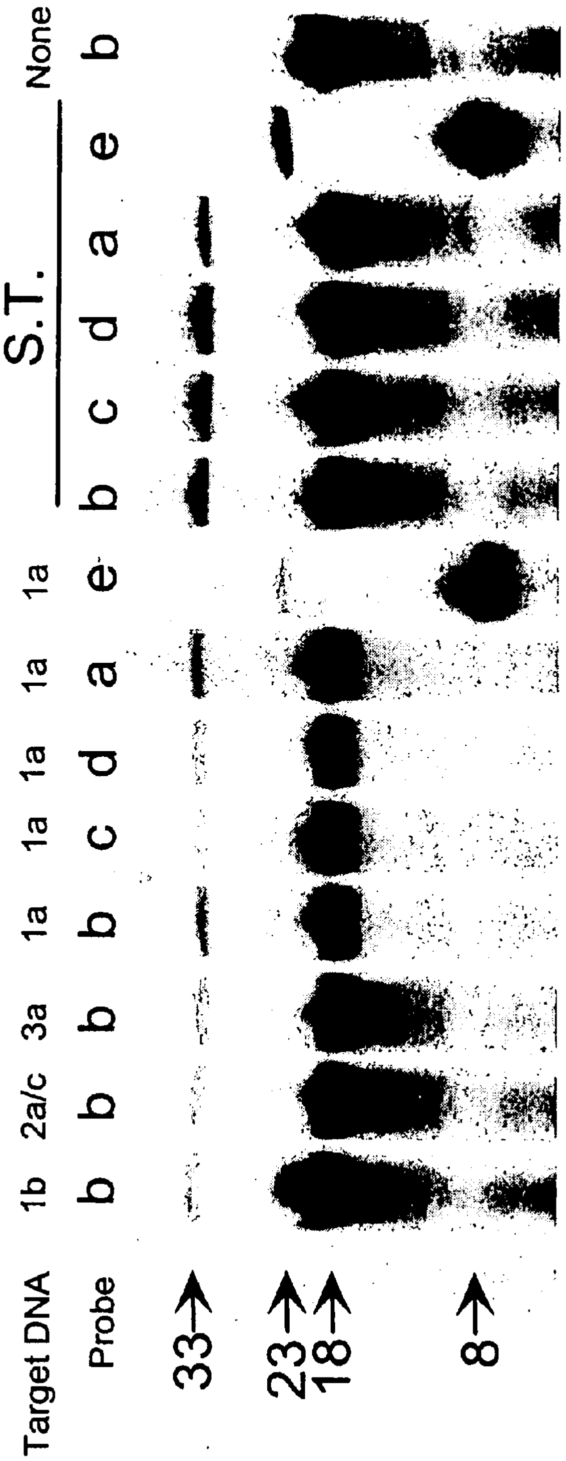
FIG. 27 shows a fluorescence imager scan of the products of ligation reactions using the probes and targets depicted in FIGS. 24 and 26. The unreacted probes are indicated at 8 and 18 nt by arrows on the left. Arrows indicates the 33 nt product of ligation between the probe “f” and “a”, “b”, “c” or “d”, and the 23 nt product of ligation between “f” and “e”.

Each ligation reaction contained 200 fmole of the target DNA, 1 pmole each of the bridging and ligation oligonucleotides, 100 units of AMPLI-LIGASE (Epicenter) in 10 μl of 1×AMPLI-LIGASE buffer (Epicenter). A control reaction was performed without target DNA. Reactions were assembled with all components except the enzyme and the enzyme buffer, heated to 95° C. for 3 minutes, then cooled to the reaction temperature of 45° C. The ligation reactions were started with the addition of the enzyme and the enzyme buffer, and incubated for 1 hour. The reactions were terminated by the addition of 4 μl of 95% formamide with 10 mM EDTA and 0.02% Methyl Violet. The products were heated at 90° C. for 1 minute, and aliquots were resolved by electrophoresis through 15% denaturing polyacrylamide gel (19:1 cross link) with 7 M urea in a buffer of 45 mM Tris-Borate, pH 8.3, 1.4 mM EDTA. The gel was visualized using the M.D. Scanner (Molecular Dynamics, Sunnyvale, Calif.). The resulting image is shown in the panel of FIG. 27. The sizes in nucleotides of each band is indicated on the left side of the panel.

The labeled, unreacted probes are visible as either an 18 nt band (a-d; i.e., probes corresponding to SEQ ID NOS:52, 53, 57, and 58) or an 8 nt band (e; i.e., probe corresponding to SEQ ID NO:59). The product of ligation between oligonucleotide "f" (SEQ ID NO:62) and bridge probes "a" through "c" (SEQ ID NOS:52, 53, and 57, respectively), is visible as a 33 nt band near the top of the panel, while the product of ligation between "f" (SEQ ID NO:62) and "e" (SEQ ID NO:59) is indicated as a 23 nt band. It can be seen from these data that all of the bridge oligonucleotides are able to use the folded target at a template to correctly align for ligation. The efficiency of the ligation can be assessed by comparing the product intensity in each lane to the intensity from ligation of the non-bridging oligonucleotide "a" (SEQ ID NO:52). Probe "b" (SEQ ID NO:53), which is fully complementary in both contact sequences shows the strongest signal on the HCV type 1a, which is consistent with the binding seen in the capture tests of these oligonucleotides. The ligation of the shortest oligonucleotide, "e" (SEQ ID NO:59) shows that even an 8 nt probe is sufficiently stable in this assay to be ligated at some level. The least amount of ligation is seen with the bridge probe having the mismatch closest to the site of ligation, reflecting a decrease in hybridization for this portion of the oligonucleotide or a decrease in activity of the ligase enzyme near a mismatch, or a combination of these effects.

As described above for the primer extension of the bridging oligonucleotide, at elevated ligation temperatures the folded structures denature, reducing the binding efficiency of the bridging oligonucleotide relative to the non-bridging oligonucleotide. To examine this effect in a ligation reaction, and to examine the effect of the folding on the discrimination of the amplicons by HCV type, additional experiments were performed on all four amplicon types, at a range of temperatures. Because the thermostable ligase activity intended for use under high-stringency conditions (e.g., at temperatures above about 45° C.), T4 DNA ligase, commonly used at 10 to 30° C., was used in the ligations performed at lower temperature.

Figure 28:
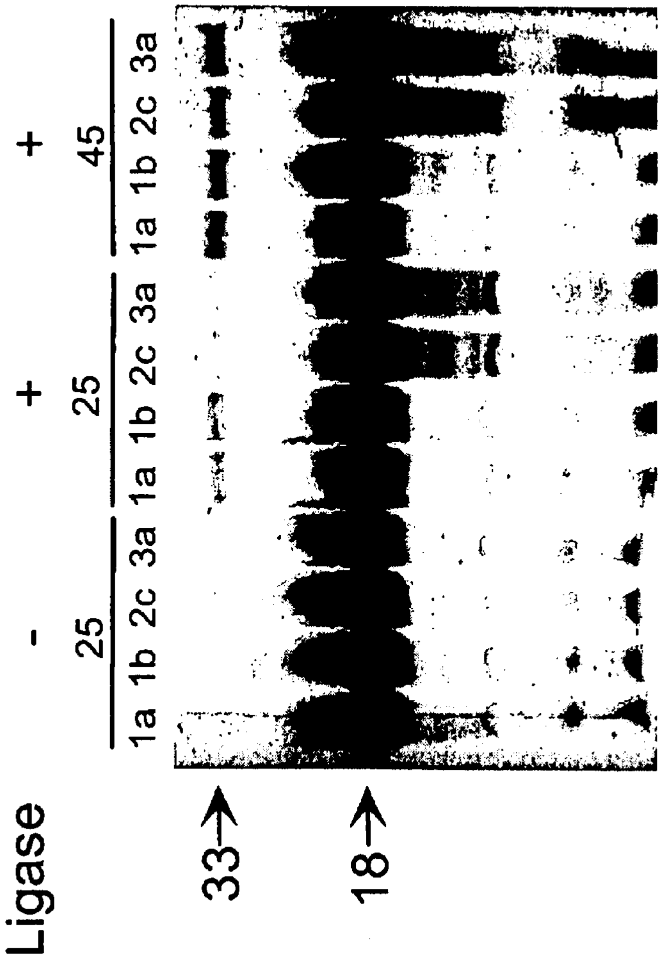
FIG. 28 shows a fluorescence imager scan of the products of ligation reactions using the ligation probe “f” and the bridging probe “b” in reactions performed at various temperatures, using target amplicons derived from HCV types 1a, 1b, 2a/c and 3a. Arrows on the left indicate the unreacted probe at 18 nt the product of ligation at 33 nt.

Each ligation reaction contained 200 fmole of the target DNA, 1 pmole of the fluorescein-labeled bridge oligonucleotide, 1 pmole of the ligation oligonucleotide and 3 units of T4 Ligase (Promega) in 10 μl of 1×T4 LIGASE buffer (Promega). Reactions were assembled with all components except the enzyme and the concentrated enzyme buffer, heated to 95° C. for 3 minutes, then cooled to the reaction temperature of either 25° C. or 45° C. The ligation reactions were started by the addition of the enzyme and the concentrated buffer to bring each of those components to the final concentrations listed above, and incubated for 1 hour. The reactions were terminated by the addition of 4 μl of 95% formamide with 10 mM EDTA and 0.02% Methyl Violet. The products were heated at 900C for 1 minute, and aliquots were resolved by electrophoresis through 15% denaturing polyacrylamide (19:1 cross link) with 7 M urea in a buffer of 45 mM Tris-Borate, pH 8.3, 1.4 mM EDTA. The gel was visualized using the M.D. Scanner (Molecular Dynamics, Sunnyvale, Calif.). The resulting image is shown in the panel of FIG. 28. The reaction temperatures are indicated at the top of the panel, and the control reactions lacking the ligase enzyme are indicated. The labeled, unreacted probes are visible as an 18 nt band. The product of ligation is visible as a 33 nt band near the top of the panel.

Examination of the product bands at the two temperatures confirms the expected increase in discrimination at the lower temperature. The signals from the 1a and 1b types are very similar, while the signals from 2a/c and 3a are much lower. While the 3a result is consistent with the capture data using the combination of the "b" and "f" probes (SEQ ID NO:53 and 62, respectively) shown in FIG. 25, the signal from 2a/c is relatively lower than in the capture. Without limitation to any particular mechanism, this effect may be attributable to the substrate specificity of the ligase at this temperature (e.g., the assumed structure may have a loop or bulge situated in a manner that inhibits the enzyme). Nonetheless, this example demonstrates that these viral types may be distinguished using ligation reactions performed under non-stringent conditions. At slightly elevated temperature, the product bands are of approximately equal, and stronger intensity. The uniformity of the signal may be attributed to the partial or complete disruption of the structure at this temperature. It was observed in the FIG. 27 that even the 8 nt "e" (SEQ ID NO:59) control molecule could be efficiently ligated to the "f" ligation oligonucleotide (SEQ ID NO:62) on the linear synthetic target ("S.T."; SEQ ID NO:63). This indicates that the ligase can join rather short oligonucleotides, even at temperatures above their estimated Tm. As the structure is unfolded in the 45° C. reaction in FIG. 28, the bridging oligonucleotide may be participating in the ligation in this manner (i.e., only its 3' end is binding), eliminating the ability to discriminate between types under these conditions. The strength of the signal may reflect increased activity of the enzyme at this temperature, the preference for the enzyme for this structure over the bridge conformation, or a combination of these or other factors.

The ligation under the lower temperature conditions demonstrates that bridging oligonucleotides can be used to identify folded target molecules in this type of a reaction. Since the contact sequence on the 3' terminus of the bridging oligonucleotides of these examples is clearly stabilized in these reactions (i.e., a mismatch in this portion, as in oligonucleotide "c" (SEQ ID NO:57), has less effect on the bridge activity of the probe than in the capture, primer extension and cleavage assays shown in other examples) it may be desirable to provide a less stable contact sequence in this region. Means for reducing oligonucleotide Tm are well known in the art, and a few methods are discussed above, in the context of PCR primer design.

Figure 35:
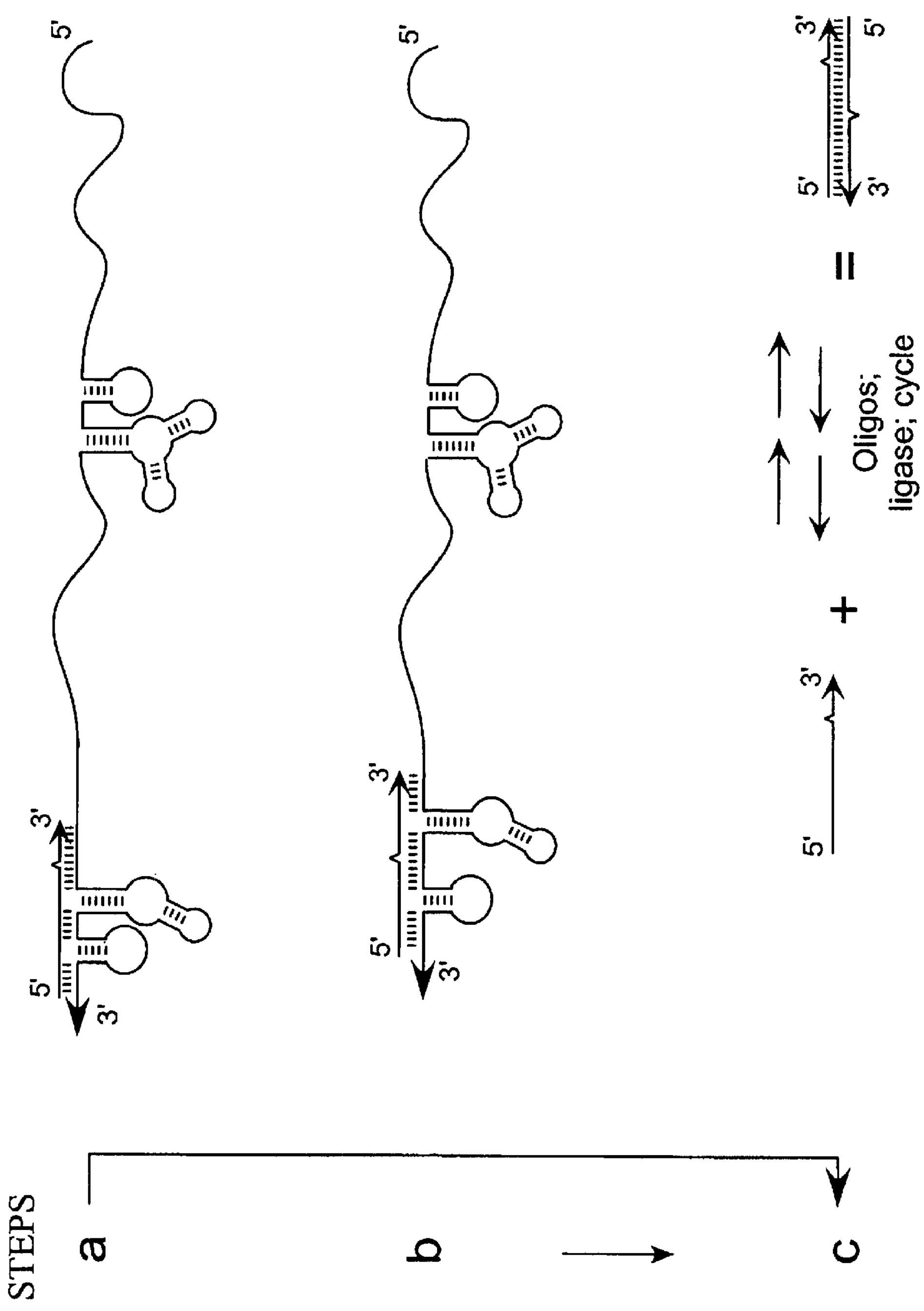
FIG. 35 is a schematic diagram showing two examples of target-dependent ligation of bridging oligonucleotides, with subsequent detection of the bridged ligation product by a ligase chain reaction. The "a–c" designations in this Figure are used to indicate the steps in the reaction, with either step a or b being followed by step c (i.e., b does not follow a in the progression of the steps).

Just as the conditions for bridge oligonucleotide primer extension can be adapted to the polymerase chain reaction for amplification of signal, the ligation of the bridge oligonucleotides can be adapted to the ligase chain reaction. The target-specific ligation event can be viewed as creating a unique molecule to be detected, even if the ligation point in not centered, as it is in the LCR. Two possible configurations are depicted schematically in FIG. 35. In all panels of this Figure, the ligation junction is represented by a carat point on the ligated nucleic acid. In the first panel, FIG. **35*a*, the bridging oligonucleotide would be extended by addition of a short sequence, such as a hexamer or an octamer. Ligation of short oligonucleotides that are stabilized by coaxial stacking is known in the art (Kaczorowski and Szybalski, Gene 179:189 [1996]), and is demonstrated by ligation of the "e" oligonucleotides (SEQ ID NO:59) shown in FIG. 27**. The configuration shown in 35b instead shows the ligation of two longer probes, each of which bridges in a structure. It is contemplated that other configurations within the scope of the present invention would be apparent to those skilled in the art, including but not limited to ligation of a non-bridging oligonucleotide to the 5' end of a bridging oligonucleotide, or ligation of more that two oligonucleotides assembled on a single folded target.

In each of the embodiments and configurations listed above, the ligation event would create a unique contiguous sequence not found in the target nucleic acid. This unique sequence may then itself be detected by a number of means, including, but not limited to the ligase chain reaction. Practice of the ligase chain reaction for the detection of specific sequences is well known in the art, and the means of adapting the bridging ligation to this amplification method are easily ascertainable from the literature (See e.g., Barany, PCR Meth. App. 1:5 [1991], and U.S. Pat. No. 5,494,810, herein incorporated by reference). The bridging oligonucleotides may also be used in modified LCR assays, such as gap-filling LCR (See e.g., U.S. Pat. No. 5,427,930, herein incorporated by reference), or other variants of the method. By combining the bridging oligonucleotides of the present invention with the ligase chain reaction an investigator can derive the benefits of structure characterization discussed above, but performed directly on samples of interest, without intervening culture or PCR amplification.

EXAMPLE 12

Target Dependent Cleavage of a Probe, Directed by an Invasive Bridging Oligonucleotide The previous examples demonstrated the ability of the bridging oligonucleotides to serve as substrate in reactions that produced a maximum of one event for each copy of a folded target. There are many applications based on the use of oligonucleotides in which the reactions are configured to produce many signals for each copy of a target nucleic acid. Such reactions include, but are not limited to ligase chain reaction, polymerase chain reaction, cycle sequencing, and nuclease detection assays such as the cycling probe reaction. We show here that such reactions can be configured to make use of noncontiguous probe binding. The use of bridging probes may in some embodiments allow the kind of structure-based typing described above to be used in a reaction that can also amplify the signal from the target. It is also well known that even single-stranded nucleic acid targets can fold such that very little sequence is actually available for probe binding for detection or for antisense applications. The ability of probes to bind to non-contiguous sites facilitates the design of probes that interact only with the outer surface of the target nucleic acid, thus allowing detection or typing of targets that could not previously be characterized by hybridization methods.

Figure 31:
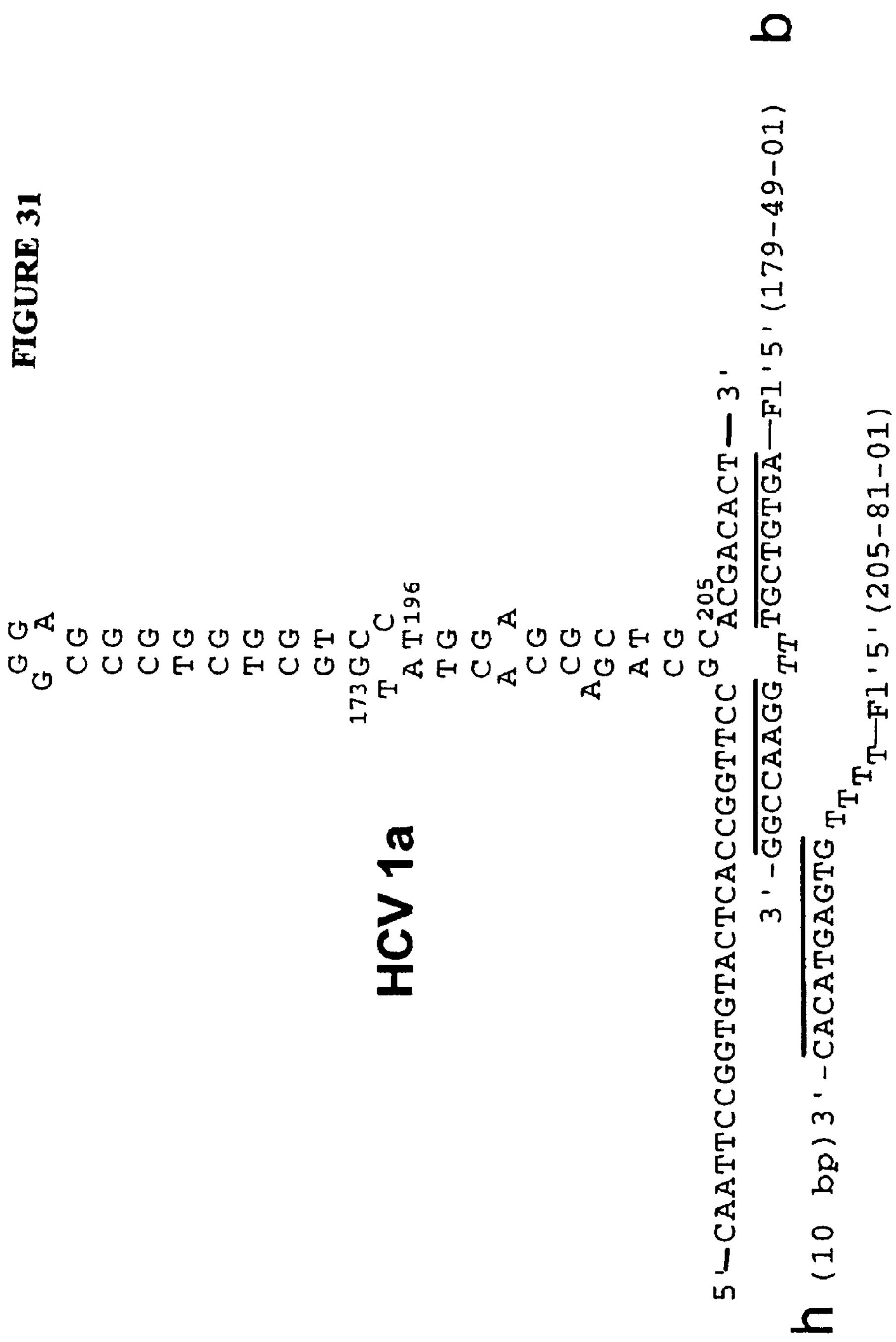
FIG. 31 shows a schematic diagram of a structure in the amplicon derived from HCV type 1a aligned with bridging probe "b" (SEQ ID NO:53) and invasive cleavage probe "h" (SEQ ID NO:61). The regions that are complementary as aligned to the target are indicated by a black line between the strands.

The INVADER reaction involves the contacting of a target nucleic acid with a pair of oligonucleotides to create a cleavage structure as described above. The signal probes can leave the structure after cleavage, to be replaced by an uncleaved copy, thus starting the cycle again, and allowing each target to create many copies of the cleaved probe during the course of the reaction. The probes and targets used for this assay are diagrammed in FIGS. 29A, 29B and 31. The effects of the signal probe ("g"; SEQ ID NO:60) on the stability of the bridge oligonucleotides was described in Example 9.

In the experiments in this Example, all invasive cleavage reactions included a mixture of 10 fmole of either the 244 bp target DNA or the synthetic linear target, 10 pmole each of a fluorescein-labeled bridge oligonucleotide and the fluorescein-labeled probe ("g" or "h" SEQ ID:60 or 61), 10 mM MOPS, 7.5 mM MgCl2, 20 ng of the 5' nuclease AfuFEN1 (i.e., a FEN1 from *Archaeoglobus fulgidus*, PCT/US97/21783, herein incorporated herein by reference), and water to a final volume of 10 μl. Reactions were assembled with all components except the enzyme and 7.5 mM $MgCl_2$, heated to 95° C. for 2 minutes. The reactions were then cooled to the indicated reaction temperatures, started with the addition of enzyme and 7.5 mM $MgCl_2$, and incubated for 1 hour. The reactions were then terminated by the addition of 10 μl of 95% formamide with 10 mM EDTA and 0.02% Methyl Violet. The products were heated at 90° C. for 1 minute, and aliquots were resolved by electrophoresis through 20% denaturing polyacrylamide gel (19:1 cross link) with 7 M urea in a buffer of 45 mM Tris-Borate, pH 8.3, 1.4 mM EDTA. The gel was visualized using the M.D. Scanner (Molecular Dynamics, Sunnyvale, Calif.).

Figure 30:
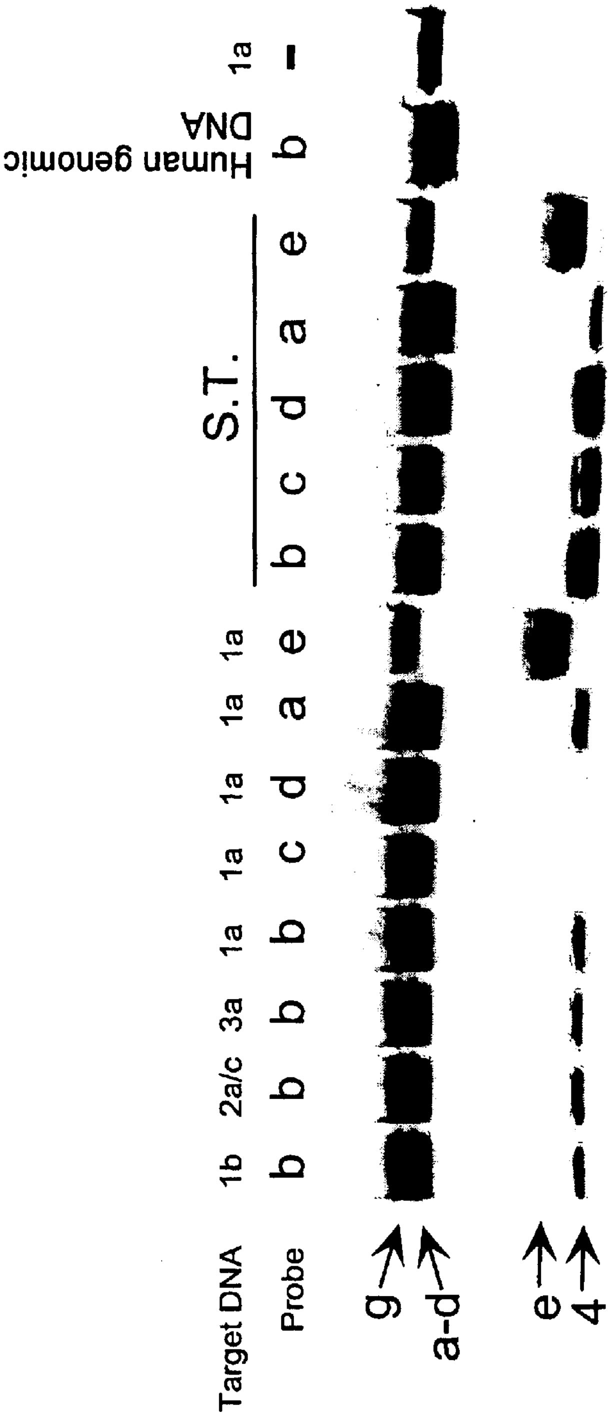
FIG. 30 shows a fluorescence imager scan of the products of invasive cleavage reactions using the probes and targets depicted in FIGS. 29A and 29B. The identities of the target DNA and probes used in each reaction (in addition to the cleavage probe "g"; SEQ ID NO:60) are indicted above each lane, and the unreacted probes are indicated by arrows and their letters on the left. An arrow indicates the 4 nucleotide (nt) product of cleavage.

The first assay tested the ability of both the HCV variants and a synthetic non-folded target to serve as a target in this assay. All reactions used the "g" signal probe (SEQ ID NO:60), and were incubated at 55° C. The resulting image is shown in FIG. 30. The type target DNA and the bridging probe used in each assay are identified above each line. In this Figure, the unreacted probes are indicated with arrows and their letters to the left of the panel, in addition, the 4-nt product of the cleavage is also indicated by arrow.

Examination of the intensity of the 4 nt band in each lane shows that on each type of folded target (1a, 1b, 2a/c and 3a) the bridging probe "b" (SEQ ID NO:53) performed nearly as well as the linear probe "a" (SEQ ID NO:52) at directing cleavage of the signal probe "g" (SEQ ID NO:60). In contrast, the bridging probes either having a mismatch in one contact sequence ("c" and "d"; SEQ ID NOS:57 and 58) or missing one contact sequence ("e"; SEQ ID NO:59) were not able to complete the cleavage structure to any significant extent. This demonstrates not only that a bridging oligonucleotide having no more than 8 bases of contiguous complementarity in any contact sequence can nonetheless specifically detect this HCV sequence, it also shows that both of the contact sequences in the probe are important to this function.

The signal generated from the non-folded synthetic target shown the maximum product yield that can be expected from these probes when essentially perfectly bound. As expected based on previous experiments conducted during the development of the present invention, the signal is stronger, although not astoundingly so. Also as expected based on previous experiments conducted during the development of the present invention, the half molecule, which does not cross a structure on the folded target, does not improve much in performance when the structure is removed, while the non bridging probe performance is decreased because has a number of mismatches to this target (See, FIG. 29B).

Figure 32:
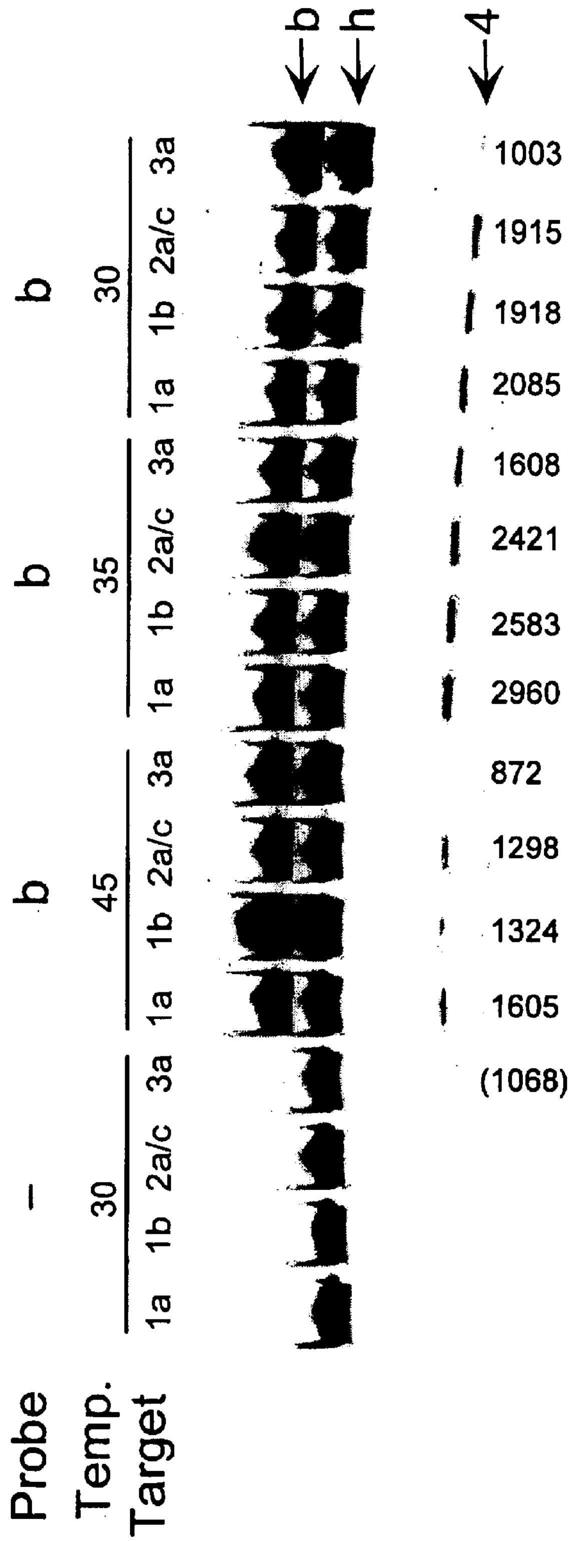
FIG. 32 shows a fluorescence imager scan of the products of invasive cleavage reactions using the probes and target depicted in FIG. 31, in reactions performed over a range of temperatures, as indicated above the lanes. The identities of the target DNA and probes used in each reaction (in addition to the cleavage probe "h"; SEQ ID NO:61) are indicted above each lane, and the unreacted probes are indicated by arrows and their letters on the right. An arrow indicates the 4 nucleotide (nt) product of cleavage.

As described above for the primer extension and ligation of the bridging oligonucleotides, at elevated temperatures the folded structures denature, reducing the binding efficiency of the bridging oligonucleotide relative to the non-bridging oligonucleotide. To examine this effect in an INVADER reaction, additional experiments were performed at a range of temperatures. Because the INVADER assay is performed near the Tm of the signal probe to allow turnover without thermal cycling, a shorter probe molecule ("h"; SEQ ID NO:61) was made for use at the lower temperatures. This is shown schematically in FIG. 31. The INVADER reactions were performed as described above, using the bridging probe "b" (SEQ ID NO:53) and the "h" signal probe (SEQ ID NO:61), with incubations done at 300, 35o and 40° C. All four HCV amplicon types were tested. The resulting image is shown in the panel of FIG. 32. The probes and targets used in each reaction, and the temperatures of the incubation are indicated above the panel. The arrow on the right indicate the unreacted probes by their letters, and the 4 nt cleavage product. The fluorescence, in arbitrary fluorescence units, measured for each of the 4 nt bands is shown below each lane; the same location in a no-probe reaction lane was counted to determine the background level (in parentheses), which was subtracted from the product count for each lane.

Examination of these data show that while the "b" (SEQ ID NO:53) bridge functions in the invasive cleavage at all temperatures, the lower temperature reactions show a greater signal differential between the HCV type 3a lane and the other types. This is consistent with the data from the capture experiments described in Examples 8 and 10, showing that the 3a type amplicon does not have the same structure in this region as the other 3 types tested. This also demonstrates that discrimination of subtle sequence differences by this method is most easily done at temperatures that encourage folding in the target molecules.

Figure 33:
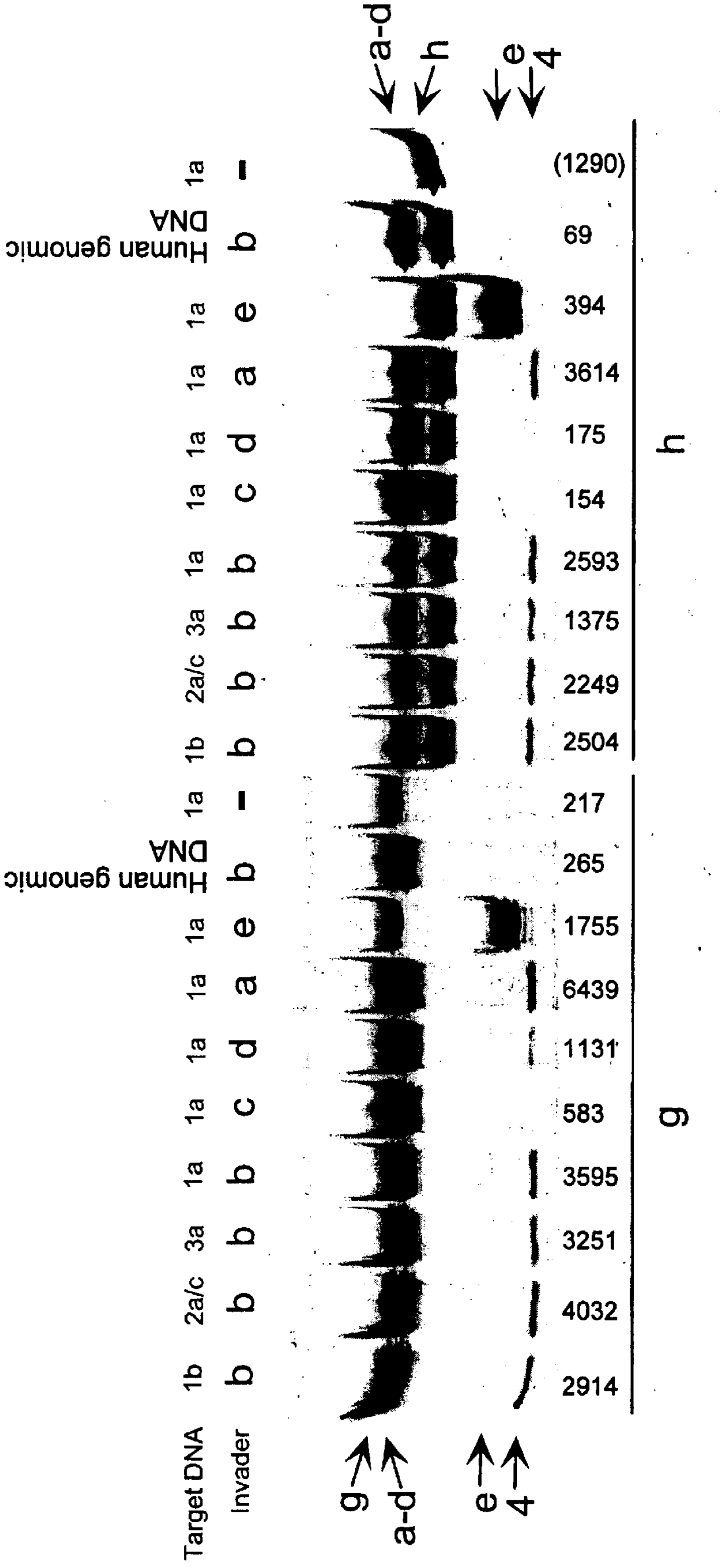
FIG. 33 shows a fluorescence imager scan of the products of invasive cleavage reactions using the probes and targets depicted in 29A and 31. The identities of the target DNA and probes used in each reaction are indicted above each lane, and the cleavage probes used ate indicated below the lanes. The unreacted probes are indicated by arrows and their letters on either side and arrows indicate the 4 nucleotide (nt) product of cleavage.

This is further supported by examination of the reactions data shown in FIG. 33. This panel compares the signals generated at two temperatures, 55° C. and 35° C., using the whole array of bridging and non-bridging probes, on a number of targets. The identities of the target DNAs and probes used in each reaction are indicted above each lane, and the cleavage probes used are indicated below the lanes. The unreacted probes are indicated by arrows and their letters on either side of the panel, and arrows indicate the 4 nucleotide (nt) product of cleavage. The fluorescence, in arbitrary fluorescence units, measured for each of the 4 nt bands is shown below each lane; the same location in a no-probe reaction lane was counted to determine the background level (in parentheses), which was subtracted from the product count for each lane.

The data shown in FIG. 33 shows the same profile of detection signal for the HCV samples as in the previous example, and further demonstrated that the mismatched bridge probes ("c" and "d"; SEQ ID NO:57 and 58) and the half probe ("e"; SEQ ID NO:59) have limited function in this assay. Similarly, the probe is not detectably cleaved when the bridging oligonucleotide is altogether omitted. Furthermore, reactions using human genomic DNA in place of the HCV target exhibit no signal that can be seen above background, demonstrating the specificity of this assay in both "stringent" and "non-stringent" conditions.

EXAMPLE 13

Structure Analysis and Bridging Probe Binding to DNA Derived from a Gene Associated with Antibiotic Resistance in *Mycobacterium tuberculosis*

In the past decade there has been a tremendous resurgence in the incidence of tuberculosis in this country and throughout the world. Worldwide, the number of new cases reported annually is forecast to increase from 7.5 million in 1990 to 10.2 million by the year 2000. An alarming feature of this resurgence in tuberculosis is the increasing numbers of patients presenting with strains of *M. tuberculosis* that are resistant to one or more anti-tuberculosis drugs (i.e., multidrug resistant tuberculosis [MDR-TB]).

Resistance to either or both of the antibiotics rifampin (rif) and isoniazid (inh) is the standard by which *M. tuberculosis* strains are judged to be multi-drug resistant. Both because of their potent bactericidal activities, and because acquisition of primary resistance to these drugs is rare (the spontaneous mutation rate of resistance to rifampin is approximately $10^{-8}$ and to isoniazid, $10^{-8}$ to $10^{-9}$), until very recently, these two antibiotics were among the most powerful front-line drugs used to combat the advance and spread of tuberculosis. However surveys of tuberculosis patients in the U.S. reveal that as many as one-third were infected with strains resistant to one or more anti-tuberculosis drugs; greater than 25% of the *M. tuberculosis* cultures isolated were resistant to isoniazid and 19% were resistant to both isoniazid and rifampin (Frieden et al., New Eng. J. Med. 328:521 [1993]). Resistance to rifampin is associated with mutation of the rpoB gene in M tuberculosis. It has been shown that key mutations in this gene can be detected and identified using the CFLP method of structure analysis, demonstrating that these mutations influence the folded conformations of these genes (Brow et al., J. Clin. Microbiol., 34:3129 [1996]; and PCT International Application No. PCT/US95/14673 [WO 96/15267]; co-pending application Ser. No. 08/484,956 and 08/520,946). We therefore chose this gene as a model to demonstrate the process of identifying non-contiguous sequences that are brought into sufficiently close proximity by strand folding for interaction with bridging probes.

The Description of the Invention outlines a step-wise procedure for analysis of a target secondary structure and for the design of bridging probes to interact with any folded nucleic acid molecule. This process comprises the steps of: a) performing CFLP analysis to identify nucleotides that are basepaired on the 5' sides of stems; b) using this partial basepair information as a "soft constraint" in a fold-prediction program such as mfold to produce schematic diagrams (or other suitable output) of possible folded conformations that are consistent with the CFLP data; c) using PCR deletion and directed mutagenesis to confirm the identities of the nucleotides on the 3' sides of stems to which the 5' side nucleotides are hydrogen bonded; d) using this full basepair information as a "hard constraint" in the fold prediction program to produce a highly refined set of predicted structures; and e) designing and testing bridging probes that interact with the predicted stems. Depending on the complexity of the data generated at each step, one or more of steps (a) through (d) may be omitted in any particular application. As noted in the Description section, a number of physical analytical methods may be combined with a number of secondary structure prediction algorithms to perform this type of analysis; the use CFLP cleavage method in conjunction with the mfold software is discussed here as a convenient example and is not presented as a limitation on the scope of the present invention.

To demonstrate the analysis on a non-viral target, DNA fragments were amplified from the rpoB gene of *M. tuberculosis*. DNA extracted from *M. tuberculosis* culture was obtained from the CDC (Center for Disease Control, Atlanta, Ga.). Genomic DNA was prepared at the CDC using siliconized glass beads as described previously (Plikaytis et al., J. Clin. Microbiol. 28:1913 [1990]). A 193-bp fragment of the rpoB gene (SEQ ID NO:69) was generated by PCR amplification of the genomic DNA sample using primers rpo 105 (forward) CGT GGA GGC GAT CAC ACC GCA GAC GT (SEQ ID NO:70) and rpo 273 (reverse) GAC CTC CAG CCC GGC ACG CTC ACG T (SEQ ID NO:71). This fragment contains the 81-bp rifampin resistance region. This amplicon was cloned using the TOPO-TA cloning kit (K4550-40, Invitrogen, Carlsbad, Calif.). A 128 bp subfragment of the rpoB gene (SEQ ID NO:72) was amplified from the resulting plasmid using a TET-labeled forward primer with the sequence 5'-CGCCGCGATCAAGGAGTTCT-3' (SEQ ID NO:73) and a reverse primer with the sequence 5'-GCTCACGTGACAGACCGCCG-3' (SEQ ID NO:74). PCR reactions were done in a final volume of 100 μl, containing: 2 ng of genomic DNA, 35 pmoles of each primer, 50 μM of each deoxyribonucleotide (Perkin Elmer, Foster City, Calif.), 1×PCR buffer (20 mM Tris-HCl pH 8.5, 50 mM KCl, 1.5 M $MgCl_2$, 0.05% Tween 20, 0.05% NP40), 1M betaine, 5% DMSO, and 2.5 units of Taq polymerase. PCR cycling conditions consisted of an initial denaturation at 95° C. for 5 minutes, 30 cycles of denaturation at 94° C. for 1 minute, annealing at 58° C. for 1 minute, and extension at 72° C. for 1 minute, with a final 7 minute extension at 72° C. Following PCR amplification, the fragments were purified by treatment with Exonuclease I (United States biochemical, Cleveland, Ohio) at 37° C. for 45 min, and followed with the High Pure PCR Product Purification Kit spin columns (Boehringer Mannheim, Indianapolis, Ind.). The purified products were quantified using the PicoGreen™ assay (Molecular Dynamics, Eugene, Oreg.) according to the manufacturers' recommended procedure. The same PCR procedure was used in the generation of the truncated and mutated amplicons described below; the forward primer was not varied, and the reverse and mismatch primers were one of the following (the primer names indicate the construct to be created): 75–121(reverse) TGACAGACCGCCGGGCCC (SEQ ID NO:75) to generate the 121 fragment (SEQ ID NO:76); 75–121(mismatch) AGACAGACCGCCGGGCCC (SEQ ID NO:77) to generate the 121 mismatch fragment (SEQ ID NO:78); 57–119(reverse) ACAGACCGCCGGGCCCCA (SEQ ID NO:79) to generate the 119 fragment (SEQ ID NO:80); 57–119(mismatch) CCAGACCGCCGGGCCCCA (SEQ ID NO:81) to generate the 119 mismatch fragment (SEQ ID NO:82); 53–118 (reverse) CAGACCGCCGGGCCCCAG (SEQ ID NO:83) to generate the 118 fragment (SEQ ID NO:84); 53–118 (mismatch) GAGACCGCCGGGCCCCAG (SEQ ID NO:85) to generate the 118 mismatch fragment (SEQ ID NO:86); 62–114(reverse) CCGCCGGGCCCCAGCGCCGA (SEQ ID NO:87) to generate the 114 fragment (SEQ ID NO:88); 62–114(mismatch) GCGCCGGGCCCCAGCGCCGA (SEQ ID NO:89) to generate the 114 mismatch fragment (SEQ ID NO:90); 63–113(mismatch) CGGCCGGGCCCCAGCGCCGA (SEQ ID NO:91) to generate the 114 mismatch(113) fragment (SEQ ID NO:92);

69–110(reverse) CGGGCCCCAGCGCCGACA (SEQ ID NO:93) to generate the 110 fragment (SEQ ID NO:94); 69–110(mismatch) AGGGCCCCAGCGCCGACA (SEQ ID NO:95) to generate the 110 mismatch fragment (SEQ ID NO:96); 78–106(reverse) CCCCAGCGCCGACAGTCG (SEQ ID NO:97) to generate the 106 fragment (SEQ ID NO:98); 78–106(mismatch) TCCCAGCGCCGACAGTCG (SEQ ID NO:99) to generate the 106 mismatch fragment (SEQ ID NO:100); 63–87(reverse) CGCTTGTGGGTCAACCCCGA (SEQ ID NO:101) to generate the 87 fragment (SEQ ID NO:102); and 63-87(mismatch) AGCTTGTGGGTCAACCCCGA (SEQ ID NO:103) to generate the 87 mismatch fragment (SEQ ID NO:104). For all rpoB capture experiments the amplicons were labeled on the sense strand with biotin instead of TET.

CFLP scanning reactions were performed using 15 ng (175 fmoles) of purified PCR product, diluted to a final volume of 15 μl with distilled water. Optimal CFLP conditions were determined as described previously. Briefly, matrices of three different reaction times (2, 4, and 6 minutes) and five temperatures (40, 45, 50, 55, and 60° C.) were examined. Conditions were chosen as optimal yielded patterns with an approximately even distribution of long and short cleavage products. The diluted amplified fragments were denatured for 15 seconds at 95° C., cooled to the reaction temperature (50° C.), and combined with 5 μl of enzyme mixture so that the final 20 μl volume contained: 25U of CLEAVASE I enzyme, 0.5 mM $MnCl_2$, 1 mM $MgCl_2$ and 1×CFLP buffer (10 mM MOPS, pH 7.5, 0.05% Tween 20, 0.05% NP40). Reactions were stopped after 4 minutes by the addition of 16 μl of stop buffer (95% formamide with 10 mM EDTA, pH 8.0 and 0.02% methyl violet). The cleavage products were resolved on a 15% denaturing PAGE (19:1 crosslink) containing 7M urea in 0.5×TBE. The resulting pattern was visualized using a Hitachi FMBIO-100 fluorescence image analyzer, equipped with a 585 nm filter.

Figure 36:
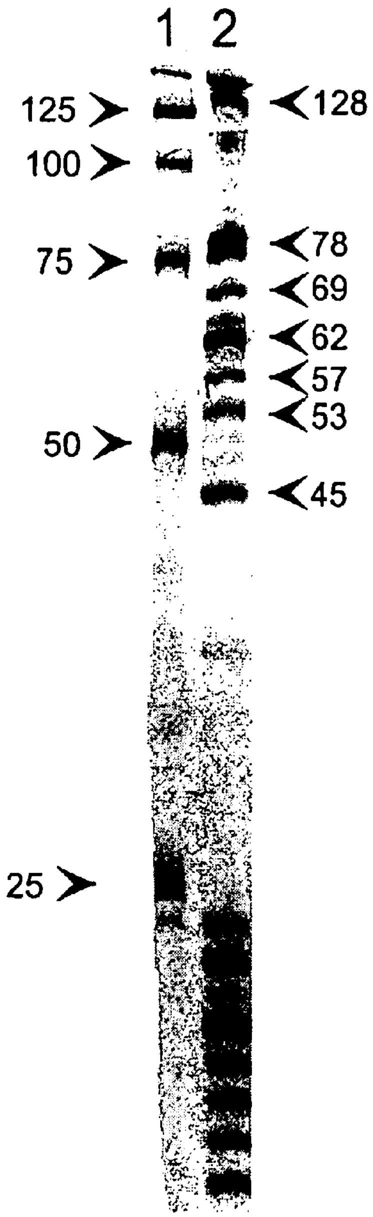
FIG. 36 shows a fluorescence imager scan of the cleavage patterns generated using the CFLP method on a 128 nucleotide fragment derived from the rpoB gene of *M. tuberculosis* (right lane). A marker having fragments of the indicated sizes (in nucleotides) is shown in the left lane and the sizes of the significant cleavage bands from the rpoB fragment are indicated to the right of the panel.

The CFLP analysis of the 128 nucleotide segment of rpoB identified key bands of 45, 53, 57, 62, 69, 75, 78, and 84 nucleotides in length, among others within the CFLP pattern, as indicated in FIG. 36. These major band positions were chosen for further analysis. As described above, the specificity of the CLEAVASE I enzyme dictates that these nucleotides are basepaired to some nucleotide downstream in the strand in the structure that is cleaved.

Structure analysis of this amplicon using the mfold 2.3 software without any added constraints from the CFLP pattern yielded only seven possible structures. Given the small number, manual analysis was sufficient to select from these 2 variants that together accounted for the major cleavage products seen in FIG. 36. The cleavage sites are indicated on structures shown in FIG. 37A (structures generated used the hard constraints from PCR walking data, described below).

The structure and cleavage analysis of the structure(s) contributing to the CFLP band at position 62 are used here to demonstrate the next steps of the process. In both of the structures shown in FIG. 37A, the C at nucleotide 62 is indicated to basepair with a G at nucleotide 114. The stem formed between these positions is the same in both structures, and is reproduced at the top of FIG. 38A. One step in confirming the interaction between these bases is to create a truncated version of this strand in which nucleotide 114 is changed to prevent pairing with nucleotide 62, and examine the resulting CFLP cleavage (this is termed "PCR walking" in this discussion). This is shown schematically as the variant number 2, the center structure at the bottom of FIG. 37B. A control molecule that is similarly truncated, but that retains the putative 62/114 base pair is shown on the left as variant 1. The CFLP patterns from these 2 molecules are shown in the gel image at the right of FIG. 37B, with an arrow indicating the band at position 62. It can be seen by the data in the first lane that the CFLP pattern gives a strong signal at position 62 in the truncated control, confirming that nucleotide 62 does not require any of the material downstream of nt 114 (deleted in this construct) to basepair. Analysis of the variant with the disrupted basepair in lane 2 shows that removal of the 62/114 basepair shifts cleavage by one position, to the 63/113 basepair. Further variation to remove the 63/113 pairing, by changing nucleotide 113 as diagrammed in variant 3 on the right, nearly eliminates this short stem region, and eliminates this particular CFLP band from the pattern altogether (lane 3; the factors contributing to the slight residual signal at this position will be discussed below). This shows how the combination of truncation and mutation combined with CFLP cleavage can be used to interrogate and confirm specific basepairs within predicted structures, thereby allowing their use as "hard constraints" in further computer-based modeling. The structures shown in FIG. 37A were generated using the hard constraints determined by such PCR walking. It is not required that further computer analysis be done before bridging probes are designed. If desired, bridge probes may be designed on the strength of the PCR walking data.

Figure 37B:
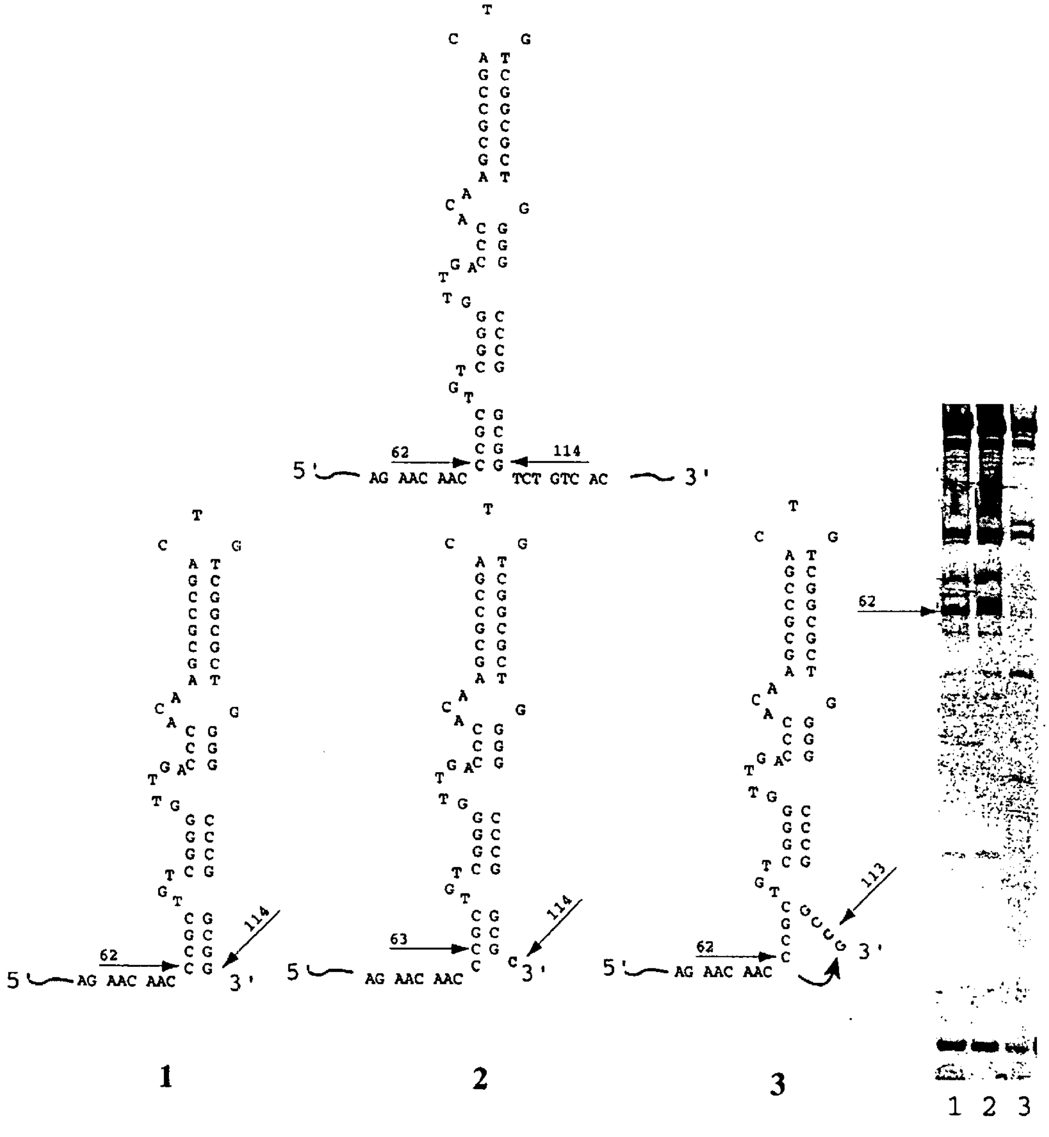
FIG. 37B shows four schematic diagrams; one is of the stem predicted to fold when nucleotide 62 of the rpoB amplicon is basepaired to nucleotide 114; three variant molecules, indicated as 1, 2, and 3, are also depicted.
Figure 38B:
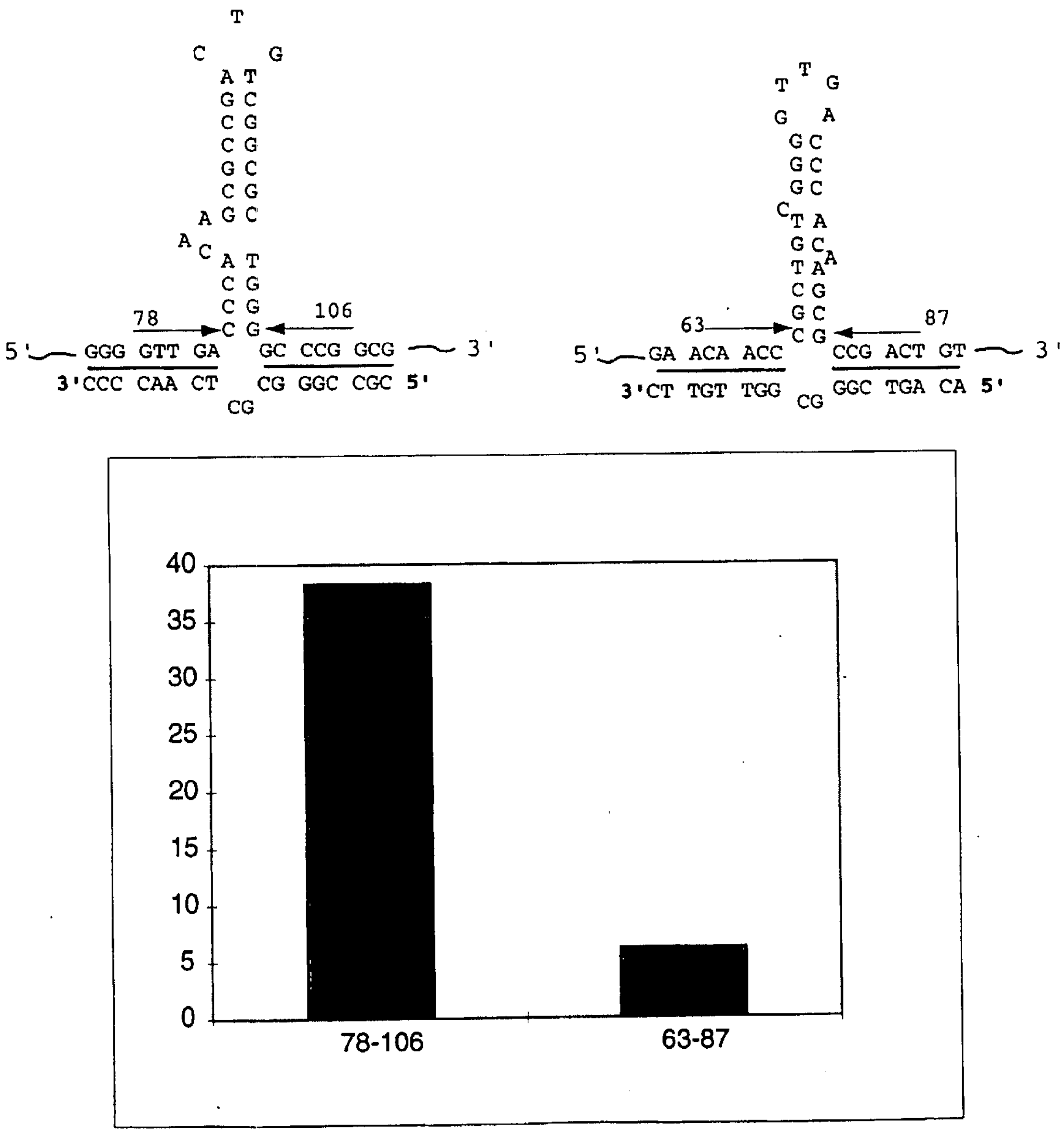
FIG. 38B shows schematic diagrams of two structured sites in the amplicon derived from the rpoB gene of *M. tuberculosis* aligned with bridging probes 78–106 and 63–87 (SEQ ID NOs:114 and 115, respectively). The regions that are complementary as aligned to the target are indicated by a black line between the strands. A graph depicts the fluorescence signal measured after the solid support capture of this amplicon by the indicated probe. The numbers identifying the probes used in each capture test are indicated below each bar, and the fluorescence signal is shown on the left of the panel as a percentage of the signal measured in experiments using a linear (non-bridging) control probe for capture of this target.

Based on the data shown in FIG. 37B, several bridging probes were designed to span the base of this stem. For all rpoB capture experiments, the amplicons were labeled on the sense strand with biotin instead of TET. In these capture analyses, the capture probes were bound to the target DNAs in solution and then the complexes were immobilized on a solid support, as described in Example 8. For each assay, a hybridization mixture was assembled containing 20 fmols of a biotin-labeled test molecule, 1.5 pmole of a fluorescein-labeled capture probe, 10 μg/ml tRNA, and 0.2% acetylated BSA, in 150 μl of 4.5×SSPE. The mixture was incubated at room temperature for 30 min.

Aliquots (100 μl) of the mixtures were then transferred to wells in a streptavidin-coated 96-well plate (Boehringer Mannheim) and incubated at room temperature for 20 min. The plate was then washed three times with TBS (25 mM Tris-Cl, 0.15 M NaCl, pH 7.2) with 0.01% TWEEN-20 non-ionic detergent. Then, 100 μl of a 1:5000 dilution of 0.75 u/ml anti-fluorescein antibody conjugated with alkaline-phosphatase in 0.2% I-block buffer (Tropix, Bedford, Mass.) was added to each well. After 20 minutes at room temperature, the plate was washed three times with TBS with 0.01% TWEEN-20. Then, 100 μl of Attophos fluorescent substrate (JBL, San Louis Obisbo, Calif.) were added to each well and the plate was incubated at 37° C. for 1 hour, before fluorescence readings were taken using a Perkin-Elmer Cytofluor-4000 set to excite at 450/50 nm and to and detect emission at 580/50 nm. Each assay was performed in duplicate with the standard deviation represented by the black bar at the top of each column in each graph.

The oligonucleotides designed to bind this stem are shown schematically in FIG. 37C, aligned with the 62/114 structure. Several different approaches were used to link the contact sequences, including direct linkage without a spacer (shown as a gap in oligonucleotide 62-114b; SEQ ID NO:105), several different dinucleotides, as shown (62-114a [SEQ ID NO:106]; 62-114c [SEQ ID NO:107]; 62-114d [SEQ ID NO:108]), or d-spacers (62-114e [SEQ ID NO:109]) (Glen Research Corp. (Sterling, Va.)), indicated as "D"s, using one D for each spacer group (i.e., DD indicates two such spacers used in sequence).

The efficacy of these probes in binding the folded target is shown graphically at the bottom of FIG. 37C. The letters below each bar indicate the identity of the space, with "NS" indicating no spacer. The capture reactions were performed as described above, and the numbers at the left of the panel indicate the fluorescence measured from the captured target DNA/probe complex, shown as a percentage of the signal measured when the same amplicons capture a linear (nonbridging) control oligonucleotide 5'-FL TCC TTG ATC GCG G-3' (SEQ ID NO:123). It can be seen from these data that a combination of CFLP, computer fold modeling, and PCR walking can be used to successfully design probes capable of binding to non-contiguous sites on the target molecule. Bridge probes having the "TT" spacer and mismatches to the target within either contact sequence, similar to those demonstrated in the bridge probes in Example 7, show very little binding to the rpoB DNA (signal equal to no-target background; data not shown), confirming that interaction of both contact sequences is necessary.

In selection of a probe to span this structure, some spacers show better performance than others. While the binding performance of the probes in FIG. 37C is well above background, it is possible that a different spacer might enhance binding without changing the contact sequences. Similarly, different spacers may perform differently in the enzymatic reactions described in Examples 9–11. If finding the optimal spacer is desired for any given application of these bridging probes, a more comprehensive comparison may be performed. For example, a simple, yet broad test would be to assess all possible dinucleotide arrangements, 16 possibilities in all, in addition to the no spacer and non-nucleotide spacer options. While other lengths of contact sequence may be used, the use of contact sequences of eight nucleotides on either side of the stem is convenient for a first test and gives a reasonable probability of success. If desired, shorter contact sequences may be tried, either in the first test or after an optimal spacer arrangement has been identified. Given the ease and low cost of current methods of automated oligonucleotide synthesis, the creation of this number of test probes would not be burdensome.

Figure 38C:
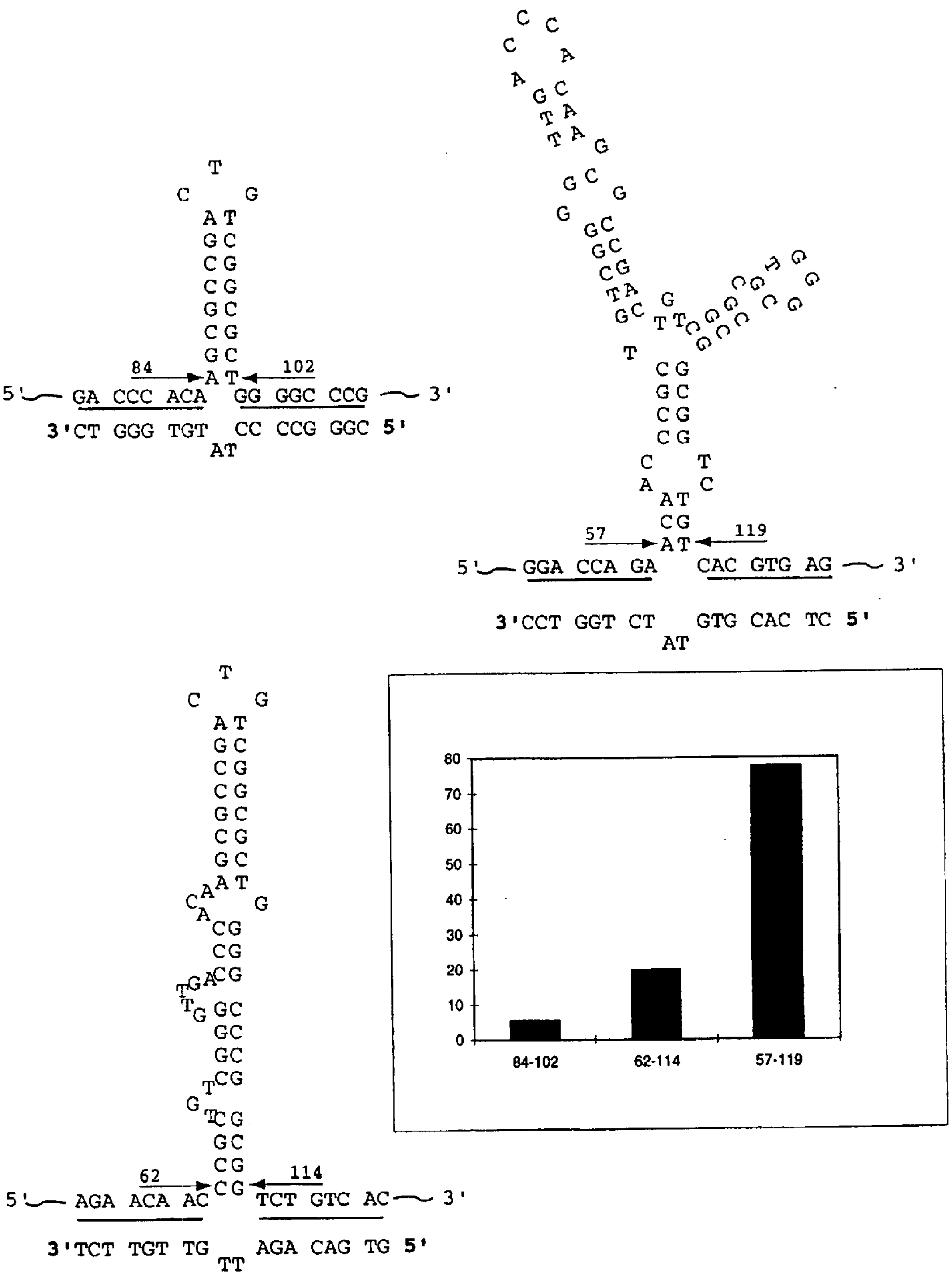
FIG. 38C shows schematic diagrams of three structured sites in the amplicon derived from the rpoB gene of *M. tuberculosis* aligned with bridging probes 84–102, 57–119 or 84–102 (SEQ ID NOs:116, 117, and 118, respectively). The regions that are complementary as aligned to the target are indicated by a black line between the strands. A graph depicts the fluorescence signal measured after the solid support capture of this amplicon by the indicated probe. The numbers identifying the probes used in each capture test are indicated below each bar, and the fluorescence signal is shown on the left of the panel as a percentage of the signal measured in experiments using a linear (non-bridging) control probe for capture of this target.

Similar approaches were used in the design of bridging probes to other predicted structures within the rpoB amplicon. Some of these structures are shown schematically in FIGS. 38A, 38B, and 38C. For comparison, the 62-114 structure with oligonucleotide 62-114 (a) (SEQ ID NO:106) is reproduced in FIG. 38C. In each of these figures the base pair analyzed by CFLP, PCR walking, and folding predictions is at the base of the depicted stem, and the nucleotide positions measured from the 5' end of the DNA fragment are indicated by arrows. The corresponding bridging probes (53-118(cg) [SEQ ID NO:110]; 69-110(cg) [SEQ ID NO:111]; 75-121(a)(ta) [SEQ ID NO:112]; 75-121(b)(ta) [SEQ ID NO:113]; 78-106(cg) [SEQ ID NO:114]; 63-87(gc) [SEQ ID NO:115]; 84-102(at) [SEQ ID NO:116]; 57-119(at) [SEQ ID NO:117]; 62-113 [SEQ ID NO:118]; and 62-98 [SEQ ID NO:119]) are identified by these same basepair numbers (e.g, the probe designed to span the basepair formed between nucleotides 75 and 121 is termed 75-121). If two probes were targeted to the same basepair the probes are further distinguished by lower case letters (e.g., 75-121 (a) and 75-121(b)). In the case of the 75-121 probes, the target material did not have a full 8 nucleotides 3' of the base of the structure, so a bridging probe having only 7 nucleotides at this position was created (75-121 (a); SEQ ID NO: 112). Because PCR products may include a non-templated "A" nucleotide at the 3' ends (shown in parentheses), a bridging probe have an extra "T" nucleotide was created. The presence of this basepair would extend this contact sequence duplex to 8 nucleotides. All probes were designed with two 8 nucleotide contact sequences (complementary to the target) flanking a 2 nucleotide spacer. Each of these three figures includes a graph of the fluorescence signal measured after the solid support capture of each amplicon by the indicated probe. The numbers identifying the probes used in each capture test are indicated below each bar. The signal is shown as a percentage of the signal detected by binding of a linear (non-bridging) fully complementary probe. While some of these probes have poor binding properties (i.e., less than about 5% of the signal from the linear control oligonucleotide), these data further demonstrate the efficacy of this method at identifying non-contiguous target sequences that can be bound by a single bridging probe.

Figure 39:
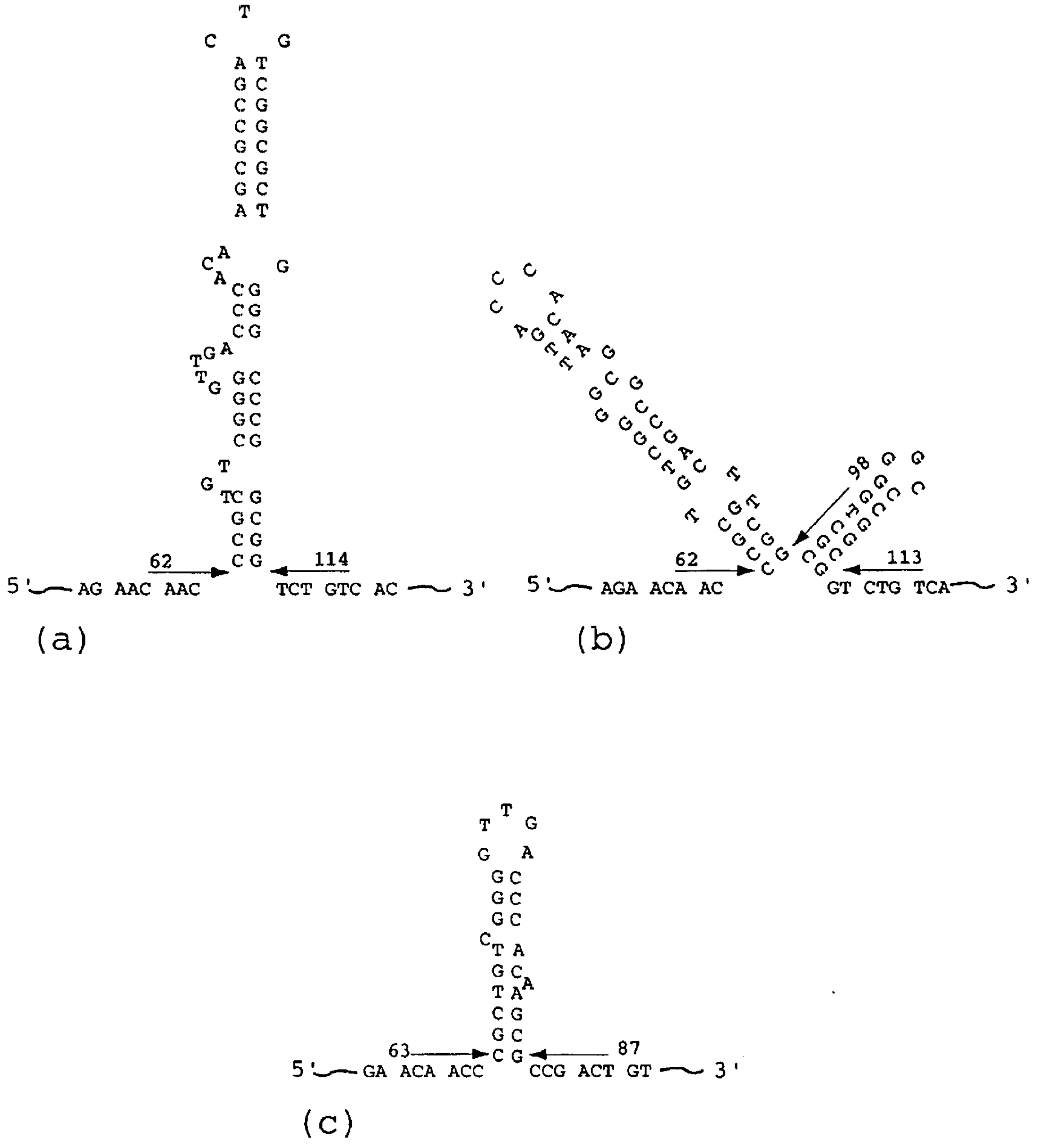
FIG. 39 shows schematic diagrams of three possible structures ("a", "b", and "c") formed by the amplicon derived from the rpoB gene of *M tuberculosis*. Each of these three structures could cause CFLP cleavage 62 to 63 nucleotides from the 5' end of this fragment, contributing signal in this region of the CFLP gel pattern.

As noted above, it is possible for several different structural conformers to contribute a single band in a CFLP cleavage pattern. This means that the nucleotide upstream of the cleavage site can pair with several different downstream nucleotides at different times, or on different copies of the nucleic acid molecule in a population. Recalling PCR walking data from the investigation of the pairing partners for nucleotide 62 and 63 in the rpoB amplicon, shown in FIG. 37B, it was seen that there was residual cleavage at position 62 even when the preferred structure was disrupted by deletion and mutation in the amplicon. This indicates that there might be other, less favored folded conformations contributing to cleavage at this site. One way of looking for such alternative conformations is to carefully examine the less energetically favored structures predicted by a program such as mfold. Such analysis was done to identify other regions to which nucleotides 62 and 63 might pair. The primary 62/114 structure and two less favorable variants are shown schematically in FIG. 39. Bridging probes were designed to test the for the presence of each of these variant structures. These are shown schematically in FIGS. 40–42.

It was recognized that representation of these alternative structures in the molecule populations, as measured by bridge probe binding, was likely to be influenced by the length of the target molecule by any one of a number of mechanisms, including but not limited to the following: longer molecules may have a more diverse population of possible structures, making any one sub-optimal structure a lower percentage of the signal; the additional sequences present may provide regions of complementarity that compete with the some portion of the less favored structure, thereby reducing its presence in the population; additional sequences may form additional stems that do not interact directly with the less favored structure, but that nonetheless inhibit probe binding by steric or other interactions. To investigate this effect the bridges designed to bind to the structures depicted in FIG. 39 were tested using target molecules of several lengths. The full length (i.e., the 128-mer) amplicon (SEQ ID NO:72) allows the most favored structure shown in FIG. 39(*a*) to form, and allows a full 8 nucleotides of contact with probe 62-114 on either side of the structure. Deletion of the target to 121 nucleotides SEQ ID NO:76) reduces the downstream contact of the 62-114 probe to 7 nucleotides, vet allows a full 8 nucleotides of hybridization for the 62-113 probe designed to bind to variant 39(*b*). Binding of a probe to this structure would create a four way "Holliday" junction. Even though nucleotides 62 and 113 are not basepaired in this structure, this nomenclature is used for the probes oligonucleotide to reflect the positions of the contact sequences within the target strand. To explore even less favored structures, the target was further truncated to 113 nucleotides, eliminating regions complementary to both the 62-114 and 62-113 probes. The substitution of a C for the wild-type G at position 113 ("113 MM", SEQ ID NO:92) causes mismatches in the basepairing of nucleotide 113 in both strictures 39(*a*) and 39(*b*), although with different putative pairing partners.

Figure 41:
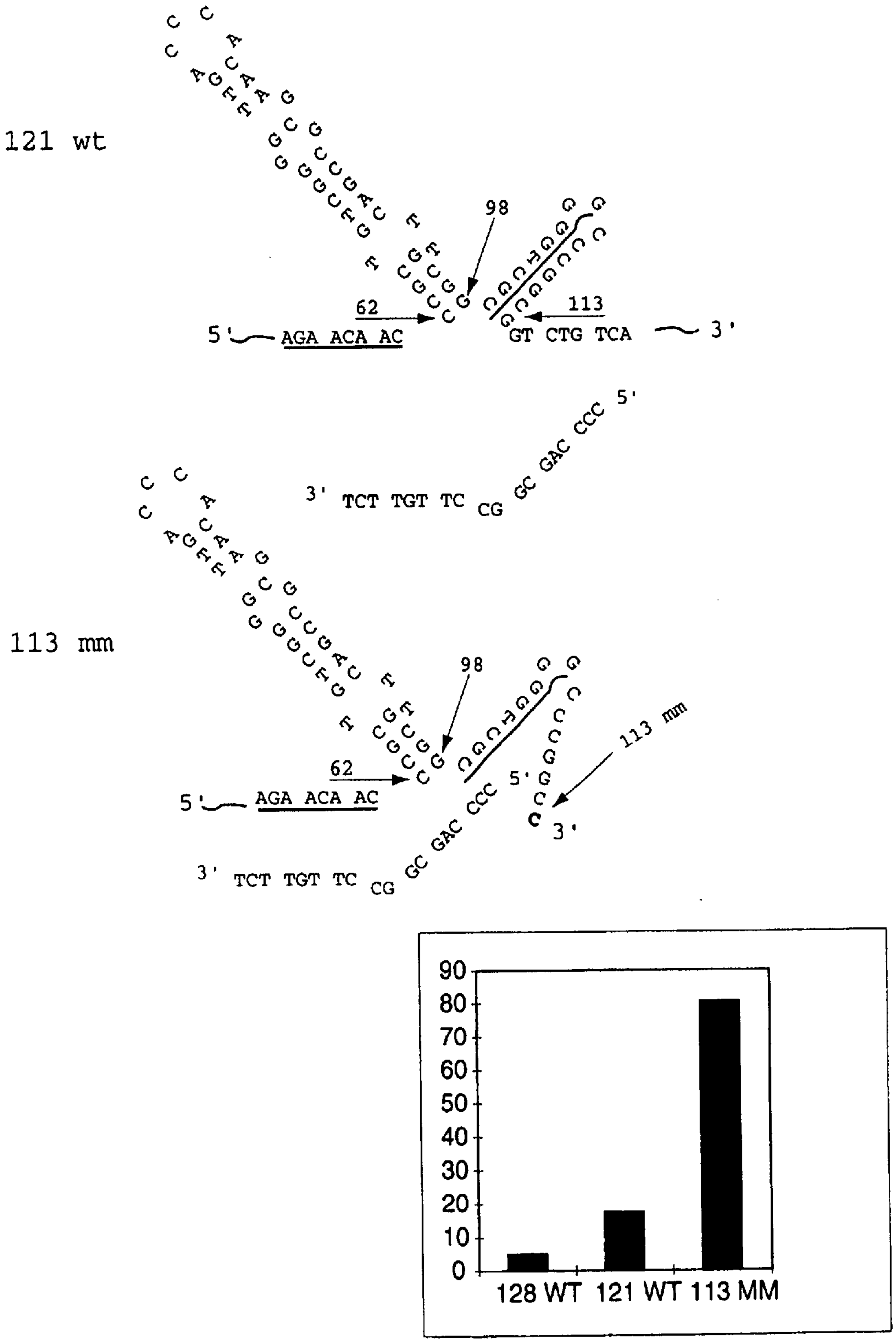
FIG. 41 shows schematic diagrams of structure "b" from FIG. 39, either unaltered, or truncated and mutated to destabilize the shorter stem. Also depicted is bridging probe 62–98 (SEQ ID NO:119), designed to hybridize across the longer remaining stem, and a graph depicting the fluorescence signal measured after the solid support capture of the shortened amplicon by the indicated probe. The fluorescence signal is shown on the left of the panel as a percentage of the signal measured in experiments using a linear (non-bridging) control probe for capture of this target.

Each of FIGS. 40, 41, and 42 includes a graph of the fluorescence signal measured after the solid support capture of each amplicon by the indicated probe. The numbers identifying the version of the target molecule used in each capture test are indicated below each bar. The signal is shown as a percentage of the signal detected by binding of a linear (non-bridging) fully complementary probe.

The capture data in FIG. 4 suggests that a structure bridging probe can be made 10) to cross the base of a sequence capable of forming 2 hairpins. The increase in signal observed when the 121 nucleotide amplicon is targeted suggests that this truncation increases the percentage of the population that is adopting this conformation. The shorted variant, 113 MM, was not tested with this probe because one of the two contact sites on the target is deleted in this variant, so binding would not be expected.

A bridging probe designed to cross only one of the two stems of conformation 39(*b*) was also designed (62-98, SEQ ID NO:119), and is shown schematically in FIG. 41. With this probe the presence of the second, shorter stem in this conformation would be expected to weaken or block binding. The target variant having the "C" nucleotide at position 113 would have a less stable, shorter stem and would be expected to show more binding to this probe. The capture data with this probe demonstrates that the majority of the full length amplicon assumes a structure that does not allow binding of this probe. When the target is shortened to 121, more of the molecules fold, such that these binding sequences are accessible. Finally, when the molecule is shortened to 113 nucleotides and the alternative conformations are destabilized, the binding signal from the 62-98 bridging probe is over 80% of the signal from the non-bridging control, verifying that the percentage of the molecular population adopting this previously sub-optimal conformation has dramatically increased.

Another sub-optimal conformer is predicted in addition to that depicted in FIG. 41 This other variant is shown schematically in FIG. 42, and predicts basepairing between nucleotide 63 and nucleotide 87. Binding of the 63-87 probe (SEQ ID NO: 115) follows a profile similar to that observed with the 62-98 probe; this structure does not appear to form in a significant population of either the 128-mer or 121-mer target molecules When the target is both shortened, and the 113 "C" mutation is added, the binding at this site is markedly increased, yielding a signal about 13% of that from the non-bridging control. It is not surprising that it does not increase to the same extent as the 62-98 structure, because it represents an alternative conformer of the same molecule (the 113 MM target) and, absent any conformational shift actually promoted by the binding of the probe, the presence of the 62-98 structure would block binding of this probe.

These data clearly show that distal sequences can have an effect on local structures, which is consistent with earlier observations (Brow, et al. supra). The structure analysis method of the present invention provides a way of clearly identifying the regions of structural interaction. However, it is envisioned that this method has utility beyond the design and optimization of bridging probes. This type of structure analysis can also be used to improve the performance of other analysis methods based on structure. For example, some regions of genes are refractory to CFLP and/or SSCP analysis because the mutations do not detectably alter the conformations of the folded target nucleic acids In other applications a sites on a molecule that would be useful for hybridization (e.g., for detection, analysis, or antisense purposes) might be inaccessible due to strand folding. The knowledge gained in using the structure analysis method described herein allows selection of target materials or sites more amenable to these methods. For example, PCR primers used to generate the materials for the CFLP and SSCP analysis may be relocated to eliminate undesirable structural interactions, or they may include mutations or extra sequences chosen to specifically alter the folding behavior of the material. PCR primers might include a region of complementarity to a selected part of the resulting amplicon strand, the sequestration of which would cause a site of interest to be disposed in a more desirable conformation (i.e., more revealing of mutation or polymorphism, or more accessible to hybridization for other purposes). In another embodiment, undesirable structures may be disrupted by the provision of an additional hybridization probe. Clearly, such disrupting probes need not interact directly with, or adjacent to the site of interest; it is envisioned that binding of such disrupting probes may be at a far removed location from the site of interest. The only requirement is that the binding of the probe cause a favorable change in the conformation assumed by the nucleic acid of interest. Such effect may be fairly direct (e.g., by direct blocking of the formation of an undesirable structure) or may be indirect (e.g., by precipitating a chain of conformational shifts that ultimately result in the elimination of an undesirable structure). This latter embodiment, in which the disrupter sequence is not made to be a part of the same strand as the sequence of interest, would have particular application in antisense applications in vivo.

EXAMPLE 14

Bridging Oligonucleotides

Figure 43A:
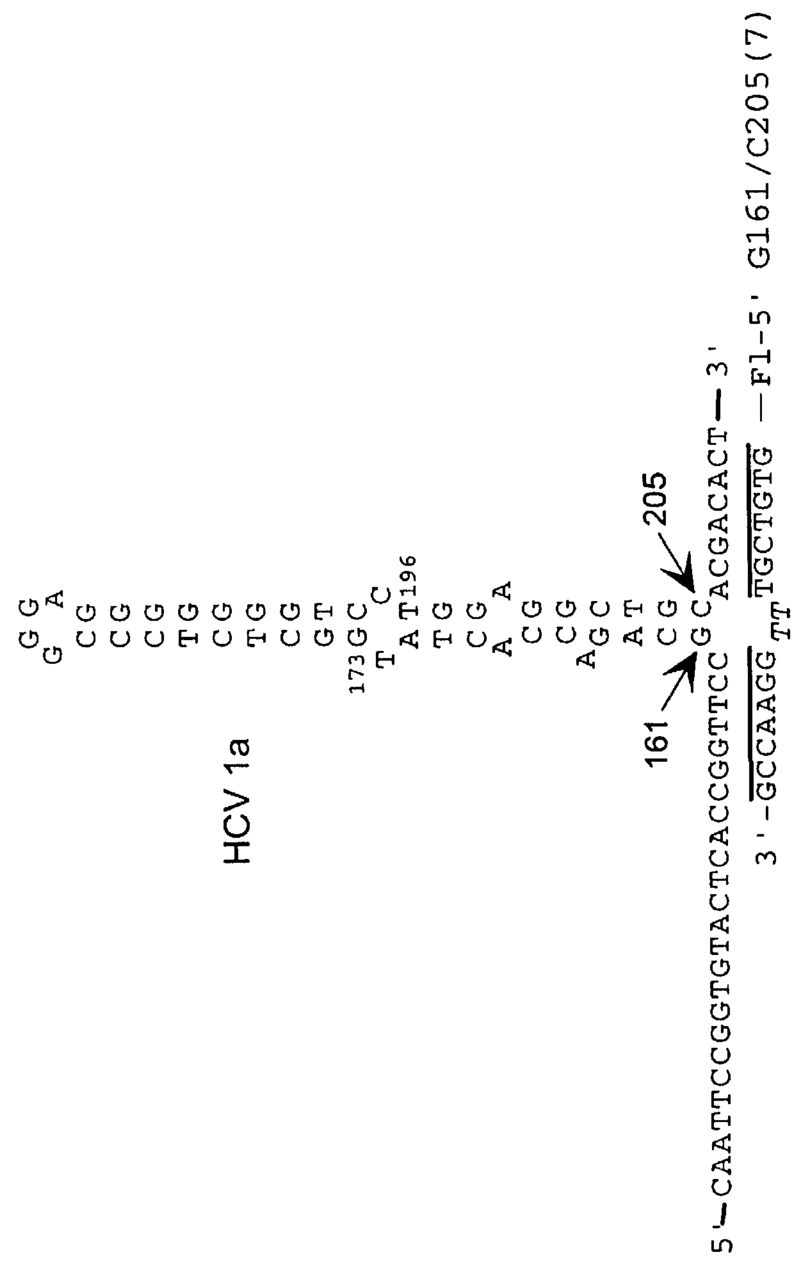
FIG. 43A shows a schematic diagram of a structure in the amplicon derived from HCV type 1a aligned with bridging probe having two seven-nucleotide regions of complementarity (SEQ ID NO:120). The regions that are complementary as aligned to the target are indicated by a black line between the strands.
Figure 43B:
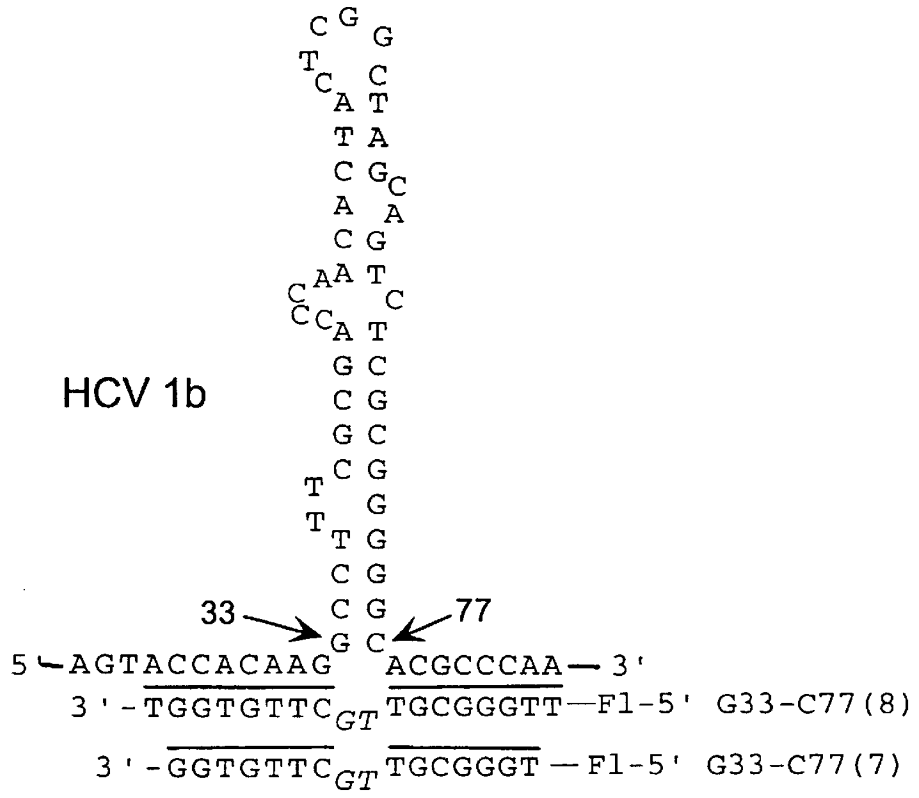
FIG. 43B shows a schematic diagram of a structure in the amplicon derived from HCV type 1b aligned with bridging probe having two 7 or 8 nucleotide regions of complementarity (SEQ ID NOS:121 and 122, respectively). The regions that are complementary as aligned to the target are indicated by a black line between the strands.

Using the structure analysis methods described above, new bridging oligonucleotides were designed for the target HCV 244 bp DNA, which is the same target used before. One set of probes was designed to span a structure predicted to form with a base pair between 161 and 205 (FIG. 43A), while the other was designed to span a newly identified structure formed with the base pair between 33 and 77 (FIG. 43B).

Three bridging oligonucleotides, shown as G161/C205 (7), G33/C77 (7) and G33/C77 (8) (SEQ ID NOS:120,121, and 122, respectively), were used, and these had 7 or 8 nucleotides of complementarity, respectively, to each side of hairpins formed in the HCV targets, subtypes 1a, 1b, 2a/c, and 3a (SEQ ID NOS:26–29). They were synthetically labeled with fluorescein at their 5' ends and purified by gel-electrophoresis. A hybridization mixture was assembled containing 10–20 fmols of a biotin-labeled test HCV amplicon, (prepared as described in Example 3, but using the biotinylated primer described in Example 8) 1.5 pmole of one of the fluorescein-labeled capture probes, 0.01 mg/ml tRNA and 0.2% acetylated BSA, in 150 μl of 4.5×SSPE. The mixture was incubated at room temperature for 30 minutes.

Figure 44A:
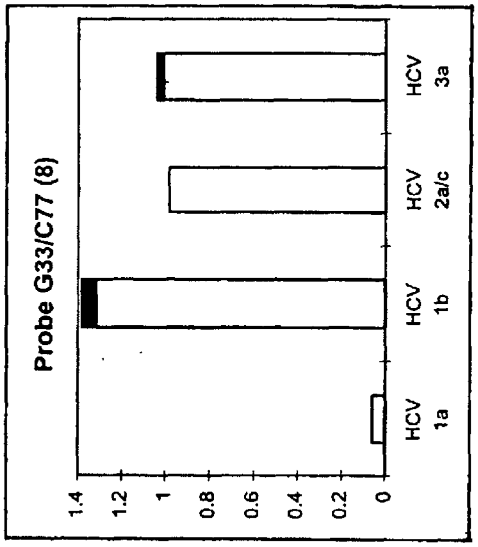
FIG. 44A shows a graph depicting the fluorescence signal measured after the solid support capture of the amplicons derived from HCV types 1a, 1b, 2a/c and 3a by the indicated probe. The amplicons used in each capture test are indicated below each bar. The fluorescence signal is shown on the left of the panel as a percentage of the signal measured in experiments using a linear (non-bridging) control probe for capture of this target, with 1 being 100 percent.

Aliquots (100 μl) of the mixtures were then transferred to wells in a streptavidin-coated 96-well plate (Boehringer Mannheim) and incubated at room temperature for 20 minutes. The plate was then washed three times with TBS (25 mM Tris-Cl, 0.15 M NaCl, pH 7.2) with 0.01% TWEEN-20 non-ionic detergent. Then, 100 µl of a 1:5000 dilution of 0.75 u/ml anti-fluorescein antibody conjugated with alkaline-phosphatase in 0.2% I-block buffer (Tropix, Bedford, Mass.) was added to each well. After 20 minutes at room temperature, the plate was washed three times with TBS with 0.01% TWEEN-20. Then, 100 µl of Attophos fluorescent substrate (JBL, San Louis Obisbo, Calif.) were added to each well and the plate was incubated at 37° C. for 1 hour, before fluorescence readings were taken using a Perkin-Elmer Cytofluor4000 set to excite at 450/50 nm and to and detect emission at 580/50 nm. Each assay was performed in duplicate with the standard deviation represented by the black bar at the top of each column in the FIGS. 44A and 44B, the fluorescence intensity is indicated in arbitrary fluorescence units.

Figure 44B:
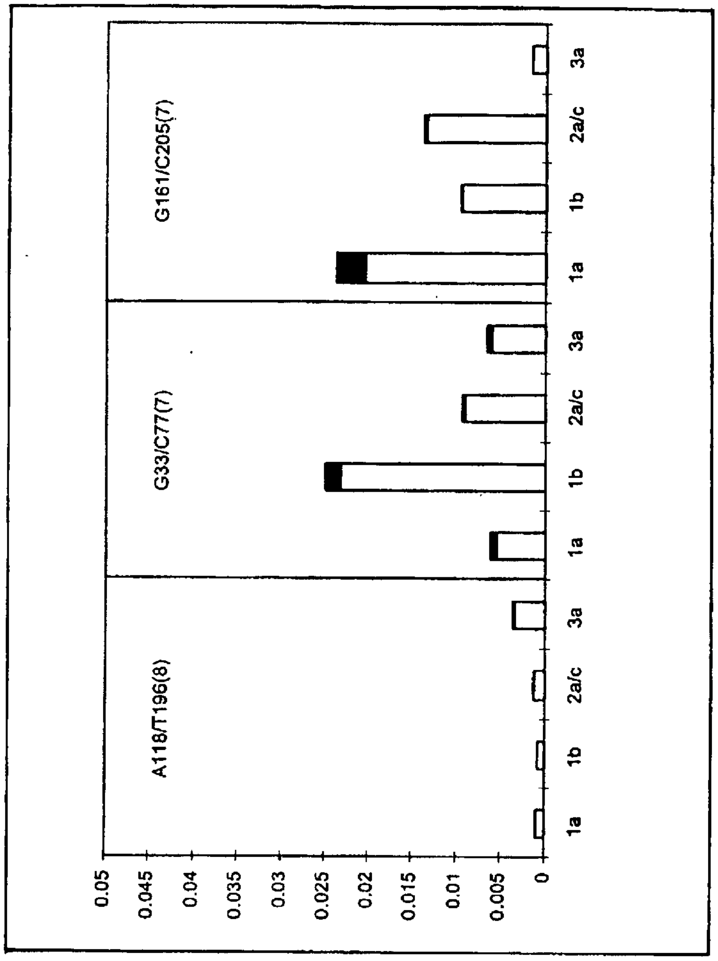
FIG. 44B shows a graph depicting the fluorescence signal measured after the solid support capture of the amplicons derived from HCV types 1a, 1b, 2a/c and 3a by the probes indicated at the top of each panel. The amplicons used in each capture test are indicated below each bar. The fluorescence signal is shown on the left of the panel as a percentage of the signal measured in experiments using a linear (non-bridging) control probe for capture of this target, with 1 being 100 percent.

These data show that the use of shorter contact sequences can enhance the discriminating power of the structure probing of variants using bridge probes. The data from capture by the G33/C77 (8) probe (SEQ ID NO:122), shown in FIG. 44A, can be compared to the center panel of FIG. 44B, which shows the signals from the G33/C77 (7) probe (SEQ ID NO:121). The latter probe binds the same structure as the former, but has only 7 nt of complementarity on either side of the spacer. Even though the total fluorescence signal is reduced, the use of shorter probe results in a greater difference in signal between the different HCV genotypes, allowing more accurate identification of these types. Similarly, the use of the G161/C205 (7) probe (SEQ ID NO:120), which is similar to probe "b" (SEQ ID NO:53) described in Example 8 but is one nt shorter on either terminus, shows the same effect. Examination of the binding of "b" to the same four types of HCV, shown in FIGS. 19 and 25 demonstrates that types 1a, 1b and 2a/c produce similar amounts of signal compared to the non-bridging control shown in each panel; 3a does not efficiently bind probe "b". In comparison, the capture signals from the shorter probe G161 !C205 (7), shown in the right hand panel of FIG. 44B show much greater discrimination between the 1a, 1b and 2a/c normalized signals, each being distinct from the others. These data demonstrate that the use of probes having shorter contact sequences can allow more sensitive distinction between the structures assumed by closely related nucleic acid molecules (i.e., those differing in sequence by only one or a few nucleotides).

It is also clear from the above that the present invention provides methods for the analysis of secondary structure within nucleic acids, without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within genes obtained from various organisms, including humans.

EXAMPLE 15

Determining Extendible Sites from RT Extension Products

A. Reverse Transcription and PCR; Deoxyoligonucleotide Synthesis and Purification Deoxyoligonucleotides were synthesized on solid support using standard phosphoramidites chemistry on an Expedite 8909 (PE Biosystems) synthesizer. Equal amounts of amidites were mixed and used for synthesis of degenerate bases. For fluorescently labeled oligonucleotide, the fluorescent label tetracholorofluorecsein (TET) was added to the 5'-end of the oligonucleotides as a phosphoramidite (Glen Research).

After completion of the synthesis, oligonucleotides were deblocked and deprotected by treatment with concentrated ammonia at 60° C. for 5 hrs. Oligonucleotides were further purified by electrophoresis on a 20% denaturing polyacrylamide gel (19:1) in a buffer of 7M urea, 45 mM Tris-borate, pH 8.3, 1.4 mM EDTA. After excision of the major band, the DNA was eluted in 0.5 M ammonium acetate, 10 mM Mg acetate, 0.1% SDS at 37° C. overnight. Oligonucleotides were then desalted using NAP-10 size exclusion column (Amersham-Pharmacia Biotech) and UV absorption at 260 nm was used to determine their final concentrations.

B. RNA Synthesis cDNA clones used in this study were generated using standard RT-PCR methods with Access RNA kit (Promega Corp., Madison, Wis.) on total RNA isolated from human T cells. cDNAs were then cloned into pGEM-T easy vectors (Promega Corp., Madison, Wis.), transformed into *E. coli* TOP10A (Invitrogen, Carlsbad, Calif.) cells. Plasmid DNA was Isolated from transformed colonies using standard procedures and the sequence of the cDNA inserts was confirmed by sequencing on a 377 ABI Prism sequencer. Transcription was used to prepare all RNA used in this study using T7-MEGAshortscript transcription kit (Ambion) following the vendors recommended procedure. T7 promoter sequence was added to the sense strand primer of the PCR reaction to generate DNA transcription templates from plasmid DNA containing cDNA inserts.

After completion of the transcription reactions, transcription templates were removed from RNA transcripts by addition of DNase I. RNA transcripts were further purified on 8% denaturing PAGE and visualized by UV shadowing, excised, and eluted in 0.5 M ammonium acetate, 10 mM Magnesium acetate, 0.1% SDS at 37° C. overnight. RNA transcripts were finally desalted by ethanol precipitation.

Unless otherwise indicated, Moloney-Murine Leukemia virus (MMLV) reverse transcriptase (Promega Corp., Madison, Wis.) was used for all RT experiments (100 units/reaction). RT reactions were performed in 20 µL volumes with the final pre-hybridized oligomer-RNA mixtures diluted in a 1:10 ratio resulting in buffer concentrations of 10 mM Tris-HCl, 50 mM KCl, 1.5 mM $MgCl_2$, 0.5 mM and 0.25 mM concentrations of deoxynucleotide triphosphates (Promega Corp., Madison, Wis.) were used for RT and PCR reactions, respectively. Reverse transcription was performed for 30–60 minutes at 42° C. followed by a heating step to 92° C. for 10 minutes and a cool down to 4° C. Taq DNA polymerase (PE Biosystems, Foster City, Calif.) (5 units/reaction) was used for PCR amplification of the RT products in a reaction buffer containing 10 mM Tris-HCl, 50 mM KCl, and 1.5 mM $MgCl_2$ using 30 cycles with a denaturing temperature of 95° C. for 45 seconds, an annealing temperature of 50° C. for 45 seconds, and an extension temperature of 72° C. for 2 minutes. Sense-strand primers used for PCR amplifications were target cDNA specific designed to have a melting temperature of approximately 50° C. (Allawi and SantaLucia, Biochemistry 36:10581 [1997]). Antisense-strand primers were 5'-tag specific (see above) and had the following sequences: 5'-CTTAAGGTAGGACTAC-3' (SEQ ID NO:124) for Tag-A and 5'-CATTTTCCAACCTTAA-3' (SEQ ID NO:125) for Tag-B. 0.5 µM final concentration of 5'-TET labeled sense strand primers and tag specific antisense primers were used. RT-PCR products were loaded on a 6% denaturing PAGE (19:1) and scanned and analyzed on an FMBIO-100 fluorescent gel scanner (Hitachi) using a 585 nm emission filter. For RT reactions containing 2'-O-methylated antitags, 2.5 µM final concentrations of oligonucleotides with same sequences as the anti-sense PCR primers for each 5'-tag were added to the degenerate oligomers-RNA mixtures prior to the RT reactions.

C. Sequencing Reactions

Figure 46:
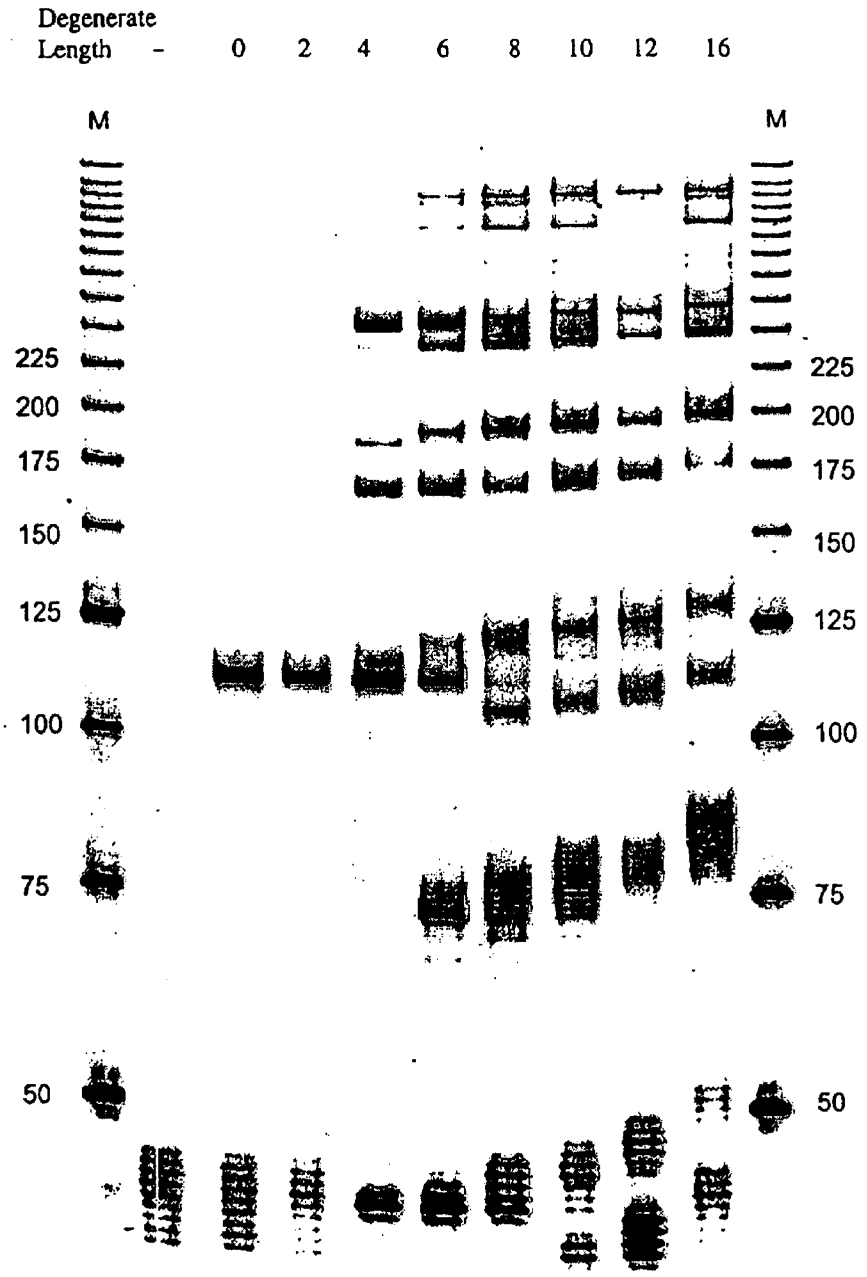
FIG. 46 shows an analysis of the effect of 3'-degenerate nucleotide length, from 0 to 16 nt, on primer extension using human interferon (HFE)-γ mRNA as a template.

Thermosequenase sequencing kit (Amersham Pharmacia Biotech) was used for sequencing reactions. Approximately 250–500 ng of cDNA and one unit of Thermosequenase in a buffer containing 65 mM Tris-HCl, 1 mM $MgCl_2$ were used for sequencing reactions. Four reactions with 0.25 μM 5'-TET labeled sequencing primers (for FIG. 47, ladder primer SEQ ID NO:140 was used) and 75 and 7.5 mM of each of the four dNTP and ddNTP, respectively were cycled 70 times using a denaturing step at 95° C. for 30 seconds, an annealing step at 50° C. for 30 seconds, and an extension at 72° C. for 2 minute. Sequencing products were then loaded on a 8% denaturing PAGE (19:1) and scanned and analyzed as described above. FIG. 46 shows PCR-amplified extension products obtained for human interferon-γ mRNA (hIFN-γ) (SEQ ID NO:141) using RT with oligonucleotides having degenerate portions ranging in lengths from 0 to 16 (SEQ ID NOs:126–133), each linked to a 16 nucleotide 5'-tag (in combination with primer SEQ ID NO:140). Close examination of FIG. 46 reveals several features. It is observed that when the degenerate oligonucleotide length is below six, fewer RT products are present, and those that arise do not correlate with the products arising from reactions using primers with longer degenerate regions. When the length of the degenerate oligonucleotides is above 6 nucleotides, a clear pattern is observed, which is maintained when longer regions of degeneracy are used.

It is also noticeable that the RT products become longer by the length difference between each degenerate oligonucleotide used. In other words, adding two nucleotides to the primer length produces an RT product that is, on average, two nucleotides longer. This indicates that the 3' ends of each degenerate oligonucleotide are hybridizing to the same accessible sites on the RNA, and the added bases in the primer are added to the length of the final amplicon. The fact that consistent RT product bands are observed for degenerate oligomers of larger than six residues suggests a minimum of about six base pairs of primer/RNA target heteroduplex are needed for stability and perhaps for reverse transcriptase recognition.

Figure 47:
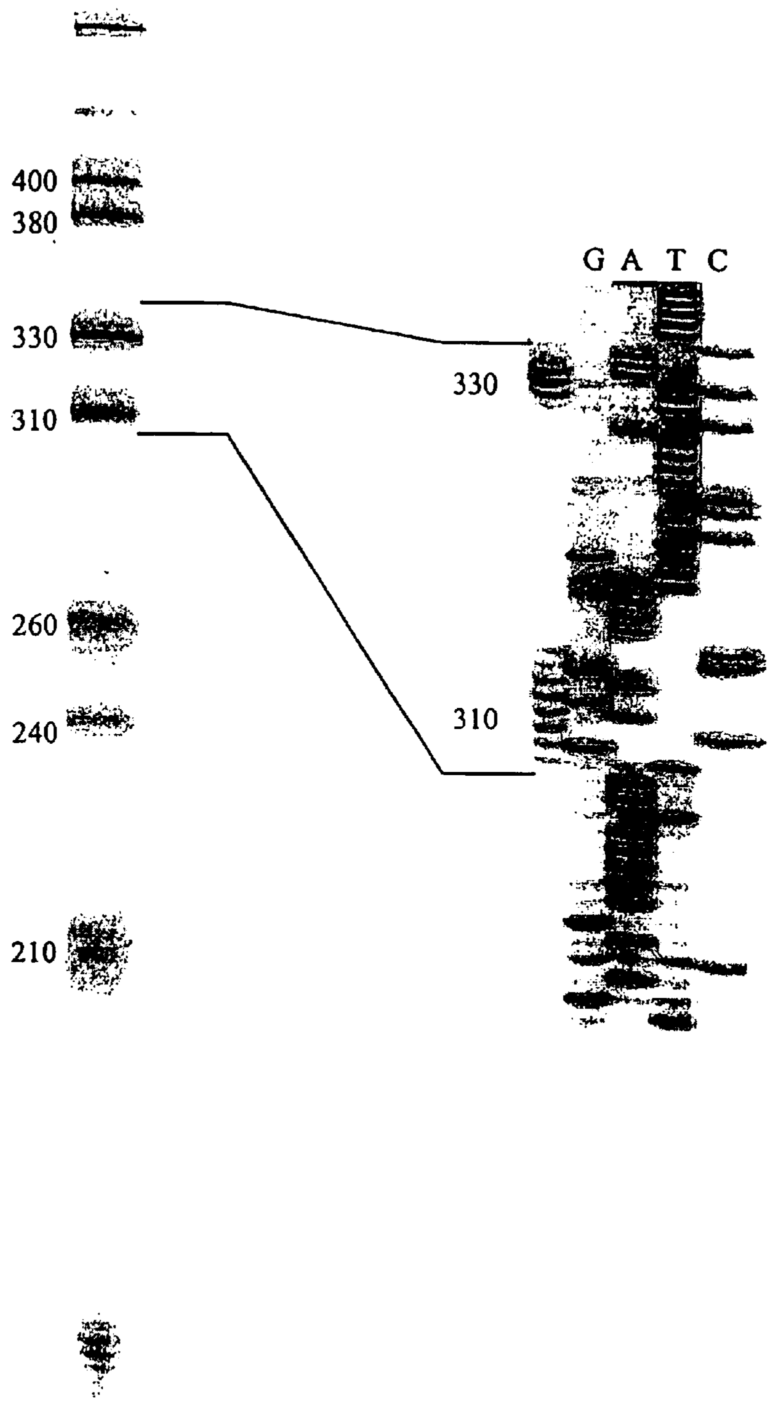
FIG. 47 shows mapping analysis of the products of the degenerate-primer RT-PCR by comparison of the position to a sequencing ladder.

To map the position at which the 3'-end of the degenerate primer bound and extended on the target RNA, a sequencing ladder was used. It can be presumed that each product band on the gel (FIG. 46) corresponds to an RT product resulting from a degenerate primer binding and extending at an accessible region of the RNA. FIG. 47 shows an example of how a sequencing ladder was used to map the positions of two RT products of the hIFN-γ. To do so, the RT product band(s) are simply aligned with the sequencing ladder and the sequence is read. This sequence is assumed to correspond to the fragment size of the RT-PCR product, the length of which is a sum of the lengths of the 5'-tag, the degenerate regions, and the distance between the binding site and the 5' end of the transcript. Thus to determine the position where the 3'-end of the degenerate primer bound the RNA and extended, the length of the tag and the degenerate oligonucleotide are subtracted from the corresponding nucleotide position on the sequencing ladder and the position is obtained. For example, for a 10mer degenerate oligonucleotides linked to a 16mer 5'-tag (total length 26 nucleotides) the nucleotide position at which the 3'-end of the degenerate primer bound and extended on the RNA is simply the corresponding position on the sequencing ladder minus 25 nucleotide. 25 is used instead of 26 because the last nucleotide at 3'-end of the degenerate primer is where the primer bound and extended.

It is important to note that the intensity of the RT-PCR product on PAGE may not correlate with the extent of accessibility of the site. This is because of PCR artifacts that may amplify certain RT fragments more efficiently than others, thus making them appear to be more abundant. Additionally, it should be noted that the RT products obtained using DP-RT may not be individual bands, but rather may be a collection of bands that each differ in length by a single nucleotide. These collections of products indicate, with a one-to-two nucleotide resolution, the span of that accessible region of the mRNA. Each band is a position on the mRNA where a 3'-end of a degenerate primer found access for hybridization and was extended. Some accessible regions could be as wide as ten nucleotides or as narrow as two or three nucleotides (FIG. 47).

D. 5'-Tag Sequence Effect

Figure 48:
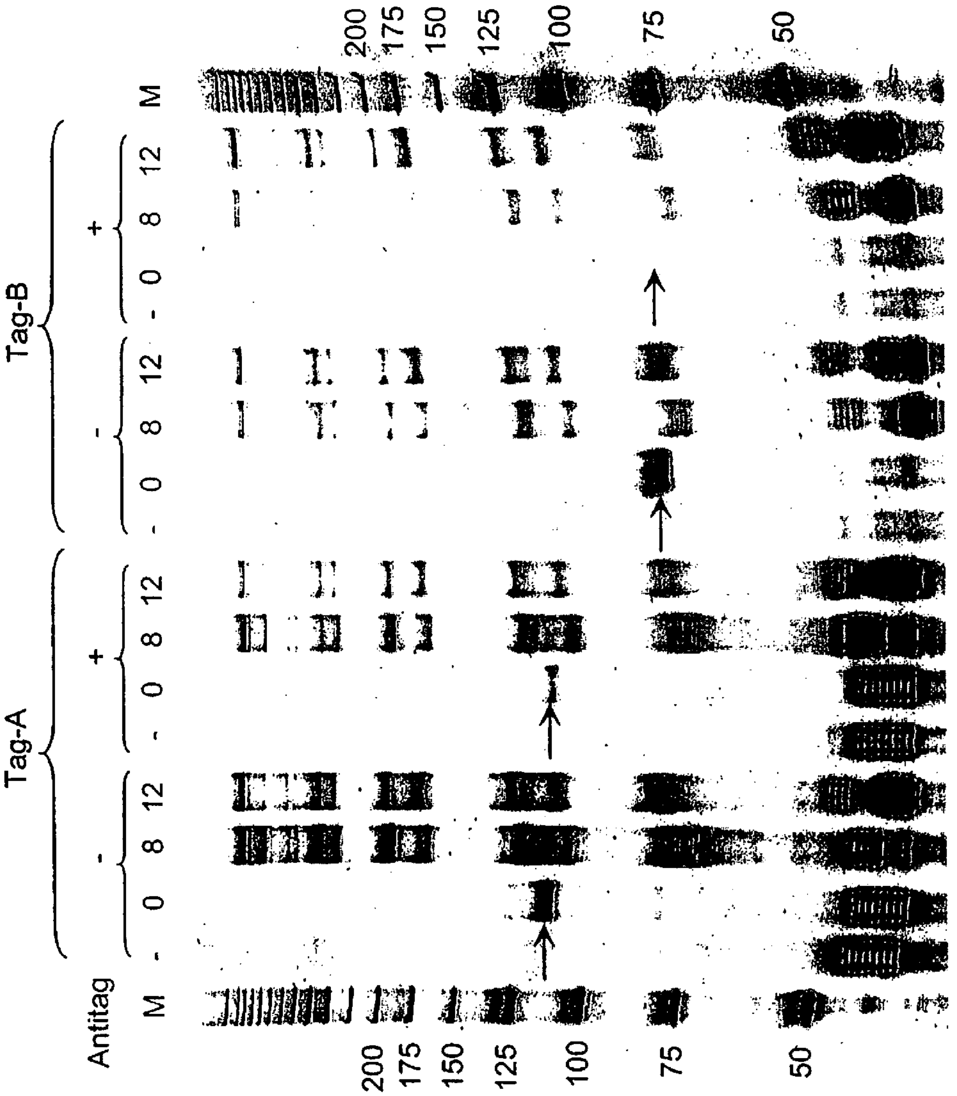
FIG. 48 shows an analysis of the effects on the RT-PCR extension profile of hIFN-γ of using two different 5'-tag sequences on a partially degenerate primer.

It was also examined whether the use of different 5' tag sequences would alter the accessible sites detected using this method. The 5'-tag linked to the degenerate part of the primers used in DP-RT is needed for purposes of PCR amplification of the RT products, as it provides a known sequence unrelated to the RNA for binding of a PCR primer FIG. 48 shows the sites identified using either TagA with 0, 8, or 12 degenerate bases (SEQ ID NO:126, 130, or 132) or TagB with 0, 8, or 12 degenerate bases (SEQ ID NO:134, 135, or 136). Reactions included an anti-tag primer as indicated. It is not intended that the 5'-tag hybridize to the RNA and, therefore it is expected that the RT-PCR primer extension pattern of a specific RNA target would generally be independent of the tag used. This was observed to be true in most cases, although some sites were observed that appeared or disappeared, depending on the tag sequence, indicated by the arrows in FIG. 48. While not limiting the present invention to any particular mechanism, and an understanding of the mechanism in not necessary to practive the present invention, these products are believed to be due to partial homology between the tag sequence and some regions of the RNA target. To overcome this effect, an excess of 2'-O-methylated oligonucleotides complementary to the tag sequence, referred to as "anti-tags," were included in the RT reaction where indicated. The anti-tagA is SEQ ID NO:137 and the anti-tagB is SEQ ID NO138. It is contemplated that the ant-tags hybridize to the tag sequence, thereby preventing it from binding the RNA. The patterns in the indicated lanes of FIG. 48 show that the false priming bands are substantially reduced, while the effect on the true primer extension patterns is minimal, even when the anti-tag concentrations are 5 times or more greater than the degenerate-tagged oligonucleotides.

To ensure that all RT extension sites for a given RNA target are truly accessible sites and not tag artifacts, a modified procedure was devised in which two different tags, each with three different degenerate oligonucleotide lengths (N8, N10, and N12), are used (TagA oligonucleotides SEQ ID NOs:130, 131, and 132, respectively; TagB oligonucleotides SEQ ID NOs:135, 139 and 136, respectively). Any extension products that are not common between the two tags are then considered to be potentially false extension, or mis-priming sites that are not necessarily indicative of accessibility of the RNA at that site, while those that are observed for both tags are considered truly accessible. The three different lengths of degenerate regions used with each tag serve the purpose of reassuring that observed accessible sites are measured from true RT products and not PCR or tag sequence artifacts, since the true RT products resulting from different length degenerate primers finding accessible sites will have distinctive and reproducible length differences between them.

E. Choice of Enzymes (Reverse Transcriptase) and RT Temperature

To ensure that extension profiles obtained for a given RNA target are not dependent on the enzyme used for reverse transcription, the extension patterns obtained using several enzymes were compared, including viral reverse transcriptases such as MMLV and AMV, and bacterial DNA polymerases having reverse transcriptase activity, such as *Thermus thermophilus* (Tth) DNA polymerase. Even when used under slightly different conditions, primer extension by the different polymerases resulted in the same extension profile. The effects of the temperature at which the RT is performed was also examined, varying reactions from 37 to 55° C. While the overall RT extension pattern remained consistent over a wide range of temperatures, higher temperatures resulted in extension from fewer sites and in the requirement for oligonucleotides having longer degenerate regions.

F. Effect of Hybridization Conditions

Figure 49:
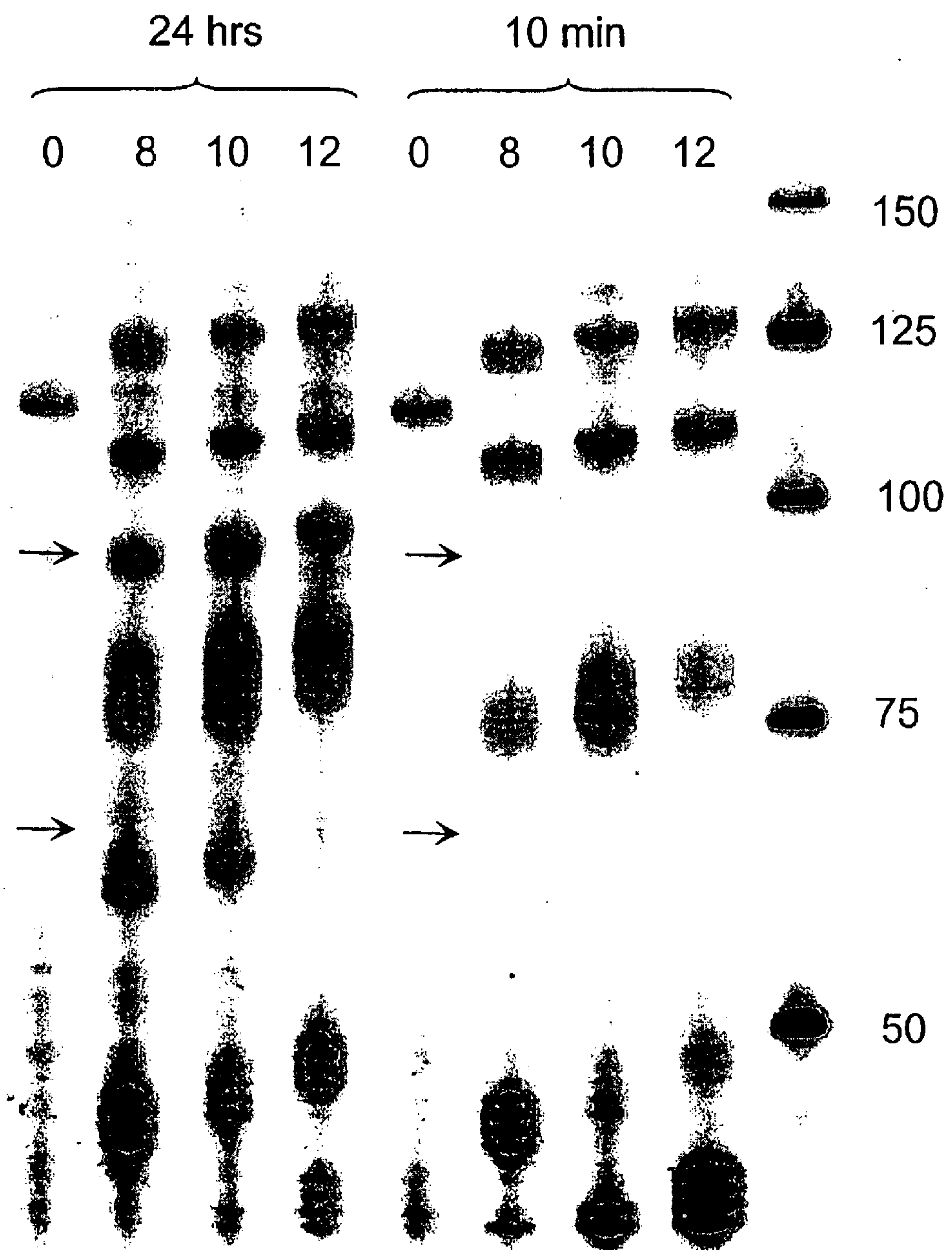
FIG. 49 shows an analysis of the effects on the RT-PCR extension profile of hIFN-γ of the time of hybridization prior to reverse transcription.

To test the effect of different salt and buffer conditions on the RT-PCR accessible sites pattern observed for a given RNA, degenerate oligonucleotide primers were hybridized to RNA targets in different buffers for different periods of times, prior to RT reactions. Varying salt concentrations in the hybridization buffers from 100 mM NaCl, 0 $MgCl_2$ to 5 mM NaCl, 50 mM $MgCl_2$ did not have noticeable effect on accessible sites maps. However, for some RNA targets, minor differences were observed depending on the length of the hybridization period. FIG. 49 shows the RT-PCR products observed using 10 min and 24 hr hybridization periods between hIFN-γ mRNA (SEQ ID NO:141) and the degenerate primers. Allowing 24 hrs of hybridization prior to RT resulted in the appearance of new products of 90 and 60 base pairs, (regions showing presence and absence are indicated by arrows), which did not appear when only 10 min were allowed for hybridization prior to the initiation of the RT. While not limiting the present invention to any particular mechanism, and an understanding of the mechanims is not necessary to practice the present invention, it appears that some accessible sites may allow DNA hybridization at relatively slower rates than other sites. Interestingly, many of the sites products were not altered by the shorter hybridization time, indicating that a brief hybridization may be preferable for some embodiments of the present invention. For example, if rapid hybridization is preferable for an antisense therapeutic oligonucleotide, a comparison such as this can provide a means for distinguishing sites that are immediately accessible from those that require prolonged exposure to the hybridizing oligonucleotide.

G. Target RNA Concentration

To determine how much RNA is needed to obtain an accessible sites map, the RNA concentrations in the RT reactions was varied from 5 μM (100 pmoles) to 0.5 nM (1 fmole). Detection of accessible sites required approximately 10 fmoles (5 nM) of RNA and was dependent on the quality, purity, and integrity of the RNA target. Since the extended primers are subsequently amplified by PCR, optimizations of enzyme, primer, and salt concentrations along with RT time and PCR cycles allows this detection limit to be further reduced and allows the method to be easily adapted to be carried out on total cellular mRNA.

EXAMPLE 16

Correlation Between Accessibility of RNA as Measured by Extendibility of Degenerate Primers with Accessibility of RNA Previously Reported To further understand the nature of the sites that are observed in a given RNA to be accessible for primer extension, RNA targets that have been the characterized in previous studies were examined, with site accessibility being determined by either hybridization followed by RNase H digestion (Ha-ras mRNA) (Lima et al., Biochemistry 31:12055 [1992]; Bruice and Lima, Biochemistry 36:5004 [1997]), or by hybridization to libraries of oligonucleotides arrays (rabbit β-globin mRNA) (Milner et al., Nature Biotechnology 15:537 [1997]). For the present examples, association and dissociation constants for hybridization reactions of oligonucleotides to RNA were previously determined using gel shift assays as described (Lima et al., Biochemistry 31:12055 [1992]; Fried and Crothers, Nucleic Acids Res., 9:6505 [1981]). Briefly, hybridization reactions were performed in 100 mM NaCl, 5 mM $MgCl_2$, 10 mM Tris-HCl pH 7.5 in 10 μL volumes Equal concentrations of the oligonucleotide and RNA target (100–10 nM) were used. The hybridization was carried out by heating the reaction mixture to 75° C. for 3 minutes and slowly cooling down to 37° C. and incubating at that temperature for 1 to 24 hours. Reactions were then transferred to an ice bath and 2 μL of a gel loading buffer containing 50% glycerol and bromophenol blue in 10 mM Tris-HCl, 0.1 mM EDTA, pH 8.0 pre-cooled to 0° C., were then added. 5 μL of each hybridization mixture were loaded or a nondenaturing polyacrylamide gel (10%) in a buffer containing 1×TBE with 5 mM $MgCl_2$, at pre-equilibrated to 4° C., and run at that temperature at 100 volts for 1–2 hours. The resolved products were scanned and analyzed as described above.

1. Ha-ras mRNA

To compare accessible sites results obtained using the DP-RT method of the present invention with those obtained using RNase H footprinting, a 47-nucleotide transcript model of a mutant ha-ras mRNA hairpin loop corresponding to residues +18 to +64 of human ha-ras gene was chosen. Intensive studies were carried out previously on this 47 nucleotide hairpin loop by Bruice and Lima (Lima et al., Biochemistry 31:12055 [1992]; Bruice and Lima, Biochemistry 36:5004 [1997]). Bruice and Lima used RNase I footprinting and gel shift binding studies to determine favorable hybridization sites on the ras mRNA.

Figure 50A:
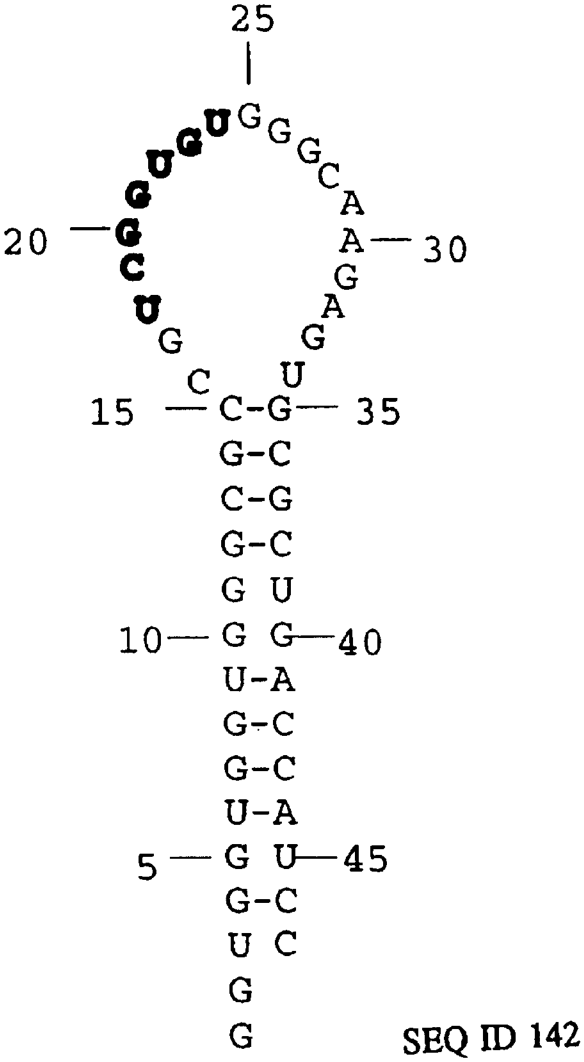
FIG. 50A shows a schematic diagram of a proposed secondary structure of a 47 nucleotide region of ha-ras mRNA. Nucleotides shown in bold correspond to a regions from which the degenerate primers of the present invention were able to bind and extend in an RT-PCR reaction.
Figure 50B:
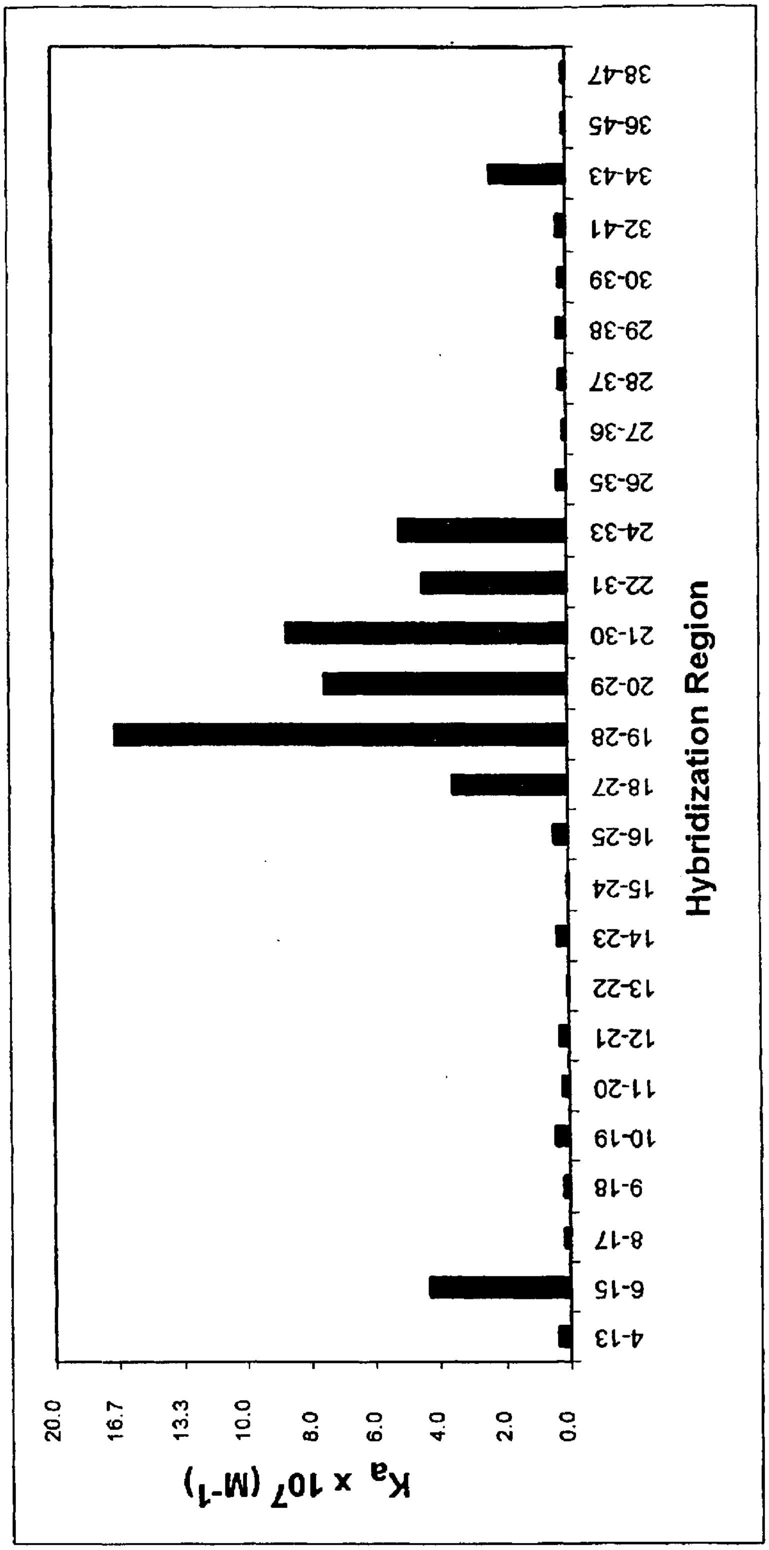
FIG. 50B shows a plot of binding constants ($K_a$, $M^{-1}$) as determined from gel-shift assay experiments for 10-mer oligonucleotide probes complementary to the ha-ras mRNA, and walking its full 47 nucleotide length.

FIG. 50A shows the secondary structure of the 47mer ha-ras mRNA (SEQ ID NO 142) with the extendible sites obtained using DP-RT highlighted in bold type. Compared to the Bruice and Lima results, the extension sites using the methods of the present invention are in complete agreement with their maximum accessibility results for nucleotides 18 to 24 of the ras RNA. Furthermore, when comparing binding constants for twenty-six 12mer DNA oligonucleotides designed to complement the RNA with a one or two nucleotide step, it is observed that, with the exception of the 5' and 3' ends of the ras mRNA, appreciable binding and thus $K_a$ values are obtained for only oligonucleotides that have their 3-ends at nucleotides 18 to 24 of ras RNA (FIG. 50B). This suggests that sites on RNA from which degenerate primers can be extended using the DP-RT method of the present invention can be classified as accessible sites on a target RNA for oligonucleotides that have their 3'-ends at the extendible site. This correlation between the 3'-end positioning of the complementary oligonucleotide and the DP-RT extendible sites makes sense, since RT extension occurs when the 3'-end of the degenerate primer binds and accessible region of the RNA. Thus the accessible sites obtained using the methods of the present invention correlate with positions along an mRNA where 3'-end of oligonucleotide hybridization is favorable.

2. Rabbit β-globin

Rabbit β-globin mRNA (SEQ ID NO:143) was the target for determining its accessible sites by Milner et al. (Milner et al., Nature Biotechnology 15:537 [1997]). The authors used a library of deoxyoligonucleotide microarrays complementary to bases 1–122 of the mRNA and concluded that regions from approximately bases 38–48, 64–73, and 93–116 are accessible, and observed maximum hybridization efficiency for oligonucleotides having their 3'-ends at position 46 of the rabbit β-globin mRNA. To compare results, the accessible sites on this RNA were mapped using the DP-RT method of the present invention. FIG. 51 shows the accessible sites map obtained for the first 200 nucleotides of the rabbit p-globin mRNA, made using the 593 nucleotide full-length mRNA (SEQ ID NO:143). Three major regions of the RNA were observed to be accessible regions 44–50, 64–68, and 88–97. With minor variations on the span of these accessible regions, these results agree with the observations of Milner et al., confirming the correlation between extension of the degenerate primers and location of accessible sites on mRNA targets.

EXAMPLE 17

Correlation Between Antisense Inhibition and Accessible Sites Determined Using DP-RT Human intercellular adhesion molecule 1 mRNA (hICAM-1) was the target for intensive antisense oligonucleotide targeting studies carried out by groups at ISIS Pharmaceuticals and the Sczakiel laboratory (Patzel et al., Nucleic Acids Res., 27:4328 [1999]; Yacyshyn et al., Gastroenterology 114:1133 [1998]; Chiang et al., J. Biol. Chem., 266:18162 [1991]; Bennett et al., J. Pharmacol. Exp. Ther., 280:988 [1997]). This made hICAM-1a suitable candidate for assessing the applicability of accessible sites determined using DP-RT to the design of antisense reagents and therapeutics. A DP-RT accessible sites determination study was carried out on hICAM-1 mRNA corresponding to nucleotides 1 through 2,881 of the gene (GenBank accession NM_000201; SEQ ID NO:144). FIG. 52 shows the accessible sites results of the hICAM-1, indicated by the bold type.

Comparison with previous studies revealed that, with a few minor exceptions, the DP-RT results were in agreement with published observations (Patzel et al., Nucleic Acids Res., 27:4328 [1999]; Yacyshyn et al., Gastroenterology 114:1133 [1998]; Chiang et al., J. Biol. Chem., 266:18162 [1991]; Bennett et al., J. Pharmacol. Exp. Ther., 280:988 [1997]) in that antisense oligonucleotides exhibiting a high degree of inhibition lie in regions that DP-RT analysis determines to be accessible, and that oligonucleotides that show insignificant control over gene expression are in regions that DP-RT determines to be inaccessible. For example, oligonucleotide ISIS 1939 (SEQ ID NO:145), which has been shown to have the strongest control over ICAM-1 gene expression of the studied oligonucleotides (Chiang et al., J. Biol. Chem., 266:18162 [1991]; Bennett et al., J. Immunol., 152:3530 [1994]), has its 3'-end in a region indicated as accessible by DP-RT (region 1939-1945). Similarly, ISIS 1570 (SEQ ID NO:146), which also showed appreciable inhibition (Bennett et al., J. Immunol., 152:3530 [1994]), coincides with regions determined to be accessible by DP-RT (region 45-64). ISIS 1571 (SEQ ID NO:147) and ISIS 1934 (SEQ ID NO:148), which span regions 8–25 and 337–356, respectively, exhibit poor inhibition (Chiang et al., J. Biol. Chem., 266:18162 [1991]) and both lie in regions that DP-RT does not show as accessible. These data show that regions indicated to be accessible using DP-RT are excellent candidates for successful antisense oligonucleotide design and targeting.

An exception to the agreement between DP-RT results and antisense efficacy was ISIS 2302 (SEQ ID NO: 149). ISIS 2302 has been shown to have a relatively high degree of inhibition (Yacyshyn et al., Gastroenterology 114:1133 [1998]; Bennett et al., J. Immunol., 152:3530 [1994]) but does not lie in an accessible region that is detected using DP-RT. It is interesting to note, however, that ISIS 2302 lies in a region that is flanked by two accessible regions (ISIS 2302 spans nucleotides 2100–2119 which is in between accessible regions 2083–2091 and 2129–2136). Thus it could be the case that the proximity of these two accessible regions allowed for the successful hybridization of ISIS 2302.

Another major study performed on hICAM-1 was carried out by Patzel and coworkers (Patzel et al., Nucleic Acids Res., 27:4328 [1999]). The authors used a computer algorithm for predicting accessible regions of the hICAM-1 RNA. They predicted six regions to be accessible, out of which three around nucleotides 596, 1376, and 1616 were deemed "highly" accessible. Experimental antisense inhibition results on these three regions, especially the region around position 1616, were successful in terms of inhibiting gene expression. Nonetheless, the authors screened a large number of oligonucleotides for each site region to find these effective antisense oligonucleotides. For example, for sites 596, 1376, and 1616, a total of twenty one oligonucleotides were tested. The reason for testing such a large number of antisense oligonucleotides was due to the fact that moving antisense oligonucleotides by one nucleotide upstream or downstream on the mRNA target caused a dramatic change in their efficacy and thus "fine-tuning" the position of the most effective antisense oligonucleotide was needed.

FIG. 52 shows the ICAM gene sequence aligned with the ISIS antisense oligonucleotides. Regions determined to be accessible in the ICAM RNA using the method of the present invention are shown in bold type. When comparing the results obtained using the methods of the present invention with the Patzel et al. study, an excellent agreement between accessible sites determined using DP-RT and antisense inhibition was observed. All regions predicted and successfully tested by Patzel et al. for antisense inhibition (596, 1206, 1376, 1616, and 1846) coincided with accessible regions determined using DP-RT. Interestingly, antisense oligonucleotides tested for site 1616, which were shown to have the highest degree of inhibition compared to all others including ISIS's, lie in a three consecutive and closely spaced accessible regions as determined by DP-RT, further evidence that the DP-RT is an effective tool for determining accessible sites in RNA for antisense purposes.

EXAMPLE 18

Application of Accessible Sites Selection for INVADER Assay Oligonucleotide Design FIG. 53 shows the accessible sites profile for hIFN-γ mRNA (GenBank accession X01992, SEQ ID NO: 141) obtained using the DP-RT procedure. In this RNA target, the methods of the present invention indicate that there are 18 sites accessible for degenerate primer extension. The sites for a shorter transcript that spans nucleotides 174 to 591 of the full length RNA and were also mapped. In agreement with previous observations on other RNA targets (Sohail et al., RNA 5:646 [1999]), accessible sites in the shorter transcript were identical to those mapped in the full-length RNA. To assess the correlation between accessible sites obtained using the methods of the present invention and the level of performance of the INVADER assay, INVADER experiments were performed on the accessible site around residue 331 (referred to as site 330) of the hIFN-γ. A walking approach was tested, which comprises testing multiple oligonucleotide probes, the first having a 3'-end hybridizing to position 315 and the other probes hybridizing to sites that shift in one nucleotide steps to position 335 of the hIFN-γ.

A. INVADER Assays

INVADER assays were performed in 10 μL total reaction volumes using 10 ng of CLEAVASE TTH DN (Third Wave Technologies; See PCT Publication WO 98/23774, herein incorporated by reference in its entirety), 1 nM of RNA, and 1 μM of 5'-labeled fluorescence probe and INVADER oligonucleotides in a final reaction buffer containing 500 ng/μL tRNA, 10 mM MOPS pH 7.5, 0.1 M KCl, and 5 mM $MgCl_2$. To determine the optimal reaction temperature for each probe/INVADER oligonucleotide set, temperature optimization were performed on a gradient thermocycler. Once the optimal temperature was determined, a one hour INVADER reaction was carried out, followed by cooling to 4° C. and addition of 2 μL of gel loading dye containing 90% formamide, and bromophenol blue in 10 mM Tris-HCl, 0.1 mM EDTA, pH 8. 5 μL of each reaction were then loaded on a 20% denaturing PAGE and allowed to run for 20 minutes and scanned as described above, using a 505 nm emission filter. Turnover rates were determined from the percentage of cleaved probe, as calculated from band intensities integrated using FMBIO-100 scanner software.

Figure 54A:
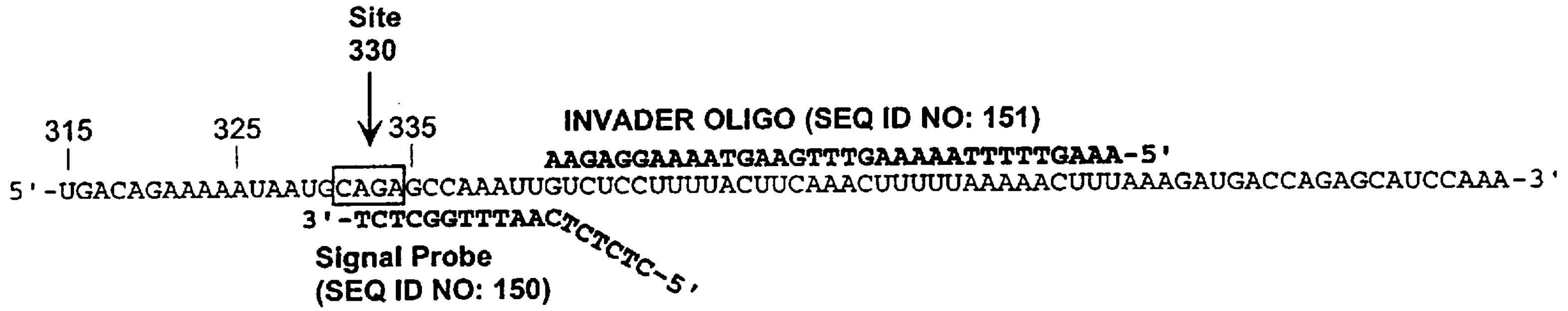
FIG. 54A shows an example of INVADER design for site 330 of hIFN-γ. Note that the 3'-end of the probe was walked across the accessible site by a one nucleotide step from nucleotides 315 to 335 on the mRNA for a total 21 probe/INVADER oligonucleotide design. Probe oligonucleotides were designed to have an optimal reaction temperature of approximately 50° C. and INVADER oligonucleotides were designed to have a 10° C. higher stability than their corresponding probe.
Figure 54B:
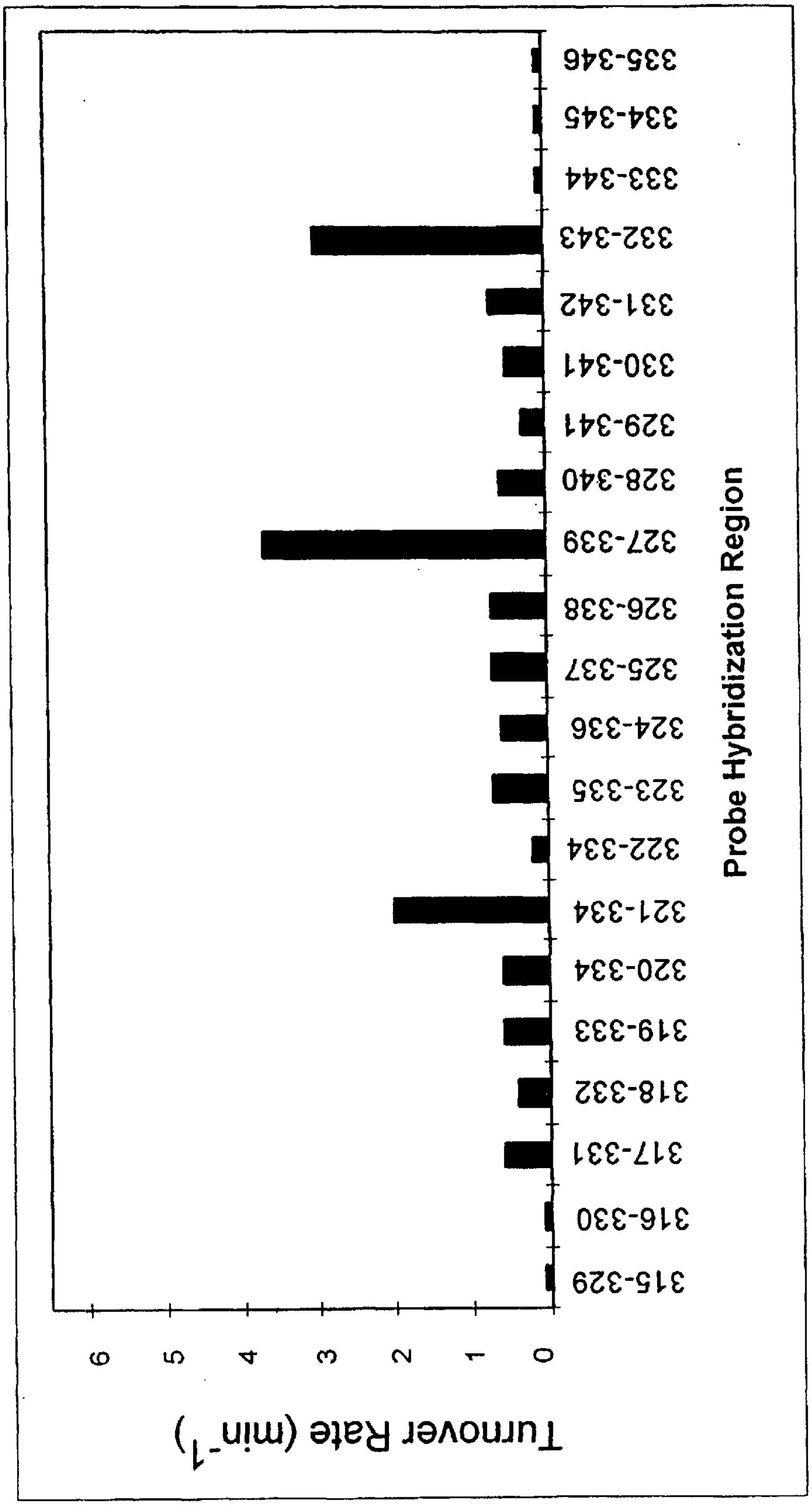
FIG. 54B shows probe turnover rates ($min^{-1}$) as determined in the INVADER assay.

FIG. 54A shows the design of one of the INVADER substrates for site 330 in the hIFN-γ (signal probe SEQ ID NO:150; INVADER probe SEQ ID NO:151); other probes were shifted across the accessible site as described above. INVADER assay results (FIG. 54B) show that substantial cleavage, measured by the number of cleaved probes per minutes per target molecule (turnover rate), is obtained in three cases: when the probe 3'-end is at the accessible site (probe hybridization region 332–343), when the INVADER oligonucleotide 3'-end and/or the probe 5'-end are at the accessible site (probe hybridization region 321–334), and when the middle of the probe hybridizing region is at the accessible site (region 327–339). These results are consistant with the quality of the information obtained from DP-RT, showing that the placing of the 3'-ends of either the probe or the INVADER oligonucleotide at the accessible site results in high INVADER assay turnover rates. The extension map obtained using DP-RT indicates positions along the RNA where the 3'-end of the primers could bind and be extended. The results in which a high cleavage rate occurred when the middle of the probe was placed at the accessible region suggest that probe cycling kinetics may be a factor in the level of signal observed, since the INVADER reaction requires not only probe hybridization, but also requires probes turnover so that the cleaved probe may be replaced by an intact probe.

In addition to hIFN-γ, high turnover rates at accessible sites first identified using the DP-RT methods of the present invention were also observed for several other targets, such as human PSP94 and human ubiquitin, while negligible turnover rates were observed in control experiments that tested numerous probe and INVADER oligomers that spanned or 'walked' across non-accessible control regions (e.g., regions where no degenerate primer extension was observed). Thus, it is contemplated that accessible sites identified using DP-RT can be selected as targets sites for INVADER probes without further verification of the accessibility of the sites.

EXAMPLE 19

Application of Accessible Sites Selection for INVADER Assay Oligonucleotide Design for the General Detection of HIV-1

The accessible sites method was employed in the design of probes for the INVADER assay-based detection of human immunodeficiency virus 1 (HIV-1). The detection of HIV-derived RNA presents an additional challenge in that this virus is known to be highly polymorphic, so known and potential variations in the target sequence must be taken into account if the intention is to design a probe or probe set that can be used without advance knowledge of the sequence of the particular variant to be detected. The method employed involved several steps.

First, regions of greatest homology between the different genetic sub-types of HIV-1 were determined. This was done by visually inspecting the alignments of approximately 140 different HIV-1 genomes using the 1998 and 1999 Compendium (Los Alamos HIV-1 database) and targeting the 2 most conserved regions (i.e., regions with the lowest density of nucleotide differences among the genomes) for analysis. Initial investigations were done using the p5' HIV-1 construct [the p5' reagent was obtained from the AIDS Research and Reference Reagent Program, Division of AIDS, NIAID, NIH, from Drs. Dean Winslow and Lee Bacheler. (Winslow D L, Anton E D, Horlick P R, Zagursky R J, Tritch R J, Scamati H, Ackerman K, Bacheler L T. Construction of infectious molecular clones of HIV-1 containing defined mutations in the protease gene. *Biochem Biophys Res Commun* 205:1651–1657, 1994)].

Synthetic RNA transcripts spanning these conserved regions [bases 455–2076 of the gag gene, termed transcript 1 (SEQ ID NO:158) and bases 3300–5070 of the pol gene, termed transcript 3 (SEQ ID NO:159)] were prepared by established methods, outlined below, using the p5' HIV-1 reagent as template. All base positions are numbered relative to HXB2CG (Korber, et al., HIV Sequence Database, Los Alamos National Laboratories, Reviews [1998]).

The regions of p5' HIV-1 to be analyzed were first amplified using PCR. For the pol gene region, amplification was done using a T7 promoter sequence in the forward PCR primer: 5'-GGTAATACGACTCACTATAGGCTGGACTGT CAATGACATACAGAAGTTAGTG GG-3' (SEQ ID NO:160, hybridizing to position 3300–3334), in conjunction with the reverse primer: 5'-CACAATCATCACCTGCCATCTGTTTTCCATAATC-3' (SEQ ID NO:161, hybridizing to position 5037–5070). Amplification of the gag region was done using the T7 promoter sequence in the forward PCR primer: 5'-GGTAATACGACTCACTATAGGTCTCTCTCTGG TTAGACC-3'(SEQ ID NO:162, hybridizing to position 455–472) in conjunction with the reverse primer: 5'-CTCTCAGTACAATCTTTCAT-3' (SEQ ID NO:163, hybridizing to position 2056–2076). PCR reactions were performed in 50 μl final volume and contained 5 μl of 10×PCR reaction buffer (Perkin Elmer GeneAmp PCR Kit, Cat. # JO843), 200 μm dNTP's, 100 nM forward primer, 100 nM reverse primer, 2.5 units of AmpliTaq or AmpliTaq Gold (Applied Biosystems), 40–43 ng p5' HIV-1 clone, and water to 50 μl. 50 μl of CHILLOUT liquid wax (MJ Research) was added and the reactions were denatured at 95° C. for 12 minutes, then cycled at 95° C. for 45 seconds, 60° for 45 seconds, and 72° degrees for 60 seconds. This was repeated 30 times. Samples were then incubated for 10 minutes at 72° and cooled to 4° C.

PCR products were then used as templates in in vitro transcription assays. The T7-MEGAshortscript transcription kit (Ambion) was used according to the vendor's recommended procedure. After completion of the transcription reactions, DNA templates were removed from the RNA transcripts by the addition of DnaseI.

Transcripts were purified by trizol RNA extraction as follows. RNA samples were heated to 95° C. for 1 min., then cooled on ice. 500 μl trizol was added and reaction tubes were shaken by hand for 15 seconds. Reactions were incubated at room temperature for 2–3 minutes and centrifuged at 10,000 rpm for 15 minutes and 4° C. The upper, aqueous phase (about 400 μl) was transferred to a fresh tube, and an equal volume of isopropanol was added. Samples were incubated at room temperature for 10 min then centrifuged at 10,000 rpm for 10 minutes at 4° C. The supernatants were discarded and the pellets were dried. Each was dissolved in 100 μl of nuclease-free water. Finally, samples were purified using the RNeasy Mini Kit (Qiagen) according to the manufacturer's instructions. Samples were quantitated via absorbance at 260 nm.

Accessible sites were identified on both the pol and the gag transcripts using the DP-RT method described in Example 15. Buffer conditions and target RNA:oligonucleotide ratios for the RT reaction were as described in Example 15, though reaction volume was doubled to 40 μl.

For the gag transcript, 5 μl of the RT reaction were transferred into each of 8 tubes and PCR components were added to final conditions described in Example 15. Each reaction received one of eight different, target-cDNA specific, sense-strand, fluorescently labeled PCR primers, and a 5' tag specific antisense primer, as described in

EXAMPLE 15

The sense primers were designed to have a melting temperature of approximately 60° C. and are spaced approximately ~100–200 nucleotides apart (shown underlined in FIG. 55). PCR reaction products were run on a 6% denaturing PAGE alongside a sequence ladder, and the results imaged as detailed in Example 15. Accessible sites were identified as described above, and are indicated as bold type in FIG. 55. For INVADER assay probe design, sites that were found to be in exceptionally variable regions of the HIV genome were passed over in favor of sites showing less polymorphism:

Primer 4: Accessible sites were detected around 1080, 1100, 1160, and 1200 nt;

Primer 5: Accessible sites were detected at 1320, 1370 and 1400;

Primer 6: Accessible sites were detected at positions 1460 and 1480;

Primer 7: Accessible sites detected at positions 1700, 1720, 1730, and 1800; this site was noted to be exceptionally good with respect to sequence conservation;

Primer 8: Excellent accessible sites detected at 1840–1850 (excellent because it is long, close (contiguous) to another site, with few polymorphisms in the immediate area. This region is known to be conserved with only scattered polymorphisms. Additional sites were detected at 1920 and 1980.

Figure 56:
FIG. 56 shows mapping analysis of HIV transcript 1 (SEQ ID NO:158) in the 1840–1850 region using degenerate oligonucleotides of 0, 8, 10, or 12 nucleotides, in combination with 2 different tag sequences, Tag A and Tag B, by comparison to a sequencing ladder.

FIG. 56 shows the analysis of these sites using primer 8 and degenerate oligonucleotides of 0, 8, 10, or 12 nucleotides, in combination with 2 different tag sequences, tag A and tag B (see example 15 for tag sequence).

Figure 58:
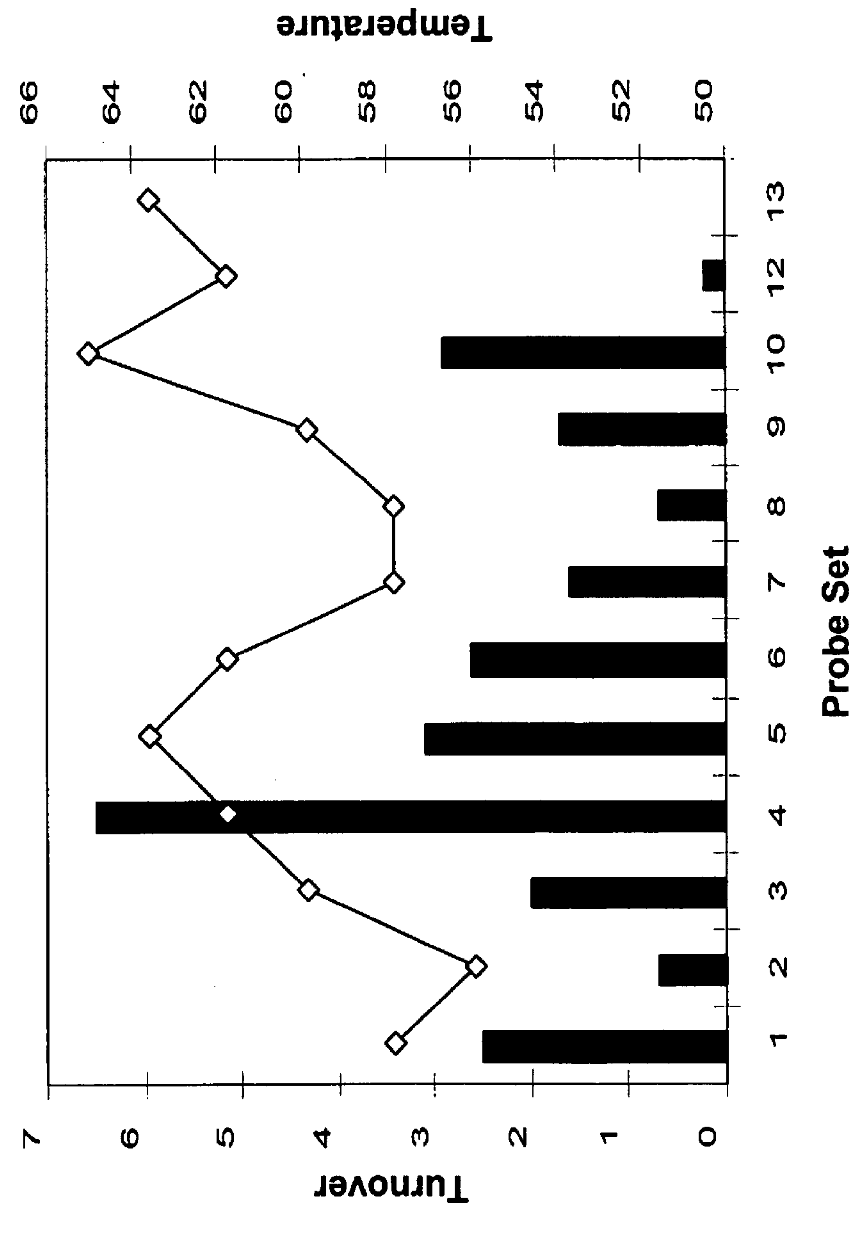
FIG. 58 shows probe turnover rates ($min^{-1}$) as determined in the INVADER assay.
Figure 59:
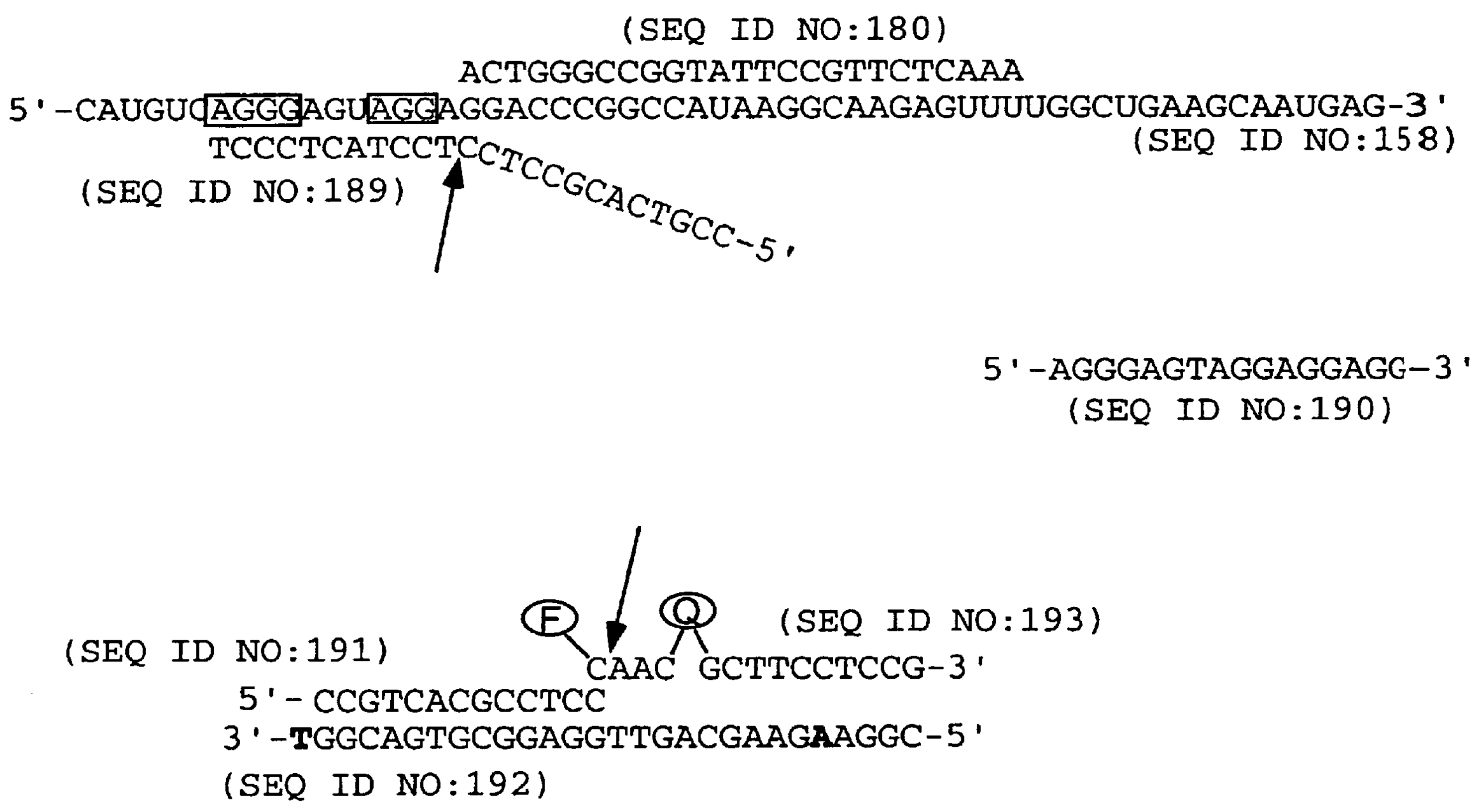
FIG. 59 shows a schematic diagram of an INVADER oligonucleotide (SEQ ID NO: 180), primary probe oligonucleotide (SEQ ID NO: 189), an ARRESTOR oligonucleotide (SEQ ID NO: 190), a secondary target oligonucleotide (SEQ ID NO: 192) and FRET probe (SEQ ID NO: 193) for the detection of HIV RNA. The primary probe and INVADER oligonucleotides are shown aligned with a portion of HIV transcript 1 (SEQ ID NO: 158). Cleavage of the primary probe oligonucleotide produces the arm oligonucleotide having SEQ ID NO:191.

The site identified using primer 8, the 1840–1850 site, was chosen as a target site for the design of INVADER/signal probe sets probe sets. Multiple pairs of probes were designed to determine an optimal position for the signal probe with respect to the detected accessible site. These probe sets are diagrammed in FIG. 57; each signal probe included the 'A' 5' arm and a 5' fluorescein as indicated on Signal Probe 13, and each was used with the INVADER oligonucleotide having the same number (i.e., Signal Probe 12 was used with INVADER oligonucleotide 12). INVADER assay reactions were performed as described in Example 18 using transcript #1 prepared as described above, with the additional step of purification on a 6% denaturing PAGE. The turnover rates were measured as the number of enzymatic cleavage events per target, per minute, and are charted in FIG. 58.

The probe set showing the greatest rate of signal accumulation (set 4 from FIG. 57) was used to detect HIV viral RNA at a range of concentrations using the INVADER-squared assay format, described above. Viral RNA was isolated from HIV-positive plasma samples using the QIAamp Viral RNA Kit (Qiagen) with the following protocol modifications. A dilution series was created by diluting purified HIV viral particles (strain IIIB, Advanced Biotechnologies, Inc.) in negative plasma (Lampire Biological Laboratories, Pipersville, Pa.). The plasma was certified to be negative for Hepatitis B surface antigen, HIV, Hepatitis C Virus, and syphilis. One ml of each plasma sample was first subjected to high-speed centrifugation at 23,500×g for 1 h at 4° C. to concentrate the virus, 930 μl of supernatant was removed and discarded. To lyse the particles, 280 μl of QIAgen buffer AVL were added and samples were incubated at 25° C. for 10 min. The lysate was applied to the spin column after the addition of 280 μl 100% ethanol, followed by one wash with 500 μl QIAgen AW2. 50 μl of heated distilled $H_2O$ (70° C.) were added, columns were incubated at 70° C. for 5 min, and the eluted RNA was collected by centrifugation.

Figure 60:
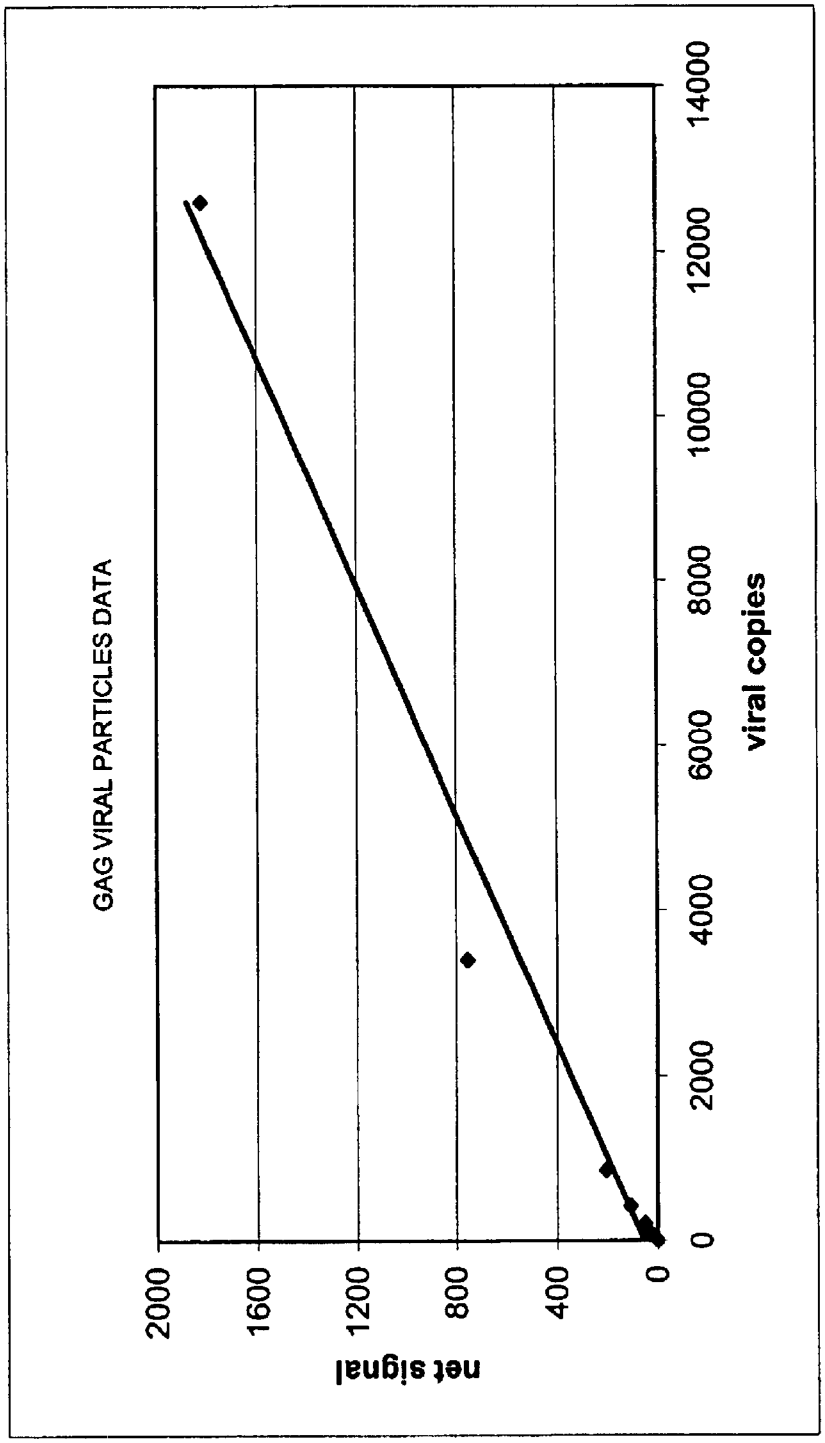
FIG. 60 shows the accumulated fluorescence signal from INVADER assay reactions comprising 53 to 13,600 copies of HIV viral RNA per reaction.

The INVADER assay reactions were performed as follows. Primary reaction components were combined to final concentrations of 4% PEG, 10 mM MOPS pH 7.5, 0.05% Tween-20, 0.05% NP-40, 12.5 mM $MgSO_4$, 1 μM primary probe, 0.5 μM INVADER oligonucleotide, and 20 ng CLEAVASE IX enzyme (Third Wave) per 5 μl. For each reaction, 5 μl of HIV-1 RNA (53–13,600 copies per reaction) were added to 5 μl of primary mix, covered with 10 μl of clear CHILL OUT liquid wax. Reactions were incubated at 65° C. for 2 hours. During the primary reaction, the secondary components were combined to a final concentration of 0.4 μM secondary target oligonucleotide, 2 μM FRET oligonucleotide, 10 mM MOPS pH 7.5, 0.05% Tween 20, 0.05% NP-40, and 8 μM ARRESTOR oligonucleotide, in a final volume of 5 μl per reaction. After the primary reaction, 5 μl of the secondary reaction mix were added to the primary reaction, and samples were incubated for 1 hour at 60° C. Results were read using a standard fluorescence microtiter plate reader at a gain of 40, and excitation/emission 485/530. The accumulated signal and the data are summarized in FIG. 60. The target amounts are indicated as copies per reaction and four replicates were performed for each target amount.

The pol gene transcripts were analyzed similarly to the gag gene, except each reaction received one of nine different target-cDNA specific, sense-strand, fluorescently labeled PCR primers, and a 5' tag specific antisense primer, as described in Example 15 (see FIGS. 61A–C; primer sequences are underlined). Reaction products were analyzed as described above for the gag region (data not shown). Sites found to be both accessible and in regions showing less polymorphism were found within primers 1, 2, 4, 5, 6, 7, 8 and 9, with 8 and 9 having the best sites due to lack of regional polymorphisms and proximity to additional extendible sites. Of the accessible sites found within primers 8 and 9, two general regions, (4790–4810, termed site 4800 and found in primer 8, and 4910–4960, termed 4900 and found in primer 9) were chosen as target sites for the design of INVADER/signal probe sets. Multiple pairs of oligonucleotides were designed to determine an optimal position for the signal probe with respect to each detected accessible site. Eight different INVADER/probe sets were designed for the accessible site around pol site 4900 (FIGS. 62 and 63), and 4 different INVADER oligonucleotide/probe sets were designed for the pol site 4800 (FIG. 64). Reactions were tested with and without stacking oligonucleotides present, to determine if a greater turnover rate could be obtained.

As seen in FIG. 64, for the pol site 4800, only 4 different INVADER/probe oligonucleotide sets were tested (with and without stacking oligonucleotides). All of the designs position the probe oligonucleotide directly in the accessible site. Designs 1, 2 and 4 position the probe cleavage site within the accessible site, while Design 3 positions the cleavage site just downstream of the accessible site, so that only the 3' end of the probe is in the accessible site. Basic INVADER assay reactions without stacking oligonucleotides were performed as described in Example 18. Reactions containing stacking oligonucleotides were performed as described in Example 18, with the addition of 50 pmoles of a stacking oligonucleotide to the reaction. Results of the different designs and different reactions are represented graphically in FIG. 65. Design 3 used with stacking oligonucleotides gives the highest turnover rate, with the other 3 designs being comparable in performance. All four oligonucleotide sets performed better with the stacker than without, with the improvement being most dramatic in oligonucleotide sets 1 and 3. While not limiting the present invention to any particular mechanism, and while an understanding of these mechanisms is not necessary for the practice of the methods of the present invention, it is observed that the stacker oligonucleotides used for sets 1 and 3 are positioned to overlap or completely cover the adjacent accessible site, while the stackers for sets 2 and 4 cover sequence determined to be not accessible by the DP-RT method. Probe sets showing the greatest rate of signal accumulation (sets 1 and 3 from FIG. 65) were used to design a sequential INVADER assay (See e.g., U.S. Pat. No. 5,994,069 and PCT Publication WO 98/42873).

In testing different primary arms and secondary system sequences, set 3 proved problematic due to sequence similarity with the secondary systems and primary arms, resulting in aberrant hybridization. Set 1 was therefore used to detect HIV particles at a range of concentrations, with probe designs shown in FIG. 66. The viral samples were prepared as detailed above for the 1840 site, and the INVADER assay reactions were performed as described, with the resulting data shown in FIG. 67.

Probe sets were also designed for the Pol 4900 site. As shown in the FIGS. 62 and 63, two INVADER/probe oligonucleotide sets were designed for sites 4910 and 4930, and 4 sets were designed for site 4960. In each case, the cleavage site, indicated by an arrow, was positioned over the accessible site, with the two different sets being displaced by a single base. All 8 designs were tested with and without stacking oligonucleotides, as described above, and those designs showing the best turnover rate (see FIG. 68) were selected for further analysis. Set 5 gave the best turnover rates in studies testing different primary arms and the associated secondary systems, and was therefore used to detect HIV-1 RNA at a range of concentrations using the probe set diagrammed in FIG. 69, with the results shown in FIG. 70.

The data from analysis of these accessible sites show that the DP-RT method of determining site accessibility produces improved INVADER assays for the detection of HIV RNA. In addition, these results show that information from accessible sites analysis performed on in vitro transcripts is transferable to the design of assays for the detection of the genomic RNA of HIV viral particles.

EXAMPLE 20

Kits for Performing the mRNA INVADER Assay

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). By way of example, and not intending to limit the kits of the present invention to any particular configuration or combination of components, the following section describes one embodiment of a kit for practicing the present invention:

In some embodiments, the kits of the present invention provide the following reagents:

| | |
|---|---|
| CLEAVASE enzyme (e.g., CLEAVASE IX enzyme, Third Wave Technologies) | Primary Oligos |
| RNA Primary Buffer 1 | Secondary Oligos |
| RNA Secondary Buffer 1 | RNA Standard [100 amol/μl] |
| tRNA Carrier [20 ng/μl] | 10X Cell Lysis Buffer 1 |
| $T_{10}e_{0.1}$ Buffer [10 mM TrisoHCl, pH 8, 0.1 mM EDTA] | |

Examples of Primary Oligonucleotides and Secondary Oligonucleotides suitable for use with the methods of the present invention are provided in FIGS. 54A, 57, 59, 62, 63, 64, 66, and 69. While the oligonucleotides shown therein may find use in a number of the methods, and variations of the methods, of the present invention, these INVADER assay oligonucleotide sets find particular use with kits of the present invention. The oligonucleotide sets may be used as individual sets to detect individual target RNAs, or may be combined in biplex or multiplex reactions for the detection of two or more analytes or controls in a single reaction. It is contemplated that the designs of these probes sets (e.g., the oligonucleotides and/or their sequences) may be adapted for use in DNA detection assays, using the guidelines for reaction design and optimization provided herein. Additional oligonucleotides that find use in detection assays and kits of the present invention, including, e.g., for use with the RNAs mapped for accessible sites shown in FIGS. 71–83B, may be designed and used according to the guidelines and methods provided hereinabove.

In some embodiments, a kit of the present invention provides a list of additional components (e.g., reagents, supplies, and/or equipment) to be supplied by a user in order to perform the methods of the invention. For example, and without intending to limit such additional components lists to any particular components, one embodiment of such a list comprises the following:

RNase-free (e.g., DEPC-treated) $H_2O$

Clear CHILLOUT-14 liquid wax (MJ Research) or RNase-free, optical grade mineral oil (Sigma, Cat. No. M-5904)

Phosphate-buffered saline (no $MgCl_2$, no $CaCl_2$)

96-well polypropylene microplate (MJ Research, Cat. No. MSP-9601)

0.2-ml thin-wall tubes

Thermaseal well tape (e.g., GeneMate, Cat. No. T-2417-5)

Multichannel pipets (0.5–10 μl, 2.5–20 μl, 20–200 μl)

Thermal cycler or other heat source (e.g., lab oven or heating block).

Fluorescence microplate reader (a preferred plate reader is top-reading, equipped with light filters have the following characteristics:

| Excitation (Wavelength/Bandwidth) | Emission (Wavelength/Bandwidth) |
|---|---|
| 485 nm/20 nm | 530 nm/25 nm |
| 560 nm/20 nm | 620 nm/40 nm |

In some embodiments, a kit of the present invention provides a list of optional components (e.g., reagents, supplies, and/or equipment) to be supplied by a user to facilitate performance of the methods of the invention. For example, and without intending to limit such optional components lists to any particular components, one embodiment of such a list comprises the following:

tRNA Solution, 20 ng/μl (Sigma, R-5636)

1×Stop Solution (10 mM Tris.HCl, pH 8, 10 mM EDTA)

Black opaque, 96-well microplate (e.g., COSTAR, Cat. No. 3915)

Electronic repeat pipet (250 μl)

In some embodiments of a kit, detailed protocols are provided. In preferred embodiments, protocols for the assembly of INVADER assay reactions (e.g., formulations and preferred procedures for making reaction mixtures) are provided. In particularly preferred embodiments, protocols for assembly of reaction mixtures include computational or graphical aids to reduce risk of error in the performance of the methods of the present invention (e.g., tables to facilitate calculation of volumes of reagents needed for multiple reactions, and plate-layout guides to assist in configuring multi-well assay plates to contain numerous assay reactions). By way of example, and without intending to limit such protocols to any particular content or format, kits of the present invention may comprise the following protocol:

I. Detailed mRNA Invader Assay Protocol

1. Plan the microplate layout for each experimental run. An example microplate layout for 40 samples, 6 standards, and a No Target Control is shown in FIG. 40. Inclusion of a No Target Control (tRNA Carrier or 1×Cell Lysis Buffer 1) and quantitation standards are required for absolute quantitation.
2. Prepare the Primary Reaction Mix for either the single or biplex assay format. To calculate the volumes of reaction components needed for the assay (X Volume), multiply the number of reactions (for both samples and controls) by 1.25 [X Volume (μl)=# reactions×1.25]. Vortex the Primary Reaction Mix briefly after the last reagent addition to mix thoroughly. Aliquot 5 μl of the Primary Reaction Mix per microplate well (an electronic repeat pipet is recommended for this step).

Primary Reaction Mix

| Reaction Components | 1X Volume | X Volume |
|---|---|---|
| Single Assay Format | | |
| RNA Primary Buffer 1 | 4.0 μl | |
| Primary Oligos | 0.25 μl | |
| $T_{10}e_{0.1}$ Buffer | 0.25 μl | |
| CLEAVASE enz. enzyme | 0.5 μl | |
| Total Mix Volume (1X) | 5.0 μl | |
| Biplex Assay Format | | |
| RNA Primary Buffer 1 | 4.0 μl | |
| Primary Oligos | 0.25 μl | |
| Housekeeping Primary Oligos | 0.25 μl | |
| CLEAVASE enzyme | 0.5 μl | |
| Total Mix Volume (1X) | 5.0 μl | |

3. Add 5 μl of each No Target Control, standard, or sample (total RNA or cell lysate) to the appropriate well and mix by pipetting up and down 1–2 times. Overlay each reaction with 10 μl of clear CHILLOUT or mineral oil. Seal microplate with Thermaseal well tape.
4. Incubate reactions for 90 minutes at 60° C. in a thermal cycler or oven.
5. While the primary reaction is incubating, prepare the Secondary FRET Reaction Mix for the single or biplex format. Calculate the component volumes required (X Volume) by multiplying the number of reactions (for both samples and controls) by 1.25 [X Volume (μl)=# reactions×1.25 (μl)]. Aliquot the Secondary FRET Reaction Mix into multiple 0.2-ml thin-wall tubes or an 8-well strip (70 μl/tube is sufficient for a row of 12 reactions).

Secondary FRET Reaction Mix

| Reaction Components | 1X Volume | X Volume |
|---|---|---|
| Single Assay Format | | |
| RNA Secondary Buffer 1 | 2.0 μl | |
| Secondary Oligos | 1.5 μl | |
| $T_{10}e_{0.1}$ Buffer | 1.5 μl | |
| Total Mix Volume (1X) | 5.0 μl | |
| Biplex Assay Format | | |
| RNA Secondary Buffer 1 | 2.0 μl | |
| Secondary Oligos | 1.5 μl | |
| Housekeeping Secondary Oligos | 1.5 μl | |
| Total Mix Volume (1X) | 5.0 μl | |

6. After the primary reaction incubation is completed, remove the microplate seal, and add 5 μl Secondary FRET Reaction Mix per well using a multichannel pipet. Mix by pipetting up and down 1–2 times. Reseal the microplate with the well tape and incubate the microplate at 60° C. for 60 or 90 minutes, as indicated in each Product Information Sheet. The secondary reaction incubation time can be varied. See sections 2 of the PROCEDURAL NOTES FOR OPERATION OF THE mRNA INVADER ASSAY for details.
7. Reactions can be read using one of two procedures: Direct Read or Stop and Transfer.

NOTE: Remove the microplate seal before reading the microplate.

Direct Read Procedure

This procedure enables collection of multiple data sets to extend the assay's dynamic range. During the secondary INVADER reaction, read the microplate directly in a top-reading fluorescence microplate reader.

Recommended settings for a PerSeptive Biosystem Cytofluor 4000 instrument are as follows:

| Specific Gene Signal: | | Housekeeping Gene Signal: | |
|---|---|---|---|
| Excitation: | 485/20 nm | Excitation: | 560/20 nm |
| Emission: | 530/25 nm | Emission: | 620/40 nm |
| Reads/Well: | 10 | Reads/Well: | 10 |
| Gain: | 40 | Gain: | 45 |
| Temperature: | 25° C. | Temperature: | 25° C. |

NOTE: Because the optimal gain setting can vary between instruments, adjust the gain as needed to give the best signal/background ratio (sample raw signal divided by the No Target Control signal) or No Target Control sample readings of ~100 RFUs. Fluorescence microplate readers that use a xenon lamp source generally produce higher RFUs. For directly reading the microplates, the probe height of, and how the plate is positioned in, the fluorescence microplate reader may need to be adjusted according to the manufacturer's recommendations.

Stop and Transfer Procedure

1. Prepare 1×Stop Solution (10 mM Tris.HCl, pH 8, 10 mM EDTA) with RNase-free $H_2O$. Add 100 μl per well with a multichannel pipet.
2. Transfer 100 μl of the diluted reactions to a black microplate (e.g., COSTAR (Corning), Cat. No. 3915).
3. Read the microplate using the same parameters as the Direct Read Procedure, but adjust the gain to give No Target Control sample readings of ~100 RFUs (see NOTE above).

In some embodiments, supplementary documentation, such as protocols for ancillary procedures, e.g., for the preparation of additional reagents, or for preparation of samples for use in the methods of the present invention, are provided. In preferred embodiments, supplementary documentation includes guidelines and lists of precautions provided to facilitate successful use of the methods and kits by unskilled or inexperienced users. In particularly preferred embodiments, supplementary documentation includes a troubleshooting guide, e.g., a guide describing possible problems that may be encountered by users, and providing suggested solutions or corrections to intended to aid the user in resolving or avoiding such problems.

For example, and without intending to limit such supplementary documentation to any particular content, kits of the present invention may comprise any of the following procedures and guidelines:

II. Avoidance of RNase Contamination

To avoid RNase contamination during sample preparation and testing, in one embodiment, the user is cautioned to observe the following precautions:

- Wear disposable gloves at all times to avoid contact with samples and reagents.
- Use certified RNase-free disposables, including thin-wall polypropylene tubes and aerosol-barrier pipet tips, for preparing samples and assay reagents, to avoid cross-contamination.
- Use RNase-free (DEPC-treated) $H_2O$ for diluting samples and/or reagents.
- Keep RNA samples and controls on ice during assay setup.

III. Sample and Control Preparation

NOTE: Dilute both standards and samples to concentrations that correspond to a 5-μl addition per reaction.

EXAMPLE 1

The concentration of a 5-attomole standard is 1 amol/μl. 1 amol=$10^{-18}$ mole=602,000 molecules.

EXAMPLE 2

The concentration of a 100-ng sample should be 20 ng/μl

A. Control Preparation

No Target Control:

- Total RNA Format: tRNA Carrier (20 ng/μl)
- Cell Lysate Format: 1×Cell Lysis Buffer 1 (dilute 10×Cell Lysis Buffer 1 to 1×with RNase-free $H_2O$)

Positive Control: RNA Standard (Std) (100amol/μl in vitro transcript)

1. Prepare RNA standards by diluting the positive controls with tRNA Carrier (when running total RNA samples) or with 1×Cell Lysis Buffer 1 [10×Cell Lysis Buffer 1 diluted with RNase-free $H_2O$] (when running cell lysate samples). The Product Information Sheet included in each kit indicates the recommended standard test levels and preparation methods.
2. Using a fresh set of standards for each run is recommended. Store the standards on ice during reaction setup.

B. Total RNA Sample Preparation

1. Prepare total RNA from cells or tissue according to manufacturer's instructions for the selected preparation method. Recommended methods include TRIZOL (Life Technologies, Rockville, Md.), RNEASY (Qiagen, Valencia, Calif.), and RNA WIZ (Ambion, Austin, Tex.).
2. Dilute total RNA samples with RNase-free $H_2O$ to the appropriate concentration.

C. Cell Lysate Sample Preparation—96-Well Microplate Format

NOTE: This cell lysate detection format is used for adherent cells cultured in 96-well tissue culture microplates. Cells are typically seeded at 10,000–40,000 cells per well. Different seeding densities may be required depending on cell type and/or mRNA expression levels. See Procedural Notes for more details. For cells exhibiting high expression, the following methods can be used to attenuate the signal from the cell lysates:

- plate fewer cells per well;
- dilute the cell lysates with 1×Cell Lysis Buffer 1 before addition to the reaction (e.g., 2.5 μl lysate+2.5 μl 1×Cell Lysis Buffer 1);
- read the reaction microplate 15–30 minutes after addition of the Secondary FRET Reaction Mix instead of the recommended 60–90 minutes;

1. Dilute 10×Cell Lysis Buffer 1 to a 1×concentration with RNase-free $H_2O$.
2. Using a multichannel pipet, carefully remove the culture medium from the wells of adherent cells without disturbing the cell monolayer.
3. Wash the cells once with 200 μl PBS (no $MgCl_2$, no $CaCl_2$) and carefully remove the residual PBS with the multichannel pipet.
4. Add 40 μl 1×Cell Lysis Buffer 1 per well. Lyse cells at room temperature for 3–5 minutes.
5. Using a multichannel pipet, carefully transfer 25 μl of each lysate sample into a 96-well microplate. Avoid transferring cellular material from the bottom of the well.
6. Overlay each lysate sample with 10 μl clear CHILLOUT or mineral oil (overlaying is not necessary if using a heated-lid thermal cycler).
7. Seal microplate with Thermaseal well tape. Immediately heat lysates at 75–80° C. for 15 minutes in a thermal cycler or oven to inactivate cellular nucleases.

8. During the heating step, proceed with the reaction setup. See DETAILED mRNA INVADER ASSAY PROTOCOL (above) for instructions.
9. After the heat inactivation step, add the lysate samples immediately to the reaction microplate. Alternatively, the lysate samples can be quickly transferred to a −70° C. freezer for later testing (long-term stability has not been established and may differ for each cell type).

IV. Procedural Notes for Operation of the mRNA Invader Assay

1. RNA Sample Types and Optimization of RNA Sample Amount.

The assay is optimized for performance with total RNA samples prepared from either tissue or cells. Several total RNA preparation methods/kits have been validated for performance in the mRNA INVADER assay:

TRIZOL (Life Technologies, Rockville, Md.)

RNeasy (Qiagen, Valencia, Calif.)

RNA WIZ (Ambion, Austin, Tex.)

It is important to use a method or kit that minimizes the level of genomic DNA, which can inhibit signal generation. Performance of a preliminary experiment is recommended to determine the amount of total RNA sample (typically 1–200 ng, depending on the gene's expression level) that provides the best limit of detection and dynamic range.

The assay has also been validated with lysate samples from a number of cell types. Recommended cell densities in a 96-well tissue culture microplate are 10,000–40,000 cells per well depending on cell type and expression level of the gene of interest. Performance of a preliminary experiment is recommended for any given cell line and/or gene being monitored. Such an experiment should include different cell density levels and/or dilution of the lysate samples with 1×Cell Lysis Buffer 1 (e.g. a 1 μl test level is prepared by mixing 1 μl lysate sample+4 μl 1×Cell Lysis Buffer 1 for a 5 μl sample addition).

2. Dynamic Range Modulation: Variable Secondary Reaction Incubation Times.

The length of the secondary reaction incubation time listed in the protocol is sufficient for most analytes. However, the linear detection range (Signal/Background<15–25) can be adjusted by reading the reaction microplate at variable times after addition of the secondary FRET reagents. For example, high expression samples can often be detected in 15–30 minutes. The Direct Read method (DETAILED mRNA INVADER ASSAY PROTOCOL, step 7) enables simple optimization of the secondary reaction time as the reaction microplate can be incubated further if an early time read does not provide enough signal from the samples being tested.

Monitoring the secondary reaction fluorescence signal with time can also extend the dynamic range of the assay. The Direct Read method at multiple time points can be applied using low-cost instrumentation. Alternatively, real-time fluorescence instrumentation can be used to achieve comparable dynamic ranges exhibited by other mRNA quantitation methods.

3. Dynamic Range Modulation: Variable Sample Levels.

While the FRET detection method greatly simplifies the assay, the dynamic range is typically limited to 2–3 logs when using an endpoint read method. However, since mRNA INVADER assay signal is generated linearly with both target level and time, the easiest method for extending the dynamic range beyond 3 logs (as may be required, e.g., for highly induced genes) is to adjust total RNA sample levels. Fold changes in gene expression (treated sample signal divided by untreated sample signal) can be reliably calculated using normalized sample signals. This is accomplished by testing sample levels that give signal within the linear detection range defined by the standard curve. For example, the fold induction for a highly induced sample can be calculated as follows:

Fold induction=(Net Signal for 1 ng treated sample×100)/Net Signal for 100 ng untreated sample V. Troubleshooting Guide

| Problem | Possible Solution |
|---|---|
| No signal | Check that the fluorescence microplate reader has been set up correctly and that the appropriate excitation and emission filters are in place.<br>Perform mRNA INVADER assay with the provided standard as a positive control.<br>Potential RNase contamination of the samples and reagents. Discard suspect reagents.<br>Use only reagents and oligonucleotides supplied in the kit. Do not mix reagents or oligonucleotides between kits. |
| High variation between replicates | Always work with master primary and secondary reaction mixes.<br>Thoroughly mix all master mixes and samples.<br>Pipet in a similar manner across all the controls and samples.<br>Calibrate pipets frequently. |
| Lack of low target level detection | Calibrate thermal cycler or heat block.<br>Minimize assay variability (see above), i.e. CVs are less than 5% for the sample replicates. This is particularly important for detecting low target levels. |
| Lack of discrimination between high signal samples | Decrease secondary reaction incubation time to achieve detection within the linear range of the assay.<br>Use less total RNA per reaction.<br>Attenuate cell lysate sample signal (see NOTE, Sample and Control Preparation, Part C). |
| Signal inhibition | Run samples on an agarose gel to check for presence of genomic DNA. Alter the RNA sample isolation method to minimize genomic DNA or presence of other inhibitors. The same isolation procedure should be used throughout an experiment.<br>If using the cell lysate format, residual PBS can be inhibitory. Be sure to remove residual PBS from the tissue culture microplate. Do not use PBS that contains $MgCl_2$ or $CaCl_2$, which inhibits the assay. |

APPENDIX A:

mRNA Invader Single Assay Worksheet mRNA Invader Assay Procedure

Prepare samples and controls.

Prepare Primary Reaction Mix. Vortex briefly and aliquot 5 μl per well.

Add 5 μl sample or control per well and pipet up and down 1–2 times.

Add 10 μl CHILLOUT or mineral oil per well.

Incubate primary reaction at 60° C. for 90 minutes.

Prepare Secondary FRET Reaction Mix, vortex briefly.

Using a multichannel pipet, aliquot 5 μl per well and pipet up and down 1–2 times.

Incubate secondary reaction at 60° C. for 60 or 90 minutes.

Read microplate in fluorescence microplate reader (FAM Dye: Ex. 485 nm/Em. 530 nm).

| Reaction Components | 1X Volume | _X Volume (No. of reactions × 1.25) |
|---|---|---|
| PRIMARY REACTION MIX | | |
| RNA Primary Buffer 1 | 4.0 µl | |
| Primary Oligos | 0.25 µl | |
| $T_{10}e_{0.1}$ Buffer | 0.25 µl | |
| CLEAVASE enzyme | 0.5 µl | |
| Total Mix Volume (1X) | 5.0 µl | |
| SECONDARY FRET REACTION MIX | | |
| RNA Secondary Buffer 1 | 2.0 µl | |
| Secondary Oligos | 1.5 µl | |
| $T_{10}e_{0.1}$ Buffer | 1.5 µl | |
| Total Mix Volume (1X) | 5.0 µl | |

APPENDIX B:

mRNA Invader Biplex Assay Worksheet mRNA Invader Assay Procedure

Prepare samples and controls.

Prepare Primary Reaction Mix. Vortex briefly and aliquot 5 µl per well.

Add 5 µl sample or control per well and pipet up and down 1–2 times.

Add 10 µl CHILLOUT or mineral oil per well.

Incubate primary reaction at 60° C. for 90 minutes.

Prepare Secondary FRET Reaction Mix, vortex briefly.

Using a multichannel pipet, aliquot 5 µl per well and pipet up and down 1–2 times.

Incubate secondary reaction at 60° C. for 60 or 90 minutes.

Read microplate in fluorescence microplate reader (FAM Dye: Ex. 485 nm/Em. 530 nm and red dye: Ex. 560 nm/Em. 620 nm).

| Reaction Components | 1X Volume | _X Volume (No. of reactions × 1.25) |
|---|---|---|
| PRIMARY REACTION MIX | | |
| RNA Primary Buffer 1 | 4.0 µl | |
| Primary Oligos | 0.25 µl | |
| Housekeeping Primary Oligos | 0.25 µl | |
| CLEAVASE IX enzyme | 0.5 µl | |
| Total Mix Volume (1X) | 5.0 µl | |
| SECONDARY FRET REACTION MIX | | |
| RNA Secondary Buffer 1 | 2.0 µl | |
| Secondary Oligos | 1.5 µl | |
| Housekeeping Secondary Oligos | 0.25 µl | |
| Total Mix Volume (1X) | 5.0 µl | |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method for selecting a primer, comprising:

a) providing:

i) a target nucleic acid having at least one accessible site and at least one inaccessible site;

ii) a plurality of extension primers, each of said primers comprising a first region, wherein said first regions of said plurality of primers differ in sequence from each other, and wherein said plurality of primers comprise first regions that are complementary to different portions of said target nucleic acid; and iii) a template-dependent nucleic acid extension agent;

b) exposing said plurality of extension primers and said extension agent to said target nucleic acid under conditions wherein primers comprising first regions that are complementary only to an inaccessible site in said target nucleic acid are not extended by said extension agent, and wherein primers comprising first regions that are complementary to at least one accessible site of said target nucleic acid form an extension product;

c) selecting a primer complementary to at least one accessible site by identifying a member of said plurality of primers that forms an extension product.

2. The method of claim 1, wherein said target nucleic acid comprises DNA.

3. The method of claim 1, wherein said target nucleic acid comprises RNA.

4. The method of claim 1, wherein said plurality of primers further comprise a second region, said second region located 5' of said first region.

5. The method of claim 4, wherein said second regions of said plurality of primers are identical in sequence to one another.

6. The method of claim 5, further comprising providing:

i) first and second amplification primers, said first amplification primer complementary to at least a portion of said second regions of said plurality of extension primers and said second amplification primer capable of hybridizing to a sequence complementary to a first domain of said target nucleic acid; and ii) an amplification agent;

and further comprising the step of treating said extension products with said first and second amplification primers and said amplification agents to produce amplification products prior to said selecting step.

7. The method of claim 1, wherein said plurality of primers comprises at least 10 different primers.

8. The method of claim 1, wherein said plurality of primers comprises at least 100 different primers.

9. The method of claim 1, wherein said plurality of primers comprises at least 1000 different primers.

10. The method of claim 1, wherein said plurality of primers comprises a sufficient number of primers to encompass every sequence variation within said first region.

11. The method of claim 1, wherein said first region is six or more nucleotides in length.

12. The method of claim 11, wherein said first region is six nucleotides in length.

13. The method of claim 1, wherein said template-dependent nucleic acid extension agent comprises a polymerase.

14. The method of claim 1, wherein said template-dependent nucleic acid extension agent comprises a reverse transcriptase.

15. A method for identifying accessible sites on a target nucleic acid comprising:

a) providing:
   i) a target nucleic acid having at least one accessible site and at least one inaccessible site;
   ii) a plurality of extension primers, each of said primers comprising a first region, wherein said first regions of said plurality of primers differ in sequence from each other, and wherein said plurality of primers comprise first regions that are complementary to different portions of said target nucleic acid; and
   iii) a template-dependent nucleic acid extension agent;

b) exposing said plurality of extension primers and said extension agent to said target nucleic acid under conditions wherein primers comprising first regions that are complementary only to an inaccessible site in said target nucleic acid are not extended by said extension agent, and wherein primers comprising first regions that are complementary to at least one accessible site of said target nucleic acid form an extension product that is complementary to said target nucleic acid adjacent to said accessible site;

c) determining at least a portion of the sequence of an extension product; and d) identifying said accessible site by locating a region of said target nucleic acid adjacent to sequence that is complementary to said extension product.

16. The method of claim 15, wherein said target nucleic acid comprises DNA.

17. The method of claim 15, wherein said target nucleic acid comprises RNA.

18. The method of claim 15, wherein said plurality of primers comprises at least 10 different primers.

19. The method of claim 15, wherein said plurality of primers comprises at least 100 different primers.

20. The method of claim 15, wherein said plurality of primers comprises at least 1000 different primers.

21. The method of claim 15, wherein said plurality of primers comprises a sufficient number of primers to encompass every sequence variation within said first region.

22. The method of claim 15, wherein said first region is six or more nucleotides in length.

23. The method of claim 22, wherein said first region is six nucleotides in length.

24. The method of claim 15, wherein said template-dependent nucleic acid extension agent comprises a polymerase.

25. The method of claim 15, wherein said template-dependent nucleic acid extension agent comprises a reverse transcriptase.

26. A method of locating accessible sites on a target nucleic acid comprising:

a) providing:
   i) a target nucleic acid having at least one accessible site and at least one inaccessible site wherein said accessible site is located a set distance from a first domain of said target nucleic acid;
   ii) a plurality of extension primers, each of said primers comprising first region and second regions, wherein said first regions of said plurality of primers differ in sequence from each other, wherein said plurality of primers comprise first regions that are complementary to different portions of said target nucleic acid, and wherein said second region is located 5' of said first region;
   iii) a template-dependent nucleic acid extension agent;
   iv) an amplification agent; and
   v) first and second amplification primers, said first amplification primer complementary to at least a portion of said second regions of said plurality of extension primers and said second amplification primer capable of hybridizing to a sequence complementary to a first domain of said target nucleic acid;

b) exposing said plurality of extension primers and said extension agent to said target nucleic acid under conditions wherein primers comprising first regions that are complementary only to an inaccessible site in said target nucleic acid are not extended by said extension agent, and wherein primers comprising first regions that are complementary to at least one accessible site of said target nucleic acid form an extension product;

c) treating said extension products with said amplification agent and said first and second amplification primers to generate one or more amplification products, said amplification products having a length, wherein said length of said amplification products is equal to said distance of said accessible site on said target nucleic acid from said first domain of said target nucleic acid; and d) determining a location of one or more accessible sites on said target nucleic acid using said distance.

27. The method of claim 26, wherein said using said distance comprises determining said size of one or more of said amplification products.

28. The method of claim 26, wherein said target nucleic acid comprises DNA.

29. The method of claim 26, wherein said target nucleic acid comprises RNA.

30. The method of claim 26, wherein said plurality of primers comprises at least 10 different primers.

31. The method of claim 26, wherein said plurality of primers comprises at least 100 different primers.

32. The method of claim 26, wherein said plurality of primers comprises at least 1000 different primers.

33. The method of claim 26, wherein said plurality of primers comprises a sufficient number of primers to encompass every sequence variation within said first region.

34. The method of claim 26, wherein said first region is six or more nucleotides in length.

35. The method of claim 34, wherein said first region is six nucleotides in length.

36. The method of claim 26, wherein said template-dependent nucleic acid extension agent comprises a polymerase.

37. The method of claim 26, wherein said template-dependent nucleic acid extension agent comprises a reverse transcriptase.

38. The method of claim 26, wherein said amplification agent comprises a polymerase.

39. The method of claim 38, wherein said polymerase comprises a thermostable polymerase.

40. The method of claim 26, wherein said treating said extension products with said amplification agent and said first and second amplification primers comprises a polymerase chain reaction.

* * * * *